(12) United States Patent
Wu et al.

(10) Patent No.: US 8,546,135 B2
(45) Date of Patent: Oct. 1, 2013

(54) IN VIVO GENOME-WIDE MUTAGENESIS

(75) Inventors: Sen Wu, Salt Lake City, UT (US);
Mario R. Capecchi, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 515 days.

(21) Appl. No.: 12/522,075

(22) PCT Filed: Feb. 8, 2008

(86) PCT No.: PCT/US2008/053446
§ 371 (c)(1),
(2), (4) Date: Feb. 11, 2010

(87) PCT Pub. No.: WO2008/098181
PCT Pub. Date: Aug. 14, 2008

(65) Prior Publication Data
US 2010/0178696 A1     Jul. 15, 2010

Related U.S. Application Data

(60) Provisional application No. 60/889,149, filed on Feb. 9, 2007.

(51) Int. Cl.
*C12N 15/00*     (2006.01)
*C07H 21/04*     (2006.01)

(52) U.S. Cl.
USPC ........................ 435/320.1; 536/23.1; 536/24.1

(58) Field of Classification Search
None
See application file for complete search history.

(56) References Cited

U.S. PATENT DOCUMENTS

| | | | |
|---|---|---|---|
| 4,959,317 A | 9/1990 | Sauer et al. | |
| 5,434,066 A | 7/1995 | Bebee et al. | |
| 6,277,608 B1 | 8/2001 | Hartley et al. | |
| 7,105,343 B1 | 9/2006 | Fraser, Jr. et al. | |
| 2002/0173634 A1* | 11/2002 | Fraser et al. | 536/23.1 |
| 2003/0143578 A1 | 7/2003 | Pruitt et al. | |
| 2005/0066376 A1 | 3/2005 | Craig et al. | |
| 2006/0212949 A1 | 9/2006 | Alphey | |
| 2006/0218652 A1 | 9/2006 | Horn et al. | |

FOREIGN PATENT DOCUMENTS

| | | |
|---|---|---|
| EP | 2113029 | 2/2008 |
| WO | WO 2006/122442 | 11/2006 |
| WO | WO 2008/098181 | 2/2008 |

OTHER PUBLICATIONS

GenBank Accession No. J04364.2, GI: 23963667, publicly available Oct. 2002.*
Ishida et al. RET: a poly A-trap retrovirus vector for reversible disruption and expression monitoring of genes in living cells. Nucleic Acids Research, vol. 27, No. 24, p. e35, printed as pp. 1/8-8/8.*
Ishida et al. RET: A poly A-trap retrovirus vector for reversible disruption and expression monitoring of genes in living cells. Nucleic Acids Research, vol. 27, No. 24, p. e35, 1999, printed as pp. 1/8-8/8.*
Wu S, Ying G, Wu Q, Capecchi MR. (2007) Toward simpler and faster genome-wide mutagenesis in mice. Nat Genet. 39(7): 922-930.
Yu Y, Bradley A. (2001) Engineering chromosomal rearrangements in mice. Nat Rev Genet. 2(10): 780-790.
Supplementary European Search Report for EP Application No. 08729412.0, mailed May 6, 2010.
International Search Report and Written Opinion for PCT/US08/53446, mailed Sep. 23, 2008.
Abremski, K. et al. Studies on the properties of P1 site-specific recombination: evidence for topologically unlinked products following recombination. *Cell* 32:1301-1311 (1983).
Accili, D. "Correspondence: A note of caution on the Knockout Mouse Project." *Nat Genet* 36(11):1132 (2004).
Adams, D. et al. "A genome-wide, end-sequenced 129Sv BAC library resource for targeting vector construction." *Genomics* 86:753-8 (2005).
Adams, D.J. et al. "Mutagenic insertion and chromosome engineering resource (MICER)." *Nat Genet* 36(8):867-71 (2004).
Alvarado-Urbina, G. et al. "Automated Synthesis of Gene Fragments." *Science* 214:270 (1981).
Angrand, P. et al. "Simplified generation of targeting constructs using ET recombination." *Nucleic Acids Res* 27(17): e16(i)-e16(vi) (1999).
Austin, C. P. et al. "The knockout mouse project." *Nat Genet* 36(9):921-4 (2004).
Auwerx, J. et al. "The European dimension for the mouse genome mutagenesis program." *Nat Genet* 36(9):, 925-7 (2004).
Bangs, C. and Donlon, T. "Metaphase Chromosome preparation from Cultured Peripheral Blood Cells." *Current Protocols in Human Genetics* 4.1.1-4.1.19 (2005).
Baudin, A. et al. A simple and efficient method for direct gene deletion in *Saccharomyces cerevisiae*. *Nucleic Acids Res* 21(14):3329-30 (1993).
Bejerano, G. et al. "Ultraconserved elements in the human genome." *Science* 304:1321-5 (2004).
Bejerano, G. et al. "Into the heart of darkness: large-scale clustering of human non-coding DNA." *Bioinformatics* 20 Suppl 1, i40-i48 (2004).
Boffelli, D. et al. Comparative genomics at the vertebrate extremes. Nat Rev Genet 5, 456-65 (2004).
Bolivar, F. et al. Construction and characterization of new cloning vehicles. II. A multipurpose cloning system. Gene 2, 95-113 (1977).
Bolivar, F. et al. Construction and characterization of new cloning vehicles. III. Derivatives of Plasmid pBR322 carrying unique *EcoI* RI sites for selection of *Eco* RI generated recombinant DHA molecules. Gene 4:121-136 (1978).
Bonin, C. P. & Mann, R. S. A piggyBac transposon gene trap for the analysis of gene expression and function in *Drosophila*. Genetics 167, 1801-11 (2004).
Bradshaw, M. et al. A new vector for recombinationbased cloning of large DNA fragments from yeast artificial chromosomes. Nucleic Acids Res 23(23):4850-6 (1995).

(Continued)

*Primary Examiner* — Jennifer Dunston
(74) *Attorney, Agent, or Firm* — Ballard Spahr LLP

(57) ABSTRACT

Disclosed herein are compositions and methods for deleting or duplicating DNA in a mammalian genome. Also disclosed are compositions and methods for generating a random genome-wide chromosome rearrangement. Also disclosed are compositions and methods for streamlined construction of gene targeting vectors.

3 Claims, 31 Drawing Sheets

(56) References Cited

OTHER PUBLICATIONS

Branda, C.S. & Dymecki, S.M. "Talking about a revolution: The impact of sitespecific recombinases on genetic analyses in mice." *Dev Cell* 6:7-28 (2004).
Buchholz, F. et al. "Inducible chromosomal translocation of AML1 and ETO genes through Cre/loxP-mediated recombination in the mouse." *EMBO Rep* 1, 133-9 (2000).
Bunting, M. et al. "Targeting genes for self-excision in the germ line." *Genes Dev* 13, 1524-8 (1999).
Capecchi, M.R. "Altering the genome by homologous recombination." *Science* 244:1288-92 (1989b).
Capecchi, M.R. "The new mouse genetics: altering the genome by gene targeting." *Trends Genet* 5(3):70-6 (1989a).
Cary, L. C. et al. "Transposon mutagenesis of baculoviruses: analysis of Trichoplusia ni transposon IFP2 insertions within the FP-locus of nuclear polyhedrosis viruses." *Virology* 172:156-69 (1989).
Chan, W. et al. "A recombineering based approach for high-throughput conditional knockout targeting vector construction." *Nucleic Acids Res* 35: e64 (2007).
Chang, A.C., and Cohen, S.N. "Construction and characterization of amplifiable multicopy DNA cloning vehicles derived from the P15A cryptic miniplasmid." *J Bacteriol* 134:1141-1156 (1978).
Chomczynski, P. "One-hour downward alkaline capillary transfer for blotting of DNA and RNA." *Anal Biochem* 201:134-9 (1992).
Collins, E. et al. "Inter-chromosomal recombination of M11 and Af9 genes mediated by cre-loxP in mouse development." *EMBO Rep 1*, 127-32 (2000).
Copeland, N. et al. "Recombineering: a powerful new tool for mouse functional genomics." *Nat Rev Genet* 2:769-79 (2001).
Datsenko, K. A. & Wanner, B. L. "One-step inactivation of chromosomal genes in *Escherichia coli* K-12 using PCR products." *Proc Natl Acad Sci U S A* 97:6640-5 (2000).
Deng, C. & Capecchi, M.R. "Reexamination of gene targeting frequency as a function of the extent of homology between the targeting vector and the target locus." *Mol Cell Biol* 12:3365-71 (1992).
Dermitzakis, E. et al. "Conserved non-genic sequences—an unexpected feature of mammalian genomes." *Nat Rev Genet* 6:151-7 (2005).
Ding, S. et al. "Efficient transposition of the piggyBac (PB) transposon in mammalian cells and mice." *Cell* 122:473-83 (2005).
Elick et al. "Excision of the piggyBac transposable element in vitro is a precise event that is enhanced by the expression of its encoded transposase." Genetica 98(1):33-41.1996a.
Ellis et al. "High efficiency mutagenesis, repair, and engineering of chromosomal DNA using single-stranded oligonucleotides." *Proc. Natl. Acad. Sci*, 98:6742-6746, 2001.
Fraser, M. J. et al. "Precise excision of TTAA-specific lepidopteran transposons piggyBac (IFP2) and tagalong (TFP3) from the baculovirus genome in cell lines from two species of Lepidoptera." *Insect Mol Biol* 5:141-51 (1996.
Friedrich, G. & Soriano, P. "Promoter traps in embryonic stem cells: a genetic screen to identify and mutate developmental genes in mice." *Genes Dev* 5:1513-23 (1991).
Genoud, N. et al. "Disruption of Doppel prevents neurodegeneration in mice with extensive Prnp deletions." *Proc Natl Acad Sci U S A* 101:4198-203 (2004).
George, S.H. et al. "Developmental and adult phenotyping directly from mutant embryonic stem cells." *Proc Natl Acad Sci U S A* 104:4455-60 (2007).
Golic, K. G. & Golic, M. M. "Engineering the *Drosophila* genome: chromosome rearrangements by design" *Genetics* 144:1693-711 (1996).
Hambsch, B. et al. "{gamma}-Protocadherins, presenilin-mediated release of C-terminal fragment promotes locus expression." *J Biol Chem* 280:15888-97 (2005).
Hamilton, C.M. et al. "New method for generating deletions and gene replacements in *Escherichia coli*." *J Bacteriol* 171:4617-22 (1989).
Hamilton, D.L. et al. "Site-specific recombination by the bacteriophage P1 lox-Cre system." *J. Mol. Biol.* 178:481-486 (1984).

Handler, A. M. & Harrell, R. A., 2nd. "Transformation of the Caribbean fruit fly, *Anastrepha suspensa*, with a piggyBac vector marked with polyubiquitin-regulated GFP." *Insect Biochem Mol Biol* 31:199-205 (2001).
Hansen, J. et al. "A large-scale, gene-driven mutagenesis approach for the functional analysis of the mouse genome." *Proc Natl Acad Sci U S A* 100, 9918-22 (2003).
Harfe, B.D. et al. "Evidence for an expansion-based temporal Shh gradient in specifying vertebrate digit identities." *Cell* 118:517-28 (2004).
Hartley, J.L. et al. "DNA cloning using in vitro sitespecific recombination." *Genome Res* 10:1788-95 (2000).
Herault, Y. et al. "Engineering chromosomes in mice through targeted meiotic recombination (TAMERE)." *Nat Genet* 20:381-4 (1998).
Hoess, R. et al. "Interaction of the bacteriophage P1 recombinase Cre with the recombining site loxP." *Proc. Natl. Acad. Sci. USA* 81:1026-1029 (1984).
Hoess, R. et al "P1 site-specific recombination: Nucleotide sequence of the recombining sites.". *Proc. Natl. Acad. Sci. USA* 79:3398-3402 (1982).
Huber, A. B. et al. "Distinct roles for secreted semaphorin signaling in spinal motor axon guidance." *Neuron* 48:949-64 (2005).
Inoue, H. et al. "High efficiency transformation of *Escherichia coli* with plasmids." *Gene* 96, 23-8 (1990).
Ito et al. "Solid phase synthesis of polynucleotides. VI. Further studies on polystyrene copolymers for the solid support." *Nuc. Acid. Res.* 10(5):1755 (1982).
Jossin, Y. et al. "The central fragment of Reelin, generated by proteolytic processing in vivo, is critical to its function during cortical plate development." *J Neurosci.* 24:514-21 (2004).
Kahn, M. et al. "Plasmid cloning vehicles derived from plasmids ColE1, F, R6K, and RK2." *Methods in enzymology* 68:268-280 (1979).
Kmita, M. et al. "Serial deletions and duplications suggest a mechanism for the collinearity of Hoxd genes in limbs." *Nature* 420:145-50 (2002).
Kohmura, N. et al. "Diversity revealed by a novel family of cadherins expressed in neurons at a synaptic complex." *Neuron* 20, 1137-51 (1998).
Landy A. "Dynamic structural, and regljlatory aspects of λ sitespecific recombination" *Annu. Rev. Biochem.* 58:913 (1989).
Lee, E.C. et al. "A highly efficient *Escherichia coli*-based chromosome engineering system adapted for recombinogenic targeting and subcloning of BAC DNA." *Genomics* 73, 56-65 (2001).
Li, X. et al. "piggyBac internal sequences are necessary for efficient transformation of target genomes." *Insect Mol Biol* 14: 17-30 (2005).
Lin, F. et al. "Homologous Recombination in Mouse L Cells.". Cold Spring Harbor Symp. Quant. Biol. vol. XLIX Recombination at the DNA Level, pp. 139-149 (1984).
Liu, P. et al. "Efficient Cre-loxP-induced mitotic recombination in mouse embryonic stem cells." *Nat Genet* 30:66-72 (2002).
Liu, P. et al. "A highly efficient recombineering-based method for generating conditional knockout mutations." *Genome Res* 13: 476-84 (2003).
Mansour, S.L. et al. "Disruption of the proto-oncogene int-2 in mouse embryo-derived stem cells: a general strategy for targeting mutations to non-selectable genes." *Nature* 336:348-52 (1988).
Margulies, E. H. et al. << Comparative sequencing provides insights about the structure and conservation of marsupial and monotreme genomes. *Proc Natl Acad Sci U S A* 102:3354-9 (2005).
Mills, A. A. & Bradley, A. "From mouse to man: generating megabase chromosome rearrangements." *Trends Genet* 17:331-9 (2001).
Moon, A.M. & Capecchi, M.R. "Fgf8 is required for outgrowth and patterning of the limbs." *Nat Genet* 26:455-9 (2000).
Nagae, S. et al. "Temporal and spatial expression profiles of the Fat3 protein, a giant cadherin molecule, during mouse development." *Dev Dyn* 236:534-43 (2007).
Nagy, A. "Cre recombinase: the universal reagent for genome tailoring." *Genesis* 26: 99-109 (2000).
Nakayama, M. et al. "MEGF1/fat2 proteins containing extraordinarily large extracellular domains are localized to thin parallel fibers of cerebellar granule cells." *Mol Cell Neurosci* 20:563-78 (2002).

Nobrega, M. et al. "Megabase deletions of gene deserts result in viable mice." *Nature* 431:988-93 (2004).

Oliner, J.D. et al. "In vivo cloning of PCR products in *E. coli*". *Nucleic Acids Res* 21:5192-7 (1993).

Phillips, G. R. et al. Gamma-protocadherins are targeted to subsets of synapses and intracellular organelles in neurons. *J Neurosci* 23:5096-104 (2003).

Price, S.R. et al. "Regulation of motor neuron pool sorting by differential expression of type II cadherins." *Cell* 109:205-16 (2002).

Ryder, E. et al. "The DrosDel collection: a set of P-element insertions for generating custom chromosomal aberrations in *Drosophila melanogaster*." *Genetics* 167:797-813 (2004).

Sandelin, A. et al. "Arrays of ultraconserved non-coding regions span the loci of key developmental genes in vertebrate genomes." *BMC Genomics* 5:99 (2004).

Schmidt, E. et al. "Illegitimate Cre-dependent chromosome rearrangements in transgenic mouse spermatids." *Proc Natl Acad Sci U S A* 97:13702-7 (2000).

Senzaki, K. et al. "Proteins of the CNR family are multiple receptors for Reelin." *Cell* 99:635-47 (1999).

Shima, Y. et al. "Regulation of dendritic maintenance and growth by a mammalian 7-pass transmembrane cadherin." *Dev Cell* 7:205-16 (2004).

Skarnes, W.C. et al. <<A public gene trap resource for mouse functional genomics. *Nat Genet* 36:543-4 (2004).

Spitz, F. et al. "Inversion-induced disruption of the Hoxd cluster leads to the partition of regulatory landscapes." *Nat Genet* 37:889-893 (2005).

Sternberg, N. et al. "Site-specific Recombination and its ole in the life cycle of bacteriophage P1." Cold Spring Harbor Symp. Quant. Biol. vol. XLV Movable Genetic Elements, pp. 297-309 (1981).

Sugino, H. et al. "Genomic organization of the family of CNR cadherin genes in mice and humans." *Genomics* 63:75-87 (2000).

Takeichi, M. "The cadherin superfamily in neuronal connections and interactions." *Nat Rev Neurosci* 8:11-20 (2007).

Tang, S. et al. "A Cre/loxP-deleter transgenic line in mouse strain 129S1/SvImJ." *Genesis* 32:199-202 (2002).

te Riele, H. et al. "A. Highly efficient gene targeting in embryonic stem cells through homologous recombination with isogenic DNA constructs." *Proc Natl Acad Sci U S A* 89:5128-32 (1992).

Testa, G. et al. "Engineering the mouse genome with bacterial artificial chromosomes to create multipurpose alleles." *Nat Biotechnol* 21:443-7 (2003).

The International Mouse Knockout Consortium. A mouse for all reasons. Cell 128, 9-13 (2007).

Thomas, K. et al. "High frequency targeting of genes to specific sites in the mammalian genome." *Cell* 44: 419-28 (1986).

Thomas, K.R. & Capecchi, M.R. "Site-directed mutagenesis by gene targeting in mouse embryo-derived stem cells." *Cell* 51:503-12 (1987).

Tissir, F. & Goffinet, A. M. "Reelin and brain development." *Nat Rev Neurosci* 4: 496-505 (2003).

Tissir, F. et al. "Protocadherin Celsr3 is crucial in axonal tract development." *Nat Neurosci* 8:451-7 (2005).

Truett, G.E. et al. "Preparation of PCR-quality mouse genomic DNA with hot sodium hydroxide and tris (HotSHOT)." *Biotechniques* 29:52-54 (2000).

Tvrdik, P. & Capecchi, M.R. "Reversal of Hox1 gene subfunctionalization in the mouse." *Dev Cell* 11:239-50 (2006).

Valenzuela, D.M. et al. "High-throughput engineering of the mouse genome coupled with high-resolution expression analysis." *Nat Biotechnol* 21(6):652-9 (2003).

Vavouri, T. et al. "Defining a genomic radius for long-range enhancer action: duplicated conserved non-coding elements hold the key." *Trends Genet* 22:5-10 (2006).

Ventura, A. et al. "Restoration of p53 function leads to tumour regression in vivo." *Nature* 445:661-5 (2007).

Wang, X. et al. "Gamma protocadherins are required for survival of spinal interneurons." *Neuron* 36:843-54 (2002).

Weiner, J. et al. "Gamma protocadherins are required for synaptic development in the spinal cord." *Proc Natl Acad Sci U S A* 102:8-14 (2005).

Wu, S. et al. Motoneurons and oligodendrocytes are sequentially generated from neural stem cells but do not appear to share common lineage-restricted progenitors in vivo. Development 133: 581-90 (2006).

Wu, Q. "Comparative genomics and diversifying selection of the clustered vertebrate protocadherin genes." *Genetics* 169:2179-88 (2005).

Wu, Q. et al. "Comparative DNA sequence analysis of mouse and human protocadherin gene clusters." *Genome Res* 11:389-404 (2001).

Wu, Q. & Maniatis, T. "Large exons encoding multiple ectodomains are a characteristic feature of protocadherin genes." *Proc Natl Acad Sci U S A* 97:3124-9 (2000).

Wu, Q. & Maniatis, T. "A striking organization of a large family of human neural cadherin-like cell adhesion genes." *Cell* 97:779-90 (1999).

Yang, X. et al. "Homologous recombination based modification in *Escherichia coli* and germline transmission in transgenic mice of a bacterial artificial chromosome." *Nat Biotechnol* 15:859-65 (1997).

Yang, Y. & Seed, B. "Site-specific gene targeting in mouse embryonic stem cells with intact bacterial artificial chromosomes." *Nat Biotechnol* 21: 447-51 (2003).

Yu, D. et al. "An efficient recombination system for chromosome engineering in *Escherichia coli*." *Proc Natl Acad Sci U S A* 97:5978-83 (2000).

Zhang, P. et al. "Towards genetic genome projects: genomic library screening and gene-targeting vector construction in a single step." *Nat Genet* 30:31-9 (2002).

Zhang, Y. et al. "A new logic for DNA engineering using recombination in *Escherichia coli*." *Nat Genet* 20:123-8 (1998).

Zhang, Y. et al. "DNA cloning by homologous recombination in *Escherichia coli*." *Nat Biotechnol* 18:1314-7 (2000).

Zheng, B. et al. "Engineering mouse chromosomes with Cre-loxP: range, efficiency, and somatic applications." *Mol Cell Biol* 20:648-55 (2000).

\* cited by examiner

Southern blot

US 8,546,135 B2

IN VIVO GENOME-WIDE MUTAGENESIS

CROSS-REFERENCE TO RELATED APPLICATIONS

This application claims benefit of U.S. Provisional Application No. 60/889,149, filed Feb. 9, 2007, which is hereby incorporated herein by reference in its entirety.

STATEMENT REGARDING FEDERALLY SPONSORED RESEARCH

This invention was made with government support under Grant 2 RO1 GM021168-33 awarded by the National Institutes of Health. The government has certain rights in the invention.

BACKGROUND

International efforts to generate knockouts of all mouse genes (Austin, C. P. et al. 2004; Auwerx, J. et al. 2004), such as the NIH Knockout Mouse Project (KOMP), have been initiated, however these efforts will concentrate on coding regions, representing about 2.5% of the genome. The remaining 97.5% non-coding region is often referred to as "junk DNA". Based upon comparisons between the newly sequenced mammalian genomes, as well as partial sequencing of other vertebrate genomes, more than 300,000 conserved non-coding elements (CNEs) (also referred to as conserved non-genic sequences, CNGs) have been identified within this presumed "junk DNA". Many of these CNEs show greater sequence conservation among disparate vertebrate species than do the average protein-coding sequence (Dermitzakis, E. T., et al. 2005; Bejerano, G. et al. 2004; Boffelli, D., et al. 2004; Sandelin, A. et al. 2004; Margulies, E. H. et al. 2005; Vavouri, T., et al. 2006; Bejerano, G., et al. 2004). Increasing evidence suggests that such non-coding regions play important regulatory roles, particularly for genes controlling development. In many cases mutations in these regions cause significant disease phenotypes. However, in order to assess their functions directly, it is currently unrealistic to generate specific deletions of all of these CNEs in the mouse. A more practical approach to dissect the functional roles of such non-coding regions can be to systematically generate relatively large deletions of up to several hundred kilobase pairs (kb) that encompass multiple CNEs.

In *Drosophila*, the transposon-based gene-trap has been used to generate a large collection of FRT-bearing alleles, allowing investigators to use FLP/FRT site-specific recombination to mediate trans recombinations in vivo between homologous chromosomes in order to generate large deletions and duplications covering the entire genome (Ryder, E. et al. 2004; Golic, K. G. & Golic, M. M. 1996). In the mouse, an in vitro Cre/loxP-based method in embryonic stem (ES) cells has been used to generate megabase size deletions and duplications (Zheng, B., et al. 2000; Mills, A. A. & Bradley, A. 2001). However, this in vitro protocol is very labor-intensive and requires multiple rounds of ES cell genomic manipulations. An in vivo Cre/loxP method, named TAMERE, that uses the Sycp1-Cre driver, and takes advantage of homologous chromosome paring during meiosis, has been used to generate trans-allelic recombination in mice (Herault, Y., et al. 1998). Although this method was successful in generating deletions and duplications for the closely-linked Hoxd genes (Kmita, M., et al. 2002), it has been limited to generating only relatively small deletions of up to about 15 kb (Genoud, N. et al. 2004). Since deletions of this size can be readily achieved by conventional gene targeting/knockout technology, TAMERE does not offer more advantages. Another in vivo Cre/loxP method, named STRING (Spitz, F., 2005), that also uses the Sycp1-Cre driver and very tedious and lengthy breeding, has been able to generate super-large deletions of more than several megabase pairs. The main problem of TAMERE and STRING is that the deletions they generate are either too small or too big, the most useful deletions of from 20 kb to 2 Mb would be very difficult to create by TAMERE or STRING, if not impossible. Needed is a simple and efficient strategy for the generation of large deletions and duplications at most useful resolutions of 20 kb to 2 Mb. Needed also is a simple and efficient strategy for in vivo generation of translocations.

The development of phage based homologous recombination systems has greatly simplified the generation of transgenic and knockout constructs, making it possible to engineer large segments of genomic DNA, such as those carried on BACs or P1 artificial chromosomes (PACs), that replicate at low-copy number in *Escherichia coli*. Using phage recombination to carry out genetic engineering has been called recombinogenic engineering or recombineering. Needed are improved compositions and methods of recombineering to facilitate large scale construction of target vectors.

BRIEF SUMMARY

In accordance with the purpose of this invention, as embodied and broadly described herein, this invention relates to compositions and methods for deleting or duplicating DNA in a mammalian genome. Also disclosed are compositions and methods for generating a random genome-wide chromosome rearrangement. Also disclosed are compositions and methods for streamlined construction of gene targeting vectors.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1 shows generation of mouse Pcdh alleles.

FIG. 2 shows generation of large deletions and duplications by Cre/loxP-mediated in trans recombination.

FIG. 3 shows generation of a Cre/loxP-mediated germline translocation between non-homologous chromosomes.

FIG. 4 shows successful piggyBac transposition for multipurpose gene-trapping.

FIG. 5 shows germline transposition.

FIG. 6 shows targeting vector design and construction. FIG. 6G shows the final targeting vector is made by a Gateway recombination of the vectors shown in FIG. 6F.

FIG. 7 shows Gateway-compatible vectors.

FIG. 8A shows to insert the first loxP site, two oligos are designed for PCR amplifying a resistance gene (cat). The forward oligo has this formula: 50 nt for homologous recombination, loxP site, a unique restriction enzyme site (E), and 20-25 nt as PCR primer. The reverse oligo has similar formula but without the loxP site. It should be noted that site E is also designed for use in Southern screening of ES cells, ensuring that 5' loxP site is targeted. The PCR and Redrecombination conditions are the same as those described for generations of simple loss of-function alleles. FIG. 8B shows the resulting plasmid from (a) is cut with the unique restriction enzyme E, and self-ligates to obtain the plasmid (b). FIG. 8C shows To insert the second loxP site and neo cassette, the forward oligo has this formula: 50 nt for homologous recombination, a unique restriction enzyme site (B), and 20-25 nt as PCR primer. The reverse oligo has similar formula: 50 nt for homologous recombination, loxP site, a unique restriction enzyme site (B), and 20-25 nt as PCR primer. The PCR and Red-recombination conditions are the same as above. FIG. 8D shows the resulting plasmid in (c) is cut with the unique restriction enzyme B, and ligated to a site B-flanked FRT-neo-FRT cassette to obtain the plasmid in (d). The negative selection cassette TK is add in a similar manner as for the simple loss-of-function targeting vectors by Gateway recombination. FIG. 8E shows a HSV-TK vector to be used in Gateway recombination with the vector created in (d). FIG. 8F shows the resulting vector from the Gateway recombination of the vectors shown in (d) and (e).

FIG. 9 shows three examples of the knockout mice generated: $Fat2^{EGFP}$, $Fat3^{nlacZ}$ and $Fat4^{EGFP}$ knockout mice.

FIG. 10 shows alleles generated for the clustered protocadherin genes in this study.

DETAILED DESCRIPTION

Figure 1A:
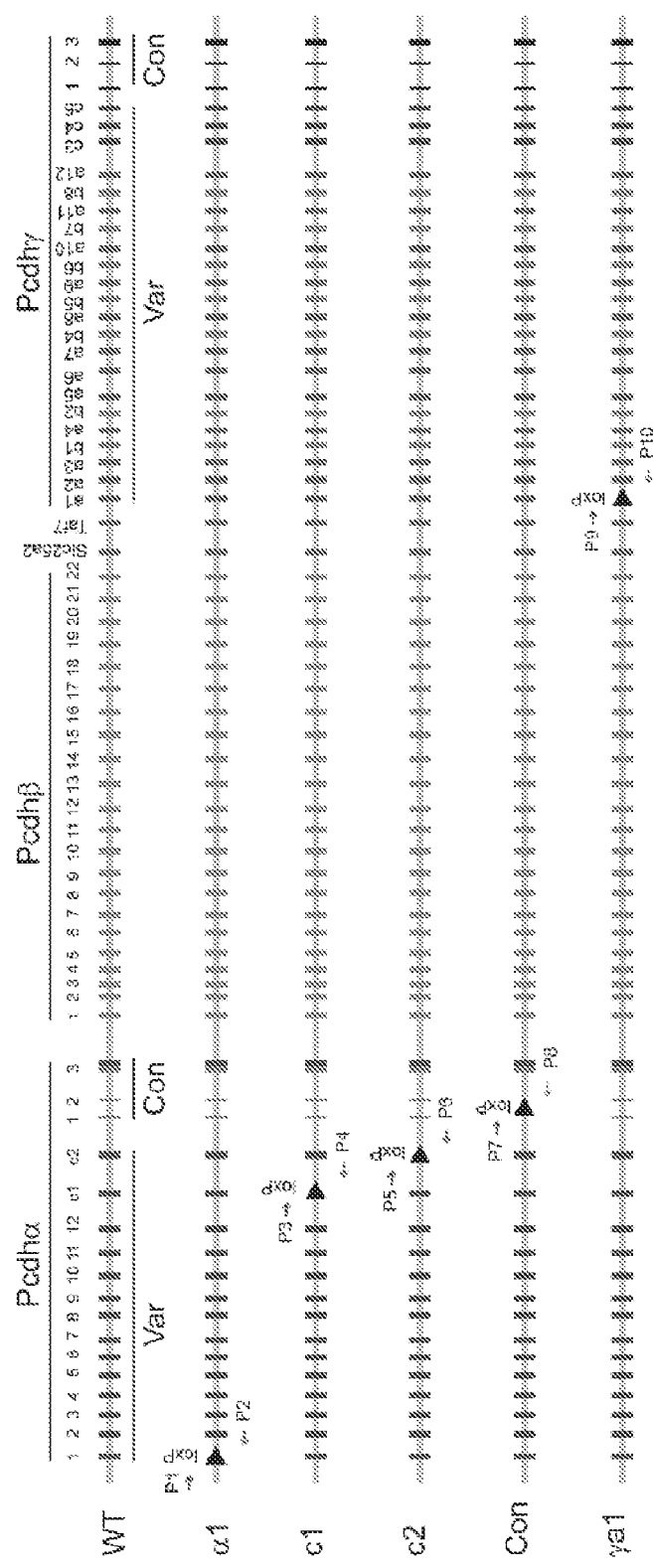
FIG. 1A shows the wildtype mouse Pcdh clusters along with five gene-targeted mutant alleles. In the wildtype locus, α and γ clusters share similar genomic structures; each of the 14 α and 22γ variable exons are separately spliced to the three α and γ constant exons, respectively; However, the β cluster has no constant exons. Five mutant alleles are: α1, c1, c2, Con, and γa1. All of these alleles contain a loxP site, whose orientation is shown by a black triangle. The positions of the PCR primers used to characterize the mutant alleles are indicated by the small arrows.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a vector is disclosed and discussed and a number of modifications that can be made to a number of molecules including the vector are discussed, each and every combination and permutation of vector and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a vector" includes a plurality of such vectors, reference to "the vector" is a reference to one or more vectors and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

C. Method of Recombineering

Recombineering (recombinogenic engineering) is a powerful molecular biology technique based on homologous recombination systems in *E. coli* to modify DNA. Recombineering has been successful using the bacteriophage lambda Red recombination system and the Rac-encoded RecET system. These homologous recombination systems mediate the efficient recombination of a target fragment (with homology sequences as short as 50 bps) into the DNA construct. The sequence homologies (or arms) flanking the desired modifications are homologous to regions 5' and 3' to the region to be modified. Positive and negative selections might be employed to increase the efficiency of this process.

In the first stage of recombineering, a selection marker cassette is introduced to replace the region to be modified. In the second stage, the selection marker is selected against following introduction of a target fragment containing the desired modification. Alternatively, the target fragment could be flanked by loxP or FRT sites, which could be removed later simply by the expression of the Cre or FLP recombinases, respectively.

The biggest advantage of recombineering is that it obviates the need for conveniently positioned restriction sites, whereas conventional DNA modification are often restricted by the availability of unique restriction sites. In large constructs of >100 kb, such as the Bacterial Artificial Chromosomes (BACs), this became a necessity. Recombineering could generate the desired modifications without leaving any 'footprints' behind. It also forgoes multiple cloning stages for generating intermediate vectors and therefore could be used to modify DNA constructs in a fairly short time-frame.

Provided herein is an improved recombineering method of inserting a target DNA fragment into an expression vector that is simpler, faster, and more reproducible than prior methods. Generally, the method can first involve designing oligonucleotide primers that have (1) sequences complementary to regions flanking the target DNA and (2) sequences complementary to the entry vector. The method can further involve amplifying the entry vector by polymerase chain reaction (PCR) using the disclosed primers such that the amplified PCR product comprises the homologous regions of the target DNA at each end. The method can further involve delivering the amplified PCR product to a recombination-competent cell, such as a bacteria cell, comprising the target DNA. The method can further involve selectively growing the cells comprising the entry vector. The method further involves isolating the entry vector comprising the target DNA from said bacterial cells.

1. Primers

The method can comprise designing a first and second oligonucleotide primer that each comprise at least 5, 6, 7, 8, 9, 10, 11, 12, 13, 14, 15, 16, 17, 18, 19, 20, 25, 30 or more nucleic acids comprising a sequence having at least about 70%, at least about 75%, at least about 80%, at least about 85%, at least about 90%, at least about 95%, at least about 96%, at least about 97%, at least about 98%, at least about 99%, or at least about 100% sequence identity to regions 5' and 3' to the target DNA, or complement thereof.

The first and second oligonucleotide primer can each further comprise at least 5, 6, 7, 8, 9, 10, 11, 12, 13, 14, 15, 16, 17, 18, 19, 20, 25, 30 or more nucleic acids comprising a sequence having at least about 70%, at least about 75%, at least about 80%, at least about 85%, at least about 90%, at least about 95%, at least about 96%, at least about 97%, at least about 98%, at least about 99%, or at least about 100% sequence identity to the backbone of an entry vector.

2. Entry Vector

The origin of replication (ori) is a unique DNA sequence at which DNA replication is initiated. DNA replication may proceed from this point bidirectionally or unidirectionally. The specific structure of the origin of replication varies somewhat from species to species, but all share some common characteristics. The origin of replication binds a member of the pre-replication complex—a protein complex that binds, unwinds, and begins to copy DNA.

Prokaryotes have a single circular molecule of DNA, and typically only a single ori. Eukaryotes often have multiple origins of replication on each chromosome. Having many origins of replication helps to speed the duplication of their (usually) much larger store of genetic material. The segment of DNA that is copied starting from each unique replication origin is called a replicon.

Origins of replication are typically assigned names containing "ori." For example, the E. coli replication origin is known as oriC. In E. coli, the oriC consists of 13 mer repeats followed by 9 mer repeats. A protein, DnaA would bind to the 9 mer repeats, and the DNA would then coil around the protein complex (many DnaA) forming a protein core. This coiling stimulates the AT rich region in the 13 mer sequence to unwind, thus allowing enzymes and other factors to bind and replication would start.

Origins of replication origin can be categorized as either narrow or broad host range and as either high- or low-copy number. Thus, in one aspect, the entry vector comprises a low-copy origin of replication. Examples of origins of replication that confer low-copy number are known in the art and include pMB1 (Bolivar F., 1977), colE1 (Kahn, 1979), and p15A (Chang A. C., 1978). Thus, the herein disclosed entry vector can be replicated in a bacterial cell such that the cell comprises on average about 1-50 copies of the entry vector per cell.

3. Target DNA

The herein disclosed recombineering method is not limited by the source of target DNA, which can be any source of DNA for which recombination is desired. For example, the target DNA can be located in a chromosome (i.e., genomic DNA) or can be in a vector, such as from a library.

As disclosed and exemplified herein, the target DNA can be in a bacterial artificial chromosome (BAC) vector. BACs have been developed to hold much larger pieces of DNA than can a plasmid. BAC vectors were originally created from part of an unusual plasmid present in some bacteria called the F' plasmid, which helps bacteria transfer its genome to another bacteria when under a lot of stress. F' can hold up to a million basepairs of DNA from another bacteria. Also, F' has origins of replication, and bacteria have a way to control how F' is copied. BAC vectors are able to hold up to 350 kb of DNA and have all of the tools that a vector needs to work properly, like replication origins, antibiotic resistance genes, and convenient places where clone DNA can insert itself. With these vectors it is possible to study larger genes, several genes at once, or entire viral genomes. By using a vector that can hold larger pieces of DNA, the number of clones required to cover the human genome six times theoretically could drop from 1.8 billion to about 50 million, about 10 million, about 1 million, or about 100,000.

4. Bacteria Cell

In one aspect, the cell of the disclosed recombineering cell can be any cell competent for recombination. In one aspect the disclosed cell can be a prokaryote. In another aspect the disclosed cell can be a eukaryote. For example, the cell can be a bacterial cell or a yeast cell that is recombination-competent. Compositions and methods for modifying cells, such as bacterial cells, to make them competent for homologous recombination are known in the art and described herein.

i. Early Strategies for DNA Engineering in *E. coli*

Unlike in yeast, linear dsDNA is unstable in *E. coli* due to the presence of the ATP-dependent, linear-dsDNA exonuclease RecBCD. However, *E. coli* strains that lack RecBCD by virtue of a recBC mutation can be transformed by linear dsDNA, provided that they also have sbcB and sbcC mutations, which restore recombination activity to recBC mutants. These exonuclease-deficient strains provided one of the first in vivo cloning systems for *E. coli* and have been used for several applications.

RecBCD-exonuclease-deficient strains have also been used to subclone PCR products into plasmids by a process called in vivo cloning. In vivo cloning is similar to yeast gap repair; linear PCR products with terminal sequences that match those at the two ends of a linearized plasmid vector are co-transfected with vector DNA into *E. coli* recBC-sbcBC- cells. Recombination between the two sets of homologies generates a circular plasmid by gap repair that can replicate and be selected in *E. coli*. This cloning method removes the need for enzymatic treatment of the PCR product or for in vitro ligation.

RecBCD does not degrade circular DNA. Therefore, genomes can be modified in wild-type *E. coli* strains using circular dsDNA targeting cassettes, provided that they are also wild-type for recA (recA+), as RecA function is essential for integrating circular DNA by homologous recombination. Because the *E. coli* host that is used to generate most BAC libraries (DH10B) is defective for recA, modifying BAC DNA in this host is done through a vector that carries the wild-type recA gene. When *E. coli* is transformed with this vector, it becomes competent to carry out homologous recombination.

ii. Phage-Encoded Recombination Systems

PCR-amplified linear dsDNA, flanked by short (42-bp) regions of homology to a plasmid, can be efficiently targeted to a plasmid by electroporating the dsDNA into recBC sbcA strains, which results in a more flexible *E. coli* homologous recombination system. sbcA is a mutation that activates expression of the recE and recT genes, which are encoded by part of the cryptic RAC prophage that is present in *E. coli* K12 strains. recE- and recT-encoded recombination functions enable genomic DNA to be modified directly with PCR-generated linear dsDNA targeting cassettes, rather than by using targeting cassettes that carry long homologies generated by a multi-step process including subcloning into plasmids.

Cloning through recE recT (called ET cloning or RecET cloning) was initially studied in a recA recBC sbcA host so that the targeting cassette would not be degraded by the RecBCD nuclease. However, many useful strains are recBC+, including strains that are commonly used for carrying P1, BAC or PAC plasmids. To allow ET cloning in recBC+ strains, the pBAD-ETγ plasmid was developed. pBADETγ contains the recE gene under the control of the ARABINOSE-inducible pBAD promoter, the recT gene expressed from the constitutive EM7 promoter, and the bacteriophage-λ gam gene expressed from the constitutive Tn5 promoter. The addition of arabinose activates recE expression and establishes higher recombination activity in the cell.

Bacteriophage-λ also contains a homologous recombination system termed Red, which is functionally analogous to the RecET recombination system of Rac. Like RecET, Red recombination requires two genes: redα (or exo), which is analogous to recE, and redβ (or bet), which is analogous to recT.

Exo is a 5'-3' exonuclease that acts on linear dsDNA. Beta binds to the ssDNA overhangs that are created by Exo and stimulates annealing to a complementary strand, but cannot promote strand invasion and exchange on its own. The recombination functions of Exo and Beta are again assisted by bacteriophage-λ-encoded Gam, which inhibits the RecBCD activity of the host cell. λ-Red-mediated recombination events can be 10-100 times more efficient than those observed in recBC sbcBC or recD strains. Because homologous recombination is increased by introducing phage-encoded protein functions to the host, this procedure is applicable to any *E. coli* strain and to other bacterial species as well.

Thus, as disclosed herein, a bacteria cell can be made recombination-competent by delivering to said cell a Redα and Redβ-expressing plasmid or a RedE and RedT-expressing plasmid.

5. Modifications

The method can further comprise modifying the target DNA incorporated into the entry vector. For example, the method can further comprise modifying the target DNA to incorporate a reporter cassette. Thus, the method can further comprise inserting a nucleic acid comprising one or more restriction enzyme cleavage site(s) into a region of the target DNA. The method can further comprise replacing a region of the target with a nucleic acid comprising one or more DNA restriction enzyme cleavage site(s). In addition, the enzyme cleavage sites can flank a selection gene. These cleavage sites can be used to insert nucleic acid cassettes of interest. For example, the method can further comprise inserting a reporter cassette into the entry vector at the restriction enzyme cleavage site(s).

6. Cloning System

The herein disclosed method of recombineering can further comprise the use of a cloning system to transfer the target DNA and optional reporter cassette into a desired expression vector. In one aspect of the disclosed recombineering method, any suitable cloning system can be used to transfer the target DNA into a desired expression vector. In a preferred aspect, the method comprises the use of the GATEWAY® Cloning Technology (Invitrogen, Carlsbad, Calif.), which provides a versatile system for transferring DNA segments between vectors. Once in the system, DNA segments can be transferred from an Entry Clone into numerous vectors (e.g., for protein expression) or from the Expression vector back into Entry Clones.

The recombination reactions of the GATEWAY® Cloning Technology are based on the site-specific recombination reactions of bacteriophage λ in *E. coli*. They can be represented as follows: attBxattP←—→attLxattR (where "x" signifies recombination).

The four att sites contain binding sites for the proteins that mediate the reactions. The wild type attP, attB, attL, and attR sites contain 243, 25, 100, and 168 base pairs, respectively. The attBxattP reaction (integration) is mediated by the proteins Int and IHF. The attLxattR reaction (excision) is mediated by the proteins Int, IHF, and Xis. Int (integrase) and Xis (excisionase) are encoded by the λ genome, while IHF (integration host factor) is an *E. coli* protein. For a general review of lambda recombination, see Landy, A. (1989) Annu. Rev. Biochem. 58, 913.

By using a combination of the LR and BP reactions, a gene or DNA segment can be easily moved between Entry Clones and Expression Clones. This versatility provides an operating system in which genes can be transferred easily into different vector backbones.

The LR Reaction is a recombination reaction between an Entry Clone and a Destination Vector (e.g., pDEST™), mediated by a mix of recombination proteins (e.g., LR CLONASE® mix). This reaction transfers DNA segments (e.g., cDNA, genomic DNA, or gene sequences) in the Entry Clone to the Destination Vector, to create an Expression Clone.

The gene in an Expression Clone can be flanked by attB1 and attB2 sites. The orientation of the gene is maintained throughout the subcloning, because attL1 reacts only with attR1, and attL2 reacts only with attR2. The unreacted Destination Vector can comprise a gene lethal to *E. coli*, such as ccdB to select for the entry vector.

Essentially the reverse of the LR Reaction, the BP Reaction transfers the gene in the Expression Clone (between attB sites) into a Donor vector (containing attP sites), to produce a new Entry Clone (attL sites). This reaction is also catalyzed by a mix of recombination proteins (e.g., BP CLONASE® mix). Once a gene is flanked by attL sites as an Entry Clone, it can be transferred into new expression vectors by recombination with Destination Vectors (via the LR Reaction).

A major use of the BP Reaction is for cloning PCR products as Entry Clones. PCR products made with primers containing terminal attB sites (e.g., 25 nucleotides+4 Gs) are efficient substrates for the BP reaction. The result is an Entry Clone containing the PCR fragment. Such Entry Clones can be readily recombined with Destination Vectors (through the LR Reaction) to yield Expression Clones of the PCR product.

Thus, the entry vector can comprise a first and second recombination site for bacteriophage λ. For example, the first and second recombination site for bacteriophage λ can be attL1 and attL2.

The method can further comprise delivering to a cell, such as a bacterial cell, the entry vector (1) a destination vector comprising a third and fourth recombination site for bacteriophage λ, and (2) bacteriophage recombination proteins, wherein the entry vector and the destination vector recombine to form an expression vector comprising the target DNA. For example, the third and fourth recombination site for bacteriophage λ can be attR1 and attR2. The method can further comprise selectively growing the cells comprising the expression vector and isolating the expression vector comprising the target DNA from said cells.

D. Method of Cre-Mediated Deletions and Duplications

Also provided herein is a method of deleting, duplicating, or translocating DNA in a mammalian genome. The method can comprise deleting, duplicating, or translocating any size of DNA. For example, the method can comprise deleting, duplicating, or translocating from about 20 kb to about 2,000 kb, including about 20 kb, about 30 kb, about 40 kb, about 50 kb, about 60 kb, about 70 kb, about 80 kb, about 90 kb, about 100 kb, about 200 kb, about 300 kb, about 400 kb, about 500 kb, about 600 kb, about 700 kb, about 800 kb, about 900 kb, about 1000 kb, about 1500 kb, or about 2000 kb of DNA. In some aspects, deletion, duplication, or translocation is germline transmissible.

Generally, the method involves breeding a first mammal comprising two or more germline transmissible loxP sites in the genome with a sexually compatible second mammal comprising germline transmissible Cre-recombinase functionally linked to a strong promoter.

U.S. Pat. No. 4,959,317 and U.S. Pat. No. 5,434,066 are incorporated herein by reference for their teaching of the use of Cre recombinase in the site-specific recombination of DNA in eukaryotic cells. The term "Cre" recombinase, as used herein, refers to a protein having an activity that is substantially similar to the site-specific recombinase activity of the Cre protein of bacteriophage P1 (Hamilton, D. L., et al., J. Mol. Biol. 178:481-486 (1984), herein incorporated by reference for its teaching of Cre recombinase). The Cre protein of bacteriophage P1 mediates site-specific recombination between specialized sequences, known as "loxP" sequences. Hoess, R., et al., Proc. Natl. Acad. Sci. USA 79:3398-3402 (1982) and Sauer, B. L., U.S. Pat. No. 4,959,317 are herein incorporated by reference for their teaching of the lox sequences. The loxP site has been shown to consist of a double-stranded 34 bp sequence (SEQ ID NOS:90 and 91):

```
                                          (SEQ ID NO: 90)
   5' ATAACTTCGTATAATGTATGCTATACGAAGTTAT 3'

(SEQ ID NO: 91)
   5' ATAACTTCGTATAGCATACATTATACGAAGTTAT 3'
```

This sequence contains two 13 bp inverted repeat sequences which are separated from one another by an 8 bp spacer region. Other suitable lox sites include LoxB, LoxL and LoxR sites which are nucleotide sequences isolated from E. coli. These sequences are disclosed and described by Hoess et al., Id, herein incorporated by reference for the teaching of lox sites. Lox sites can also be produced by a variety of synthetic techniques which are known in the art. For example, synthetic techniques for producing lox sites are disclosed by Ito et al., Nuc. Acid Res., 10:1755 (1982) and Ogilvie et al., Science 214:270 (1981), the disclosures of which are incorporated herein by reference for their teaching of these synthetic techniques.

The Cre protein mediates recombination between two loxP sequences (Sternberg, N., et al., Cold Spring Harbor Symp. Quant. Biol. 45:297-309 (1981)). These sequences may be present on the same DNA molecule, or they may be present on different molecules. Because the internal spacer sequence of the loxP site is asymmetrical, two loxP sites can exhibit directionality relative to one another (Hoess, R. H., et al., Proc. Natl. Acad, Sci. 81:1026-1029 (1984)). Thus, when two sites on the same DNA molecule are in a directly repeated orientation, Cre will excise the DNA between the sites (Abremski, K., et al., Cell 32:1301-1311 (1983)). However, if the sites are inverted with respect to each other, the DNA between them is not excised after recombination but is simply inverted. Thus, a circular DNA molecule having two loxP sites in direct orientation will recombine to produce two smaller circles, whereas circular molecules having two loxP sites in an inverted orientation simply invert the DNA sequences flanked by the loxP sites.

Thus, in one aspect, the loxP sites of the provided method are on homologous chromosomes. In another aspect, the loxP sites can be on non-homologous chromosomes.

E. Methods of PiggyBac Gene-Trapping

The TTAA-specific transposon piggyBac is rapidly becoming a highly useful transposon for genetic engineering of a wide variety of species. The TTAA-specific, short repeat elements are a group of transposons that share similarity of structure and properties of movement. These elements were originally defined in the order Lepidoptera, but appear to be common among other animals as well.

A nucleic acid sequences for wildtype piggyBac transposase is shown in SEQ ID NO:92. A codon-optimized piggyBac transposase is shown in SEQ ID NO:93. Thus, the piggyBac transposase of the disclosed compositions and methods can comprise SEQ ID NO:92 or 93, or a fragment or conservative variant thereof of at least 10, 50, 100, 500, 1000 nucleotides in length. Thus, the piggyBac transposase of the disclosed compositions and methods can comprise a nucleic acid of at least 10, 50, 100, 500, 1000 nucleotides in length that can hybridize under stringent conditions with SEQ ID NO:92 or 93. Thus, the piggyBac transposase of the disclosed compositions and methods can comprise a nucleic acid with at least about 70%, about 75%, about 80%, about 85%, about 90%, about 95%, about 96%, about 97%, about 98%, about 99%, about 100% sequence identity to SEQ ID NO:92 or 93.

Spontaneous plaque morphology mutants of baculoviruses were observed to arise during propagation of these viruses in the TN-368 cell line. Genetic characterization of these mutations often revealed an associated insertion of host-derived DNAs, some of which appeared to be transposons. Evidence is accumulating that suggests a superfamily of TTAA-specific mobile elements exists in a diversity of organisms, and that piggyBac-related sequences may be present in a diversity of species.

The piggyBac element is 2.5 kb in length and terminates in 13 bp perfect inverted repeats, with additional internal 19 bp inverted repeats located asymmetrically with respect to the ends (Cary et al. 1989). The initial sequence analysis of the piggyBac element revealed a potential RNA polymerase II promoter sequence configuration, typical Kozak translational start signal, and two apparently overlapping long open reading frames. Primer extension analysis with polyadenylated mRNA positioned the 5' end of the piggyBac transcript near the identified consensus promoter region (Cary et al.1989). Subsequent Northern analyses, and RT-PCR and sequencing of piggyBac-specific RNA transcripts from TN-368 cells confirmed that the major transcript is unspliced (Elick et al. 1996a). Re-examination of additional piggyBac sequences amplified from the TN-368 cell genome, as well as the plasmid p3E1.2, confirmed an error of a single base in the original sequence, and the corrected sequence could be read as a single open reading frame encoding a polypeptide with a predicted size of 64 Kd.

Thus, also provided is a method of generating a random genome-wide chromosome rearrangement in vivo in a mammal comprising the use of piggyBac transposase. For example, the method can comprise breeding a first mammal with a second mammal comprising (1) a germline transmissible nucleic acid comprising a piggyBac construct having a splice acceptor site linked to a reporter sequence and substantially lacking a splice donor site and (2) a germline transmissible nucleic acid comprising a piggyBac transposase functionally linked to a protamine promoter. In one aspect, the first mammal is female and the second mammal is male. The methods can further comprise selecting offspring expressing the reporter sequence. In addition, the splice acceptor site and reporter sequence can be flanked by a first and second loxP site.

The piggyBac construct can further comprise a second reporter construct functionally linked to an expression control sequence positioned between the first and second loxP sites, wherein the second reporter construct, expression control sequence, and second loxP site are flanked by a first and second FRT site.

The method can further comprise breeding the offspring with a sexually compatible third mammal comprising germline transmissible Cre-recombinase functionally linked to a strong promoter. For example, disclosed is the use of a CAG promoter (human cytomeglovirus immediate early enhancer and chicken β-actin/rabbit β-globin hybrid promoter). For example, a strong promoter can produce a level of Cre protein that is non-toxic but sufficient to induce recombination of loxP sites in vivo.

F. Gene-Trap Vector

Also provided herein is a gene-trap vector comprising wild type piggyBac or simplified piggyBac, an adenovirus splice acceptor site and substantially lacking a splice donor site. In some aspects, the gene-trap vector can comprise an insert of at least 0.5, 1.0, 1.5, 2, 3, 4, 5, 6, 7, 8, 9, 10, 11, 12, 13, 14, 15, 16, 17, 18, 19, or 20 kb. In some aspects, the gene-trap vector substantially lacks cryptic RNA splicing.

In some aspects, the gene-trap vector comprises a 3' transposon terminal sequence from a piggyBac transposon comprising the 3' inverted terminal repeat (3'ITR) and less than about 933, 932, 931, 930, 925, 920, 915, 910, 905, 900, 895, 890, 885, 880, 875, 870, 865, 860, 855, 850, 845, 840, 835, 830, 825, 820, 815, 810, 805, 800, 795, 790, 785, 780, 775, 770, 765, 760, 755, 750, 745, 740, 735, 730, 725, 720, 715, 710, 705, 700, 695, 690, 685, 680, 675, 670, 665, 660, 655, 650, 645, 640, 635, 630, 625, 620, 615, 610, 605, 600, 595, 590, 585, 580, 575, 570, 565, 560, 555, 550, 545, 540, 535, 530, 525, 520, 515, 510, 505, 500, 495, 490, 485, 480, 475, 470, 465, 460, 459, 458, 457, 456, 455, 454, 453, 452, 451, 450, 449, 448, 447, 446, 445, 440, 435, 430, 425, 420, 415, 410, 405, 400, 395, 390, 385, 380, 375, 370, 365, 360, 355, 350, 345, 340, 335, 330, 325, 320, 315, 310, 305, 300, 290, 280, 270, 260, 250, 240, 230, 220, 210, 200, 190, 180 170, 160, 150, 140, 130, 120, 110, 100, 90, 80, 70, 60, 50, 40, 30, 20, or 10 nucleic acids from the adjacent internal sequence.

In some aspects, the 3'ITR comprises a nucleic acid sequence having at least 95% sequence identity to SEQ ID NO:95. In some aspects, the 3'ITR and adjacent internal sequence consist essentially of the nucleic acid sequence SEQ ID NO:238.

In some aspects, the 3' transposon terminal sequence consist essentially nucleic acids 1-453 of the sequence SEQ ID NO:238. In some aspects, the 3' transposon terminal sequence consist essentially nucleic acids 1-354 of the sequence SEQ ID NO:238. In some aspects, the 3' transposon terminal sequence does not comprise one or more of the splice donor sites represented by nucleic acids 78-79, 466-467, 475-476, 479-480, 860-861, or 944-945 of SEQ ID NO:238.

In some aspects, the 5' transposon terminal sequence from a piggyBac transposon comprising the 5' inverted terminal repeat (5'ITR) and less than 681 or 330 nucleic acids from the adjacent internal sequence.

In some aspects, the 5'ITR comprises the nucleic acid sequence SEQ ID NO:96. In some aspects, the 5'ITR comprises a nucleic acid sequence having at least 95% sequence identity to SEQ ID NO:96.

In some aspects, the 5' transposon terminal sequence consist essentially of the nucleic acid sequence SEQ ID NO:239.

In some aspects, the 5' transposon terminal sequence consist essentially of nucleic acids 352-680 of the sequence SEQ ID NO:239.

For example, provided is a gene-trap vector comprising the formula:

$$3'TR\text{-lox-SA-}R^1\text{-lox-5'TR}$$

wherein 3'TR and 5'TR are piggyBac 3' and 5' terminal repeats, respectively; wherein the lox sites are in the same orientation; wherein SA is a splice acceptor; and wherein $R^1$ is first reporter sequence linked to SA. The lox sites can be loxP sites.

As another example, provided is a gene-trap vector comprising the formula:

$$3'TR\text{-loxP-SA-}R^1\text{—X—}R^2\text{-loxP-X-5'TR}$$

wherein 3'TR and 5'TR are piggyBac 3' and 5' terminal repeats, respectively; wherein the loxP sites are in the same orientation; wherein SA is a splice acceptor; wherein $R^1$ is first reporter sequence linked to SA; wherein $R^2$ is a second reporter sequence functionally linked to an expression control sequence; and wherein X is a recombination site. Examples of recombination sites include FRT and attB or attP.

As another example, provided is a gene-trap vector comprising the formula:

$$3'TR\text{-lox-SA-}R^1\text{—X—}R^2\text{—X-lox-5'TR.}$$

Also disclosed is a byproduct of a gene-trap vector disclosed herein based on recombination at the X receombination sites, wherein the byproduct comprises the formula:

$$3'TR\text{-lox-SA-}R^1\text{—X-5'TR.}$$

For example, wherein the X recombination site is FRT, the byproduct of Flp recombinase is referred to herein as a "Flp allele."

Also disclosed is a byproduct of a gene-trap vector disclosed herein based on Cre recombination at the lox sites, wherein the byproduct comprises the formula:

$$3'TR\text{-lox-X-5'TR.}$$

The byproduct of Cre recombinase is referred to herein as a "Cre allele."

The splice acceptor of the disclosed gene-trap vector can comprise a nucleic acid having the nucleic acid sequence SEQ ID NO:94. The splice acceptor can comprise SEQ ID NO:94, or a fragment or conservative variant thereof of at least 10, 50, 100, 500, 1000 nucleotides in length. The splice acceptor can comprise a nucleic acid of at least 10, 50, 100, 500, 1000 nucleotides in length that can hybridize under stringent conditions with SEQ ID NO:94. The splice acceptor can comprise a nucleic acid with at least about 70%, about 75%, about 80%, about 85%, about 90%, about 95%, about 96%, about 97%, about 98%, about 99%, about 100% sequence identity to SEQ ID NO:94.

The loxP sites of the disclosed gene-trap vector can comprise a nucleic acid having the nucleic acid sequence SEQ ID NO:90 or 91. The loxP sites can comprise SEQ ID NO:90 or 91, or a fragment or conservative variant thereof of at least 10, 50, 100, 500, 1000 nucleotides in length. The loxP sites can comprise a nucleic acid of at least 10, 50, 100, 500, 1000 nucleotides in length that can hybridize under stringent conditions with SEQ ID NO:90 or 91. The loxP sites can comprise a nucleic acid with at least about 70%, about 75%, about 80%, about 85%, about 90%, about 95%, about 96%, about 97%, about 98%, about 99%, about 100% sequence identity to SEQ ID NO:90 or 91.

The 3'TR and 5'TR of the disclosed gene-trap vector are piggyBac 3' and 5' terminal repeats can comprise a nucleic acid having the nucleic acid sequence SEQ ID NO:95 and 96, respectively. The 3'TR and 5'TR are piggyBac 3' and 5' terminal repeats can comprise SEQ ID NO:95 and 96 respectively, or a fragment or conservative variant thereof of at least 10, 50, 100, 500, 1000 nucleotides in length. The 3'TR and 5'TR are piggyBac 3' and 5' terminal repeats can comprise a nucleic acid of at least 10, 50, 100, 500, 1000 nucleotides in length that can hybridize under stringent conditions with SEQ ID NO:95 and 96 respectively. The 3'TR and 5'TR are piggyBac 3' and 5' terminal repeats can comprise a nucleic acid with at least about 70%, about 75%, about 80%, about 85%, about 90%, about 95%, about 96%, about 97%, about 98%, about 99%, about 100% sequence identity to SEQ ID NO:95 and 96 respectively.

The FRT of the disclosed gene-trap vector can comprise a nucleic acid having the nucleic acid sequence SEQ ID NO:97 or 98. The FRT can comprise SEQ ID NO:97 or 98, or a fragment or conservative variant thereof of at least 10, 50, 100, 500, 1000 nucleotides in length. The FRT can comprise a nucleic acid of at least 10, 50, 100, 500, 1000 nucleotides in length that can hybridize under stringent conditions with SEQ ID NO:97 or 98. The FRT can comprise a nucleic acid with at least about 70%, about 75%, about 80%, about 85%, about 90%, about 95%, about 96%, about 97%, about 98%, about 99%, about 100% sequence identity to SEQ ID NO:97 or 98.

Examples of reporter sequences include, but are not limited to, the *E. Coli* lacZ gene (SEQ ID NO:99), which encodes 13-galactosidase, adenosine phosphoribosyl transferase (APRT), and hypoxanthine phosphoribosyl transferase (HPRT). Fluorescent proteins can also be used as markers and marker products. Examples of fluorescent proteins include green fluorescent protein (GFP; SEQ ID NO:100), green reef coral fluorescent protein (G-RCFP), cyan fluorescent protein (CFP; SEQ ID NO:102), red fluorescent protein (RFP or dsRed2; SEQ ID NO:101), yellow fluorescent protein (YFP; SEQ ID NO:103), and mCherry (SEQ ID NO:104). Other reporter sequences are known in the art and contemplated for use herein.

Example gene-trap vectors disclosed herein are referred to as ZG-l, ZG-m, and ZG-s. Sequences for these vectors are described in GenBank Accession No. EF591488, EF591489, and EF591490, respectively. Thus, disclosed is a gene-trap vector comprising the nucleic acid sequence set forth in SEQ ID NO:105, 106 or 107. Also disclosed is a gene-trap vector comprising SEQ ID NO:105, 106 or 107, or a fragment or conservative variant thereof of at least 10, 50, 100, 500, 1000 nucleotides in length. As another example, disclosed is a gene-trap vector comprising a nucleic acid of at least 10, 50, 100, 500, 1000 nucleotides in length that can hybridize under stringent conditions with SEQ ID NO:105, 106 or 107. As another example, disclosed is a gene-trap vector comprising a nucleic acid with at least about 70%, about 75%, about 80%, about 85%, about 90%, about 95%, about 96%, about 97%, about 98%, about 99%, about 100% sequence identity to SEQ ID NO:105, 106 or 107.

Also provided herein are mammals comprising the disclosed vectors and/or made by the disclosed methods. For example, provided herein is a transgenic mouse comprising germline transmissible expression of a piggyBac vector comprising a splice acceptor site linked to a reporter sequence and substantially lacking a splice donor site and a nucleic acid encoding a piggyBac transposase functionally linked to an expression control sequence.

G. Nucleic Acids

1. Nucleotides and Related Molecules

There are a variety of molecules disclosed herein that are nucleic acid based. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

2. Sequences

A variety of sequences are provided herein and these and others can be found in Genbank at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

3. Primers and Probes

Disclosed are compositions including primers and probes, which are capable of interacting with a target gene as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the gene or region of the gene or they hybridize with the complement of the gene or complement of a region of a target gene.

The size of the primers or probes for interaction with the target gene in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

5. Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

H. Peptides

Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 1 and are referred to as conservative substitutions.

TABLE 1

Amino Acid Substitutions
Original Residue Exemplary Conservative
Substitutions, others are known in the art.

| Original Residue | Exemplary Conservative Substitutions |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn;Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 1. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —CH$_2$NH—, —CH$_2$S—, —CH$_2$—CH$_2$—, —CH═CH— (cis and trans), —COCH$_2$—, —CH(OH) CH$_2$—, and —CHH$_2$SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH$_2$NH—, CH$_2$CH$_2$—); Spatola et al. Life Sci 38:1243-1249 (1986) (—CHH$_2$—S); Hann J. Chem. Soc Perkin Trans. I 307-314 (1982) (—CH—CH—, cis and trans); Almquist et al. J. Med. Chem. 23:1392-1398 (1980) (—COCH$_2$—); Jennings-White et al. Tetrahedron Lett 23:2533 (1982) (—COCH$_2$—); Szelke et al. European Appln, EP 45665 CA (1982): 97:39405 (1982) (—CH(OH)CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

I. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing the expression vectors using the herein disclosed methods, the kit comprising pSTART-K, pSTART-C2, pKD46, pKD3, pGFP-ACN, pYFP-ACN, pCFP-ACN, pRFP-ACN, pLacZ-ACN, pAP-ACN, pWS-TK2, pWS-TK3, and pWS-TK6. This kit would be useful for small-scale or large-scale production of targeting vectors for generation of conventional knockout mice.

J. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

The nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process Claims for Making the Compositions

Disclosed are processes for making the compositions as well as making the intermediates leading to the compositions. For example, disclosed are nucleic acids in SEQ ID NOs:1-119. There are a variety of methods that can be used for making these compositions, such as synthetic chemical methods and standard molecular biology methods. It is understood that the methods of making these and the other disclosed compositions are specifically disclosed.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

K. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Simpler and Faster Genome-Wide Mutagenesis in Mice

The clustered Protocadherin (Pcdh) genes provide an ideal locus to test methods for generating genomic manipulations such as the generation of large deletions and duplications. This unusual locus (FIG. 1A) in the mouse contains 58 very similar genes, encoding trans-plasma membrane adhesion molecules, that are arranged into three sequentially-linked clusters ($\alpha$, $\beta$ and $\gamma$), spanning a region about one megabase pairs of DNA (Wu, Q. & Maniatis, T. 1999; Wu, Q. et al. 2001; Wu, Q. et al. 2005). The protein products from this locus are generally localized to synaptic junctions in the central nervous system (Kohmura, N. et al. 1998; Wang, X. et al. 2002; Phillips, G. R. et al. 2003), and have been proposed to play roles in the establishment and maintenance of neuronal connections. The $\alpha$ and $\gamma$ proteins are thought to have distinct intracellular signalling pathways, due to their highly divergent intracellular domains (Wu, Q. & Maniatis, T. 1999). Recently, the $\gamma$ cluster deletion (Wang, X. et al. 2002), generated by in vitro Cre/loxP-mediated recombination (Zheng, B., et al. 2000; Mills, A. A. & Bradley, A. 2001), and a $\gamma$ constant region deletion (Weiner, J. A., et al. 2005; Hambsch, B., 2005) have been shown to cause neonatal lethality in the mouse. Initial analysis of these mice suggests that the $\gamma$ cluster is required for synapse development, as well as for survival of interneurons in the spinal cord and for specific neurons in the brain (Wang, X. et al. 2002; Weiner, J. A., et al. 2005). However, the function of the Pcdh $\alpha$ and $\beta$ clusters, or for that matter, of any individual Pcdh gene, is still undefined.

In the current study, a simple modular protocol was developed to rapidly produce 5 distinct knockout alleles in the Pcdh clusters. Using these loxP-containing alleles and a powerful Cre driver, the result is a highly efficient trans-allelic recombination between homologous chromosomes in somatic cells and in the germline. This methodology was used to generate germline alleles containing large deletions and duplications, including the $\alpha$ cluster deletion and the $\alpha$ through $\alpha$ cluster deletion. Remarkably, mice homozygous for the $\alpha$ cluster deletion manifest no apparent gross phenotypes. Germline translocations between non-homologous chromosomes, bearing loxP sites, can be similarly generated by simple breeding.

The piggyBac transposon derived from the cabbage looper moth, *Trichoplusia ni*, has been demonstrated to transpose very efficiently in mammalian cells and in the mouse (Ding, S. et al. 2005). To extend the above-described Cre/loxP-mediated methodology to the entire mouse genome, a piggyBac-based gene-trap strategy was designed that provides not only the means for very efficient introductions of loxP sites throughout the mouse genome simply by breeding, but also allows in vivo generation of genome-wide gene-trap alleles that complement the more conventional gene knockout strategy.

i. Results

Streamlined Cloning and the Creation of Pcdh Mutant Alleles:

A limiting factor of conventional gene targeting is the construction of targeting vectors. Recently developed recombineering methods (Zhang, Y., et al. 1998; Zhang, Y., et al. 2000; Hartley, J. L., et al. 2000; Datsenko, K. A. & Wanner, B. L. 2000; Lee, E. C. et al. 2001), e.g., ET cloning and Gateway cloning, have greatly simplified these procedures. These two recombineering strategies were combined into a standardized and streamlined method that can facilitate large-scale construction of targeting vectors. This procedure reduces targeting vector construction time by approximately fifty fold. The method starts with identification of a BAC (bacterial artificial chromosome) clone that contains the genomic region of interest as defined in the public sequence databases. A genomic fragment to be used for targeting vector construction is isolated from the BAC by ET recombination into a low-copy replicating Gateway pStart-K plasmid. Next, the isolated genomic DNA is modified through ET cloning by insertion of a unique restriction site into the target region, that allows introduction of a repertoire of reporter/selection cassettes. To facilitate subsequent removal of neomycin resistance gene (neo), which may adversely affect expression of neighboring genes in the intact animal, all of the reporter/selection cassettes are designed for automatic germline self-excision of the neo cassette (Bunting, M., et al. 1999). Finally, in a simple Gateway recombination step, the modified vectors are shuttled into a TK (thymidine kinase) vector to allow inclusion of negative selection during the ES cell targeting procedure (Mansour, S. L., et al. 1988).

To validate this cloning protocol, it was used to generate a series of targeting vectors that allows systematic genetic dissection of the function of the α and β clusters of the Pcdh genes. For this analysis 12 mouse lines (FIG. 1A) were created that deleted individual genes or potential regulatory elements within the Pcdh clusters. In the Pcdhα1 (α1) allele, the α1 variable region were replaced in frame by a GFP reporter gene. The Pcdhαc1 (c1) allele is an alkaline phosphatase (AP) knockin that replaces in frame the c1 variable exon. The Pcdhαc2 (c2) allele is a lacZ knockin that replaces the c2 variable exon. Each of these alleles permit determination of, as well as internal comparisons of, individual Pcdhα gene expression patterns in the embryonic or adult animal. The Pcdhα conditional allele was created by flanking the first two constant exons with loxP sites. Cre-mediated recombination of this conditional allele generates the Con allele, which is a deletion of a constant exons 1 and 2. The Pcdhγa1 (γa1) allele is an hrGFP knockin that replaces the γa1 variable exon.

The Mid allele deleted 7 conserved non-coding elements (CNEs), that are highly conserved between mouse and human and located between the variable and constant regions of the α cluster. The CIE allele deleted the most conserved CNE (Wu, Q. et al. 2001). Alternative splicing within constant exon 3 normally generates two sets of mRNAs, type A and type B (Sugino, H. et al. 2000). The $A^{cfp}$ allele has a CFP gene fused in-frame to the last amino acid of the type A sequence with type B deleted. The $B^{yfp}$ allele has a YFP fusion to the last amino acid of the type B sequence with type A deleted. The delA and delB alleles were simple deletions of type A and type B, respectively. The Down allele, a deletion of 9.7 kb region downstream of the α cluster, was designed to test for potential regulatory functions of this region.

Figure 1B:
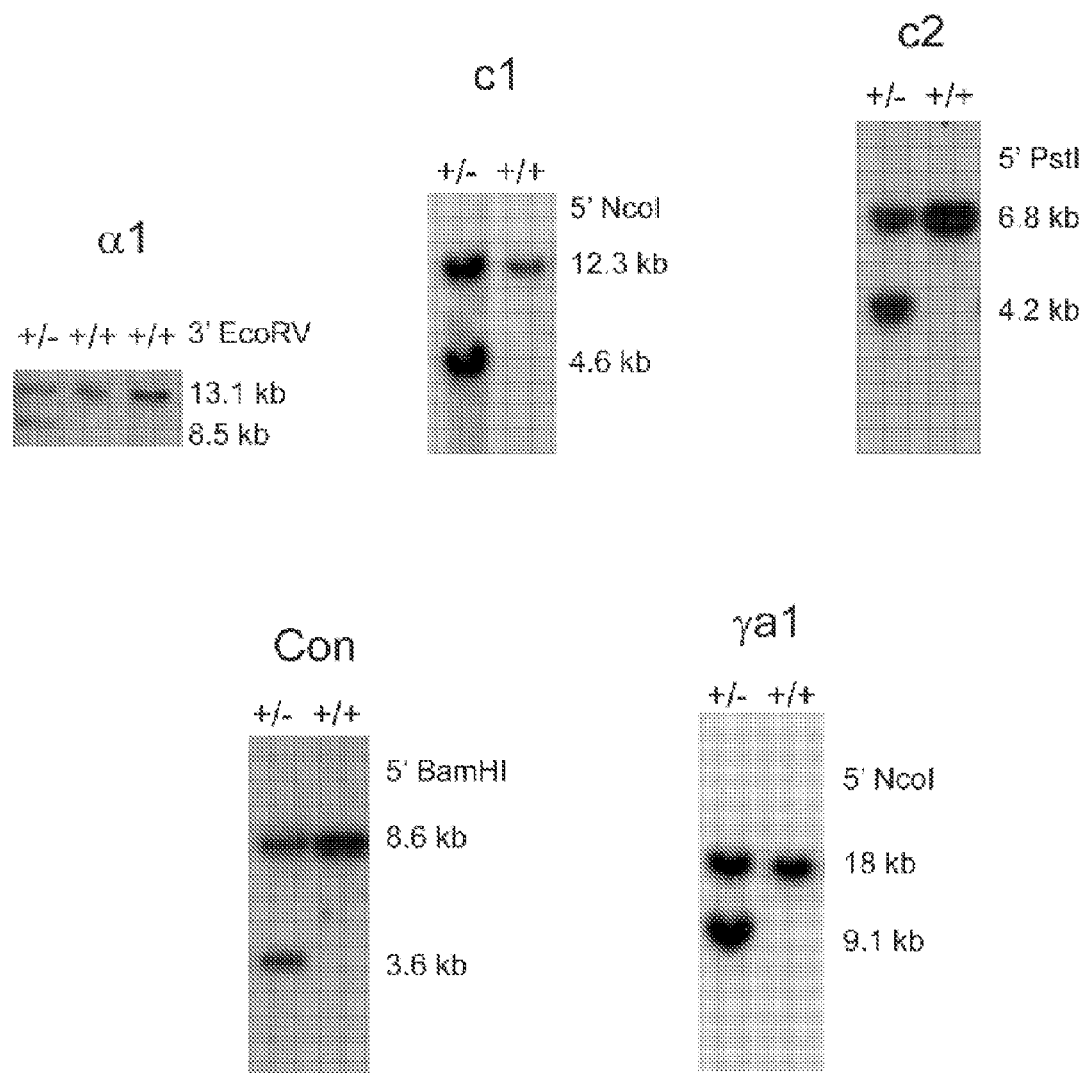
FIG. 1B shows southern transfer analysis used to confirm the gene structure for each of the 5 mutant alleles.

Each allele was confirmed to carry the prescribed genetic alterations by southern blot analysis (FIG. 1B). Genotyping of these alleles were performed by PCR (Table 2). Since all of these alleles contain a loxP site, they were used to identify an efficient Cre-driver for in vivo generation of large deletions and duplications.

TABLE 2

| \multicolumn{3}{c}{Genotyping primers for all alleles in this study} | | |
|---|---|---|
| a1 | comF: 5'-ATCTTGGTGTGACAGCGATACG<br>wtR: 5'-CTCAGTTCAAGCGAAAGGGATT<br>mutR: 5'-AGATGAACTTCAGGGTCAGCTTGC<br>202 bp for mutant; 635 bp for WT | SEQ ID NO: 1<br>SEQ ID NO: 2<br>SEQ ID NO: 3 |
| c1 | comF: 5'-TTTCCAGTCTCCTCTCCAGGAGTTC<br>wtR: 5'-TAGTTGGAAAGGAAGCGAAAGTTCC<br>mutR: 5'-TTGTATGTCTTGGACAGAGCCACAT<br>399 bp for mutant; 258 bp for WT | SEQ ID NO: 4<br>SEQ ID NO: 5<br>SEQ ID NO: 6 |
| c2 | comF: 5'-TTGTAGTGCGTGAGAGGTGAAG<br>wtR: 5'-CATTGGTCAAGTCCAGTTCCAG<br>mutR: 5'-CAAACCTCCACTCTCCATTGAG<br>312 bp for mutant, 408 bp for WT | SEQ ID NO: 7<br>SEQ ID NO: 8<br>SEQ ID NO: 9 |
| Mid | comF: 5'-GCCATAACAGTGTTTGAGAAGTGAGG<br>wtR: 5'-AGGGGTAACCACATAGCTCTGGAAG<br>mutR: 5'-CAGGCACACCTTCAGTCCTGTAGTC<br>330 bp for mutant; 224 bp for WT | SEQ ID NO: 10<br>SEQ ID NO: 11<br>SEQ ID NO: 12 |
| CIE | comF: 5'-CAGAAAGAGTTGGAGTCCTTGTGGA<br>wtR: 5'-GACAACAGCCTCTTCAACTGATGGA<br>mutR: 5'-ACGAAGTTATGAATTCGCCCTTGTT<br>269 bp for mutant; 205 bp for WT | SEQ ID NO: 13<br>SEQ ID NO: 14<br>SEQ ID NO: 15 |
| α conditional | F1: 5'-AGGCTGAATAACGTGCACAGCTAAG<br>comR: 5'-TGCAGATTGGTTCAATGGAGTCTTT<br>343 bp for unrecombined allele;<br>219 bp for WT | SEQ ID NO: 16<br>SEQ ID NO: 17 |
| Con | F1: 5'-AGGCTGAATAACGTGCACAGCTAAG<br>comR: 5'-TGCAGATTGGTTCAATGGAGTCTTT<br>F2: 5'-CCCTTTCCTAGATTCCCCTCAAAAA<br>440 bp for recombined; 219 for WT | SEQ ID NO: 18<br>SEQ ID NO: 19<br>SEQ ID NO: 20 |

TABLE 2-continued

Genotyping primers for all alleles in this study

| Allele | Primers | SEQ ID NO |
|---|---|---|
| A$^{cfp}$ | comF: 5'-GGAGCCTGCTAACAACCAAATTGAC<br>wtR: 5'-GAGGGCTCATGTCATAGGAGAAAGG<br>mutR: 5'-CACTGCACGCCCCAGGTCAG<br>366 bp for mutant; 253 bp for WT | SEQ ID NO: 21<br>SEQ ID NO: 22<br>SEQ ID NO: 23 |
| B$^{yfp}$ | comF: 5'-AAGCAGACCCAGGTTTCCTTTCTCC<br>wtR: 5'-CTCTTGGTAGCCACACATACCCAGT<br>mutR: 5'-AAGCACTGCAGGCCGTAGCC<br>281 bp for Byfb; 188bp for WT | SEQ ID NO: 24<br>SEQ ID NO: 25<br>SEQ ID NO: 26 |
| delA | comF: 5'-GGATATTTCCTGTCTTGTTCCCAGGT<br>wtR: 5'-ACCAAATGGAAACAAGCCACTTAGC<br>mutR: 5'-GGCTGGGAAGCTTCTCCTTTGC<br>386 bp for mutant; 276 for WT | SEQ ID NO: 27<br>SEQ ID NO: 28<br>SEQ ID NO: 29 |
| delB | comF: 5'-AATGGAAACAAGCCACTTAGCCAGT<br>wtR: 5'-GGCTGGGAAGCTTCTCCTTTGC<br>mutR: 5'-CGAAGTTATGAATTCGCCCTTGTTA<br>211 bp for mutant; 272 bp for WT | SEQ ID NO: 30<br>SEQ ID NO: 31<br>SEQ ID NO: 32 |
| Down | comF: 5'-GCTTGAGAGAGGGAGTGACAAAGTG<br>wtR: 5'-TCCCTTACACAATGTGGCAGAAGTT<br>mutR: 5'-GAGCACGTACCCAGATATGGAATTG<br>426 bp for mutant; 287 bp for WT | SEQ ID NO: 33<br>SEQ ID NO: 34<br>SEQ ID NO: 35 |
| ya1 | comF: 5'-GCTGGTGTGTCTTTCTCTGGAGCTA<br>wtR: 5'-GGATGTTAAAGCTGACGACACATGG<br>mutR: 5'-AGCTCTGGATGAAGAAGTCGCTGAT<br>398 bp for mutant; 284 bp for WT | SEQ ID NO: 36<br>SEQ ID NO: 37<br>SEQ ID NO: 38 |
| del(c1-c2) | P3: 5'-CCACTGCTCCCTGAGATCGAAT<br>P6: 5'-CTGGAAGACACTTGGATCACCATCT<br>566 bp | SEQ ID NO: 39<br>SEQ ID NO: 40 |
| dup(c1-c2) | P5: 5'-CAGTTATCTGCTGGCAGGTACCACT<br>P4: 5'-TGCCAGAGGAGTCAAACCACATAAT<br>595 bp | SEQ ID NO: 41<br>SEQ ID NO: 42 |
| del(α) | P1: 5'-CCCCCTGAACCTGAAACATAAAATG<br>P8: 5'-TGCAGATTGGTTCAATGGAGTCTTT<br>P11: AGGCTGAATAACGTGCACAGCTAAG<br>383 bp for mutant; 219 bp for WT | SEQ ID NO: 43<br>SEQ ID NO: 44<br>SEQ ID NO: 45 |
| dup(α) | P7: 5'-CCCTTTCCTAGATTCCcCTCAAAAA<br>P2: 5'-CCCTAACACCACCACTACCCAAAAT<br>591 bp | SEQ ID NO: 46<br>SEQ ID NO: 47 |
| del(α-β) | P1: 5'-ACAACCACTACCTGAGCACCCAGTC<br>P10: 5'-AAAGCTGCGACCTACCTCTGGAAAC<br>517 bp | SEQ ID NO: 48<br>SEQ ID NO: 49 |
| dup(α-β) | P9: 5'-AAGGACTTCCCCGAGTACCACTTC<br>P2: 5'-AGCCACAGCTCAAATTTGGACTTAC<br>708 bp | SEQ ID NO: 50<br>SEQ ID NO: 51 |
| Chr(16; 18) | P11: 5'-CCACTGCTCCCTGAGATCGAAT<br>P14: 5'-CTGGAAGACACTTGGATCACCATCT<br>566bp | SEQ ID NO: 52<br>SEQ ID NO: 53 |
| Chr(18; 16) | P13: 5'-CAGTTATCTGCTGGCAGGTACCACT<br>P12: 5'-TGCCAGTGTCTGAAGGAGATGC<br>923 bp | SEQ ID NO: 54<br>SEQ ID NO: 55 |

Each of the above described Pcdh alleles were bred to homozygosity. All genotypes were obtained at the expected Mendelian ratio, and homozygotes were viable and fertile. All reporter cassettes used in these alleles could be detected efficiently. No gross phenotypes with respect to viability and histology have been detected for any of these homozygotes. These mice are analyzed in detail for changes in neural circuitry and behaviour associated with the individual mutant alleles.

Somatic in Trans Cre/loxP Recombination In Vivo:

Although Cre/loxP-mediated recombination between homologous or non-homologous chromosomes during mitotic divisions has been reported in ES cells and somatic tissues, the low efficiency of these events precluded its use for identifying in vivo germline transmissions of these events (Zheng, B., et al. 2000; Herault, Y., et al. 1998; Collins, E. C., et al. 2000; Liu, P., et al. 2002; Buchholz, F., et al. 2000). Whereas the former in vitro approaches take advantage of drug selection protocols to identify the rare site-specific recombination events, in vivo approaches cannot readily do so.

Figure 2A:
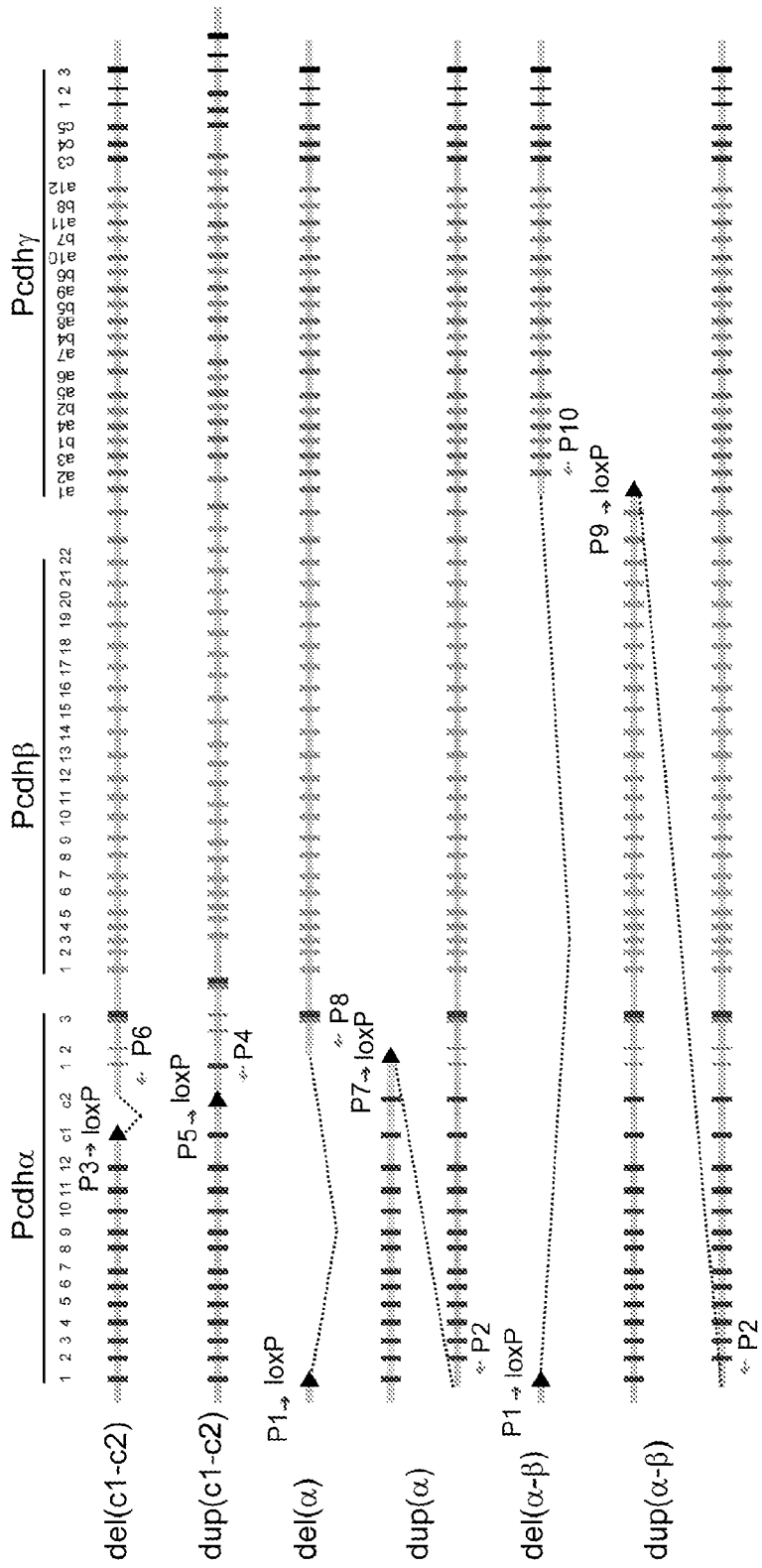
FIG. 2A shows a1, c1, c2, Con and γa1 alleles were used for in vivo generation of large deletions and duplications. Schematic in panel A shows genomic structures of deletions and duplications that could be generated by Cre/loxP-mediated in trans recombination.
Figure 2B:
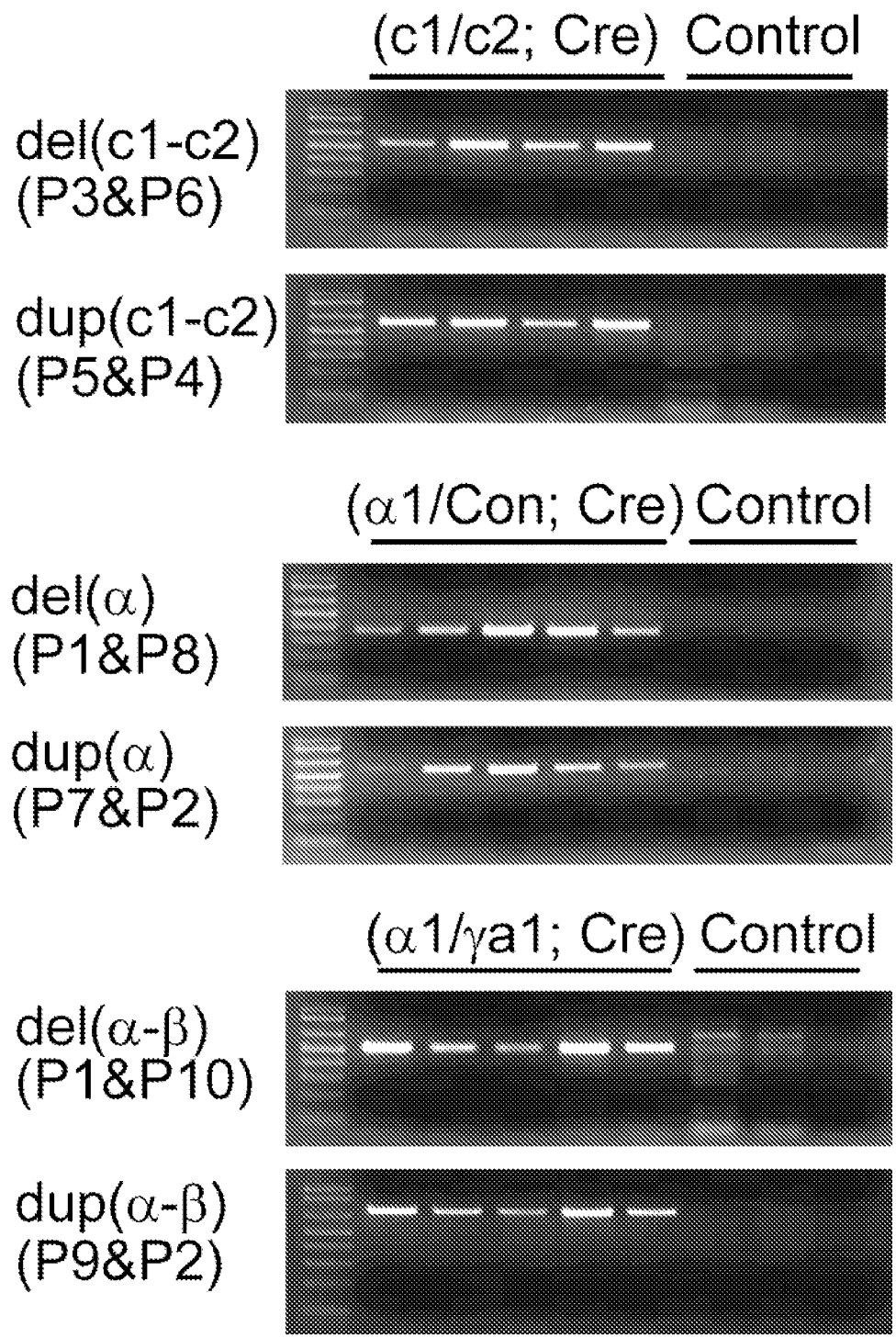
FIG. 2B shows Cre/loxP mediates efficient in trans recombination between chosen Pcdh mutant alleles in somatic cells. Tail DNA from mice containing (c1/c2; Hprt-Cre/+), (α1/Con; Hprt-Cre/+), or (α1/γa1; Hprt-Cre/+) alleles, respectively, were subject to PCR analysis to detect the corresponding deletion and duplication alleles. The predicted del and dup alleles were detected in tail DNA of every male containing the appropriate Pcdh loxP alleles and Hprt-Cre.
Figure 2C:
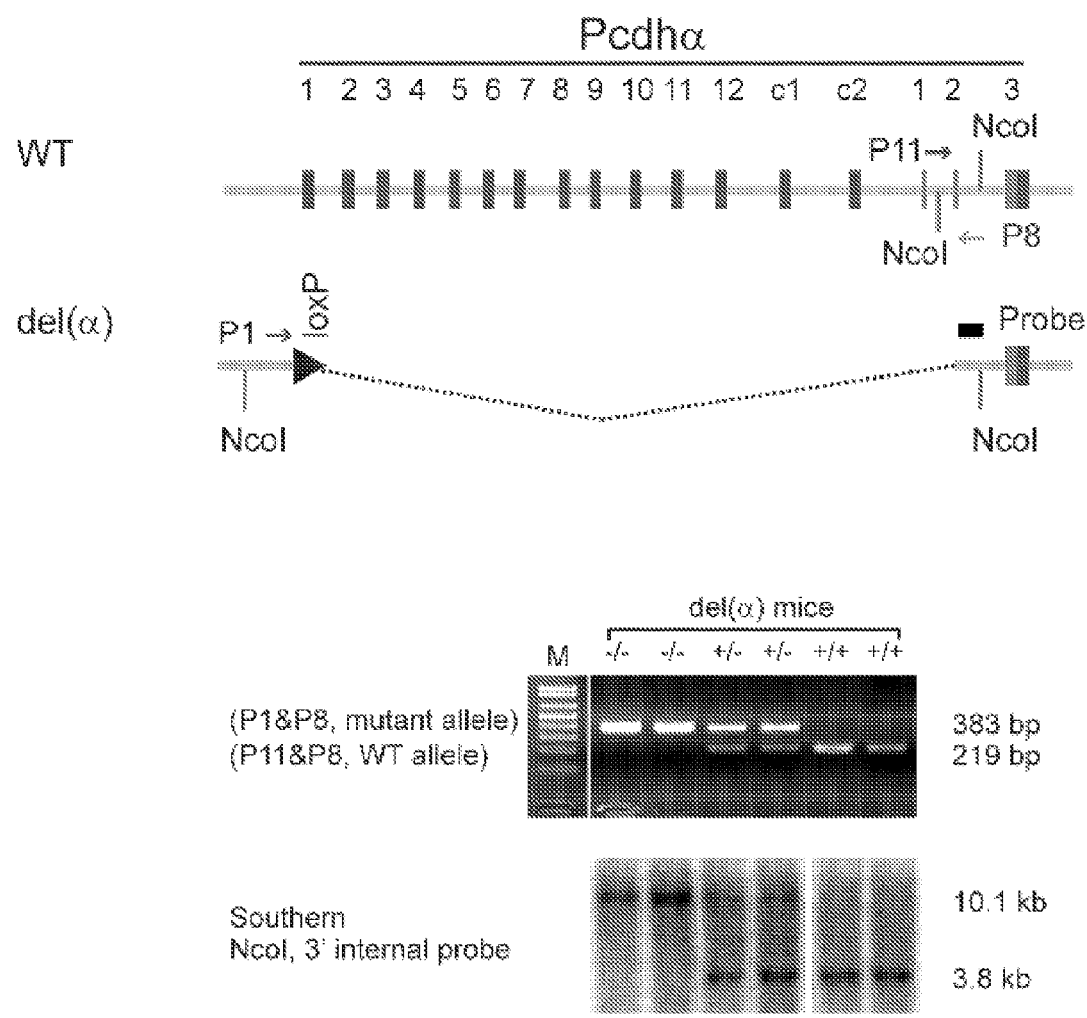
FIG. 2C shows a germline transmission of the recombined deletion allele del(α) confirmed by both PCR and Southern blot.

Since Cre recombinase activity is dosage-dependent, a strong, constitutively expressed Cre transgene can efficiently drive trans-allelic recombination during both mitotic and meiotic cell divisions. Hprt-Cre (Tang, S. H., et al. 2002; Schmidt, E. E., et al. 20), in which Cre production is driven by the human cytomeglovirus immediate early enhancer and chicken β-actin/rabbit β-globin hybrid promoter (CAG promoter), appeared to be a good candidate for this purpose. To test this hypothesis, Pcdh alleles: α1, c1, c2, Con, and γa1 were used because they all harbor loxP sites with the same chromosomal orientation. The appropriate Pcdh alleles were first crossed with Hprt-Cre to generate compound heterozygous males that contained the following sets of alleles (c1/c2; Hprt-Cre/+), (α1/Con; Hprt-Cre/+), and (α1/γa1; Hprt-Cre/+), respectively. Tail DNA from these mice were then analyzed using PCR to detect the corresponding Cre-mediated deletion and duplication alleles. It was demonstrated that each mouse had undergone the predicted Cre/loxP-mediated trans-allelic recombination event in somatic cells, and that both the deletion and duplication alleles were present (FIG. 2A, B). All the PCR products were sequenced and the presence of the predicted junction sequences generated by the Cre-mediated site-specific recombination events confirmed. Although these experiments could not provide the frequencies of these long-range trans-allelic recombination events, these results encouraged evaluation of germline transmission of these events.

Large Deletions and Duplications in Germ Line:

Heterozygous males containing the above described combinations of Pcdh alleles and Hprt-Cre, were mated to wild type C57BL/6J females. Germline transmission was not detected at remarkably high frequencies in the offspring of all six recombined alleles [del(c1-c2), dup(c1-c2), del(α), dup (α), del(α-β), and dup(α-β)](FIG. 2A, C). As expected, the Cre-mediated trans-chromosomal recombination frequency between loxP sites separated by the shortest distance (54 kb, between c1 and c2 alleles) yielded the highest frequency (~10%, Table 3. However, even with the loxP sites in the α1 and γa1 alleles being separated by over 700 kb, the trans-chromosomal recombination frequency was still remarkably high (i.e. ~5%). These results indicate that large genome-wide deletions and duplications ranging from tens to hundreds of kilobase pairs can be similarly generated using this simple breeding procedure.

TABLE 3

Frequency of germline transmission of the corresponding duplication and deletion alleles.

|  | Distance | Frequency |
| --- | --- | --- |
| del(c1-c2) | 54 kb | 9/97 |
| dup(c1-c2) |  | 12/97 |
| del(α) | 228 kb | 7/201 |
| dup(α) |  | 4/201 |
| del(α-β) | 730 kb | 3/64 |
| dup(α-β) |  | 3/64 |

The Pcdh α Cluster is not Essential for Survival:

To determine the function of the α cluster, mice heterozygous for the del(α) allele were bred to homozygosity. Surprisingly, these homozygotes are viable and fertile with no apparent gross phenotype. Histochemical analysis with Nissel staining revealed apparent normal gross anatomy of the mutant mouse brain. For example, the thickness and layering of the cerebral cortex appears normal. Nissl staining showed similar staining patterns in the control and mutant mice. The same results were obtained for the Con/Con homozygotes. The gross wiring in the peripheral and central nervous system was also examined by whole-mount antibody staining with neurofilament antibody, and no gross changes in the mutants could be detected. Antibodies against the presynaptic marker synpaptophysin, the excitatory postsynaptic marker PSD-95, and the inhibitory synaptic marker GAD65 also showed similar immunostaining patterns in del(α) homozygous and in control mice in all adult brain regions examined, such as cortex, hippocampus, and cerebellum, suggesting normal gross synaptic formation in the mutant brain. The Pcdhα cytoplasmic domain has been suggested to interact with Fyn tyrosine kinase (Kohmura, N. et al. 1998), and Fyn knockout mice show an abnormal dendrite phenotype in the hippocampus. Brain sections were therefore stained with the dendritic marker MAP2 antibody. Again no obvious dendritic defects were observed in the hippocampus and other brain regions of adult del(α)/del(α) mice.

Adults homozygous for dup(α-β), a duplication of 37 genes, were obtained. No obvious phenotypes have been detected in these mice. In contrast, homozygous del(α-β) mutants embryos die before day 9 of gestation. However, the analysis of del(α-β) homozygotes is complicated by the fact that two non-Pcdh genes (Slc25a2 and Taf7) were also deleted in these mice.

Figure 3A:
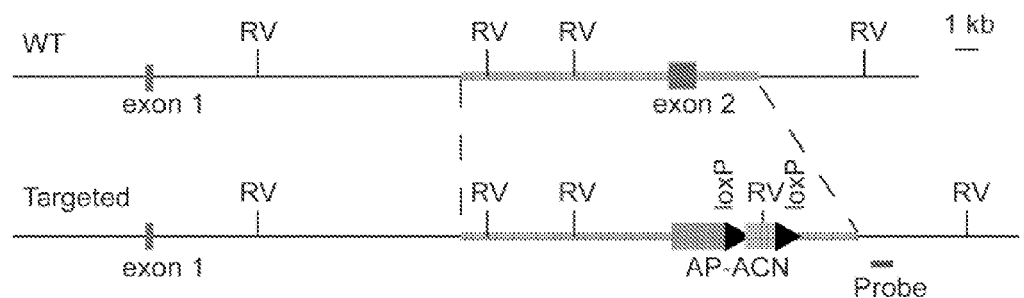
FIG. 3A shows gene targeting in Nogo Receptor (NgR, Rtn4r) locus. To generate a loss-of-function allele of the NgR gene, an alkaline phosphatase reporter/selection cassette replaced more than 95% of the amino acids of NgR. Southern transfer analysis, using EcoRV (RV) digest and a 3' flanking probe, identified a 12.9 kb band for wildtype and the predicted 8.8 kb band for targeted allele.
Figure 3A:
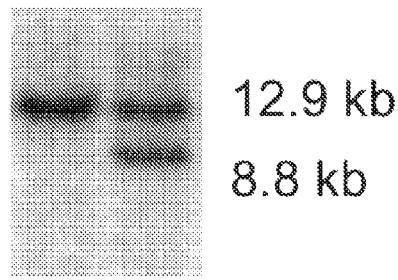
Figure 3B:
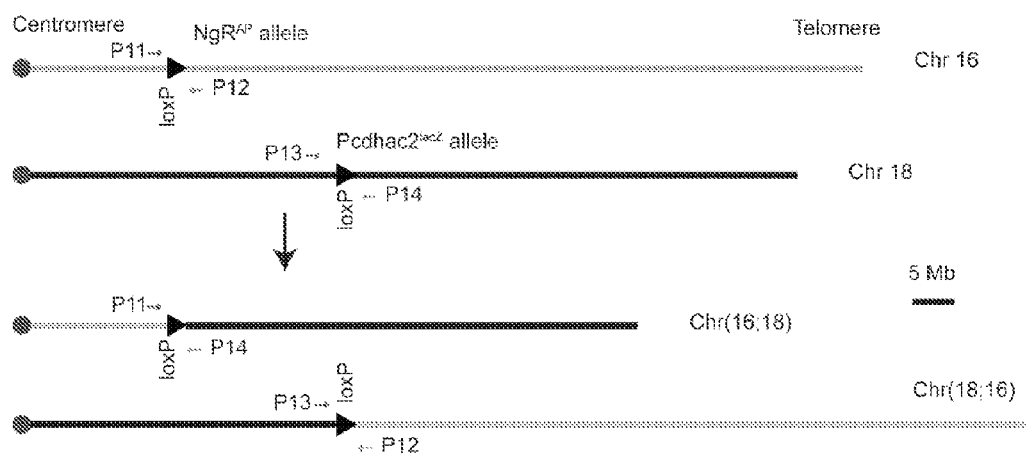
FIG. 3B shows both loxP sites in the NgR-AP allele and the Pcdhαc2 alleles have the same orientation relative to their centromeres. Cre/loxP-mediated recombination between these loci generated a translocation between these chromosomes.
Figure 3C:
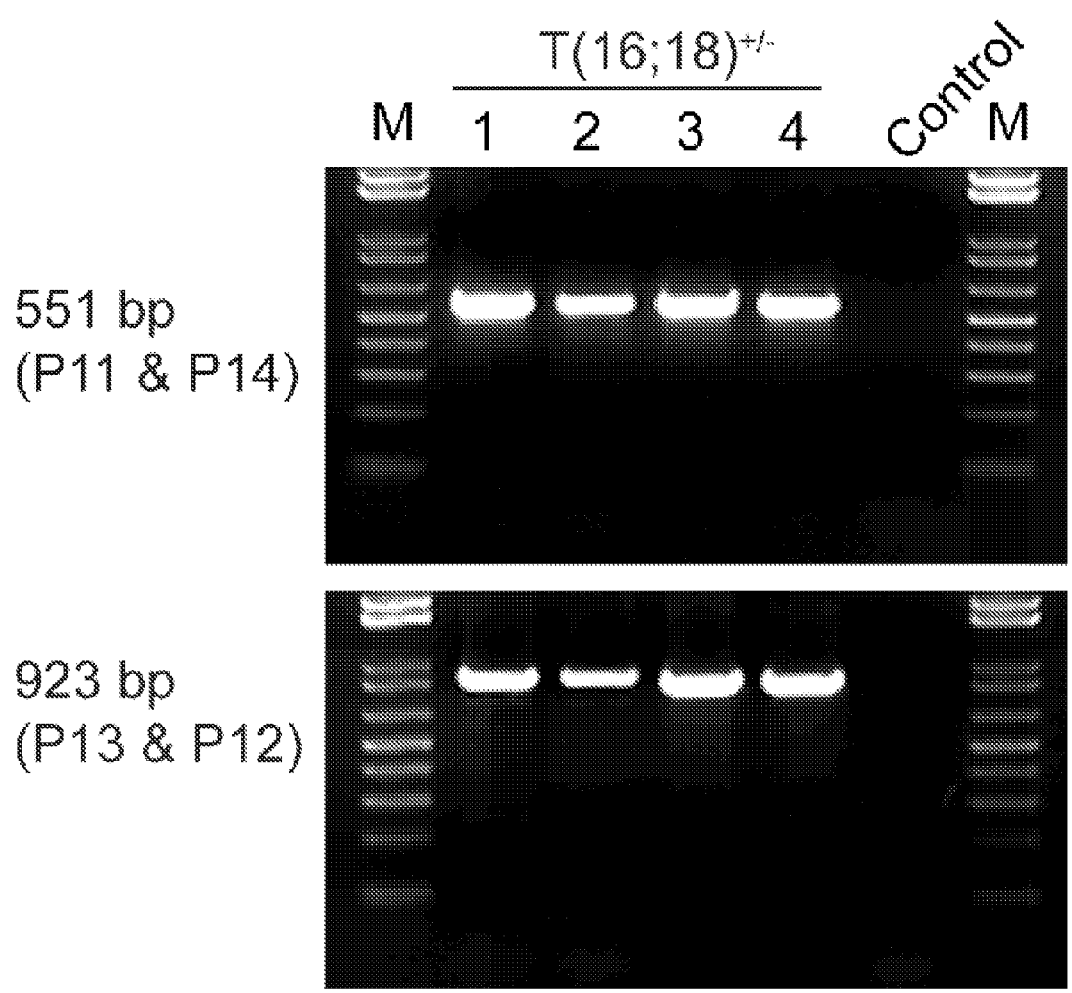
FIG. 3C shows germline transmission of reciprocal T(16; 18) translocations was confirmed by PCR. Lanes 1 and 2 are two F1 adult mice, Lanes 3 and 4 are two 2-week-old F2 offspring from a cross of F1 mouse to wild type, and they are all heterozygous for the reciprocal translocation T(16; 18).
Figure 3D:
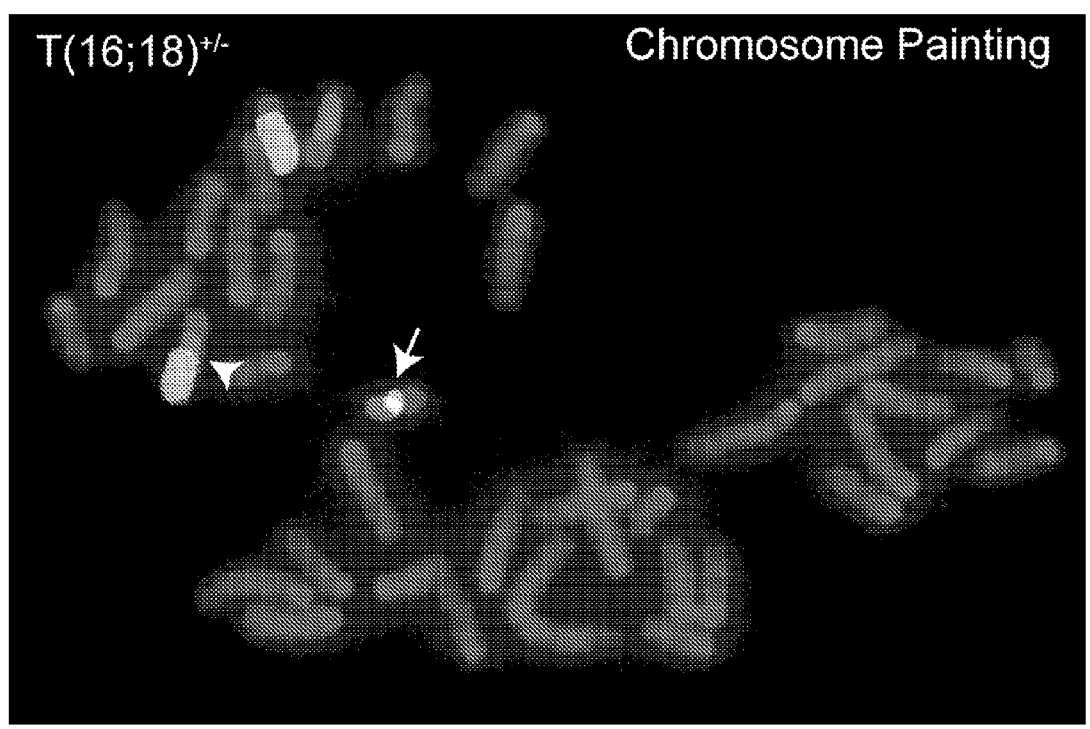
FIG. 3D shows chromosome painting of metaphase chromosomes prepared from heterozygous E16 F2 fibroblast culture. Arrow: Chr(16; 18); Arrowhead: Chr (18; 16).

Germline Generation of Chromosomal Translocations:

To examine whether the same breeding strategy can generate germline translocations between non-homologous chromosomes, the Pcdhαc2 allele on mouse chromosome 18 was bred to a NgR-AP allele on chromosome 16 (FIG. 3A), in which the Nogo receptor gene is replaced by an alkaline phosphatase reporter gene, and to Hprt-Cre mice to produce compound heterozygous males (c2/+; NgR-AP/+; Hprt-Cre/+). The Pcdhαc2 and NgR alleles each contain loxP sites in the same chromosomal orientation relative to the centromeres. These males were then crossed to C57BL/6J wild-type females. To date, 2 out of 182 offspring have been detected to inherit a germline transmission of the balanced reciprocal T(16; 18) and T(18; 16) translocations (FIG. 3b-c). The two mice appear normal, healthy, and fertile. It appears that T(16; 18) and T(18; 16) translocations always cosegregate, because non-reciprocal translocation were never detected alone, even among the next generation (FIG. 3c). This result indicates that non-reciprocal translocation can cause embryonic lethality. Two out of 182 offspring were shown to inherit a germline transmission of the balanced reciprocal T(16; 18) translocations (FIG. 3B-C). The two mice appear normal, healthy, and fertile, having swapped 81.6% of chromosome 16 with 58.9% of chromosome 18 and vice versa. In living mice it appears that the reciprocal translocations always co-segregate together, since non-reciprocal transmission of these translocation products was not detected in the next generation (FIG. 3C-D). Among 27 F2 offspring generated from crosses of F1 to wild-type mice, 14 reciprocal translocations were detected while mice containing individual translocations were not detected. This result indicates that being either haploid or trisomic for these portions of chromosome 16 and 18 causes embryonic lethality.

Gene-Trap Using the piggyBac Transposon:

Genome-wide chromosome rearrangements can be accomplished using loxP sites distributed throughout the mouse genome. The efficient transposition of the piggyBac transposon in the mouse germline (Ding, S. et al. 2005) offered an ideal method for achieving this goal. A piggyBac gene-trap strategy was designed that would produce multi-purpose loss-of-function and conditional alleles, in addition to providing a broad distribution of loxP sites in the mouse genome (FIG. 4).

Figure 4A:
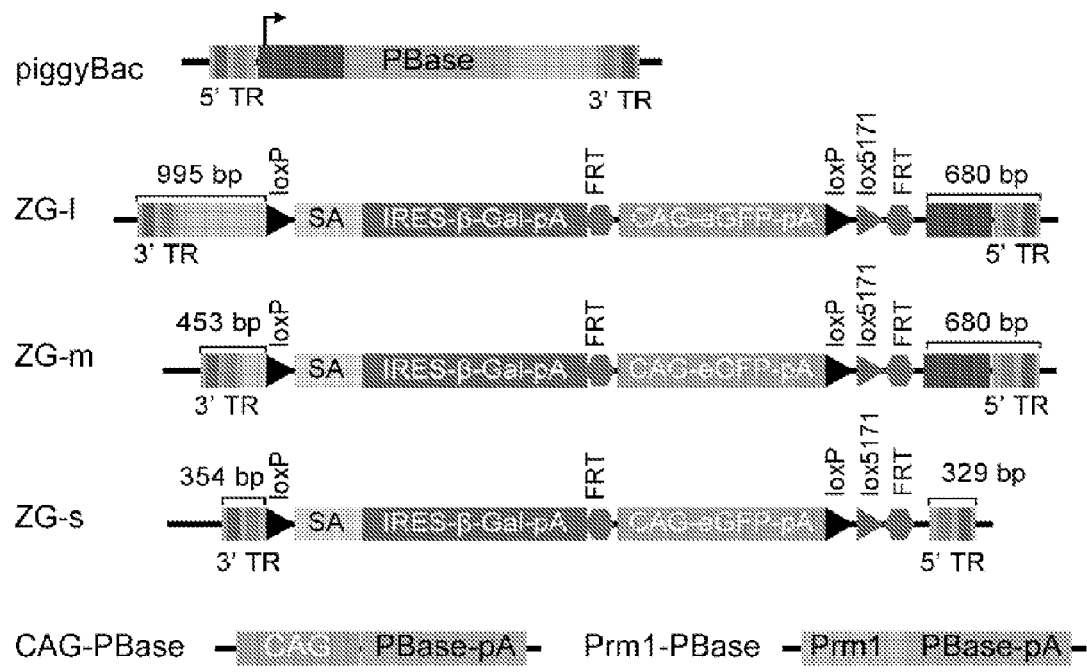
FIG. 4A shows three gene-trap vectors (ZG-l, ZG-m and ZG-s) and two transposase constructs (CAG-PBase-SEQ ID NO:118 and Prm1-PBase-SEQ ID NO:119).

To maximize the utility of the piggyBac gene-trap vector, it was first sought to define which transposon sequences are required for efficient transposition, and which sequences could be deleted in order to increase cargo size, and at the same time minimize cryptic RNA splicing through transposon sequences. Based on this consideration, three gene-trap vectors were constructed ZG-1 (SEQ ID NO:105), ZG-m (SEQ ID NO:106) and ZG-s (SEQ ID NO:107) (FIG. 4A). ZG-l has the 63 bp of 3' terminal repeats with the adjacent 932 bp internal sequences, and 35 bp of 5' terminal repeats with the adjacent 645 bp internal sequences. Compared to ZG-l, ZG-m excludes 542 bp of 3' internal sequence, deleting all but one of the cryptic splice donor (SD) sites. ZG-s deletes all potential SD sites, and an additional 450 bp of more internal sequences.

fluorescent as expected because all three constructs harbor a constitutive CAG promoter-driven GFP. Sequencing of the inverse PCR products, generated from genomic DNA from each founder, confirmed that most of the integrations are precise piggyBac-mediated transpositions (Table 4. Since lack of internal sequences in ZG-s did not appear to affect the transposition efficiency, ZG-s, which has no cryptic SD sites, was chosen for all subsequent germline transposition studies.

TABLE 4 piggyBac transpositions in founder mice

| Founder | Insertion site | SEQ ID NO: | Location | Chr |
|---|---|---|---|---|
| 17_1(ZG-1) | TTAAGAGAGGAGGA ATTTATTCTG | SEQ ID NO: 56 | intergenic | 11 |
| 17-2(ZG-1) | TTAAGAAGGCTGTC GTGCTGACC | SEQ ID NO: 57 | intron | 5 |
| 45(ZG-1) | random insertion (nontransposition) | | | |
| 64(ZG-m) | TTAATGGTGTTATT TGATTTCTG | SEQ ID NO: 58 | intergenic | 1 |
| 67(ZG-m) | TTAAAATGAACTCT AGAACCTCCT | SEQ ID NO: 59 | intron | 2 |
| 78(ZG-m) | random insertion (nontransposition) | | | |
| 90_1(ZGs) | TTAAAAGATTTATT TATTTTATTT | SEQ ID NO: 60 | intron | 5 |
| 90_2(ZG-s) | TTAAAGGCGTGCGC CACCACAACC | SEQ ID NO: 61 | intron | 9 |
| 94_1(ZG-s) | TTAAATGTATTTAC TTACTTATTT | SEQ ID NO: 62 | intergenic | 4 |
| 94_2(ZG-s) | TTAAAGAATAAAAG ATGGTGTCTT | SEQ ID NO: 63 | intergenic | 17 |
| 105(ZG-s) | TTAAACAAGGATAA AAGCAATCTA | SEQ ID NO: 64 | intron | 11 |

Figure 4B:
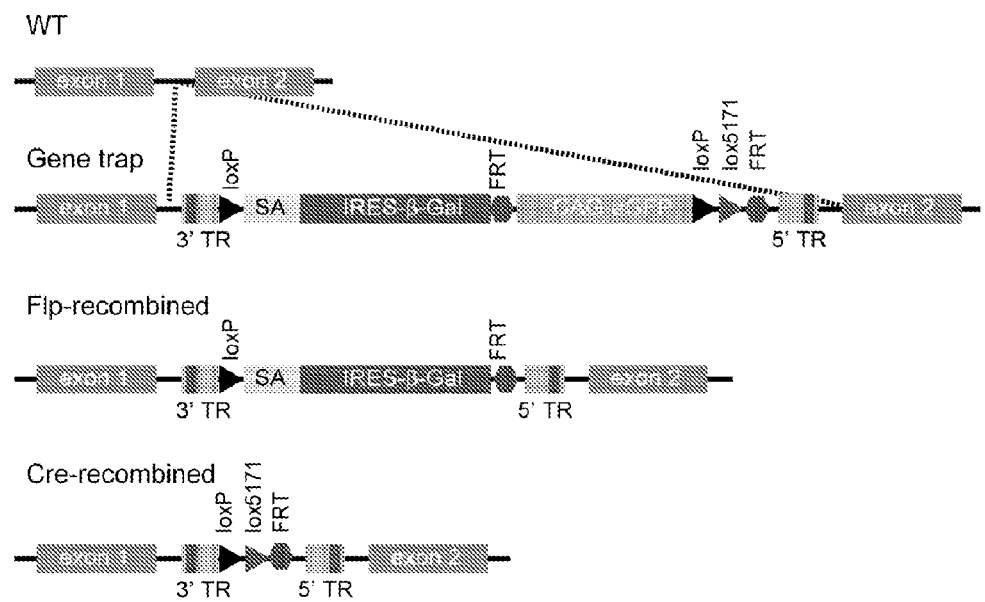
FIG. 4B shows successful piggyBac transposition into an intron of an endogenous gene produces a gene-trap allele. The presence of loxP and FRT sites allows for further in vivo manipulation of this gene-trap allele.
Figure 4C:
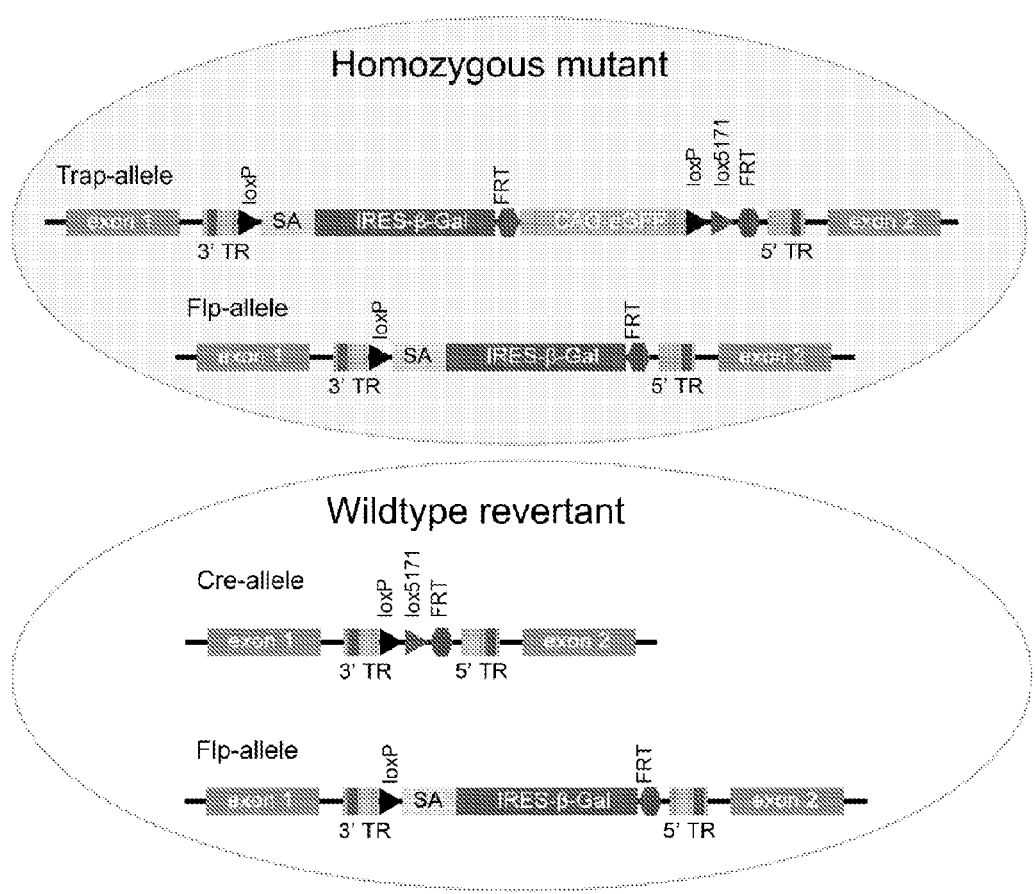
FIG. 4C shows gene-trap alleles can be used as conditional alleles.
Figure 4D:
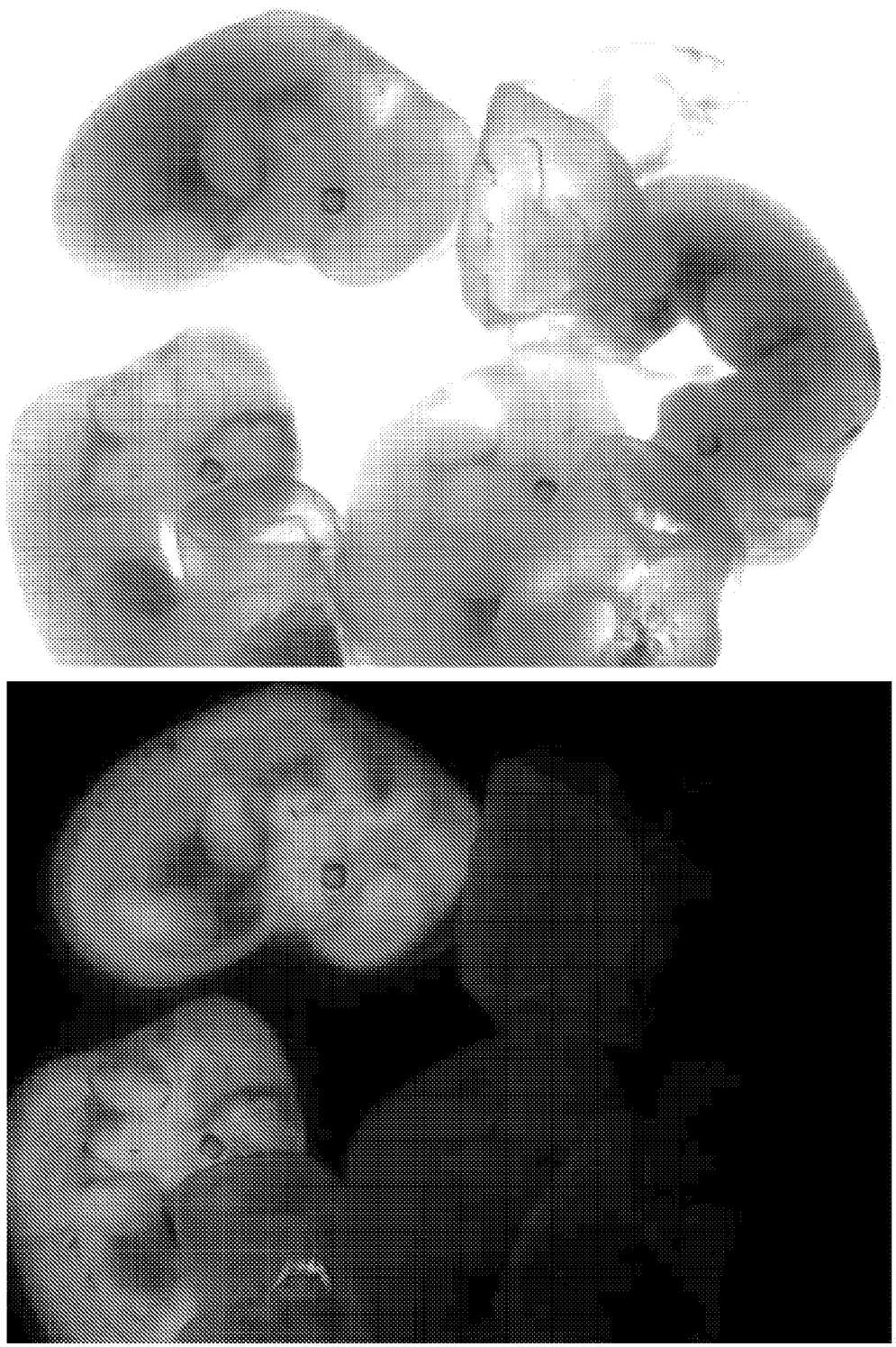
FIG. 4D shows embryonic day 12 (E12) embryos containing Ror2 gene-trap alleles are fluorescent, due to the presence of CAG-eGFP reporter in the ZG-s gene-trap construct.
Figure 4E:
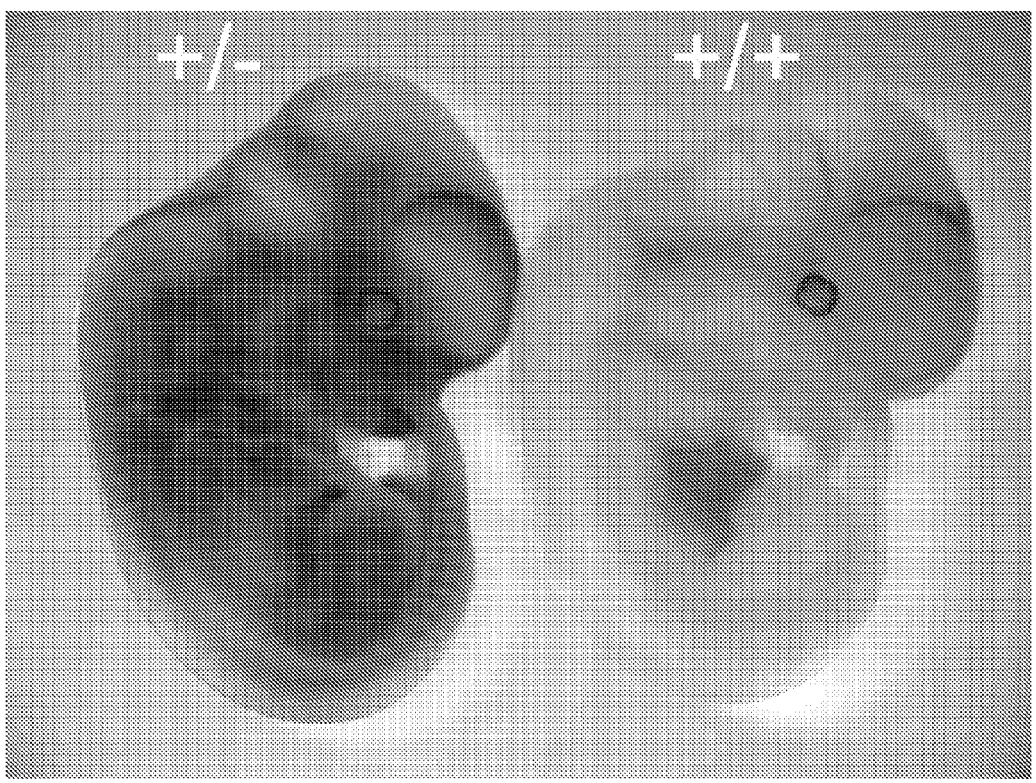
FIG. 4E shows a heterozygous embryo from FIG. 4D is stained for β-galactosidase, and shows strong expression in developing bones and forebrain.
Figure 4F:
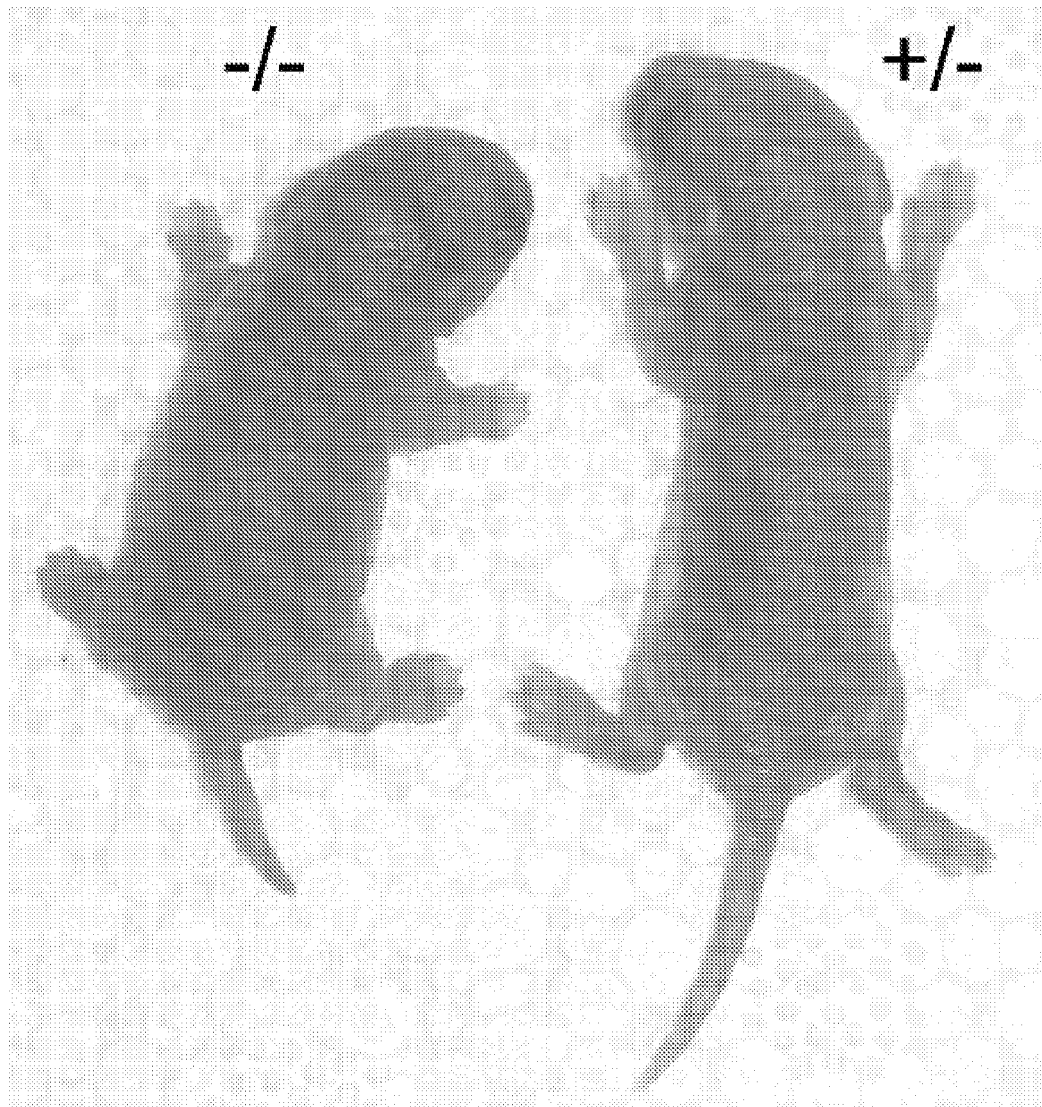
FIG. 4F shows postnatal day 0 animals homozygous for the Ror2 gene-trap allele have shortened body, limbs and tail.
Figure 4G:
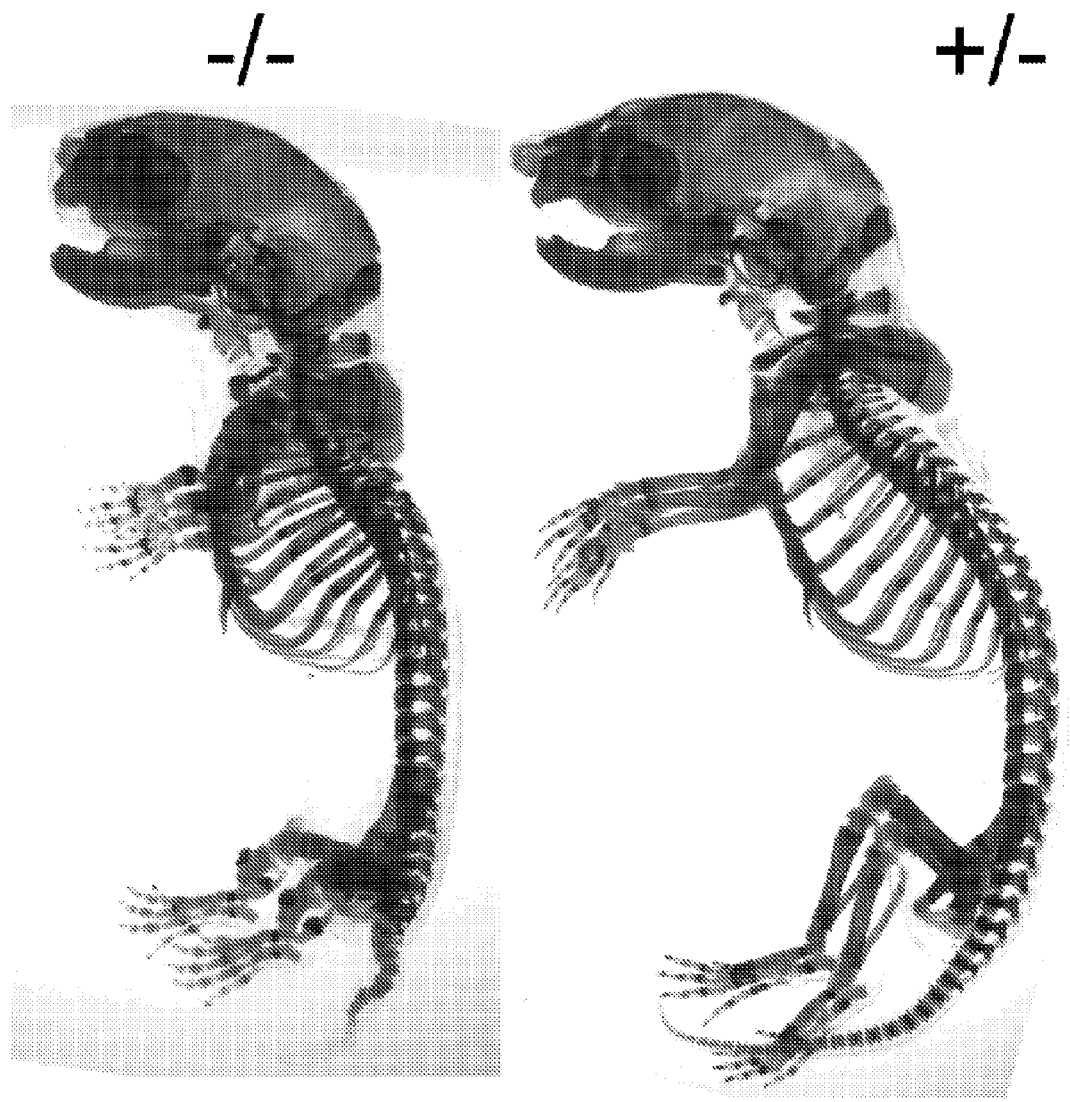
FIG. 4G shows skeleton preparation of the two animals in FIG. 4F further confirms the extensive abnormalities in the bones.

The disclosed gene-trap design generates multi-purpose alleles (FIG. 4B). First, successful piggyBac transposition into an intron of an endogenous gene should produce a loss-of-function gene-trap allele (trap-allele). Second, it provides for easy removal of sequences flanked by the two FRT sites by Flp recombinase generating the flp-allele. In contrast to the gene-trap allele, this flp-allele can be bred to any Cre drivers without concern for unexpected germline Cre-mediated recombination involving these alleles. Third, because the splice acceptor in the trap-allele is flanked by two loxP sites, Cre-mediated recombination of this allele should generate a wild type revertant allele (cre-allele), since the remaining sequence at the locus, without a splice acceptor site, is very likely to be innocuous. Therefore, the trap-allele can be used as a conditional allele (FIG. 4B, C).

Figure 5A:
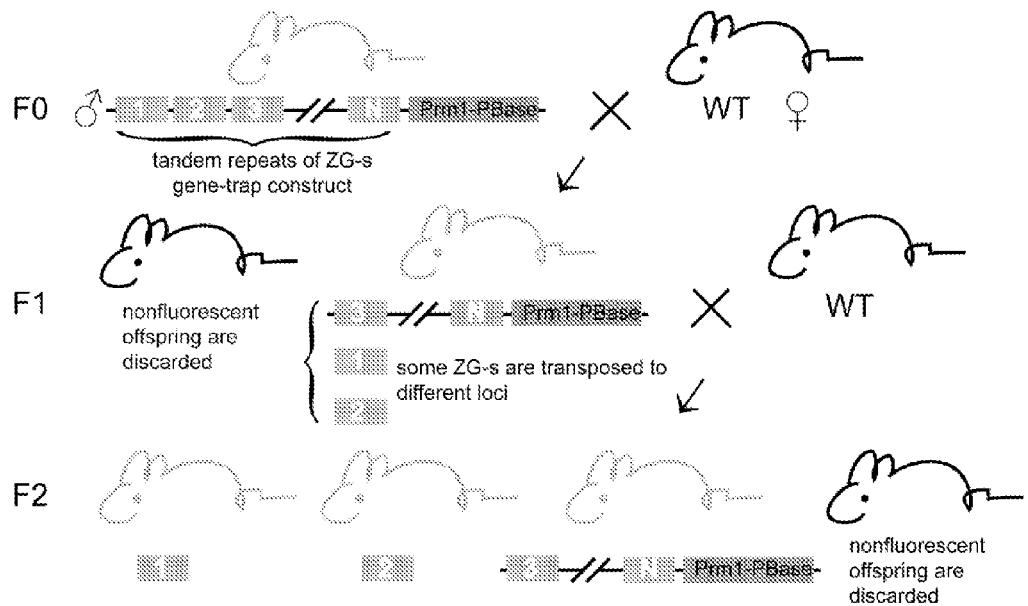
FIG. 5A shows schematic showing a breeding scheme to generate new piggyBac gene-trap alleles by germline transposition. Male founders (F0) containing tandem ZG-s and Prm1-PBase (in the same locus) were bred to wild type C57BL/6J females. New transposition events (shown as boxes 1 and 2) in the F1 generation can be separated as F1 gametes, and stable alleles are obtained in the F2 generation.
Figure 5B:
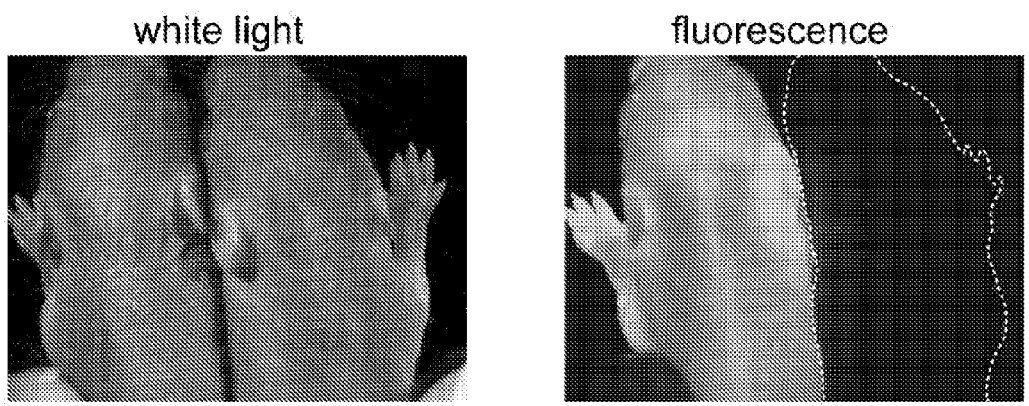
FIG. 5B shows newborns harboring a ZG-s gene-trap construct can be easily detected under fluorescence.

To compare the three gene-trap constructs in the mouse, transgenic mice were created through pronuclear injection of circular plasmid containing a strong CAG promoter-driven piggyBac transposase (CAG-PBase; SEQ ID NO:118), with a circular plasmid containing the ZG-l, ZG-m or ZG-s sequences, respectively. Transgenic founder mice containing only ZG-l (two lines), ZG-m (three lines) or ZG-s (three lines) without CAG-PBase were obtained. All of these founders are To produce large numbers of loxP-bearing gene-trap alleles by germline transposition, double transgenic mouse lines were next created through pronuclear co-injection of ZG-s, and protamine promoter driven-piggyBac transposase (Prm1-PBase; SEQ ID NO:119), which expresses piggyBac transposase in the male germline only (Ding, S. et al. 2005; Schmidt, E. E., et al. 2000). Eighteen founder mice (12 males and 6 females) were obtained. After confirming that the Prm1 promoter is only active in male founders, female founders were used to maintain a line and produce more male founders. Male founders were used for crossing with wildtype C57BL/6J females to generate new transposition events. Since the Prm1 promoter is only active after meiosis, only those offspring (about half) that inherit the transgenes (Prm1-PBase and ZG-s) can have new transpositions (FIG. 5A). Since ZG-s gene-trap construct includes a constitutively expressed GFP (FIG. 4A), it is very convenient to tell which offspring contain new transposition events (FIG. 5B). Results from inverse PCR confirmed that new transposition events indeed occurred in germline through simple breeding (Table 5. On average one new transposition event was obtained per offspring per generation.

TABLE 5 piggyBac transpositions in germline through breeding

| Mouse ID | Insertion site | Gene | Location | Chr |
|---|---|---|---|---|
| 340_1 | TTAACATATAGTAACTGTGTGTAT | SEQ ID NO: 65 | intergenic | 7 |
| 340_2 | TTAAGGAGACTAGTGAAAGTGAAC | SEQ ID NO: 66 | intergenic | 11 |
| 340_3 | TTAATAAATTAATCAGTCACTTAA | SEQ ID NO: 67 | intron | 17 |
| 340_4 | TTAACTAGATCCTCTACATATTTG | SEQ ID NO: 68 | intergenic | 8 |
| 340_5 | TTAAGTAATACAGGAAAAGAGGAA | SEQ ID NO: 69 | intergenic | 1 |
| 340_6 | TTAAATCTGGGTCTAGATTTTCGG | SEQ ID NO: 70 | intron | 8 |
| 381_1 | TTAAGGTGTCTCTATGTAGTCTTG | SEQ ID NO: 71 | intron | 4 |
| 381_2 | TTAAGCAACCTGCTGAATCAAACC | SEQ ID NO: 72 | intergenic | 11 |
| 381_3 | TTAAGGACCATTCACAAAATATGG | SEQ ID NO: 73 | intron | 11 |
| 381_4 | TTAAGCTGCTTGCTGGATCTTTTG | SEQ ID NO: 74 | intergenic | 5 |
| 390_1 | TTAAAGAAGAGTGCTGCTTCTATG | SEQ ID NO: 75 | intergenic | 9 |
| 390_2 | TTAAATAAAACCAGTTAAAAATAA | SEQ ID NO: 76 | intergenic | 1 | ii. Methods

Creation of Mutant Pcdh and NgR Alleles:

In the method for the construction of the targeting vectors is described as a general protocol, a total of 8-15 kb homology to the target locus was used, with each homology arm being greater than 1 kb. If both homology arms contained an excess of repetitive DNA sequence, then the targeting frequency can be low.

To construct the targeting vectors, two ET cloning oligos were designed to permit isolation of the targeting vector homology arms from the chosen BAC clone and to transfer the BAC fragment to the plasmid, pStart-K (SEQ ID NO:108). For example, for the Pcdhαc1 targeting vector the upstream oligo sequence was: CTAGATCATATCCAAGTTTTTTATC-CTCTGAAGCCATTAAAATTAAGTTGcgactg aattggttcctt-taaagcc (SEQ ID NO:77) and the downstream oligo sequence was: GACCAACCAACTTCTC-CTGGGCATGGGGCCTGCCCTGGAGTGTG-GTTTACgccgc actcgagatatctagaccca (SEQ ID NO:78). The uppercase sequences within each oligo are homologous to 50 bps at the two junctions of the desired BAC fragment. The lowercase oligo sequences match the backbone of pStart-K. These two oligos were used in conjunction with the polymerase chain reaction to amplify the plasmid template pStart-K. (5×25 µl reactions. pStart-K, 50 ng; 10× buffer, 12.5 µl; 25 mM MgCl$_2$, 10 µl; primers, 2.5 µl each at 10 pmoles/µl; 10 mM dNTP, 2.5 µl; Taq, 1.25 µl; H$_2$O was added to a total volume of 125 µl). PCR conditions were: 94° C. 30 seconds, 59° C. 30 seconds, and 72° C. 90 seconds for 30 cycles. The amplified PCR product was purified on a Qiagen column and digested with DpnI for 1-2 hours. The reaction was re-purified on a Qiagen column, and eluted with 40 µl H$_2$O. DH10B bacteria containing the corresponding BAC were made ET-recombination competent by transformation with a Redα and Red β-expressing plasmid pKD46 (Zhang, Y., et al. 1998; Datsenko, K. A. & Wanner, B. L. 2000). 5-10 µl of purified PCR product (200 ng to 1000 ng) were electroporated into 50 µl of the above competent cells. The parameters for electroporation with a Genepulser (Biorad) were: 0.1 cm cuvettes, 1.8 kV, 25 µF capacitance, and 200 ohms. Immediately after electroporation, the cells were transferred to 1 ml of SOC medium, incubated at 37° C. for 1 hour, and plated onto Kanamycin LB-agar. 8 small Kan$^r$ colonies were picked and grown in 5 ml of SOB medium at 37° C. overnight for preparation of DNA minipreps. These DNA preps were analyzed by restriction enzyme mapping. The resulting positive clones, designated pStart-K-Pcdhαc1, were further confirmed by sequencing. Primers for the sequencing reactions were WS275: TAAACTGCCAGGCATCAAACTAAGC (SEQ ID NO:79); WS276: AGTCAGCCCCATACGATATAAGTTG (SEQ ID NO:80).

Next oligos were designed to delete the Pcdhαc1 variable exon and concomitantly introduce an AscI restriction enzyme site at this position. The upstream oligo sequence was: GAGCATGGTCCCGGGTCGCCGCAACTG-GAGCGTGGAGGCCGAAAGGGAGGAT GGT GGCGCGCCagcattacacgtcttgagcgattgt (SEQ ID NO:81) and the downstream oligo sequence was: TAGTAACTATCTCCTTGCCAGAGGAGT-CAAACCACATAATATGTGCTTAC GGCGCGCCcacttaacggctgacatgggaatta (SEQ ID NO:82). Uppercase sequences are 50 bp homology for ET recombination. The underlined portion (GGCGCGCC) is the AscI consensus sequence. Lowercase sequences are primers for the choloramphenicol resistance gene in pKD3 (Datsenko, K. A. & Wanner, B. L. 2000). PCR was performed as described above. 5 µl of purified PCR product plus pStart-K-Pcdhαc1 was added to a tube of ET competent DH5α/pKD46 cells. Electroporation was performed as above. 1 ml of SOC was added and the mixture incubated in 37° C. with shaking for 1 hour. The bacteria were spread onto chloramphenicol plates, and incubated at 37° C. overnight. 4 medium-to-large colonies were picked and grown in 5 ml SOB medium at 37° C. overnight for preparation of DNA minipreps. Two minipreps with the correct restriction patterns were sequenced to confirm the presence of the predicted junction regions using primers WS187: ATGCCGCTGGCGATTCAGGTTC (SEQ ID NO:83) and WS188: GCCGATCAACGTCTCATTTTCG (SEQ ID NO:84). The resulting plasmid was designated pStart-K-Pcdhαc1 Asc, which was subject to insertion of a pre-cut AscI-AP-ACN-AscI cassette or other reporter cassettes. Characterized clones from this step were designated pStart-K-Pcdhαc1-AP.

Finally, introduction of the HSV-thymidine kinase gene into the targeting vector implemented a Gateway (Invitrogen) recombination reaction. The reaction mixture contained: (LR Reaction Buffer (5×), 1 μl; pStart-K-Pcdhαc1 AP (e.g.), 2 μl; pWS-TK6/linearized with SalI, 1 μl; LR clonase enzyme mix, 1 μl). After incubation at 25° C. for one hour, 0.5 μl of Proteinase K Solution was added and reaction incubated for 10 minutes at 37° C. 100 μl of chemically competent DH5α cells (>$10^8$ transformants/μg) were transformed with 2 μl of the above DNA by heat shock. No incubation is needed for this step. 10 μl and 90 μl of the transformed bacteria were plated on LB plates containing 100 μg/ml ampicillin. The plates were incubated at 32° C. for 20-30 hours. Two colonies were picked for culture and preparation of DNA minipreps. The correct clone was named pTV-Pcdhαc1AP. Conveniently, the TK vectors contain many engineered sites for linearization of the targeting vector, which is required for efficient targeting of ES cells (Thomas, K. R., et al. 1986). The other targeting vectors were generated using very similar methods.

The above procedure allows for quick and precise modification of cloned genomic DNA, thus enabling the production of sophisticated targeting vectors containing point mutations, in-frame fusions, and/or reporter genes. In addition, it was found that the use of pStart-K or other low-copy replicating plasmid has many advantages. First, due to the presence of repetitive DNA sequences some genomic DNAs are difficult to maintain as high-copy plasmids. Second, modification of high-copy plasmids by ET cloning often generate concatemers, containing both original and modified plasmids that are difficult to separate. With this procedure it is possible for one to construct as many as 30 distinct targeting vectors in approximately one month.

Immunohistochemistry:

The following primary antibodies were used: rabbit anti-GAD 65 (Chemicon, 1: 500), monoclonal anti-MAP2 (Sigma, clone HM-2, 1:500), 2H3 monoclonal anti-neurofilament (Developmental Studies Hybridoma Bank, 1:100), monoclonal anti-PSD-95 (Upstate, clone K28/43, 1: 2000), and monoclonal anti-synaptophysin (Chemicon, clone SY38, 1:1000). Whole-mount immunostaining with 2H3 antibody was performed as previously described (Huber, A. B. et al. 2005).

Chromosome Painting:

Fibroblasts were derived from an embryonic day 16 embryo containing the reciprocal T(16; 18) translocations. Metaphase chromosomes were prepared according to standard protocol (Dracopoli, N. C. et al. 2006). Chromosome hybridization was performed using green chromosome 16 and red chromosome 18 paints, following instructions from the manufacturer (Applied Spectral Imaging).

Generation of piggyBac Transgenic Mice:

The full-length piggyBac element is a 2472 bp autonomous transposon flanked by inverted repeats and encoding a functional transposase (PBase) (Cary, L. C. et al. 1989; Fraser, M. J., et al. 1996). It specifically inserts into a TTAA target site (Fraser, M. J., et al. 1996). In addition to the 5' and 3' inverted terminal repeats, the PBase requires internal sequences for efficient transposition (Li, X. et al. 2005). However, the minimal requirements for these internal sequences have not been determined in the mouse. The 5' end of piggyBac has a residual promoter, and was not put before a reporter gene in the disclosed gene-trap design. The 3' end of piggyBac has a few cryptic splice donor (SD) sites, which could also compromise gene-trapping, as has been observed in *Drosophila* (Bonin, C. P. & Mann, R. S. 2004).

To construct the gene-trap vector, the piggyBac transposon 5' and 3' sequences were derived from the plasmid C4-PBss (R. Mann, Columbia University). The IRES sequence was derived from pIRES2-EGFP (Clontech). The adenovirus splice acceptor was derived from pBigT (F. Constantini, Columbia University). A codon-optimized lacZ was derived from the nls-lacZ (nuclear localization signal β-galactosidase) in pBroad2-LacZnls (Invivogen), and the sequence for nuclear localization was removed by PCR-mutagenesis. All three gene-trap constructs were designed as follows. The splice acceptor (SA) is a widely-used adenovirus SA (Friedrich, G. & Soriano, P. 1991). The lacZ reporter is preceded by an internal ribosomal entry site (IRES) sequence from the encephalomyocarditis virus, which enables lacZ translation independent of the trapped endogenous genes. The IRES-lacZ is followed by CAG promoter-driven GFP. The entire gene-trap cassette is flanked by two loxP sites. An independent lox5171 site is also included for potential increased trans-allelic recombination efficiency (Liu, P., et al. 2002). Standard cloning and ET cloning were used to assemble all the components into the full-length gene-trap vector ZG-l. ZG-l was further modified by ET recombination and PCR-based mutagenesis to obtain the medium-sized ZG-m and the small-sized ZG-s gene-trap vectors. PBase was derived from the plasmid 286 (Handler, A. M. & Harrell, R. A., 2001) for construction of CAG-PBase and Prm1-PBase vectors. The sequences of the final vectors were confirmed by sequencing. Transgenic mouse lines containing the above vectors were created by standard pronuclear injection methodology.

Inverse PCR to Identify piggyBac Insertion Sites:

To isolate genomic DNA for inverse PCR or for southern blot analysis, about half centimeter pieces of tail were put into 480 μl lysis buffer (50 mM TRIS pH8; 100 mM EDTA; 1% SDS; 100 mM NaCl). 25 μl proteinase K (20 mg/ml stock) was added and the mixture incubated at 55° C. overnight. 0.25 ml 6M NaCl was added and kept on ice for 10 minutes. The reaction mixture was then shaken vigorously for 2 minutes and spun at 14,000 rpm for 10 minutes at 4° C. The supernatant was transferred to a new Eppendorf tube, and ~1 ml 100% ethanol added. A capillary tube was used to spool out the DNA and washed in 70% ethanol. The DNA was dissolved in 200 μl TE. Twenty μl (about 5 μg) of the DNA was digested with the appropriate restriction enzyme in 50 μl reaction for 2 hours. The enzyme digestion is purified on a Qiagen column, and eluted with 50 μl $H_2O$, which was used for ligation at room temperature for 2 hours. The ligation reaction was purified on a Qiagen column, and eluted with 50 μl $H_2O$. Three μl were used in a 25 μl PCR reaction. For identifying the ZG-l 3' junction, the DNA was digested with MspI and the PCR primers were: PB37inv3R (5'-CCTCGATATACAGAC-CGATAAAACACATGC-3'; SEQ ID NO:85) and PB38inv3F (5'-AGTCAGTCAGAAACAACTTTGGCACATATC-3'; SEQ ID NO:86). For identifying the ZG-m junction the DNA was digested with MspI digestion, the primers were: PB39inv3F (5'-GTCAGTCAGAAACAACTTTGGCA-CATATC-3'; SEQ ID NO:87) and PB37inv3R. For ZG-s, MspI digest was used for 3' junction. Primers were: PB40inv3R (5'-CAGATCGATAAAACACATGCGT-CAATTT-3'; SEQ ID NO:88) and PB41inv3F (5'-TAA-CAAAACTTTTAAACATTCTCTCTTTTAC-3'; SEQ ID NO:89). The Roche Expand long template PCR kit was used for all inverse PCR reactions. PCR conditions were as follows: 92° C. for 2 min; 30 cycles of (92° C. for 10 sec, 55° C.

for 30 sec and 68° C. for 3 min); 68° C. for 10 min. Starting from 10$^{th}$ cycle, extension is increased to 20 sec for each successive cycle.

2. Example 2

A Streamlined Protocol for Construction of Gene Targeting Vectors: Generating Knockout Mice for the Cadherin Family and Beyond i. Introduction Gene targeting, the use of homologous recombination in mouse embryonic stem (ES) cells to precisely modify mouse genes (Thomas, K. R., et al. 1987; Mansour, S. L., et al. 1988), allows researchers to create virtually any desired modification in its genome. The predominant use of gene targeting is to generate mice with loss-of-function mutations, so called "knockout mice." To date, thousands of mouse genes have been disrupted by gene targeting (The International Mouse Knockout Consortium. 2007; Austin, C. P., et al. 2004). Three major international programs have been initiated with the goal to disrupt every gene in mouse ES cells.

Despite the large numbers of loss-of-function alleles generated in the past 20 years, construction of targeting vectors still remains a significant technical challenge. Because most targeting vectors are plasmids of well over 20 kb in size, they can be difficult and time-consuming to construct by conventional restriction enzyme-based cloning methods. In addition, PCR-based methods, though straightforward, are generally avoided for this purpose because they almost invariably introduce unwanted mutations when amplifying the large DNA templates required for generating the homology arms.

A number of recombination-based methods in bacteria and yeast have been used for molecular cloning (Hamilton, C. M., et al. 1989; Yang, X. W., et al. 1997; Bradshaw, M. S., et al. 1995; Baudin, A., et al. 1993; Oliner, J. D., et al. 1993). An improved method which utilized the Rac prophage recombinase pair (RecE and RecT) (Zhang, Y., et al. 1998; Zhang, Y., et al. 2000), requires only ~50 bp of homology arms to mediate the desired recombination events in bacteria. However, the efficiency of this procedure is reduced when used for generating large DNA constructs, required for gene targeting vector construction (Liu, P., et al. 2003). Later, another improvement was introduced by expressing λ phage Red-recombinant; Yu, D., et al. 2000; Lee, E. C., et al. 2001). Both improved recombination methods (also known as recombineering) have been used extensively for targeting vector construction (Liu, P., et al. 2003; Angrand, P. O., et al. 1999; Copeland, N. G., et al. 2001). Although the latter method (Liu, P., et al. 2003) is more efficient, it requires use of relatively long homology arms (200-500 bp each) to mediate the recombination events, which entails several additional cloning steps thereby negating many of the advantages associated with the simplicity of recombineering protocols (Chan, W., et al. 2007).

Though not ideal, recombineering has prompted several attempts to develop high-throughput methods for targeting vector construction. An example is the REC method (Zhang, P., et al. 2002), which couples library screening with targeting vector construction. However, the REC method requires relatively complex phage manipulation. Further, the homology arms screened out from the library may not be compatible with subsequent confirmation analysis (e.g., Southern blot strategy). Therefore, the adoption of REC has been limited. In another high-throughput method, BAC clones are directly modified to create targeting vectors (Valenzuela, D. M., et al. 2003) through Red-recombination. However, manipulation of BAC clones can be technically challenging (Valenzuela, D. M., et al. 2003; Testa, G., et al. 2003; Yang, Y., et al. 2003). And Southern blot or PCR screening of ES cells modified with these vectors is very difficult (Valenzuela, D. M., et al. 2003). Further, BAC vectors are not as versatile as plasmid-based targeting vectors, which allow introduction of more sophisticated modifications into the target locus.

The high-throughput approaches (Chan, W., et al. 2007; Valenzuela, D. M., et al. 2003) utilized by the major Knock-out Projects, inevitably emphasize production speed, rather than individual researchers' needs for modifying their genes of interest (Accili, D., et al. 2004). Previous large-scale efforts have produced mutant ES cell libraries that cover a significant portion of mouse genes (Adams, D. J., et al. 2004; Skarnes, W. C., et al. 2004; Hansen, J., et al. 2003), yet researchers have been reluctant to use these lines to produce mice. Apart from the cost, an important factor is that investigators are often more invested in research-oriented designs that best meet their experimental requirements, rather than settle for simple loss-of-function alleles.

A good fully-tested protocol for targeting vector construction is arguably one that is simple and efficient, that creates high quality research-oriented alleles, and is compatible with multiple modifications—such as the generation of reporter alleles, Cre drivers, and conditional alleles from the same locus. Disclosed herein is an improvement of the Red-recombination method, where Red recombinases are expressed from a very-low copy plasmid pKD46 (Datsenko, K. A., et al. 2000). Secondly, disclosed is a series of modules to streamline the construction procedure. Together, these components generate a flexible new protocol for targeting vector construction that incorporates the use of both Red-recombination and Gateway recombination (Hartley, J. L., et al. 2000), with different self-excision neo cassettes, and many small yet important technical details. To illustrate the efficacy of this modular cloning protocol, disclosed are examples of systematic generation of loss-of-function mouse lines for members of the cadherin gene family.

ii. Experimental Design

A knockout mouse is typically produced in two steps. First, principally in ES cells derived from agouti brown mice (strain 129Sv), designed modifications engineered in genomic DNA of a targeting vector are transferred into the endogenous locus by homologous recombination (FIG. 6). ES cell clones containing the modified DNA are enriched by positive and negative selection (Mansour, S. L., et al. 1988), and identified by Southern blot analysis. Second, targeted ES cells are injected into blastocysts derived from black mice (C57BL/6J) to generate chimeric mice. When targeted ES cells contribute to formation of the germ line of chimeric mice, progeny with the desired mutations are obtained.

A foundation for an efficient targeting vector design is the ability to use both positive and negative selection (Mansour, S. L., et al. 1988; Capecchi, M. R., et al. 1989a; Capecchi, M. R., et al. 1989b). Although there is no single design that fits all needs, there are some general principles that can help design a good targeting strategy and avoid mistakes. To design an efficient targeting strategy, the sequences of both the mouse and human genomes and any functional studies of the gene of interest should be incorporated into the planning. Many genes have complex genomic structures, with multiple introns and exons spanning hundreds of kilobases. However, gene targeting, in its current most-utilized form, can only efficiently delete up to about 15 kb in ES cells. Therefore, prior knowledge about the genomic organization of a gene is often useful to decide which part of the gene to modify. The known genomic sequence can also be used to position the homology arms so as to reduce the repetitive DNA sequences contained within the targeting vector. The presence of excessive repetitive DNA can significantly reduce the targeting frequency.

In the simple loss-of-function approach (FIG. 6A), a reporter gene, e.g., green fluorescent protein (GFP) or β-galactosidase, is often used to replace a part or all of the coding sequence of a gene. By placing the reporter gene in frame with the endogenous start codon AUG, the expression pattern of the endogenous gene can be easily followed in vivo. For most genes, replacing the coding sequence a few amino acids after the start codon AUG with a reporter cassette ensures a null allele and recapitulates the endogenous gene expression pattern. But for more complex genes with multiple promoters and/or alternative splicing, a reporter with a strong transcription stop might be needed to ensure a true null allele. An alternative strategy to obtain a loss-of-function allele for such complicated genes is to replace their most important domains with a reporter.

Cre recombinase, as a reporter, has become increasingly popular for many investigators since they can be used for lineage analysis, conditional mutagenesis, and conditional cell ablation (Wu, S., et al. 2006). Previously, these so-called Cre drivers were mostly created through pronuclear injection-based transgenesis (Branda, C. S., et al. 2004). Recently, growing numbers of Cre drivers are created through gene targeting as a knockin/null allele, or as an internal ribosomal entry site (IRES) version without disrupting the endogenous gene function. In the knockin design, Cre gene is used to replace in frame the endogenous gene coding sequence, concurrently generating a null allele. In the IRES version, Cre gene is inserted after the endogenous gene coding sequence, and is transcribed contiguously with the endogenous transcript. Since the IRES sequence allows translation initiation in the middle of the mRNA, the IRES-Cre created through gene targeting, like the knockin Cre allele, faithfully recapitulates the endogenous gene expression. Due to its usefulness, several modifications of Cre have been generated. These include GFP-Cre fusion protein, CreER, and CreERt2 (Branda, C. S., et al. 2004; Harfe, B. D., et al. 2004). However, a few things should be considered when designing a Cre allele. First, the best position to insert an IRES-Cre is probably right after the stop codon (this is also true for other IRES-reporters); the cloning for this can again be readily realized by recombineering in bacteria. Generally, a knockin Cre driver has stronger expression than the IRES-Cre for the same locus. For many genes, Cre expression from either knockin Cre or IRES-Cre is sufficient to effect efficient recombination, resulting in the same expression pattern and lineage pattern when analyzed with the Rosa26 reporters (S. W., Y. W. and M. R. C., unpublished). Second, CreER or CreERt2 is generally not 100% efficient in terms of induction, and can be leaky in certain situations.

Figure 6A:
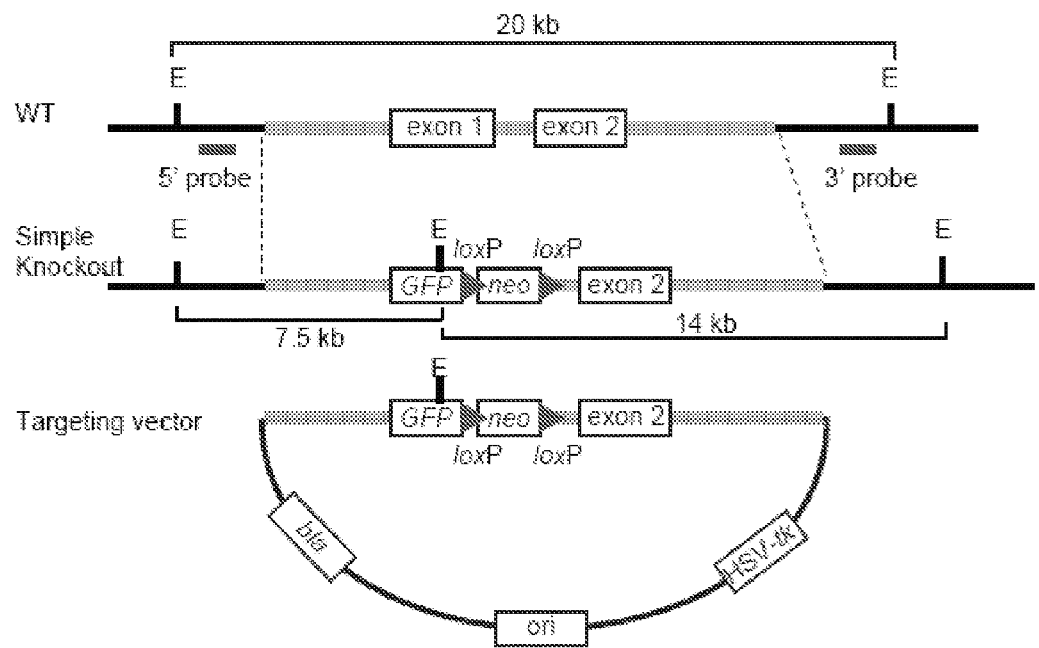
FIG. 6A shows schematic showing general design of a loss-of-function allele.
Figure 6B:
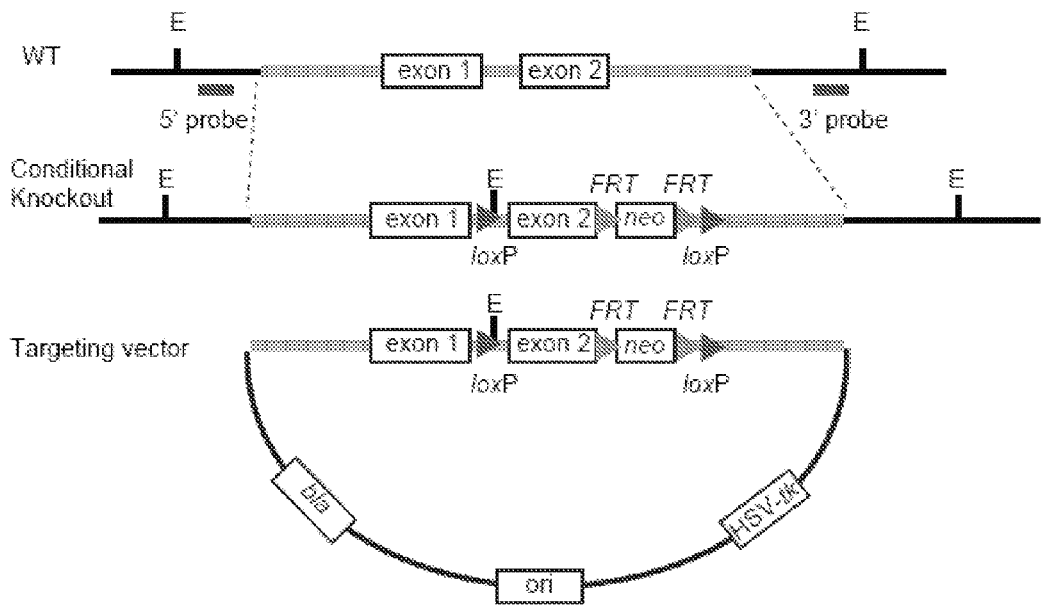
FIG. 6B shows schematic showing general design of a conditional knockout allele. A Southern blotting strategy for ES cell screening can be designed before construction of targeting vector. A good Southern strategy can easily distinguish between correctly targeted allele and random integrations. Generally, a downshifted band for the targeted allele is easier to identify than an upshifted band, as the latter could often be hidden in the noise from a suboptimal Southern blot. The principle of Southern blot is illustrated by a simplified example in panel (a), where a restriction enzyme (E) is used for digestion of DNA isolated from ES cells, for 5', 3' and internal neo probes. For 5' flanking probe, a 7.5 kb band (downshift) is expected for the targeted allele, compared to the 20 kb wt band (Size limit is ~25-30 kb for efficient gel separation and transfer.). For 3' flanking probe, a 14 kb band (downshift) is expected for the targeted allele, compared to the 20 kb wt band. For the internal neo probe, a 14 kb band is expected for the targeted allele, while random integrations can show variations.

Since a significant portion of the ~25,000 mouse genes are essential for survival, loss-of-function alleles often results in embryonic or postembryonic lethality, precluding analysis of that gene's function at stages past lethality. A conditional allele overcomes this limitation by flanking the gene of interest with loxP sites (FIG. 6B). In this way, the gene of interest is only disrupted when Cre recombinase is provided. Since many Cre drivers, each with specific expression in different tissues and developmental stages, have been generated (Nagy, A., et al. 2000), the loxP-flanked gene can be excised in multiple tissues and developmental periods.

In addition to the loss-of-function and conditional alleles, researchers are also using gene targeting to generate precise point mutations, gain-of-function alleles, and other alterations to recapitulate human genetic diseases.

To design an efficient targeting vector for the above purposes, a total of 8-15 kb homology to the target locus is normally used, with each homology arm being greater than 1 kb (Deng, C., et al. 1992). If both homology arms contain an excess of repetitive DNA sequences, then the targeting frequency will be low, and longer arms or a shift in the position of the targeting vector can be required to obtain a successful targeting. Most ES cell lines currently used for gene targeting are derived from strain 129Sv. The finished mouse genome sequence was performed on C57BL/6J DNA, although other strains are being sequenced. As these two strains have sequence variations from gene to gene that can affect gene targeting efficiency, the use of isogenic DNA for targeting vector construction is often very beneficial (Deng, C., et al. 1992; Adams, D. J., et al. 2005; to Riele, H., et al. 1992). However, in a 129Sv and C57BL/6J hybrid ES cell line (e.g., G4), genomic DNA from either 129Sv or C57BL/6J can be used to generate homology arms for the targeting vectors (George, S. H., et al. 2007).

After introduction of a targeting vector with only positive selection (neo) into ES cells, on average ~1 in 1,000 G418 resistant clones are products of a homologous recombination event, while the others are random integration events. To enrich for targeting events, inclusion of a negative selection cassette adjacent to one end or two ends of the homology arms on the targeting vector can be very useful. During homologous recombination, the negative selection cassette is lost. If random integration occurs, the negative selection cassette is incorporated into the genome. By selecting against cells containing the negative selection cassette, cells with homologous recombination events are enriched. The most widely used negative selection cassette in ES cells is the herpes simplex virus thymidine kinase gene (HSV-tk)(Mansour, S. L., et al. 1988).

Despite the enrichment many of the selected ES clones still contains nonhomologous recombination products. To identify clones that result from homologous recombination, Southern blot analysis is usually used and a strategy should be considered during the designing phase of targeting vector construction. Not all restriction enzymes are equally efficient in digesting genomic DNA from ES cells. Some good sites that have been tested in our lab include Acc65I, BamHI, BglI, BglII, BsrGI, ClaI, EcoRI, EcoRV, HindIII, Asp718, NcoI, PstI, RsrII, SpeI, SphI, ScaI (Roche), SstI and XbaI. Template used for Southern probe can be 200 bp to 2,000 bp, but should not contain repetitive sequences, as they give rise to high background signals. Ideally, an alternate Southern screening strategy should also be designed. Probes that will be used for Southern transfer analysis should be tested prior to starting construction of the targeting vector.

iii. Materials

Plasmids: pAP-CAN, pECFPpA-ACN, pEGFPpA-CAN, pEYFPpA-CAN, pKD3, pKD46, pnlacZ-CAN, pStart-C2, pStart-K, pStart-T2, pWS-TK2, pWS-TK3, pWS-TK6.

Agarose, GenePure ME (ISC BioExpress, cat. no. E-3121-500), Ampicillin (American Pharmaceutical Partners, Inc.), Bromophenol Blue (Sigma, cat. no. B7021), BSA (Sigma, cat. no. A-3912), $CaCl_2$ (Sigma, cat. no. C-3881), Chloramphenicol (Sigma, cat. no. C-0378), Chloroform (Fisher, cat. no. C298-500), DH5α (Invitrogen), DMSO (Sigma, cat. no. D-8779), dNTP mix (Fermentas, cat. no. R0192), EDTA (Sigma, cat. no. E5134-1KG), Formamide (Fisher, cat. no. BP227-500), Glycerol (Fisher, cat. no. BP229-4), Herring sperm DNA(Sigma, cat. no. D-3159), Kanamycin (Sigma, cat. no. K1377-25G), KCl (Fisher, cat. no. BP366-500), L-Arabinose (Difco, cat. no. 0159-15), $MnCl_2$ (Sigma, cat. no. M-3634), $Na_2HPO_4$ (Fisher, cat. no. BP393-3), NaCl (Fisher, cat. no. S640-10), NaH$_2$PO$_4$ (Fisher, cat. no. BP329-1), NaOH (Fisher, cat. no. BP359-500), Phenol (Sigma, cat. no. P-4557), Pipes (Sigma, P1851-500G), Proteinase K (Invitrogen, cat. no. 25530-031), QIAprep Spin Miniprep Kit (Qiagen, cat. No. 27106), Random primer labeling kit (Stratagene, cat. no. 300385), Restriction enzymes (NEB), SDS (Roche, cat. no. 11667262001), Shrimp alkaline phosphatase (Roche, cat. no. 1758250), Spermidine 3-HCl (Sigma, cat. no. S-2501), T4 DNA ligase (Fermentas, cat. no. EL0011), Taq DNA polymerase (Fermentas, cat. no. EL0402), TOPO-TA cloning kit (Invitrogen, cat. no. 45-0640), Tris base (Roche, cat. no. 11814273001), Tris HCl (Roche, cat. no. 10812846001), Trisodium citrate (Sigma, cat. no. S4641-1KG), Xylene Cyanol (Kodak, cat. no. T1579), Centrifuge (J2-21M, Beckman), Centrifuge (J-6M, Beckman), Electroporation device (BIO-RAD, Gene Pulser Xcell™), G50 columns (Amersham, ProbeQuant G-50 micro columns), Gel documentation system (Alpha Innotech), GeneAmp PCR system 9700 (AppliedBiosystems), Glass capillary (Kimble, cat. no. KIMAX-51), Hybond-N+ nylon membrane (Amersham), Hybridization oven (Techne, cat. no. Hybridiser HB-1D), Refrigerated benchtop centrifuge (5417R, Eppendorf), UV crosslinker (UV Stratalinker 1800, Stratagene), UV tranilluminator for agarose gel cutting, UV-Visible spectrophotometer (CARY 50 Bio, Varian Analytical Instruments).

20×SSC: 300 mM trisodium citrate, 3 M NaCl; adjust pH to 7.0 with a few drops of 10 M NaOH. SOB medium: For 1 liter, Bacto tryptone 20 g, Bacto yeast extract 5 g, NaCl 0.5 g, 1 M KCl 2.5 ml. Autoclave and cool to room temperature. Just before use, add 10 ml of sterile 1 M MgCl$_2$. SOC medium: add 2 ml of sterile 1 M glucose to 100 ml of SOB medium. Sodium Phosphate Buffer 1 M, pH6.5: mix 1 M Na$_2$HPO$_4$ and 1 M NaH$_2$PO$_4$ to obtain pH6.5.

iv. Procedures a. Overview of Steps

Figure 7A:
FIG. 7A shows although it is possible to use the commercially available high-copy Gateway plasmid (e.g., pENTR1a, Invitrogen) to subclone a genomic fragment by recombineering, it is often difficult to grow high-copy plasmid with some mammalian genomic DNA in bacteria. One simple solution is to use low-copy plasmids such as those with p15A origin of replication. Therefore, disclosed is a series of Gateway-compatible, low-copy vectors from the plasmids pACYC177 and pACYC184 (New England Biolabs). Panel (a) shows three of these vectors, pStart-K, pStart-C2, and pStart-T2, which can all be used to pull out a genomic fragment from an existing plasmid or BAC clone.

With the disclosed targeting vector construction protocol, the first step was to subclone a genomic fragment of the chosen gene from a BAC clone that can be used to generate the homology arms. To facilitate this and subsequent steps, a series of vectors were created: pStart-C2 (Chloramphenicol resistant, Cam$^r$), pStart-K (Kanamycin resistant, Kan$^r$), pStart-T2 (Tetracycline resistant, Tet$^r$) and others (FIG. 7). The different resistance genes in these Gateway-compatible, low-copy-number replicating plasmids provide choices for subcloning DNA from different sources.

To capture a fragment from the chosen BAC clone (usually Cam$^r$) using the pStart-K vector, two oligonucleotides of ~75 nt, including 50 nt homology to the 5' or 3' end points of the BAC region of interest (FIG. 6C), were used to amplify pStart-K to obtain a linear PCR product, which was in turn used to recombine out the genomic region of interest from the BAC. All subsequent modifications of the target locus were performed on this plasmid, thereby avoiding difficult manipulation of intact BAC clones (Chan, W., et al. 2007; Valenzuela, D. M., et al. 2003).

To insert a neo cassette into the BAC subcloned fragment, again two oligos with homology to the insertion site 5' and 3' ends were used to PCR amplify a different resistance gene (e.g., cat). The desired deletion and two AscI (rare cutter) sites were introduced into the genomic DNA captured by pStart-K (FIG. 6D) through the use of Red-mediated recombination. Next, through a standard restriction enzyme-based cloning, a reporter/neo cassettes can be readily inserted into the AscI sites in the genomic DNA of pStart-K. A series of convenient reporter/neo cassettes were constructed that are all flanked by AscI sites (FIG. 6E). Because the presence of neo can affect neighboring gene expression, most current protocols use a loxP-flanked neo cassette for selection in ES cells that can subsequently be removed by crossing founders to a Cre deleter mouse (Tang, S. H., et al. 2002). To shorten this time-consuming breeding process (>5 months), a very effective neo cassette (designated ACN) using Cre-loxP system was developed for automatic self-excision of the neo gene in the male germ line (Bunting, M., et al. 1999). This useful tool was used to build a series of reporter/neo self-excision cassettes (FIG. 6E).

In the final step, one or two tk cassettes were add to the targeting vector for negative selection in ES cells (Mansour, S. L., et al. 1988). A series of Gateway-compatible HSV-tk vectors were constructed (FIG. 6F and FIG. 7), with either high-copy or low-copy origins of replication. For stable genomic DNA, high-copy TK vectors can be used to facilitate DNA preparation, while low-copy TK vectors can be used to reduce potential problems with growth of vectors carrying unstable genomic DNA. Although including two tk genes, one at each end of the two homology arms, on a targeting vector increases enrichment of homologous recombinants (Capecchi, M. R., et al. 1989b), this configuration can cause instability during bacterial culture for some genomic DNA (FIG. 6F and FIG. 6). All TK vectors contain several engineered restriction sites for linearization of the targeting vector, prior to ES cell electroporation (Thomas, K. R., et al. 1986). Through a simple Gateway recombination reaction, the modified genomic DNA with its reporter/neo cassette was transferred from pStart-K to a TK-containing vector.

Figure 8:
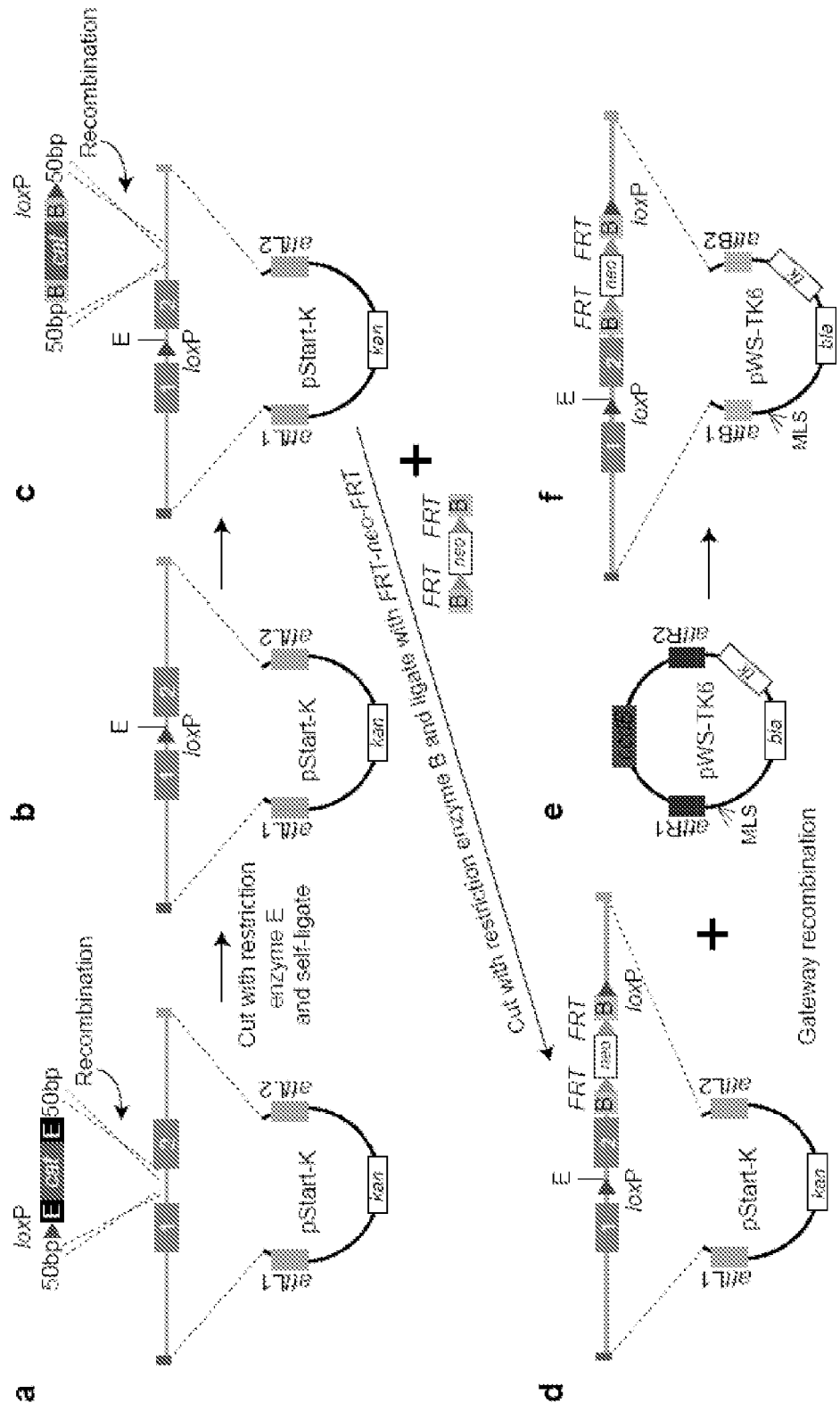
FIG. 8 shows schematic for the construction of conditional targeting vectors. Most common conditional vectors use a design that includes two loxP sites to flank the region of interest. When choosing positions for inserting loxP sites and the neo cassette, care should be taken not to disrupt the endogenous transcription, translation, and splicing. If possible, the first loxP site should be placed within an intron. If the first loxP has to be inserted before the start codon, it can be inserted about 10 nt before the ATG (insertion to further upstream might affect transcription), minimizing the potential effect on the Kozak sequence and translation. Since loxP sequence in one orientation has two ATG's that could potentially be used as start codons, it is better to use the other orientation that has no ATG in the reading frame. When possible, the second loxP site and neo are also inserted within an intron. Another possible position for the second loxP is right after the stop codon. Conditional alleles can also be designed to offer more creative uses in many unique ways. For some conditional alleles, a reporter (e.g. EGFP) can be engineered that is not expressed before Cre-mediated recombination, but expressed from the endogenous locus after Cre-mediated recombination (Moon, A. M., et al. 2000). Conditional rescue alleles can be equally informative if designed well (Ventura, A., et al. 2007).

The same cloning strategy described above for generating null alleles can be used for constructing conditional allele vectors, with only minor modifications (FIG. 8).

b. Preparation of Red-Competent Bacteria/BAC•TIMING 1 Day

1. Bacteria containing the BAC clone of interest were inoculated into 5 ml of SOB, 20 µg/ml Chloramphenicol, and grown at 37° C. for 3-5 h or overnight.

2. The cells were centrifuged at 2000 g in J-6M (Beckman) for 5 min at 4° C.

3. The supernatant was decanted. The cells were resuspend (by pipetting up and down) in 1 ml of 10% ice cold glycerol, transferred into a 1.7 ml Eppendorf tube, and centrifuged at 8000 g and 4° C. in a bench-top centrifuge for 10 s.

4. The supernatant was decanted. The cells were resuspended in 1 ml of 10% ice cold glycerol, and centrifuged at 8000 g and 4° C. in bench-top centrifuge for 10 s.

5. The supernatant was discarded and the cells resuspended in 100 µl of 10% cold glycerol, and divided into two 50-µl aliquots.

■PAUSE POINT One aliquot was stored directly in −80° C. as a backup, and the other was kept on ice for immediate use.

6. 10 ng of pKD46 was transformed to one tube of the above freshly made electrocompetent cells. The electroporation conditions were 0.1 cm cuvette, 1.8 kV, 25 µF capacitance, and 200 ohms (BIO-RAD, Gene Pulser Xcell™).

7. Immediately after the pulse (within seconds), 1 ml of SOC medium was added and the cells transferred into an Eppendorf tube. Without incubation, 100 µl and 900 µl of the cells were directly spread on two LB-agar plates (100 µg/ml Ampicillin; 20 µg/ml Chloramphenicol).

8. The plates were incubated at 30-32° C. for 24-30 h (pKD46 is temperature sensitive, so they were not grown at 37° C.).

9. Single/several colonies were inoculated from the above plate into a 15 ml tube containing 5 ml of SOB medium (100

μg/ml Ampicillin; 20 μg/ml Chloramphenicol), and incubated at 30-32° C. overnight with vigorous shaking.

10. After determining the $OD_{600}$, an appropriate amount was inoculated into a 250 ml flask containing 50 ml of SOB medium (100 μg/ml Ampicillin; 20 μg/ml Chloramphenicol) to reach a final $OD_{600}$ of ~0.1-0.2.

11. To induce the λ red recombination systems, L-arabinose was added to a final concentration of 0.1%, and the bacteria incubated at 30-32° C. with shaking. Doubling time is about 1.5-2 h. (Not 37° C.).

12. When $OD_{600}$ was 0.4-0.8, the culture was transfer into a 50 ml conical tube, and left on ice for 10 min with occasional swirling.

13. The cells were centrifuged for 15 min at 2,000 g and 4° C.

14. The supernatant was decanted and the cells were resuspended gently in 50 ml of ice cold 10% glycerol, and then centrifuged at 2,000 g and 4° C. for 15 min. (10% ice cold glycerol was prepared ahead of time in milliQ water without autoclave or filtration).

15. The supernatant was decanted and the cells were resuspended gently in 25 ml of ice cold 10% glycerol, and then centrifuged at 2000 g and 4° C. for 15 min.

16. The supernatant was decanted and the cells were resuspended gently in 25 ml ice cold 10% glycerol, and centrifuge at 2000 g for 15 min at 4° C.

17. Finally, the supernatant was decanted and any remaining liquid was remove by pipetting. 100 μl of fresh ice cold 10% glycerol was added to resuspend the pellet. The cells were then divided into 50-100 μl aliquots. One tube was kept one ice for immediate use. The remaining tubes were frozen directly in −80° C. (no dry ice or liquid nitrogen is required.).

c. Subcloning of Genomic Fragment into pStart-K•TIMING 2 Days

18. Two oligonucleotides were designed for PCR amplification of the pStart-K vector. For example, in the case of the Pcdh1 targeting vector construction, the upstream oligo sequence was:

(SEQ ID NO: 120)
CCCTATCTCCCAGAACCGGCTATTAGCCTCTGCAGGCTTCCATGCACCTG cgactgaattggttcctttaaagc;

and the downstream oligo sequence was:

(SEQ ID NO: 121)
GCGCTGTCTGTATGTCCGGTAGCAAGCACCAGACTTTAAGATATATGTCT gccgcactcgagatatctagaccca.

The uppercase sequence within each oligo matches 50 bp at the two junctions of the desired BAC fragment. The lowercase oligo sequence matches the backbone of pStart-K.

The use of a low-copy replicating plasmid as the carrier of the BAC subcloned fragment has many advantages. First, in bacteria some mammalian DNA sequences are difficult to maintain in high-copy replicating plasmids, whereas in low-copy replicating plasmids many of these difficult DNA's are tolerated. Second, modifications of high-copy plasmids (containing colE1, pUC, or similar origins of DNA replication) by Red-mediated recombination almost always generates concatimers (Liu, P., et al. 2003; Yu, D., et al. 2000), containing both the original and modified plasmids that are very difficult to separate. Again, use of a low-copy plasmid (containing an original DNA replication such as p15A) eliminates such problems.

19. The two oligos were then used to amplify the plasmid template pStart-K by PCR (5×25 μl reactions. pStart-K, 50 ng; 10× buffer, 12.5 μl; 25 mM $MgCl_2$, 10 μl; primers, 2.5 μl each at 10 μM; 10 mM dNTP, 2.5 μl; Taq, 1.25 μl; $H_2O$ was added to a total volume of 125 μl). PCR conditions were: 94° C. 2 min; 30 cycles of 94° C. 30 s, 59° C. 30 s, and 72° C. 90 s; 72° C. 7 min.

For PCR involving long oligos, it is better to use regular Taq polymerase, since proof-reading polymerases (e.g. Pfu) tend to be much less efficient.

20. The amplified PCR products were combined, purified with a single Qiagen column, and digested with DpnI for 1-2 h. The reaction was re-purified on a Qiagen column, and eluted with 40 μl $H_2O$. DNA concentration was normally ~200 ng/μl or higher.

21. The purified PCR product (5-10 μl) was electroporate into 50 μl of the above Red-competent Bacteria containing the desired BAC. The parameters for electroporation were: 0.1 cm cuvette, 1.8 kV, 25 μF capacitance, and 200 ohms.

22. Immediately after the pulse, the cells were transferred to 1 ml of SOC medium, incubated at 37° C. for 1 h, and spread onto LB-agar plates (50 μg/ml Kanamycin).

23. Eight small $Kan^r$ (NOT BIG) colonies were picked and grown in 5 ml of SOB medium at 37° C. overnight for preparation of DNA minipreps.

Large colonies are usually self-recombined pStart-K. Qiagen spin columns can be used for DNA minipreps, as plasmid DNA prepared without columns can often have contaminations of BAC DNA.

24. These DNA preps were analyzed by restriction enzyme mapping.

25. The resulting positive clones were further confirmed by sequencing and designated pStart-KPcdh1. Universal primers for the sequencing reactions were WS275 and WS276 (present on the backbone of pStart-K; Table 6.

After the homology arms were cloned into a pStart vector, the next step was to introduce the desired changes to the region of interest, such as deletion, insertion, point mutation, and so on, which again was done by λ phage Red-mediated recombination. For this step, Red-competent DH5α/pKD46 cells were used.

TABLE 6

Oligonucleotides used in this study

| Gene | Oligonucleotides | SEQ ID |
|---|---|---|
| Pcdhb1 | | |
| Pcdhb1_out_1 | AAACATATCACTGAATTATCTTATTGTTGTGACTTAAAGGCTAA ATAAGTcgactgaattggttcctttaaagc | SEQ ID NO: 124 |
| Pcdhb1_out_2 | CAATTGTCCAATTAAAAGACATAGGCTAACAGACT GGATCTATAAACAGGtcgagatatctagaccagctttc | SEQ ID NO: 125 |

TABLE 6-continued

Oligonucleotides used in this study

| Gene | Oligonucleotides | SEQ ID |
|---|---|---|
| Pcdhb1_in_1 | GAGCTGGCGGCAGCTGAGGGGAGTGCACTGGTGAGGAATCATG GGAGCTTCTAGAGggcgcgcctacctgtgacg | SEQ ID NO: 126 |
| Pcdhb1_in_2 | GATGGACTATAACATCCTGTTTCTCTTCTCATGAGAGATGTTAGC CAGAAggcgcgccttacgccccg | SEQ ID NO: 127 |
| Pcdhb22 | | |
| Pcdhb22_out_1 | TTTTAGTAAGGATGTGTTGATGCAGTATTGGATGATTTGGAGAA AATATTcgactgaattggttcctttaaagc | SEQ ID NO: 128 |
| Pcdhb22_out_2 | ACTTGTACTCATTTCTGGAAGGTCCTGTCATGGGAAGAGAGTGT GCAAAGtcgagatatctagacccagctttc | SEQ ID NO: 129 |
| Pcdhb22_in_1 | GTCTGGATACCCTTGTACCCTGGGTGCAGAAGCAAAGATGAAGA TTGGAAGGCGCGCCagcattacacgtcttgagcgattgt | SEQ ID NO: 130 |
| Pcdhb22_in_2 | GTTTTGAGTAGAAACGCAGTGCCAACAGGGCTATTCTCTATGAT TTTCACGGCGCGCCcacttaacggctgacatgggaattag | SEQ ID NO: 131 |
| Celsr2 | | |
| Celsr2_out_1 | TTAATCCAGCGGATCACAACTGGACAAACCGCTAAGAATAAAT AACGAGTcgactgaattggttcctttaaagc | SEQ ID NO: 132 |
| Celsr2_out_2 | CCGCTAGTATTTAAGATGGAGATAACCAATTTATGTAGGTCAAA AGTTGCtcgagatatctagacccagctttc | SEQ ID NO: 133 |
| Celsr2_in_1 | CGCCGCGGCTGTTGACCCGGCTGGCCGGGAACAGGGAGAGATG CGGAGCCggcgcgcctacctgtgacg | SEQ ID NO: 134 |
| Celsr2_out_2 | CTCCTGAACTTTGGGGTTGCCTTGGTGACTGACTCTAAGGGTCA GGGCTGggcgogccttacgccccg | SEQ ID NO: 135 |
| Celsr3 | | |
| Celsr3_out_1 | GTCGCTCCCAATGCACTTCCTGGAAAGAGAAAAATGAGGAGCCT AAAGGAcgactgaattggttcctttaaagcC | SEQ ID NO: 136 |
| Celsr3_out_2 | GTTTTGGCCACAGTACCCTGTACCCCGGGGGGCCTTGGGTGAGT ATGTGGgccgcactcgagatatctagaccca | SEQ ID NO: 137 |
| Celsr3_in_1 | CCCGGGCGGGGGCGGCGGAGGCCGTGACGGGAGGCGGGGGTG ATGGCGAGGCGCGCCagcattacacgtcttgagcgattgt | SEQ ID NO: 138 |
| Celsr3_in_2 | AGCTCTGTCTCACAGAAGTCTCCCGTGAAGCCAGGAGGGCAGCG GCAGCGACTAGTGGCGCGCCcacttaacggctgacatgggaatta | SEQ ID NO: 139 |
| Fat2 | | |
| Fat2_out_1 | GTTGTAAGGTCCCCCGGACTCATTCAGGCATGGCTCTCTGAACT ATATACcgactgaattggttcctttaaagc | SEQ ID NO: 140 |
| Fat2_out_2 | CAGGTGAGGCCCAGAAAGCTGGAGGAACAGGGATATATAGATC TACAAAGtcgagatatctagacccagctttc | SEQ ID NO: 141 |
| Fat2_in_1 | ACCTGAACCCTTTCCCTCTTCTTACCCAGGAGCTTTCACCATGAC GCTTGggcgcgcctacctgtgacg | SEQ ID NO: 142 |
| Fat2_in_2 | CCTGAGTTCAAATCTCAGCAACCACATGGTGGCTCACAACCACC CATAATggcgcgccttacgccccg | SEQ ID NO: 143 |
| Fat3 | | |
| Fat3_out_1 | ACTGTGAAGTATTCATCTTCTGGTAGTGAGTTTAAGTATGTGAAT TTAACcgactgaattggttcctttaaagc | SEQ ID NO: 144 |
| Fat3_out_2 | TATTTTAGAATAAAGATCAAATTTGGCAAATATTTCATTTCCAA AATCTAtcgagatatctagacccagctttc | SEQ ID NO: 145 |
| Fat3_in_1 | ACGGACATGTGATATGATGAGTGTGACTATGGGACACTGTATGG GCACAAGGATCCggcgcgcctacatgtgacg | SEQ ID NO: 146 |
| Fat3_in_2 | AGCCATTCTAAGACATGTCATTTCTACTCAAATGGAGACTTCCC CATCTGGAATTCggcgcgccttacgccccg | SEQ ID NO: 147 |
| Fat4 | | |
| Fat4_out_1 | CACCAAATCGTAATTAGTTATGAAAATGGTTGTCAAGTCAGAGC TTTAACcgactgaattggttcctttaaagc | SEQ ID NO: 148 |
| Fat4_out_2 | GGCCCTCTTATGTTCCCTTGAAACTCTCCAAGGGCTTCCTGATGA AGAgccgcactcgagatatctagaccca | SEQ ID NO: 149 |
| Fat4_in_1 | TCTTCTTCTCCAGGTTCCTGGAAACTAGGACCATGAACTTGGCC GCAAACGGATCCCGGCGCGCCagcattacacgtcttgagcgattg t | SEQ ID NO: 150 |
| Fat4_in_2 | AGAAAAGAATTTTTAAGCCTATTGAGAACAAATAAAAGAATAC AAGCTCTagaGGCGCGCCcacttaacggctgacatgggaattag | SEQ ID NO: 151 |

TABLE 6-continued

Oligonucleotides used in this study

| Gene | Oligonucleotides | SEQ ID |
|---|---|---|
| Dscam (5' allele) | | |
| Dscam_5'out_1 | CACAACCCACAGAAGGTGATAGACCCATAATGATAGAGACTGG TCAAGACcgactgaattggttccttttaaagc | SEQ ID NO: 152 |
| Dscam_5'out_2 | CCACGGCAGAACACCATGGGGATGGAATCAACGCAAGCTTTCA GAGAACAgccgcactcgagatatctagaccca | SEQ ID NO: 153 |
| Dscam_5'in_1 | GCTCGCTGGCTCGCTGGCTCGCGGGAGGCCGGGCAGCAGCAGG GGCATGTGGCGCGCCagcattacacgtcttgagcgattgt | SEQ ID NO: 154 |
| Dscam_5'in_2 | CCATCCCCGGGCCCCTTCCCAGACAGGAATCAGCACAGACCGC AAGGCTCGGCGCGCCcacttaacggctgacatgggaattag | SEQ ID NO: 155 |
| Dscam_3'out_1 | CCTTCTCCTAACTAGTCAGCATACAGATGTAATTACTGCCTCCCT GATCCcgactgaattggttccttttaaagc | SEQ ID NO: 156 |
| Dscam_3'out_2 | GCACCCTTGATGACTGGGGACAAGAGGATAGCATCCTCCTGATG CCTACAgccgcactcgagatatctagaccca | SEQ ID NO: 157 |
| Dscam_3'in_1 | CGGGGCCATTTGAAAGGAAACAATCCCTACGCAAAATCTTACAC CTTGGTAGGGCGCGCCagcattacacgtcttgagcgattgt | SEQ ID NO: 158 |
| Dscam_3'in_2 | CTCGTTTAAATTGTATTTACAACCGCTGTCCATCAGGTGCCATG TGTTAGGCGCGCCcacttaacggctgacatgggaattag | SEQ ID NO: 159 |
| DscamL1 (5' allele) | | |
| Dscam11_5'out_1 | TTGCTGTATGGCTTTGTTGTAAAAAGGATCAGCTGCAGAAACAA CCTAAGcgactgaattggttccttttaaagc | SEQ ID NO: 160 |
| Dscam11_5'out_2 | ATGAGGGCAGCCTGGTCAGAGAGCTCTGCCCAAGGACTCTACC CGTGTGgccgcactcgagatatctagaccca | SEQ ID NO: 161 |
| Dscam11_5'in_1 | CCCACATGCCCCAGGACCCCCCAGCATCCGGGCAATGAGGAAC ATCACGGGGCGCGCCagcattacacgtcttgagcgattgt | SEQ ID NO: 162 |
| Dscam11_5_'in_2 | ACCTGTGCCAGCAGCCTAGGAGGCAGGCAGGCTGCAGGCGGGG AGGGACCTGGCGCGCCcacttaacggctgacatgggaattag | SEQ ID NO: 163 |
| DscamL1 (3' allele) | | |
| Dscam11_3'out_1 | GCAATTTGGAAGTACACTTTTAGCCCCACTGCAGCAGACTACTG AACGAAcgactgaattggttccttttaaagc | SEQ ID NO: 164 |
| Dscam11_3'out_2 | CACTGGTTTTCCCCCTTAGTAAGATGCACAAGGTCTAGAAATTC AGATAGgccgcactcgagatatctagaccca | SEQ ID NO: 165 |
| Dscam11_3'in_1 | TTCTCAGAAACAGGGGGCTGGCGCGCTATTCCAAATCCTACACCC TGGTGGGGCGCGCCagcattacacgtcttgagcgattgt | SEQ ID NO: 166 |
| Dscam11_3'in_2 | GAGGCGCAGAGGTCCAGTGTGGAGCCCTTCTCCATTTGTCGGC CATCCTAGGCGCGCCcacttaacggctgacatgggaattag | SEQ ID NO: 167 |
| Dchs1 | | |
| Dchs1_5'out_1 | TGTCCTACCAAAGACGTGTTTCCAAGAGGCACTCCAGGGAGAGG CTGAGGcgactgaattggttccttttaaagc | SEQ ID NO: 168 |
| Dchs1_5'out_2 | CAGCAGTGTAATGAATACTTTCTGTAAAGATCAGACATATATGC TGGAATgccgcactcgagatatctagaccca | SEQ ID NO: 169 |
| Dchs1_5_'in_1 | GTCTGGTGTGGAGCTGGAGCTTCAGCTGGACTGGCCCTGCCATG CAGAAGGGGCGCGCCagcattacacgtcttgagcgattgt | SEQ ID NO: 170 |
| Dchs1_5Th_2 | CCTCTGTGACCCTCACACCCACTGCTGCTCACAGTGCTGTGGAC AGGGGCGCGCCcacttaacggctgacatgggaatta | SEQ ID NO: 171 |
| Dchs2 | | |
| Dchs2_5'out_1 | CATGTCATTAATGTTGGCTCAAGAAACTACCCAGTCTGCCTTCG GTAGGCcgactgaattggttccttttaaagc | SEQ ID NO: 172 |
| Dchs2_5'out_2 | GAAAACTTAAGACAAAACACACTGCCACCTCGCACCTAAGAC ATATTGAgccgcactcgagatatctagaccca | SEQ ID NO: 172 |
| Dchs2_5'in_1 | GCATTGACACACTGTCTTATTTTTCAGGCACCATATTCACTACTA ATTCTGGGCGCGCCagcattacacgtcttgagcgattgt | SEQ ID NO: 174 |
| Dchs2_5'in_2 | TGTCTGAGCTGAGAGATGGGCGAGCAGGcACGGAGTCAGCATC AGGTCTAGGCGCGCCcacttaacggctgacatgggaatta | SEQ ID NO: 175 |
| Cdh8 | | |
| Cdh8_out_1 | GTGCACATGCCCAGCTGAGCAACCTGATTCATTATAATACCACT GGCTCAcgactgaattggttccttttaaagc | SEQ ID NO: 176 |
| Cdh8_out_2 | GAGCATCATCTTGAGAGGCCTCTGCAGTAAGGGAGTCAGCAGAT AGAGAGgccgcactcgagatatctagaccca | SEQ ID NO: 177 |
| Cdh8_in_1 | AATTGTCTCATTTTCGCGCTGATTTGCTTAACTGGTGGGACCATG CCAGAAAGGCGCGCCagcattacacgtcttgagcgattgt | SEQ ID NO: 178 |
| Cdh8_in_2 | CATTTAAAGACCAGGAACAGGCCCTGAAATGGTAGTTTTAAAT GAAGCTTGGCGCGCCcacttaacggctgacatgggaatta | SEQ ID NO: 179 |

TABLE 6-continued

Oligonucleotides used in this study

| Gene | Oligonucleotides | SEQ ID |
|---|---|---|
| Cdh13 | | |
| Cdh13_out_1 | CAATGGCAGGCCAGCCAAGTCCAAGTCTCAAGAGGCCCTCTCTG CTTCAGcgactgaattggttcctttaaagc | SEQ ID NO: 180 |
| Cdh13_out_2 | GTTGCATGGGCATGGGGTATTGGCCCTGTGGGTAAGAGTGTTTG TTGTACgccgcactcgagatatctagaccca | SEQ ID NO: 181 |
| Cdh13_in_1 | GAATGCAAACGCCGCCAGGCGCTTCTTCTAGTCGGGCAAGATGC AGCCGAGGCGCGCCagcattacacgtcttgagcgattgt | SEQ ID NO: 182 |
| Cdh13_in_2 | CTGAATGCAGAAAGCTGGTGGGAGCGCGCTGACTGCGGCTCAC ATTCCCTGGCGCGCCcacttaacggctgacatgggaatta | SEQ ID NO: 183 |
| Cdh18 | | |
| Cdh18_out_1 | CACATTTTCTGGTAACATAGAGAAAGCTACTGTAGAAGACACCA GAATTTcgactgaattggttcctttaaagc | SEQ ID NO: 184 |
| Cdh18_out_2 | GAATGGAAAGATATGTTTACAGGGTGTGGAATTTTGGAATATG GTGGGAgccgcactcgagatatctagaccca | SEQ ID NO: 185 |
| Cdh18_in_1 | CAGGCCACGAAGACAAGAAGGACTGTGAACGGGAAGCGATCTT ACAATGAGGCGCGCCagcattacacgtcttgagcgattgt | SEQ ID NO: 186 |
| Cdh18_in_2 | CTCAAGAGAGAAAAACTAACAATCAATTCCAAAGAAATCAAAA CAAACTTGGCGCGCCcacttaacggctgacatgggaatta | SEQ ID NO: 187 |
| Cdh19 | | |
| Cdh19_out_1 | ATGAACATATCTGACGTTACTCATAGAACAACATGGCTTCAGAG TTTAGAcgactgaattggttcctttaaagc | SEQ ID NO: 188 |
| Cdh19_out_2 | TAGAATGAGGTGCAGTGAATTTGTATTTCTTAACTGAATTTAATT TTAAGgccgcactcgagatatctagaccca | SEQ ID NO: 189 |
| Cdh19_in_1 | CCTTTCTAGATAGAGCTGGATCCTAATACACACCAGAATGA ATTATTGGCGCGCCagcattacacgtcttgagcgattgt | SEQ ID NO: 190 |
| Cdh19_in_2 | CACTTCACATCTTTACAAATTCATCTATTGTAACTTTTTCAGAAA ACAAGTGGCGCGCCcacttaacggctgacatgggaatta | SEQ ID NO: 191 |
| Cdh20 | | |
| Cdk20_out_1 | ACCTGCCACAGACAGTCGAGAAGAGCCTGTACAAGGAGTGAAA CAGGTGGcgactgaattggttcctttaaagc | SEQ ID NO: 192 |
| Cdh20_out_2 | TCCAATGCCTGTTAGTTCTGAGTTCTTAAGATTCAAAGACATGA ACAATGgccgcactcgagatatctagaccca | SEQ ID NO: 193 |
| Cdh20_in_1 | CATTCTACTTGACTTCTGAAACTCCTGCAAGCCCATGTGGACTAC GGGTAGGCGCGCCagcattacacgtcttgagcgattgt | SEQ ID NO: 194 |
| Cdh20_in_2 | CATCTCAACACCAGAGACCCTGAGAATTTCTCTTTCTCCTGGGC ACATCTTGGCGCGCCcacttaacggctgacatgggaatta | SEQ ID NO: 195 |
| Cdh22 | | |
| Cdh22_out_1 | ATTCATCCCCTTGCTTCTTCCACTTGACACTGCAGGCTTATGTGT GTCCTcgactgaattggttcctttaaagc | SEQ ID NO: 196 |
| Cdh22_out_2 | GACAGGAAAGGAATGCTGATTCACAGTAAGAACCTACTGTGTG CTGTGAGgccgcactcgagatatctagaccca | SEQ ID NO: 197 |
| Cdh22_in_1 | CTCTGGTCCATGCTCAGGGGCTTGGCCAGCGCCATCAAGCATGA GGCCACGGCGCGCCagcattacacgtcttgagcgattgt | SEQ ID NO: 198 |
| Cdh22_in_2 | GAACCGGGACTACCAGTGGGTGTCCCCAGAGTCGGGGCTGGAC AGTGGGCGCGCCcacttaacggctgacatgggaatta | SEQ ID NO: 199 |
| Cdh24 | | |
| Cdh24_out_1 | AGTCTCCCTGCTGCTGCAATGCCCTCCATCTGCCCACACTGCTCA CAGGAcgactgaattggttcctttaaagc | SEQ ID NO: 200 |
| Cdh24_out_2 | GTCTGTCTCCTGCCCACATGTCCCTCCCTTCTCTTTGAGTCCCTG TGACTGgccgcactcgagatatctagaccca | SEQ ID NO: 201 |
| Cdh24_in_1 | CCTGGGGCCAGTGAACAAGAGCCCTGGCTGGATTACAAAACATGT GGGGCCGGCGCGCCagcattacacgtcttgagcgattgt | SEQ ID NO: 202 |
| Cdh24_in_2 | ACATCCAGGGATAGCTCTCTGTATGGTGCTCCTTAGGGCCCAGG GCTTCTCGGCGCGCCcacttaacggctgacatgggaatta | SEQ ID NO: 203 |
| Pcdh1 | | |
| Pcdh1_out_1 | CCCTATCTCCCAGAACCGGCTATTAGCCTCTGCAGGCTTCCATGC ACCTGcgactgaattggttcctttaaagc | SEQ ID NO: 204 |
| Pcdh1_out_2 | GCGCTGTCTGTATGTCCGGTAGCAAGCACCAGACTTTAAGATAT ATGTCTgccgcactcgagatatctagaccca | SEQ ID NO: 205 |
| Pcdh1_in_1 | GTCTTCTTGTAGTTCTCCTGATTCTGGAGCCTGCCAGGATGGGC CTCTGAGGCGCGCCagcattacacgtcttgagcgattgt | SEQ ID NO: 206 |
| Pcdh1_in_2 | CTCCCTCATGATCTAGTCGATCATGGCGGGTAAGACACACCTGC TCTATCAGGCGCGCCcacttaacggctgacatgggaatta | SEQ ID NO: 207 |

TABLE 6-continued

Oligonucleotides used in this study

| Gene | Oligonucleotides | SEQ ID |
|---|---|---|
| Pcdh7 | | |
| Pcdh7_out_1 | TACAGCCTATTGGCTAACTGTAAAACACAGACACAAGGCCAGTGTGATACcgactgaattggttcctttaaagc | SEQ ID NO: 208 |
| Pcdh7_out_2 | ATACTCTGTCTTCACCTTGCTTCTACGACACCTGCTGGAGCCTGCCCTTGgccgcactcgagatatctagaccca | SEQ ID NO: 209 |
| Pcdh7_in_1 (MluI) | GGTTAGAAGGAGCAGTAGCAGCAGCAGCAAGAGAAGATGCTGAGGATGCGACGCGTagcattacacgtcttgagcgattgt | SEQ ID NO: 210 |
| Pcdh7_in_2 (MluI) | CTGAGTGATCAGCCCTCTCTGGGGTATGTAAACACATCTGGGATCTATCTTACGCGTcacttaacggctgacatgggaatta | SEQ ID NO: 211 |
| Pcdh10 | | |
| Pcdh10_out_1 | AGACAGAGACCTCTAGAGGTACAGTAAGATTCATCTGAATCGCCAGCATGcgactgaattggttcctttaaagc | SEQ ID NO: 212 |
| Pcdh10_out_2 | ACGAGAAATAGATCCACTCATTTTACTGATAAAACTGGTGAAATACTCAGgccgcactcgagatatctagaccca | SEQ ID NO: 213 |
| Pcdh10_in_1 | GGCTGGCTGGCTACAGGGGAGCTGCTTCCTTTTCCTTTTGGAAATGATTGGGCGCGCCagcattacacgtcttgagcgattgt | SEQ ID NO: 214 |
| Pcdh10_in_2 | GCTAACACCTGAAAATACACAGTGCACCAGAAGAGATGCAGGGCCGGGCTAGGCGCGCCcacttaacggctgacatgggaattag | SEQ ID NO: 215 |
| Pcdh17 | | |
| Pcdh17_out_1 | ACCATAGGATTAACTCAGCAAAGACATGCAAACTAAACCTGTGAGGAATTcgactgaattggttcctttaaagc | SEQ ID NO: 216 |
| Pcdh17_out_2 | GTATTTGGCTACGCGTTTTATGCCAAGAAGATGCCACTGGATTAGTCTATgccgcactcgagatatctagaccca | SEQ ID NO: 217 |
| Pcdh17_in_1 | AGTCCGGCTGCTCCTGTTCCCACCCCACCGGTCTGGGATGTACCTTTCCAGGCGCGCCagcattacacgtcttgagcgattgt | SEQ ID NO: 218 |
| Pcdh17_in_2 | TGGAGTTAAGTGGAGGGGAGCCCCCGTCCCGGGCCACAATGGTCACATTGTGGCGCGCCcacttaacggctgacatgggaattag | SEQ ID NO: 219 |
| Pcdh18 | | |
| Pcdh18_out_1 | GCTATGAGGCTGTTTTCTGGAAATCCAGATGCTTAGCTCTTTGCTACTCAcgactgaattggttcctttaaagc | SEQ ID NO: 220 |
| Pcdh18_out_2 | TGTTGCTAGGGGCTGTAGAAAGAAATCAACACTTAGGAGTACTGAAGTCTgccgcactcgagatatctagaccca | SEQ ID NO: 221 |
| Pcdh18_in_1 | CTAACTCGCCCTGAGAAGGGAATCTAGCAACTGACCAATGCACCAAATGAGGCGCGCCagcattacacgtcttgagcgattgt | SEQ ID NO: 222 |
| Pcdh18_in_2 | GCCTCTGAGCATCAGCATCTGGCTTGACCAGGCCCTGTAGTGTCTGATCTTGGCGCGCCcacttaacggctgacatgggaattag | SEQ ID NO: 223 |
| Pcdh19 | | |
| Pcdh19_out_1 | CTAGACCTCACAAGTGGCTTTATGTAGTTCCTTAGGACTTCCAGCTGCTCcgactgaattggttcctttaaagc | SEQ ID NO: 224 |
| Pcdh19_out_2 | TCTTCCCAGATCTTCTAGAGCTGCTTACTATCCCATGGGACACTCTGGAGgccgcactcgagatatctagaccca | SEQ ID NO: 225 |
| Pcdh19_in_1 | TCGGAGGGGTGTGGAGAGGCGAGGCAAGGCAGAGCCCCGCGCAGCCATGGAACGCGTagcattacacgtcttgagcgattgt | SEQ ID NO: 226 |
| Pcdh19_in_2 | CATATCTTACTCACTCAAAACACAGAAGAAAAGAAGAAAAACTTGGCTCTACGCGTcacttaacggctgacatgggaattag | SEQ ID NO: 227 |
| Pcdh20 | | |
| Pcdh20_out_1 | ATTTGAATTTCACGTTCTTCTTTCTCACTTCTGGCAGAGGTGATAATGAGcgactgaattggttcctttaaagc | SEQ ID NO: 228 |
| Pcdh20_out_2 | GCACAGTTTAAAAATTATAGAATTGGTACAAAACAGTTTGATAGGCAGTCgccgcactcgagatatctagaccca | SEQ ID NO: 229 |
| Pcdh20_in_1 | CCACCCTCCCTTCTGGAGCGCTCTGACTGCAGCCTCCCAGGGAATGCGCGGGCGCGCCagcattacacgtcCtgagcgattgt | SEQ ID NO: 230 |
| Pcdh20_in_2 | GACTACCTATGGCAGTTACAATGTCCCTCCATGTTATTCCACAATGGCATAGGCGCGCCcacttaacggctgacatgggaattag | SEQ ID NO: 231 |
| Primers | | |
| WS187 | ATGCCGCTGGCGATTCAGGTTC | SEQ ID NO: 83 |
| WS188 | GCCGATCAACGTCTCATTTTCG | SEQ ID NO: 84 |
| W5275 | TAAACTGCCAGGCATCAAACTAAGC | SEQ ID NO: 79 |
| WS276 | AGTCAGCCCCATACGATATAAGTTG | SEQ ID NO: 80 |
| p1 | TAGTGAAACAGGGGCAATGGTG | SEQ ID NO: 232 |
| p2 | CATGGATGCAGAGCAGTGTTTG | SEQ ID NO: 233 |
| p3 | GCCTTCTTGACGAGTTCTTCTGAGG | SEQ ID NO: 234 |
| p4 | TACCTTCTTGGGCAGGAAGCAG | SEQ ID NO: 235 |

TABLE 6-continued

Oligonucleotides used in this study

| Gene | Oligonucleotides | SEQ ID |
|------|------------------|--------|
| p5 | TTTCTTTCCAGGCATTCCCTCA | SEQ ID NO: 236 |
| p6 | TTCTTGCGAACCTCATCACTCG | SEQ ID NO: 237 |

Note:
The construction of targeting vectors for del(Mid), del(CIE), ACFP, BYFP, delA, delB, and del(Down) alleles is slightly different for the other vectors in this study.
Underlined sequences indicate restriction sites.
Sequences in lowercase are PCR primers for either pStart-K or pKD3 template.
Other sequences in uppercase (~50 nt) are homology for recombination in bacteria.
All these XXX_out_1 and XXX_out_2 oligonucleotides use pStart-K as a template for PCR.
All these XXX_in_1 and XXX_in2 oligonucleotides use pKLD3 as a template for PCR.
Pcdhb1, Celsr2, Fat2, and Fat3 use different primers for amplifying pStart-K and pKD3 templates.
However, the primer sequences (sequences in lowercase) used for other genes appear to be more robust. The latter primer sequences are now routinely use for oligonucleotides.

d. Preparation of Chemically Competent DH5α Cells•TIMING 2 Days

26. Even with recombineering, standard restriction enzyme-based cloning can be used. Chemically super-competent DH5α cells (>1×10$^8$ transformants/μg DNA) are useful in cloning of targeting vectors. The Inoue method (Inoue, H., et al. 1990) was used with slight modifications for preparation of chemically competent DH5α cells.

27. DH5α was streaked on an LB-agar plate, and incubated at 37° C. overnight.

28. 10 large colonies were picked and grown in 250 ml SOB medium in a 1 L flask at room temperature (RT) (21-23° C.) until OD$_{600}$=0.6.

29. The culture was transferred to a centrifuge tube and kept on ice for 10 min with occasional shaking.

30. The bacteria was centrifuge at 2,500 g and 4° C. for 10 min. The pellet was gently resuspended in 80 ml of ice cold transformation buffer (TB) (10 mM Pipes, from 0.5M pH6.7 stock; 55 mM MnCl2; 15 mM CaCl2; 250 mM KCl), on ice for 10 min.

31. The bacteria was centrifuged for 10 min at 2500 g and 4° C. The pellet was gently resuspended in 20 ml of ice cold TB.

32. DMSO (1.4 ml) was added to the tube and mixed well. the tube was kept on ice for 10 min.

33. The bacteria was divide into 0.5-1 ml aliquots, frozen in liquid nitrogen, and stored at −80° C.

Note: this protocol produces 10 folds more competent cells than many other commonly-used protocols, yet the efficiency of the cells are still as high as 1-5×10$^8$ cfu/μg plasmid DNA. If stored at −80° C., cells are good for at least 3 years. When thawed for use, the 0.5-1 ml aliquot can be further aliquoted and refrozen without noticeable reduction of transformation efficiency.

e. Preparation of Red-Competent DH5α/pKD46 Cells•TIMING 2 Days 34. 50 μl of chemically competent DH5α cells were transformed with pKD46 (~10 ng) by 42° C. heat shock for 1 min. The transformed cells were directly spread onto an LB-agar plate (100 μg/ml Ampicillin) and grown at 30-32° C. for about 24-30 h.

35. Several big colonies were picked and grown in 20 ml of SOB medium overnight at 30-32° C.

36. About 10 ml was transfer into 250 ml of SOB medium to obtain (OD$_{600}$ of ~0.1-0.2, and 0.25 g L-arabinose powder was added to the culture to induce Red-protein expression. The culture was incubate at 30-32° C. with shaking for another 2-4 h.

37. When the OD$_{600}$ of the cells reached ~0.4-0.8, the culture was transferred into a large centrifuge tube, and left on ice for 10-20 min with occasional shaking.

38. The cells were centrifuge for 5 min at 4,000 g and 4° C. The supernatant was discarded and the pellet resuspended gently in 200 ml of ice cold 10% glycerol.

39. The cells were centrifuge for 10 min at 4,000 g and 4° C. The supernatant was discarded and the pellet resuspended gently in 200 ml of ice cold 10% glycerol.

40. The cells were centrifuge for 10 min at 4,000 g and 4° C. The supernatant was discarded and the pellet resuspended gently in 100 ml of ice cold 10% glycerol.

41. Finally the cells were centrifuge at 4,000 g for 10 min at 4° C. The supernatant was discarded the residual liquid removed by pipetting. The pellet was gently resuspended in a fresh 0.5 ml of ice cold 10% glycerol. The cells were divided into 50 μl aliquots, and snap frozen in liquid nitrogen.

Cells were stored at −80° C. (good for at least 3 years). When possible, all the steps were performed in a 4° C. cold room to ensure very high transformation efficiency. The procedure above can be easily scaled up if the cells are needed for many targeting vectors.

f. Insertion of Reporter/Neo Cassette•TIMING 3 Days

42. For the simple loss-of-function allele of Pcdh1, oligos were designed to delete the Pcdh1 exon 1 and concomitantly introduce an AscI restriction enzyme site at this position. Other enzyme sites can also be used. An AscI site was used because all the other reporter cassettes (FIG. 6E) are similarly flanked by AscI. Because AscI is a rare cutter, and its overhang is compatible with a few other restriction enzymes like MluI, it is possible to use AscI-flanked reporter/neo for virtually any gene.

43. The upstream oligo sequence was:

(SEQ ID NO: 122)
GTCTTCTTGTAGTTCTCCTGATTCTGGAGCCTGCCAGGATGGGGCCTCTG

AGGCGCGCCagcattacacgtcttgagcgattgt and the downstream oligo sequence was:

(SEQ ID NO: 123)
CTCCCTCATGATCTAGTCGATCATGGCGGGTAAGACACACCTGCTCTATC

AGGCGCGCCcacttaacggctgacatgggaatta.

Uppercase sequences are 50 nt homology to flanking genomic DNA of Pcdh1 exon 1—homology arms for Red-recombination. The GGCGCGCC is the AscI consensus sequence. Lowercase sequences are primers for the chloramphenicol resistance gene in pKD3 (Datsenko, K. A., et al. 2000).

44. PCR was performed and products purified as described in the previous step.

45. The purified PCR product (2-5 µl, ~200-500 ng) plus pStart-KPcdh1 (2-5 µl, ~200-500 ng) was electroporated into 50 µl of Red-competent DH5α/pKD46 cells. Electroporation conditions are as above.

46. The electroporated cells were transferred into 1 ml of SOC medium and the mixture incubated at 37° C. with shaking for 1 h. The bacteria were spread onto LB-agar plates (30 µg/ml Chloramphenicol), and incubated at 37° C. overnight.

For difficult DNA, incubation can also be at 30-32° C.

47. Four medium-large colonies (>90% are recombinants) were picked and grown in 5 ml of SOB medium at 37° C. overnight for DNA minipreps.

48. To confirm the presence of the predicted junction regions, two
minipreps were sequenced with the correct restriction patterns using primers WS187 and WS188. The resulting plasmid were designated pStart-K-Pcdh1Asc.

49. 2-5 µg of pStart-K-Pcdh1Asc were cut with AscI restriction enzyme and separated on 0.8% agarose gel.

50. The large fragment was gel purified with a Qiagen column, and eluted with 48 µl H$_2$O. 51. The eluted DNA (~43 µl) was mixed with 5 µl of 10× Shrimp Alkaline Phosphatase buffer and 2 µl of Shrimp Alkaline Phosphatase (Roche) in a total volume of 50 µl for dephosphorylation at 37° C. for 10 min. The reaction was inactivated at 65° C. for 15 min.

52. A standard ligation was set up to insert a pre-cut AscI-EGFP-ACN-AscI cassette or other reporter cassettes (FIG. 6E). 12 µl (~200-500 ng) of above purified recipient DNA, 5 µl (~200 ng) of pre-cut AscI-EGFP-ACN-AscI cassette, 2 µl of T4 DNA ligase buffer, and 1 µl of T4 DNA ligase (Fermentas, EL0011) in a total volume of 20 µl for ligation reaction at RT (21-23° C.) for 2 h.

53. Chemically competent DH5α cells (100 µl, >10$^8$ transformants/µg) were transformed with 10 µl of the above reaction mixture by heat shock at 42° C. for 1 min. 1 ml of SOC medium was added and incubated at 37° C. for 1 h. Aupernatant was centrifuged and decanted. The pellet resuspended in the remaining liquid of ~100 µl and spread on LB-agar plates (50 µg/ml Kanamycin). 4-8 colonies were picked for culture and preparation of DNA minipreps. The correct clones from this step were designated pStart-K-Pcdh1-EGFP (FIG. 6F).

g. Gateway Recombination•TIMING 2 Days

54. Finally, introduction of the HSV-tk gene into the targeting vector implemented a Gateway recombination reaction.

55. A reaction mixture was set up that contained: (LR Reaction Buffer (5×), 1 µl; pStart-K-Pcdh1-EGFP (e.g.), 2 µl; pWS-TK6/linearized with SalI, 1 µl; LR clonase enzyme mix, 1 µl).

56. This was incubated at 25° C. for 1 h, 0.5 µl of Proteinase K Solution was added and the reaction incubated for 10 min at 37° C.

57. Chemically competent DH5α cells (100 µl, >10$^8$ transformants/m) were transform with 2 µl of the above reaction mixture by heat shock at 42° C. for 1 min. Without adding SOC medium or incubation, 10 and 90 µl of the transformed bacteria were spread on LB-agar plates (100 µg/ml Ampicillin).

58. The plates were incubated at 30-32° C. (NOT 37° C. or higher) for 20-30 h. Two colonies (>90% were usually correct) were picked for culture and preparation of DNA minipreps. The correct clone was the final targeting vector for Pcdh1 and was designated pTV-Pcdh1-EGFP.

h. Preparation of DNA for Electroporation of ES Cells•TIMING 6 h

59. Targeting vectors were linearized for electroporation of ES cells.

60. To prepare about 100-150 µg of clean DNA, 200 µg of targeting vector DNA (assuming a 70% recovery) was digested with appropriate restriction enzyme at 1-2 units/µg DNA in a total volume of 500-µl reaction for about 4 h.

61. To determine the completeness of the digest by agarose gel electrophoresis, ~50 ng of digested DNA were run along with 50 ng of uncut targeting vector and ladder. If the gel is run long enough, uncut DNA should be found to migrate at a slower speed.

62. To purify the 500 µl DNA digest, one volume of phenol (Sigma, P-4557) and one volume of chloroform were added. The tube was hand-shaken vigorously, and centrifuged at 14,000 rpm (20,000 g) for 3-5 min at RT (21-23° C.) in a benchtop centrifuge.

63. The supernatant was transferred to a new tube, and an equal volume of chloroform added. The tube was hand-shaken vigorously, and centrifuged at 14,000 rpm (20,000 g) for 3-5 min at RT.

64. The supernatant was transfer to a new Eppendorf tube. 1.6 to 2 volumes of ethanol were added (without adding salt). The tube was mixed by gentle inversions, and DNA become cloudy.

65. The tube was centrifuge at 3,000 g (Higher speed makes the pellet hard to dissolve later.) for 2 min, and the supernatant was discarded.

66. The DNA pellet was rinse with 500 µl of 70% ethanol by shaking. The tube was centrifuge at 3,000 g for 2 min, and the supernatant discarded.

67. The tube was centrifuge briefly, and residual liquid removed by pipetting. The linearized DNA pellet needs was suspended well (by gentle pipetting up and down) in 100 µl of TE (pH7.5, filtered). Note: if DNA is not fully dissolved in TE, it will affect targeting efficiency in ES cells.

68. To determine the concentration, 1 µl of resuspend DNA was used to check OD$_{260/280}$. The concentration was adjusted to 1 µg/µl.

The linearized DNA was store at 4° C. until use (long-term storage should be at −20° C.).

i. Preparation of Genomic DNA from ES Cells for Southern Blot or PCR•TIMING 8 h

69. To prepare DNA from ES cells for Southern blot analysis or PCR, cells were lysed in 1.7 ml Eppendorf tubes in ~500 µl of ES cell lysis buffer (100 mM NaCl; 20 mM Tris, pH7.6; 10 mM EDTA; 0.5% SDS).

70. 5 µl of proteinase K (from 20 mg/ml stock) was added to a final concentration 0.2 mg/ml, and the tubes incubated at 37° C. for 2-4 h without shaking.

71. 250 µl of saturated NaCl (~6 M) was added to each tube, and hand-shaken vigorously 100-200 times.

72. The tubes were left on ice for 10 min, and centrifuged on a benchtop centrifuge at 14,000 rpm (20,000 g) for 10 min.

73. Supernatant (~700 µl) was collected into a new 2 ml Eppendorf tube. ~1.2 ml 100% ethanol was added.

74. A glass capillary (Kimble, KIMAX-51®, 1.5-1.8×90 mm) was used for each tube to spool out the DNA. The DNA normally sticks to the tip of glass capillary.

75. The DNA was washed briefly by dipping into another tube containing 70% ethanol.

76. Each DNA was dissolved in 150 µl TE (pH7.5, 10 mM Tris, 1 mM EDTA).

j. Southern Blot Screening of ES Cells•TIMING 3 Days

77. When designing probe templates for Southerns, the Blat (genome.ucsc.edu/cgi-bin/hgBlat) or RepeatMasker (www.repeatmasker.org/) was used to check the template sequence and to avoid using regions with repeats, since repeats in probes usually resulted in very high background signal.

78. PCR product can be directly used as a probe template, but it is better to perform a TOPO-TA cloning (Invitrogen) of the PCR product because using a template cut out from a plasmid generate cleaner Southerns.

79. To prepare radio-labeled probe, Stratagene Prime-It® II Random Primer Labeling Kit (Catalog #300385) or the Ready-To-Go DNA Labelling Beads (Amersham) was used following the manufacturer's instructions.

80. Probes were purified with G50 columns (e.g., ProbeQuant™ G-50 Micro Columns from Amersham).

81. The DNA digest was set up, 5-10 µg of genomic DNA (usually 10-15 µl) were digested with restriction enzyme in 25-µl reactions in the presence of 4 mM Spermidine (100 mM, pH7.0 Spermidine stock: 127 mg of Spermidine 3-HCl (Sigma S-2501), 5 ml of ddH$_2$O, and 1 drop of 1 M NaOH.) for 12-20 h at appropriate temperature for the enzyme.

82. To separate the digested DNA, 10× loading buffer was added (95% Formamide; 10 mM EDTA; 0.025% SDS; 0.17% Xylene Cyanol; 0.17% Bromophenol Blue), the samples heated at 65° C. for 10 min, and loaded on 0.8-1% agarose gel in 1× TAE. DNA standard (e.g. 1 kb plus DNA from Invitrogen) can also be included.

83. The samples were electrophoresed overnight at 20-50 Volts. The gel was photographed under UV light along with a fluorescent ruler.

84. DNA was transfer to Hybond-N+ nylon membrane (Amersham) by downward capillary transfer using a protocol described previously (Tvrdik, P., et al. 2006; Chomczynski, P., et al. 1992).

85. The gel was denatured in 3 M NaCl, 0.4 M NaOH for 1 h, and blot DNA onto Hybond N+ membrane in 3 M NaCl, 8 mM NaOH for 2 h to overnight.

86. The nylon membrane was neutralized in 0.2 M sodium phosphate, pH 6.5, and UV crosslinked.

87. The wet membrane was used directly for hybridization. Alternatively the membrane was dried at RT (21-23° C.) for later use.

88. To hybridize, the membrane was placed into a large hybridization tube, and prehybridized in an oven (Hybridiser HB-1D, Techne) at 42° C. in about 25 ml of hybridization solution (50% Formamide; 5×SSC; 5×Denhardt; 0.05M Sodium Phosphate, pH6.5; 0.5% SDS; 100 µg/ml Herring sperm DNA, Sigma D3159).

89. After 1 h of prehybridization, the solution was discarded.

90. The membrane was hybridized with a radioactive probe (the probe was boiled for 10 min and snap cooled on ice before use) in about 15 ml hybridization solution at 42° C. overnight.

91. The hybridized membrane was washed twice in 2×SSC, 0.1% SDS at RT (21-23° C.) for 15 min, and once in 0.2×SSC, 0.1% SDS at 42° C. for 10-15 min.

92. The membrane was placed into a Kodak film cassette with film at −80° C. for overnight to several days. Alternatively, the membrane was placed into a phosphor imaging cassette at RT (21-23° C.) for a few hours to overnight and visualized with Typhoon PhosphorImager (GE).

93. The hybridized membrane can also be stripped for hybridization with another probe. To strip the membrane, it was placed in 0.5% SDS, 100° C. until the signal disappears (from a few seconds to several minutes).

k. pCR Screening of ES Cells•TIMING 6-8 h

94. For ES cell screening, Southern blot method is generally more robust than PCR. However, PCR can be a simple non-radiation alternative method. If primers are not optimal, PCR can be very difficult.

95. Several pairs of primers were designed for testing. It is essential to obtain a good flanking primer outside the homology arms.

96. The same good internal primers (e.g. primers from neo or GFP) were preferably used. The Roche Expand long template PCR kit (#11681842001) was used for all PCR reactions.

97. 2 µl of genomic DNA prepared from ES cells as described above was diluted in 20 µl of lysis solution (25 mM NaOH; 0.2 mM EDTA).

98. It was then boiled for 15 min, and neutralized with 20 µl of 40 mM TrisCl.

99. 2 µl of the neutralized DNA was used in a 12.5-µl PCR reaction. PCR was performed according to the manufacturer's instruction.

l. Preparation of Tail (or Other Tissue) DNA for Southern Blot and PCR•TIMING 1 Day 100. To confirm germline transmission of a gene-targeted allele, Southern blot analysis is usually needed. Once confirmed by Southern blot, PCR is used for routine genotyping of mice from subsequent breeding.

101. To isolate genomic DNA from tails or other tissues for Southern blot analysis and PCR, tails (~0.5 centimetre) were put into 1.7 ml Eppendorf tubes containing 480 µl Tail Lysis Buffer (50 mM Tris, pH8; 100 mM EDTA; 1% SDS; 100 mM NaCl).

102. proteinase K (25 µl from 20 mg/ml stock) was added and the mixture incubated at 55° C. overnight.

103. NaCl (0.25 ml from 6M stock) was added to each tube, and left on ice for 10 min.

104. The tubes were shaken vigorously for 2 min and centrifuge at 14,000 rpm for 10 min at 4° C.

105. The supernatant was transferred to a new Eppendorf tube, and ~1 ml 100% ethanol added.

106. A capillary tube was used to spool out the DNA, which was washed by dipping in a tube containing 70% ethanol. DNA was dissolved in 200 µl TE.

m. Quick Preparation of Tail (or Other Tissue) DNA for PCR Genotyping•TIMING 2 h 107. 1-1.5 mm long tails were cut and boiled in 100 µl lysis solution (25 mM NaOH; 0.2 mM EDTA) for 1 h, and neutralized with 100 µl of 40 mM TrisCl (Truett, G. E., et al. 2000).

108. An aliquot of 2 µl was used for PCR genotyping in a 12.5-µl reaction.

v. Trouble Shooting

For molecular cloning of targeting vectors or other large constructs, software such as Gene Construction Kit (GCK, www.textco.com) or Vector NTI (www.invitrogen.com) can be used. They can help speed up the cloning procedure by taking advantage of the fully sequenced mouse genome information.

The combined use of low-copy-plasmid (15-20 copies per bacterial cell) for cloning and low temperature (30-32° C. instead of 37° C.) for bacterial growth can solve many problems associated with large construct cloning.

All of the oligos up to 130 nt in this study were synthesized at a normal 40 nmoles scale, and no purification such as HPLC or PAGE was necessary (Although mutations can occur during synthesis of long oligos, the correct ones are selected during recombination.).

Figure 6C:
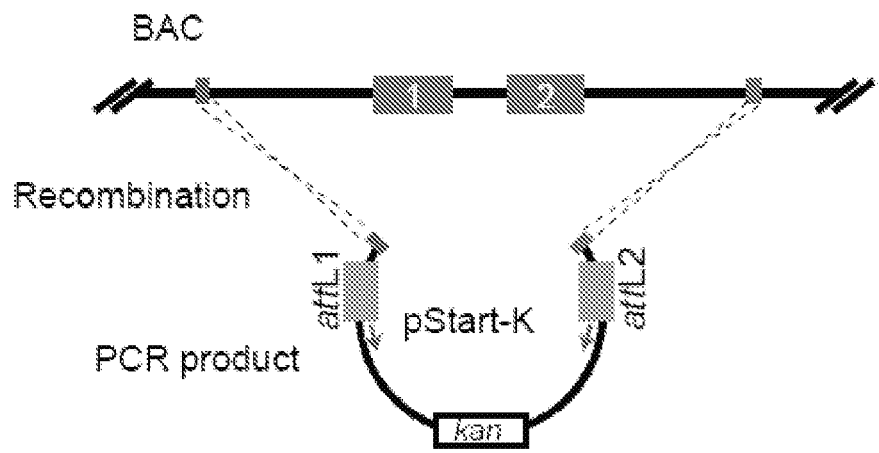
FIG. 6C shows Red-recombination is first used to pull out a genomic fragment from a chosen BAC clone that can be used for the homology arms in the targeting vector. pStart-K is created as a Gateway-compatible vector, with a low-copy origin for DNA replication.
Figure 6D:
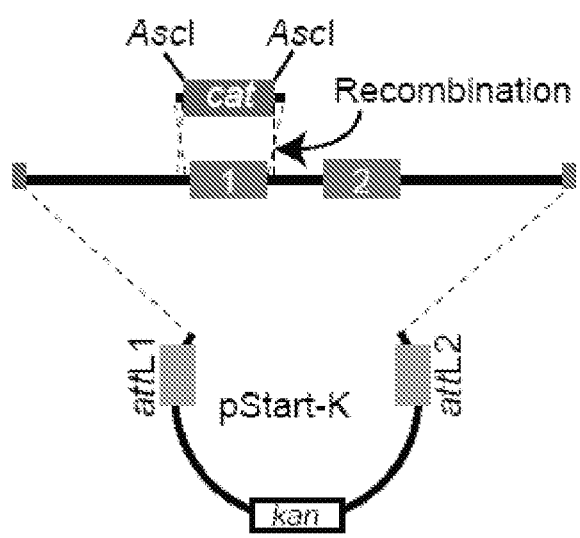
FIG. 6D shows the region of interest (e.g., exon 1) is replaced by an AscI-flanked chloramphenicol resistance gene (cat) by another round of Red-recombination.
Figure 6E:
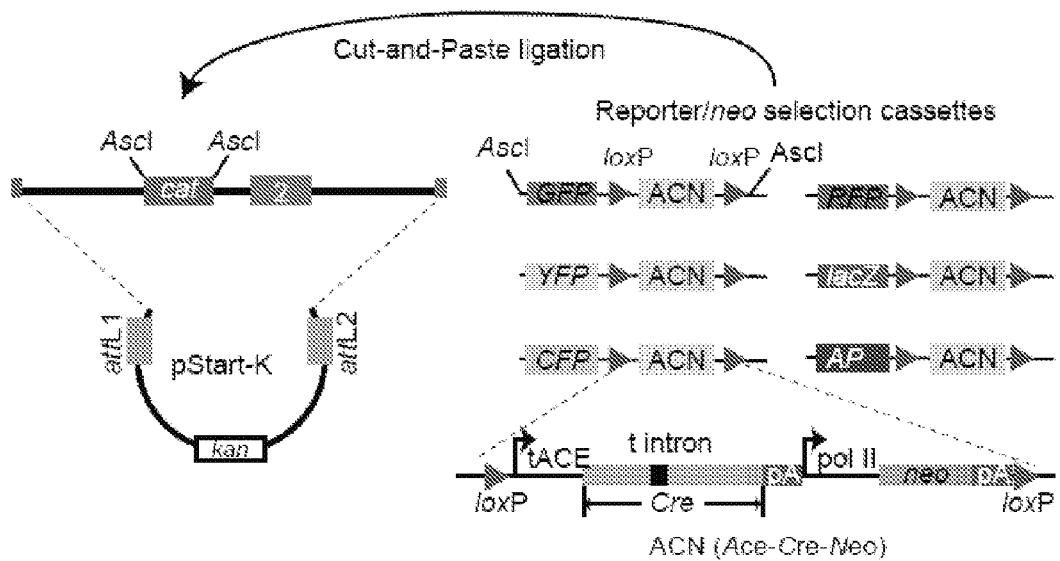
FIG. 6E shows a set of AscI-flanked reporter cassettes. They all contain a self-excision neo cassette (ACN) used for selection in mouse ES cells, which is subsequently automatically deleted in the male germline (Bunting, M., et al. 1999). If endogenous polyadenylation signal is preferred, a series of reporter/neo cassettes that do not carry a polyadenylation signal were also designed.
Figure 6F:
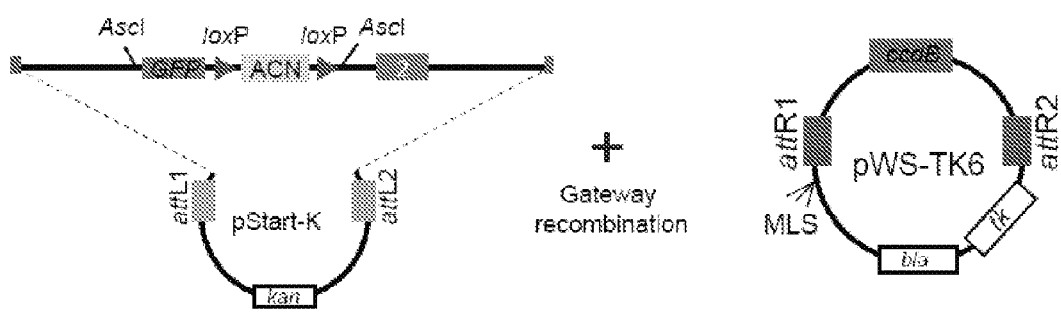
FIG. 6F shows a subcloning of any reporter cassette from panel (e) into the AscI site of vector shown in panel (e) will result in the vector shown in panel (f).
Figure 6G:
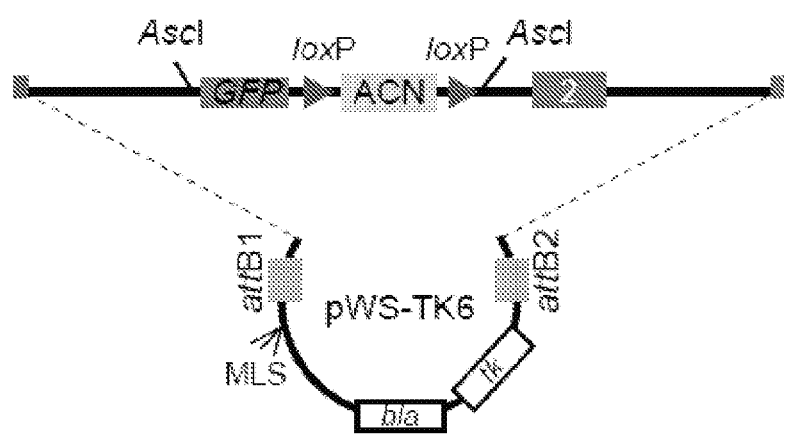
FIG. 6G shows HSV-TK vectors were created as Gateway-compatible vectors and also contain multiple restriction sites for linearization (MLS) of the targeting vector.

To capture difficult genomic regions, it is better to leave out the almost identical attL1 and attL2 sites (identities=93/95) in pStart-K in the PCR product (that is, if oligonucleotides are designed to match arrows in FIG. 6C), and the background of self-recombined pStart-K is greatly reduced. However, this extra background was tolerated because the resulting positive products enable direct cloning into TK vectors in subsequent steps.

Restriction enzyme-based cloning. Miniprep DNA from 5 ml culture in SOB medium is enough for intermediate cloning steps, e.g., restriction analysis, sequencing, ligation and so on. Qiagen miniprep spin columns can also be reliably used for gel purification of DNA up to 20 kb. Although it seems more convenient to dephosphorylate DNA in the same tube of restriction enzyme digest by Shrimp alkaline phosphatase (Roche Cat#1758250), dephosphorylation usually works much better after gel purification. For ligation of a large construct, it is better to use a larger amount of DNA, e.g., a few hundred nanograms of DNA for the backbone vector or the insert.

vi. Results: Targeting Cadherin Gene Family

The above described protocol for construction of gene targeting vectors was used to systematically disrupt members of the cadherin family (Table 7. The cadherin family of cell adhesion genes is one of the largest gene families in the mouse genome, containing more than 100 clustered and dispersed members (Wu, Q., et al. 1999; Wu, Q., et al. 2000). These genes are important players in construction of the body plan during development, playing disparate roles in processes such as the epithelial-mesenchymal transitions, synaptic formation, axon guidance and neural circuit establishment (Price, S. R., et al. 2002), planar cell polarity and organ shape formation, cell sorting and tissue morphogenesis (Takeichi, M., et al. 2007). Mutations in members of the cadherin family can lead to dramatic phenotypes including neuronal diseases and tumor metastasis. Despite two decades of extensive work in this area, functional studies in the mouse for many of these genes are still lacking.

TABLE 7

Targeted alleles of cadherin and protocadherin genes

| Gene Name | Allele Name | Targeting vector | Germline transmission |
|---|---|---|---|
| Pcdha (Mid) | del(Mid) | Yes | Yes |
| Pcdha (CIE) | del(CIE) | Yes | Yes |
| Pcdha Type A | $A^{CFP}$ | Yes | Yes |
| Pcdha Type B | $B^{YFP}$ | Yes | Yes |
| Pcdha Type A | delA | Yes | Yes |
| Pcdha Type B | delB | Yes | Yes |
| Pcdha (Down) | del(Down) | Yes | Yes |
| Pcdhb1 | Pcdhb1$^{EGFP}$ | Yes | In progress |
| Pcdhb22 | Pcdhb22$^{EGFP}$ | Yes | In progress |
| Celsr2 | Celsr2$^{EGFP}$ | Yes | Yes |
| Celsr3 | Celsr3$^{EGFP}$ | Yes | Yes |
| Fat2 | Fat2$^{EGFP}$ | Yes | Yes |
| Fat3 | Fat3$^{nlacZ}$ | Yes | Yes |
| Fat4 | Fat4$^{EGFP}$ | Yes | Yes |
| Dscam | Dscam$^{EGFP5'}$ | Yes | In progress |
| Dscam | Dscam$^{EGFP3'}$ | Yes | In progress |
| DscamL1 | DscamL1$^{EGFP5'}$ | Yes | In progress |
| DscamL1 | DscamL1$^{EGFP3'}$ | Yes | In progress |
| Dchs1 | Dchs1$^{EGFP}$ | Yes | In progress |
| Dchs2 | Dchs2$^{EGFP}$ | Yes | In progress |

TABLE 7-continued

Targeted alleles of cadherin and protocadherin genes

| Gene Name | Allele Name | Targeting vector | Germline transmission |
|---|---|---|---|
| Cdh8 | Cdh8$^{EGFP}$ | Yes | In progress |
| Cdh13 | Cdh13$^{EGFP}$ | Yes | In progress |
| Cdh18 | Cdh18$^{EGFP}$ | Yes | In progress |
| Cdh19 | Cdh19$^{EGFP}$ | Yes | In progress |
| Cdh20 | Cdh20$^{EGFP}$ | Yes | In progress |
| Cdh22 | Cdh22$^{EGFP}$ | Yes | In progress |
| Cdh24 | Cdh24$^{EGFP}$ | Yes | In progress |
| Pcdh1 | Pcdh1$^{EGFP}$ | Yes | In progress |
| Pcdh7 | Pcdh7$^{EGFP}$ | Yes | In progress |
| Pcdh10 | Pcdh10$^{EGFP}$ | Yes | In progress |
| Pcdh17 | Pcdh17$^{EGFP}$ | Yes | In progress |
| Pcdh18 | Pcdh18EGFP | Yes | In progress |
| Pcdh19 | Pcdh19EGFP | Yes | In progress |
| Pcdh20 | Pcdh20EGFP | Yes | In progress |

Figure 7B:
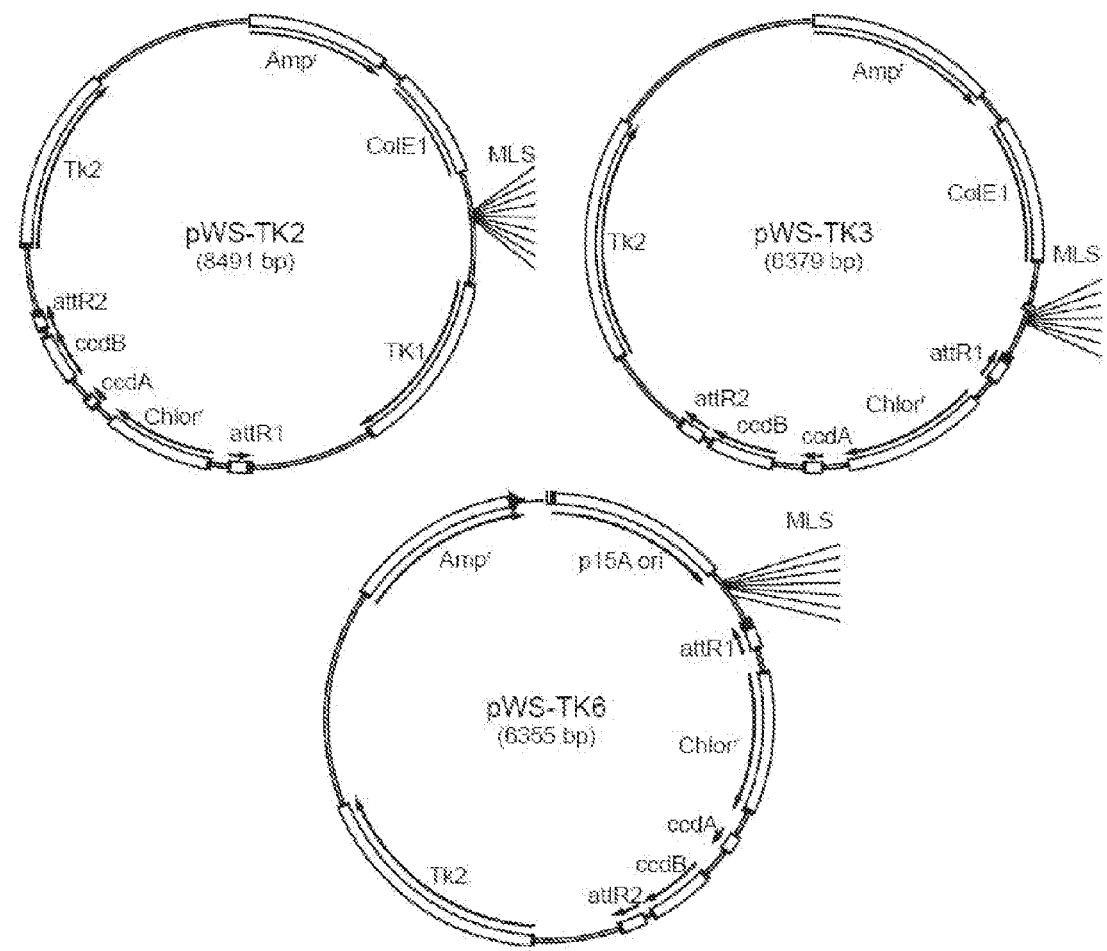
FIG. 7B shows a series of Gateway destination vectors that can be used to add negative selection cassettes, as well as linearization sites, for targeting vectors. pWS-TK2 is a highcopy plasmid with two TK genes. pWS-TK3 is a high-copy plasmid with one TK gene. pWS-TK6 is a low-copy plasmid with one TK gene. All three TK vectors have multiple restriction sites for linearization (MLS).
Figure 9A:
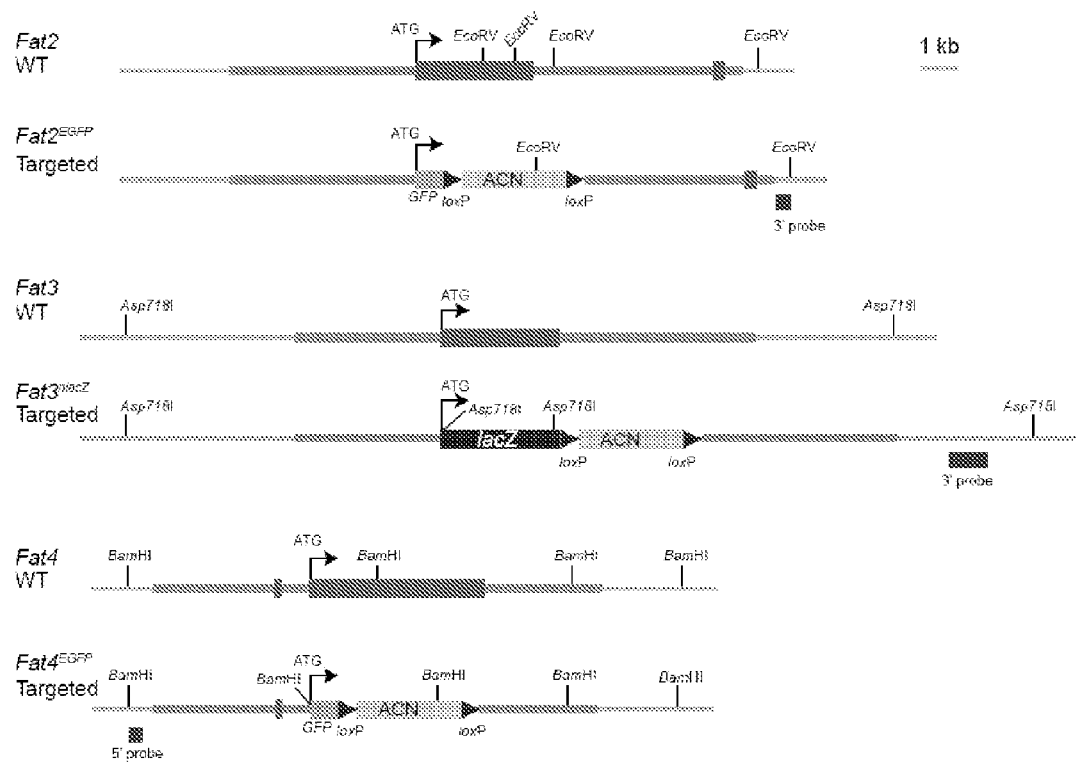
FIG. 9A shows targeting strategies for $Fat2^{EGFP}$, $Fat3^{nlacZ}$ and $Fat4^{EGFP}$ alleles.
Figure 9B:
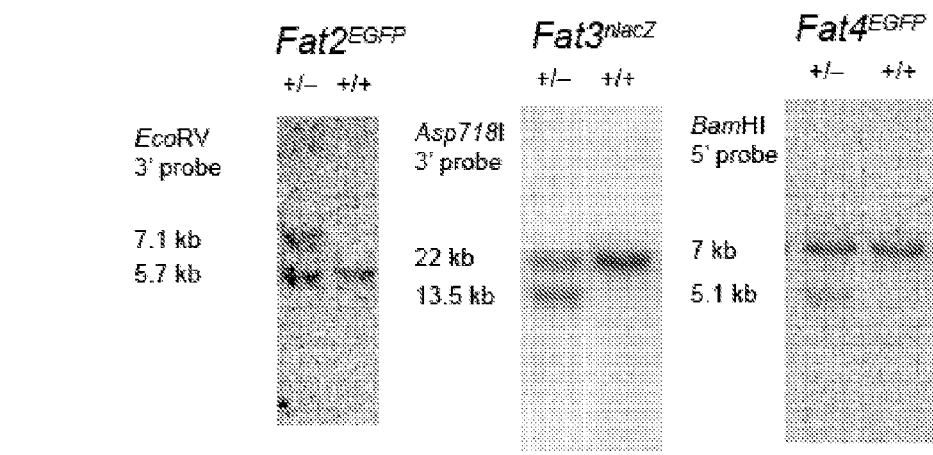
FIG. 9B shows Southern blot analysis of ES cells for $Fat2^{EGFP}$, $Fat3^{nlacZ}$ and $Fat4^{EGFP}$ alleles.
Figure 10A:
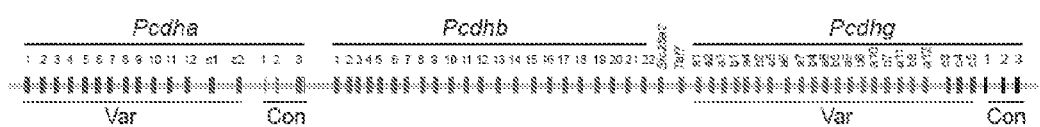
FIG. 10A shows schematic of the three closely-linked Pcdh clusters. The Pcdha and Pcdhg (α and γ) cluster has an interesting genomic structure, each of the 14 α and 22 γ variable exons share the three α and γ constant exons, respectively. In contrast, however, the Pcdhb (β) cluster has no constant exons. Described below is the creation of nine mutant alleles delA, delB, $A^{CFP}$, $B^{YFP}$, del(Mid), del (CIE), del(Down), $Pcdhb1^{EGFP}$ and $Pcdhb22^{EGFP}$.
Figure 10B:
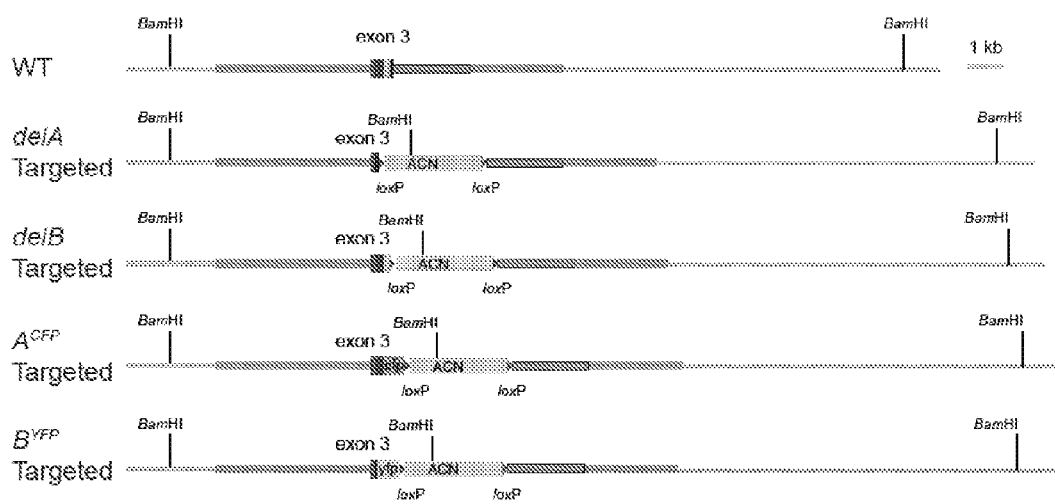
FIGS. 10B and 10C show alternative splicing within a constant exon 3 normally generates two sets of mRNAs, type A and type B 57. To use fluorescent markers to distinguish the expression profiles of Type A and B proteins in vivo, the $A^{CFP}$ and $B^{YFP}$ alleles were created. The $A^{CFP}$ allele has an ECFP gene fused in-frame to the last amino acid of the type A sequence with type B deleted. The $B^{YFP}$ allele has an EYFP fusion to the last amino acid of the type B sequence with type A deleted. Further created were simple deletions of type A and type B, the delA and delB alleles respectively, as internal controls.
Figure 10C:
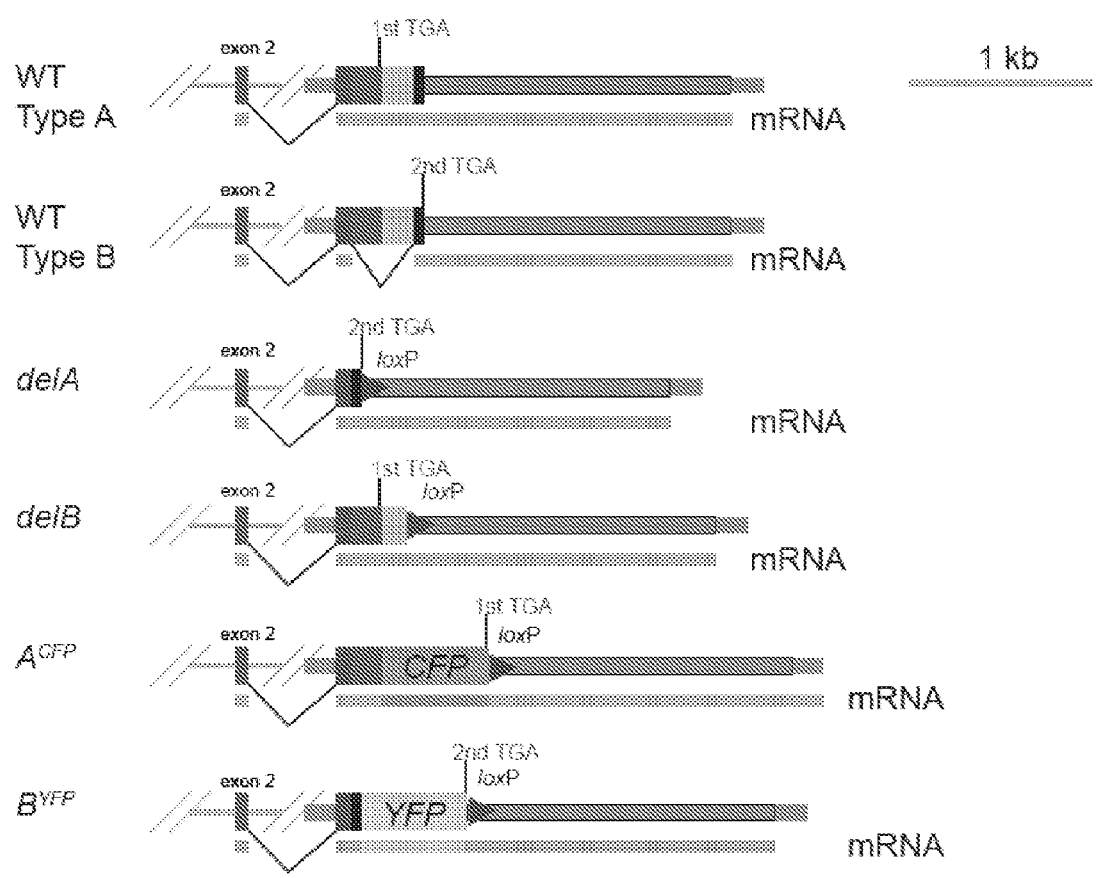
Figure 10D:
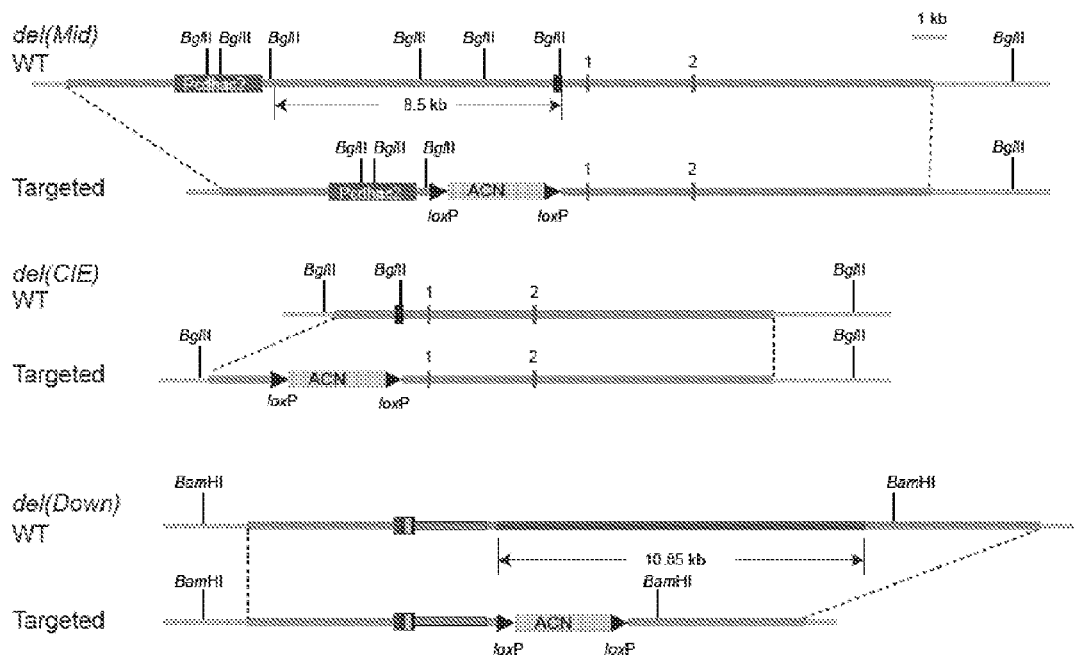
FIG. 10D shows the del(Mid) allele deletes 7 conserved non-coding elements (CNEs; also referred to as conserved non-genic sequences or CNGs), that are highly conserved between mouse and human and located between the variable and constant regions of the α cluster. The CIE allele deletes the most conserved CNE (Wu, Q., et al. 2001). The Down allele, a deletion of 10.85 kb region downstream of the α cluster, is designed to test for potential regulatory functions of this region.
Figure 10E:
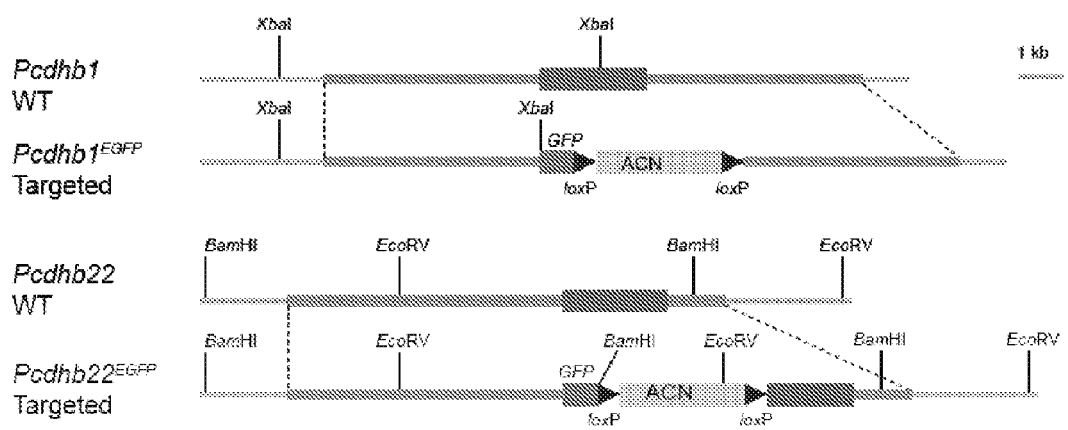
FIG. 10E shows the $Pcdhb1^{EGFP}$ allele is a GFP knockin that replaces the Pcdhb1 variable exon. The $Pcdhb22^{EGFP}$ allele is a GFP knockin that replaces the Pcdhb22 variable exon.
Figure 10F:
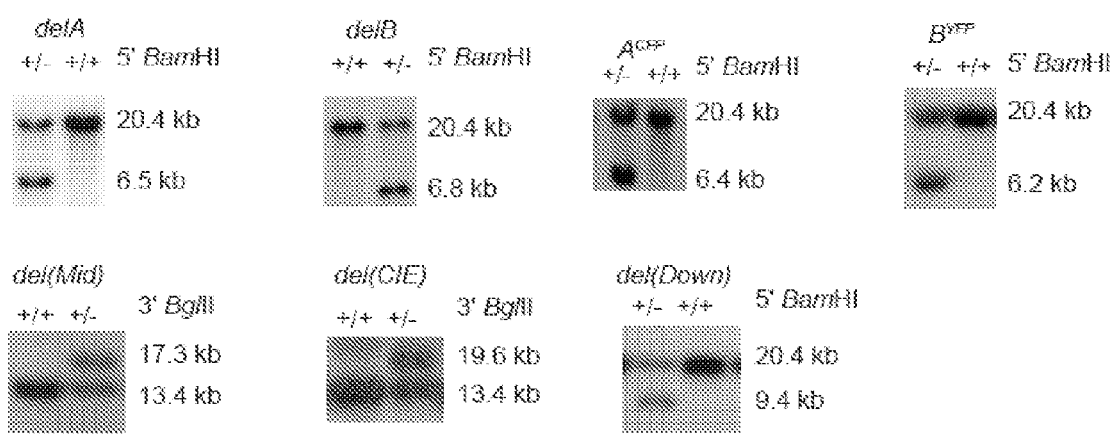
FIG. 10F shows Southern transfer analysis was used to confirm the gene structure for these mutant alleles.
Figure 11A:
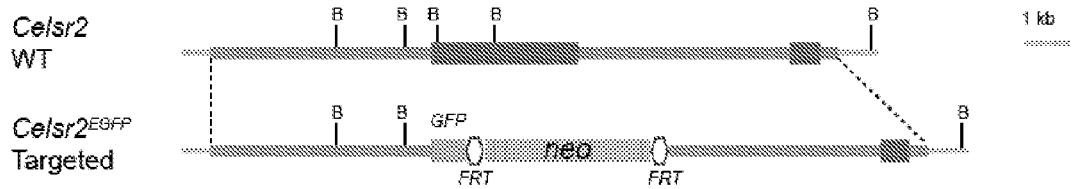
FIGS. 11A-V show the maps of vector maps of twenty-two of the knockout mice that were generated for $Celsr2^{EGFP}$, $Celsr3^{EGFP}$, $Dchs1^{EGFP}$, $Dchs2^{EGFP}$, $Dscam^{EGFP5'}$, $Dscam^{EGFP3'}$, $DscamL1^{EGFP5'}$, $DscamL1^{EGFP3'}$, $Cdh8^{EGFP}$, $Cdh13^{EGFP}$, $Cdh18^{EGFP}$, $Cdh19^{EGFP}$, $Cdh20^{EGFP}$, $Cdh22^{EGFP}$, $Cdh24^{EGFP}$, $Pcdh1^{EGFP}$, $Pcdh7^{EGFP}$, $Pcdh10^{EGFP}$, $Pcdh17^{EGFP}$, $Pcdh18^{EGFP}$, $Pcdh19^{EGFP}$, and $Pcdh20^{EGFP}$, respectively.
Figure 11B:
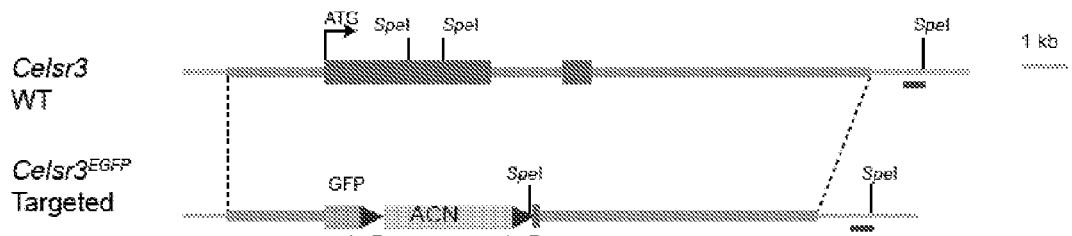
FIG. 11 shows alleles generated for nonclustered cadherin genes in this study.
Figure 11C:
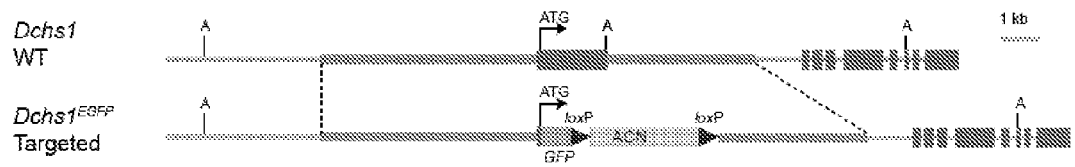
Figure 11D:
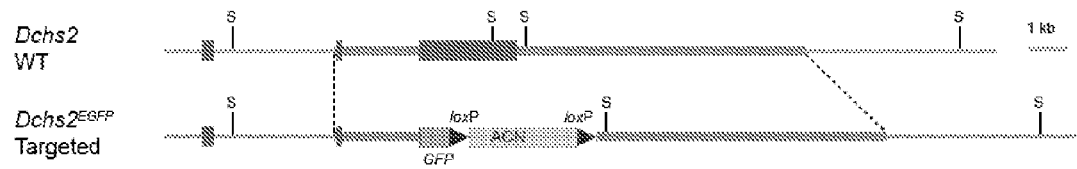
Figure 11E:
Figure 11F:
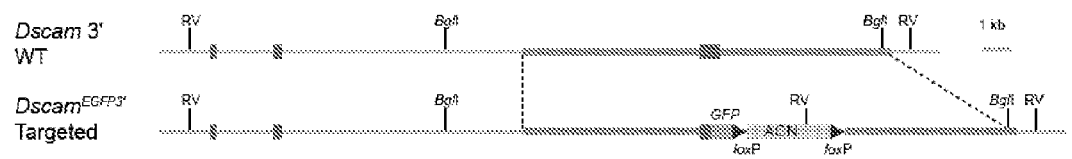
Figure 11G:
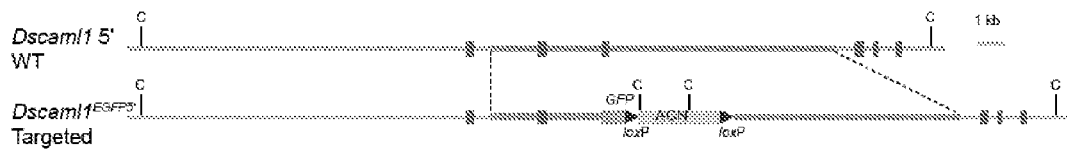
Figure 11H:
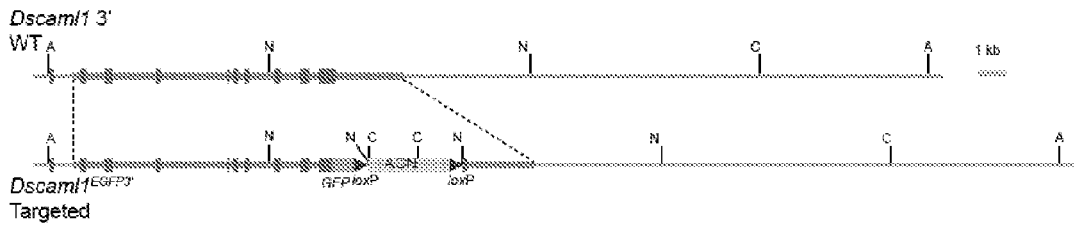
Figure 11I:
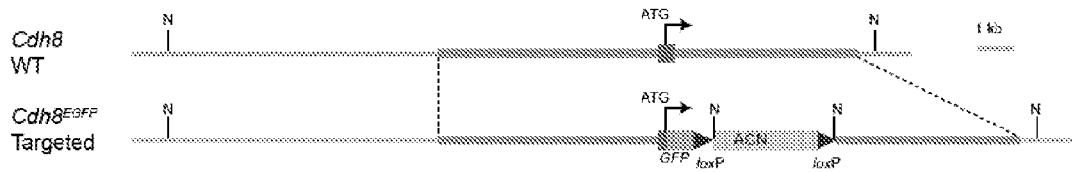
Figure 11J:
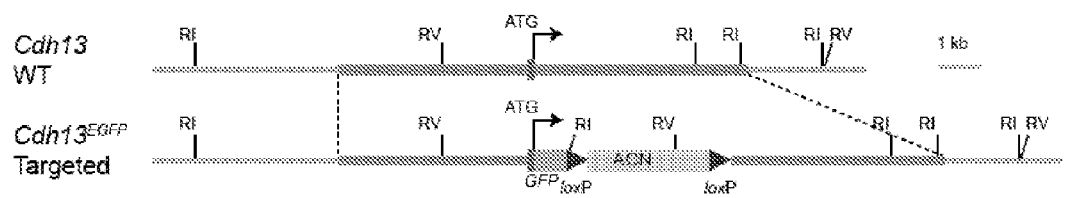
Figure 11K:
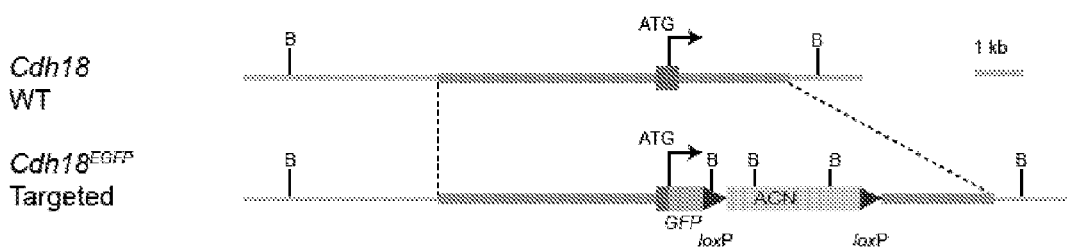
Figure 11L:
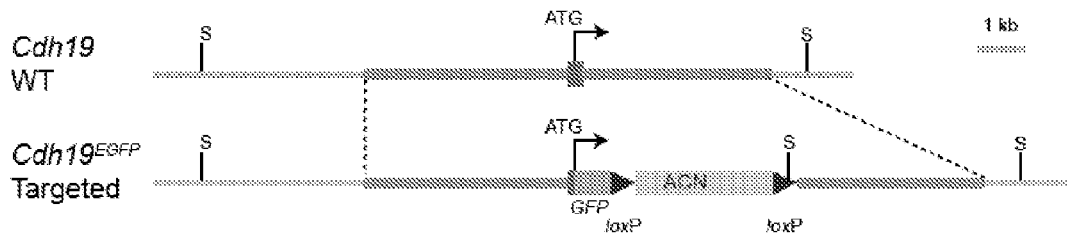
Figure 11M:
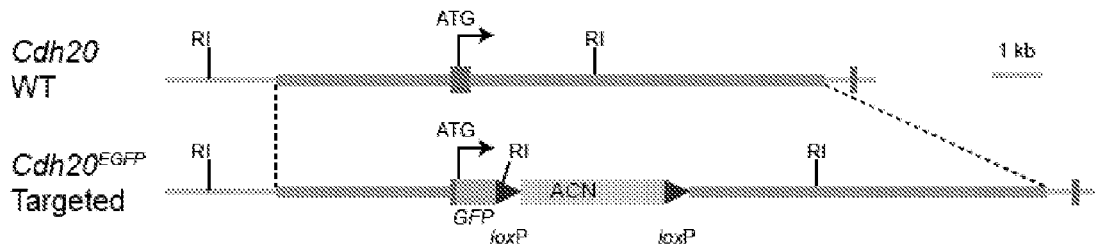
Figure 11N:
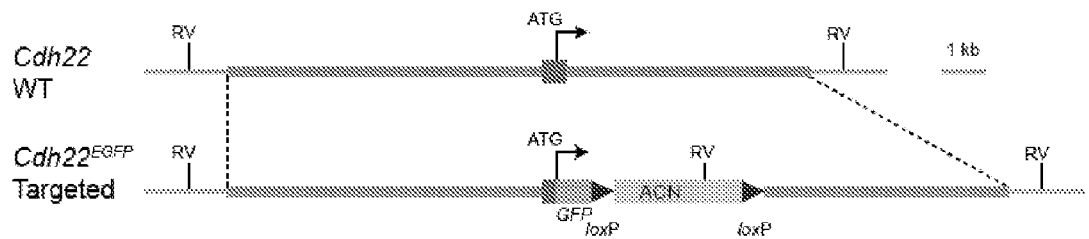
Figure 11O:
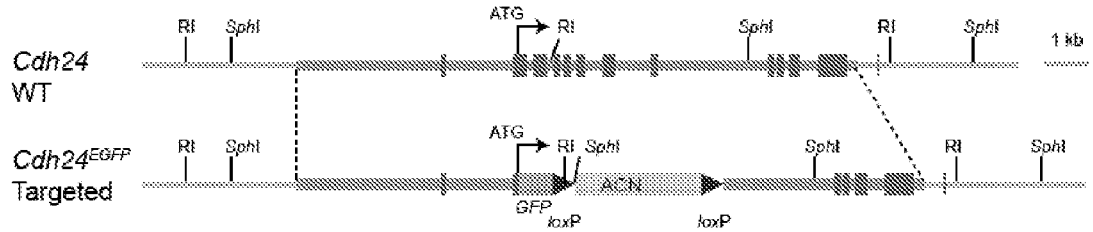
Figure 11P:
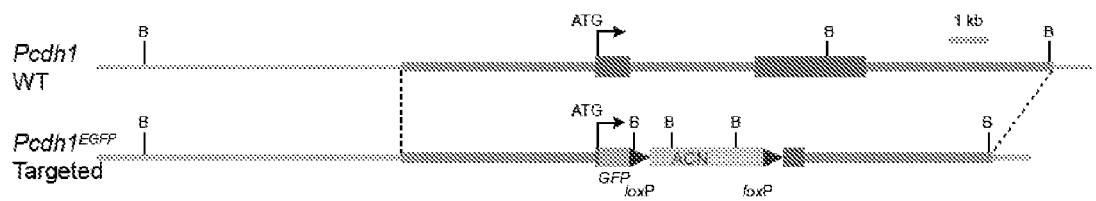
Figure 11Q:
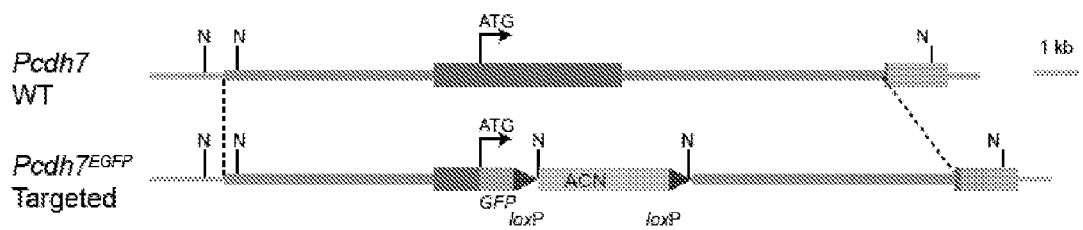
Figure 11R:
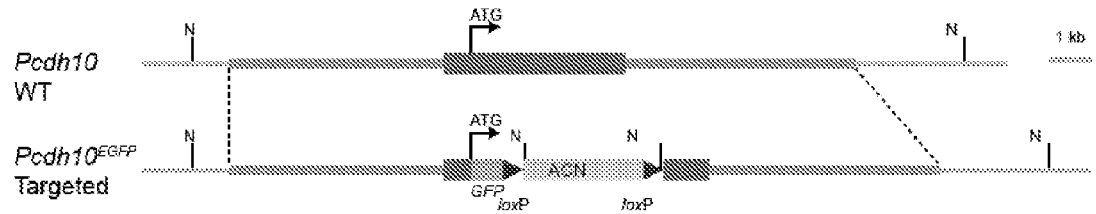
Figure 11S:
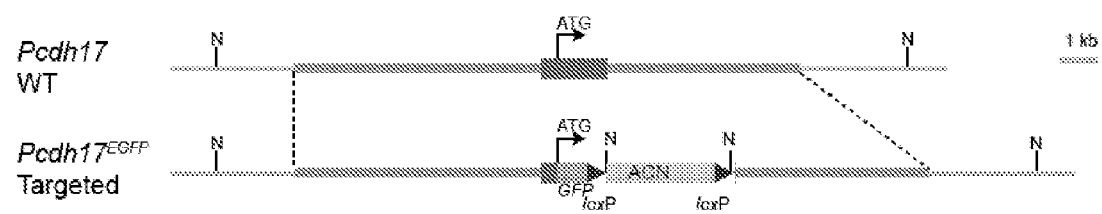
Figure 11T:
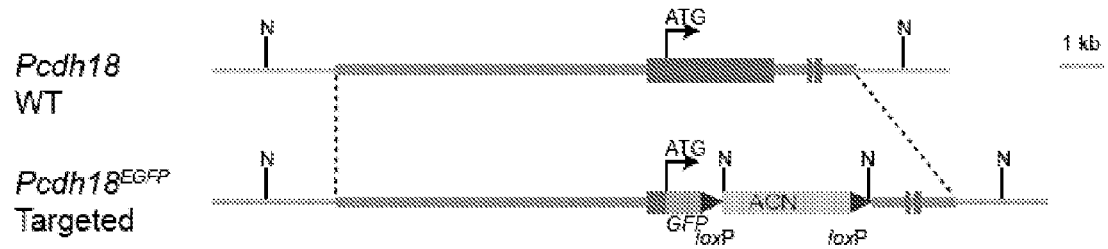
Figure 11U:
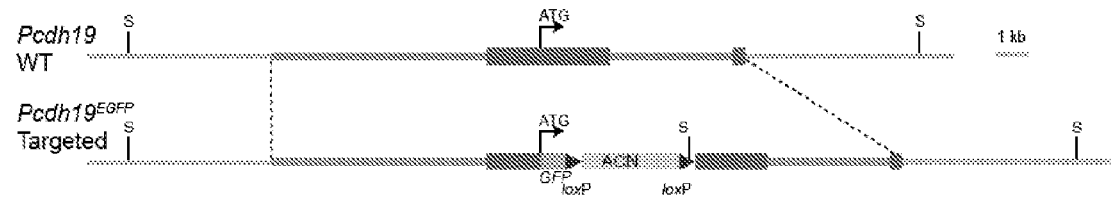
Figure 11V:
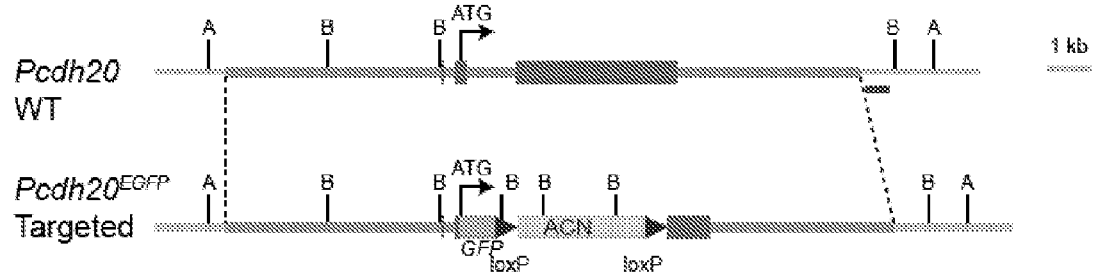

The generation of mouse loss-of-function alleles for individual members of the protocadherin gene clusters have been reported, as well as long-range deletions that cover 14 Pcdha genes and 22 Pcdhb genes (Wu, S., et al. 2007). Targeting strategies were designed for disrupting 34 additional classic cadherin and protocadherin genes (Table 7 FIG. 9-11), following the principles outlined above. To create these targeting vectors, BAC clones containing the desired genomic regions were used (bacpac.chori.org/). The modular nature of the disclosed cloning method made it possible to handle dozens of targeting vectors at a time. It was possible to subclone genomic regions for these genes into the pStart-K vector with an average efficiency of >40% (4 out 10 colonies picked contained the genomic region of interest) (FIG. 6C). For the next step (FIG. 6D), Red-competent DH5α/pKD46 cells were used. With only 50 nt homology for recombination, this step (FIG. 6d) had greater than 90% efficiency. Restriction enzyme-based cloning was next used to insert the reporter/neo cassette into the AscI site (FIG. 6E). Although this was non-directional cloning (single AscI site), almost all of the transformants in this ligation step contained an insert, with ~50% having the desired orientation. For the final step (FIG. 6F,G), a series of TK vectors could be chosen (FIG. 7B). Since Gateway recombination (Invitrogen) is very efficient, virtually every clone contained the desired insert (that is, homology arms with reporter/neo cassette).

All of the targeting vectors listed in Table 7 were constructed using the method outlined above. When these plasmid-based vectors were electroporated into mouse ES cells by electroporation, the overall targeting efficiency was 7.0%, higher than the reported targeting frequency obtained with targeting vectors generated from intact BACs (3.8%) (Valenzuela, D. M., et al. 2003). To date, germline transmission has been obtained for 12 of the targeted cell lines (Table 7. To further compare the different reporter/systems in vivo, the expression patterns of these knockout alleles was analyzed.

In general, all of the reporter/neo cassettes tested could be used to examine the endogenous gene expression pattern. However, different reporters showed different properties in vivo. Expression patterns of Fat2 and Fat3 revealed by knockin reporter alleles. Fat2 was mainly expressed in the cerebellum and pontine nuclei. Weak expression was also observed in distinct neurons in the glomerular layer of the olfactory bulb and in the pontine central gray and the vestibular nucleus. Fat3 expression was strong in the forebrain, but weak in the midbrain and hindbrain in a sagittal section. Many regions in the forebrain including the mitral cell layer of the olfactory bulb and anterior olfactory nuclei, and the hippocampus, have strong Fat3 expression. In the hippocampus, Fat3 is expressed strongly in the CA1 and the dentate gyrus, but at a very low level in the CA3 and dentate hilus. Fat3 shows a layer-specific expression pattern in the cortex in a coronal section. Strong labeling is mainly localized to layers 4 and 5 of the neocortex. Strong signals are also observed in striatum.

Pcdha types A and B have similar expression pattern in the brain. In the olfactory bulb, Pcdha types A and B were strongly expressed in the olfactory nerve layer and glomerular layer but very weak in other layers. In the hippocampus, the signal was observed in the pyramidal cell layer and granule cell layer and hilus. In the cerebellum, both types A and B were strongly expressed in the Purkinje cell layer and molecular layer, but weakly in the granular cell layer. Both were also strongly expressed in the midbrain Raphe nucleus.

Pcdhac1 was widely expressed at various brain regions throughout rostra-caudal levels, including olfactory bulb, cortex, striatum and septum, cortex, hippocampus and thalamus, midbrain, and cerebellum and pons. At P10, the strongest expression was in the olfactory bulb, basal ganglia, midbrain, and cerebellar nucleus and Pons; while at adult, the expression was evenly distributed throughout the brain. In the P10 cortex, Pcdhac1 showed an interesting patch-like expression pattern in the sensory cortical region, possibly in layer 2/3. This pattern was no longer seen in the adult cortex, where Pcdhac1 was localized in all layers. Note that no expression was detected in the hippocampal pyramidal cells, dentate granule cells, and cerebellar granule cells in either P10 or adult brain. AP staining using P10 wt brain was negative. As a separate example, AP expression was examined in an NgR$^{AP}$ allele. NgR was expressed in the nervous system.

The results indicate that EGFP and nlacZ (lacZ containing a nuclear localization signal) reporters were superior to others tested. While EGFP can usually be observed directly by fluorescence microscopy without immunostaining, the nlacZ reporter yields very high resolution at the cellular level. For example, in the Fat2$^{EGFP}$ allele, EGFP is very strongly expressed in the cerebellum and pons, in a pattern very similar to the previously reported Fat2 antibody staining pattern (Nakayama, M., et al. 2002). In the Fat3$^{nlacZ}$ allele, nlacZ is widely expressed in the nervous system of adults. Due to the robustness of lacZ, it was possible to obtain a clearer expression pattern for Fat3 than the previously reported antibody staining patterns (Nagae, S., et al. 2007). In contrast to EGFP and nlacZ, the alkaline phosphatase (AP) reporter yielded lower resolution patterns, especially in the nervous system.

Homozygosity for many of these mutant alleles resulted in interesting phenotypes. For example, homozygotes of Fat4$^{EGFP}$ die as newborns, with a curly tail that indicates a role for this gene in the planar cell polarity pathway. Homozygotes for the Celsr3$^{EGFP}$ allele also died as newborns, similar to the recently reported allele (Tissir, F., et al. 2005). However, the built-in EGFP reporter in the examined allele allowed examination of the fate of Celsr3 expressing cells in vivo. On the other hand, Celsr2$^{EGFP}$ homozygotes showed no detectable phenotypes in the development of dendritic tree, in marked contrast to the reported RNA interference (RNAi) study (Shima, Y., et al. 2004). Detailed studies of Celsr2$^{EGFP}$ and Celsr3$^{EGFP}$ alleles as well as the others will be reported separately.

Disclosed is a procedure that allows for rapid production of sophisticated targeting vectors. This procedure breaks down the complexity of targeting vector construction into a few simple modular steps that can be used for the routine generation of custom-designed targeting vectors. It has been fully tested and has been used to generate a broad spectrum of knockout mouse lines. This protocol makes it possible for a single investigator with basic molecular cloning experience to construct targeting vectors at a high speed of up to several hundred vectors per year. In addition, the same modular cassettes and cloning methods described here have been used to generate targeting vectors for use in other mammalian cell types with similar targeting frequencies to those for mouse ES cells.

Different reporters were compared in vivo: EGFP, EYFP, ECFP, Cre, LacZ, and AP. It appears that EGFP, lacZ and Cre are good choices. If higher resolution is required, the inclusion of a nuclear localization signal for the reporter gene is beneficial. For the purpose of visually labeling neurons and their projections, a tau-EGFP reporter has also been used (Tvrdik, P., et al. 2006).

Gene targeting is experiencing an ever greater demand in the post-genomic era. The readily available DNA sequence data can be used to optimize positioning of targeting vectors so as to avoid regions containing excessive repetitive DNA content. Knockout alleles can be created for every mouse gene (The International Mouse Knockout Consortium. 2007; Austin, C. P., et al. 2004; Auwerx, J., et al. 2004). For these large-scale projects, the disclosed streamlined approach can be useful. The use of self-excision neo cassettes such as the ACN (Bunting, M., et al. 1999), and Flp-FRT-based cassettes, on a large scale can save years of mouse husbandry work. Even with the completion of the large-scale knockout mouse projects (The International Mouse Knockout Consortium. 2007), the need for more custom-designed loss- or gain-of-function alleles, such as point mutations, gene-swaps, Cre-drivers, and many others will inevitably continue to rise.

L. References

Accili, D. A note of caution on the Knockout Mouse Project. Nat Genet 36, 1132 (2004).
Adams, D. J. et al. A genome-wide, end-sequenced 129Sv BAC library resource for targeting vector construction. Genomics 86, 753-8 (2005).
Adams, D. J. et al. Mutagenic insertion and chromosome engineering resource (MICER). Nat Genet 36, 867-71 (2004).
Angrand, P. O., Daigle, N., van der Hoeven, F., Scholer, H. R. & Stewart, A. F. Simplified generation of targeting constructs using ET recombination. Nucleic Acids Res 27, e16 (1999).
Austin, C. P. et al. The knockout mouse project. Nat Genet 36, 921-4 (2004).
Auwerx, J. et al. The European dimension for the mouse genome mutagenesis program. Nat Genet 36, 925-7 (2004).
Baudin, A., Ozier-Kalogeropoulos, O., Denouel, A., Lacroute, F. & Cullin, C. A simple and efficient method for direct gene deletion in Saccharomyces cerevisiae. Nucleic Acids Res 21, 3329-30 (1993).
Bejerano, G. et al. Ultraconserved elements in the human genome. Science 304, 1321-5 (2004).
Bejerano, G., Haussler, D. & Blanchette, M. Into the heart of darkness: large-scale clustering of human non-coding DNA. Bioinformatics 20 Suppl 1, I40-I48 (2004).
Boffelli, D., Nobrega, M. A. & Rubin, E. M. Comparative genomics at the vertebrate extremes. Nat Rev Genet 5, 456-65 (2004).
Bolivar, F., Rodriguez, R. L., Greene, P. J., Betlach, M. C., Heyneker, H. L., and Boyer, H. W. (1977). Construction and characterization of new cloning vehicles. II. A multipurpose cloning system. Gene 2, 95-113.

Bonin, C. P. & Mann, R. S. A piggyBac transposon gene trap for the analysis of gene expression and function in *Drosophila*. Genetics 167, 1801-11 (2004).

Bradshaw, M. S., Bollekens, J. A. & Ruddle, F. H. A new vector for recombination based cloning of large DNA fragments from yeast artificial chromosomes. Nucleic Acids Res 23, 4850-6 (1995).

Branda, C. S. & Dymecki, S. M. Talking about a revolution: The impact of site specific recombinases on genetic analyses in mice. Dev Cell 6, 7-28 (2004).

Buchholz, F., Refaeli, Y., Trumpp, A. & Bishop, J. M. Inducible chromosomal translocation of AML1 and ETO genes through Cre/loxP-mediated recombination in the mouse. EMBO Rep 1, 133-9 (2000).

Bunting, M., Bernstein, K. E., Greer, J. M., Capecchi, M. R. & Thomas, K. R. Targeting genes for self-excision in the germ line. Genes Dev 13, 1524-8 (1999).

Capecchi, M. R. Altering the genome by homologous recombination. Science 244, 1288-92 (1989b).

Capecchi, M. R. The new mouse genetics: altering the genome by gene targeting. Trends Genet 5, 70-6 (1989a).

Cary, L. C. et al. Transposon mutagenesis of baculoviruses: analysis of *Trichoplusia ni* transposon IFP2 insertions within the FP-locus of nuclear polyhedrosis viruses. Virology 172, 156-69 (1989).

Chan, W. et al. A recombineering based approach for high-throughput conditional knockout targeting vector construction. Nucleic Acids Res 35, e64 (2007).

Chang, A. C., and Cohen, S. N. (1978). Construction and characterization of amplifiable multicopy DNA cloning vehicles derived from the P15A cryptic miniplasmid. J Bacteriol 134, 1141-1156.

Chomczynski, P. One-hour downward alkaline capillary transfer for blotting of DNA and RNA. Anal Biochem 201, 134-9 (1992).

Collins, E. C., Pannell, R., Simpson, E. M., Forster, A. & Rabbitts, T. H. Inter-chromosomal recombination of M11 and Af9 genes mediated by cre-loxP in mouse development. EMBO Rep 1, 127-32 (2000).

Copeland, N. G., Jenkins, N. A. & Court, D. L. Recombineering: a powerful new tool for mouse functional genomics. Nat Rev Genet 2, 769-79 (2001).

Datsenko, K. A. & Wanner, B. L. One-step inactivation of chromosomal genes in *Escherichia coli* K-12 using PCR products. Proc Natl Acad Sci USA 97, 6640-5 (2000).

Deng, C. & Capecchi, M. R. Reexamination of gene targeting frequency as a function of the extent of homology between the targeting vector and the target locus. Mol Cell Biol 12, 3365-71 (1992).

Dermitzakis, E. T., Reymond, A. & Antonarakis, S. E. Conserved non-genic sequences—an unexpected feature of mammalian genomes. Nat Rev Genet 6, 151-7 (2005).

Ding, S. et al. Efficient transposition of the piggyBac (PB) transposon in mammalian cells and mice. Cell 122, 473-83 (2005).

Dracopoli, N. C. et al. Current Protocols in Human Genetics. 1, 4.1.1-4.1.4 (2006).

Ellis et al. Proc. Natl. Acad. Sci, 98:6742-6746.

Fraser, M. J., Ciszczon, T., Elick, T. & Bauser, C. Precise excision of TTAA-specific lepidopteran transposons piggyBac (IFP2) and tagalong (TFP3) from the baculovirus genome in cell lines from two species of Lepidoptera. Insect Mol Biol 5, 141-51 (1996).

Friedrich, G. & Soriano, P. Promoter traps in embryonic stem cells: a genetic screen to identify and mutate developmental genes in mice. Genes Dev 5, 1513-23 (1991).

Genoud, N. et al. Disruption of Doppel prevents neurodegeneration in mice with extensive Prnp deletions. Proc Natl Acad Sci USA 101, 4198-203 (2004).

George, S. H. et al. Developmental and adult phenotyping directly from mutant embryonic stem cells. Proc Natl Acad Sci USA 104, 4455-60 (2007).

Golic, K. G. & Golic, M. M. Engineering the *Drosophila* genome: chromosome rearrangements by design. Genetics 144, 1693-711 (1996).

Hambsch, B., Grinevich, V., Seeburg, P. H. & Schwarz, M. K. {gamma}-Protocadherins, presenilin-mediated release of C-terminal fragment promotes locus expression. J Biol Chem 280, 15888-97 (2005).

Hamilton, C. M., Aldea, M., Washburn, B. K., Babitzke, P. & Kushner, S. R. New method for generating deletions and gene replacements in *Escherichia coli*. J Bacteriol 171, 4617-22 (1989).

Handler, A. M. & Harrell, R. A., 2nd. Transformation of the Caribbean fruit fly, *Anastrepha suspensa*, with a piggyBac vector marked with polyubiquitin-regulated GFP. Insect Biochem Mol Biol 31, 199-205 (2001).

Hansen, J. et al. A large-scale, gene-driven mutagenesis approach for the functional analysis of the mouse genome. Proc Natl Acad Sci USA 100, 9918-22 (2003).

Harfe, B. D. et al. Evidence for an expansion-based temporal Shh gradient in specifying vertebrate digit identities. Cell 118, 517-28 (2004).

Hartley, J. L., Temple, G. F. & Brasch, M. A. DNA cloning using in vitro site specific recombination. Genome Res 10, 1788-95 (2000).

Herault, Y., Rassoulzadegan, M., Cuzin, F. & Duboule, D. Engineering chromosomes in mice through targeted meiotic recombination (TAMERE). Nat Genet 20, 381-4 (1998).

Huber, A. B. et al. Distinct roles for secreted semaphorin signaling in spinal motor axon guidance. Neuron 48, 949-64 (2005).

Inoue, H., Nojima, H. & Okayama, H. High efficiency transformation of *Escherichia coli* with plasmids. Gene 96, 23-8 (1990).

Jossin, Y. et al. The central fragment of Reelin, generated by proteolytic processing in vivo, is critical to its function during cortical plate development. J Neurosci 24, 514-21 (2004).

Kahn, M., Kolter, R., Thomas, C., Figurski, D., Meyer, R., Remaut, E., and Helinski, D. R. (1979). Plasmid cloning vehicles derived from plasmids ColE1, F, R6K, and RK2. Methods in enzymology 68, 268-280.

Kmita, M., Fraudeau, N., Herault, Y. & Duboule, D. Serial deletions and duplications suggest a mechanism for the collinearity of Hoxd genes in limbs. Nature 420, 145-50 (2002).

Kohmura, N. et al. Diversity revealed by a novel family of cadherins expressed in neurons at a synaptic complex. Neuron 20, 1137-51 (1998).

Lee, E. C. et al. A highly efficient *Escherichia coli*-based chromosome engineering system adapted for recombinogenic targeting and subcloning of BAC DNA. Genomics 73, 56-65 (2001).

Li, X. et al. piggyBac internal sequences are necessary for efficient transformation of target genomes. Insect Mol Biol 14, 17-30 (2005).

Liu, P., Jenkins, N. A. & Copeland, N. G. Efficient Cre-loxP-induced mitotic recombination in mouse embryonic stem cells. Nat Genet 30, 66-72 (2002).

Liu, P., Jenkins, N. A. & Copeland, N. G. A highly efficient recombineering-based method for generating conditional knockout mutations. Genome Res 13, 476-84 (2003).

Mansour, S. L., Thomas, K. R. & Capecchi, M. R. Disruption of the proto-oncogene int-2 in mouse embryo-derived stem cells: a general strategy for targeting mutations to non-selectable genes. Nature 336, 348-52 (1988).

Margulies, E. H. et al. Comparative sequencing provides insights about the structure and conservation of marsupial and monotreme genomes. Proc Natl Acad Sci USA 102, 3354-9 (2005).

Mills, A. A. & Bradley, A. From mouse to man: generating megabase chromosome rearrangements. Trends Genet 17, 331-9 (2001).

Moon, A. M. & Capecchi, M. R. Fgf8 is required for outgrowth and patterning of the limbs. Nat Genet 26, 455-9 (2000).

Nagae, S., Tanoue, T. & Takeichi, M. Temporal and spatial expression profiles of the Fat3 protein, a giant cadherin molecule, during mouse development. Dev Dyn 236, 534-43 (2007).

Nagy, A. Cre recombinase: the universal reagent for genome tailoring. Genesis 26, 99-109 (2000).

Nakayama, M., Nakajima, D., Yoshimura, R., Endo, Y. & Ohara, O. MEGF1/fat2 proteins containing extraordinarily large extracellular domains are localized to thin parallel fibers of cerebellar granule cells. Mol Cell Neurosci 20, 563-78 (2002).

Nobrega, M. A., Zhu, Y., Plajzer-Frick, I., Afzal, V. & Rubin, E. M. Megabase deletions of gene deserts result in viable mice. Nature 431, 988-93 (2004).

Oliner, J. D., Kinzler, K. W. & Vogelstein, B. In vivo cloning of PCR products in E. coli. Nucleic Acids Res 21, 5192-7 (1993).

Phillips, G. R. et al. Gamma-protocadherins are targeted to subsets of synapses and intracellular organelles in neurons. J Neurosci 23, 5096-104 (2003).

Price, S. R., De Marco Garcia, N. V., Ranscht, B. & Jessell, T. M. Regulation of motor neuron pool sorting by differential expression of type II cadherins. Cell 109, 205-16 (2002).

Ryder, E. et al. The DrosDel collection: a set of P-element insertions for generating custom chromosomal aberrations in *Drosophila melanogaster*. Genetics 167, 797-813 (2004).

Sandelin, A. et al. Arrays of ultraconserved non-coding regions span the loci of key developmental genes in vertebrate genomes. BMC Genomics 5, 99 (2004).

Schmidt, E. E., Taylor, D. S., Prigge, J. R., Barnett, S. & Capecchi, M. R. Illegitimate Cre-dependent chromosome rearrangements in transgenic mouse spermatids. Proc Natl Acad Sci USA 97, 13702-7 (2000).

Senzaki, K., Ogawa, M. & Yagi, T. Proteins of the CNR family are multiple receptors for Reelin. Cell 99, 635-47 (1999).

Shima, Y., Kengaku, M., Hirano, T., Takeichi, M. & Uemura, T. Regulation of dendritic maintenance and growth by a mammalian 7-pass transmembrane cadherin. Dev Cell 7, 205-16 (2004).

Skarnes, W. C. et al. A public gene trap resource for mouse functional genomics. Nat Genet 36, 543-4 (2004).

Spitz, F., Herkenne, C., Morris, M. A., and Duboule, D. (2005). Inversion-induced disruption of the Hoxd cluster leads to the partition of regulatory landscapes. Nat Genet. 37, 889-893.

Sugino, H. et al. Genomic organization of the family of CNR cadherin genes in mice and humans. Genomics 63, 75-87 (2000).

Takeichi, M. The cadherin superfamily in neuronal connections and interactions. Nat Rev Neurosci 8, 11-20 (2007).

Tang, S. H., Silva, F. J., Tsark, W. M. & Mann, J. R. A Cre/loxP-deleter transgenic line in mouse strain 129S1/SvImJ. Genesis 32, 199-202 (2002).

te Riele, H., Maandag, E. R. & Berns, A. Highly efficient gene targeting in embryonic stem cells through homologous recombination with isogenic DNA constructs. Proc Natl Acad Sci USA 89, 5128-32 (1992).

Testa, G. et al. Engineering the mouse genome with bacterial artificial chromosomes to create multipurpose alleles. Nat Biotechnol 21, 443-7 (2003).

The International Mouse Knockout Consortium. A mouse for all reasons. Cell 128, 9-13 (2007).

Thomas, K. R., Folger, K. R. & Capecchi, M. R. High frequency targeting of genes to specific sites in the mammalian genome. Cell 44, 419-28 (1986).

Thomas, K. R. & Capecchi, M. R. Site-directed mutagenesis by gene targeting in mouse embryo-derived stem cells. Cell 51, 503-12 (1987).

Tissir, F. & Goffinet, A. M. Reelin and brain development. Nat Rev Neurosci 4, 496-505 (2003).

Tissir, F., Bar, I., Jossin, Y., De Backer, O. & Goffinet, A. M. Protocadherin Celsr3 is crucial in axonal tract development. Nat Neurosci 8, 451-7 (2005).

Truett, G. E. et al. Preparation of PCR-quality mouse genomic DNA with hot sodium hydroxide and tris (HotSHOT). Biotechniques 29, 52, 54 (2000).

Tvrdik, P. & Capecchi, M. R. Reversal of Hox1 gene subfunctionalization in the mouse. Dev Cell 11, 239-50 (2006).

Valenzuela, D. M. et al. High-throughput engineering of the mouse genome coupled with high-resolution expression analysis. Nat Biotechnol 21, 652-9 (2003).

Vavouri, T., McEwen, G. K., Woolfe, A., Gilks, W. R. & Elgar, G. Defining a genomic radius for long-range enhancer action: duplicated conserved non-coding elements hold the key. Trends Genet 22, 5-10 (2006).

Ventura, A. et al. Restoration of p53 function leads to tumour regression in vivo. Nature 445, 661-5 (2007).

Wang, X. et al. Gamma protocadherins are required for survival of spinal interneurons. Neuron 36, 843-54 (2002).

Weiner, J. A., Wang, X., Tapia, J. C. & Sanes, J. R. Gamma protocadherins are required for synaptic development in the spinal cord. Proc Natl Acad Sci USA 102, 8-14 (2005).

Wu, Q. & Maniatis, T. A striking organization of a large family of human neural cadherin-like cell adhesion genes. Cell 97, 779-90 (1999).

Wu, Q. & Maniatis, T. Large exons encoding multiple ectodomains are a characteristic feature of protocadherin genes. Proc Natl Acad Sci USA 97, 3124-9 (2000).

Wu, Q. Comparative genomics and diversifying selection of the clustered vertebrate protocadherin genes. Genetics 169, 2179-88 (2005).

Wu, Q. et al. Comparative DNA sequence analysis of mouse and human protocadherin gene clusters. Genome Res 11, 389-404 (2001).

Wu, S., Wu, Y. & Capecchi, M. R. Motoneurons and oligodendrocytes are sequentially generated from neural stem cells but do not appear to share common lineage-restricted progenitors in vivo. Development 133, 581-90 (2006).

Wu, S., Ying, G., Wu, Q. & Capecchi, M. R. Toward simpler and faster genomewide mutagenesis in mice. Nat Genet (2007).

Yang, X. W., Model, P. & Heintz, N. Homologous recombination based modification in *Escherichia coli* and germline transmission in transgenic mice of a bacterial artificial chromosome. Nat Biotechnol 15, 859-65 (1997).

Yang, Y. & Seed, B. Site-specific gene targeting in mouse embryonic stem cells with intact bacterial artificial chromosomes. Nat Biotechnol 21, 447-51 (2003).

Yu, D. et al. An efficient recombination system for chromosome engineering in *Escherichia coli*. Proc Natl Acad Sci USA 97, 5978-83 (2000).

Zhang, P., Li, M. Z. & Elledge, S. J. Towards genetic genome projects: genomic library screening and gene-targeting vector construction in a single step. Nat Genet 30, 31-9 (2002).

Zhang, Y., Buchholz, F., Muyrers, J. P. & Stewart, A. F. A new logic for DNA engineering using recombination in *Escherichia coli*. Nat Genet 20, 123-8 (1998).

Zhang, Y., Muyrers, J. P., Testa, G. & Stewart, A. F. DNA cloning by homologous recombination in *Escherichia coli*. Nat Biotechnol 18, 1314-7 (2000).

Zheng, B., Sage, M., Sheppeard, E. A., Jurecic, V. & Bradley, A. Engineering mouse chromosomes with Cre-loxP: range, efficiency, and somatic applications. Mol Cell Biol 20, 648-55 (2000).

M. Sequences

```
1. SEQ ID NO: 1
ATCTTGGTGTGACAGCGATACG

2. SEQ ID NO: 2
CTCAGTTCAAGCGAAAGGGATT

3. SEQ ID NO: 3
AGATGAACTTCAGGGTCAGCTTGC

4. SEQ ID NO: 4
TTTCCAGTCTCCTCTCCAGGAGTTC

5. SEQ ID NO: 5
TAGTTGGAAAGGAAGCGAAAGTTCC

6. SEQ ID NO: 6
TTGTATGTCTTGGACAGAGCCACAT

7. SEQ ID NO: 7
TTGTAGTGCGTGAGAGGTGAAG

8. SEQ ID NO: 8
CATTGGTCAAGTCCAGTTCCAG

9. SEQ ID NO: 9
CAAACCTCCACTCTCCATTGAG

10. SEQ ID NO: 10
GCCATAACAGTGTTTGAGAAGTGAGG

11. SEQ ID NO: 11
AGGGGTAACCACATAGCTCTGGAAG

12. SEQ ID NO: 12
CAGGCACACCTTCAGTCCTGTAGTC

13. SEQ ID NO: 13
CAGAAAGAGTTGGAGTCCTTGTGGA

14. SEQ ID NO: 14
GACAACAGCCTCTTCAACTGATGGA

15. SEQ ID NO: 15
ACGAAGTTATGAATTCGCCCTTGTT

16. SEQ ID NO: 16
AGGCTGAATAACGTGCACAGCTAAG

17. SEQ ID NO: 17
TGCAGATTGGTTCAATGGAGTCTTT

18. SEQ ID NO: 18
AGGCTGAATAACGTGCACAGCTAAG

19. SEQ ID NO: 19
TGCAGATTGGTTCAATGGAGTCTTT

20. SEQ ID NO: 20
CCCTTTCCTAGATTCCCCTCAAAAA

21. SEQ ID NO: 21
GGAGCCTGCTAACAACCAAATTGAC

22. SEQ ID NO: 22
GAGGGCTCATGTCATAGGAGAAAGG

23. SEQ ID NO: 23
CACTGCACGCCCCAGGTCAG

24. SEQ ID NO: 24
AAGCAGACCCAGGTTTCCTTTCTCC

25. SEQ ID NO: 25
CTCTTGGTAGCCACACATACCCAGT

26. SEQ ID NO: 26
AAGCACTGCAGGCCGTAGCC

27. SEQ ID NO: 27
GGATATTTCCTGTCTTGTTCCCAGGT

28. SEQ ID NO: 28
ACCAAATGGAAACAAGCCACTTAGC

29. SEQ ID NO: 29
GGCTGGGAAGCTTCTCCTTTGC

30. SEQ ID NO: 30
AATGGAAACAAGCCACTTAGCCAGT

31. SEQ ID NO: 31
GGCTGGGAAGCTTCTCCTTTGC

32. SEQ ID NO: 32
CGAAGTTATGAATTCGCCCTTGTTA

33. SEQ ID NO: 33
GCTTGAGAGAGGGAGTGACAAAGTG

34. SEQ ID NO: 34
TCCCTTACACAATGTGGCAGAAGTT

35. SEQ ID NO: 35
GAGCACGTACCCAGATATGGAATTG

36. SEQ ID NO: 36
GCTGGTGTGTCTTTCTCTGGAGCTA

37. SEQ ID NO: 37
GGATGTTAAAGCTGACGACACATGG

38. SEQ ID NO: 38
AGCTCTGGATGAAGAAGTCGCTGAT

39. SEQ ID NO: 39
CCACTGCTCCCTGAGATCGAAT

40. SEQ ID NO: 40
CTGGAAGACACTTGGATCACCATCT

41. SEQ ID NO: 41
CAGTTATCTGCTGGCAGGTACCACT

42. SEQ ID NO: 42
TGCCAGAGGAGTCAAACCACATAAT

43. SEQ ID NO: 43
CCCCCTGAACCTGAAACATAAAATG

44. SEQ ID NO: 44
TGCAGATTGGTTCAATGGAGTCTTT
```

-continued

45. SEQ ID NO: 45
AGGCTGAATAACGTGCACAGCTAAG

46. SEQ ID NO: 46
CCCTTTCCTAGATTCCCCTCAAAAA

47. SEQ ID NO: 47
CCCTAACACCACCACTACCCAAAAT

48. SEQ ID NO: 48
ACAACCACTACCTGAGCACCCAGTC

49. SEQ ID NO: 49
AAAGCTGCGACCTACCTCTGGAAAC

50. SEQ ID NO: 50
AAGGACTTCCCCGAGTACCACTTC

51. SEQ ID NO: 51
AGCCACAGCTCAAATTTGGACTTAC

52. SEQ ID NO: 52
CCACTGCTCCCTGAGATCGAAT

53. SEQ ID NO: 53
CTGGAAGACACTTGGATCACCATCT

54. SEQ ID NO: 54
CAGTTATCTGCTGGCAGGTACCACT

55. SEQ ID NO: 55
TGCCAGTGTCTGAAGGAGATGC

56. SEQ ID NO: 56
TTAAGAGAGGAGGAATTTATTCTG

57. SEQ ID NO: 57
TTAAGAAGGCTGTCTGTGCTGACC

58. SEQ ID NO: 58
TTAATGGTGTTATTTGATTTTCTG

59. SEQ ID NO: 59
TTAAAATGAACTCTAGAACCTCCT

60. SEQ ID NO: 60
TTAAAAGATTTATTTATTTTATTT

61. SEQ ID NO: 61
TTAAAGGCGTGCGCCACCACAACC

62. SEQ ID NO: 62
TTAAATGTATTTACTTACTTATTT

63. SEQ ID NO: 63
TTAAAGAATAAAAGATGGTGTCTT

64. SEQ ID NO: 64
TTAAACAAGGATAAAAGCAATCTA

65. SEQ ID NO: 65
TTAACATATAGTAACTGTGTGTAT

66. SEQ ID NO: 66
TTAAGGAGACTAGTGAAAGTGAAC

67. SEQ ID NO: 67
TTAATAAATTAATCAGTCACTTAA

68. SEQ ID NO: 68
TTAACTAGATCCTCTACATATTTG

69. SEQ ID NO: 69
TTAAGTAATACAGGAAAAGAGGAA

70. SEQ ID NO: 70
TTAAATCTGGGTCTAGATTTTCGG

71. SEQ ID NO: 71
TTAAGGTGTCTCTATGTAGTCTTG

-continued

72. SEQ ID NO: 72
TTAAGCAACCTGCTGAATCAAACC

73. SEQ ID NO: 73
TTAAGGACCATTCACAAAATATGG

74. SEQ ID NO: 74
TTAAGCTGCTTGCTGGATCTTTTG

75. SEQ ID NO: 75
TTAAAGAAGAGTGCTGCTTCTATG

76. SEQ ID NO: 76
TTAAATAAAACCAGTTAAAAATAA

77. SEQ ID NO: 77
CTAGATCATATCCAAGTTTTTTATCCTCTGAAGCCATTAAAATTAAGTTG

CGACTGAATTGGTTCCTTTAAAGCC

78. SEQ ID NO: 78
GACCAACCAACTTCTCCTGGGCATGGGGCCTGCCCTGGAGTGTGGTTTAC

GCCGCACTCGAGATATCTAGACCCA

79. SEQ ID NO: 79
TAAACTGCCAGGCATCAAACTAAGC

80. SEQ ID NO: 80
AGTCAGCCCCATACGATATAAGTTG

81. SEQ ID NO: 81
GAGCATGGTCCCGGGTCGCCGCAACTGGAGCGTGGAGGCCGAAAGGGAGG

ATGGTGGCGCGCCAGCATTACACGTCTTGAGCGATTGT

82. SEQ ID NO: 82
TAGTAACTATCTCCTTGCCAGAGGAGTCAAACCACATAATATGTGCTTAC

GGCGCGCCCACTTAACGGCTGACATGGGAATTA

83. SEQ ID NO: 83
ATGCCGCTGGCGATTCAGGTTC

84. SEQ ID NO: 84
GCCGATCAACGTCTCATTTTCG

85. SEQ ID NO: 85
CCTCGATATACAGACCGATAAAACACATGC

86. SEQ ID NO: 86
AGTCAGTCAGAAACAACTTTGGCACATATC

87. SEQ ID NO: 87
GTCAGTCAGAAACAACTTTGGCACATATC

88. SEQ ID NO: 88
CAGATCGATAAAACACATGCGTCAATTT

89. SEQ ID NO: 89
TAACAAAACTTTTAAACATTCTCTCTTTTAC

90. SEQ ID NO: 90
ATAACTTCGTATAATGTATGCTATACGAAGTTAT

91. SEQ ID NO: 91
ATAACTTCGTATAGCATACATTATACGAAGTTAT

92. SEQ ID NO: 92
(Wildtype piggyBac transposase)
ATGGGTAGTTCTTTAGACGATGAGCATATCCTCTCTGCTCTTCTGCAAAG

CGATGACGAGCTTGTTGGTGAGGATTCTGACAGTGAAATATCAGATCACG

TAAGTGAAGATGACGTCCAGAGCGATACAGAAGAAGCGTTTATAGATGAG

GTACATGAAGTGCAGCCAACGTCAAGCGGTAGTGAAATATTAGACGAACA

AAATGTTATTGAACAACCAGGTTCTTCATTGGCTTCTAACAGAATCTTGA

CCTTGCCACAGAGGACTATTAGAGGTAAGAATAAACATTGTTGGTCAACT

```
TCAAAGTCCACGAGGCGTAGCCGAGTCTCTGCACTGAACATTGTCAGATC
TCAAAGAGGTCCGACGCGTATGTGCCGCAATATATATGACCCACTTTTAT
GCTTCAAACTATTTTTTACTGATGAGATAATTTCGGAAATTGTAAAATGG
ACAAATGCTGAGATATCATTGAAACGTCGGGAATCTATGACAGGTGCTAC
ATTTCGTGACACGAATGAAGATGAAATCTATGCTTTCTTTGGTATTCTGG
TAATGACAGCAGTGAGAAAAGATAACCACATGTCCACAGATGACCTCTTT
GATCGATCTTTGTCAATGGTGTACGTCTCTGTAATGAGTCGTGATCGTTT
TGATTTTTTGATACGATGTCTTAGAATGGATGACAAAAGTATACGGCCCA
CACTTCGAGAAAACGATGTATTTACTCCTGTTAGAAAAATATGGGATCTC
TTTATCCATCAGTGCATACAAAATTACACTCCAGGGGCTCATTTGACCAT
AGATGAACAGTTACTTGGTTTTAGAGGACGGTGTCCGTTTAGGATGTATA
TCCCAAACAAGCCAAGTAAGTATGGAATAAAAAATCCTCATGATGTGTGAC
AGTGGTACGAAGTATATGATAAATGGAATGCCTTATTTGGGAAGAGGAAC
ACAGACCAACGGAGTACCACTCGGTGAATACTACGTGAAGGAGTTATCAA
AGCCTGTGCACGGTAGTTGTCGTAATATTACGTGTGACAATTGGTTCACC
TCAATCCCTTTGGCAAAAAACTTACTACAAGAACCGTATAAGTTAACCAT
TGTGGGAACCGTGCGATCAAACAAACGCGAGATACCGGAAGTACTGAAAA
ACAGTCGCTCCAGGCCAGTGGGAACATCGATGTTTTGTTTTGACGGACCC
CTTACTCTCGTCTCATATAAACCGAAGCCAGCTAAGATGGTATACTTATT
ATCATCTTGTGATGAGGATGCTTCTATCAACGAAAGTACCGGTAAACCGC
AAATGGTTATGTATTATAATCAAACTAAAGGCGGAGTGGACACGCTAGAC
CAAATGTGTTCTGTGATGACCTGCAGTAGGAAGACGAATAGGTGGCCTAT
GGCATTATTGTACGGAATGATAAACATTGCCTGCATAAATTCTTTTATTA
TATACAGCCATAATGTCAGTAGCAAGGGAGAAAAGGTTCAAAGTCGCAAA
AAATTTATGAGAAACCTTTACATGAGCCTGACGTCATCGTTTATGCGTAA
GCGTTTAGAAGCTCCTACTTTGAAGAGATATTTGCGCGATAATATCTCTA
ATATTTTGCCAAATGAAGTGCCTGGTACATCAGATGACAGTACTGAAGAG
CCAGTAATGAAAAAACGTACTTACTGTACTTACTGCCCCTCTAAAATAAG
GCGAAAGGCAAATGCATCGTGCAAAAAATGCAAAAAAGTTATTTGTCGAG
AGCATAATATTGATATGTGCCAAAGTTGTTTCTAA
```

93. SEQ ID NO: 93
(codon-optimized piggyBac transposase)
```
ATGGGCAGCAGCTGGACGACGAGCACATCCTGAGCGCCCTGCTGCAGAG
CGACGACGAGCTGGTGGGCGAGGACAGCGACAGCGAGATCAGCGACCACG
TGAGCGAGGACGACGTGCAGAGCGACACCGAGGAGGCCTTCATCGACGAG
GTGCACGAGGTGCAGCCCACCAGCAGCGGCAGCGAGATCCTGGACGAGCA
GAACGTGATCGAGCAGCCCGGCAGCAGCCTGGCCAGCAACAGGATCCTGA
CCCTGCCCCAGAGGACCATCAGGGGCAAGAACAAGCACTGCTGGAGCACC
AGCAAGAGCACCAGGAGGAGCAGGGTGAGCGCCCTGCACATCGTGAGGAG
CCAGAGGGGCCCCACCAGGATGTGCAGGAACATCTACGACCCCCTGCTGT
GCTTCAAGCTGTTCTTCACCGACGAGATCATCAGCGAGATCGTGAAGTGG
ACCAACGCCGAGATCAGCCTGAAGAGGAGGGAGAGCATGACCGGCGCCAC
```

```
CTTCAGGGACACCAACGAGGACGAGATCTACGCCTTCTTCGGCATCCTGG
TGATGACCGCCGTGAGGAAGGACAACCACATGAGCACCGACGACCTGTTC
GACAGGAGCCTGAGCATGGTGTACGTGAGCGTGATGAGCAGGGACAGGTT
CGACTTCCTGATCAGGTGCCTGAGGATGGACGACAAGAGCATCAGGCCCA
CCCTGAGGGAGAACGACGTGTTCACCCCCGTGAGGAAGATCTGGGACCTG
TTCATCCACCAGTGCATCCAGAACTACACCCCCGGCGCCCACCTGACCAT
CGACGAGCAGCTGCTGGGCTTCAGGGGCAGGTGCCCCTTCAGGATGTACA
TCCCCAACAAGCCCAGCAAGTACGGCATCAAGATCCTGATGATGTGCGAC
AGCGGCACCAAGTACATGATCAACGGCATGCCCTACCTGGGCAGGGGCAC
CCAGACCAACGGCGTGCCCCTGGGCGAGTACTACGTGAAGGAGCTGAGCA
AGCCCGTGCACGGCAGCTGCAGGAACATCACCTGCGACAACTGGTTCACC
AGCATCCCCCTGGCCAAGAACCTGCTGCAGGAGCCCTACAAGCTGACCAT
CGTGGGCACCGTGAGGAGCAACAAGAGGGAGATCCCCGAGGTGCTGAAGA
ACAGCAGGAGCAGGCCCGTGGGCACCAGCATGTTCTGCTTCGACGGCCCC
CTGACCCTGGTGAGCTACAAGCCCAAGCCCGCCAAGATGGTGTACCTGCT
GAGCAGCTGCGACGAGGACGCCAGCATCAACGAGAGCACCGGCAAGCCCC
AGATGGTGATGTACTACAACCAGACCAAGGGCGGCGTGGACACCCTGGAC
CAGATGTGCAGCGTGATGACCTGCAGCAGGAAGACCAACAGGTGGCCCAT
GGCCCTGCTGTACGGCATGATCAACATCGCCTGCATCAACAGCTTCATCA
TCTACAGCCACAACGTGAGCAGCAAGGGCGAGAAGGTGCAGAGCAGGAAG
AAGTTCATGAGGAACCTGTACATGAGCCTGACCAGCAGCTTCATGAGGAA
GAGGCTGGAGGCCCCCACCCTGAAGAGGTACCTGAGGGACAACATCAGCA
ACATCCTGCCCAACGAGGTGCCCGGCACCAGCGACGACAGCACCGAGGAG
CCCGTGATGAAGAAGAGGACCTACTGCACCTACTGCCCCAGCAAGATCAG
GAGGAAGGCCAACGCCAGCTGCAAGAAGTGCAAGAAGGTGATCTGCAGGG
AGCACAACATCGACATGTGCCAGAGCTGCTTCTAA
```

94. SEQ ID NO: 94
(Splice Acceptor)
```
TAGGGCGCAGTAGTCCAGGGTTTCCTTGATGATGTCATACTTATCCTGTC
CCTTTTTTTTCCACAGCTCGCGGTTGAGGACAAACTCTTCGCGGTCTTTC
CAGT
```

95. SEQ ID NO: 95
(3' TR)
```
CCCTAGAAAGATAATCATATTGTGACGTACGTTAAAGATAATCATGCGTA
AAATTGACGCATG
```

96. SEQ ID NO: 96
(5' TR)
```
CATGCGTCAATTTTACGCAGACTATCTTTCTAGGG
```

97. SEQ ID NO: 97
(FRT: 5')
```
GAAGTTCCTATTCTCTAGAAAGTATAGGAACTTC
```

98. SEQ ID NO: 98
(FRT: 5')
```
GAAGTTCCTATACTTTCTAGAGAATAGGAACTTC
```

99. SEQ ID NO: 99
(lacZ)
ATGGACCCTGTTGTGCTGCAAAGGAGAGACTGGGAGAACCCTGGAGTGAC
CCAGCTCAACAGACTGGCTGCCCACCCTCCCTTTGCCTCTTGGAGGAACT
CTGAGGAAGCCAGGACAGACAGGCCCAGCCAGCAGCTCAGGTCTCTCAAT
GGAGAGTGGAGGTTTGCCTGGTTCCCTGCCCCTGAAGCTGTGCCTGAGTC
TTGGCTGGAGTGTGACCTCCCAGAGGCTGACACTGTTGTGGTGCCAAGCA
ACTGGCAGATGCATGGCTATGATGCCCCCATCTACACCAATGTCACCTAC
CCCATCACTGTGAACCCCCCTTTTGTGCCCACTGAGAACCCCACTGGCTG
CTACAGCCTGACCTTCAATGTTGATGAGAGCTGGCTGCAAGAAGGCCAGA
CCAGGATCATCTTTGATGGAGTCAACTCTGCCTTCCACCTCTGGTGCAAT
GGCAGGTGGGTTGGCTATGGCCAAGACAGCAGGCTGCCCTCTGAGTTTGA
CCTCTCTGCCTTCCTCAGAGCTGGAGAGAACAGGCTGGCTGTCATGGTGC
TCAGGTGGTCTGATGGCAGCTACCTGGAAGACCAAGACATGTGGAGGATG
TCTGGCATCTTCAGGGATGTGAGCCTGCTGCACAAGCCCACCACCCAGAT
TTCTGACTTCCATGTTGCCACCAGGTTCAATGATGACTTCAGCAGAGCTG
TGCTGGAGGCTGAGGTGCAGATGTGTGGAGAACTCAGAGACTACCTGAGA
GTCACAGTGAGCCTCTGGCAAGGTGAGACCCAGGTGGCCTCTGGCACAGC
CCCCTTTGGAGGAGAGATCATTGATGAGAGGAGGCTATGCTGACAGAG
TCACCCTGAGGCTCAATGTGGAGAACCCCAAGCTGTGGTCTGCTGAGATC
CCCAACCTCTACAGGGCTGTTGTGGAGCTGCACACTGCTGATGGCACCCT
GATTGAAGCTGAAGCCTGTGATGTTGGATTCAGAGAAGTCAGGATTGAGA
ATGGCCTGCTGCTGCTCAATGGCAAGCCTCTGCTCATCAGGGGAGTCAAC
AGGCATGAGCACCACCCTCTGCATGGACAAGTGATGGATGAACAGACAAT
GGTGCAAGATATCCTGCTAATGAAGCAGAACAACTTCAATGCTGTCAGGT
GCTCTCACTACCCCAACCACCCTCTCTGGTACACCCTGTGTGACAGGTAT
GGCCTGTATGTTGTTGATGAAGCCAACATTGAGACACATGGCATGGTGCC
CATGAACAGGCTCACAGATGACCCCAGGTGGCTGCCTGCCATGTCTGAGA
GAGTGACCAGGATGGTGCAGAGAGACAGGAACCACCCCTCTGTGATCATC
TGGTCTCTGGGCAATGAGTCTGGACATGGAGCCAACCATGATGCTCTCTA
CAGGTGGATCAAGTCTGTTGACCCCAGCAGACCTGTGCAGTATGAAGGAG
GTGGAGCAGACACCACAGCCACAGACATCATCTGCCCCATGTATGCCAGG
GTTGATGAGGACCAGCCCTTCCCTGCTGTGCCCAAGTGGAGCATCAAGAA
GTGGCTCTCTCTGCCTGGAGAGACCAGACCTCTGATCCTGTGTGAATATG
CACATGCAATGGGCAACTCTCTGGGAGGCTTTGCCAAGTACTGGCAAGCC
TTCAGACAGTACCCCAGGCTGCAAGGAGGATTTGTGTGGGACTGGGTGGA
CCAATCTCTCATCAAGTATGATGAGAATGGCAACCCCTGGTCTGCCTATG
GAGGAGACTTTGGTGACACCCCCAATGACAGGCAGTTCTGCATGAATGGC
CTGGTCTTTGCAGACAGGACCCCTCACCCTGCCCTCACAGAGGCCAAGCA
CCAGCAACAGTTCTTCCAGTTCAGGCTGTCTGGACAGACCATTGAGGTGA
CATCTGAGTACCTCTTCAGGCACTCTGACAATGAGCTCCTGCACTGGATG
GTGGCCCTGGATGGCAAGCCTCTGGCTTCTGGTGAGGTGCCTCTGGATGT
GGCCCCTCAAGGAAAGCAGCTGATTGAACTGCCTGAGCTGCCTCAGCCAG
AGTCTGCTGGACAACTGTGGCTAACAGTGAGGGTGGTTCAGCCCAATGCA
ACAGCTTGGTCTGAGGCAGGCCACATCTCTGCATGGCAGCAGTGGAGGCT
GGCTGAGAACCTCTCTGTGACCCTGCCTGCTGCCTCTCATGCCATCCCTC
ACCTGACAACATCTGAAATGGACTTCTGCATTGAGCTGGGCAACAAGAGA
TGGCAGTTCAACAGGCAGTCTGGCTTCCTGTCTCAGATGTGGATTGGAGA
CAAGAAGCAGCTCCTCACCCCTCTCAGGGACCAATTCACCAGGGCTCCTC
TGGACAATGACATTGGAGTGTCTGAGGCCACCAGGATTGACCCAAATGCT
TGGGTGGAGAGGTGGAAGGCTGCTGGACACTACCAGGCTGAGGCTGCCCT
GCTCCAGTGCACAGCAGACACCCTGGCTGATGCTGTTCTGATCACCACAG
CCCATGCTTGGCAGCACCAAGGCAAGACCCTGTTCATCAGCAGAAAGACC
TACAGGATTGATGGCTCTGGACAGATGGCAATCACAGTGGATGTGGAGGT
TGCCTCTGACACACCTCACCCTGCAAGGATTGGCCTGAACTGTCAACTGG
CACAGGTGGCTGAGAGGGTGAACTGGCTGGGCTTAGGCCCTCAGGAGAAC
TACCCTGACAGGCTGACAGCTGCCTGCTTTGACAGGTGGGACCTGCCTCT
GTCTGACATGTACACCCCTTATGTGTTCCCTTCTGAGAATGGCCTGAGGT
GTGGCACCAGGGAGCTGAACTATGGTCCTCACCAGTGGAGGGGAGACTTC
CAGTTCAACATCTCCAGGTACTCTCAGCAACAGCTCATGGAAACCTCTCA
CAGGCACCTGCTCCATGCAGAGGAGGGAACCTGGCTGAACATTGATGGCT
TCCACATGGGCATTGGAGGAGATGACTCTTGGTCTCCTTCTGTGTCTGCT
GAGTTCCAGTTATCTGCTGGCAGGTACCACTATCAGCTGGTGTGGTGCCA
GAAGTAA 100. SEQ ID NO: 100
(EGFP)
ATGGTGAGCAAGGGCGAGGAGCTGTTCACCGGGGTGGTGCCCATCCTGGT
CGAGCTGGACGGCGACGTAAACGGCCACAAGTTCAGCGTGTCCGGCGAGG
GCGAGGGCGATGCCACCTACGGCAAGCTGACCCTGAAGTTCATCTGCACC
ACCGGCAAGCTGCCCGTGCCCTGGCCCACCCTCGTGACCACCCTGACCTA
CGGCGTGCAGTGCTTCAGCCGCTACCCCGACCACATGAAGCAGCACGACT
TCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGG
CGACACCCTGGTGAACCGCATCGAGCTGAAGGGCATCGACTTCAAGGAGG
ACGGCAACATCCTGGGGCACAAGCTGGAGTACAACTACAACAGCCACAAC
GTCTATATCATGGCCGACAAGCAGAAGAACGGCATCAAGGTGAACTTCAA
GATCCGCCACAACATCGAGGACGGCAGCGTGCAGCTCGCCGACCACTACC
AGCAGAACACCCCCATCGGCGACGGCCCCGTGCTGCTGCCCGACAACCAC
TACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCA
TGGACGAGCTGTACAAGTAA 101. SEQ ID NO: 101
(dsRed monomer)
ATGGACAACACCGAGGACGTCATCAAGGAGTTCATGCAGTTCAAGGTGCG

CATGGAGGGCTCCGTGAACGGCCACTACTTCGAGATCGAGGGCGAGGGCG

AGGGCAAGCCCTACGAGGGCACCCAGACCGCCAAGCTGCAGGTGACCAAG

GGCGGCCCCCTGCCCTTCGCCTGGGACATCCTGTCCCCCCAGTTCCAGTA

CGGCTCCAAGGCCTACGTGAAGCACCCCGCCGACATCCCCGACTACATGA

AGCTGTCCTTCCCCGAGGGCTTCACCTGGGAGCGCTCCATGAACTTCGAG

GACGGCGGCGTGGTGGAGGTGCAGCAGGACTCCTCCCTGCAGGACGGCAC

CTTCATCTACAAGGTGAAGTTCAAGGGCGTGAACTTCCCCGCCGACGGCC

CCGTAATGCAGAAGAAGACTGCCGGCTGGGAGCCCTCCACCGAGAAGCTG

TACCCCCAGGACGGCGTGCTGAAGGGCGAGATCTCCCACGCCCTGAAGCT

GAAGGACGGCGGCCACTACACCTGCGACTTCAAGACCGTGTACAAGGCCA

AGAAGCCCGTGCAGCTGCCCGGCAACCACTACGTGGACTCCAAGCTGGAC

ATCACCAACCACAACGAGGACTACACCGTGGTGGAGCAGTACGAGCACGC

CGAGGCCCGCCACTCCGGCTCCCAGTAG

102. SEQ ID NO: 102
(ECFP)
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTG

GGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACATCAGCCACAAC

GTCTATATCACCGCCGACAAGCAGAAGAACGGCATCAAGGCCAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA

103. SEQ ID NO: 103
(EYFP)
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCTTCGGCTA

CGGCCTGCAGTGCTTCGCCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCTACCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA

104. SEQ ID NO: 104
(mCherry)
ATGGTGAGCAAGGGCGAGGAGGACAACATGGCCATCATCAAGGAGTTCAT

GCGCTTCAAGGTGCACATGGAGGGCTCCGTGAACGGCCACGAGTTCGAGA

TCGAGGGCGAGGGCGAGGGCCGCCCCTACGAGGGCACCCAGACCGCCAAG

CTGAAGGTGACCAAGGGCGGCCCCCTGCCCTTCGCCTGGGACATCCTGTC

CCCTCAGTTCATGTACGGCTCCAAGGCCTACGTGAAGCACCCCGCCGACA

TCCCCGACTACTTGAAGCTGTCCTTCCCCGAGGGCTTCAAGTGGGAGCGC

GTGATGAACTTCGAGGACGGCGGCGTGGTGACCGTGACCCAGGACTCCTC

CCTGCAGGACGGCGAGTTCATCTACAAGGTGAAGCTGCGCGGCACCAACT

TCCCCTCCGACGGCCCCGTAATGCAGAAGAAGACCATGGGCTGGGAGGCC

TCCTCCGAGCGGATGTACCCCGAGGACGGCGCCCTGAAGGGCGAGATCAA

GCAGAGGCTGAAGCTGAAGGACGGCGGCCACTACGACGCCGAGGTCAAGA

CCACCTACAAGGCCAAGAAGCCCGTGCAGCTGCCCGGCGCCTACAACGTC

AACATCAAGCTGGACATCACCTCCCACAACGAGGACTACACCATCGTGGA

ACAGTACGAGCGCGCCGAGGGCCGCCACTCCACCGGCGGCATGGACGAGC

TGTACAAGTAA

105. SEQ ID NO: 105
(ZG-1)
TTAACCCTAGAAAGATAATCATATTGTGACGTACGTTAAAGATAATCATG

CGTAAAATTGACGCATGTGTTTTATCGGTCTGTATATCGAGGTTTATTTA

TTAATTTGAATAGATATTAAGTTTTATTATATTTACACTTACATACTAAT

AATAAATTCAACAAACAATTTATTTTATGTTTATTTATTTATTAAAAAAAA

ACAAAAACTCAAAATTTCTTCTATAAAGTAACAAAACTTTTAAACATTCT

CTCTTTTACAAAAATAAACTTATTTTGTACTTTAAAAACAGTCATGTTGT

ATTATAAAATAAGTAATTAGCTTAACTTATACATAATAGAAACAAATTAT

ACTTATTAGTCAGTCAGAAACAACTTTGGCACATATCAATATTATGCTCT

CGACAAATAACTTTTTTGCATTTTTTGCACGATGCATTTGCCTTTCGCCT

TATTTTAGAGGGGCAGTAAGTACAGTAAGTACGTTTTTTCATTACTGGCT

CTTCAGTACTGTCATCTGATGTACCAGGCACTTCATTTGGCAAAATATTA

GAGATATTATCGCGCAAATATCTCTTCAAAGTAGGAGCTTCTAAACGCTT

ACGCATAAACGATGACGTCAGGCTCATGTAAAGGTTTCTCATAAATTTTT

TGCGACTTTGAACCTTTTCTCCCTTGCTACTGACATTATGGCTGTATATA

ATAAAAGAATTTATGCAGGCAATGTTTATCATTCCGTACAATAATGCCAT

AGGCCACCTATTCGTCTTCCTACTGCAGGTCATCACAGAACACATTTGGT

CTAGCGTGTCCACTCCGCCTTTAGTTTGATTATAATACATAACCATTTGC

GGTTTACCGGTACTTTCGTTGATAGAAGCATCCTCATCACAAGATGATAA

-continued

```
TAAGTATACCATCTTAGCTGGCTTCGGTTTATATGAGACGAGAGTAAGGG
GTCCGTCAAAACAAAACATCGATGTTCCCACTGGCCTGGAGCGACTGTTA
ATAACTTCGTATAATGTATGCTATACGAAGTTATGCGATTAAGGGATCTG
TAGGGCGCAGTAGTCCAGGGTTTCCTTGATGATGTCATACTTATCCTGTC
CCTTTTTTTTCCACAGCTCGCGGTTGAGGACAAACTCTTCGCGGTCTTTC
CAGTGGGGATCGACGGTATCGTAGAGTCGAGGCCGCTCTAGCGGATCTGC
CCCTCTCCCTCCCCCCCCCCTAACGTTACTGGCCGAAGCCGCTTGGAATA
AGGCCGGTGTGCGTTTGTCTATATGTTATTTTCCACCATATTGCCGTCTT
TTGGCAATGTGAGGGCCCGGAAACCTGGCCCTGTCTTCTTGACGAGCATT
CCTAGGGGTCTTTCCCCTCTCGCCAAAGGAATGCAAGGTCTGTTGAATGT
CGTGAAGGAAGCAGTTCCTCTGGAAGCTTCTTGAAGACAAACAACGTCTG
TAGCGACCCTTTGCAGGCAGCGGAACCCCCCACCTGGCGACAGGTGCCTC
TGCGGCCAAAAGCCACGTGTATAAGATACACCTGCAAAGGCGGCACAACC
CCAGTGCCACGTTGTGAGTTGGATAGTGTGGAAAGAGTCAAATGGCTCT
CCTCAAGCGTATTCAACAAGGGGCTGAAGGATGCCCAGAAGGTACCCCAT
TGTATGGGATCTGATCTGGGGCCTCGGTGCACATGCTTTACATGTGTTTA
GTCGAGGTTAAAAAAACGTCTAGGCCCCCCGAACCACGGGGACTGGTTT
TCCTTTGAAAAACGATGATAATATGGCCACAACCATGGACCCTGTTGT
GCTGCAAAGGAGAGACTGGGAGAACCCTGGAGTGACCCAGCTCAACAGAC
TGGCTGCCCACCCTCCCTTTGCCTCTTGGAGGAACTCTGAGGAAGCCAGG
ACAGACAGGCCCAGCCAGCAGCTCAGGTCTCTCAATGGAGAGTGGAGGTT
TGCCTGGTTCCCTGCCCCTGAAGCTGTGCCTGAGTCTTGGCTGGAGTGTG
ACCTCCCAGAGGCTGACACTGTTGTGGTGCCAAGCAACTGGCAGATGCAT
GGCTATGATGCCCCCATCTACACCAATGTCACCTACCCCATCACTGTGAA
CCCCCCTTTTGTGCCCACTGAGAACCCCACTGGCTGCTACAGCCTGACCT
TCAATGTTGATGAGAGCTGGCTGCAAGAAGGCCAGACCAGGATCATCTTT
GATGGAGTCAACTCTGCCTTCCACCTCTGGTGCAATGGCAGGTGGGTTGG
CTATGGCCAAGACAGCAGGCTGCCCTCTGAGTTTGACCTCTCTGCCTTCC
TCAGAGCTGGAGAGAACAGGCTGGCTGTCATGGTGCTCAGGTGGTCTGAT
GGCAGCTACCTGGAAGACCAAGACATGTGGAGGATGTCTGGCATCTTCAG
GGATGTGAGCCTGCTGCACAAGCCCACCACCCAGATTTCTGACTTCCATG
TTGCCACCAGGTTCAATGATGACTTCAGCAGAGCTGTGCTGGAGGCTGAG
GTGCAGATGTGTGGAGAACTCAGAGACTACCTGAGAGTCACAGTGAGCCT
CTGGCAAGGTGAGACCCAGGTGGCCTCTGGCACAGCCCCCTTTGGAGGAG
AGATCATTGATGAGAGGAGGCTATGCTGACAGAGTCACCCTGAGGCTC
AATGTGGAGAACCCCAAGCTGTGGTCTGCTGAGATCCCCAACCTCTACAG
GGCTGTTGTGGAGCTGCACACTGCTGATGGCACCCTGATTGAAGCTGAAG
CCTGTGATGTTGGATTCAGAGAAGTCAGGATTGAGAATGGCCTGCTGCTG
CTCAATGGCAAGCCTCTGCTCATCAGGGGAGTCAACAGGCATGAGCACCA
CCCTCTGCATGGACAAGTGATGGATGAACAGACAATGGTGCAAGATATCC
TGCTAATGAAGCAGAACAACTTCAATGCTGTCAGGTGCTCTCACTACCCC
```

-continued

```
AACCACCCTCTCTGGTACACCCTGTGTGACAGGTATGGCCTGTATGTTGT
TGATGAAGCCAACATTGAGACACATGGCATGGTGCCCATGAACAGGCTCA
CAGATGACCCCAGGTGGCTGCCTGCCATGTCTGAGAGAGTGACCAGGATG
GTGCAGAGAGACAGGAACCACCCCTCTGTGATCATCTGGTCTCTGGGCAA
TGAGTCTGGACATGGAGCCAACCATGATGCTCTCTACAGGTGGATCAAGT
CTGTTGACCCCAGCAGACCTGTGCAGTATGAAGGAGGTGGAGCAGACACC
ACAGCCACAGACATCATCTGCCCCATGTATGCCAGGGTTGATGAGGACCA
GCCCTTCCCTGCTGTGCCCAAGTGGAGCATCAAGAAGTGGCTCTCTCTGC
CTGGAGAGACCAGACCTCTGATCCTGTGTGAATATGCACATGCAATGGGC
AACTCTCTGGGAGGCTTTGCCAAGTACTGGCAAGCCTTCAGACAGTACCC
CAGGCTGCAAGGAGGATTTGTGTGGGACTGGGTGGACCAATCTCTCATCA
AGTATGATGAGAATGGCAACCCCTGGTCTGCCTATGGAGGAGACTTTGGT
GACACCCCCAATGACAGGCAGTTCTGCATGAATGGCCTGGTCTTTGCAGA
CAGGACCCCTCACCCTGCCCTCACAGAGGCCAAGCACCAGCAACAGTTCT
TCCAGTTCAGGCTGTCTGGACAGACCATTGAGGTGACATCTGAGTACCTC
TTCAGGCACTCTGACAATGAGCTCCTGCACTGGATGGTGGCCCTGGATGG
CAAGCCTCTGGCTTCTGGTGAGGTGCCTCTGGATGTGGCCCCTCAAGGAA
AGCAGCTGATTGAACTGCCTGAGCTGCCTCAGCCAGAGTCTGCTGGACAA
CTGTGGCTAACAGTGAGGGTGGTTCAGCCCAATGCAACAGCTTGGTCTGA
GGCAGGCCACATCTCTGCATGGCAGCAGTGGAGGCTGGCTGAGAACCTCT
CTGTGACCCTGCCTGCTGCCTCTCATGCCATCCCTCACCTGACAACATCT
GAAATGGACTTCTGCATTGAGCTGGGCAACAAGAGATGGCAGTTCAACAG
GCAGTCTGGCTTCCTGTCTCAGATGTGGATTGGAGACAAGAAGCAGCTCC
TCACCCCTCTCAGGGACCAATTCACCAGGGCTCCTCTGGACAATGACATT
GGAGTGTCTGAGGCCACCAGGATTGACCCAAATGCTTGGGTGGAGAGGTG
GAAGGCTGCTGGACACTACCAGGCTGAGGCTGCCCTGCTCCAGTGCACAG
CAGACACCCTGGCTGATGCTGTTCTGATCACCACAGCCCATGCTTGGCAG
CACCAAGGCAAGACCCTGTTCATCAGCAGAAAGACCTACAGGATTGATGG
CTCTGGACAGATGGCAATCACAGTGGATGTGGAGGTTGCCTCTGACACAC
CTCACCCTGCAAGGATTGGCCTGAACTGTCAACTGGCACAGGTGGCTGAG
AGGGTGAACTGGCTGGGCTTAGGCCCTCAGGAGAACTACCCTGACAGGCT
GACAGCTGCCTGCTTTGACAGGTGGGACCTGCCTCTGTCTGACATGTACA
CCCCTTATGTGTTCCCTTCTGAGAATGGCCTGAGGTGTGGCACCAGGGAG
CTGAACTATGGTCCTCACCAGTGGAGGGGAGACTTCCAGTTCAACATCTC
CAGGTACTCTCAGCAACAGCTCATGGAAACCTCTCACAGGCACCTGCTCC
ATGCAGAGGAGGGAACCTGGCTGAACATTGATGGCTTCCACATGGGCATT
GGAGGAGATGACTCTTGGTCTCCTTCTGTGTCTGCTGAGTTCCAGTTATC
TGCTGGCAGGTACCACTATCAGCTGGTGTGGTGCCAGAAGTAAACCTAAT
CTAGCAGCTCGCTGATCAGCCTCGACTGTGCCTTCTAGTTGCCAGCCATC
TGTTGTTTGCCCCTCCCCCGTGCCTTCCTTGACCCTGGAAGGTGCCACTC
CCACTGTCCTTTCCTAATAAAATGAGGAAATTGCATCGCATTGTCTGAGT
```

-continued

```
AGGTGTCATTCTATTCTGGGGGGTGGGGTGGGGCAGGACAGCAAGGGGGA
GGATTGGGAAGACAATAGCAGGCATGCTGGGGATGCGGTGGGCTCTATGG
CTTCTGAGGCGGAAAGAACCAGCTGGGGCTCGATCCTCTAGTTGGCGCGT
CATGGTCCATATGAATATCCTCCTTAGTTCCTATTCCGAAGTTCCTATTC
TCTAGAAAGTATAGGAACTTCGGCGCGTCGACATTGATTATTGACTAGTT
ATTAATAGTAATCAATTACGGGGTCATTAGTTCATAGCCCATATATGGAG
TTCCGCGTTACATAACTTACGGTAAATGGCCCGCCTGGCTGACCGCCCAA
CGACCCCCGCCCATTGACGTCAATAATGACGTATGTTCCCATAGTAACGC
CAATAGGGACTTTCCATTGACGTCAATGGGTGGACTATTTACGGTAAACT
GCCCACTTGGCAGTACATCAAGTGTATCATATGCCAAGTACGCCCCCTAT
TGACGTCAATGACGGTAAATGGCCCGCCTGGCATTATGCCCAGTACATGA
CCTTATGGGACTTTCCTACTTGGCAGTACATCTACGTATTAGTCATCGCT
ATTACCATGGGTCGAGGTGAGCCCCACGTTCTGCTTCACTCTCCCCATCT
CCCCCCCCTCCCCACCCCCAATTTTGTATTTATTTATTTTTTAATTATTT
TGTGCAGCGATGGGGGCGGGGGGGGGGGGCGCGCGCCAGGCGGGGCGG
GGCGGGGCGAGGGCGGGGCGGGGCGAGGCGGAGAGGTGCGGCGGCAGCC
AATCAGAGCGGCGCGCTCCGAAAGTTTCCTTTTATGGCGAGGCGGCGGCG
GCGGCGGCCCTATAAAAAGCGAAGCGCGCGGCGGGCGGGAGTCGCTGCGT
TGCCTTCGCCCCGTGCCCCGCTCCGCGCCGCCTCGCGCCGCCCGCCCCGG
CTCTGACTGACCGCGTTACTCCCACAGGTGAGCGGGCGGGACGGCCCTTC
TCCTCCGGGCTGTAATTAGCGCTTGGTTTAATGACGGCTCGTTTCTTTTC
TGTGGCTGCGTGAAAGCCTTAAAGGGCTCCGGGAGGGCCCTTTGTGCGGG
GGGGAGCGGCTCGGGGGTGCGTGCGTGTGTGTGCGTGGGGAGCGCCG
CGTGCGGCCCGCGCTGCCCGGCGGCTGTGAGCGCTGCGGGCGCGGCGCGG
GGCTTTGTGCGCTCCGCGTGTGCGCGAGGGGAGCGCGGCCGGGGGCGGTG
CCCCGCGGTGCGGGGGGGCTGCGAGGGGAACAAAGGCTGCGTGCGGGGTG
TGTGCGTGGGGGGGGTGAGCAGGGGGTGTGGGCGCGGCGGTCGGGCTGTAA
CCCCCCCCCTGCACCCCCCTCCCCGAGTTGCTGAGCACGGCCCGGCTTCGG
GTGCGGGGCTCCGTGCGGGGCGTGGCGCGGGGCTCGCCGTGCCGGGCGGG
GGGTGGCGGCAGGTGGGGGTGCCGGCGGGGCGGGGCCGCCTCGGGCCGG
GGAGGGCTCGGGGAGGGCGCGGCGGCCCCGGAGCGCCGGCGGCTGTCG
AGGCGCGGCGAGCCGCAGCCATTGCCTTTTATGGTAATCGTGCGAGAGGG
CGCAGGGACTTCCTTTGTCCCAAATCGGCGGAGCCGAAATCTGGGAGGC
GCCGCCGCACCCCCTCTAGCGGGCGCGGGCGAAGCGGTGCGGCGCCGGCA
GGAAGGAAATGGGCGGGAGGGCCTTCGTGCGTCGCCGCGCCGCCGTCCC
CTTCTCCATCTCCAGCCTCGGGCTGCCGCAGGGGGACGGCTGCCTTCGG
GGGGGACGGGGCAGGGCGGGGTTCGGCTTCTGGCGTGTGACCGGCGGCTC
TAGAGCCTCTGCTAACCATGTTCATGCCTTCTTCTTTTTCCTACAGCTCC
TGGGCAACGTGCTGGTTATTGTGCTGTCTCATCATTTTGGCAAAGAATTC
GCCACCATGGTGAGCAAGGGCGAGGAGCTGTTCACCGGGGTGGTGCCCAT
CCTGGTCGAGCTGGACGGCGACGTAAACGGCCACAAGTTCAGCGTGTCCG
```

-continued

```
GCGAGGGCGAGGGCGATGCCACCTACGGCAAGCTGACCCTGAAGTTCATC
TGCACCACCGGCAAGCTGCCCGTGCCCTGGCCCACCCTCGTGACCACCCT
GACCTACGGCGTGCAGTGCTTCAGCCGCTACCCCGACCACATGAAGCAGC
ACGACTTCTTCAAGTCCGCCATGCCCGAAGGCTACGTCCAGGAGCGCACC
ATCTTCTTCAAGGACGACGGCAACTACAAGACCCGCGCCGAGGTGAAGTT
CGAGGGCGACACCCTGGTGAACCGCATCGAGCTGAAGGGCATCGACTTCA
AGGAGGACGGCAACATCCTGGGGCACAAGCTGGAGTACAACTACAACAGC
CACAACGTCTATATCATGGCCGACAAGCAGAAGAACGGCATCAAGGTGAA
CTTCAAGATCCGCCACAACATCGAGGACGGCAGCGTGCAGCTCGCCGACC
ACTACCAGCAGAACACCCCCATCGGCGACGGCCCCGTGCTGCTGCCCGAC
AACCACTACCTGAGCACCCAGTCCGCCCTGAGCAAAGACCCCAACGAGAA
GCGCGATCACATGGTCCTGCTGGAGTTCGTGACCGCCGCCGGGATCACTC
TCGGCATGGACGAGCTGTACAAGTAAAGCGGCCGCGACTCTAGATCATAA
TCAGCCATACCACATTTGTAGAGGTTTTACTTGCTTTAAAAAACCTCCCA
CACCTCCCCCTGAACCTGAAACATAAAATGAATGCAATTGTTGTTGTTAA
CTTGTTTATTGCAGCTTATAATGGTTACAAATAAAGCAATAGCATCACAA
ATTTCACAAATAAAGCATTTTTTTCACTGCATTCTAGTTGTGGTTTGTCC
AAACTCATCAATGTATCTTAAGATAACTTCGTATAATGTATGCTATACGA
AGTTATATAACTTCGTATAATGTGTACTATACGAAGTTATAAATGAAGTT
CCTATTCCGAAATTCCTATTCTCTAGAAAGTATAGGAACTTCGAAGCAGC
TCCAGCCTACACAATGCTCAAGACGTGTAATGCTCTATGGTAGGTCGAT
ATAATAGCAATCAACGCAAGCAAATGTGTCAGTCCTGCTTACAGGAACGA
TTCTATTTAGTAATTTTCGTTGTATAAAGTAATTATGTATGTATGTAAGC
CCCATAAATCTGAAACAATTAGGCAAAACCATGCGACGGCCGATCTCGAG
AGATCTGACAATGTTCAGTGCAGAGACTCGGCTACGCCTCGTGGACTTTG
AAGTTGACCAACAATGTTTATTCTTACCTCTAATAGTCCTCTGTGGCAAG
GTCAAGATTCTGTTAGAAGCCAATGAAGAACCTGGTTGTTCAATAACATT
TTGTTCGTCTAATATTTCACTACCGCTTGACGTTGGCTGCACTTCATGTA
CCTCATCTATAAACGCTTCTTCTGTATCGCTCTGGACGTCATCTTCACTT
ACGTGATCTGATATTTCACTGTCAGAATCCTCACCAACAAGCTCGTCATC
GCTTTGCAGAAGAGCAGAGAGGATATGCTCATCGTCTAAAGAACTACCCA
TTTTATTATATATTAGTCACGATATCTATAACAAGAAAATATATATATAA
TAAGTTATCACGTAAGTAGAACATGAAATAACAATATAATTATCGTATGA
GTTAAATCTTAAAAGTCACGTAAAAGATAATCATGCGTCATTTTGACTCA
CGCGGTCGTTATAGTTCAAAATCAGTGACACTTACCGCATTGACAAGCAC
GCCTCACGGGAGCTCCAAGCGGCGACTGAGATGTCCTAAATGCACAGCGA
CGGATTCGCGCTATTTAGAAAGAGAGAGCAATATTTCAAGAATGCATGCG
TCAATTTTACGCAGACTATCTTTCTAGGGTTAAAAAAGATTTGCGCTTTA
CTCGACCTAAACTTTAAACAGGTCATAGAATCTTCGTTTGACAAAAACCA
CATTGTGGGGTACCGAGCTCGAATTCATCGATGATATCAGATCTGCCGGT
CTCCCTATAGTGAGTCGTATTAATTTCGATAAGCCAGGTTAACCTGCATT
```

AATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAG
GGGATAACGCAGGAAGAACATGTGAGCAAAAGGCCAGCAAAAGGCCAGG
AACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGA
CAGGACTATAAAGATACCAGGCGTTTCCCCCTGGAAGCTCCCTCGTGCGC
TCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCC
GGTAAGACACGACTTATCGCCACTGGCAGCAGCCACTGGTAACAGGATTA
GCAGAGCGAGGTATGTAGGCGGTGCTACAGAGTTCTTGAAGTGGTGGCCT
AACTACGGCTACACTAGAAGAACAGTATTTGGTATCTGCGCTCTGCTGAA
GCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGA
CGCTCAGTGGAACGAAAACTCACGTTAAGGGATTTTGGTCATGAGATTAT
CAAAAAGGATCTTCACCTAGATCCTTTTAAATTAAAAATGAAGTTTTAAA
TCAATCTAAAGTATATATGAGTAAACTTGGTCTGACAGTTACCAATGCTT
AATCAGTGAGGCACCTATCTCAGCGATCTGTCTATTTCGTTCATCCATAG
TTGCCTGACTCCCCGTCGTGTAGATAACTACGATACGGGAGGGCTTACCA
TCTGGCCCCAGTGCTGCAATGATACCGCGAGACCCACGCTCACCGGCTCC
AGATTTATCAGCAATAAACCAGCCAGCCGGAAGGGCCGAGCGCAGAAGTG
GTCCTGCAACTTTATCCGCCTCCATCCAGTCTATTAATTGTTGCCGGGAA
GCTAGAGTAAGTAGTTCGCCAGTTAATAGTTTGCGCAACGTTGTTGCCAT
TGCTACAGGCATCGTGGTGTCACGCTCGTCGTTTGGTATGGCTTCATTCA
GCTCCGGTTCCCAACGATCAAGGCGAGTTACATGATCCCCCATGTTGTGC
AAAAAAGCGGTTAGCTCCTTCGGTCCTCCGATCGTTGTCAGAAGTAAGTT
GGCCGCAGTGTTATCACTCATGGTTATGGCAGCACTGCATAATTCTCTTA
CTGTCATGCCATCCGTAAGATGCTTTTCTGTGACTGGTGAGTACTCAACC
AAGTCATTCTGAGAATAGTGTATGCGGCGACCGAGTTGCTCTTGCCCGGC
GTCAATACGGGATAATACCGCGCCACATAGCAGAACTTTAAAAGTGCTCA
TCATTGGAAAACGTTCTTCGGGGCGAAAACTCTCAAGGATCTTACCGCTG
TTGAGATCCAGTTCGATGTAACCCACTCGTGCACCCAACTGATCTTCAGC
ATCTTTTACTTTCACCAGCGTTTCTGGGTGAGCAAAAACAGGAAGGCAAA
ATGCCGCAAAAAAGGGAATAAGGGCGACACGGAAATGTTGAATACTCATA
CTCTTCCTTTTTCAATATTATTGAAGCATTTATCAGGGTTATTGTCTCAT
GAGCGGATACATATTTGAATGTATTTAGAAAAATAAACAAATAGGGGTTC
CGCGCACATTTCCCCGAAAAGTGCCACCTGACGTCTAAGAAACCATTATT
ATCATGACATTAACCTATAAAAATAGGCGTATCACGAGGCCCTTTCGTCT

CGCGCGTTTCGGTGATGACGGTGAAAACCTCTGACACATGCAGCTCCCGG
AGACGGTCACAGCTTGTCTGTAAGCGGATGCCGGGAGCAGACAAGCCCGT
CAGGGCGCGTCAGCGGGTGTTGGCGGGTGTCGGGGCTGGCTTAACTATGC
GGCATCAGAGCAGATTGTACTGAGAGTGCACCATATGGACATATTGTCGT
TAGAACGCGGCTACAATTAATACATAACCTTATGTATCATACACATACGA
TTTAGGTGACACTATAGAACTCGACCTCGAGGCTGGCACGACAGGTTTCC
CGACTGGAAAGCGGGCAGTGAGCGCAACGCAATTAATGTGAGTTAGCTCA
CTCATTAGGCACCCCAGGCTTTACACTTTATGCTTCCGGCTCGTATGTTG
TGTGGAATTGTGAGCGGATAACAATTTCACACAGGAAACAGCTATGACCA
TGATTACGCCAAGCTCGAAATTAACCCTCACTAAAGGGAACAAAAGCTGG
AGCTCGTCTTTGATCAAAACGCAAATCGACGAAAATGTGTCGGACAATAT
CAAGTCGATGAGCGAAAAACTAAAAAGGCTAGAATACGACAATCTCACAG
ACAGCGTTGAGATATACGGTATTCACGACAGCAGGCTGAATAATAAAAAA
ATTAGAAACTATTAT

106. SEQ ID NO: 106
(ZG-m)

TTAACCCTAGAAAGATAATCATATTGTGACGTACGTTAAAGATAATCATG
CGTAAAATTGACGCATGTGTTTTATCGGTCTGTATATCGAGGTTTATTTA
TTAATTTGAATAGATATTAAGTTTTATTATATTTACACTTACATACTAAT
AATAAATTCAACAAACAATTTATTTATGTTTATTTATTTATTAAAAAAAA
ACAAAAACTCAAAATTTCTTCTATAAAGTAACAAAACTTTTAAACATTCT
CTCTTTTCAAAAATAAACTTATTTTGTACTTTAAAAACAGTCATGTTGT
ATTATAAAATAAGTAATTAGCTTAACTTATACATAATAGAAACAAATTAT
ACTTATTAGTCAGTCAGAAACAACTTTGGCACATATCAATATTATGCTCT
CGACAAATAACTTTTTTGCATTTTTTGCACGATGCATTTGCCTTTCGCCT
TATTTTAATCGCATAACTTCGTATAATGTATGCTATACGAAGTTATGCGA
TTAAGGGATCTGTAGGGCGCAGTAGTCCAGGGTTTCCTTGATGATGTCAT
ACTTATCCTGTCCCTTTTTTTTCCACAGCTCGCGGTTGAGGACAAACTCT
TCGCGGTCTTTCCAGTGGGGATCGACGGTATCGTAGAGTCGAGGCCGCTC
TAGCGGATCTGCCCCTCTCCCTCCCCCCCCCCTAACGTTACTGGCCGAAG
CCGCTTGGAATAAGGCCGGTGTGCGTTTGTCTATATGTTATTTTCCACCA
TATTGCCGTCTTTTGGCAATGTGAGGGCCCGGAAACCTGGCCCTGTCTTC
TTGACGAGCATTCCTAGGGGTCTTTCCCCTCTCGCCAAAGGAATGCAAGG
TCTGTTGAATGTCGTGAAGGAAGCAGTTCCTCTGGAAGCTTCTTGAAGAC
AAACAACGTCTGTAGCGACCCTTTGCAGGCAGCGGAACCCCCCACCTGGC
GACAGGTGCCTCTGCGGCCAAAAGCCACGTGTATAAGATACACCTGCAAA
GGCGGCACAACCCCAGTGCCACGTTGTGAGTTGGATAGTTGTGGAAAGAG
TCAAATGGCTCTCCTCAAGCGTATTCAACAAGGGGCTGAAGGATGCCCAG
AAGGTACCCCATTGTATGGGATCTGATCTGGGGCCTCGGTGCACATGCTT
TACATGTGTTTAGTCGAGGTTAAAAAAACGTCTAGGCCCCCCGAACCACG
GGGACGTGGTTTTCCTTTGAAAAACACGATGATAATATGGCCACAACCAT
GGACCCTGTTGTGCTGCAAAGGAGAGACTGGGAGAACCCTGGAGTGACCC

-continued

```
AGCTCAACAGACTGGCTGCCCACCCTCCCTTTGCCTCTTGGAGGAACTCT
GAGGAAGCCAGGACAGACAGGCCCAGCCAGCAGCTCAGGTCTCTCAATGG
AGAGTGGAGGTTTGCCTGGTTCCCTGCCCCTGAAGCTGTGCCTGAGTCTT
GGCTGGAGTGTGACCTCCCAGAGGCTGACACTGTTGTGGTGCCAAGCAAC
TGGCAGATGCATGGCTATGATGCCCCCATCTACACCAATGTCACCTACCC
CATCACTGTGAACCCCCTTTTGTGCCCACTGAGAACCCCACTGGCTGCT
ACAGCCTGACCTTCAATGTTGATGAGAGCTGGCTGCAAGAAGGCCAGACC
AGGATCATCTTTGATGGAGTCAACTCTGCCTTCCACCTCTGGTGCAATGG
CAGGTGGGTTGGCTATGGCCAAGACAGCAGGCTGCCCTCTGAGTTTGACC
TCTCTGCCTTCCTCAGAGCTGGAGAGAACAGGCTGGCTGTCATGGTGCTC
AGGTGGTCTGATGGCAGCTACCTGGAAGACCAAGACATGTGGAGGATGTC
TGGCATCTTCAGGGATGTGAGCCTGCTGCACAAGCCCACCACCCAGATTT
CTGACTTCCATGTTGCCACCAGGTTCAATGATGACTTCAGCAGAGCTGTG
CTGGAGGCTGAGGTGCAGATGTGTGGAGAACTCAGAGACTACCTGAGAGT
CACAGTGAGCCTCTGGCAAGGTGAGACCCAGGTGGCCTCTGGCACAGCCC
CCTTTGGAGGAGAGATCATTGATGAGAGAGGAGGCTATGCTGACAGAGTC
ACCCTGAGGCTCAATGTGGAGAACCCCAAGCTGTGGTCTGCTGAGATCCC
CAACCTCTACAGGGCTGTTGTGGAGCTGCACACTGCTGATGGCACCCTGA
TTGAAGCTGAAGCCTGTGATGTTGGATTCAGAGAAGTCAGGATTGAGAAT
GGCCTGCTGCTGCTCAATGGCAAGCCTCTGCTCATCAGGGGAGTCAACAG
GCATGAGCACCACCCTCTGCATGGACAAGTGATGATGAACAGACAATGG
TGCAAGATATCCTGCTAATGAAGCAGAACAACTTCAATGCTGTCAGGTGC
TCTCACTACCCCAACCACCCTCTCTGGTACACCCTGTGTGACAGGTATGG
CCTGTATGTTGTTGATGAAGCCAACATTGAGACACATGGCATGGTGCCCA
TGAACAGGCTCACAGATGACCCCAGGTGGCTGCCTGCCATGTCTGAGAGA
GTGACCAGGATGGTGCAGAGAGACAGGAACCACCCCTCTGTGATCATCTG
GTCTCTGGGCAATGAGTCTGGACATGGAGCCAACCATGATGCTCTCTACA
GGTGGATCAAGTCTGTTGACCCCAGCAGACCTGTGCAGTATGAAGGAGGT
GGAGCAGACACCACAGCCACAGACATCATCTGCCCCATGTATGCCAGGGT
TGATGAGGACCAGCCCTTCCCTGCTGTGCCCAAGTGGAGCATCAAGAAGT
GGCTCTCTCTGCCTGGAGAGACCAGACCTCTGATCCTGTGTGAATATGCA
CATGCAATGGGCAACTCTCTGGGAGGCTTTGCCAAGTACTGGCAAGCCTT
CAGACAGTACCCCAGGCTGCAAGGAGGATTTGTGTGGGACTGGGTGGACC
AATCTCTCATCAAGTATGATGAGAATGGCAACCCCTGGTCTGCCTATGGA
GGAGACTTTGGTGACACCCCCAATGACAGGCAGTTCTGCATGAATGGCCT
GGTCTTTGCAGACAGGACCCCTCACCCTGCCCTCACAGAGGCCAAGCACC
AGCAACAGTTCTTCCAGTTCAGGCTGTCTGGACAGACCATTGAGGTGACA
TCTGAGTACCTCTTCAGGCACTCTGACAATGAGCTCCTGCACTGGATGGT
GGCCCTGGATGGCAAGCCTCTGGCTTCTGGTGAGGTGCCTCTGGATGTGG
CCCCTCAAGGAAAGCAGCTGATTGAACTGCCTGAGCTGCCTCAGCCAGAG
TCTGCTGGACAACTGTGGCTAACAGTGAGGGTGGTTCAGCCCAATGCAAC
```

-continued

```
AGCTTGGTCTGAGGCAGGCCACATCTCTGCATGGCAGCAGTGGAGGCTGG
CTGAGAACCTCTCTGTGACCCTGCCTGCTGCCTCTCATGCCATCCCTCAC
CTGACAACATCTGAAATGGACTTCTGCATTGAGCTGGGCAACAAGAGATG
GCAGTTCAACAGGCAGTCTGGCTTCCTGTCTCAGATGTGGATTGGAGACA
AGAAGCAGCTCCTCACCCCTCTCAGGGACCAATTCACCAGGGCTCCTCTG
GACAATGACATTGGAGTGTCTGAGGCCACCAGGATTGACCCAAATGCTTG
GGTGGAGAGGTGGAAGGCTGCTGGACACTACCAGGCTGAGGCTGCCCTGC
TCCAGTGCACAGCAGACACCCTGGCTGATGCTGTTCTGATCACCACAGCC
CATGCTTGGCAGCACCAAGGCAAGACCCTGTTCATCAGCAGAAAGACCTA
CAGGATTGATGGCTCTGGACAGATGGCAATCACAGTGGATGTGGAGGTTG
CCTCTGACACACCTCACCCTGCAAGGATTGGCCTGAACTGTCAACTGGCA
CAGGTGGCTGAGAGGGTGAACTGGCTGGGCTTAGGCCCTCAGGAGAACTA
CCCTGACAGGCTGACAGCTGCCTGCTTTGACAGGTGGGACCTGCCTCTGT
CTGACATGTACACCCCTTATGTGTTCCCTTCTGAGAATGGCCTGAGGTGT
GGCACCAGGGAGCTGAACTATGGTCCTCACCAGTGGAGGGGAGACTTCCA
GTTCAACATCTCCAGGTACTCTCAGCAACAGCTCATGGAAACCTCTCACA
GGCACCTGCTCCATGCAGAGGAGGGAACCTGGCTGAACATTGATGGCTTC
CACATGGGCATTGGAGGAGATGACTCTTGGTCTCCTTCTGTGTCTGCTGA
GTTCCAGTTATCTGCTGGCAGGTACCACTATCAGCTGGTGTGGTGCCAGA
AGTAAACCTAATCTAGCAGCTCGCTGATCAGCCTCGACTGTGCCTTCTAG
TTGCCAGCCATCTGTTGTTTGCCCCTCCCCGTGCCTTCCTTGACCCTGG
AAGGTGCCACTCCCACTGTCCTTTCCTAATAAAATGAGGAAATTGCATCG
CATTGTCTGAGTAGGTGTCATTCTATTCTGGGGGGTGGGTGGGCAGGA
CAGCAAGGGGAGGATTGGGAAGACAATAGCAGGCATGCTGGGGATGCGG
TGGGCTCTATGGCTTCTGAGGCGGAAAGAACCAGCTGGGGCTCGATCCTC
TAGTTGGCGCGTCATGGTCCATATGAATATCCTCCTTAGTTCCTATTCCG
AAGTTCCTATTCTCTAGAAAGTATAGGAACTTCGGCGCGTCGACATTGAT
TATTGACTAGTTATTAATAGTAATCAATTACGGGGTCATTAGTTCATAGC
CCATATATGGAGTTCCGCGTTACATAACTTACGGTAAATGGCCCGCCTGG
CTGACCGCCCAACGACCCCCGCCCATTGACGTCAATAATGACGTATGTTC
CCATAGTAACGCCAATAGGGACTTTCCATTGACGTCAATGGGTGGACTAT
TTACGGTAAACTGCCCACTTGGCAGTACATCAAGTGTATCATATGCCAAG
TACGCCCCCTATTGACGTCAATGACGGTAAATGGCCCGCCTGGCATTATG
CCCAGTACATGACCTTATGGGACTTTCCTACTTGGCAGTACATCTACGTA
TTAGTCATCGCTATTACCATGGTCGAGGTGAGCCCCACGTTCTGCTTCA
CTCTCCCCATCTCCCCCCCCTCCCCACCCCCAATTTTGTATTTATTTATT
TTTTAATTATTTTGTGCAGCGATGGGGGCGGGGGGGGGGGGCGCGCGC
CAGGCGGGGCGGGCGGGCGAGGGCGGGCGGGCGAGGCGGAGAGGT
GCGGCGGCAGCCAATCAGAGCGGCGCGCTCCGAAAGTTTCCTTTTATGGC
GAGGCGGCGGCGGCGGCGGCCCTATAAAAAGCGAAGCGCGCGGCGGGCGG
GAGTCGCTGCGTTGCCTTCGCCCCGTGCCCCGCTCCGCGCCGCCTCGCGC
```

-continued

```
CGCCCGCCCCGGCTCTGACTGACCGCGTTACTCCCACAGGTGAGCGGGCG
GGACGGCCCTTCTCCTCCGGGCTGTAATTAGCGCTTGGTTTAATGACGGC
TCGTTTCTTTTCTGTGGCTGCGTGAAAGCCTTAAAGGGCTCCGGGAGGGC
CCTTTGTGCGGGGGGGAGCGGCTCGGGGGGTGCGTGCGTGTGTGTGCG
TGGGGAGCGCCGCGTGCGGCCCGCGCTGCCCGGCGGCTGTGAGCGCTGCG
GGCGCGGCGCGGGGCTTTGTGCGCTCCGCGTGTGCGCGAGGGGAGCGCGG
CCGGGGGCGGTGCCCCGCGGTGCGGGGGGGCTGCGAGGGGAACAAAGGCT
GCGTGCGGGGTGTGTCGTGGGGGGGTGAGCAGGGGGTGTGGGCGCGGCG
GTCGGGCTGTAACCCCCCCTGCACCCCCCTCCCCGAGTTGCTGAGCACG
GCCCGGCTTCGGGTGCGGGGCTCCGTGCGGGGCGTGGCGCGGGGCTCGCC
GTGCCGGGCGGGGGGTGGCGGCAGGTGGGGGTGCCGGGCGGGGCGGGGCC
GCCTCGGGCCGGGGAGGGCTCGGGGGAGGGGCGCGGCGGCCCCGGAGCGC
CGGCGGCTGTCGAGGCGCGGCGAGCCGCAGCCATTGCCTTTTATGGTAAT
CGTGCGAGAGGGCGCAGGGACTTCCTTTGTCCCAAATCTGGCGGAGCCGA
AATCTGGGAGGCGCCGCCGCACCCCCTCTAGCGGGCGCGGGCGAAGCGGT
GCGGCGCCGGCAGGAAGGAAATGGGCGGGGAGGGCCTTCGTGCGTCGCCG
CGCCGCCGTCCCCTTCTCCATCTCCAGCCTCGGGGCTGCCGCAGGGGGAC
GGCTGCCTTCGGGGGGGACGGGGCAGGGCGGGGTTCGGCTTCTGGCGTGT
GACCGGCGGCTCTAGAGCCTCTGCTAACCATGTTCATGCCTTCTTCTTTT
TCCTACAGCTCCTGGGCAACGTGCTGGTTATTGTGCTGTCTCATCATTTT
GGCAAAGAATTCGCCACCATGGTGAGCAAGGGCGAGGAGCTGTTCACCGG
GGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACC
CTGAAGTTCATCTGCACCACCGGCAAGCTGCCCGTGCCCTGGCCCACCCT
CGTGACCACCCTGACCTACGGCGTGCAGTGCTTCAGCCGCTACCCCGACC
ACATGAAGCAGCACGACTTCTTCAAGTCCGCCATGCCCGAAGGCTACGTC
CAGGAGCGCACCATCTTCTTCAAGGACGACGGCAACTACAAGACCCGCGC
CGAGGTGAAGTTCGAGGGCGACACCCTGGTGAACCGCATCGAGCTGAAGG
GCATCGACTTCAAGGAGGACGGCAACATCCTGGGGCACAAGCTGGAGTAC
AACTACAACAGCCACAACGTCTATATCATGGCCGACAAGCAGAAGAACGG
CATCAAGGTGAACTTCAAGATCCGCCACAACATCGAGGACGGCAGCGTGC
AGCTCGCCGACCACTACCAGCAGAACACCCCCATCGGCGACGGCCCCGTG
CTGCTGCCCGACAACCACTACCTGAGCACCCAGTCCGCCCTGAGCAAAGA
CCCCAACGAGAAGCGCGATCACATGGTCCTGCTGGAGTTCGTGACCGCCG
CCGGGATCACTCTCGGCATGGACGAGCTGTACAAGTAAAGCGGCCGCGAC
TCTAGATCATAATCAGCCATACCACATTTGTAGAGGTTTTACTTGCTTTA
AAAAACCTCCCACACCTCCCCCTGAACCTGAAACATAAAATGAATGCAAT
TGTTGTTGTTAACTTGTTTATTGCAGCTTATAATGGTTACAAATAAAGCA
ATAGCATCACAAATTTCACAAATAAAGCATTTTTTTCACTGCATTCTAGT
TGTGGTTTGTCCAAACTCATCAATGTATCTTAAGATAACTTCGTATAATG
TATGCTATACGAAGTTATATAACTTCGTATAATGTGTACTATACGAAGTT

ATAAATGAAGTTCCTATTCCGAAGTTCCTATTCTCTAGAAAGTATAGGAA
CTTCGAAGCAGCTCCAGCCTACACAATCGCTCAAGACGTGTAATGCTCTA
TGGTAGGTCGATATAATAGCAATCAACGCAAGCAAATGTGTCAGTCCTGC
TTACAGGAACGATTCTATTTAGTAATTTTCGTTGTATAAAGTAATTATGT
ATGTATGTAAGCCCCATAAATCTGAAACAATTAGGCAAAACCATGCGACG
GCCGATCTCGAGAGATCTGACAATGTTCAGTGCAGAGACTCGGCTACGCC
TCGTGGACTTTGAAGTTGACCAACAATGTTTATTCTTACCTCTAATAGTC
CTCTGTGGCAAGGTCAAGATTCTGTTAGAAGCCAATGAAGAACCTGGTTG
TTCAATAACATTTTGTTCGTCTAATATTTCACTACCGCTTGACGTTGGCT
GCACTTCATGTACCTCATCTATAAACGCTTCTTCTGTATCGCTCTGGACG
TCATCTTCACTTACGTGATCTGATATTTCACTGTCAGAATCCTCACCAAC
AAGCTCGTCATCGCTTTGCAGAAGAGCAGAGAGGATATGCTCATCGTCTA
AAGAACTACCCATTTTATTATATATTAGTCACGATATCTATAACAAGAAA
ATATATATATAATAAGTTATCACGTAAGTAGAACATGAAATAACAATATA
ATTATCGTATGAGTTAAATCTTAAAAGTCACGTAAAAGATAATCATGCGT
CATTTTGACTCACGCGGTCGTTATAGTTCAAAATCAGTGACACTTACCGC
ATTGACAAGCACGCCTCACGGGAGCTCCAAGCGGCGACTGAGATGTCCTA
AATGCACAGCGACGGATTCGCGCTATTTAGAAAGAGAGAGCAATATTTCA
AGAATGCATGCGTCAATTTTACGCAGACTATCTTTCTAGGGTTAAAAAAG
ATTTGCGCTTTACTCGACCTAAACTTTAAACAGGTCATAGAATCTTCGTT
TGACAAAAACCACATTGTGGGGTACCGAGCTCGAATTCATCGATGATATC
AGATCTGCCGGTCTCCCTATAGTGAGTCGTATTAATTTCGATAAGCCAGG
TTAACCTGCATTAATGAATCGGCCAACGCGCGGGGAGAGGCGGTTTGCGT
ATTGGGCGCTCTTCCGCTTCCTCGCTCACTGACTCGCTGCGCTCGGTCGT
TCGGCTGCGGCGAGCGGTATCAGCTCACTCAAAGGCGGTAATACGGTTAT
CCACAGAATCAGGGGATAACGCAGGAAAGAACATGTGAGCAAAAGGCCAG
CAAAAGGCCAGGAACCGTAAAAAGGCCGCGTTGCTGGCGTTTTTCCATAG
GCTCCGCCCCCTGACGAGCATCACAAAAATCGACGCTCAAGTCAGAGGT
GGCGAAACCCGACAGGACTATAAAGATACCAGGCGTTTCCCCCTGGAAGC
TCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCT
TGAGTCCAACCCGGTAAGACACGACTTATCGCCACTGGCAGCAGCCACTG
GTAACAGGATTAGCAGAGCGAGGTATGTAGGCGGTGCTACAGAGTTCTTG
AAGTGGTGGCCTAACTACGGCTACACTAGAAGAACAGTATTTGGTATCTG
CGCTCTGCTGAAGCCAGTTACCTTCGGAAAAAGAGTTGGTAGCTCTTGAT
CCGGCAAACAAACCACCGCTGGTAGCGGTGGTTTTTTTGTTTGCAAGCAG
CAGATTACGCGCAGAAAAAAAGGATCTCAAGAAGATCCTTTGATCTTTTC
TACGGGGTCTGACGCTCAGTGGAACGAAAACTCACGTTAAGGGATTTTGG
TCATGAGATTATCAAAAAGGATCTTCACCTAGATCCTTTTAAATTAAAAA
```

```
TGAAGTTTTAAATCAATCTAAAGTATATATGAGTAAACTTGGTCTGACAG
TTACCAATGCTTAATCAGTGAGGCACCTATCTCAGCGATCTGTCTATTTC
GTTCATCCATAGTTGCCTGACTCCCCGTCGTGTAGATAACTACGATACGG
GAGGGCTTACCATCTGGCCCCAGTGCTGCAATGATACCGCGAGACCCACG
CTCACCGGCTCCAGATTTATCAGCAATAAACCAGCCAGCCGGAAGGGCCG
AGCGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGGTA
TGGCTTCATTCAGCTCCGGTTCCCAACGATCAAGGCGAGTTACATGATCC
CCCATGTTGTGCAAAAAAGCGGTTAGCTCCTTCGGTCCTCCGATCGTTGT
CAGAAGTAAGTTGGCCGCAGTGTTATCACTCATGGTTATGGCAGCACTGC
ATAATTCTCTTACTGTCATGCCATCCGTAAGATGCTTTTCTGTGACTGGT
GAGTACTCAACCAAGTCATTCTGAGAATAGTGTATGCGGCGACCGAGTTG
CTCTTGCCCGGCGTCAATACGGGATAATACCGCGCCACATAGCAGAACTT
TAAAAGTGCTCATCATTGGAAAACGTTCTTCGGGGCGAAAACTCTCAAGG
ATCTTACCGCTGTTGAGATCCAGTTCGATGTAACCCACTCGTGCACCCAA
CTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGT
TGAATACTCATACTCTTCCTTTTTCAATATTATTGAAGCATTTATCAGGG
TTATTGTCTCATGAGCGGATACATATTTGAATGTATTTAGAAAAATAAAC
AAATAGGGGTTCCGCGCACATTTCCCCGAAAAGTGCCACCTGACGTCTAA
GAAACCATTATTATCATGACATTAACCTATAAAAATAGGCGTATCACGAG
GCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGC
AGACAAGCCCGTCAGGGCGCGTCAGCGGGTGTTGGCGGGTGTCGGGGCTG
GCTTAACTATGCGGCATCAGAGCAGATTGTACTGAGAGTGCACCATATGG
ACATATTGTCGTTAGAACGCGGCTACAATTAATACATAACCTTATGTATC
ATACACATACGATTTAGGTGACACTATAGAACTCGACCTCGAGGCTGGCA
CGACAGGTTTCCCGACTGGAAAGCGGGCAGTGAGCGCAACGCAATTAATG
TGAGTTAGCTCACTCATTAGGCACCCCAGGCTTTACACTTTATGCTTCCG
GCTCGTATGTTGTGTGGAATTGTGAGCGGATAACAATTTCACACAGGAAA
CAGCTATGACCATGATTACGCCAAGCTCGAAATTAACCCTCACTAAAGGG
AACAAAAGCTGGAGCTCGTCTTTGATCAAAACGCAAATCGACGAAAATGT
GTCGGACAATATCAAGTCGATGAGCGAAAAACTAAAAAGGCTAGAATACG
ACAATCTCACAGACAGCGTTGAGATATACGGTATTCACGACAGCAGGCTG
AATAATAAAAAAATTAGAAACTATTAT
```

107. SEQ ID NO: 107
(ZG-s)

```
TTAACCCTAGAAAGATAATCATATTGTGACGTACGTTAAAGATAATCATG
CGTAAAATTGACGCATGTGTTTTATCGATCTGTATATCGAGGTTTATTTA
TTAATTTGAATAGATATTAAGTTTTATTATATTTACACTTACATACTAAT
AATAAATTCAACAAACAATTTATTTATGTTTATTTATTTATTAAAAAAAA
```

```
ACAAAAACTCAAAATTTCTTCTATAAAGTAACAAAACTTTTAAACATTCT
CTCTTTTACAAAAATAAACTTATTTTGTACTTTAAAAACAGTCATGTTGT
ATTATAAAATAAGTAATTAGCTTAACTTATACATAATAGAAACAAATTAT
ACTTATTAATCGCATAACTTCGTATAATGTATGCTATACGAAGTTATGCG
ATTAAGGGATCTGTAGGGCGCAGTAGTCCAGGGTTTCCTTGATGATGTCA
TACTTATCCTGTCCCTTTTTTTTCCACAGCTCGCGGTTGAGGACAAACTC
TTCGCGGTCTTTCCAGTGGGGATCGACGGTATCGTAGAGTCGAGGCCGCT
CTAGCGGATCTGCCCCTCTCCCTCCCCCCCCCCTAACGTTACTGGCCGAA
GCCGCTTGGAATAAGGCCGGTGTGCGTTTGTCTATATGTTATTTTCCACC
ATATTGCCGTCTTTTGGCAATGTGAGGGCCCGGAAACCTGGCCCTGTCTT
CTTGACGAGCATTCCTAGGGGTCTTTCCCCTCTCGCCAAAGGAATGCAAG
GTCTGTTAATGTCGTGAAGGAAGCAGTTCCTCTGGAAGCTTCTTGAAGA
CAAACAACGTCTGTAGCGACCCTTTGCAGGCAGCGGAACCCCCCACCTGG
CGACAGGTGCCTCTGCGGCCAAAAGCCACGTGTATAAGATACACCTGCAA
AGGCGGCACAACCCCAGTGCCACGTTGTGAGTTGGATAGTTGTGGAAAGA
GTCAAATGGCTCTCCTCAAGCGTATTCAACAAGGGGCTGAAGGATGCCCA
GAAGGTACCCCATTGTATGGGATCTGATCTGGGGCCTCGGTGCACATGCT
TTACATGTGTTTAGTCGAGGTTAAAAAAACGTCTAGGCCCCCCGAACCAC
GGGGACGTGGTTTTCCTTTGAAAAACACGATGATAATATGGCCACAACCA
TGGACCCTGTTGTGCTGCAAAGGAGAGACTGGGAGAACCCTGGAGTGACC
CAGCTCAACAGACTGGCTGCCCACCCTCCCTTTGCCTCTTGGAGGAACTC
TGAGGAAGCCAGGACAGACAGGCCCAGCCAGCAGCTCAGGTCTCTCAATG
GAGAGTGGAGGTTTGCCTGGTTCCCTGCCCCTGAAGCTGTGCCTGAGTCT
TGGCTGGAGTGTGACCTCCCAGAGGCTGACACTGTTGTGGTGCCAAGCAA
CTGGCAGATGCATGGCTATGATGCCCCCATCTACACCAATGTCACCTACC
CCATCACTGTGAACCCCCCTTTTGTGCCCACTGAGAACCCCACTGGCTGC
TACAGCCTGACCTTCAATGTTGATGAGAGCTGGCTGCAAGAAGGCCAGAC
CAGGATCATCTTTGATGGAGTCAACTCTGCCTTCCACCTCTGGTGCAATG
GCAGGTGGGTTGGCTATGGCCAAGACAGCAGGCTGCCCTCTGAGTTTGAC
CTCTCTGCCTTCCTCAGAGCTGGAGAGAACAGGCTGGCTGTCATGGTGCT
CAGGTGGTCTGATGGCAGCTACCTGGAAGACCAAGACATGTGGAGGATGT
CTGGCATCTTCAGGGATGTGAGCCTGCTGCACAAGCCCACCACCCAGATT
TCTGACTTCCATGTTGCCACCAGGTTCAATGATGACTTCAGCAGAGCTGT
GCTGGAGGCTGAGGTGCAGATGTGTGGAGAACTCAGAGACTACCTGAGAG
TCACAGTGAGCCTCTGGCAAGGTGAGACCCAGGTGGCCTCTGGCACAGCC
CCCTTTGGAGGAGATCATTGATGAGAGGAGGCTATGCTGACAGAGT
CACCCTGAGGCTCAATGTGGAGAACCCCAAGCTGTGGTCTGCTGAGATCC
CCAACCTCTACAGGGCTGTTGTGGAGCTGCACACTGCTGATGGCACCCTG
ATTGAAGCTGAAGCCTGTGATGTTGGATTCAGAGAAGTCAGGATTGAGAA
TGGCCTGCTGCTGCTCAATGGCAAGCCTCTGCTCATCAGGGGAGTCAACA
GGCATGAGCACCACCCTCTGCATGGACAAGTGATGGATGAACAGACAATG
```

```
GTGCAAGATATCCTGCTAATGAAGCAGAACAACTTCAATGCTGTCAGGTG
CTCTCACTACCCCAACCACCCTCTCTGGTACACCCTGTGTGACAGGTATG
GCCTGTATGTTGTTGATGAAGCCAACATTGAGACACATGGCATGGTGCCC
ATGAACAGGCTCACAGATGACCCCAGGTGGCTGCCTGCCATGTCTGAGAG
AGTGACCAGGATGGTGCAGAGAGACAGGAACCACCCCTCTGTGATCATCT
GGTCTCTGGGCAATGAGTCTGGACATGGAGCCAACCATGATGCTCTCTAC
AGGTGGATCAAGTCTGTTGACCCCAGCAGACCTGTGCAGTATGAAGGAGG
TGGAGCAGACACCACAGCCACAGACATCATCTGCCCCATGTATGCCAGGG
TTGATGAGGACCAGCCCTTCCCTGCTGTGCCCAAGTGGAGCATCAAGAAG
TGGCTCTCTCTGCCTGGAGAGACCAGACCTCTGATCCTGTGTGAATATGC
ACATGCAATGGGCAACTCTCTGGGAGGCTTTGCCAAGTACTGGCAAGCCT
TCAGACAGTACCCCAGGCTGCAAGGAGGATTTGTGTGGGACTGGGTGGAC
CAATCTCTCATCAAGTATGATGAGAATGGCAACCCCTGGTCTGCCTATGG
AGGAGACTTTGGTGACACCCCCAATGACAGGCAGTTCTGCATGAATGGCC
TGGTCTTTGCAGACAGGACCCCTCACCCTGCCCTCACAGAGGCCAAGCAC
CAGCAACAGTTCTTCCAGTTCAGGCTGTCTGGACAGACCATTGAGGTGAC
ATCTGAGTACCTCTTCAGGCACTCTGACAATGAGCTCCTGCACTGGATGG
TGGCCCTGGATGGCAAGCCTCTGGCTTCTGGTGAGGTGCCTCTGGATGTG
GCCCCTCAAGGAAAGCAGCTGATTGAACTGCCTGAGCTGCCTCAGCCAGA
GTCTGCTGGACAACTGTGGCTAACAGTGAGGGTGGTTCAGCCCAATGCAA
CAGCTTGGTCTGAGGCAGGCCACATCTCTGCATGGCAGCAGTGGAGGCTG
GCTGAGAACCTCTCTGTGACCCTGCCTGCTGCCTCTCATGCCATCCCTCA
CCTGACAACATCTGAAATGGACTTCTGCATTGAGCTGGGCAACAAGAGAT
GGCAGTTCAACAGGCAGTCTGGCTTCCTGTCTCAGATGTGGATTGGAGAC
AAGAAGCAGCTCCTCACCCCTCTCAGGGACCAATTCACCAGGGCTCCTCT
GGACAATGACATTGGAGTGTCTGAGGCCACCAGGATTGACCCAAATGCTT
GGGTGGAGAGGTGGAAGGCTGCTGGACACTACCAGGCTGAGGCTGCCCTG
CTCCAGTGCACAGCAGACACCCTGGCTGATGCTGTTCTGATCACCACAGC
CCATGCTTGGCAGCACCAAGGCAAGACCCTGTTCATCAGCAGAAAGACCT
ACAGGATTGATGGCTCTGGACAGATGGCAATCACAGTGGATGTGGAGGTT
GCCTCTGACACACCTCACCCTGCAAGGATTGGCCTGAACTGTCAACTGGC
ACAGGTGGCTGAGAGGGTGAACTGGCTGGGCTTAGGCCCTCAGGAGAACT
ACCCTGACAGGCTGACAGCTGCCTGCTTTGACAGGTGGGACCTGCCTCTG
TCTGACATGTACACCCCTTATGTGTTCCCTTCTGAGAATGGCCTGAGGTG
TGGCACCAGGGAGCTGAACTATGGTCCTCACCAGTGGAGGGGAGACTTCC
AGTTCAACATCTCCAGGTACTCTCAGCAACAGCTCATGGAAACCTCTCAC
AGGCACCTGCTCCATGCAGAGGAGGGAACCTGGCTGAACATTGATGGCTT
CCACATGGGCATTGGAGGAGATGACTCTTGGTCTCCTTCTGTGTCTGCTG
AGTTCCAGTTATCTGCTGGCAGGTACCACTATCAGCTGGTGTGGTGCCAG
AAGTAAACCTAATCTAGCAGCTCGCTGATCAGCCTCGACTGTGCCTTCTA
GTTGCCAGCCATCTGTTGTTTGCCCCTCCCCCGTGCCTTCCTTGACCCTG
```

```
GAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGG
ACAGCAAGGGGGAGGATTGGGAAGACAATAGCAGGCATGCTGGGGATGCG
GTGGGCTCTATGGCTTCTGAGGCGGAAAGAACCAGCTGGGGCTCGATCCT
CTAGTTGGCGCGTCATGGTCCATATGAATATCCTCCTTAGTTCCTATTCC
GAAGTTCCTATTCTCTAGAAAGTATAGGAACTTCGGCGCGTCGACATTGA
TTATTGACTAGTTATTAATAGTAATCAATTACGGGGTCATTAGTTCATAG
CCCATATATGGAGTTCCGCGTTACATAACTTACGGTAAATGGCCCGCCTG
GCTGACCGCCCAACGACCCCCGCCCATTGACGTCAATAATGACGTATGTT
CCCATAGTAACGCCAATAGGGACTTTCCATTGACGTCAATGGGTGGACTA
TTTACGGTAAACTGCCCACTTGGCAGTACATCAAGTGTATCATATGCCAA
GTACGCCCCCTATTGACGTCAATGACGGTAAATGGCCCGCCTGGCATTAT
GCCCAGTACATGACCTTATGGGACTTTCCTACTTGGCAGTACATCTACGT
ATTAGTCATCGCTATTACCATGGGTCGAGGTGAGCCCCACGTTCTGCTTC
ACTCTCCCCATCTCCCCCCCCTCCCCACCCCCAATTTTGTATTTATTTAT
TTTTTAATTATTTTGTGCAGCGATGGGGGCGGGGGGGGGGGGCGCGCG
CCAGGCGGGGCGGGCGGGCGAGGGGCGGGCGGGGCGAGGCGGAGAGG
TGCGGCGGCAGCCAATCAGAGCGGCGCGCTCCGAAAGTTTCCTTTTATGG
CGAGGCGGCGGCGGCGGCCCTATAAAAAGCGAAGCGCGCGGCGGGCG
GGAGTCGCTGCGTTGCCTTCGCCCCGTGCCCCGCTCCGCGCCGCCTCGCG
CCGCCCGCCCCGGCTCTGACTGACCGCGTTACTCCCACAGGTGAGCGGGC
GGGACGGCCCTTCTCCTCCGGGCTGTAATTAGCGCTTGGTTTAATGACGG
CTCGTTTCTTTTCTGTGGCTGCGTGAAAGCCTTAAAGGGCTCCGGGAGGG
CCCTTTGTGCGGGGGGAGCGGCTCGGGGGGTGCGTGCGTGTGTGTGTGC
GTGGGGAGCGCCGCGTGCGGCCCGCGCTGCCCGGCGGCTGTGAGCGCTGC
GGGCGCGGCGCGGGGCTTTGTGCGCTCCGCGTGTGCGCGAGGGGAGCGCG
GCCGGGGCGGTGCCCCGCGGTGCGGGGGGGCTGCGAGGGGAACAAAGGC
TGCGTGCGGGGTGTGTGCGTGGGGGGGTGAGCAGGGGGTGTGGGCGCGGC
GGTCGGGCTGTAACCCCCCCCTGCACCCCCCTCCCCGAGTTGCTGAGCAC
GGCCCGGCTTCGGGTGCGGGCTCCGTGCGGGCGTGGCGCGGGGCTCGC
CGTGCCGGGCGGGGGTGGCGGCAGGTGGGGGTGCCGGGCGGGCGGGC
CGCCTCGGGCCGGGAGGGCTCGGGGAGGGGCGCGCGGCCCCGGAGCG
CCGGCGGCTGTCGAGGCGCGGCGAGCCGCAGCCATTGCCTTTTATGGTAA
TCGTGCGAGAGGGCGCAGGGACTTCCTTTGTCCCAAATCGGCGGAGCCG
AAATCTGGGAGGCGCCGCCGCACCCCCTCTAGCGGGCGCGGGCGAAGCGG
TGCGGCGCCGGCAGGAAGGAAATGGGCGGGAGGGCCTTCGTGCGTCGCC
GCGCCGCCGTCCCCTTCTCCATCTCCAGCCTCGGGGCTGCCGCAGGGGGA
CGGCTGCCTTCGGGGGGACGGGGCAGGGCGGGGTTCGGCTTCTGGCGTG
TGACCGGCGGCTCTAGAGCCTCTGCTAACCATGTTCATGCCTTCTTCTTT
TTCCTACAGCTCCTGGGCAACGTGCTGGTTATTGTGCTGTCTCATCATTT
TGGCAAAGAATTCGCCACCATGGTGAGCAAGGGCGAGGAGCTGTTCACCG
```

-continued

```
GGGTGGTGCCCATCCTGGTCGAGCTGGACGGCGACGTAAACGGCCACAAG
TTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCC
TCGTGACCACCCTGACCTACGGCGTGCAGTGCTTCAGCCGCTACCCCGAC
CACATGAAGCAGCACGACTTCTTCAAGTCCGCCATGCCCGAAGGCTACGT
CCAGGAGCGCACCATCTTCTTCAAGGACGACGGCAACTACAAGACCCGCG
CCGAGGTGAAGTTCGAGGGCGACACCCTGGTGAACCGCATCGAGCTGAAG
GGCATCGACTTCAAGGAGGACGGCAACATCCTGGGGCACAAGCTGGAGTA
CAACTACAACAGCCACAACGTCTATATCATGGCCGACAAGCAGAAGAACG
GCATCAAGGTGAACTTCAAGATCCGCCACAACATCGAGGACGGCAGCGTG
CAGCTCGCCGACCACTACCAGCAGAACACCCCCATCGGCGACGGCCCCGT
GCTGCTGCCCGACAACCACTACCTGAGCACCCAGTCCGCCCTGAGCAAAG
ACCCCAACGAGAAGCGCGATCACATGGTCCTGCTGGAGTTCGTGACCGCC
GCCGGGATCACTCTCGGCATGGACGAGCTGTACAAGTAAAGCGGCCGCGA
CTCTAGATCATAATCAGCCATACCACATTTGTAGAGGTTTTACTTGCTTT
AAAAAACCTCCCACACCTCCCCCTGAACCTGAAACATAAAATGAATGCAA
TTGTTGTTGTTAACTTGTTTATTGCAGCTTATAATGGTTACAAATAAAGC
AATAGCATCACAAATTTCACAAATAAAGCATTTTTTTCACTGCATTCTAG
TTGTGGTTTGTCCAAACTCATCAATGTATCTTAAGATAACTTCGTATAAT
GTATGCTATACGAAGTTATATAACTTCGTATAATGTGTACTATACGAAGT
TATAAATGAAGTTCCTATTCCGAAGTTCCTATTCTCTAGAAAGTATAGGA
ACTTCGAAGCAGCTCCAGCCTACACAATCGCTCAAGACGTGTAATGCTTT
TATTATATATTAGTCACGATATCTATAACAAGAAAATATATATATAATAA
GTTATCACGTAAGTAGAACATGAAATAACAATATAATTATCGTATGAGTT
AAATCTTAAAAGTCACGTAAAAGATAATCATGCGTCATTTTGACTCACGC
GGTCGTTATAGTTCAAAATCAGTGACACTTACCGCATTGACAAGCACGCC
TCACGGGAGCTCCAAGCGGCGACTGAGATGTCCTAAATGCACAGCGACGG
ATTCGCGCTATTTAGAAAGAGAGCAATATTTCAAGAATGCATGCGTCA
ATTTTACGCAGACTATCTTTCTAGGGTTAAAAAAGATTTGCGCTTTACTC
GACCTAAACTTTAAACACGTCATAGAATCTTCGTTTGACAAAAACCACAT
TGTGGGGTACCGAGCTCGAATTCATCGATGATATCAGATCTGCCGGTCTC
CCTATAGTGAGTCGTATTAATTTCGATAAGCCAGGTTAACCTGCATTAAT
GAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGG
ATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAG
GACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAG
CCCGACCGCTGCGCCTTATCCGGTAACTATCGTCTTGAGTCCAACCCGGT
AAGACACGACTTATCGCCACTGGCAGCAGCCACTGGTAACAGGATTAGCA
GAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCC
AGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGC
TCAGTGGAACGAAAACTCACGTTAAGGGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCT
CCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTG
TCATGCCATCCGTAAGATGCTTTTCTGTGACTGGTGAGTACTCAACCAAG
TCATTCTGAGAATAGTGTATGCGGCGACCGAGTTGCTCTTGCCCGGCGTC
AATACGGGATAATACCGCGCCACATAGCAGAACTTTAAAGTGCTCATCA
TTGGAAAACGTTCTTCGGGGCGAAAACTCTCAAGGATCTTACCGCTGTTG
AGATCCAGTTCGATGTAACCCACTCGTGCACCCAACTGATCTTCAGCATC
TTTTACTTTCACCAGCGTTTCTGGGTGAGCAAAAACAGGAAGGCAAAATG
CCGCAAAAAAGGGAATAAGGGCGACACGGAAATGTTGAATACTCATACTC
TTCCTTTTTCAATATTATTGAAGCATTTATCAGGGTTATTGTCTCATGAG
CGGATACATATTTGAATGTATTTAGAAAAATAAACAAATAGGGGTTCCGC
GCACATTTCCCCGAAAAGTGCCACCTGACGTCTAAGAAACCATTATTATC
ATGACATTAACCTATAAAAATAGGCGTATCACGAGGCCCTTTCGTCTCGC
GCGTTTCGGTGATGACGGTGAAAACCTCTGACACATGCAGCTCCCGGAGA
CGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGC
ATCAGAGCAGATTGTACTGAGAGTGCACCATATGGACATATTGTCGTTAG
AACGCGGCTACAATTAATACATAACCTTATGTATCATACACATACGATTT
AGGTGACACTATAGAACTCGACCTCGAGGCTGGCACGACAGGTTTCCCGA
CTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGT
GGAATTGTGAGCGGATAACAATTTCACACAGGAAACAGCTATGACCATGA
```

-continued

TTACGCCAAGCTCGAAATTAACCCTCACTAAAGGGAACAAAAGCTGGAGC
TCGTCTTTGATCAAAACGCAAATCGACGAAAATGTGTCGGACAATATCAA
GTCGATGAGCGAAAAACTAAAAAGGCTAGAATACGACAATCTCACAGACA
GCGTTGAGATATACGGTATTCACGACAGCAGGCTGAATAATAAAAAAATT
AGAAACTATTAT

108. SEQ ID NO: 108
(pSTART-k)
CCAAATAATGATTTTATTTTGACTGATAGTGACCTGTTCGTTGCAACAAA
TTGATAAGCAATGCTTTTTTATAATGCCAACTTTGTACAAAAAAGCAGGC
TTTAAAGGAACCAATTCAGTCGACTGGATCCGGTACCGAATTCGCTTACT
AAAAGCCAGATAACAGTATGCGTATTTGCGCGCTGATTTTTGCGGTATAA
GAATATATACTGATATGTATACCCGAAGTATGTCAAAAGAGGTGTGCTT
CTAGAATGCAGTTTAAGGTTTACACCTATAAAAGAGAGAGCCGTTATCGT
CTGTTTGTGGATGTACAGAGTGATATTATTGACACGCCCGGGCGACGGAT
AGTGATCCCCCTGGCCAGTGCACGTCTGCTGTCAGATAAAGTCTCCCGTG
AACTTTACCCGGTGGTGCATATCGGGGATGAAAGCTGGCGCATGATGACC
ACCGATATGGCCAGTGTGCCGGTCTCCGTTATCGGGGAAGAAGTGGCTGA
TCTCAGCCACCGCGAAAATGACATCAAAAACGCCATTAACCTGATGTTCT
GGGGAATATAGAATTCGCGGCCGCACTCGAGATATCTAGACCCAGCTTTC
TTGTACAAAGTTGGCATTATAAGAAAGCATTGCTTATCAATTTGTTGCAA
CGAACAGGTCACTATCAGTCAAAATAAAATCATTATTTGCCATCCAGCTG
Cagctgtcaaacatgagaattacaacttatatcgtatgggctgacttca
ggtgctacatttgaagagataaattgcactgaaatctagaaatattttat
ctgattaataagatgatcttcttgagatcgttttggtctgcgcgtaatct
cttgctctgaaaacgaaaaaaccgccttgcagggcggttttttcgaaggtt
ctctgagctaccaactcttttgaaccgaggtaactggcttggaggagcgca
gtcaccaaaacttgtcctttcagtttagccttaaccggcgcatgacttca
agactaactcctctaaatcaattaccagtggctgctgccagtggtgcttt
tgcatgtctttccgggttggactcaagacgatagttaccggataaggcgc
agcggtcggactgaacgggggggttcgtgcatacagtccagcttggagcga
actgcctacccggaactgagtgtcaggcgtggaatgagacaaacgcggcc
ataacagcggaatgacaccggtaaaccgaaaggcaggaacaggagagcgc
acgagggagccgccaggggggaaacgcctggtatctttatagtcctgtcgg
gtttcgccaccactgatttgagcgtcagatttcgtgatgcttgtcagggg
ggcggagcctatggaaaaacggctttgccgcggccctctcacttccctgt
taagtatcttcctggcatcttccaggaaatctccgccccgttcgtaagcc
atttccgctcgccgcagtcgaacgaccgagcgtagcgagtcagtgagcga
ggaagcggaatatatcctgtatcacatattctgctgacgcaccggtgcag
ccttttttctcctgccacatgaagcacttcactgacaccctcatcagtgc
caacatagtaagccagtatacactccgctagcgctGAGGTCTGCCTCGTG
AAGAAGGTGTTGCTGACTCATACCAGGCCTGAATCGCCCCATCATCCAGC
CAGAAAGTGAGGGAGCCACGGTTGATGAGAGCTTTGTTGTAGGTGGACCA GTTGGTGATTTTGAACTTTTGCTTTGCCACGGAACGGTCTGCGTTGTCGG
GAAGATGCGTGATCTGATCCTTCAACTCAGCAAAAGTTCGATTTATTCAA
CAAAGCCACGTTGTGTCTCAAAATCTCTGATGTTACATTGCACAAGATAA
AAATATATCATCATGAACAATAAAACTGTCTGCTTACATAAACAGTAATA
CAAGGGGTGTTATGAGCCATATTCAACGGGAAACGTCTTGCTCGAGGCCG
CGATTAAATTCCAACATGGATGCTGATTTATATGGGTATAAATGGGCTCG
CGATAATGTCGGGCAATCAGGTGCGACAATCTATCGATTGTATGGGAAGC
CCGATGCGCCAGAGTTGTTTCTGAAACATGGCAAAGGTAGCGTTGCCAAT
GATGTTACAGATGAGATGGTCAGACTAAACTGGCTGACGGAATTTATGCC
TCTTCCGACCATCAAGCATTTTATCCGTACTCCTGATGATGCATGGTTAC
TCACCACTGCGATCCCCGGGAATACAGCATTCCAGGTATTAGAAGAATAT
CCTGATTCAGGTGAAAATATTGTTGATGCGCTGGCAGTGTTCCTGCGCCG
GTTGCATTCGATTCCTGTTTGTAATTGTCCTTTTAACAGCGATCGCGTAT
TTCGTCTCGCTCAGGCGCAATCACGAATGAATAACGGTTTGGTTGATGCG
AGTGATTTTGATGACGAGCGTAATGGCTGGCCTGTTGAACAAGTCTGGAA
AGAAATGCATAAGCTTTTGCCATTCTCACCGGATTCAGTCGTCACTCATG
GTGATTTCTCACTTGATAACCTTATTTTTGACGAGGGGAAATTAATAGGT
TGTATTGATGTTGGACGAGTCGGAATCGCAGACCGATACCAGGATCTTGC
CATCCTATGGAACTGCCTCGGTGAGTTTTCTCCTTCATTACAGAAACGGC
TTTTTCAAAAATATGGTATTGATAATCCTGATATGAATAAATTGCAGTTT
CATTTGATGCTCGATGAGTTTTTCTAATCAGAcATGTTCTTTCCTGCGTT
ATCCCCTGATTCTGTGGATAACCGTATTACCGCTAGCATGGATCTCGGGG
ACGTCTAACTACTAAGCGAGAGTAGGGAACTGCCAGGCATCAAATAAAAC
GAAAGGCTCAGTCGGAAGACTGGGCCTTTCGTTTTATCTGTTGTTTGTCG
GTGAACGCTCTCCTGAGTAGGACAAATCCGCCGGGAGCGGATTTGAACGT
TGTGAAGCAACGGCCCGGAGGGTGGCGGGCAGGACGCCCGCCATAAACTG
CCAGGCATCAAACTAAGCAGAAGGCCATCCTGACGGATGGCCTTTTTGCG
TTTCTACAAACTCTTCCTGTTAGTTAGTTACTTAAGCTCGGGCC 109. SEQ ID NO: 109
(pSTART-C2)
AGAAGGCCATCCTGACGGATGGCCTTTTTGCGTTTCTACAAACTCTTCCT
GTTAGTTAGTTACTTAAGCTCGGGCCCCAAATAATGATTTTATTTTGACT
GATAGTGACCTGTTCGTTGCAACAAATTGATAAGCAATGCTTTTTTATAA
TGCCAACTTTGTACAAAAAAGCAGGCTTTAAAGGAACCAATTCAGTCGAC
TGGATCCGGTACCGAATTCGCTTACTAAAAGCCAGATAACAGTATGCGTA
TTTGCGCGCTGATTTTTGCGGTATAAGAATATATACTGATATGTATACCC
GAAGTATGTCAAAAGAGGTGTGCTTCTAGAATGCAGTTTAAGGTTTACA
CCTATAAAAGAGAGCCGTTATCGTCTGTTTGTGGATGTACAGAGTGAT
ATTATTGACACGCCCGGGCGACGGATAGTGATCCCCCTGGCCAGTGCACG
TCTGCTGTCAGATAAAGTCTCCCGTGAACTTTACCCGGTGGTGCATATCG
GGGATGAAAGCTGGCGCATGATGACCACCGATATGGCCAGTGTGCCGGTC
TCCGTTATCGGGGAAGAAGTGGCTGATCTCAGCCACCGCGAAAATGACAT -continued CAAAAACGCCATTAACCTGATGTTCTGGGGAATATAGAATTCGCGGCCGC
ACTCGAGATATCTAGACCCAGCTTTCTTGTACAAAGTTGGCATTATAAGA
AAGCATTGCTTATCAATTTGTTGCAACGAACAGGTCACTATCAGTCAAAA
TAAAATCATTATTTGCCATCCAGCTGCagctgtcaaacatgagaattaca
acttatatcgtatgggctgacttcaggtgctacatttgaagagataaat
tgcactgaaatctagaaatattttatctgattaataagatgatcttcttg
agatcgttttggtctgcgcgtaatctcttgctctgaaaacgaaaaaccg
ccttgcagggcggttttttcgaaggttctctgagctaccaactCtttgaac
cgaggtaactggcttggaggagcgcagtcaccaaaacttgtcctttcagt
ttagccttaaccggcgcatgacttcaagactaactcctctaaatcaatta
ccagtggctgctgcagtggtgcttttgcatgtctttccgggttggactc
aagacgatagttaccggataaggcgcagcggtcggactgaacgggggtt
cgtgcatacagtccagcttggagcgaactgcctaccggaactgagtgtc
aggcgtggaatgagacaaacgcggccataacagcggaatgacaccggtaa
accgaaaggcaggaacaggagagcgcacgagggagccgcaggggggaaac
gcctggtatctttatagtcctgtcgggtttcgccaccactgatttgagcg
tcagatttcgtgatgcttgtcaggggggcggagcctatgaaaaacggct
ttgccgcggccctctcacttccctgttaagtatcttcctggcatcttcca
ggaaatctccgcccgttcgtaagccatttccgctcgccgcagtcgaacg
accgagcgtagcgagtcagtgagcgaggaagcggaatatatcctgtatca
catattctgctgacgcaccggtgcagcctttttttctcctgccacatgaag
cacttcactgacaccctcatcagtgccaacatagtaagccagtatacact
ccgctagcgctgatgtccggcggtgcttttgccgttacgcaccaccccgt
cagtagctgaacaggagggacagctgatagaaacagaagccactggagca
cctcaaaaacaccatcatacactaaatcagtaagttggcagcatcacccg
acgcactttgcgccgaataaatacctgtgacggaagatcacttcgcagaa
taaataaatcctggtgtccctgttgataccgggaagccctgggccaactt
ttggcgaaaatgagacgttgatcggcacgtaagaggttccaactttcacc
ataatgaaataagatcactaccgggcgtattttttgagttatcgagattt
tcaggagctaaggaagctaaaatggagaaaaaaatcactggatataccac
cgttgatatatcccaatggcatcgtaaagaacattttgaggcatttcagt
cagttgctcaatgtacctataaccagaccgttcagctggatattacggcc
ttttaaagaccgtaaagaaaataagcacaagttttatccggcctttat
tcacattcttgcccgcctgatgaatgctcatccggaattccgtatggcaa
tgaaagacggtgagctggtgatatgggatagtgttcaccttgttacacc
gttttccatgagcaaactgaaacgttttcatcgctctggagtgaatacca
cgacgatttccggcagtttctacacatatattcgcaagatgtggcgtgtt
acggtgaaaacctggcctatttccctaaagggtttattgagaatatgttt
ttcgtctcagccaatccctgggtgagtttcaccagttttgatttaaacgt
ggccaatatggacaacttcttcgcccccgttttcaccatgggcaaatatt
atacgcaaggcgacaaggtgctgatgccgctggcgattcaggttcatcat -continued gccgtctgtgatggcttccatgtcggcagaatgcttaatgaattacaaca
gtactgcgatgagtggcagggcggggcgtaattttttttaaggcagttatt
ggtgcccttaaacATGTTCTTTCCTGCGTTATCCCCTGATTCTGTGGATA
ACCGTATTACCGCTAGCATGGATCTCGGGGACGTCTAACTACTAAGCGAG
AGTAGGGAACTGCCAGGCATCAAATAAAACGAAAGGCTCAGTCGGAAGAC
TGGGCCTTTCGTTTTATCTGTTGTTTGTCGGTGAACGCTCTCCTGAGTAG
GACAAATCCGCCGGGAGCGGATTTGAACGTTGTGAAGCAACGGCCCGGAG
GGTGGCGGGCAGGACGCCCGCCATAAACTGCCAGGCATCAAACTAAGC 110. SEQ ID NO: 110
(pGFP-CAN)
GAACtcgacggcgcgccgcgatTaacCCCAAGAAGAAGAGGAAGGTGAGC
AAGCAGATCCTGAAGAACACCGGCCTGCAGGAGATCATGAGCTTCAAGGT
GAACCTGGAGGGCGTGGTGAACAACCACGTGTTCACCATGGAGGGCTGCG
GCAAGGGCAACATCCTGTTCGGCAACCAGCTGGTGCAGATCCGCGTGACC
AAGGGCGCCCCCCTGCCCTTCGCCTTCGACATCCTGAGCCCCGCCTTCCA
GTACGGCAACCGCACCTTCACCAAGTACCCCGAGGACATCAGCGACTTCT
TCATCCAGAGCTTCCCCGCCGGCTTCGTGTACGAGCGCACCCTGCGCTAC
GAGGACGGCGGCCTGGTGGAGATCCGCAGCGACATCAACCTGATCGAGGA
GATGTTCGTGTACCGCGTGGAGTACAAGGGCCGCAACTTCCCCAACGACG
GCCCCGTGATGAAGAAGACCATCACCGGCCTGCAGCCCAGCTTCGAGGTG
GTGTACATGAACGACGGCGTGCTGGTGGGCCAGGTGATCCTGGTGTACCG
CCTGAACAGCGGCAAGTTCTACAGCTGCCACATGCGCACCCTGATGAAGA
GCAAGGGCGTGGTGAAGGACTTCCCCGAGTACCACTTCATCCAGCACCGC
CTGGAGAAGACCTACGTGGAGGACGGCGGCTTCGTGGAGCAGCACGAGAC
CGCCATCGCCCAGCTGACCAGCCTGGGCAAGCCCCTGGGCAGCCTGCACG
AGTGGGTGTAATAGGAATTCGCCCTTGttaattaagcggcgcgccGTGAG
CAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGC
GATGCCACCTACGGCAAGCTGACCCTGAAGTTCATCTGCACCACCGGCAA
GCTGCCCGTGCCCTGGCCCACCCTCGTGACCACCCTGACCTACGGCGTGC
AGTGCTTCAGCCGCTACCCCGACCACATGAAGCAGCACGACTTCTTCAAG
TCCGCCATGCCCGAAGGCTACGTCCAGGAGCGCACCATCTTCTTCAAGGA
CGACGGCAACTACAAGACCCGCGCCGAGGTGAAGTTCGAGGGCGACACCC
TGGTGAACCGCATCGAGCTGAAGGGCATCGACTTCAAGGAGGACGGCAAC
ATCCTGGGGCACAAGCTGGAGTACAACTACAACAGCCACAACGTCTATAT
CATGGCCGACAAGCAGAAGAACGGCATCAAGGTGAACTTCAAGATCCGCC
ACAACATCGAGGACGGCAGCGTGCAGCTCGCCGACCACTACCAGCAGAAC
ACCCCCATCGGCGACGGCCCCGTGCTGCTGCCCGACAACCACTACCTGAG
CACCCAGTCCGCCCTGAGCAAAGACCCCAACGAGAAGCGCGATCACATGG
TCCTGCTGGAGTTCGTGACCGCCGCCGGGATCACTCTCGGCATGGACGAG
CTGTACAAGTAAAGCGGCCGCGACTCTAGATCATAATCAGCCATACCACA
TTTGTAGAGGTTTTACTTGCTTTAAAAAACCTCCCACACCTCCCCCTGAA -continued

```
CCTGAAACATAAAATGAATGCAATTGTTGTTGTTAACTTGTTTATTGCAG
CTTATAATGGTTACAAATAAAGCAATAGCATCACAAATTTCACAAATAAA
GCATTTTTTTCACTGCATTCTAGTTGTGGTTTGTCCAAACTCATCAATGT
ATCTTAAGGATCCGCCGATAAGGGCGaattcataacttcgtataatgtat
gctatacgaagttatggatctgtcgatcgacggatcgatccgaacaaacg
acccaacacccgtgcgttttattctgtctttttattgccgatcccctcag
aagaactcgtcaagaaggcgatagaaggcgatgcgctgcgaatcgggagc
ggcgataccgtaaagcacgaggaagcggtcagcccattcgccgccaagct
cttcagcaatatcacgggtagccaacgctatgtcctgatagcggtccgcc
acacccagccggccacagtcgatgaatccagaaaagcggccattttccac
catgatattcggcaagcaggcatcgccatgggtcacgacgagatcctcgc
cgtcgggcatgcgcgccttgagcctggcgaacagttcggctggcgcgagc
ccctgatgctcttcgtccagatcatcctgatcgacaagaccggcttccat
ccgagtacgtgctcgctcgatgcgatgtttcgcttggtggtcgaatgggc
aggtagccggatcaagcgtatgcagccgccgcattgcatcagccatgatg
gatactttctcggcaggagcaaggtgagatgacaggagatcctgccccgg
cacttcgcccaatagcagccagtccttccccgcttcagtgacaacgtcga
gcacagctgcgcaaggaacgcccgtcgtggccagccacgatagccgcgct
gcctcgtcctgcagttcattcagggcaccggacaggtcggtcttgacaaa
aagaaccgggcgcccctgcgctgacagccggaacacggcggcatcagagc
agccgattgtctgttgtgcccagtcatagccgaatagcctctccacccaa
gcggccggagaacctgcgtgcaatccatcttgttcaatggccgatcccat
attggctgcacggatcctgaacggcagaggttacggcagtttgtctctcc
cccttccgggagccaccttcttctccaaccgtcccggtcgcgctctcggc
gcttctgaggagagaactggctgagtgacgcccttatagattcgccctt
gtgtcccgcccttcctttccgccctcccttgcgctacggggccgcccg
caccggcctacacgagcgcgcgcggcggagttgttgacgctagggctcc
ggctccctggttgggtgttctttctgacgcgacaggaggaggagaatgtc
ctggtcctgtcgtcctcctttcggtttcccgtgcactcaaaccgaggac
ttacagaacggaggataaagttaggccattttttactcagcttcggagttc
aggctcattttttcagctaaagtctctcattagtatccccccacacacatc
gggaaaatggtttgtcctacgcatcggtaatgaaggcggggcccttcggg
tcctccggagcgggttccgggggtgggggaaggagggagggacgggacg
ggcctcgttcatgaatattcagttcaccgctgaatatgcataaggcaggc
aagatggcgcgtccaatcaattggaagtagccgttattagtggagaggcc
ccaggacgttggggcaccgcctgtgctctagtagctttacggagccctgg
cgctcgatgttcaagcccaagctttcgcgagctcgaccgaacaaacgacc
caacacccgtgcgttttattctgtctttttattgccgctcagctttacag
tgacaatgacggctggcgactgaatattagtgcttacagacagcactaca
tattttccgtcgatgttgaaatcctttctcatatgtcaccataaatatca
aataattatagcaatcatttacgcgttaatggctaatcgccatcttccag
```

-continued

```
caggcgcaccattgcccctgtttcactatccaggttacggatatagttca
tgacaatatttacattggtccagccaccagcttgcatgatctccggtatt
gaaactccagcgcgggccatatctcgcgcggctccgacacgggcactgtg
tccagaccaggccaggtatctctgaccagagtcatcctaaaatacacaaa
caattagaatcagtagtttaacacattatacacttaaaaattttatattt
accttagcgccgtaaatcaatcgatgagttgcttcaaaaatcccttccag
ggcgcgagttgatagctggctggtggcagatggcgcggcaacaccatttt
ttctgacccggcaaaacaggtagttattcggatcatcagctacaccagag
acggaaatccatcgctcgaccagtttagttaccccaggctaagtgcctt
ctctacacctgcggtgctaaccagcgttttcgttctgccaatatggatta
acattctcccaccgtcagtacgtgagatatctttaaccctgatcctggca
atttcggctatacgtaacagggtgttataagcaatccccagaaatgccag
attacgtatatcctggcagcgatcgctattttccatgagtgaacgaacct
ggtcgaaatcagtgcgttcgaacgctagagcctgttttgcacgttcaccg
gcatcaacgttttcttttcggatccgccgcataaccagtgaaacagcatt
gctgtcacttggtcgtggcagcccggaccgacgatgaagcatgtttagct
ggcccaaatgttgctggatagttttactgccagaccgcgcgcctgaaga
tatagaagataatcgcgaacatcttcaggttctgcgggaaaccatttccg
gttattcaacttgcaccatgccgcccacgaccggcaaacggacagaagca
ttttccaggtatgctcagaaaacgcctggcgatccctgaacatgtccatc
aggttcttgcgaacctcatcactcgttgcatcgaccggtaatgcaggcaa
attttggtgtacggtcagtaaattggacaccttcctcttcttcttgggca
tggccgcaggaaagcagagccctgaagctcccatcaccggccaataagag
ccaagcctgcagtgtgacctcatagagcaatgtgccagccagcctgaccc
caagggccctcaggcttgggcacactgtctctaggaccctgagagaaaga
catacccatttctgcttagggccctgaggatgagcccaggggtggcttgg
cactgaagcaaaggacactggggctcagctggcagcaaagtgaccaggat
gctgaggctttgacccagaagccagaggccagaggccaggacttctcttg
gtcccagtccaccctcactcagagctttaccaatgccctctggatagttg
tcgggtaacggtggacgccactgattctctgccagcctaggacttcgcc
attccgctgattctgctcttccagccactggctgaccggttggaagtact
ccagcagtgccttggcatccagggcatctgagcctaccaggtccttcagt
acctcctgccagggcctggagcagccagcctgcaacacctgcctgccaag
cagagtgaccactgtgggcacaggggacacagggtggggcccacaacagc
accattgtccacttgtccctcactagtaaaagaactctagggttgcgggg
ggtggggaggtctctgtgaggctggtaagggatatttgcctggcccatg
gagatccataacttcgtataatgtatgctatacgaagttataagctttcg
cgagctcgagatcctgcaggcgcgccgGATCTGCCGGTCTCCCTATAGTG
AGTCGTATTAATTTCGATAAGCCAGGTTAACCTGCATTAATGAATCGGCC
AACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGC
```

-continued

TCACTCAAAGGCGGTAATACGGTTATCCACAGAATCAGGGGATAACGCAG
GAAAGAACATGTGAGCAAAAGGCCAGCAAAAGGCCAGGAACCGTAAAAAG
GCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGA
CTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTAC
ACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAA
CGAAAACTCACGTTAAGGGATTTTGGTCATGAGATTATCAAAAAGGATCT
TCACCTAGATCCTTTTAAATTAAAAATGAAGTTTTAAATCAATCTAAAGT
ATATATGAGTAAACTTGGTCTGACAGTTACCAATGCTTAATCAGTGAGGC
ACCTATCTCAGCGATCTGTCTATTTCGTTCATCCATAGTTGCCTGACTCC
CCGTCGTGTAGATAACTACGATACGGGAGGGCTTACCATCTGGCCCCAGT
GCTGCAATGATACCGCGAGACCCACGCTCACCGGCTCCAGATTTATCAGC
AATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCAT
CGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTT
ATCACTCATGGTTATGGCAGCACTGCATAATTCTCTTACTGTCATGCCAT
CCGTAAGATGCTTTTCTGTGACTGGTGAGTACTCAACCAAGTCATTCTGA
GAATAGTGTATGCGGCGACCGAGTTGCTCTTGCCCGGCGTCAATACGGGA
TAATACCGCGCCACATAGCAGAACTTTAAAAGTGCTCATCATTGGAAAAC
GTTCTTCGGGGCGAAAACTCTCAAGGATCTTACCGCTGTTGAGATCCAGT
TCGATGTAACCCACTCGTGCACCCAACTGATCTTCAGCATCTTTTACTTT
CACCAGCGTTTCTGGGTGAGCAAAAACAGGAAGGCAAAATGCCGCAAAAA
AGGGAATAAGGGCGACACGGAAATGTTGAATACTCATACTCTTCCTTTTT
CAATATTATTGAAGCATTTATCAGGGTTATTGTCTCATGAGCGGATACAT
ATTTGAATGTATTTAGAAAAATAAACAAATAGGGGTTCCGCGCACATTTC
CCCGAAAAGTGCCACCTGACGTCTAAGAAACCATTATTATCATGACATTA
ACCTATAAAAATAGGCGTATCACGAGGCCCTTTCGTCTCGCGCGTTTCGG
TGATGACGGTGAAAACCTCTGACACATGCAGCTCCCGGAGACGGTCACAG
CTTGTCTGTAAGCGGATGCCGGGAGCAGACAAGCCCGTCAGGGCGCGTCA

-continued

GCGGGTGTTGGCGGGTGTCGGGGCTGGCTTAACTATGCGGCATCAGAGCA
GATTGTACTGAGAGTGCACCATATGGACATATTGTCGTTAGAACGCGGCT
ACAATTAATACATAACCTTATGTATCATACACATACGATTTAGGTGACAC
TATA

111. SEQ ID NO: 111
(pCFP-CAN)
GAACtcgacggcgcgccgcgatTaacCCCAAGAAGAAGAGGAAGGTGAGC
AAGCAGATCCTGAAGAACACCGGCCTGCAGGAGATCATGAGCTTCAAGGT
GAACCTGGAGGGCGTGGTGAACAACCACGTGTTCACCATGGAGGGCTGCG
GCAAGGGCAACATCCTGTTCGGCAACCAGCTGGTGCAGATCCGCGTGACC
AAGGGCGCCCCCCTGCCCTTCGCCTTCGACATCCTGAGCCCCGCCTTCCA
GTACGGCAACCGCACCTTCACCAAgTACCCCGAGGACATCAGCGACTTCT
TCATCCAGAGCTTCCCCGCCGGCTTCGTGTACGAGCGCACCCTGCGCTAC
GAGGACGGCGGCCTGGTGGAGATCCGCAGCGACATCAACCTGATCGAGGA
GATGTTCGTGTACCGCGTGGAGTACAAGGGCCGCAACTTCCCCAACGACG
GCCCCGTGATGAAGAAGACCATCACCGGCCTGCAGCCCAGCTTCGAGGTG
GTGTACATGAACGACGGCGTGCTGGTGGGCCAGGTGATCCTGGTGTACCG
CCTGAACAGCGGCAAGTTCTACAGCTGCCACATGCGCACCCTGATGAAGA
GCAAGGGCGTGGTGAAGGACTTCCCCGAGTACCACTTCATCCAGCACCGC
CTGGAGAAGACCTACGTGGAGGACGGCGGCTTCGTGGAGCAGCACGAGAC
CGCCATCGCCCAGCTGACCAGCCTGGGCAAGCCCCTGGGCAGCCTGCACG
AGTGGGTGTAATAGGAATTCGCCCTTGttaattaagcggcgcgccGTGAG
CAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGC
GATGCCACCTACGGCAAGCTGACCCTGAAGTTCATCTGCACCACCGGCAA
GCTGCCCGTGCCCTGGCCCACCCTCGTGACCACCCTGACCTGGGGCGTGC
AGTGCTTCAGCCGCTACCCCGACCACATGAAGCAGCACGACTTCTTCAAG
TCCGCCATGCCCGAAGGCTACGTCCAGGAGCGCACCATCTTCTTCAAGGA
CGACGGCAACTACAAGACCCGCGCCGAGGTGAAGTTCGAGGGCGACACCC
TGGTGAACCGCATCGAGCTGAAGGGCATCGACTTCAAGGAGGACGGCAAC
ATCCTGGGGCACAAGCTGGAGTACAACTACATCAGCCACAACGTCTATAT
CACCGCCGACAAGCAGAAGAACGGCATCAAGGCCAACTTCAAGATCCGCC
ACAACATCGAGGACGGCAGCGTGCAGCTCGCCGACCACTACCAGCAGAAC
ACCCCCATCGGCGACGGCCCCGTGCTGCTGCCCGACAACCACTACCTGAG
CACCCAGTCCGCCCTGAGCAAAGACCCCAACGAGAAGCGCGATCACATGG
TCCTGCTGGAGTTCGTGACCGCCGCCGGGATCACTCTCGGCATGGACGAG
CTGTACAAGTAAAGCGGCCGCGACTCTAGATCATAATCAGCCATACCACA
TTTGTAGAGGTTTTACTTGCTTTAAAAAACCTCCCACACCTCCCCCTGAA
CCTGAAACATAAAATGAATGCAATTGTTGTTGTTAACTTGTTTATTGCAG
CTTATAATGGTTACAAATAAAGCAATAGCATCACAAATTTCACAAATAAA
GCATTTTTTTCACTGCATTCTAGTTGTGGTTTGTCCAAACTCATCAATGT
ATCTTAAGGATCCGCCGATAAGGGCGaattcataacttcgtataatgtat -continued gctatacgaagttatggatctgtcgatcgacggatcgatccgaacaaacg
acccaacacccgtgcgttttattctgtctttttattgccgatcccctcag
aagaactcgtcaagaaggcgatagaaggcgatgcgctgcgaatcgggagc
ggcgataccgtaaagcacgaggaagcggtcagcccattcgccgccaagct
cttcagcaatatcacgggtagccaacgctatgtcctgatagcggtccgcc
acacccagccgccacagtcgatgaatccagaaaagcggccattttccac
catgatattcggcaagcaggcatcgccatgggtcacgacgagatcctcgc
cgtcgggcatgcgcgccttgagcctggcaacagttcggctggcgcgagc
ccctgatgctcttcgtccagatcatcctgatcgacaagaccggcttccat
ccgagtacgtgctcgctcgatgcgatgtttcgcttggtggtcgaatgggc
aggtagccggatcaagcgtatgcagccgccgcattgcatcagccatgatg
gatactttctcggcaggagcaaggtgagatgacaggagatcctgccccgg
cacttcgcccaatagcagccagtcccttcccgcttcagtgacaacgtcga
gcacagctgcgcaaggaacgcccgtcgtggccagccacgatagccgcgct
gcctcgtcctgcagttcattcagggcaccggacaggtcggtcttgacaaa
aagaaccgggcgcccctgcgctgacagccggaacacggcggcatcagagc
agccgattgtctgttgtgcccagtcatagccgaatagcctctccacccaa
gcggccggagaacctgcgtgcaatccatcttgttcaatggccgatcccat
attggctgcacggatcctgaacggcagaggttacggcagtttgtctctcc
cccttccgggagccaccttcttctccaaccgtcccggtcgcgctctcggc
gcttctgaggagagaactggctgagtgacgccctttatagattcgccctt
gtgtcccgccccttcctttccgccctcccttgcgctacggggccgcccg
caccggcctacacggagcgcgcgcggcggagttgttgacgctagggctcc
ggctccctggttgggtgttctttctgacgcgacaggaggaggagaatgtc
ctggtcctgtcgtcctcctttcggggttcccgtgcactcaaaccgaggac
ttacagaacggaggataaagttaggccattttttactcagcttcggagttc
aggctcattttttcagctaaagtctctcattagtatccccccacacacatc
gggaaaatggtttgtcctacgcatcggtaatgaaggcggggcccttcggg
tcctccggagcgggttccgggggtgggggaaggagggagggacgggacg
ggcctcgttcatgaatattcagttcaccgctgaatatgcataaggcaggc
aagatgcgcgtccaatcaattggaagtagccgttattagtggagaggcc
ccaggacgttggggcaccgcctgtgctctagtagctttacggagccctgg
cgctcgatgttcaagcccaagctttcgcgagctcgaccgaacaaacgacc
caacacccgtgcgttttattctgtctttttattgccgctcagctttacag
tgacaatgacggctggcgactgaatattagtgcttacagacagcactaca
tatttttccgtcgatgttgaaatcctttctcatatgtcaccataaatatca
aataattatagcaatcatttacgcgttaatggctaatcgccatcttccag
caggcgcaccattgcccctgtttcactatccaggttacggatatagttca
tgacaatatttacattggtccagccaccagcttgcatgatctccggtatt
gaaactccagcgcgggccatatctcgcgcggctccgacacgggcactgtg
tccagaccaggccaggtatctctgaccagagtcatcctaaaatacacaaa -continued caattagaatcagtagtttaacacattatacacttaaaaattttatattt
accttagcgccgtaaatcaatcgatgagttgcttcaaaaatcccttccac
ggcgcgagttgatagctggctggtggcagatggcgcggcaacaccatttt
ttctgaccggcaaaacaggtagttattcggatcatcagctacaccagag
acggaaatccatcgctcgaccagtttagttaccccccaggctaagtgcctt
ctctacacctgcggtgctaaccagcgttttcgttctgccaatatggatta
acattctcccaccgtcagtacgtgagatatctttaaccctgatcctggca
atttcggctatacgtaacagggtgttataagcaatcccccagaaatgccag
attacgtatatcctggcagcgatcgctatttttccatgagtgaacgaacct
ggtcgaaatcagtgcgttcgaacgctagagcctgttttgcacgttcaccg
gcatcaacgttttcttttcggatccgccgcataaccagtgaaacagcatt
gctgtcacttggtcgtggcagcccggaccgacgatgaagcatgtttagct
ggcccaaatgttgctggatagttttttactgccagaccgcgcgcctgaaga
tatagaagataatcgcgaacatcttcaggttctgcgggaaaccatttccg
gttattcaacttgcaccatgccgcccacgaccggcaaacggacagaagca
ttttccaggtatgctcagaaaacgcctggcgatccctgaacatgtccatc
aggttcttgcgaacctcatcactcgttgcatcgaccggtaatgcaggcaa
attttggtgtacggtcagtaaattggacaccttcctcttcttcttgggca
tggccgcaggaaagcagagccctgaagctcccatcaccggccaataagag
ccaagcctgcagtgtgacctcatagagcaatgtgccagccagcctgaccc
caagggccctcaggcttgggcacactgtctctaggaccctgagagaaga
catacccatttctgcttagggccctgaggatgagcccaggggtggcttgg
cactgaagcaaaggacactggggctcagctggcagcaaagtgaccaggat
gctgaggctttgacccagaagccagaggccagaggccaggacttctcttg
gtcccagtccaccctcactcagagctttaccaatgccctctggatagttg
tcgggtaacggtggacgccactgattctctggccagcctaggacttcgcc
attccgctgattctgctcttccagccactggctgaccggttggaagtact
ccagcagtgccttggcatccagggcatctgagcctaccaggtccttcagt
acctcctgccagggcctggagcagccagcctgcaacacctgcctgccaag
cagagtgaccactgtgggcacaggggacacagggtggggcccacaacagc
accattgtccacttgtccctcactagtaaaagaactctagggttgcgggg
ggtggggaggtctctgtgaggctggtaagggatatttgcctggcccatg
gagatcctaaacttcgtataatgtatgctatacgaagttataagctttcg
cgagctcgagatcctgcaggcgcgccgGATCTGCCGGTCTCCCTATAGTG
AGTCGTATTAATTTCGATAAGCCAGGTTAACCTGCATTAATGAATCGGCC
AACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGC
TCACTCAAAGGCGGTAATACGGTTATCCACAGAATCAGGGGATAACGCAG
GAAAGAACATGTGAGCAAAAGGCCAGCAAAAGGCCAGGAACCGTAAAAAG
GCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAA

```
GATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGA
CTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTAC
ACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAA
CGAAAACTCACGTTAAGGGATTTTGGTCATGAGATTATCAAAAAGGATCT
TCACCTAGATCCTTTTAAATTAAAAATGAAGTTTTAAATCAATCTAAAGT
ATATATGAGTAAACTTGGTCTGACAGTTACCAATGCTTAATCAGTGAGGC
ACCTATCTCAGCGATCTGTCTATTTCGTTCATCCATAGTTGCCTGACTCC
CCGTCGTGTAGATAACTACGATACGGGAGGGCTTACCATCTGGCCCCAGT
GCTGCAATGATACCGCGAGACCCACGCTCACCGGCTCCAGATTTATCAGC
AATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCAT
CGTGGTGTCACGCTCGTCGTTTGGTATGGCTTCATTCAGCTCCGGTTCCC
AACGATCAAGGCGAGTTACATGATCCCCCATGTTGTGCTAAAAAGCGGTT
AGCTCCTTCGGTCCTCCGATCGTTGTCAGAAGTAAGTTGGCCGCAGTGTT
ATCACTCATGGTTATGGCAGCACTGCATAATTCTCTTACTGTCATGCCAT
CCGTAAGATGCTTTTCTGTGACTGGTGAGTACTCAACCAAGTCATTCTGA
GAATAGTGTATGCGGCGACCGAGTTGCTCTTGCCCGGCGTCAATACGGGA
TAATACCGCGCCACATAGCAGAACTTTAAAAGTGCTCATCATTGGAAAAC
GTTCTTCGGGGCGAAAACTCTCAAGGATCTTACCGCTGTTGAGATCCAGT
TCGATGTAACCCACTCGTGCACCCAACTGATCTTCAGCATCTTTTACTTT
CACCAGCGTTTCTGGGTGAGCAAAAACAGGAAGGCAAAATGCCGCAAAAA
AGGGAATAAGGGCGACACGGAAATGTTGAATACTCATACTCTTCCTTTTT
CAATATTATTGAAGCATTTATCAGGGTTATTGTCTCATGAGCGGATACAT
ATTTGAATGTATTTAGAAAAATAAACAAATAGGGGTTCCGCGCACATTTC
CCCGAAAAGTGCCACCTGACGTCTAAGAAACCATTATTATCATGACATTA
ACCTATAAAAATAGGCGTATCACGAGGCCCTTTCGTCTCGCGCGTTTCGG
TGATGACGGTGAAAACCTCTGACACATGCAGCTCCCGGAGACGGTCACAG
CTTGTCTGTAAGCGGATGCCGGGAGCAGACAAGCCCGTCAGGGCGCGTCA
GCGGGTGTTGGCGGGTGTCGGGGCTGGCTTAACTATGCGGCATCAGAGCA
GATTGTACTGAGAGTGCACCATATGGACATATTGTCGTTAGAACGCGGCT
ACAATTAATACATAACCTTATGTATCATACACATACGATTTAGGTGACAC
TATA
```

112. SEQ ID NO: 112
(pYFP-CAN)

```
GAACtcgacggcgcgccgcgatTaacCCCAAGAAGAAGAGGAAGGTGAGC
AAGCAGATCCTGAAGAACACCGGCCTGCAGGAGATCATGAGCTTCAAGGT
GAACCTGGAGGGCGTGGTGAACAACCACGTGTTCACCATGGAGGGCTGCG
GCAAGGGCAACATCCTGTTCGGCAACCAGCTGGTGCAGATCCGCGTGACC
AAGGGCGCCCCCCTGCCCTTCGCCTTCGACATCCTGAGCCCCGCCTTCCA
GTACGGCAACCGCACCTTCACCAAGTACCCCGAGGACATCAGCGACTTCT
TCATCCAGAGCTTCCCCGCCGGCTTCGTGTACGAGCGCACCCTGCGCTAC
GAGGACGGCGGCCTGGTGGAGATCCGCAGCGACATCAACCTGATCGAGGA
GATGTTCGTGTACCGCGTGGAGTACAAGGGCCGCAACTTCCCCAACGACG
GCCCCGTGATGAAGAAGACCATCACCGGCCTGCAGCCCAGCTTCGAGGTG
GTGTACATGAACGACGGCGTGCTGGTGGGCCAGGTGATCCTGGTGTACCG
CCTGAACAGCGGCAAGTTCTACAGCTGCCACATGCGCACCCTGATGAAGA
GCAAGGGCGTGGTGAAGGACTTCCCCGAGTACCACTTCATCCAGCACCGC
CTGGAGAAGACCTACGTGGAGGACGGCGGCTTCGTGGAGCAGCACGAGAC
CGCCATCGCCCAGCTGACCAGCCTGGGCAAGCCCCTGGGCAGCCTGCACG
AGTGGGTGTAATAGGAATTCGCCCTTGttaattaagcggcgcgccGTGAG
CAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGC
GATGCCACCTACGGCAAGCTGACCCTGAAGTTCATCTGCACCACCGGCAA
GCTGCCCGTGCCCTGGCCCACCCTCGTGACCACCTTCGGCTACGGCCTGC
AGTGCTTCGCCCGCTACCCCGACCACATGAAGCAGCACGACTTCTTCAAG
TCCGCCATGCCCGAAGGCTACGTCCAGGAGCGCACCATCTTCTTCAAGGA
CGACGGCAACTACAAGACCCGCGCCGAGGTGAAGTTCGAGGGCGACACCC
TGGTGAACCGCATCGAGCTGAAGGGCATCGACTTCAAGGAGGACGGCAAC
ATCCTGGGGCACAAGCTGGAGTACAACTACAACAGCCACAACGTCTATAT
CATGGCCGACAAGCAGAAGAACGGCATCAAGGTGAACTTCAAGATCCGCC
ACAACATCGAGGACGGCAGCGTGCAGCTCGCCGACCACTACCAGCAGAAC
ACCCCCATCGGCGACGGCCCCGTGCTGCTGCCCGACAACCACTACCTGAG
CTACCAGTCCGCCCTGAGCAAAGACCCCAACGAGAAGCGCGATCACATGG
TCCTGCTGGAGTTCGTGACCGCCGCCGGGATCACTCTCGGCATGGACGAG
CTGTACAAGTAAAGCGGCCGCGACTCTAGATCATAATCAGCCATACCACA
TTTGTAGAGGTTTTACTTGCTTTAAAAAACCTCCCACACCTCCCCCTGAA
CCTGAAACATAAAATGAATGCAATTGTTGTTGTTAACTTGTTTATTGCAG
CTTATAATGGTTACAAATAAAGCAATAGCATCACAAATTTCACAAATAAA
GCATTTTTTCACTGCATTCTAGTTGTGGTTTGTCCAAACTCATCAATGT
ATCTTAAGGATCCGCCGATAAGGGCGaattcataacttcgtataatgtat
gctatacgaagttatggatctgtcgatcgacggatcgatccgaacaaacg
acccaacacccgtgcgttttattctgtcttttattgccgatcccctcag
aagaactcgtcaagaaggcgatagaaggcgatgcgctgcgaatcgggagc
ggcgataccgtaaagcacgaggaagcggtcagcccattcgccgccaagct
```

-continued

```
cttcagcaatatcacgggtagccaacgctatgtcctgatagcggtccgcc
acacccagccggccacagtcgatgaatccagaaaagcggccattttccac
catgatattcggcaagcaggcatcgccatgggtcacgacgagatcctcgc
cgtcgggcatgcgcgccttgagcctggcgaacagttcggctggcgcgagc
ccctgatgctcttcgtccagatcatcctgatcgacaagaccggcttccat
ccgagtacgtgctcgctcgatgcgatgtttcgcttggtggtcgaatgggc
aggtagccggatcaagcgtatgcagccgccgcattgcatcagccatgatg
gatactttctcggcaggagcaaggtgagatgacaggagatcctgccccgg
cacttcgcccaatagcagccagtcccttcccgcttcagtgacaacgtcga
gcacagctgcgcaaggaacgcccgtcgtggccagccacgatagccgcgct
gcctcgtcctgcagttcattcagggcaccggacaggtcggtcttgacaaa
aagaaccgggcgccctgcgctgacagccggaacacggcggcatcagagc
agccgattgtctgttgtgcccagtcatagccgaatagcctctccacccaa
gcggccggagaacctgcgtgcaatccatcttgttcaatggccgatcccat
attggctgcacggatcctgaacggcagaggttacggcagtttgtctctcc
cccttccgggagccaccttcttctccaaccgtcccggtcgcgctctcggc
gcttctgaggagagaactggctgagtgacgccctttatagattcgcctt
gtgtcccgcccttcctttccgccctcccttgcgctacggggccgcccg
caccggcctacacggagcgcgcgcggcggagttgttgacgctaggctcc
ggctccctggttgggtgttctttctgacgcgacaggaggaggagaatgtc
ctggtcctgtcgtcctcctttcgggtttcccgtgcactcaaaccgaggac
ttacagaacggaggataaagttaggccatttttactcagcttcggagttc
aggctcattttcagctaaagtctctcattagtatcccccacacacatc
gggaaaatggtttgtcctacgcatcggtaatgaaggcggggcccttcggg
tcctccggagcgggttccggggtggggggaaggagggagggacgggacg
ggcctcgttcatgaatattcagttcaccgctgaatatgcataaggcaggc
aagatgcgcgtccaatcaattggaagtagccgttattagtggagaggcc
ccaggacgttggggcaccgcctgtgctctagtagctttacggagccctgg
cgctcgatgttcaagcccaagctttcgcgagctcgaccgaacaaacgacc
caacacccgtgcgttttattctgtcttttattgccgctcagctttacag
tgacaatgacggctggcgactgaatattagtgcttacagacagcactaca
tattttccgtcgatgttgaaatcctttctcatatgtcaccataaatatca
aataattatagcaatcatttacgcgttaatggctaatcgccatcttccag
caggcgcaccattgcccctgtttcactatccaggttacggatatagttca
tgacaatatttacattggtccagccaccagcttgcatgatctccggtatt
gaaactccagcgcgggccatatctcgcgcggctccgacacgggcactgtg
tccagaccaggccaggtatctctgaccagagtcatcctaaaatacacaaa
caattagaatcagtagtttaacacattatacacttaaaaatttttatattt
acccttagcgccgtaaatcaatcgatgagttgcttcaaaaatcccttccag
ggcgcgagttgatagctggctggtggcagatggcgcggcaacaccatttt
ttctgacccggcaaaacaggtagttattcggatcatcagctacaccagag
```

-continued

```
acggaaatccatcgctcgaccagtttagttaccccaggctaagtgcctt
ctctacacctgcggtgctaaccagcgttttcgttctgccaatatggatta
acattctcccaccgtcagtacgtgagatatctttaaccctgatcctggca
atttcggctatacgtaacagggtgttataagcaatccccagaaatgccag
attacgtatatcctggcagcgatcgctattttccatgagtgaacgaacct
ggtcgaaatcagtgcgttcgaacgctagagcctgttttgcacgttcaccg
gcatcaacgttttcttttcggatccgccgcataaccagtgaaacagcatt
gctgtcacttggtcgtggcagcccggaccgacgatgaagcatgtttagct
ggcccaaatgttgctggatagttttactgccagaccgcgcgcctgaaga
tatagaagataatcgcgaacatcttcaggttctgcggtatgctcagaaaa
cgcctggcgatccctgaacatgtccatcaggttcttgcgaacctcatcac
tcgttgcatcgaccggtaatgcaggcaaattttggtgtacggtcagtaaa
ttggacaccttcctcttcttcttgggcatggccgcaggaaagcagagccc
tgaagctcccatcaccggccaataagagccaagcctgcagtgtgacctca
tagagcaatgtgccagccagcctgaccccaagggccctcaggcttgggca
cactgtctctaggaccctgagagaaagacatacccatttctgcttaggc
cctgaggatgagcccaggggtggcttggcactgaagcaaaggacactggg
gctcagctggcagcaaagtgaccaggatgctgaggctttgacccagaagc
cagaggccagaggccaggacttctcttggtcccagtccaccctcactcag
agctttaccaatgccctctggatagttgtcgggtaacggtggacgccact
gattctctggccagcctaggacttcgccattccgctgattctgctcttcc
agccactggctgaccggttggaagtactccagcagtgccttggcatccag
ggcatctgagcctaccaggtccttcagtacctcctgccagggcctggagc
agccagcctgcaacacctgcctgccaagcagagtgaccactgtgggcaca
ggggacacagggtggggcccacaacagcaccattgtccacttgtccctca
ctagtaaaagaactctagggttgcggggggtgggggaggtctctgtgagg
ctggtaagggatatttgcctggcccatggagatccataacttcgtataat
gtatgctatacgaagttataagctttcgcgagctcgagatcctgcaggcg
cgccgaTCTGCCGGTCTCCCTATAGTGAGTCGTATTAATTTCGATAAGC
CAGGTTAACCTGCATTAATGAATCGGCCAACGCGCGGGGAGAGGCGGTTT
GCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGG
TTATCCACAGAATCAGGGGATAACGCAGGAAAGAACATGTGAGCAAAAGG
CCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAG
AGGTGGCGAAACCCGACAGGACTATAAAGATACCAGGCGTTTCCCCCTGG
AAGCTCCCTCGTGCGCTCTCCTGTTCCGACCCTGCCGCTTACCGGATACC
TGTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATC
GTCTTGAGTCCAACCCGGTAAGACACGACTTATCGCCACTGGCAGCAGCC
```

ACTGGTAACAGGATTAGCAGAGCGAGGTATGTAGGCGGTGCTACAGAGTT
CTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCT
TGATCCGGCAAACAAACCACCGCTGGTAGCGGTGGTTTTTTTGTTTGCAA
GCAGCAGATTACGCGCAGAAAAAAAGGATCTCAAGAAGATCCTTTGATCT
TTTCTACGGGGTCTGACGCTCAGTGGAACGAAAACTCACGTTAAGGGATT
TTGGTCATGAGATTATCAAAAGGATCTTCACCTAGATCCTTTTAAATTA
AAAATGAAGTTTTAAATCAATCTAAAGTATATATGAGTAAACTTGGTCTG
ACAGTTACCAATGCTTAATCAGTGAGGCACCTATCTCAGCGATCTGTCTA
TTTCGTTCATCCATAGTTGCCTGACTCCCCGTCGTGTAGATAACTACGAT
ACGGGAGGGCTTACCATCTGGCCCCAGTGCTGCAATGATACCGCGAGACC
CACGCTCACCGGCTCCAGATTTATCAGCAATAAACCAGCCAGCCGGAAGG
GCCGAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTT
GGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCG
TTGTCAGAAGTAAGTTGGCCGCAGTGTTATCACTCATGGTTATGGCAGCA
CTGCATAATTCTCTTACTGTCATGCCATCCGTAAGATGCTTTTCTGTGAC
TGGTGAGTACTCAACCAAGTCATTCTGAGAATAGTGTATGCGGCGACCGA
GTTGCTCTTGCCCGGCGTCAATACGGGATAATACCGCGCCACATAGCAGA
ACTTTAAAAGTGCTCATCATTGGAAAACGTTCTTCGGGGCGAAAACTCTC
AAGGATCTTACCGCTGTTGAGATCCAGTTCGATGTAACCCACTCGTGCAC
CCAACTGATCTTCAGCATCTTTTACTTTCACCAGCGTTTCTGGGTGAGCA
AAAACAGGAAGGCAAAATGCCGCAAAAAAGGGAATAAGGGCGACACGGAA
ATGTTGAATACTCATACTCTTCCTTTTTCAATATTATTGAAGCATTTATC
AGGGTTATTGTCTCATGAGCGGATACATATTTGAATGTATTTAGAAAAAT
AAACAAATAGGGGTTCCGCGCACATTTCCCCGAAAAGTGCCACCTGACGT
CTAAGAAACCATTATTATCATGACATTAACCTATAAAAATAGGCGTATCA
CGAGGCCCTTTCGTCTCGCGCGTTTCGGTGATGACGGTGAAAACCTCTGA
CACATGCAGCTCCCGGAGACGGTCACAGCTTGTCTGTAAGCGGATGCCGG
GAGCAGACAAGCCCGTCAGGGCGCGTCAGCGGGTGTTGGCGGGTGTCGGG
GCTGGCTTAACTATGCGGCATCAGAGCAGATTGTACTGAGAGTGCACCAT
ATGGACATATTGTCGTTAGAACGCGGCTACAATTAATACATAACCTTATG
TATCATACACATACGATTTAGGTGACACTATA

113. SEQ ID NO: 113
(pAP-CAN)
TCATTAATGCAGGTTAACCTGGCTTATCGAAATTAATACGACTCACTATA
GGGAGACCGGCAGATCcggcgcgcctgcagGATCTCCTGCTGCTGCTGCT
GCTGCTGGGCCTGAGGCTACAGCTCTCCCTGggcatcatcccagttgagg
aggagaaccccgacttctggaaccgcgaggcagccgaggccctgggtgcc
gccaagaagctgcagcctgcacagacagccgccaagaacctcatcatctt cctgggcgatgggatgggggtgtctacggtgacagctgccaggatcttaa
aagggcagaagaaggacaaactggggcctgagataccccctggccatggac
cgcttcccatatgtggctctgtccaagacatacaatgtagacaaacatgt
gccagacagtggagccacagccacggcctacctgtgcgggtcaagggca
acttccagaccattggcttgagtgcagccgcccgctttaaccagtgcaac
acgacacgcggcaacgaggtcatctccgtgatgaatcgggccaagaaagc
agggaagtcagtgggagtggtaaccaccacacgagtgcagcacgcctcgc
cagccggcacctacgcccacacggtgaaccgcaactggtactcggacgcc
gacgtgcctgccTCGGCCCGCCAGGAGGGGTGCCAGGACATCGCTACGCA
GCTCATCTCCAACATGgacattgacgtgatcctaggtggaggccgaaagt
acatgtttcgcatgggaaccccagaccctgagtacccagatgactacagc
caaggtgggaccaggctggacgggaagaatctggtgcaggaatggctggc
gaagcgccagggtgcccggtatgtgtggaaccgcactgagctcatgcagg
cttccctggacccgtctgtgacccatctcatgggtctctttgagcctgga
gacatgaaatacgagatccaccgagactccacactggacccctccctgat
ggagatgacagaggctgccctgcgcctgctgagcaggaaccccgcggct
tcttcctcttcgtggagggtggtcgcatcgaccatggtcatcatgaaagc
agggcttaccgggcactgactgagacgatcatgttcgacgacgccattga
gagggcgggccagctcaccagcgaggaggacacgctgagcctcgtcactg
ccgaccactcccacgtcttctccttcggaggctaccccctgcgagggagc
tccatcttcgggctggcccctggcaaggcccgggacaggaaggcctacac
ggtcctcctatacggaaacggtccaggctatgtgctcaaggacggcgccc
ggccggatgttaccgagagcgagagcgggagccccgagtatcggcagcag
tcagcagtgcccctggacgaagagacccacgcaggcgaggacgtggcggt
gttcgCGCGCGGCCCGCAGGCGCACCTGGTTCACGCGTGCAGGAGCAGA
CCTTCATAGCGCACGTCATGGCCTTCGCCGCCTGCCTGGAGCCCTACACC
GCCTGCGACCTGGCGCCCCCGCCGGCACCACCGACGCCGCGCACCCGGG
GCGGTCCGTGGTCCCCGCGTTGCTTCCTCTGCTGGCCGGGACCCTGCTGC
TGCTGGAGACGGCCACTGCTCCCTGAGATCGAATTAATTCGATAGCTTCT
AGAAGCTCGCTTTCTTGCTGTCCAATTTCTATTAAAGGTTCCTTTGTTCC
CTAAGTCCAACTACTAAACTGGGGGATATTATGAAGGGCCTTGAGCATCT
GGATTCTGCCTAATAAAAAACATTTATTTTCATTGCAATGATGTATTTAA
ATTATTTCTGAATATTTTACTAAAAAGGGAATGTGGGAGGTCAGTGCATT
TAAAACATAAAGAAATGAAGAGCTAGTTCAAACCTTGGGAAAATACACTA
TATCTTAAACTCCATGAAAGAAGGTGAGGCTGCAAACAGCTAATGCACAT
TGGCAACAGCCCCTGATGCCTATGCCTTATTCATCCCTCAGAAAAGGATT
CAAGTAGAGGCTTGATTTGGAGGTTAAAGTTTTGCTATGCTGTATTTTAA
TTAAGaattcataacttcgtataatgtatgctatacgaagttatggatct
gtcgatcgacggatcgatccgaacaaacgacccaacaccgtgcgttttta
ttctgtcttttattgccgatcccctcagaagaactcgtcaagaaggcga
tagaaggcgatgcgctgcgaatcgggagcggcgataccgtaaagcacgag -continued

```
gaagcggtcagcccattcgccgccaagctcttcagcaatatcacgggtag
ccaacgctatgtcctgatagcggtccgccacacccagccggccacagtcg
atgaatccagaaaagcggccattttccaccatgatattcggcaagcaggc
atcgccatgggtcacgacgagatcctcgccgtcgggcatgcgcgccttga
gcctggcgaacagttcggctggcgcgagccctgatgctcttcgtccaga
tcatcctgatcgacaagaccggcttccatccgagtacgtgctcgctcgat
gcgatgtttcgcttggtggtcgaatgggcaggtagccggatcaagcgtat
gcagccgccgcattgcatcagccatgatggatactttctcggcaggagca
aggtgagatgacaggagatcctgccccggcacttcgcccaatagcagcca
gtcccttcccgcttcagtgacaacgtcgagcacagctgcgcaaggaacgc
ccgtcgtggccagccacgatagccgcgctgcctcgtcctgcagttcattc
agggcaccggacaggtcggtcttgacaaaaagaaccgggcgcccctgcgc
tgacagccgaacacggcggcatcagagcagccgattgtctgttgtgccc
agtcatagccgaatagcctctccacccaagcggccggagaacctgcgtgc
aatccatcttgttcaatggccgatcccatattggctgcacggatcctgaa
cggcagaggttacggcagtttgtctctcccccttccgggagccaccttct
tctccaaccgtcccggtcgcgctctcggcgcttctgaggagagaactggc
tgagtgacgccctttatagattcgccttgtgtcccgcccttccttttcc
cgccctcccttgcgctacggggccgccgcaccggcctacacggagcgcg
cgcggcggagttgttgacgctagggctccggctccctggttgggtgttct
ttctgacgcgacaggaggaggagaatgtcctggtcctgtcgtcctccttt
cgggtttcccgtgcactcaaaccgaggacttacagaacggaggataaagt
taggccatttttactcagcttcggagttcaggctcattttttcagctaaag
tctctcattagtatccccccacacacatcgggaaaatggtttgtcctacg
catcggtaatgaaggcggggcccttcgggtcctccggagcggggttccggg
ggtgggggaaggagggagggacgggacggcctcgttcatgaatattca
gttcaccgctgaatatgcataaggcaggcaagatggcgcgtccaatcaat
tggaagtagccgttattagtggagaggcccaggacgttggggcaccgcc
tgtgctctagtagctttacggagccctggcgctcgatgttcaagcccaag
cttttcgcgagctcgaccgaacaaacgacccaacacccgtgcgttttattc
tgtcttttttattgccgctcagctttacagtgacaatgacggctggcgact
gaatattagtgcttacagacagcactacatattttccgtcgatgttgaaa
tcctttctcatatgtcaccataaatatcaaataattatagcaatcattta
cgcgttaatggctaatcgccatcttccagcaggcgcaccattgcccctgt
ttcactatccaggttacggatatagttcatgacaatatttacattggtcc
agccaccagcttgcatgatctccggtattgaaactccagcgcgggccata
tctcgcgcggctccgacacgggcactgtgtccagaccaggccaggtatct
ctgaccagagtcatcctaaaatacacaaacaattagaatcagtagtttaa
cacattatacacttaaaaattttatatttaccttagcgccgtaaatcaat
cgatgagttgcttcaaaaatcccttccagggcgcgagttgatagctggct
ggtggcagatggcgcggcaacaccattttttctgaccggcaaaacaggt
```

-continued

```
agttattcggatcatcagctacaccagagacggaaatccatcgctcgacc
agtttagttaccccaggctaagtgccttctctacacctgcggtgctaac
cagcgttttcgttctgccaatatggattaacattctcccaccgtcagtac
gtgagatatctttaaccctgatcctggcaatttcggctatacgtaacagg
gtgttataagcaatccccagaaatgccagattacgtatatcctggcagcg
atcgctattttccatgagtgaacgaacctggtcgaaatcagtgcgttcga
acgctagagcctgttttgcacgttcaccggcatcaacgttttcttttcgg
atccgccgcataaccagtgaaacagcattgctgtcacttggtcgtggcag
cccggaccgacgatgaagcatgtttagctggcccaaatgttgctggatag
ttttactgccagaccgcgcgcctgaagatatagaagataatcgcgaaca
tcttcaggttctgcgggaaaccatttccggttattcaacttgcaccatgc
cgcccacgaccggcaaacggacagaagcattttccaggtatgctcagaaa
acgcctggcgatccctgaacatgtccatcaggttcttgcgaacctcatca
ctcgttgcatcgaccggtaatgcaggcaaattttggtgtacggtcagtaa
attggacaccttcctcttcttcttgggcatggccgcaggaaagcagagcc
ctgaagctcccatcaccggccaataagagccaagcctgcagtgtgacctc
atagagcaatgtgccagccagcctgaccccaagggccctcaggcttgggc
acactgtctctaggaccctgagagaaagacatacccatttctgcttaggg
ccctgaggatgagcccaggggtggcttggcactgaagcaaaggacactgg
ggctcagctggcagcaaagtgaccaggatgctgaggctttgacccagaag
ccagaggccagaggccaggacttctcttggtcccagtccaccctcactca
gagctttaccaatgccctctggatagttgtcgggtaacggtggacgccac
tgattctctggccagcctaggacttcgccattccgctgattctgctcttc
cagccactggctgaccggttggaagtactccagcagtgccttggcatcca
gggcatctgagcctaccaggtccttcagtacctcctgccagggcctggag
cagccagcctgcaacacctgcctgccaagcagagtgaccactgtgggcac
aggggacacagggtggggcccacaacagcaccattgtccacttgtccctc
actagtaaaagaactctagggttgcgggggtgggggaggtctctgtgag
gctggtaagggatatttgcctggcccatggagatccataacttcgtataa
tgtatgctatacgaagttataagctttcgcgagctcgagatcccagtcag
tcagtctcgagcgatcgcggcgcgccgtcgaGTTCTATAGTGTCACCTAA
ATCGTATGTGTATGATACATAAGGTTATGTATTAATTGTAGCCGCGTTCT
AACGACAATATGTCCATATGGTGCACTCTCAGTACAATCTGCTCTGATGC
CGCATAGTTAAGCCAGCCCCGACACCCGCCAACACCCGCTGACGCGCCCT
GACGGGCTTGTCTGCTCCCGGCATCCGCTTACAGACAAGCTGTGACCGTC
TCCGGGAGCTGCATGTGTCAGAGGTTTTCACCGTCATCACCGAAACGCGC
GAGACGAAAGGGCCTCGTGATACGCCTATTTTTATAGGTTAATGTCATGA
TAATAATGGTTTCTTAGACGTCAGGTGGCACTTTCGGGGAAATGTGCGC
GGAACCCCTATTTGTTTATTTTTCTAAATACATTCAAATATGTATCCGCT
CATGAGACAATAACCCTGATAAATGCTTCAATAATATTGAAAAGGAAGA
GTATGAGTATTCAACATTTCCGTGTCGCCCTTATTCCCTTTTTTGCGGCA
```

-continued

```
TTTTGCCTTCCTGTTTTTGCTCACCCAGAAACGCTGGTGAAAGTAAAGA
TGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGA
CGCCGGGCAAGAGCAACTCGGTCGCCGCATACACTATTCTCAGAATGACT
TGGTTGAGTACTCACCAGTCACAGAAAAGCATCTTACGGATGGCATGACA
GTAAGAGAATTATGCAGTGCTGCCATAACCATGAGTGATAACACTGCGGC
CAACTTACTTCTGACAACGATCGGAGGACCGAAGGAGCTAACCGCTTTTT
TGCACAACATGGGGGATCATGTAACTCGCCTTGATCGTTGGGAACCGGAG
CTGAATGAAGCCATACCAAACGACGAGCGTGACACCACGATGCCTGTAGC
AATGGCAACAACGTTGCGCAAACTATTAACTGGCGAACTACTTACTCTAG
CTTCCCGGCAACAATTAATAGACTGGATGGAGGCGGATAAAGTTGCAGGA
CCACTTCTGCGCTCGGCCCTTCCGGCTGGCTGGTTTATTGCTGATAAATC
TGGAGCCGGTGAGCGTGGGTCTCGCGGTATCATTGCAGCACTGGGGCCAG
ATGGTAAGCCCTCCCGTATCGTAGTTATCTACACGACGGGGAGTCAGGCA
ACTATGGATGAACGAAATAGACAGATCGCTGAGATAGGTGCCTCACTGAT
TAAGCATTGGTAACTGTCAGACCAAGTTTACTCATATATACTTTAGATTG
ATTTAAAACTTCATTTTTAATTTAAAAGGATCTAGGTGAAGATCCTTTTT
GATAATCTCATGACCAAAATCCCTTAACGTGAGTTTTCGTTCCACTGAGC
GTCAGACCCCGTAGAAAAGATCAAAGGATCTTCTTGAGATCCTTTTTTTC
TGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGG
CTTCAGCAGAGCGCAGATACCAAATACTGTTCTTCTAGTGTAGCCGTAGT
TAGGCCACCACTTCAAGAACTCTGTAGCACCGCCTACATACCTCGCTCTG
CTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCT
GAACGGGGGGTTCGTGCACACAGCCCAGCTTGGAGCGAACGACCTACACC
GAACTGAGATACCTACAGCGTGAGCTATGAGAAAGCGCCACGCTTCCCGA
AGGGAGAAAGGCGGACAGGTATCCGGTAAGCGGCAGGGTCGGAACAGGAG
AGCGCACGAGGGAGCTTCCAGGGGGAAACGCCTGGTATCTTTATAGTCCT
GTCGGGTTTCGCCACCTCTGACTTGAGCGTCGATTTTTGTGATGCTCGTC
AGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCC
CCTGATTCTGTGGATAACCGTATTACCGCCTTTGAGTGAGCTGATACCGC
TCGCCGCAGCCGATCGACCGAGCGCAGCGAGTCAGTGAGCGAGGAAGCGG
AAGAGCGCCCAATACGCAAACCGCCTCTCCCCGCGCGTTGGCCGAT
```

114. SEQ ID NO: 114
(pLacZ-CAN)

```
TCATTAATGCAGGTTAACCTGGCTTATCGAAATTAATACGACTCACTATA
GGGAGACCGGCAGATCcggcgcgcctgcagGCCATGGACCCTGTTGTGCT
GCAAAGGAGAGACTGGGAGAACCCTGGAGTGACCCAGCTCAACAGACTGG
CTGCCCACCCTCCCTTTGCCTCTTGGAGGAACTCTGAGGAAGCCAGGACA
GACAGGCCCAGCCAGCAGCTCAGGTCTCTCAATGGAGAGTGGAGGTTTGC
CTGGTTCCCTGCCCCTGAAGCTGTGCCTGAGTCTTGGCTGGAGTGTGACC
TCCCAGAGGCTGACACTGTTGTGGTGCCAAGCAACTGGCAGATGCATGGC
TATGATGCCCCCATCTACACCAATGTCACCTACCCCATCACTGTGAACCC
CCCTTTTGTGCCCACTGAGAACCCCACTGGCTGCTACAGCCTGACCTTCA
ATGTTGATGAGAGCTGGCTGCAAGAAGGCCAGACCAGGATCATCTTTGAT
GGAGTCAACTCTGCCTTCCACCTCTGGTGCAATGGCAGGTGGGTTGGCTA
TGGCCAAGACAGCAGGCTGCCCTCTGAGTTTGACCTCTCTGCCTTCCTCA
GAGCTGGAGAGAACAGGCTGGCTGTCATGGTGCTCAGGTGGTCTGATGGC
AGCTACCTGGAAGACCAAGACATGTGGAGGATGTCTGGCATCTTCAGGGA
TGTGAGCCTGCTGCACAAGCCCACCACCCAGATTTCTGACTTCCATGTTG
CCACCAGGTTCAATGATGACTTCAGCAGAGCTGTGCTGGAGGCTGAGGTG
CAGATGTGTGGAGAACTCAGAGACTACCTGAGAGTCACAGTGAGCCTCTG
GCAAGGTGAGACCCAGGTGGCCTCTGGCACAGCCCCCTTTGGAGGAGAGA
TCATTGATGAGAGGAGGCTATGCTGACAGAGTCACCCTGAGGCTCAAT
GTGGAGAACCCCAAGCTGTGGTCTGCTGAGATCCCCAACCTCTACAGGGC
TGTTGTGGAGCTGCACACTGCTGATGGCACCCTGATTGAAGCTGAAGCCT
GTGATGTTGGATTCAGAGAAGTCAGGATTGAGAATGGCCTGCTGCTGCTC
AATGGCAAGCCTCTGCTCATCAGGGGAGTCAACAGGCATGAGCACCACCC
TCTGCATGGACAAGTGATGGATGAACAGACTATGGTGCAAGATATCCTGC
TAATGAAGCAGAACAACTTCAATGCTGTCAGGTGCTCTCACTACCCCAAC
CACCCTCTCTGGTACACCCTGTGTGACAGGTATGGCCTGTATGTTGTTGA
TGAAGCCAACATTGAGACACATGGCATGGTGCCCATGAACAGGCTCACAG
ATGACCCCAGGTGGCTGCCTGCCATGTCTGAGAGAGTGACCAGGATGGTG
CAGAGAGACAGGAACCACCCCTCTGTGATCATCTGGTCTCTGGGCAATGA
GTCTGGACATGGAGCCAACCATGATGCTCTCTACAGGTGGATCAAGTCTG
TTGACCCCAGCAGACCTGTGCAGTATGAAGGAGGTGGAGCAGACACCACA
GCCACAGACATCATCTGCCCCATGTATGCCAGGGTTGATGAGGACCAGCC
CTTCCCTGCTGTGCCCAAGTGGAGCATCAAGAAGTGGCTCTCTCTGCCTG
GAGAGACCAGACCTCTGATCCTGTGTGAATATGCACATGCAATGGGCAAC
TCTCTGGGAGGCTTTGCCAAGTACTGGCAAGCCTTCAGACAGTACCCCAG
GCTGCAAGGAGGATTTGTGTGGGACTGGGTGGACCAATCTCTCATCAAGT
ATGATGAGAATGGCAACCCCTGGTCTGCCTATGGAGGACTTTGGTGAC
ACCCCCAATGACAGGCAGTTCTGCATGAATGGCCTGGTCTTTGCAGACAG
GACCCCTCACCCTGCCCTCACAGAGGCCAAGCACCAGCAACAGTTCTTCC
AGTTCAGGCTGTCTGGACAGACCATTGAGGTGACATCTGAGTACCTCTTC
AGGCACTCTGACAATGAGCTCCTGCACTGGATGGTGGCCCTGGATGGCAA
GCCTCTGGCTTCTGGTGAGGTGCCTCTGGATGTGGCCCCTCAAGGAAAGC
AGCTGATTGAACTGCCTGAGCTGCCTCAGCCAGAGTCTGCTGGACAACTG
TGGCTAACAGTGAGGGTGGTTCAGCCCAATGCAACAGCTTGGTCTGAGGC
AGGCCACATCTCTGCATGGCAGCAGTGGAGGCTGGCTGAGAACCTCTCTG
```

-continued

```
TGACCCTGCCTGCTGCCTCTCATGCCATCCCTCACCTGACAACATCTGAA
ATGGACTTCTGCATTGAGCTGGGCAACAAGAGATGGCAGTTCAACAGGCA
GTCTGGCTTCCTGTCTCAGATGTGGATTGGAGACAAGAAGCAGCTCCTCA
CCCCTCTCAGGGACCAATTCACCAGGGCTCCTCTGGACAATGACATTGGA
GTGTCTGAGGCCACCAGGATTGACCCAAATGCTTGGGTGGAGAGGTGGAA
GGCTGCTGGACACTACCAGGCTGAGGCTGCCCTGCTCCAGTGCACAGCAG
ACACCCTGGCTGATGCTGTTCTGATCACCACAGCCCATGCTTGGCAGCAC
CAAGGCAAGACCCTGTTCATCAGCAGAAAGACCTACAGGATTGATGGCTC
TGGACAGATGGCAATCACAGTGGATGTGGAGGTTGCCTCTGACACACCTC
ACCCTGCAAGGATTGGCCTGAACTGTCAACTGGCACAGGTGGCTGAGAGG
GTGAACTGGCTGGGCTTAGGCCCTCAGGAGAACTACCCTGACAGGCTGAC
AGCTGCCTGCTTTGACAGGTGGGACCTGCCTCTGTCTGACATGTACACCC
CTTATGTGTTCCCTTCTGAGAATGGCCTGAGGTGTGGCACCAGGGAGCTG
AACTATGGTCCTCACCAGTGGAGGGGAGACTTCCAGTTCAACATCTCCAG
GTACTCTCAGCAACAGCTCATGGAAACCTCTCACAGGCACCTGCTCCATG
CAGAGGAGGGAACCTGGCTGAACATTGATGGCTTCCACATGGGCATTGGA
GGGAGATGACTCTTGGTCTCCTTCTGTGTCTGCTGAGTTCCAGTTATCTGC
TGGCAGGTACCACTATCAGCTGGTGTGGTGCCAGAAGTAAACCTAATCTA
GAAGCTCGCTTTCTTGCTGTCCAATTTCTATTAAAGGTTCCTTTGTTCCC
TAAGTCCAACTACTAAACTGGGGGATATTATGAAGGGCCTTGAGCATCTG
GATTCTGCCTAATAAAAAACATTTATTTTCATTGCAATGATGTATTTAAA
TTATTTCTGAATATTTTACTAAAAAGGGAATGTGGGAGGTCAGTGCATTT
AAAACATAAAGAAATGAAGAGCTAGTTCAAACCTTGGGAAAATACACTAT
ATCTTAAACTCCATGAAAGAAGGTGAGGCTGCAAACAGCTAATGCACATT
GGCAACAGCCCCTGATGCCTATGCCTTATTCATCCCTCAGAAAAGGATTC
AAGTAGAGGCTTGATTTGGAGGTTAAAGTTTTGCTATGCTGTATTTTAAT
TAAGaattcataacttcgtataatgtatgctatacgaagttatggatctg
tcgatcgacggatcgatccgaacaaacgacccaacacccgtgcgtttat
tctgtctttttattgccgatccctcagaagaactcgtcaagaaggcgat
agaaggcgatgcgctgcgaatcgggagcggcgataccgtaaagcacgagg
aagcggtcagcccattcgccgccaagctcttcagcaatatcacgggtagc
caacgctatgtcctgatagcggtccgccacacccagccggccacagtcga
tgaatccagaaaagcggccattttccaccatgatattcggcaagcaggca
tcgccatgggtcacgacgagatcctcgccgtcgggcatgcgcgccttgag
cctggcgaacagttcggctggcgcgagcccctgatgctcttcgtccagat
catcctgatcgacaagaccggcttccatccgagtacgtgctcgctcgatg
cgatgtttcgcttggtggtcgaatgggcaggtagccggatcaagcgtatg
cagccgccgcattgcatcagccatgatggatactttctcggcaggagcaa
ggtgagatgacaggagatcctgccccggcacttcgcccaatagcagccag
tcccttcccgcttcagtgacaacgtcgagcacagctgcgcaaggaacgcc
cgtcgtggccagccacgatagccgcgctgcctcgtcctgcagttcattca
```

-continued

```
gggcaccggacaggtcggtcttgacaaaaagaaccgggcgcccctgcgct
gacagccggaacacggcggcatcagagcagccgattgtctgttgtgccca
gtcatagccgaatagcctctccacccaagcggccggagaacctgcgtgca
atccatcttgttcaatggccgatcccatattggctgcacggatcctgaac
ggcagaggttacggcagtttgtctctcccccttccgggagccaccttctt
ctccaaccgtcccggtcgcgctctcggcgcttctgaggagagaactggct
gagtgacgcccttatagattcgccttgtgtcccgcccttcctttccc
gccctcccttgcgctacggggccgcccgcaccggcctacacggagcgcgc
gcggcggagttgttgacgctagggctccggctccctggttgggtgttctt
tctgacgcgacaggaggaggagaatgtcctggtcctgtcgtcctccttc
gggtttcccgtgcactcaaaccgaggacttacagaacggaggataaagtt
aggccattttactcagcttcggagttcaggctcattttttcagctaaagt
ctctcattagtatccccccacacacatcgggaaaatggtttgtcctacgc
atcggtaatgaaggcggggcccttcgggtcctccggagcgggttccgggg
gtggggggaaggagggagggacgggacgggcctcgttcatgaatattcag
ttcaccgctgaatatgcataaggcaggcaagatggcgcgtccaatcaatt
ggaagtagccgttattagtggagaggccccaggacgttggggcaccgcct
gtgctctagtagctttacggagccctggcgctcgatgttcaagcccaagc
tttcgcgagctcgaccgaacaaacgacccaacacccgtgcgttttattct
gtcttttattgccgctcagctttacagtgacaatgacggctggcgactg
aatattgtgcttacagacagcactacatattttccgtcgatgttgaaat
cctttctcatatgtcaccataaatatcaaataattatagcaatcatttac
gcgttaatggctaatcgccatcttccagcaggcgcaccattgccctgtt
tcactatccaggttacggatatagttcatgacaatatttacattggtcca
gccaccagcttgcatgatctccggtattgaaactccagcgcgggccatat
ctcgcgcggtccgacacgggcactgtgtccagaccaggccaggtatctc
tgaccagagtcatcctaaaatacacaaacaattagaatcagtagtttaac
acattatacacttaaaaatttttatatttaccttagcgccgtaaatcaatc
gatgagttgcttcaaaaatcccttccagggcgcgagttgatagctggctg
gtggcagatggcgcggcaacaccatttttttctgacccggcaaaacaggta
gttattcggatcatcagctacaccagagacggaaatccatcgctcgacca
gtttagttaccccaggctaagtgccttctctacacctgcggtgctaacc
agcgttttcgttctgccaatatggattaacattctccaccgtcagtacg
tgagatatctttaaccctgatcctggcaatttcggctatacgtaacaggg
tgttataagcaatccccagaaatgccagattacgtatatcctggcagcga
tcgctattttccatgagtgaacgaacctggtcgaaatcagtgcgttcgaa
cgctagagcctgttttgcacgttcaccggcatcaacgttttcttttcgga
tccgccgcataaccagtgaaacagcattgctgtcacttggtcgtggcagc
ccggaccgacgatgaagcatgtttagctggcccaaatgttgctggatagt
ttttactgccagaccgcgcgcctgaagatatagaagataatcgcgaacat
cttcaggttctgcgggaaaccatttccggttattcaacttgcaccatgcc
```

-continued gcccacgaccggcaaacggacagaagcattttccaggtatgctcagaaaa
cgcctggcgatccctgaacatgtcctcaggttcttgcgaacctcatcac
tcgttgcatcgaccggtaatgcaggcaaattttggtgtacggtcagtaaa
ttggacaccttcctcttcttcttgggcatggccgcaggaaagcagagccc
tgaagctcccatcaccggccaataagagccaagcctgcagtgtgacctca
tagagcaatgtgccagccagcctgaccccaagggccctcaggcttgggca
cactgtctctaggaccctgagagaaagacatacccatttctgcttagggc
cctgaggatgagcccagggggtggcttggcactgaagcaaaggacactggg
gctcagctggcagcaaagtgaccaggatgctgaggctttgacccagaagc
cagaggccagaggccaggacttctcttggtcccagtccaccctcactcag
agctttaccaatgccctctggatagttgtcgggtaacggtggacgccact
gattctctggccagcctaggacttcgccattccgctgattctgctcttcc
agccactggctgaccggttggaagtactccagcagtgccttggcatccag
ggcatctgagcctaccaggtccttcagtacctcctgccagggcctggagc
agccagcctgcaacacctgcctgccaagcagagtgaccactgtgggcaca
ggggacacagggtggggcccacaacagcaccattgtccacttgtccctca
ctagtaaaagaactctaggggttgcgggggggtgggggaggtctctgtgagg
ctggtaagggatatttgcctggcccatggagatccataacttcgtataat
gtatgctatacgaagttataagctttcgcgagctcgagatcccagtcagt
cagtctcgagcgatcgcggcgcgccgtcgaGTTCTATAGTGTCACCTAAA
TCGTATGTGTATGACATAAGGTTATGTATTAATTGTAGCCGCGTTCTA
ACGACAATATGTCCATATGGTGCACTCTCAGTACAATCTGCTCTGATGCC
GCATAGTTAAGCCAGCCCCGACACCCGCCAACACCCGCTGACGCGCCCTG
ACGGGCTTGTCTGCTCCCGGCATCCGCTTACAGACAAGCTGTGACCGTCT
CCGGGAGCTGCATGTGTCAGAGGTTTTCACCGTCATCACCGAAACGCGCG
AGACGAAAGGGCCTCGTGATACGCCTATTTTTATAGGTTAATGTCATGAT
AATAATGGTTTCTTAGACGTCAGGTGGCACTTTTCGGGGAAATGTGCGCG
GAACCCCTATTTGTTTATTTTTCTAAATACATTCAAATATGTATCCGCTC
ATGAGACAATAACCCTGATAAATGCTTCAATAATATTGAAAAAGGAAGAG
TATGAGTATTCAACATTTCCGTGTCGCCCTTATTCCCTTTTTTGCGGCAT
TTTGCCTTCCTGTTTTTGCTCACCCAGAAACGCTGGTGAAAGTAAAAGAT
GCTGAAGATCAGTTGGGTGCACGAGTGGGTTACATCGAACTGGATCTCAA
CAGCGGTAAGATCCTTGAGAGTTTTCGCCCCGAAGAACGTTTTCCAATGA
TGAGCACTTTTAAAGTTCTGCTATGTGGCGCGGTATTATCCCGTATTGAC
GCCGGGCAAGAGCAACTCGGTCGCCGCATACACTATTCTCAGAATGACTT
GGTTGAGTACTCACCAGTCACAGAAAAGCATCTTACGGATGGCATGACAG
TAAGAGAATTATGCAGTGCTGCCATAACCATGAGTGATAACACTGCGGCC
AACTTACTTCTGACAACGATCGGAGGACCGAAGGAGCTAACCGCTTTTTT
GCACAACATGGGGGATCATGTAACTCGCCTTGATCGTTGGGAACCGGAGC
TGAATGAAGCCATACCAAACGACGAGCGTGACACCACGATGCCTGTAGCA
ATGGCAACAACGTTGCGCAAACTATTAACTGGCGAACTACTTACTCTAGC -continued TTCCCGGCAACAATTAATAGACTGGATGGAGGCGGATAAAGTTGCAGGAC
CACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAA
CTATGGATGAACGAAATAGACAGATCGCTGAGATAGGTGCCTCACTGATT
AAGCATTGGTAACTGTCAGACCAAGTTTACTCATATATACTTTAGATTGA
TTTAAAACTTCATTTTTAATTTAAAAGGATCTAGGTGAAGATCCTTTTTG
ATAATCTCATGACCAAAATCCCTTAACGTGAGTTTTCGTTCCACTGAGCG
TCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGC
TTCAGCAGAGCGCAGATACCAAATACTGTTCTTCTAGTGTAGCCGTAGTT
AGGCCACCACTTCAAGAACTCTGTAGCACCGCCTACATACCTCGCTCTGC
TAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTG
AACGGGGGGTTCGTGCACACAGCCCAGCTTGGAGCGAACGACCTACACCG
AACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGA
GCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCC
CTGATTCTGTGGATAACCGTATTACCGCCTTTGAGTGAGCTGATACCGCT
CGCCGCAGCCGAACGACCGAGCGCAGCGAGTCAGTGAGCGAGGAAGCGGA
AGAGCGCCCAATACGCAAACCGCCTCTCCCCGCGCGTTGGCCGAT 115. SEQ ID NO: 115
(pWS-TK2)
ATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATG
CTGAAGATCAGTTGGGTGCACGAGTGGGTTACATCGAACTGGATCTCAAC
AGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACG
CCGGGCAAGAGCAACTCGGTCGCCGCATACACTATTCTCAGAATGACTTG
GTTGAGTACTCACCAGTCACAGAAAAGCATCTTACGGATGGCATGACAGT
AAGAGAATTATGCAGTGCTGCCATAACCATGAGTGATAACACTGCGGCCA
ACTTACTTCTGACAACGATCGGAGGACCGAAGGAGCTAACCGCTTTTTTG
CACAACATGGGGGATCATGTAACTCGCCTTGATCGTTGGGAACCGGAGCT
GAATGAAGCCATACCAAACGACGAGCGTGACACCACGATGCCTGTAGCAA
TGGCAACAACGTTGCGCAAACTATTAACTGGCGAACTACTTACTCTAGCT
TCCCGGCAACAATTAATAGACTGGATGGAGGCGGATAAAGTTGCAGGACC
ACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGAT -continued

```
GGTAAGCCCTCCCGTATCGTAGTTATCTACACGACGGGGAGTCAGGCAAC
TATGGATGAACGAAATAGACAGATCGCTGAGATAGGTGCCTCACTGATTA
AGCATTGGTAACTGTCAGACCAAGTTTACTCATATATACTTTAGATTGAT
TTAAAACTTCATTTTTAATTTAAAAGGATCTAGGTGAAGATCCTTTTTGA
TAATCTCATGACCAAAATCCCTTAACGTGAGTTTTCGTTCCACTGAGCGT
CAGACCCCGTAGAAAAGATCAAAGGATCTTCTTGAGATCCTTTTTTTCTG
CGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCT
TCAGCAGAGCGCAGATACCAAATACTGTTCTTCTAGTGTAGCCGTAGTTA
GGCCACCACTTCAAGAACTCTGTAGCACCGCCTACATACCTCGCTCTGCT
AATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGA
ACGGGGGGTTCGTGCACACAGCCCAGCTTGGAGCGAACGACCTACACCGA
ACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTC
CTGGCCTTTTGCTGGCCTTTTGCTCACATGTTCTTTCCTGCGTTATCCCC
TGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAA
GAGCGCCCAATACGCAAACCGCCTCTCCCCGCGCGTTGGCCGATTCATTA
ATGCAGGTTAACCTGGCTTATCGAAATTAATACGACTCACTATAGGGAGA
CCGGCAGATCcggcgcgcctgcaggcgcgccactagttaattaatttaaa
tcgatgcgatcgctagcggccgcgtttaaacggcccTCGACTCTAGtcga
gcagtgtggttttcaagaggaagcaaaaagcctctccacccaggcctgga
atgtttccacccaatgtcgagcagtgtggttttgcaagaggaagcaaaaa
gcctctccacccaggcctggaatgtttccacccaatgtcgagCAAACCCC
GCCCAGCGTCTTGTCATTGGCGAATTCgaacacgcagatgcagtctgggc
ggcgcggcccgaggtccacttcgcatattaaggtgacgcgcgtggcctcg
aacagcgagcgaccctgcagcgacccgctcatcagcgtcagcagcgttcc
acaaatcctggtggcgttgaactcccgcacctctcgggcgaacgccttgt
agaagcgggtatggcttctcacgccggccaacagcacgcgcctgcgttcg
gtcaggctgctcgtgcgagcgggcctaccgacggccgcgcggcgtcccgt
cctagccatcgccaggggcctccgaagcccgcggggatccggagctgcc
cacgctgctgcgggtttatatagacggaccccacggggtggggaagacca
ccacctccgcgcagctgatggaggccctggggccgcgcgacaatatcgtc
tacgtccccgagccgatgacttactggcaggtgctggggcctccgagac
cctgacgaacatctacaacacgcagcaccgtctggaccgcggcgagatat
cggccggggaggcggcggtggtaatgaccagcgcccagataacaatgagc
acgccttatgcggcgacggacgccgttttggctcctcatatcggggggga
```

-continued

```
ggctgtgggcccgcaagccccgccccggccctcacccttgttttcgacc
ggcaccctatcgcctcctgctgtgctaccggccgcgcggtacctcatg
ggaagcatgaccccccaggccgtgttggcgttcgtggccctcatgccccc
gaccgcgcccggcacgaacctggtcctgggtgtccttccggaggccgaac
acgccgaccgcctggccagacgccaacgcccgggcgagcggcttgacctg
gccatgctgtccgccattcgccgtgtctacgatctactcgccaacacggt
gcggtacctgcagcgcggcgggaggtggcgggaggactggggccggctga
cgggggtcgccgcggcgacccgcgccccgaccccgaggacggcgcgggg
tctctgccccgcatcgaggacacgctgtttgccctgttccgcgttcccga
gctgctggcccccaacgggacttgtaccacattttttgcctgggtcttgg
acgtcttggccgaccgcctccttccgatgcatctatttgtcctggattac
gatcagtcgcccgtcgggtgtcgagacgccctgttgcgcctcaccgccgg
gatgatcccaacccgcgtcacaaccgccgggtccatcgccgagatacgcg
acctggcgcgcacgtttgcccgcgaggtgggggagtttagttcaaacac
ggaagcccgaacggaaggcctcccggcgatgacggcaataaaagaacaga
ataaaaggcattgttgtcgtgtggtgtgtccataagcgcgggggttcggg
gccaggctggcaccgtatcagcaccccaccgaaaaacggagcgggccga
tcCGTCCTTGTTTTCGGTCTGGTACTCCCTTTGTGCTTTTACCCTCACCC
CACCCCATCCTTTGGCCCGCGCTTACGGCAACAAAGGGCCTCCGATAGCC
TCCGAGGTGCGGAGCCTCTTTGGGCCGTGGGTACGGACACCCCCCCATCT
GCGGACTGGCAGCCGGGACGGACGACCATGGGCCCCGGTCTGTGGGTGGT
GATGGGGTCCTGGTGGGCGTTGCCGGGGGCCATGACACGTACTGGACGG
AGCAAATCGACCCGTGGTTTTGCACGGTCTGGGGTTGGCCCGCACGTAC
TGGCGCGACACAAACACCGGGCGTCTGTGGTTGCCCAACACCCCCGACGC
CAGCGACCCCCAGCGCGGACGCTTGGCGCCCCGGGCGAACTCAACCTGA
CTACGGCATCCGTGCCCATGCTTCGGTGGTACGCCGAGCGCTTTTGTTTC
GTGTTGGTCACCACGGCCGAGTTTCCTCGGGACCCCGGGCAGCTGCTTTA
CATCCCAAAGACCTATCTGCTCGGCCGGCCTCGGAACGCGAGCCTGCCCG
GAAGATCCCCGGGTACCGAGCTCGAATTCATcgTCACCATCACCTCGAAT
CAACAAGTTTGTACAAAAAAGCTGAACGAGAAACGTAAAATGATATAAAT
ATCAATATATTAAATTAGATTTTGCATAAAAAACAGACTACATAATACTG
TAAAACACAACATATCCAGTCACTATGGCGGCCGCATTAGGCACCCCAGG
CTTTACACTTTATGCTTCCGGCTCGTATAATGTGTGGATTTTGAGTTAGG
ATCCGTCGAGATTTTCAGGAGCTAAGGAAGCTAAAATGGAGAAAAAAATC
ACTGGATATACCACCGTTGATATATCCCAATGGCATCGTAAAGAACATTT
TGAGGCATTTCAGTCAGTTGCTCAATGTACCTATAACCAGACCGTTCAGC
TGGATATTACGGCCTTTTTAAAGACCGTAAAGAAAAATAAGCACAAGTTT
TATCCGGCCTTTATTCACATTCTTGCCCGCCTGATGAATGCTCATCCGGA
ATTCCGTATGGCAATGAAAGACGGTGAGCTGGTGATATGGGATAGTGTTC
ACCCTTGTTACACCGTTTTCCATGAGCAAACTGAAACGTTTTCATCGCTC
TGGAGTGAATACCACGACGATTTCCGGCAGTTTCTACACATATATTCGCA
```

```
AGATGTGGCGTGTTACGGTGAAAACCTGGCCTATTTCCCTAAAGGGTTTA
TTGAGAATATGTTTTTCGTCTCAGCCAATCCCTGGGTGAGTTTCACCAGT
TTTGATTTAAACGTGGCCAATATGGACAACTTCTTCGCCCCCGTTTTCAC
CATGGGCAAATATTATACGCAAGGCGACAAGGTGCTGATGCCGCTGGCGA
TTCAGGTTCATCATGCCGTCTGTGATGGCTTCCATGTCGGCAGAATGCTT
AATGAATTACAACAGTACTGCGATGAGTGGCAGGGCGGGGCGTAAAGATC
TGGATCCGGCTTACTAAAAGCCAGATAACAGTATGCGTATTTGCGCGCTG
ATTTTTGCGGTATAAGAATATATACTGATATGTATACCCGAAGTATGTCA
AAAAGAGGTGTGCTATGAAGCAGCGTATTACAGTGACAGTTGACAGCGAC
AGCTATCAGTTGCTCAAGGCATATATGATGTCAATATCTCCGGTCTGGTA
AGCACAACCATGCAGAATGAAGCCCGTCGTCTGCGTGCCGAACGCTGGAA
AGCGGAAAATCAGGAAGGGATGGCTGAGGTCGCCCGGTTTATTGAAATGA
ACGGCTCTTTTGCTGACGAGAACAGGGACTGGTGAAATGCAGTTTAAGGT
TTACACCTATAAAAGAGAGAGCCGTTATCGTCTGTTTGTGGATGTACAGA
GTGATATTATTGACACGCCCGGGCGACGGATGGTGATCCCCCTGGCCAGT
GCACGTCTGCTGTCAGATAAAGTCTCCCGTGAACTTTACCCGGTGGTGCA
TATCGGGGATGAAAGCTGGCGCATGATGACCACCGATATGGCCAGTGTGC
CGGTCTCCGTTATCGGGGAAGAAGTGGCTGATCTCAGCCACCGCGAAAAT
GACATCAAAAACGCCATTAACCTGATGTTCTGGGGAATATAAATGTCAGG
CTCCCTTATACACAGCCAGTCTGCAGGTCGACCATAGTGACTGGATATGT
TGTGTTTTACAGTATTATGTAGTCTGTTTTTTATGCAAAATCTAATTTAA
TATATTGATATTTATATCATTTTACGTTTCTCGTTCAGCTTTCTTGTACA
AAGTGGTTGATTCGAGGCTGCTAACAAAtcgagTCGAGCAtcgagcagtg
tggttttcaagaggaagcaaaaagcctctccacccaggcctggaatgttt
ccacccaatgtcgagcagtgtggttttgcaagaggaagcaaaaagcctct
ccacccaggcctggaatgtttccacccaatgtcgagCAAACCCCGCCCAG
CGTCTTGTCATTGGCGAATTCgaacacgcagatgcagtcggggcggcgcg
gtcccaggtccacttcgcatattaaggtgacgcgtgtggcctcgaacacc
gagcgaccctgcagcgaccccgcttaacagcgtcaacagcgtgccgcagat
cttggtggcgtgaaactcccgcacctcttcggccagcgccttgtagaagc
gcgtatggcttcgtaccccggccatcaacacgcgtctgcgttcgaccagg
ctgcgcgttctcgcggccatagcaaccgacgtacggcgttgcgccctcgc
cggcagcaagaagccacggaagtccgcccggagcagaaaatgcccacgct
actgcgggtttatatagacggtccccacgggatggggaaaaccaccacca
cgcaactgctggtggccctgggttcgcgcgacgatatcgtctacgtaccc
gagccgatgacttactggcgggtgctgggggcttccgagacaatcgcgaa
catctacaccacacaacaccgcctcgaccagggtgagatatcggccgggg
acgcggcggtggtaatgacaagcgcccagataacaatgggcatgccttat
gccgtgaccgacgccgttctggctcctcatatcgggggggaggctgggag
ctcacatgcccgccccgccctcaccctcatcttcgaccgccatccca
tcgccgccctcctgtgctaccccggccgcgcggtaccttatgggcagcatg acccccaggccgtgctggcgttcgtggccctcatcccgccgaccttgcc
cggcaccaacatcgtgcttggggcccttccggaggacagacacatcgacc
gcctggccaaacgccagcgccccggcgagcggctggacctggctatgctg
gctgcgattcgccgcgtttacgggctacttgccaatacggtgcggtatct
gcagtgcggcgggtcgtggcgggaggactggggacagctttcggggacgg
ccgtgccgcccagggtgccgagccccagagcaacgcgggcccacgaccc
catatcggggacacgttatttaccctgtttcgggcccccgagttgctggc
ccccaacgcgacctgtataacgtgtttgcctgggccttggacgtcttgg
ccaaacgcctccgttccatgcacgtctttatcctggattacgaccaatcg
ccgccggctgccgggacgccctgctgcaacttacctccgggatggtcca
gacccacgtcaccaccccggctccataccgacgatatgcgacctggcgc
gcacgtttgcccgggagatgggggaggctaactgaaacacggaaggagac
aataccggaaggaacccgcgctatgacggcaataaaaagacagaataaaa
cgcacgggtgttgggtcgtttgttcataaacgcggggttcggtcccaggg
ctggcactctgtcgatacccaccgagacccattgggccaatacgccc
gcgtttcttccttttccccaccccacccccaagttcgggtgaaggccca
gggctcgcagcaacgtcggggcggcaggccctgccatagccactggccc
cgtgggttagggacggggtcccccatggggaatggtttatggttcgtggg
ggttattattttgggcgttgcgtgggtcAGGTCCACGACCCAAGCTTGG
CTGCAGGTCGAGCTCGCGAAAGCTTGGCACTGGCCGTCGTTTTggcactg
gccgtcgttttacaacgtcgtgactgggaaaaccctggcgttacccaact
taatcgccttgcagcacatccccctttcgccagctggcgtaatagcgaag
aggcccgcaccgatcgcccttcccaacagttgcgcagcctgaatggcgaa
tggcgcctgatgcggtattttctccttacgcatctgtgcggtatttcaca
ccgcaTATGGTGCACTCTCAGTACAATCTGCTCTGATGCCGCATAGTTAA
GCCAGCCCCGACACCCGCCAACACCCGCTGACGCGCCCTGACGGGCTTGT
CTGCTCCCGGCATCCGCTTACAGACAAGCTGTGACCGTCTCCGGGAGCTG
CATGTGTCAGAGGTTTTCACCGTCATCACCGAAACGCGCGAGACGAAAGG
GCCTCGTGATACGCCTATTTTTATAGGTTAATGTCATGATAATAATGGTT
TCTTAGACGTCAGGTGGCACTTTTCGGGGAAATGTGCGCGGAACCCCTAT
TTGTTTATTTTTCTAAATACATTCAAATATGTATCCGCTCATGAGACAAT
AACCCTGATAAATGCTTCAATAATATTGAAAAAGGAAGAGT 116. SEQ ID NO: 116
(pWS-TK3)
ATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATG
CTGAAGATCAGTTGGGTGCACGAGTGGGTTACATCGAACTGGATCTCAAC
AGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACG
CCGGGCAAGAGCAACTCGGTCGCCGCATACACTATTCTCAGAATGACTTG
GTTGAGTACTCACCAGTCACAGAAAAGCATCTTACGGATGGCATGACAGT
AAGAGAATTATGCAGTGCTGCCATAACCATGAGTGATAACACTGCGGCCA
```

```
ACTTACTTCTGACAACGATCGGAGGACCGAAGGAGCTAACCGCTTTTTG
CACAACATGGGGATCATGTAACTCGCCTTGATCGTTGGGAACCGGAGCT
GAATGAAGCCATACCAAACGACGAGCGTGACACCACGATGCCTGTAGCAA
TGGCAACAACGTTGCGCAAACTATTAACTGGCGAACTACTTACTCTAGCT
TCCCGGCAACAATTAATAGACTGGATGGAGGCGGATAAAGTTGCAGGACC
ACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAAC
TATGGATGAACGAAATAGACAGATCGCTGAGATAGGTGCCTCACTGATTA
AGCATTGGTAACTGTCAGACCAAGTTTACTCATATATACTTTAGATTGAT
TTAAAACTTCATTTTTAATTTAAAAGGATCTAGGTGAAGATCCTTTTTGA
TAATCTCATGACCAAAATCCCTTAACGTGAGTTTTCGTTCCACTGAGCGT
CAGACCCCGTAGAAAAGATCAAAGGATCTTCTTGAGATCCTTTTTTTCTG
CGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCT
TCAGCAGAGCGCAGATACCAAATACTGTTCTTCTAGTGTAGCCGTAGTTA
GGCCACCACTTCAAGAACTCTGTAGCACCGCCTACATACCTCGCTCTGCT
AATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGA
ACGGGGGGTTCGTGCACACAGCCCAGCTTGGAGCGAACGACCTACACCGA
ACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTC
CTGGCCTTTTGCTGGCCTTTTGCTCACATGTTCTTTCCTGCGTTATCCCC
TGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAA
GAGCGCCCAATACGCAAACCGCCTCTCCCCGCGCGTTGGCCGATTCATTA
ATGCAGGTTAACCTGGCTTATCGAAATTAATACGACTCACTATAGGGAGA
CCGGCAGATCcggcgcgcctgcaggcgcgccactagttaattaatttaaa
tcgatgcgatcgctagcggccgcgtttGCTTTTGTTTCGTGTTGGTCACC
ACGGCCGAGTTTCCTCGGGACCCCGGGCAGCTGCTTTACATCCCAAAGAC
CTATCTGCTCGGCCGGCCTCGGAACGCGAGCCTGCCCGGAAGATCCCCGG
GTACCGAGCTCGAATTCATcgTCACCATCACCTCGAATCAACAAGTTTGT
ACAAAAAAGCTGAACGAGAAACGTAAAATGATATAAATATCAATATATTA
AATTAGATTTTGCATAAAAAACAGACTACATAATACTGTAAAACACAACA
TATCCAGTCACTATGGCGGCCGCATTAGGCACCCCAGGCTTTACACTTTA
TGCTTCCGGCTCGTATAATGTGTGGATTTTGAGTTAGGATCCGTCGAGAT
TTTCAGGAGCTAAGGAAGCTAAAATGGAGAAAAAAATCACTGGATATACC
ACCGTTGATATATCCCAATGGCATCGTAAAGAACATTTTGAGGCATTTCA
GTCAGTTGCTCAATGTACCTATAACCAGACCGTTCAGCTGGATATTACGG
CCTTTTTAAAGACCGTAAAGAAAAATAAGCACAAGTTTTATCCGGCCTTT
ATTCACATTCTTGCCCGCCTGATGAATGCTCATCCGGAATTCCGTATGGC
AATGAAAGACGGTGAGCTGGTGATATGGGATAGTGTTCACCCTTGTTACA
CCGTTTTCCATGAGCAAACTGAAACGTTTTCATCGCTCTGGAGTGAATAC
CACGACGATTTCCGGCAGTTTCTACACATATATTCGCAAGATGTGGCGTG
TTACGGTGAAAACCTGGCCTATTTCCCTAAAGGGTTTATTGAGAATATGT
TTTTCGTCTCAGCCAATCCCTGGGTGAGTTTCACCAGTTTTGATTTAAAC
GTGGCCAATATGGACAACTTCTTCGCCCCCGTTTTCACCATGGGCAAATA
TTATACGCAAGGCGACAAGGTGCTGATGCCGCTGGCGATTCAGGTTCATC
ATGCCGTCTGTGATGGCTTCCATGTCGGCAGAATGCTTAATGAATTACAA
CAGTACTGCGATGAGTGGCAGGGCGGGGCGTAAAGATCTGGATCCGGCTT
ACTAAAAGCCAGATAACAGTATGCGTATTTGCGCGCTGATTTTTGCGGTA
TAAGAATATATACTGATATGTATACCCGAAGTATGTCAAAAAGAGGTGTG
CTATGAAGCAGCGTATTACAGTGACAGTTGACAGCGACAGCTATCAGTTG
CTCAAGGCATATATGATGTCAATATCTCCGGTCTGGTAAGCACAACCATG
CAGAATGAAGCCCGTCGTCTGCGTGCCGAACGCTGGAAAGCGGAAAATCA
GGAAGGGATGGCTGAGGTCGCCCGGTTTATTGAAATGAACGGCTCTTTTG
CTGACGAGAACAGGGACTGGTGAAATGCAGTTTAAGGTTTACACCTATAA
AAGAGAGAGCCGTTATCGTCTGTTTGTGGATGTACAGAGTGATATTATTG
ACACGCCCGGGCGACGGATGGTGATCCCCCTGGCCAGTGCACGTCTGCTG
TCAGATAAAGTCTCCCGTGAACTTTACCCGGTGGTGCATATCGGGGATGA
AAGCTGGCGCATGATGACCACCGATATGGCCAGTGTGCCGGTCTCCGTTA
TCGGGGAAGAAGTGGCTGATCTCAGCCACCGCGAAAATGACATCAAAAAC
GCCATTAACCTGATGTTCTGGGGAATATAAATGTCAGGCTCCCTTATACA
CAGCCAGTCTGCAGGTCGACCATAGTGACTGGATATGTTGTGTTTTACAG
TATTATGTAGTCTGTTTTTTATGCAAAATCTAATTTAATATATTGATATT
TATATCATTTTACGTTTCTCGTTCAGCTTTCTTGTACAAAGTGGTTGATT
CGAGGCTGCTAACAAAtcgagTCGAGCAtcgagcagtgtggttttcaaga
ggaagcaaaaagcctctccacccaggcctggaatgtttccacccaatgtc
gagcagtgtggttttgcaagaggaagcaaaaagcctctccacccaggcct
ggaatgtttccacccaatgtcgagCAAACCCCGCCCAGCGTCTTGTCATT
GGCGAATTCgaacacgcagatgcagtcggggcggcgcggtcccaggtcca
cttcgcatattaaggtgacgcgtgtggcctcgaacaccgagcgaccctgc
agcgacccgcttaacagcgtcaacagcgtgccgcagatcttggtggcgtg
aaactcccgcacctcttcggccagcgccttgtagaagcgcgtatggcttc
gtaccccggccatcaacacgcgtctgcgttcgaccaggctgcgcgttctc
gcggccatagcaaccgacgtacgcgttgcgccctcgccggcagcaagaa
gccacggaagtccgcccggagcagaaaatgcccacgctactgcgggttta
tatagacggtccccacgggatggggaaaaccaccaccacgcaactgctgg
tggccctgggttcgcgcgacgatatcgtctacgtacccgagccgatgact
```

-continued tactggcgggtgctgggggcttccgagacaatcgcgaacatctacaccac
acaacaccgcctcgaccagggtgagatatcggccggggacgcggcggtgg
taatgacaagcgcccagataacaatgggcatgccttatgccgtgaccgac
gccgttctggctcctcatatcggggggaggctgggagctcacatgcccc
gcccccggccctcaccctcatcttcgaccgccatccatcgccgccctcc
tgtgctacccgccgcgcggtaccttatgggcagcatgacccccaggcc
gtgctggcgttcgtggccctcatcccgccgaccttgcccggcaccaacat
cgtgcttggggcccttccggaggacagacacatcgaccgcctggccaaac
gccagcgccccggcgagcggctggacctggctatgctggctgcgattcgc
cgcgtttacgggctacttgccaatacggtgcggtatctgcagtgcggcgg
gtcgtggcgggaggactggggacagctttcggggacggccgtgccgcccc
agggtgccgagcccagagcaacgcgggcccacgaccccatatcggggac
acgttatttaccctgtttcgggccccgagttgctggcccccaacgcga
cctgtataacgtgtttgcctgggccttggacgtcttggccaaacgcctcc
gttccatgcacgtctttatcctggattacgaccaatcgcccgccggctgc
cgggacgccctgctgcaacttacctccgggatggtccagacccacgtcac
cacccccggctccataccgacgatatgcgacctggcgcgcacgtttgccc
gggagatgggggaggctaactgaaacacggaaggagacaataccggaagg
aacccgcgctatgacggcaataaaaagacagaataaaacgcacgggtgtt
gggtcgtttgttcataaacgcggggttcggtcccagggctggcactctgt
cgataccccaccgagacccccattggggccaatacgcccgcgtttcttcct
tttccccacccacccccccaagttcgggtgaaggcccagggctcgcagcc
aacgtcggggcggcaggccctgccatagccactggccccgtgggttaggg
acggggtcccccatggggaatggtttatggttcgtggggttattatttt
gggcgttgcgtggggtcAGGTCCACGACCCAAGCTTGGCTGCAGGTCGAG
CTCGCGAAAGCTTGGCACTGGCCGTCGTTTTggcactggccgtcgtttta
caacgtcgtgactgggaaaaccctggcgttacccaacttaatgccttgc
agcacatcccccttcgccagctggcgtaatagcgaagaggccgcaccg
atcgcccttcccaacagttgcgcagcctgaatggcgaatggcgcctgatg
cggtattttctccttacgcatctgtgcggtatttcacaccgcaTATGGTG
CACTCTCAGTACAATCTGCTCTGATGCCGCATAGTTAAGCCAGCCCGAC
ACCCGCCAACACCCGCTGACGCGCCCTGACGGGCTTGTCTGCTCCCGGCA
TCCGCTTACAGACAAGCTGTGACCGTCTCCGGGAGCTGCATGTGTCAGAG
GTTTTCACCGTCATCACCGAAACGCGCGAGACGAAAGGGCCTCGTGATAC
GCCTATTTTTATAGGTTAATGTCATGATAATAATGGTTTCTTAGACGTCA
GGTGGCACTTTTCGGGGAAATGTGCGCGGAACCCCTATTTGTTTATTTTT
CTAAATACATTCAAATATGTATCCGCTCATGAGACAATAACCCTGATAAA
TGCTTCAATAATATTGAAAAAGGAAGAGT 117. SEQ ID NO: 117
(pWS-TK6)
TTTTCGTTCCACTGAGCGTCAGACCCCTTAATAAGATGATCTTCTTGAGA
TCGTTTTGGTCTGCGCGTAATCTCTTGCTCTGAAAACGAAAAAACCGCCT TGCAGGGCGGTTTTTCGAAGGTTCTCTGAGCTACCAACTCTTTGAACCGA
GGTAACTGGCTTGGAGGAGCGCAGTCACCAAAACTTGTCCTTTCAGTTTA
GCCTTAACCGGCGCATGACTTCAAGACTAACTCCTCTAAATCAATTACCA
GTGGCTGCTGCCAGTGGTGCTTTTGCATGTCTTTCCGGGTTGGACTCAAG
ACGATAGTTACCGGATAAGGCGCAGCGGTCGGACTGAACGGGGGGTTCGT
GCATACAGTCCAGCTTGGAGCGAACTGCCTACCCGGAACTGAGTGTCAGG
CGTGGAATGAGACAAACGCGGCCATAACAGCGGAATGACACCGGTAAACC
GAAAGGCAGGAACAGGAGAGCGCACGAGGGAGCCGCCAGGGGAAACGCCT
GGTATCTTTATAGTCCTGTCGGGTTTCGCCACCACTGATTTGAGCGTCAG
ATTTCGTGATGCTTGTCAGGGGGCGGAGCCTATGGAAAAACGGCTTTGC
CGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCG
AGCGTAGCGAGTCAGTGAGCGAGGAAGCGGAATATATCCTGTATCACATA
TTCTGCTGACGCACCGGTGCAGCCTTTTTTCTCCTGCCACATGAAGCACT
TCACTGACACCCTCATCAGTGCCAACATAGTAAGCCAGTATACACTCCGC
TAGCAACCTGGCTTATCGAAATTAATACGACTCACTATAGGGAGACCGGC
AGATCcggcgcgcctgcaggcgcgccactagttaattaatttaaatcgat
gcgatcgctagcggccgcgttTGCTTTTGTTTCGTGTTGGTCACCACGGC
CGAGTTTCCTCGGGACCCCGGGCAGCTGCTTTACATCCCAAAGACCTATC
TGCTCGGCCGGCCTCGGAACGCGAGCCTGCCCGGAAGATCCCCGGGTACC
GAGCTCGAATTCATcgTCACCATCACCTCGAATCAACAAGTTTGTACAAA
AAAGCTGAACGAGAAACGTAAAATGATATAAATATCAATATATTAAATTA
GATTTTGCATAAAAAACAGACTACATAATACTGTAAAACACAACATATCC
AGTCACTATGGCGGCCGCATTAGGCACCCCAGGCTTTACACTTTATGCTT
CCGGCTCGTATAATGTGTGGATTTTGAGTTAGGATCCGTCGAGATTTTCA
GGAGCTAAGGAAGCTAAAATGGAGAAAAAAATCACTGGATATACCACCGT
TGATATATCCCAATGGCATCGTAAAGAACATTTTGAGGCATTTCAGTCAG
TTGCTCAATGTACCTATAACCAGACCGTTCAGCTGGATATTACGGCCTTT
TTAAAGACCGTAAAGAAAAATAAGCACAAGTTTTATCCGGCCTTTATTCA
CATTCTTGCCCGCCTGATGAATGCTCATCCGGAATTCCGTATGGCAATGA
AAGACGGTGAGCTGGTGATATGGGATAGTGTTCACCCTTGTTACACCGTT
TTCCATGAGCAAACTGAAACGTTTTCATCGCTCTGGAGTGAATACCACGA
CGATTTCCGGCAGTTTCTACACATATATTCGCAAGATGTGGCGTGTTACG
GTGAAAACCTGGCCTATTTCCCTAAAGGGTTTATTGAGAATATGTTTTTC
GTCTCAGCCAATCCCTGGGTGAGTTTCACCAGTTTTGATTTAAACGTGGC
CAATATGGACAACTTCTTCGCCCCCGTTTTCACCATGGGCAAATATTATA
CGCAAGGCGACAAGGTGCTGATGCCGCTGGCGATTCAGGTTCATCATGCC
GTCTGTGATGGCTTCCATGTCGGCAGAATGCTTAATGAATTACAACAGTA
CTGCGATGAGTGGCAGGGCGGGGCGTAAAGATCTGGATCCGGCTTACTAA
AAGCCAGATAACAGTATGCGTATTTGCGCGCTGATTTTTGCGGTATAAGA
ATATATACTGATATGTATACCCGAAGTATGTCAAAAAGAGGTGTGCTATG -continued AAGCAGCGTATTACAGTGACAGTTGACAGCGACAGCTATCAGTTGCTCAA
GGCATATATGATGTCAATATCTCCGGTCTGGTAAGCACAACCATGCAGAA
TGAAGCCCGTCGTCTGCGTGCCGAACGCTGGAAAGCGGAAAATCAGGAAG
GGATGGCTGAGGTCGCCCGGTTTATTGAAATGAACGGCTCTTTTGCTGAC
GAGAACAGGGACTGGTGAAATGCAGTTTAAGGTTTACACCTATAAAGAG
AGAGCCGTTATCGTCTGTTTGTGGATGTACAGAGTGATATTATTGACACG
CCCGGGCGACGGATGGTGATCCCCCTGGCCAGTGCACGTCTGCTGTCAGA
TAAAGTCTCCCGTGAACTTTACCCGGTGGTGCATATCGGGGATGAAAGCT
GGCGCATGATGACCACCGATATGGCCAGTGTGCCGGTCTCCGTTATCGGG
GAAGAAGTGGCTGATCTCAGCCACCGCGAAAATGACATCAAAAACGCCAT
TAACCTGATGTTCTGGGGAATATAAATGTCAGGCTCCCTTATACACAGCC
AGTCTGCAGGTCGACCATAGTGACTGGATATGTTGTGTTTTACAGTATTA
TGTAGTCTGTTTTTTATGCAAAATCTAATTTAATATATTGATATTTATAT
CATTTTACGTTTCTCGTTCAGCTTTCTTGTACAAAGTGGTTGATTCGAGG
CTGCTAACAAAtcgagTCGAGCAtcgagcagtgtggttttcaagaggaag
caaaaagcctctccacccaggcctggaatgtttccacccaatgtcgagca
gtgtggttttgcaagaggaagcaaaaagcctctccacccaggcctggaat
gtttccacccaatgtcgagCAAACCCCGCCCAGCGTCTTGTCATTGGCGA
ATTCgaacacgcagatgcagtcggggcggcgcggtcccaggtccacttcg
catattaaggtgacgcgtgtggcctcgaacaccgagcgaccctgcagcga
cccgcttaacgcgtcaacagcgtgccgcagatcttggtggcgtgaaact
cccgcacctcttcggccagcgccttgtagaagcgcgtatggcttcgtacc
ccggccatcaacacgcgtctgcgttcgaccaggctgcgcgttctcgcggc
catagcaaccgacgtacggcgttgcgccctcgccggcagcaagaagccac
ggaagtccgcccggagcagaaaatgcccacgctactgcgggtttatatag
acggtccccacgggatggggaaaaccaccaccacgcaactgctggtggcc
ctgggttcgcgcgacgatatcgtctacgtacccgagccgatgacttactg
gcgggtgctgggggcttccgagacaatcgcgaacatctacaccacacaac
accgcctcgaccagggtgagatatcggccggggacgcggcggtggtaatg
acaagcgcccagataacaatgggcatgccttatgccgtgaccgacgccgt
tctggctcctcatatcggggggggaggctgggagctcacatgccccgcccc
cggccctcaccctcatcttcgaccgccatcccatcgccgccctcctgtgc
tacccggccgcgcggtaccttatgggcagcatgaccccccaggccgtgct
ggcgttcgtggccctcatcccgccgaccttgcccggcaccaacatcgtgc
ttggggcccttccggaggacagacacatcgaccgcctggccaaacgccag
cgccccggcgagcggctggacctggctatgctggctgcgattcgccgcgt
ttacgggctacttgccaatacggtgcggtatctgcagtgcggcgggtcgt
ggcgggaggactggggacagctttcggggacggccgtgccgccccagggt
gccgagcccagagcaacgcgggcccacgaccccatatcggggacacgtt
atttaccctgtttcgggccccgagttgctggccccaacgcgacctgt
ataacgtgtttgcctgggccttggacgtcttggccaaacgcctccgttcc -continued atgcacgtctttatcctggattacgaccaatcgcccgccggctgccggga
cgccctgctgcaacttacctcgggatggtccagacccacgtcaccaccc
ccggctccataccgacgatatgcgacctggcgcgcacgtttgcccgggag
atgggggaggctaactgaaacacggaaggagacaataccggaaggaaccc
gcgctatgacggcaataaaaagacagaataaaacgcacgggtgttgggtc
gtttgttcataaacgcggggttcggtcccagggctggcactctgtcgata
ccccaccgagaccccattggggcaatacgcccgcgtttcttccttttcc
ccaccccacccccaagttcgggtgaaggcccagggctcgcagccaacgt
cggggcggcaggccctgccatagccactggccccgtgggttagggacggg
gtccccatggggaatggtttatggttcgtggggttattattttgggcg
ttgcgtggggtcAGGTCCACGACCCAAGCTTGGCTGCAGGTCGAGCTCGC
GAAAGCTTGGCACTGGCCGTCGTTTTggcactggccgtcgttttacaacg
tcgtgactgggaaaaccctggcgttacccaacttaatcgccttgcagcac
atccccctttcgccagctggcgtaatagcgaagaggcccgcaccgatcgc
ccttcccaacagttgcgcagcctgaatgcgaatggcgcctgatgcggta
ttttctccttacgcatctgtgcggtatttcacaccgcaTATGGTGCACTC
TCAGTACAATCTGCTCTGATGCCGCATAGTTAAGCCAGCCCCGACACCCG
CCAACACCCGCTGACGCGCCCTGACGGGCTTGTCTGCTCCCGGCATCCGC
TTACAGACAAGCTGTGACCGTCTCCGGGAGCTGCATGTGTCAGAGGTTTT
CACCGTCATCACCGAAACGCGCGAGACGAAAGGGCCTCGTGATACGCCTA
TTTTTATAGGTTAATGTCATGATAATAATGGTTTCTTAGACGTCAGGTGG
CACTTTTCGGGGAAATGTGCGCGGAACCCCTATTTGTTTATTTTTCTAAA
TACATTCAAATATGTATCCGCTCATGAGACAATAACCCTGATAAATGCTT
CAATAATATTGAAAAGGAAGAGTATGAGTATTCAACATTTCCGTGTCGC
CCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTG
GGTTACATCGAACTGGATCTCAACAGCGGTAAGATCCTTGAGAGTTTTCG
CCCCGAAGAACGTTTTCCAATGATGAGCACTTTTAAAGTTCTGCTATGTG
GCGCGGTATTATCCCGTGTTGACGCCGGGCAAGAGCAACTCGGTCGCCGC
ATACACTATTCTCAGAATGACTTGGTTGAGTACTCACCAGTCACAGAAAA
GCATCTTACGGATGGCATGACAGTAAGAGAATTATGCAGTGCTGCCATAA
CCATGAGTGATAACACTGCGGCCAACTTACTTCTGACAACGATCGGAGGA
CCGAAGGAGCTAACCGCTTTTTTGCACAACATGGGGGATCATGTAACTCG
CCTTGATCGTTGGGAACCGGAGCTGAATGAAGCCATACCAAACGACGAGC
GTGACACCACGATGCCTGCAGCAATGGCAACAACGTTGCGCAAACTATTA
ACTGGCGAACTACTTACTCTAGCTTCCCGGCAACAATTAATAGACTGGAT
GGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGT
ATCATTGCAGCACTGGGGCCAGATGGTAAGCCCTCCCGTATCGTAGTTAT
CTACACGACGGGGAGTCAGGCAACTATGGATGAACGAAATAGACAGATCG
CTGAGATAGGTGCCTCACTGATTAAGCATTGGTAACTGTCAGACCAAGTT

TACTCATATATACTTTAGATTGATTTAAAACTTCATTTTTAATTTAAAAG

GATCTAGGTGAAGATCCTTTTTGATAATCTCATGACCAAAATCCCTTAAC

GTGAG

118. SEQ ID NO: 118
(pCAG-PBase)
TAGTTATTACTAGCGCTACCGGACTCAGATCTCGAGCTCAAGCTTCGAAT

TCTGCAGTCGACATTGATTATTGACTAGTTATTAATAGTAATCAATTACG

GGGTCATTAGTTCATAGCCCATATATGGAGTTCCGCGTTACATAACTTAC

GGTAAATGGCCCGCCTGGCTGACCGCCCAACGACCCCCGCCCATTGACGT

CAATAATGACGTATGTTCCCATAGTAACGCCAATAGGGACTTTCCATTGA

CGTCAATGGGTGGACTATTTACGGTAAACTGCCCACTTGGCAGTACATCA

AGTGTATCATATGCCAAGTACGCCCCCTATTGACGTCAATGACGGTAAAT

GGCCCGCCTGGCATTATGCCCAGTACATGACCTTATGGGACTTTCCTACT

TGGCAGTACATCTACGTATTAGTCATCGCTATTACCATGGGTCGAGGTGA

GCCCCACGTTCTGCTTCACTCTCCCCATCTCCCCCCCCTCCCCACCCCCA

ATTTTGTATTTATTTATTTTTTAATTATTTTGTGCAGCGATGGGGGCGGG

GGGGGGGGGGGCGCGCGCCAGGCGGGGCGGGGCGGGGCGAGGGGCGGGGC

GGGGCGAGGCGGAGAGGTGCGGCGGCAGCCAATCAGAGCGGCGCGCTCCG

AAAGTTTCCTTTTATGGCGAGGCGGCGGCGGCGGCGGCCCTATAAATAGC

GAAGCGCGCGGCGGGCGGGAGTCGCTGCGTTGCCTTCGCCCCGTGCCCCG

CTCCGCGCCGCCTCGCGCCGCCCGCCCCGGCTCTGACTGACCGCGTTACT

CCCACAGGTGAGCGGGCGGGACGGCCCTTCTCCTCCGGGCTGTAATTAGC

GCTTGGTTTAATGACGGCTCGTTTCTTTTCTGTGGCTGCGTGAAAGCCTT

AAAGGGCTCCGGGAGGGCCCTTTGTGCGGGGGGGAGCGGCTCGGGGGGTG

CGTGCGTGTGTGTGCGTGGGGAGCGCCGCGTGCGGCCCGCGCTGCCCG

GCGGCTGTGAGCGCTGCGGGCGCGGCGCGGGGCTTTGTGCGCTCCGCGTG

TGCGCGAGGGGAGCGCGGCCGGGGCGGTGCCCCGCGGTGCGGGGGGCT

GCGAGGGGAACAAAGGCTGCGTGCGGGGTGTGTGCGTGGGGGGGTGAGCA

GGGGGTGTGGGCGCGGCGGTCGGGCTGTAACCCCCCCCTGCACCCCCCTC

CCCGAGTTGCTGAGCACGGCCCGGCTTCGGGTGCGGGGCTCCGTGCGGGG

CGTGGCGCGGGGCTCGCCGTGCCGGGCGGGGGTGGCGGCAGGTGGGGGT

GCCGGGCGGGCGGGCCGCCTCGGGCCGGGGAGGGCTCGGGGGAGGGGC

GCGGCGGCCCCGGAGCGCCGGCGGCTGTCGAGGCGCGGCGAGCCGCAGCC

ATTGCCTTTTATGGTAATCGTGCGAGAGGGCGCAGGGACTTCCTTTGTCC

CAAATCTGGCGGAGCCGAAATCTGGGAGGCGCCGCCGCACCCCCTCTAGC

GGGCGCGGGCGAAGCGGTGCGCGCCGGCAGGAAGGAAATGGGCGGGAG

GGCCTTCGTGCGTCGCCGCGCCGCCGTCCCCTTCTCCATCTCCAGCCTCG

GGGCTGCCGCAGGGGACGGCTGCCTTCGGGGGGGACGGGGCAGGGCGGG

GTTCGGCTTCTGGCGTGTGACCGGCGGCTCTAGAGCCTCTGCTAACCATG

TTCATGCCTTCTTCTTTTTCCTACAGCTCCTGGGCAACGTGCTGGTTATT

GTGCTGTCTCATCATTTTGGCAAAGAATTCcgcggCCACCatgggtagtt ctttagacgatgagcatatcctctctgctcttctgcaaagcgatgacgag cttgttggtgaggattctgacagtgaaatatcagatcacgtaagtgaaga tgacgtccagagcgatacagaagaagcgtttatagatgaggtacatgaag tgcagccaacgtcaagcggtagtgaaatattagacgaacaaaatgttatt gaacaaccaggttcttcattggcttctaacagaatcttgaccttgccaca gaggactattagaggtaagaataaacattgttggtcaacttcaaagtcca cgaggcgtagccgagtctctgcactgaacattgtcagatctcaaagaggt ccgacgcgtatgtgccgcaatatatatgacccacttttatgcttcaaact atttttactgatgagataatttcggaaattgtaaaatggacaaatgctg agatatcattgaaaegtcgggaatctatgacaggtgctacatttcgtgac acgaatgaagatgaaatctatgctttctttggtattctggtaatgacagc agtgagaaaagataaccacatgtccacagatgacctctttgatcgatctt tgtcaatggtgtacgtctctgtaatgagtcgtgatcgttttgatttttg atacgatgtcttagaatggatgacaaaagtatacggcccacacttcgaga aaacgatgtatttactcctgttagaaaaatatgggatctctttatccatc agtgcatacaaaattacactccagggctcatttgaccatagatgaacag ttacttggttttagaggacggtgtccgtttaggatgtatatcccaaacaa gccaagtaagtatggaataaaaatcctcatgatgtgtgacagtggtacga agtatatgataaatggaatgccttatttgggaagaggaacacagaccaac ggagtaccactcggtgaatactacgtgaaggagttatcaaagcctgtgca cggtagttgtcgtaatattacgtgtgacaattggttcacctcaatcccttt tggcaaaaaacttactacaagaaccgtataagttaaccattgtgggaacc gtgcgatcaaacaaacgcgagataccggaagtactgaaaaacagtcgctc caggccagtgggaacatcgatgtttttgttttgacggacccccttactctcg tctcatataaaccgaagccagctaagatggtatacttattatcatcttgt gatgaggatgcttctatcaacgaaagtaccggtaaaccgcaaatggttat gtattataatcaaactaaaggcggagtggacacgctagaccaaatgtgtt ctgtgatgacctgcagtaggaagacgaataggtggcctatggcattattg tacggaatgataaacattgcctgcataaattctttttattatatacagcca taatgtcagtagcaagggagaaaaggttcaaagtcgcaaaaaaatttatga gaaacctttacatgagcctgacgtcatcgtttatgcgtaagcgtttagaa gctcctactttgaagagatatttgcgcgataatatctctaatattttgcc aaatgaagtgcctggtacatcagatgacagtactgaagagccagtaatga aaaaacgtacttactgtacttactgcccctctaaaataaggcgaaaggca aatgcatcgtgcaaaaaatgcaaaaagttatttgtcgagagcataatat tgatatgtgccaaagttgtttctgaTAGCGGCCGCGACTCTAGATCATAA

TCAGCCATACCACATTTGTAGAGGTTTTACTTGCTTTAAAAAACCTCCCA

CACCTCCCCCTGAACCTGAAACATAAAATGAATGCAATTGTTGTTGTTAA

CTTGTTTATTGCAGCTTATAATGGTTACAAATAAAGCAATAGCATCACAA

ATTTCACAAATAAAGCATTTTTTTCACTGCATTCTAGTTGTGGTTTGTCC

AAACTCATCAATGTATCTTAAGGCGTAAATTGTAAGCGTTAATATTTTGT

TAAAATTCGCGTTAAATTTTTGTTAAATCAGCTCATTTTTTAACCAATAG

GCCGAAATCGGCAAAATCCCTTATAAATCAAAAGAATAGACCGAGATAGG
GTTGAGTGTTGTTCCAGTTTGGAACAAGAGTCCACTATTAAAGAACGTGG
ACTCCAACGTCAAAGGGCGAAAAACCGTCTATCAGGGCGATGGCCCACTA
CGTGAACCATCACCCTAATCAAGTTTTTTGGGGTCGAGGTGCCGTAAAGC
ACTAAATCGGAACCCTAAAGGGAGCCCCCGATTTAGAGCTTGACGGGGAA
AGCCGGCGAACGTGGCGAGAAAGGAAGGGAAGAAAGCGAAAGGAGCGGGC
GCTAGGGCGCTGGCAAGTGTAGCGGTCACGCTGCGCGTAACCACCACACC
CGCCGCGCTTAATGCGCCGCTACAGGGCGCGTCAGGTGGCACTTTTCGGG
GAAATGTGCGCGGAACCCCTATTTGTTTATTTTTCTAAATACATTCAAAT
ATGTATCCGCTCATGAGACAATAACCCTGATAAATGCTTCAATAATATTG
AAAAAGGAAGAGTCCTGAGGCGGAAAGAACCAGCTGTGGAATGTGTGTCA
GTTAGGGTGTGGAAAGTCCCCAGGCTCCCCAGCAGGCAGAAGTATGCAAA
GCATGCATCTCAATTAGTCAGCAACCAGGTGTGGAAAGTCCCCAGGCTCC
CCAGCAGGCAGAAGTATGCAAAGCATGCATCTCAATTAGTCAGCAACCAT
AGTCCCGCCCCTAACTCCGCCCATCCCGCCCCTAACTCCGCCCAGTTCCG
CCCATTCTCCGCCCCATGGCTGACTAATTTTTTTATTTATGCAGAGGCC
GAGGCCGCCTCGGCCTCTGAGCTATTCCAGAAGTAGTGAGGAGGCTTTTT
TGGAGGCCTAGGCTTTTGCAAAGATCGATCAAGAGACAGGATGAGGATCG
TTTCGCATGATTGAACAAGATGGATTGCACGCAGGTTCTCCGGCCGCTTG
GGTGGAGAGGCTATTCGGCTATGACTGGGCACAACAGACAATCGGCTGCT
CTGATGCCGCCGTGTTCCGGCTGTCAGCGCAGGGGCGCCCGGTTCTTTTT
GTCAAGACCGACCTGTCCGGTGCCCTGAATGAACTGCAAGACGAGGCAGC
GCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCG
GGGCAGGATCTCCTGTCATCTCACCTTGCTCCTGCCGAGAAAGTATCCAT
CATGGCTGATGCAATGCGGCGGCTGCATACGCTTGATCCGGCTACCTGCC
CATTCGACCACCAAGCGAAACATCGCATCGAGCGAGCACGTACTCGGATG
GAAGCCGGTCTTGTCGATCAGGATGATCTGGACGAAGAGCATCAGGGGCT
CGCGCCAGCCGAACTGTTCGCCAGGCTCAAGGCGAGCATGCCCGACGGCG
AGGATCTCGTCGTGACCCATGGCGATGCCTGCTTGCCGAATATCATGGTG
GAAAATGGCCGCTTTTCTGGATTCATCGACTGTGGCCGGCTGGGTGTGGC
GGACCGCTATCAGGACATAGCGTTGGCTACCCGTGATATTGCTGAAGAGC
TTGGCGGCGAATGGGCTGACCGCTTCCTCGTGCTTTACGGTATCGCCGCT
CCCGATTCGCAGCGCATCGCCTTCTATCGCCTTCTTGACGAGTTCTTCTG
AGCGGGACTCTGGGGTTCGAAATGACCGACCAAGCGACGCCCAACCTGCC
ATCACGAGATTTCGATTCCACCGCCGCCTTCTATGAAAGGTTGGGCTTCG
GAATCGTTTTCCGGGACGCCGGCTGGATGATCCTCCAGCGCGGGGATCTC
ATGCTGGAGTTCTTCGCCCACCCTAGGGGGAGGCTAACTGAAACACGGAA
GGAGACAATACCGGAAGGAACCCGCGCTATGACGGCAATAAAAAGACAGA
ATAAAACGCACGGTGTTGGGTCGTTTGTTCATAAACGCGGGGTTCGGTCC
CAGGGCTGGCACTCTGTCGATACCCCACCGAGACCCCATTGGGGCCAATA

CGCCCGCGTTTCTTCCTTTTCCCCACCCCACCCCCCAAGTTCGGGTGAAG
GCCCAGGGCTCGCAGCCAACGTCGGGCGGCAGGCCCTGCCATAGCCTCA
GGTTACTCATATATACTTTAGATTGATTTAAAACTTCATTTTTAATTTAA
AAGGATCTAGGTGAAGATCCTTTTTGATAATCTCATGACCAAAATCCCTT
AACGTGAGTTTTCGTTCCACTGAGCGTCAGACCCCGTAGAAAAGATCAAA
GGATCTTCTTGAGATCCTTTTTTTCTGCGCGTAATCTGCTGCTTGCAAAC
AAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAAT
ACTGTCCTTCTAGTGTAGCCGTAGTTAGGCCACCACTTCAAGAACTCTGT
AGCACCGCCTACATACCTCGCTCTGCTAATCCTGTTACCAGTGGCTGCTG
CCAGTGGCGATAAGTCGTGTCTTACCGGGTTGGACTCAAGACGATAGTTA
CCGGATAAGGCGCAGCGGTCGGGCTGAACGGGGGGTTCGTGCACACAGCC
CAGCTTGGAGCGAACGACCTACACCGAACTGAGATACCTACAGCGTGAGC
TATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGG
AAACGCCTGGTATCTTTATAGTCCTGTCGGGTTTCGCCACCTCTGACTTG
AGCGTCGATTTTTGTGATGCTCGTCAGGGGGCGGAGCCTATGGAAAAAC
GCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTA
CCGCCATGCAT

119. SEQ ID NO: 119
(pPrm1-PBase)
AGTTATTACTAGCGCTACCGGACTCAGATCTCGAGCTCAAGCTTGGTACC
GAGCTCGGATCCACTAGTAACGGCCGCCAGTGTGCTGGAATTCGCCCTTg
tctagaGTTTCCTGTCCACCTTTCAGCTTCCCTCTCAGGCTGGGAGCAGG
GGCCAGTAGCAGCACCCACGTCCACCTTCTGTCTAGTAATGTCCAACACC
TCCCTCAGTCCAAACACTGCTCTGCATCCATGTGGCTCCCATTTATACCT
GAAGCACTTGATGGGCCTCAATGTTTTACTAGAGCCCACCCCCCTGCAA
CTCTGAGACCCTCTGGATTTGTCTGTCAGTGCCTCACTGGGGCGTTGGAT
AATTTCTTAAAAGGTCAAGTTCCCTCAGCAGCATTCTCTGAGCAGTCTGA
AGATGTGTGCTTTTCACAGTTCAAATCCATGTGGCTGTTTCACCCACCTG
CCTGGCCTTGGGTTATCTATCAGGACCTAGCCTAGAAGCAGGTGTGTGGC
ACTTAACACCTAAGCTGAGTGACTAACTGAACACTCAAGTGGATGCCATC
TTTGTCACTTCTTGACTGTGACACAAGCAACTCCTGATGCCAAAGCCCTG
CCCACCCCTCTCATGCCCATATTTGGACATGGTACAGGTCCTCACTGGCC
ATGGTCTGTGAGGTCCTGGTCCTCTTTGACTTCATAATTCCTAGGGGCCA
CTAGTATCTATAAGAGGAAGAGGGTGCTGGCTCCCAGGCCACAGCCCACA
AAATTCCACCTGCTCACAGGTTGGCTGGCTCGACCCAGGTGGTGTCCCCT
GCTCTGAGCCAGCTCCCGGCCAAGCCAGCcgcggCCACCatgggtagttc
tttagacgatgagcatatcctctctgctcttctgcaaagcgatgacgagc
ttgttggtgaggattctgacagtgaaatatcagatcacgtaagtgaagat
gacgtccagagcgatacagaagaagcgtttatagatgaggtacatgaagt -continued gcagccaacgtcaagcggtagtgaaatattagacgaacaaaatgttattg
aacaaccaggttcttcattggcttctaacagaatcttgaccttgccacag
aggactattagaggtaagaataaacattgttggtcaacttcaaagtccac
gaggcgtagccgagtctctgcactgaacattgtcagatctcaaagaggtc
cgacgcgtatgtgccgcaatatatgacccacttttatgcttcaaacta
ttttttactgatgagataatttcggaaattgtaaaatggacaaatgctga
gatatcattgaaacgtcgggaatctatgacaggtgctacatttcgtgaca
cgaatgaagatgaaatctatgcttctttggtattctggtaatgacagca
gtgagaaaagataaccacatgtccacagatgacctctttgatcgatcttt
gtcaatggtgtacgtctctgtaatgagtcgtgatcgttttgatttttga
tacgatgtcttagaatggatgacaaaagtatacggcccacacttcgagaa
aacgatgtatttactcctgttagaaaaatatgggatctctttatccatca
gtgcatacaaaattacactccaggggctcatttgaccatagatgaacagt
tacttggttttagaggacggtgtccgtttaggatgtatatcccaaacaag
ccaagtaagtatggaataaaaatcctcatgatgtgtgacagtggtacgaa
gtatatgataaatggaatgccttatttgggaagaggaacacagaccaacg
gagtaccactcggtgaatactacgtgaaggagttatcaaagcctgtgcac
ggtagttgtcgtaatattacgtgtgacaattggttcacctcaatccctt
ggcaaaaaacttactacaagaaccgtataagttaaccattgtgggaaccg
tgcgatcaaacaaacgcgagataccggaagtactgaaaaacagtcgctcc
aggccagtgggaacatcgatgttttgttttgacggaccccttactctcgt
ctcatataaaccgaagccagctaagatggtatacttattatcatcttgtg
atgaggatgcttctatcaacgaaagtaccggtaaaccgcaaatggttatg
tattataatcaaactaaaggcggagtggacacgctagaccaaatgtgttc
tgtgatgacctgcagtaggaagacgaataggtggcctatggcattattgt
acggaatgataaacattgcctgcataaattctttttattatatacagccat
aatgtcagtagcaagggagaaaaggttcaaagtcgcaaaaaatttatgag
aaacctttacatgagcctgacgtcatcgtttatgcgtaagcgtttagaag
ctcctactttgaagagatatttgcgcgataatatctctaatattttgcca
aatgaagtgcctggtacatcagatgacagtactgaagagccagtaatgaa
aaaacgtacttactgtacttactgcccctctaaaataaggcgaaaggcaa
atgcatcgtgcaaaaaatgcaaaaaagttatttgtcgagagcataatatt
gatatgtgccaaagttgtttctgaTAGCGGCCGCGACTCTAGATCATAAT
CAGCCATACCACATTTGTAGAGGTTTTACTTGCTTTAAAAAACCTCCCAC
ACCTCCCCCTGAACCTGAAACATAAAATGAATGCAATTGTTGTTGTTAAC
TTGTTTATTGCAGCTTATAATGGTTACAAATAAAGCAATAGCATCACAAA
TTTCACAAATAAAGCATTTTTTTCACTGCATTCTAGTTGTGGTTTGTCCA
AACTCATCAATGTATCTTAAGGCGTAAATTGTAAGCGTTAATATTTTGTT
AAAATTCGCGTTAAATTTTTGTTAAATCAGCTCATTTTTTAACCAATAGG
CCGAAATCGGCAAAATCCCTTATAAATCAAAAGAATAGACCGAGATAGGG
TTGAGTGTTGTTCCAGTTTGGAACAAGAGTCCACTATTAAAGAACGTGGA -continued CTCCAACGTCAAAGGGCGAAAAACCGTCTATCAGGGCGATGGCCCACTAC
GTGAACCATCACCCTAATCAAGTTTTTTGGGGTCGAGGTGCCGTAAAGCA
CTAAATCGGAACCCTAAAGGGAGCCCCCGATTTAGAGCTTGACGGGGAAA
GCCGGCGAACGTGGCGAGAAAGGAAGGGAAGAAAGCGAAAGGAGCGGGCG
CTAGGGCGCTGGCAAGTGTAGCGGTCACGCTGCGCGTAACCACCACACCC
GCCGCGCTTAATGCGCCGCTACAGGGCGCGTCAGGTGGCACTTTTCGGGG
ATATGTGCGCGGAACCCTATTTGTTTATTTTTCTAAATACATTCAAATA
TGTATCCGCTCATGAGACAATAACCCTGATAAATGCTTCAATAATATTGA
AAAAGGAAGAGTCCTGAGGCGGAAAGAACCAGCTGTGGAATGTGTGTCAG
TTAGGGTGTGGAAAGTCCCCAGGCTCCCCAGCAGGCAGAAGTATGCAAAG
CATGCATCTCAATTAGTCAGCAACCAGGTGTGGAAAGTCCCCAGGCTCCC
CAGCAGGCAGAAGTATGCAAAGCATGCATCTCAATTAGTCAGCAACCATA
GTCCCGCCCCTAACTCCGCCCATCCCGCCCCTAACTCCGCCCAGTTCCGC
CCATTCTCCGCCCCATGGCTGACTAATTTTTTTTATTTATGCAGAGGCCG
AGGCCGCCTCGGCCTCTGAGCTATTCCAGAAGTAGTGAGGAGGCTTTTTT
GGAGGCCTAGGCTTTTGCAAAGATCGATCAAGAGACAGGATGAGGATCGT
TTCGCATGATTGAACAAGATGGATTGCACGCAGGTTCTCCGGCCGCTTGG
GTGGAGAGGCTATTCGGCTATGACTGGGCACAACAGACAATCGGCTGCTC
TGATGCCGCCGTGTTCCGGCTGTCAGCGCAGGGGCGCCCGGTTCTTTTTG
TCAAGACCGACCTGTCCGGTGCCCTGAATGAACTGCAAGACGAGGCAGCG
CGGCTATCGTGGCTGGCCACGACGGGCGTTCCTTGCGCAGCTGTGCTCGA
CGTTGTCACTGAAGCGGGAAGGGACTGGCTGCTATTGGGCGAAGTGCCGG
GGCAGGATCTCCTGTCATCTCACCTTGCTCCTGCCGAGAAAGTATCCATC
ATGGCTGATGCAATGCGGCGGCTGCATACGCTTGATCCGGCTACCTGCCC
ATTCGACCACCAAGCGAAACATCGCATCGAGCGAGCACGTACTCGGATGG
AAGCCGGTCTTGTCGATCAGGATGATCTGGACGAAGAGCATCAGGGGCTC
GCGCCAGCCGAACTGTTCGCCAGGCTCAAGGCGAGCATGCCCGACGGCGA
GGATCTCGTCGTGACCCATGGCGATGCCTGCTTGCCGAATATCATGGTGG
AAAATGGCCGCTTTTCTGGATTCATCGACTGTGGCCGGCTGGGTGTGGCG
GACCGCTATCAGGACATAGCGTTGGCTACCCGTGATATTGCTGAAGAGCT
TGGCGGCGAATGGGCTGACCGCTTCCTCGTGCTTTACGGTATCGCCGCTC
CCGATTCGCAGCGCATCGCCTTCTATCGCCTTCTTGACGAGTTCTTCTGA
GCGGGACTCTGGGGTTCGAAATGACCGACCAAGCGACGCCCAACCTGCCA
TCACGAGATTTCGATTCCACCGCCGCCTTCTATGAAAGGTTGGGCTTCGG
AATCGTTTTCCGGGACGCCGGCTGGATGATCCTCCAGCGCGGGGATCTCA
TGCTGGAGTTCTTCGCCCACCCTAGGGGGAGGCTAACTGAAACACGGAAG
GAGACAATACCGGAAGGAACCCGCGCTATGACGGCAATAAAAAGACAGAA
TAAAACGCACGGTGTTGGGTCGTTTGTTCATAAACGCGGGGTTCGGTCCC
AGGGCTGGCACTCTGTCGATACCCCACCGAGACCCCATTGGGGCCAATAC
GCCCGCGTTTCTTCCTTTTCCCCACCCCACCCCCCAAGTTCGGGTGAAGG
CCCAGGGCTCGCAGCCAACGTCGGGGCGGCAGGCCCTGCCATAGCCTCAG

GTTACTCATATATACTTTAGATTGATTTAAAACTTCATTTTTAATTTAAA

AGGATCTAGGTGAAGATCCTTTTTGATAATCTCATGACCAAAATCCCTTA

ACGTGAGTTTTCGTTCCACTGAGCGTCAGACCCCGTAGAAAAGATCAAAG

GATCTTCTTGAGATCCTTTTTTTCTGCGCGTAATCTGCTGCTTGCAAACA

AAAAAACCACCGCTACCAGCGGTGGTTTGTTTGCCGGATCAAGAGCTACC

AACTCTTTTTCCGAAGGTAACTGGCTTCAGCAGAGCGCAGATACCAAATA

CTGTCCTTCTAGTGTAGCCGTAGTTAGGCCACCACTTCAAGAACTCTGTA

GCACCGCCTACATACCTCGCTCTGCTAATCCTGTTACCAGTGGCTGCTGC

CAGTGGCGATAAGTCGTGTCTTACCGGGTTGGACTCAAGACGATAGTTAC

CGGATAAGGCGCAGCGGTCGGGCTGAACGGGGGGTTCGTGCACACAGCCC

AGCTTGGAGCGAACGACCTACACCGAACTGAGATACCTACAGCGTGAGCT

ATGAGAAAGCGCCACGCTTCCCGAAGGGAGAAAGGCGGACAGGTATCCGG

TAAGCGGCAGGGTCGGAACAGGAGAGCGCACGAGGGAGCTTCCAGGGGGA

AACGCCTGGTATCTTTATAGTCCTGTCGGGTTTCGCCACCTCTGACTTGA

GCGTCGATTTTTGTGATGCTCGTCAGGGGGCGGAGCCTATGGAAAAACG

CCAGCAACGCGGCCTTTTTACGGTTCCTGGCCTTTTGCTGGCCTTTTGCT

CACATGTTCTTTCCTGCGTTATCCCCTGATTCTGTGGATAACCGTATTAC

CGCCATGCAT

120. SEQ ID NO: 120
CCCTATCTCCCAGAACCGGCTATTAGCCTCTGCAGGCTTCCATGCACCTG

CGACTGAATTGGTTCCTTTAAAGC

121. SEQ ID NO: 121
GCGCTGTCTGTATGTCCGGTAGCAAGCACCAGACTTTAAGATATATGTCT

GCCGCACTCGAGATATCTAGACCCA

122. SEQ ID NO: 122
GTCTTCTTGTAGTTCTCCTGATTCTGGAGCCTGCCAGGATGGGGCCTCTG

AGGCGCGCCAGCATTACACGTCTTGAGCGATTGT

123. SEQ ID NO: 123
CTCCCTCATGATCTAGTCGATCATGGCGGGTAAGACACACCTGCTCTATC

AGGCGCGCCCACTTAACGGCTGACATGGGAATTA

124. SEQ ID NO: 124
AAACATATCACTGAATTATCTTATTGTTGTGACTTAAAGGCTAAATAAGT

CGACTGAATTGGTTCCTTTAAAGC

125. SEQ ID NO: 125
CAATTGTCCAATTAAAAGACATAGGCTAACAGACTGGATCTATAAACAGG

TCGAGATATCTAGACCCAGCTTTC

126. SEQ ID NO: 126
GAGCTGGCGGCAGCTGAGGGGAGTGCACTGGTGAGGAATCATGGGAGCTT

CTAGAGGGCGCGCCTACCTGTGACG

127. SEQ ID NO: 127
GATGGACTATAACATCCTGTTTCTCTTCTCATGAGAGATGTTAGCCAGAA

GGCGCGCCTTACGCCCCG

128. SEQ ID NO: 128
TTTTAGTAAGGATGTGTTGATGCAGTATTGGATGATTTGGAGAAAATATT

CGACTGAATTGGTTCCTTTAAAGC

129. SEQ ID NO: 129
ACTTGTACTCATTTCTGGAAGGTCCTGTCATGGGAAGAGAGTGTGCAAAG

TCGAGATATCTAGACCCAGCTTTC

130. SEQ ID NO: 130
GTCTGGATACCCTTGTACCCTGGGTGCAGAAGCAAAGATGAAGATTGGAA

GGCGCGCCAGCATTACACGTCTTGAGCGATTGT

131. SEQ ID NO: 131
GTTTTGAGTAGAAACGCAGTGCCAACAGGGCTATTCTCTATGATTTTCAC

GGCGCGCCCACTTAACGGCTGACATGGGAATTAG

132. SEQ ID NO: 132
TTAATCCAGCGGATCACAACTGGACAAACCGCTAAGAATAAATAACGAGT

CGACTGAATTGGTTCCTTTAAAGC

133. SEQ ID NO: 133
CCGCTAGTATTTAAGATGGAGATAACCAATTTATGTAGGTCAAAAGTTGC

TCGAGATATCTAGACCCAGCTTTC

134. SEQ ID NO: 134
CGCCGCGGCTGTTGACCCGGCTGGCCGGGAACAGGGAGAGATGCGGAGCC

GGCGCGCCTACCTGTGACG

135. SEQ ID NO: 135
CTCCTGAACTTTGGGGTTGCCTTGGTGACTGACTCTAAGGGTCAGGGCTG

GGCGCGCCTTACGCCCCG

136. SEQ ID NO: 136
GTCGCTCCAATGCACTTCCTGGAAAGAGAAAAATGAGGAGCCTAAAGGA

CGACTGAATTGGTTCCTTTAAAGCC

137. SEQ ID NO: 137
GTTTTGGCCACAGTACCCTGTACCCCGGGGGCCTTGGGTGAGTATGTGG

GCCGCACTCGAGATATCTAGACCCA

138. SEQ ID NO: 138
CCCGGGCGGGGGCGGCGGAGGCCGTGACGGGAGGCGGGGGTGATGGCGA

GGCGCGCCAGCATTACACGTCTTGAGCGATTGT

139. SEQ ID NO: 139
AGCTCTGTCTCACAGAAGTCTCCCGTGAAGCCAGGAGGGCAGCGGCAGCG

ACTAGTGGCGCGCCCACTTAACGGCTGACATGGGAATTA

140. SEQ ID NO: 140
GTTGTAAGGTCCCCCGGACTCATTCAGGCATGGCTCTCTGAACTATATAC

CGACTGAATTGGTTCCTTTAAAGC

141. SEQ ID NO: 141
CAGGTGAGGCCCAGAAAGCTGGAGGAACAGGGATATATAGATCTACAAAG

TCGAGATATCTAGACCCAGCTTTC

142. SEQ ID NO: 142
ACCTGAACCCTTTCCCTCTTCTTACCCAGGAGCTTTCACCATGACGCTTG

GGCGCGCCTACCTGTGACG

143. SEQ ID NO: 143
CCTGAGTTCAAATCTCAGCAACCACATGGTGGCTCACAACCACCCATAAT

GGCGCGCCTTACGCCCCG

144. SEQ ID NO: 144
ACTGTGAAGTATTCATCTTCTGGTAGTGAGTTTAAGTATGTGAATTTAAC

CGACTGAATTGGTTCCTTTAAAGC

145. SEQ ID NO: 145
TATTTTAGAATAAAGATCAAATTTGGCAAATATTTCATTTCCAAAATCTA

TCGAGATATCTAGACCCAGCTTTC

146. SEQ ID NO: 146
ACGGACATGTGATATGATGAGTGTGACTATGGGACACTGTATGGGCACAA

GGATCCGGCGCGCCTACCTGTGACG

147. SEQ ID NO: 147
AGCCATTCTAAGACATGTCATTTCTACTCAAATGGAGACTTCCCCATCTG

GAATTCGGCGCGCCTTACGCCCCG

148. SEQ ID NO: 148
CACCCAAATCGTAATTAGTTATGAAAATGGTTGTCAAGTCAGAGCTTTAAC

CGACTGAATTGGTTCCTTTAAAGC

149. SEQ ID NO: 149
GGCCCTCTTATGTTCCCTTGAAACTCTCCAAGGGCTTCCTGATGAAGAGC

CGCACTCGAGATATCTAGACCCA

150. SEQ ID NO: 150
TCTTCTTCTCCAGGTTCCTGGAAACTAGGACCATGAACTTGGCCGCAAAC

GGATCCCGGCGCGCCAGCATTACACGTCTTGAGCGATTGT

151. SEQ ID NO: 151
AGAAAAGAATTTTTAAGCCTATTGAGAACAAATAAAAGAATACAAGCTCT

AGAGGCGCGCCCACTTAACGGCTGACATGGGAATTAG

152. SEQ ID NO: 152
CACAACCCACAGAAGGTGATAGACCCATAATGATAGAGACTGGTCAAGAC

CGACTGAATTGGTTCCTTTAAAGC

153. SEQ ID NO: 153
CCACGGCAGAACACCATGGGGATGGAATCAACGCAAGCTTTCAGAGAACA

GCCGCACTCGAGATATCTAGACCCA

154. SEQ ID NO: 154
GCTCGCTGGCTCGCTGGCTCGCGGGAGGCCGGGCAGCAGCAGGGGCATGT

GGCGCGCCAGCATTACACGTCTTGAGCGATTGT

155. SEQ ID NO: 155
CCATCCCCCGGGCCCCTTCCCAGACAGGAATCAGCACAGACCGCAAGGCT

CGGCGCGCCCACTTAACGGCTGACATGGGAATTAG

156. SEQ ID NO: 156
CCTTCTCCTAACTAGTCAGCATACAGATGTAATTACTGCCTCCCTGATCC

CGACTGAATTGGTTCCTTTAAAGC

157. SEQ ID NO: 157
GCACCCTTGATGACTGGGGACAAGAGGATAGCATCCTCCTGATGCCTACA

GCCGCACTCGAGATATCTAGACCCA

158. SEQ ID NO: 158
CGGGGCCATTTGAAAGGAAACAATCCCTACGCAAAATCTTACACCTTGGT

AGGGCGCGCCAGCATTACACGTCTTGAGCGATTGT

159. SEQ ID NO: 159
GCTCGTTTAAATTGTATTTACAACCGCTGTCCATCAGGTGCCATGTGTTA

GGCGCGCCCACTTAACGGCTGACATGGGAATTAG

160. SEQ ID NO: 160
TTGCTGTATGGCTTTGTTGTAAAAAGGATCAGCTGCAGAAACAACCTAAG

CGACTGAATTGGTTCCTTTAAAGC

161. SEQ ID NO: 161
ATGAGGGCAGCCTGGTGCAGAGAGCTCTGCCCAAGGACTCTACCCGTGTG

GCCGCACTCGAGATATCTAGACCCA

162. SEQ ID NO: 162
CCCACATGCCCCAGGACCCCCAGCATCCGGGCAATGAGGAACATCACGG

GGCGCGCCAGCATTACACGTCTTGAGCGATTGT

163. SEQ ID NO: 163
ACCTGTGCCAGCAGCCTAGGAGGCAGGCAGGCTGCAGGCGGGGAGGGACC

TGGCGCGCCCACTTAACGGCTGACATGGGAATTAG

164. SEQ ID NO: 164
GCAATTTGGAAGTACACTTTTAGCCCCACTGCAGCAGACTACTGAACGAA

CGACTGAATTGGTTCCTTTAAAGC

165. SEQ ID NO: 165
CACTGGTTTTCCCCCTTAGTAAGATGCACAAGGTCTAGAAATTCAGATAG

GCCGCACTCGAGATATCTAGACCCA

166. SEQ ID NO: 166
TTCTCAGAAACAGGGGCTGGCGCCTATTCCAAATCCTACACCCTGGTGG

GGCGCGCCAGCATTACACGTCTTGAGCGATTGT

167. SEQ ID NO: 167
GAGGCGCAGAGGTCCCAGTGTGGAGCCCTTCTCCATTTGTCGGCCATCCT

AGGCGCGCCCACTTAACGGCTGACATGGGAATTAG

168. SEQ ID NO: 168
TGTCCTACCAAAGACGTGTTTCCAAGAGGCACTCCAGGGAGAGGCTGAGG

CGACTGAATTGGTTCCTTTAAAGC

169. SEQ ID NO: 169
CAGCAGTGTAATGAATACTTTCTGTAAAGATCAGACATATATGCTGGAAT

GCCGCACTCGAGATATCTAGACCCA

170. SEQ ID NO: 170
GTCTGGTGTGGAGCTGGAGCTTCAGCTGGACTGGCCCTGCCATGCAGAAG

GGGCGCGCCAGCATTACACGTCTTGAGCGATTGT

171. SEQ ID NO: 171
CCTCTGTGACCCTCACACCCACTGCTGCTCACAGTGCTGTGGACAGGGGC

GCGCCCACTTAACGGCTGACATGGGAATTA

172. SEQ ID NO: 172
CATGTCATTAATGTTGGCTCAAGAAACTACCCAGTCTGCCTTCGGTAGGC

CGACTGAATTGGTTCCTTTAAAGC

173. SEQ ID NO: 173
GAAAACTTAAAGACAAAACACACTGCCACCTCGCACCTAAGACATATTGA

GCCGCACTCGAGATATCTAGACCCA

174. SEQ ID NO: 174
GCATTGACACACTGTCTTATTTTTCAGGCACCATATTCACTACTAATTCT

GGGCGCGCCAGCATTACACGTCTTGAGCGATTGT

175. SEQ ID NO: 175
TGTCTGAGCTGAGAGATGGGCGAGCAGGCACGGAGTCAGCATCAGGTCTA

GGCGCGCCCACTTAACGGCTGACATGGGAATTA

176. SEQ ID NO: 176
GTGCACATGCCCAGCTGAGCAACCTGATTCATTATAATACCACTGGCTCA

CGACTGAATTGGTTCCTTTAAAGC

177. SEQ ID NO: 177
GAGCATCATCTTGAGAGGCCTCTGCAGTAAGGGAGTCAGCAGATAGAGAG

GCCGCACTCGAGATATCTAGACCCA

178. SEQ ID NO: 178
AATTGTCTCATTTTCGCGCTGATTTGCTTAACTGGTGGGACCATGCCAGA

AAGGCGCGCCAGCATTACACGTCTTGAGCGATTGT

179. SEQ ID NO: 179
CATTTAAAGACCAGGAACAGGCCCTGAAATGGTAGTTTTAAAATGAAGCT

TGGCGCGCCCACTTAACGGCTGACATGGGAATTA

180. SEQ ID NO: 180
CAATGGCAGGCCAGCCAAGTCCAAGTCTCAAGAGGCCCTCTCTGCTTCAG

CGACTGAATTGGTTCCTTTAAAGC

181. SEQ ID NO: 181
GTTGCATGGGCATGGGGTATTGGCCCTGTGGGTAAGAGTGTTTGTTGTAC

GCCGCACTCGAGATATCTAGACCCA

182. SEQ ID NO: 182
GAATGCAAACGCCGCCAGGCGCTTCTTCTAGTCGGGCAAGATGCAGCCGA

GGCGCGCCAGCATTACACGTCTTGAGCGATTGT

183. SEQ ID NO: 183
CTGAATGCAGAAAGCTGGTGGGAGCGCGCTGACTGCGGCTCACATTCCCT

GGCGCGCCCACTTAACGGCTGACATGGGAATTA

184. SEQ ID NO: 184
CACATTTTCTGGTAACATAGAGAAAGCTACTGTAGAAGACACCAGAATTT

CGACTGAATTGGTTCCTTTAAAGC

185. SEQ ID NO: 185
GAATGGAAAGATATGTTTACAGGGTGTGGAATTTTGGAAATATGGTGGGA

GCCGCACTCGAGATATCTAGACCCA

186. SEQ ID NO: 186
CAGGCCACGAAGACAAGAAGGACTGTGAACGGGAAGCGATCTTACAATGA

GGCGCGCCAGCATTACACGTCTTGAGCGATTGT

187. SEQ ID NO: 187
CTCAAGAGAGAAAAACTAACAATCAATTCCAAAGAAATCAAAACAAACTT

GGCGCGCCCACTTAACGGCTGACATGGGAATTA

188. SEQ ID NO: 188
ATGAACATATCTGACGTTACTCATAGAACAACATGGCTTCAGAGTTTAGA

CGACTGAATTGGTTCCTTTAAAGC

189. SEQ ID NO: 189
TAGAATGAGGTGCAGTGAATTTGTATTTCTTAACTGAATTTAATTTTAAG

GCCGCACTCGAGATATCTAGACCCA

190. SEQ ID NO: 190
CCTTTCTAGAATAAGAGCTGGAATCCTAATACACACCAGAATGAATTATT

GGCGCGCCAGCATTACACGTCTTGAGCGATTGT

191. SEQ ID NO: 191
CACTTCCACATCTTTACAAATTCATCTATTGTAACTTTTTCAGAAAACAAG

TGGCGCGCCCACTTAACGGCTGACATGGGAATTA

192. SEQ ID NO: 192
ACCTGCCACAGACAGTCGAGAAGAGCCTGTACAAGGAGTGAAACAGGTGG

CGACTGAATTGGTTCCTTTAAAGC

193. SEQ ID NO: 193
TCCAATGCCTGTTAGTTCTGAGTTCTTAAGATTCAAAGACATGAACAATG

GCCGCACTCGAGATATCTAGACCCA

194. SEQ ID NO: 194
CATTCTACTTGACTTCTGAAACTCCTGCAAGCCCATGTGGACTACGGGTA

GGCGCGCCAGCATTACACGTCTTGAGCGATTGT

195. SEQ ID NO: 195
CATCTCAACACCAGAGACCCTGAGAATTTCTCTTTCTCCTGGGCACATCT

TGGCGCGCCCACTTAACGGCTGACATGGGAATTA

196. SEQ ID NO: 196
ATTCATCCCCTTGCTTCTTCCACTTGACACTGCAGGCTTATGTGTGTCCT

CGACTGAATTGGTTCCTTTAAAGC

197. SEQ ID NO: 197
GACAGGAAAGGAATGCTGATTCACAGTAAGAACCTACTGTGTGCTGTGAG

GCCGCACTCGAGATATCTAGACCCA

198. SEQ ID NO: 198
CTCTGGTCCATGCTCAGGGGCTTGGCCAGCGCCATCAAGCATGAGGCCAC

GGCGCGCCAGCATTACACGTCTTGAGCGATTGT

199. SEQ ID NO: 199
GAACCGGGACTACCAGTGGGTGTCCCCAGAGTCGGGGCTGGACAGTGGGC

GCGCCCACTTAACGGCTGACATGGGAATTA

200. SEQ ID NO: 200
AGTCTCCCTGCTGCTGCAATGCCCTCCATCTGCCCACACTGCTCACAGGA

CGACTGAATTGGTTCCTTTAAAGC

201. SEQ ID NO: 201
GTCTGTCTCCTGCCCACATGTCCCTCCCTTCTCTTTGAGTCCCTGTGACT

GGCCGCACTCGAGATATCTAGACCCA

202. SEQ ID NO: 202
CCTGGGGCCAGTGAACAAGAGCCCTGGCTGGATTACAAACATGTGGGGCC

GGCGCGCCAGCATTACACGTCTTGAGCGATTGT

203. SEQ ID NO: 203
ACATCCAGGGATAGCTCTCTGTATGGTGCTCCTTAGGGCCCAGGGCTTCT

CGGCGCGCCCACTTAACGGCTGACATGGGAATTA

204. SEQ ID NO: 204
CCCTATCTCCCAGAACCGGCTATTAGCCTCTGCAGGCTTCCATGCACCTG

CGACTGAATTGGTTCCTTTAAAGC

205. SEQ ID NO: 205
GCGCTGTCTGTATGTCCGGTAGCAAGCACCAGACTTTAAGATATATGTCT

GCCGCACTCGAGATATCTAGACCCA

206. SEQ ID NO: 206
GTCTTCTTGTAGTTCTCCTGATTCTGGAGCCTGCCAGGATGGGGCCTCTG

AGGCGCGCCAGCATTACACGTCTTGAGCGATTGT

207. SEQ ID NO: 207
CTCCCTCATGATCTAGTCGATCATGGCGGGTAAGACACACCTGCTCTATC

AGGCGCGCCCACTTAACGGCTGACATGGGAATTA

208. SEQ ID NO: 208
TACAGCCTATTGGCTAACTGTAAAACACAGACACAAGGCCAGTGTGATAC

CGACTGAATTGGTTCCTTTAAAGC

209. SEQ ID NO: 209
ATACTCTGTCTTCACCTTGCTTCTACGACACCTGCTGGAGCCTGCCCTTG

GCCGCACTCGAGATATCTAGACCCA

210. SEQ ID NO: 210
GGTTAGAAGGAGCAGTAGCAGCAGCAGCAAGAGAAGATGCTGAGGATGCG

ACGCGTAGCATTACACGTCTTGAGCGATTGT

211. SEQ ID NO: 211
CTGAGTGATCAGCCCTCTCTGGGGTATGTAAACACATCTGGGATCTATCT

TACGCGTCACTTAACGGCTGACATGGGAATTA

212. SEQ ID NO: 212
AGACAGAGACCTCTAGAGGTACAGTAAGATTCATCTGAATCGCCAGCATG

CGACTGAATTGGTTCCTTTAAAGC

213. SEQ ID NO: 213
ACGAGAAATAGATCCACTCATTTTACTGATAAAACTGGTGAAATACTCAG

GCCGCACTCGAGATATCTAGACCCA

214. SEQ ID NO: 214
GGCTGGCTGGCTACAGGGGAGCTGCTTCCTTTTCCTTTTGGAAATGATTG

GGCGCGCCAGCATTACACGTCTTGAGCGATTGT

215. SEQ ID NO: 215
GCTAACACCTGAAAATACACAGTGCACCAGAAGAGATGCAGGGCCGGGCT

AGGCGCGCCCACTTAACGGCTGACATGGGAATTAG

216. SEQ ID NO: 216
ACCATAGGATTAACTCAGCAAAGACATGCAAACTAAACCTGTGAGGAATT

CGACTGAATTGGTTCCTTTAAAGC

217. SEQ ID NO: 217
GTATTTGGCTACGCGTTTTATGCCAAGAAGATGCCACTGGATTAGTCTAT

GCCGCACTCGAGATATCTAGACCCA

218. SEQ ID NO: 218
AGTCCGGCTGCTCCTGTTCCCACCCCACCGGTCTGGGATGTACCTTTCCA

GGCGCGCCAGCATTACACGTCTTGAGCGATTGT

219. SEQ ID NO: 219
TGGAGTTAAGTGGAGGGGAGCCCCCGTCCCGGGCCACAATGGTCACATTG

TGGCGCGCCCACTTAACGGCTGACATGGGAATTAG

220. SEQ ID NO: 220
GCTATGAGGCTGTTTTCTGGAAATCCAGATGCTTAGCTCTTTGCTACTCA

CGACTGAATTGGTTCCTTTAAAGC

221. SEQ ID NO: 221
TGTTGCTAGGGGCTGTAGAAAGAAATCAACACTTAGGAGTACTGAAGTCT

GCCGCACTCGAGATATCTAGACCCA

222. SEQ ID NO: 222
CTAACTCGCCCTGAGAAGGGAATCTAGCAACTGACCAATGCACCAAATGA

GGCGCGCCAGCATTACACGTCTTGAGCGATTGT

223. SEQ ID NO: 223
GCCTCTGAGCATCAGCATCTGGCTTGACCAGGCCCTGTAGTGTCTGATCT

TGGCGCGCCCACTTAACGGCTGACATGGGAATTAG

224. SEQ ID NO: 224
CTAGACCTCACAAGTGGCTTTATGTAGTTCCTTAGGACTTCCAGCTGCTC

CGACTGAATTGGTTCCTTTAAAGC

225. SEQ ID NO: 225
TCTTCCCAGATCTTCTAGAGCTGCTTACTATCCCATGGGACACTCTGGAG

GCCGCACTCGAGATATCTAGACCCA

226. SEQ ID NO: 226
TCGGAGGGGTGTGGAGAGGCGAGGCAAGGCAGAGCCCCGCGCAGCCATGG

AACGCGTAGCATTACACGTCTTGAGCGATTGT

227. SEQ ID NO: 227
CATATCTTACTCACTCAAAACACAGAAGAAAAGAAAGAAAACTTGGCTCT

ACGCGTCACTTAACGGCTGACATGGGAATTAG

228. SEQ ID NO: 228
ATTTGAATTTCACGTTCTTCTTTCTCACTTCTGGCAGAGGTGATAATGAG

CGACTGAATTGGTTCCTTTAAAGC

229. SEQ ID NO: 229
GCACAGTTTAAAAATTATAGAATTGGTACAAAACAGTTTGATAGGCAGTC

GCCGCACTCGAGATATCTAGACCCA

230. SEQ ID NO: 230
CCACCCTCCCTTCTGGAGCGCTCTGACTGCAGCCTCCCAGGGAATGCGCG

GGCGCGCCAGCATTACACGTCTTGAGCGATTGT

231. SEQ ID NO: 231
GACTACCTATGGCAGTTACAATGTCCCTCCATGTTATTCCACAATGGCAT

AGGCGCGCCCACTTAACGGCTGACATGGGAATTAG

232. SEQ ID NO: 232
TAGTGAAACAGGGGCAATGGTG

233. SEQ ID NO: 233
CATGGATGCAGAGCAGTGTTTG

234. SEQ ID NO: 234
GCCTTCTTGACGAGTTCTTCTGAGG

235. SEQ ID NO: 235
TACCTTCTTGGGCAGGAAGCAG

236. SEQ ID NO: 236
TTTCTTTCCAGGCATTCCCTCA

237. SEQ ID NO: 237
TTCTTGCGAACCTCATCACTCG

238. SEQ ID NO: 238
CCCTAGAAAGATAATCATATTGTGACGTACGTTAAAGATAATCATGCGTA

AAATTGACGCATGTGTTTTATCGGTCTGTATATCGAGGTTTATTTATTAA

TTTGAATAGATATTAAGTTTTATTATATTTACACTTACATACTAATAATA

AATTCAACAAACAATTTATTTATGTTTATTTATTTATTAAAAAAAAACAA

AAACTCAAAATTTCTTCTATAAAGTAACAAACTTTTAAACATTCTCTCTT

TTACAAAAAATAAACTTATTTTGTACTTTAAAAACAGTCATGTTGTATTA

TAAAATAAGTAATTAGCTTAACTTATACATAATAGAAACAAATTATACTT

ATTAGTCAGTCAGAAACAACTTTGGCACATATCAATATTATGCTCTCGAC

AAATAACTTTTTTGCATTTTTTGCACGATGCATTTGCCTTTCGCCTTATT

TTAGAGGGGCAGTAAGTACAGTAAGTACGTTTTTTCATTACTGGCTCTTC

AGTACTGTCATCTGATGTACCAGGCACTTCATTTGGCAAAATATTAGAGA

TATTATCGCGCAAATATCTCTTCAAAGTAGGAGCTTCTAAACGCTTACGC

ATAAACGATGACGTCAGGCTCATGTAAAGGTTTCTCATAAATTTTTTGCG

ACTTTGAACCTTTTCTCCCTTGCTACTGACATTATGGCTGTATATAATAA

AAGAATTTATGCAGGCAATGTTTATCATTCCGTACAATAATGCCATAGGC

CACCTATTCGTCTTCCTACTGCAGGTCATCACAGAACACATTTGGTCTAG

CGTGTCCACTCCGCCTTTAGTTTGATTATAATACATAACCATTTGCGGTT

TACCGGTACTTTCGTTGATAGAAGCATCCTCATCACAAGATGATAATAAG

TATACCATCTTAGCTGGCTTCGGTTTATATGAGACGAGAGTAAGGGGTCC

GTCAAAACAAAACATCGATGTTCCCACTGGCCTGGAGCGACTGTT

239. SEQ ID NO: 239
GAGATCTGACAATGTTCAGTGCAGAGACTCGGCTACGCCTCGTGGACTTT

GAAGTTGACCAACAATGTTTATTCTTACCTCTAATAGTCCTCTGTGGCAA

GGTCAAGATTCTGTTAGAAGCCAATGAAGAACCTGGTTGTTCAATAACAT

TTTGTTCGTCTAATATTTCACTACCGCTTGACGTTGGCTGCACTTCATGT

ACCTCATCTATAAACGCTTCTTCTGTATCGCTCTGGACGTCATCTTCACT

TACGTGATCTGATATTTCACTGTCAGAATCCTCACCAACAAGCTCGTCAT

CGCTTTGCAGAAGAGCAGAGAGGATATGCTCATCGTCTAAAGAACTACCC

ATTTTATTATATATTAGTCACGATATCTATAACAAGAAAATATATATATA

ATAAGTTATCACGTAAGTAGAACATGAAATAACAATATAATTATCGTATG

AGTTAAATCTTAAAAGTCACGTAAAAGATAATCATGCGTCATTTTGACTC

ACGCGGTCGTTATAGTTCAAAATCAGTGACACTTACCGCATTGACAAGCA

CGCCTCACGGGAGCTCCAAGCGGCGACTGAGATGTCCTAAATGCACAGCG

ACGGATTCGCGCTATTTAGAAAGAGAGCAATATTTCAAGAATGCATGC

GTCAATTTTACGCAGACTATCTTTCTAGGG

What is claimed is:

1. A gene-trap vector, comprising the formula:

3'TR-lox-SA-R[1]—X—R[2]-lox-X-5'TR wherein 3'TR and 5'TR are piggyBac 3' and 5' transposon terminal sequences comprising 3' and 5' inverted terminal repeats (ITR), respectively;
wherein the lox sites are in the same orientation;
wherein SA is a splice acceptor;
wherein R[1] is a first reporter sequence linked to SA; and
wherein R[2] is a second reporter sequence functionally linked to an expression control sequence, and wherein X is a recombination site, wherein X is FRT, attB or attP.

2. A gene-trap vector, comprising the formula:

3'TR-lox-SA-R[1]—X—R[2]—X-lox-5'TR wherein 3'TR and 5'TR are piggyBac 3' and 5' transposon terminal sequences comprising 3' and 5' inverted terminal repeats (ITR), respectively;
wherein the lox sites are in the same orientation;
wherein SA is a splice acceptor;
wherein R[1] is a first reporter sequence linked to SA; and
wherein R[2] is a second reporter sequence functionally linked to an expression control sequence, and wherein X is a recombination site, wherein X is FRT, attB or attP.

3. A gene-trap vector comprising the nucleic acid sequence set forth in SEQ ID NO:105, SEQ ID NO:106, or SEQ ID NO:107.

\* \* \* \* \*

UNITED STATES PATENT AND TRADEMARK OFFICE
CERTIFICATE OF CORRECTION

PATENT NO. : 8,546,135 B2
APPLICATION NO. : 12/522075
DATED : October 1, 2013
INVENTOR(S) : Wu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 698 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 239

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 1
atcttggtgt gacagcgata cg                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 2
ctcagttcaa gcgaaaggga tt                                              22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 3
agatgaactt cagggtcagc ttgc                                            24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 4
tttccagtct cctctccagg agttc                                           25

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 5
tagttggaaa ggaagcgaaa gttcc                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 6
ttgtatgtct tggacagagc cacat                                              25

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 7
ttgtagtgcg tgagaggtga ag                                                 22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 8
cattggtcaa gtccagttcc ag                                                 22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 9
caaacctcca ctctccattg ag                                                 22

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 10
gccataacag tgtttgagaa gtgagg                                             26
```

```
<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 11
aggggtaacc acatagctct ggaag                                               25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 12
caggcacacc ttcagtcctg tagtc                                               25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 13
cagaaagagt tggagtcctt gtgga                                               25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 14
gacaacagcc tcttcaactg atgga                                               25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 15
acgaagttat gaattcgccc ttgtt                                               25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 16
aggctgaata acgtgcacag ctaag                                               25

<210> SEQ ID NO 17
<211> LENGTH: 25
```

```
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 17
tgcagattgg ttcaatggag tcttt                                           25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 18
aggctgaata acgtgcacag ctaag                                           25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 19
tgcagattgg ttcaatggag tcttt                                           25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 20
ccctttccta gattcccctc aaaaa                                           25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 21
ggagcctgct aacaaccaaa ttgac                                           25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 22
gagggctcat gtcataggag aaagg                                           25

<210> SEQ ID NO 23
<211> LENGTH: 20
<212> TYPE: DNA
<213> ORGANISM: Artificial Sequence
```

```
<220> FEATURE:
<223> OTHER INFORMATION: Description of Artificial Sequence: note =
      Synthetic Construct

<400> SEQUENCE: 23
cactgcacgc cccaggtcag                                                    20

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 24
aagcagaccc aggtttcctt tctcc                                              25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 25
ctcttggtag ccacacatac ccagt                                              25

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 26
aagcactgca ggccgtagcc                                                    20

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 27
ggatatttcc tgtcttgttc ccaggt                                             26

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 28
accaaatgga aacaagccac ttagc                                              25

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: note =
```

```
                                    Synthetic Construct

<400> SEQUENCE: 29
ggctgggaag cttctccttt gc                                            22

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 30
aatggaaaca agccacttag ccagt                                         25

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 31
ggctgggaag cttctccttt gc                                            22

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 32
cgaagttatg aattcgccct tgtta                                         25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 33
gcttgagaga gggagtgaca aagtg                                         25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 34
tcccttacac aatgtggcag aagtt                                         25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct
```

```
<400> SEQUENCE: 35
gagcacgtac ccagatatgg aattg                                              25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 36
gctggtgtgt ctttctctgg agcta                                              25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 37
ggatgttaaa gctgacgaca catgg                                              25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 38
agctctggat gaagaagtcg ctgat                                              25

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 39
ccactgctcc ctgagatcga at                                                 22

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 40
ctggaagaca cttggatcac catct                                              25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 41
```

```
cagttatctg ctggcaggta ccact                                          25
```

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 42

```
tgccagagga gtcaaaccac ataat                                          25
```

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 43

```
cccctgaac ctgaaacata aaatg                                           25
```

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 44

```
tgcagattgg ttcaatggag tcttt                                          25
```

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 45

```
aggctgaata acgtgcacag ctaag                                          25
```

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 46

```
ccctttccta gattcccctc aaaaa                                          25
```

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 47

```
ccctaacacc accactaccc aaaat                                          25
```

-continued

```
<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 48
acaaccacta cctgagcacc cagtc                                         25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 49
aaagctgcga cctacctctg gaaac                                         25

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 50
aaggacttcc ccgagtacca cttc                                          24

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 51
agccacagct caaatttgga cttac                                         25

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 52
ccactgctcc ctgagatcga at                                            22

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 53
ctggaagaca cttggatcac catct                                         25

<210> SEQ ID NO 54
```

```
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 54
cagttatctg ctggcaggta ccact                                           25

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 55
tgccagtgtc tgaaggagat gc                                              22

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 56
ttaagagagg aggaatttat tctg                                            24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 57
ttaagaaggc tgtctgtgct gacc                                            24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 58
ttaatggtgt tatttgattt tctg                                            24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 59
ttaaaatgaa ctctagaacc tcct                                            24

<210> SEQ ID NO 60
<211> LENGTH: 24
<212> TYPE: DNA
```

```
<213> ORGANISM: Artificial Sequence
<220> FEATURE:
<223> OTHER INFORMATION: Description of Artificial Sequence:  note =
      Synthetic Construct

<400> SEQUENCE: 60
ttaaaagatt tatttatttt attt                                          24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 61
ttaaaggcgt gcgccaccac aacc                                          24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 62
ttaaatgtat ttacttactt attt                                          24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 63
ttaaagaata aaagatggtg tctt                                          24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 64
ttaaacaagg ataaaagcaa tcta                                          24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 65
ttaacatata gtaactgtgt gtat                                          24

<210> SEQ ID NO 66
<211> LENGTH: 24
<212> TYPE: DNA
<213> ORGANISM: Artificial Sequence
<220> FEATURE:
```

```
<223> OTHER INFORMATION: Description of Artificial Sequence:  note =
      Synthetic Construct

<400> SEQUENCE: 66
ttaaggagac tagtgaaagt gaac                                            24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 67
ttaataaatt aatcagtcac ttaa                                            24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 68
ttaactagat cctctacata tttg                                            24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 69
ttaagtaata caggaaaaga ggaa                                            24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 70
ttaaatctgg gtctagattt tcgg                                            24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 71
ttaaggtgtc tctatgtagt cttg                                            24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct
```

```
<400> SEQUENCE: 72
ttaagcaacc tgctgaatca aacc                                              24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 73
ttaaggacca ttcacaaaat atgg                                              24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 74
ttaagctgct tgctggatct tttg                                              24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 75
ttaaagaaga gtgctgcttc tatg                                              24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 76
ttaaataaaa ccagttaaaa ataa                                              24

<210> SEQ ID NO 77
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 77
ctagatcata tccaagtttt ttatcctctg aagccattaa aattaagttg cgactgaatt       60
ggttccttta aagcc                                                        75

<210> SEQ ID NO 78
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct
```

```
<400> SEQUENCE: 78
gaccaaccaa cttctcctgg gcatggggcc tgccctggag tgtggtttac gccgcactcg    60
agatatctag accca                                                    75

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 79
taaactgcca ggcatcaaac taagc                                         25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 80
agtcagcccc atacgatata agttg                                         25

<210> SEQ ID NO 81
<211> LENGTH: 88
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 81
gagcatggtc ccgggtcgcc gcaactggag cgtggaggcc gaaagggagg atggtggcgc    60
gccagcatta cacgtcttga gcgattgt                                      88

<210> SEQ ID NO 82
<211> LENGTH: 83
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 82
tagtaactat ctccttgcca gaggagtcaa accacataat atgtgcttac ggcgcgccca    60
cttaacggct gacatgggaa tta                                           83

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 83
atgccgctgg cgattcaggt tc                                            22

<210> SEQ ID NO 84
<211> LENGTH: 22
<212> TYPE: DNA
```

```
<213> ORGANISM: Artificial Sequence
<220> FEATURE:
<223> OTHER INFORMATION: Description of Artificial Sequence:  note =
      Synthetic Construct

<400> SEQUENCE: 84
gccgatcaac gtctcatttt cg                                                  22

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 85
cctcgatata cagaccgata aaacacatgc                                          30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 86
agtcagtcag aaacaacttt ggcacatatc                                          30

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 87
gtcagtcaga acaactttg gcacatatc                                            29

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 88
cagatcgata aaacacatgc gtcaattt                                            28

<210> SEQ ID NO 89
<211> LENGTH: 31
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 89
taacaaaact tttaaacatt ctctctttta c                                        31

<210> SEQ ID NO 90
<211> LENGTH: 34
<212> TYPE: DNA
<213> ORGANISM: Artificial Sequence
<220> FEATURE:
```

<223> OTHER INFORMATION: Description of Artificial Sequence: note = Synthetic Construct

<400> SEQUENCE: 90
ataacttcgt ataatgtatg ctatacgaag ttat                              34

<210> SEQ ID NO 91
<211> LENGTH: 34
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 91
ataacttcgt atagcataca ttatacgaag ttat                              34

<210> SEQ ID NO 92
<211> LENGTH: 1785
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 92
atgggtagtt ctttagacga tgagcatatc ctctctgctc ttctgcaaag cgatgacgag    60
cttgttggtg aggattctga cagtgaaata tcagatcacg taagtgaaga tgacgtccag   120
agcgatacag aagaagcgtt tatagatgag gtacatgaag tgcagccaac gtcaagcggt   180
agtgaaatat tagacgaaca aaatgttatt gaacaaccag gttcttcatt ggcttctaac   240
agaatcttga ccttgccaca gaggactatt agaggtaaga ataaacattg ttggtcaact   300
tcaaagtcca cgaggcgtag ccgagtctct gcactgaaca ttgtcagatc tcaaagaggt   360
ccgacgcgta tgtgccgcaa tatatatgac ccacttttat gcttcaaact atttttact    420 gatgagataa tttcggaaat tgtaaaatgg acaaatgctg agatatcatt gaaacgtcgg   480
gaatctatga caggtgctac atttcgtgac acgaatgaag atgaaatcta tgctttcttt   540
ggtattctgg taatgacagc agtgagaaaa gataaccaca tgtccacaga tgacctcttt   600
gatcgatctt tgtcaatggt gtacgtctct gtaatgagtc gtgatcgttt tgattttttg   660
atacgatgtc ttagaatgga tgacaaaagt atacggccca cacttcgaga aaacgatgta   720
tttactcctg ttagaaaaat atgggatctc tttatccatc agtgcataca aaattacact   780
ccaggggctc atttgaccat agatgaacag ttacttggtt ttagaggacg tgtgtccgtttt   840 aggatgtata tcccaaacaa gccaagtaag tatggaataa aaatcctcat gatgtgtgac   900
agtggtacga agtatatgat aaatggaatg ccttatttgg gaagaggaac acagaccaac   960
ggagtaccac tcggtgaata ctacgtgaag gagttatcaa agcctgtgca cggtagttgt  1020
cgtaatatta cgtgtgacaa ttggttcacc tcaatccctt tggcaaaaaa cttactacaa  1080
gaaccgtata agttaaccat tgtgggaacc gtgcgatcaa acaaacgcga gataccggaa  1140
gtactgaaaa acagtcgctc caggccagtg ggaacatcga tgttttgttt tgacggaccc  1200
cttactctcg tctcatataa accgaagcca gctaagatgg tatacttatt atcatcttgt  1260
gatgaggatg cttctatcaa cgaaagtacc ggtaaaccgc aaatggttat gtattataat  1320
caaactaaag gcggagtgga cacgctagac caaatgtgtt ctgtgatgac ctgcagtagg  1380
aagacgaata ggtggcctat ggcattattg tacggaatga taaacattgc ctgcataaat  1440
tcttttatta tatacagcca taatgtcagt agcaagggag aaaaggttca agtcgcaaa   1500

```
aaatttatga gaaaccttta catgagcctg acgtcatcgt ttatgcgtaa gcgtttagaa    1560
gctcctactt tgaagagata tttgcgcgat aatatctcta atattttgcc aaatgaagtg    1620
cctggtacat cagatgacag tactgaagag ccagtaatga aaaaacgtac ttactgtact    1680
tactgcccct ctaaaataag gcgaaaggca aatgcatcgt gcaaaaaatg caaaaaagtt    1740
atttgtcgag agcataatat tgatatgtgc caaagttgtt tctaa                   1785
```

<210> SEQ ID NO 93
<211> LENGTH: 1785
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 93

```
atgggcagca gcctggacga cgagcacatc ctgagcgccc tgctgcagag cgacgacgag      60
ctggtgggcg aggacagcga cagcgagatc agcgaccacg tgagcgagga cgacgtgcag     120
agcgacaccg aggaggcctt catcgacgag gtgcacgagg tgcagcccac cagcagcggc     180
agcgagatcc tggacgagca gaacgtgatc gagcagcccg gcagcagcct ggccagcaac     240
aggatcctga ccctgcccca gaggaccatc aggggcaaga caagcactg ctggagcacc     300 agcaagagca ccaggaggag cagggtgagc gccctgaaca tcgtgaggag ccagaggggc     360
cccaccagga tgtgcaggaa catctacgac ccctgctgt gcttcaagct gttcttcacc     420
gacgagatca tcagcgagat cgtgaagtgg accaacgccg agatcagcct gaagaggagg     480
gagagcatga ccggcgccac cttcaggac accaacgagg acgagatcta cgccttcttc     540
ggcatcctgg tgatgaccgc cgtgaggaag acaaccaca tgagcaccga cgacctgttc     600
gacaggagcc tgagcatggt gtacgtgagc gtgatgagca gggacaggtt cgacttcctg     660
atcaggtgcc tgaggatgga cgacaagagc atcaggccca ccctgaggga gaacgacgtg     720
ttcacccccg tgaggaagat ctgggacctg ttcatccacc agtgcatcca gaactacacc     780
cccggcgccc acctgaccat cgacgagcag ctgctgggct tcaggggcag gtgcccttc      840 aggatgtaca tccccaacaa gcccagcaag tacggcatca agatcctgat gatgtgcgac     900
agcggcacca agtacatgat caacggcatg ccctacctgg caggggcac ccagaccaac     960 ggcgtgcccc tgggcgagta ctacgtgaag gagctgagca agcccgtgca cggcagctgc    1020
aggaacatca cctgcgacaa ctggttcacc agcatccccc tggccaagaa cctgctgcag    1080
gagccctaca gctgaccat cgtgggcacc gtgaggagca acaagaggga gatccccgag    1140
gtgctgaaga acagcaggag caggcccgtg ggcaccagca tgttctgctt cgacggcccc    1200 ctgacctgg tgagctacaa gcccaagccc gccaagatgg tgtacctgct gagcagctgc     1260
gacgaggacg ccagcatcaa cgagagcacc ggcaagcccc agatggtgat gtactacaac    1320
cagaccaagg gcggcgtgga caccctggac cagatgtgca gcgtgatgac ctgcagcagg    1380
aagaccaaca ggtggcccat ggccctgctg tacggcatga tcaacatcgc ctgcatcaac    1440
agcttcatca tctacagcca caacgtgagc agcaagggcg agaaggtgca gagcaggaag    1500
aagttcatga ggaacctgta catgagcctg accagcagct tcatgaggaa gaggctggag    1560 gccccaccc tgaagaggta cctgagggac aacatcagca acatcctgcc caacgaggtg    1620
cccggcacca gcgacgacag caccgaggag cccgtgatga agaagaggac ctactgcacc    1680
tactgcccca gcaagatcag gaggaaggcc aacgccagct gcaagaagtg caagaaggtg    1740
```

-continued atctgcaggg agcacaacat cgacatgtgc cagagctgct tctaa     1785

<210> SEQ ID NO 94
<211> LENGTH: 104
<212> TYPE: DNA
<213> ORGANISM: Artificial Sequence
<220> FEATURE:
<223> OTHER INFORMATION: Description of Artificial Sequence: note =
    Synthetic Construct

<400> SEQUENCE: 94
tagggcgcag tagtccaggg tttccttgat gatgtcatac ttatcctgtc ccttttttt     60 ccacagctcg cggttgagga caaactcttc gcggtctttc cagt     104

<210> SEQ ID NO 95
<211> LENGTH: 63
<212> TYPE: DNA
<213> ORGANISM: Artificial Sequence
<220> FEATURE:
<223> OTHER INFORMATION: Description of Artificial Sequence: note =
    Synthetic Construct

<400> SEQUENCE: 95
ccctagaaag ataatcatat tgtgacgtac gttaaagata atcatgcgta aaattgacgc     60
atg     63

<210> SEQ ID NO 96
<211> LENGTH: 35
<212> TYPE: DNA
<213> ORGANISM: Artificial Sequence
<220> FEATURE:
<223> OTHER INFORMATION: Description of Artificial Sequence: note =
    Synthetic Construct

<400> SEQUENCE: 96
catgcgtcaa ttttacgcag actatctttc taggg     35

<210> SEQ ID NO 97
<211> LENGTH: 34
<212> TYPE: DNA
<213> ORGANISM: Artificial Sequence
<220> FEATURE:
<223> OTHER INFORMATION: Description of Artificial Sequence: note =
    Synthetic Construct

<400> SEQUENCE: 97
gaagttccta ttctctagaa agtataggaa cttc     34

<210> SEQ ID NO 98
<211> LENGTH: 34
<212> TYPE: DNA
<213> ORGANISM: Artificial Sequence
<220> FEATURE:
<223> OTHER INFORMATION: Description of Artificial Sequence: note =
    Synthetic Construct

<400> SEQUENCE: 98
gaagttccta tactttctag agaataggaa cttc     34

<210> SEQ ID NO 99
<211> LENGTH: 3057
<212> TYPE: DNA
<213> ORGANISM: Artificial Sequence
<220> FEATURE:
<223> OTHER INFORMATION: Description of Artificial Sequence: note =
    Synthetic Construct

<400> SEQUENCE: 99

```
atggaccctg ttgtgctgca aaggagagac tgggagaacc ctggagtgac ccagctcaac    60
agactggctg cccacccctcc ctttgcctct tggaggaact ctgaggaagc caggacagac   120
aggcccagcc agcagctcag gtctctcaat ggagagtgga ggtttgcctg gttccctgcc   180
cctgaagctg tgcctgagtc ttggctggag tgtgacctcc cagaggctga cactgttgtg   240
gtgccaagca actggcagat gcatggctat gatgccccca tctacaccaa tgtcacctac   300
cccatcactg tgaacccccc ttttgtgccc actgagaacc ccactggctg ctacagcctg   360
accttcaatg ttgatgagag ctggctgcaa gaaggccaga ccaggatcat ctttgatgga   420
gtcaactctg ccttccacct ctggtgcaat ggcaggtggg ttggctatgg ccaagacagc   480
aggctgccct ctgagtttga cctctctgcc ttcctcagag ctggagagaa caggctggct   540
gtcatggtgc tcaggtggtc tgatggcagc tacctggaag accaagacat gtggaggatg   600
tctggcatct tcagggatgt gagcctgctg cacaagccca ccacccagat ttctgacttc   660
catgttgcca ccaggttcaa tgatgacttc agcagagctg tgctggaggc tgaggtgcag   720
atgtgtggag aactcagaga ctacctgaga gtcacagtga gcctctggca aggtgagacc   780
caggtggcct ctggcacagc cccctttgga ggagagatca ttgatgagag aggaggctat   840
gctgacagag tcaccctgag gctcaatgtg gagaacccca gctgtggtc tgctgagatc   900
cccaacctct acagggctgt tgtggagctg cacactgctg atggcaccct gattgaagct   960
gaagcctgtg atgttggatt cagagaagtc aggattgaga atggcctgct gctgctcaat  1020
ggcaagcctc tgctcatcag gggagtcaac aggcatgagc accaccctct gcatggacaa  1080
gtgatggatg aacagacaat ggtgcaagat atcctgctaa tgaagcagaa caacttcaat  1140
gctgtcaggt gctctcacta ccccaaccac cctctctggt acaccctgtg tgacaggtat  1200
ggcctgtatg ttgttgatga agccaacatt gagacacatg gcatggtgcc catgaacagg  1260
ctcacagatg accccaggtg gctgcctgcc atgtctgaga gagtgaccag gatggtgcag  1320
agagacagga accaccctct tgtgatcatc tggtctctgg gcaatgagtc tggacatgga  1380
gccaaccatg atgctctcta caggtggatc aagtctgttg accccagcag acctgtgcag  1440
tatgaaggag gtggagcaga caccacagcc acagacatca tctgccccat gtatgccagg  1500
gttgatgagg accagccctt ccctgctgtg cccaagtgga gcatcaagaa gtggctctct  1560
ctgcctggag agaccagacc tctgatcctg tgtgaatatg cacatgcaat gggcaactct  1620
ctgggaggct tgccaagta ctggcaagcc ttcagacagt accccaggct gcaaggagga  1680
tttgtgtggg actgggtgga ccaatctctc atcaagtatg atgagaatgg caaccctgg  1740
tctgcctatg gaggagactt tggtgacacc cccaatgaca ggcagttctg catgaatggc  1800
ctggtctttg cagacaggac ccctcacctt gccctcacag aggccaagca ccagcaacag  1860
ttcttccagt tcaggctgtc tggacagacc attgaggtga catctgagta cctcttcagg  1920
cactctgaca atgagctcct gcactggatg gtggccctgg atggcaagcc tctggcttct  1980
ggtgaggtgc ctctggatgt ggcccctcaa ggaaagcagc tgattgaact gcctgagctg  2040
cctcagccag agtctgctgg acaactgtgg ctaacagtga gggtggttca gcccaatgca  2100
acagcttggt ctgaggcagg ccacatctct gcatggcagc agtggaggct ggctgagaac  2160
ctctctgtga ccctgcctgc tgcctctcat gccatccctc acctgacaac atctgaaatg  2220
gacttctgca ttgagctggg caacaagaga tggcagttca caggcagtc tggcttcctg  2280
tctcagatgt ggattggaga caagaagcag ctcctcaccc ctctcaggga ccaattcacc  2340
```

-continued

```
agggctcctc tggacaatga cattggagtg tctgaggcca ccaggattga cccaaatgct   2400
tgggtggaga ggtggaaggc tgctggacac taccaggctg aggctgccct gctccagtgc   2460
acagcagaca ccctggctga tgctgttctg atcaccacag cccatgcttg cagcaccaa    2520 ggcaagaccc tgttcatcag cagaaagacc tacaggattg atggctctgg acagatggca   2580
atcacagtgg atgtggaggt tgcctctgac acacctcacc ctgcaaggat tggcctgaac   2640
tgtcaactgg cacaggtggc tgagagggtg aactggctgg gcttaggccc tcaggagaac   2700
taccctgaca ggctgacagc tgcctgcttt gacaggtggg acctgcctct gtctgacatg   2760 tacaccccctt atgtgttccc ttctgagaat ggcctgaggt gtggcaccag ggagctgaac   2820
tatggtcctc accagtggag gggagacttc cagttcaaca tctccaggta ctctcagcaa   2880
cagctcatgg aaacctctca caggcacctg ctccatgcag aggagggaac ctggctgaac   2940
attgatggct tccacatggg cattggagga gatgactctt ggtctccttc tgtgtctgct   3000
gagttccagt tatctgctgg caggtaccac tatcagctgg tgtggtgcca gaagtaa       3057
```

<210> SEQ ID NO 100
<211> LENGTH: 720
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 100

```
atggtgagca agggcgagga gctgttcacc ggggtggtgc ccatcctggt cgagctggac   60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 101
<211> LENGTH: 678
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 101

```
atggacaaca ccgaggacgt catcaaggag ttcatgcagt tcaaggtgcg catggagggc   60
tccgtgaacg gccactactt cgagatcgag ggcgagggcg agggcaagcc ctacgagggc   120
acccagaccg ccaagctgca ggtgaccaag ggcggccccc tgcccttcgc ctgggacatc   180
ctgtcccccc agttccagta cggctccaag gcctacgtga agcacccccgc cgacatcccc   240 gactacatga agctgtcctt ccccgagggc ttcacctggg agcgctccat gaacttcgag   300
```

```
gacggcggcg tggtggaggt gcagcaggac tcctccctgc aggacggcac cttcatctac    360
aaggtgaagt tcaagggcgt gaacttcccc gccgacggcc ccgtaatgca agaagagact    420
gccggctggg agccctccac cgagaagctg taccccagg acggcgtgct gaagggcgag     480
atctcccacg ccctgaagct gaaggacggc ggccactaca cctgcgactt caagaccgtg    540
tacaaggcca agaagcccgt gcagctgccc ggcaaccact acgtggactc caagctggac    600
atcaccaacc acaacgagga ctacaccgtg gtggagcagt acgagcacgc cgaggcccgc    660
cactccggct cccagtag                                                  678

<210> SEQ ID NO 102
<211> LENGTH: 720
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 102
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgacctg gggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg ccaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 103
<211> LENGTH: 720
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 103
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
```

```
tacctgagct accagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 104
<211> LENGTH: 711
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 104
atggtgagca agggcgagga ggacaacatg gccatcatca aggagttcat gcgcttcaag     60
gtgcacatgg agggctccgt gaacggccac gagttcgaga tcgagggcga gggcgagggc    120 cgccccctacg agggcaccca gaccgccaag ctgaaggtga ccaagggcgg cccccctgccc    180 ttcgcctggg acatcctgtc ccctcagttc atgtacggct ccaaggccta cgtgaagcac    240
cccgccgaca tccccgacta cttgaagctg tccttccccg agggcttcaa gtgggagcgc    300
gtgatgaact tcgaggacgg cggcgtggtg accgtgaccc aggactcctc cctgcaggac    360
ggcgagttca tctacaaggt gaagctgcgc ggcaccaact cccctccga cggccccgta    420 atgcagaaga gaccatggg ctgggaggcc tcctccgagc ggatgtaccc cgaggacggc    480
gccctgaagg gcgagatcaa gcagaggctg aagctgaagg acggcggcca ctacgacgcc    540
gaggtcaaga ccacctacaa ggccaagaag cccgtgcagc tgcccggcgc ctacaacgtc    600
aacatcaagc tggacatcac ctcccacaac gaggactaca ccatcgtgga acagtacgag    660
cgcgccgagg ccgccactc caccggcggc atggacgagc tgtacaagta a              711

<210> SEQ ID NO 105
<211> LENGTH: 11815
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 105
ttaaccctag aaagataatc atattgtgac gtacgttaaa gataatcatg cgtaaaattg     60
acgcatgtgt tttatcggtc tgtatatcga ggtttattta ttaatttgaa tagatattaa    120
gttttattat atttacactt acatactaat aataaattca acaaacaatt tatttatgtt    180 tatttatttat ttaaaaaaaa acaaaaactc aaaatttctt ctataaagta acaaaacttt    240
taaacattct ctcttttaca aaaataaact tattttgtac tttaaaaaca gtcatgttgt    300
attataaaat aagtaattag cttaacttat acataataga aacaaattat acttattagt    360
cagtcagaaa caactttggc acatatcaat attatgctct cgacaaataa ctttttttgca    420 tttttttgcac gatgcatttg cctttcgcct tattttagag gggcagtaag tacagtaagt    480
acgttttttc attactggct cttcagtact gtcatctgat gtaccaggca cttcatttgg    540
caaaatatta gagatattat cgcgcaaata tctcttcaaa gtaggagctt ctaaacgctt    600
acgcataaac gatgacgtca ggctcatgta aaggtttctc ataaattttt tgcgactttg    660 aacctttttct ccccttgctac tgacattatg gctgtatata ataaaagaat ttatgcaggc    720
aatgtttatc attccgtaca ataatgccat aggccaccta ttcgtcttcc tactgcaggt    780
catcacagaa cacatttggt ctagcgtgtc cactccgcct ttagtttgat tataatacat    840
aaccatttgc ggtttaccgg tactttcgtt gatagaagca tcctcatcac aagatgataa    900
```

```
taagtatacc atcttagctg gcttcggttt atatgagacg agagtaaggg gtccgtcaaa    960
acaaaacatc gatgttccca ctggcctgga gcgactgtta ataacttcgt ataatgtatg   1020
ctatacgaag ttatgcgatt aagggatctg tagggcgcag tagtccaggg tttccttgat   1080
gatgtcatac ttatcctgtc cctttttttt ccacagctcg cggttgagga caaactcttc   1140
gcggtctttc cagtggggat cgacggtatc gtagagtcga ggccgctcta gcggatctgc   1200
ccctctccct ccccccccc taacgttact ggccgaagcc gcttggaata aggccggtgt    1260
gcgtttgtct atatgttatt ttccaccata ttgccgtctt ttggcaatgt gagggcccgg   1320
aaacctggcc ctgtcttctt gacgagcatt cctaggggtc tttcccctct cgccaaagga   1380
atgcaaggtc tgttgaatgt cgtgaaggaa gcagttcctc tggaagcttc ttgaagacaa   1440
acaacgtctg tagcgaccct ttgcaggcag cggaaccccc cacctggcga caggtgcctc   1500
tgcggccaaa agccacgtgt ataagataca cctgcaaagg cggcacaacc ccagtgccac   1560
gttgtgagtt ggatagttgt ggaaagagtc aaatggctct cctcaagcgt attcaacaag   1620
gggctgaagg atgcccagaa ggtaccccat tgtatgggat ctgatctggg gcctcggtgc   1680
acatgcttta catgtgttta gtcgaggtta aaaaaacgtc taggcccccc gaaccacggg   1740
gacgtggttt tcctttgaaa aacacgatga taatatggcc acaaccatgg accctgttgt   1800
gctgcaaagg agagactggg agaaccctgg agtgacccag ctcaacagac tggctgccca   1860
ccctcccttt gcctcttgga ggaactctga ggaagccagg acagacaggc ccagccagca   1920
gctcaggtct ctcaatggag agtggaggtt tgcctggttc cctgcccctg aagctgtgcc   1980
tgagtcttgg ctggagtgtg acctcccaga ggctgacact gttgtggtgc caagcaactg   2040
gcagatgcat ggctatgatg ccccccatcta caccaatgtc acctacccca tcactgtgaa   2100
ccccccttt gtgcccactg agaacccac tggctgctac agcctgacct tcaatgttga    2160
tgagagctgg ctgcaagaag gccagaccag gatcatcttt gatggagtca actctgcctt   2220
ccacctctgg tgcaatggca ggtgggttgg ctatggccaa gacagcaggc tgccctctga   2280
gtttgacctc tctgccttcc tcagagctgg agagaacagg ctggctgtca tggtgctcag   2340
gtggtctgat ggcagctacc tggaagacca agacatgtgg aggatgtctg gcatcttcag   2400
ggatgtgagc ctgctgcaca agcccaccac ccagatttct gacttccatg ttgccaccag   2460
gttcaatgat gacttcagca gagctgtgct ggaggctgag gtgcagatgt gtggagaact   2520
cagagactac ctgagagtca cagtgagcct ctggcaaggt gagacccagg tggcctctgg   2580
cacagccccc tttggaggag agatcattga tgagagagga ggctatgctg acagagtcac   2640
cctgaggctc aatgtggaga accccaagct gtggtctgct gagatcccca acctctacag   2700
ggctgttgtg gagctgcaca ctgctgatgg caccctgatt gaagctgaag cctgtgatgt   2760
tggattcaga gaagtcagga ttgagaatgg cctgctgctg ctcaatggca agcctctgct   2820
catcagggga gtcaacaggc atgagcacca ccctctgcat ggacaagtga tggatgaaca   2880
gacaatggtg caagatatcc tgctaatgaa gcagaacaac ttcaatgctg tcaggtgctc   2940
tcactacccc aaccaccctc tctggtacac cctgtgtgac aggtatggcc tgtatgttgt   3000
tgatgaagcc aacattgaga cacatggcat ggtgcccatg aacaggctca cagatgaccc   3060
caggtggctg cctgccatgt ctgagagagt gaccaggatg gtgcagagag acaggaacca   3120
cccctctgtg atcatctggt ctctgggcaa tgagtctgga catggagcca accatgatgc   3180
tctctacagg tggatcaagt ctgttgaccc cagcagacct gtgcagtatg aaggaggtgg   3240
agcagacacc acagccacag acatcatctg ccccatgtat gccagggttg atgaggacca   3300
```

```
gcccttccct gctgtgccca agtggagcat caagaagtgg ctctctctgc ctggagagac   3360
cagacctctg atcctgtgtg aatatgcaca tgcaatgggc aactctctgg gaggctttgc   3420
caagtactgg caagccttca gacagtaccc caggctgcaa ggaggatttg tgtgggactg   3480
ggtggaccaa tctctcatca agtatgatga gaatggcaac ccctggtctg cctatggagg   3540
agactttggt gacacccca atgacaggca gttctgcatg aatggcctgg tctttgcaga    3600
caggacccct caccctgccc tcacagaggc caagcaccag caacagttct tccagttcag   3660
gctgtctgga cagaccattg aggtgacatc tgagtacctc ttcaggcact ctgacaatga   3720
gctcctgcac tggatggtgg ccctggatgg caagcctctg gcttctggtg aggtgcctct   3780
ggatgtggcc cctcaaggaa agcagctgat tgaactgcct gagctgcctc agccagagtc   3840
tgctggacaa ctgtggctaa cagtgagggt ggttcagccc aatgcaacag cttggtctga   3900
ggcaggccac atctctgcat ggcagcagtg gaggctggct gagaacctct ctgtgaccct   3960
gcctgctgcc tctcatgcca tccctcacct gacaacatct gaaatggact tctgcattga   4020
gctgggcaac aagagatggc agttcaacag gcagtctggc ttcctgtctc agatgtggat   4080
tggagacaag aagcagctcc tcacccctct cagggaccaa ttcaccaggg ctcctctgga   4140
caatgacatt ggagtgtctg aggccaccag gattgaccca aatgcttggg tggagaggtg   4200
gaaggctgct ggacactacc aggctgaggc tgccctgctc cagtgcacag cagacaccct   4260
ggctgatgct gttctgatca ccacagccca tgcttggcag caccaaggca agaccctgtt   4320
catcagcaga aagacctaca ggattgatgg ctctggacag atggcaatca cagtggatgt   4380
ggaggttgcc tctgacacac ctcaccctgc aaggattggc ctgaactgtc aactggcaca   4440
ggtggctgag agggtgaact ggctgggctt aggccctcag gagaactacc ctgacaggct   4500
gacagctgcc tgctttgaca ggtgggacct gcctctgtct gacatgtaca ccccttatgt   4560
gttcccttct gagaatggcc tgaggtgtgg caccagggag ctgaactatg gtcctcacca   4620
gtggagggga gacttccagt tcaacatctc caggtactct cagcaacagc tcatggaaac   4680
ctctcacagg cacctgctcc atgcagagga gggaacctgg ctgaacattg atggcttcca   4740
catgggcatt ggaggagatg actcttggtc tccttctgtg tctgctgagt ccagttatc    4800
tgctggcagg taccactatc agctggtgtg gtgccagaag taaacctaat ctagcagctc   4860
gctgatcagc ctcgactgtg ccttctagtt gccagccatc tgttgtttgc ccctcccccg   4920
tgccttcctt gaccctggaa ggtgccactc ccactgtcct ttcctaataa aatgaggaaa   4980
ttgcatcgca ttgtctgagt aggtgtcatt ctattctggg gggtgggtg gggcaggaca    5040
gcaaggggga ggattgggaa gacaatagca ggcatgctgg ggatgcggtg ggctctatgg   5100
cttctgaggc ggaaagaacc agctgggcgct cgatcctcta gttggcgcgt catggtccat   5160
atgaatatcc tccttagttc ctattccgaa gttcctattc tctagaaagt ataggaactt   5220
cggcgcgtcg acattgatta ttgactagtt attaatagta atcaattacg ggtcattag    5280
ttcatagccc atatatggag ttccgcgtta cataacttac ggtaaatggc ccgcctggct   5340
gaccgcccaa cgacccccgc ccattgacgt caataatgac gtatgttccc atagtaacgc   5400
caatagggac tttccattga cgtcaatggg tggactattt acggtaaact gcccacttgg   5460
cagtacatca agtgtatcat atgccaagta cgccccctat tgacgtcaat gacggtaaat   5520
ggcccgcctg gcattatgcc cagtacatga ccttatggga ctttcctact tggcagtaca   5580
tctacgtatt agtcatcgct attaccatgg gtcgaggtga gccccacgtt ctgcttcact   5640
ctccccatct cccccccctc cccacccca attttgtatt tatttatttt ttaattattt    5700
```

```
tgtgcagcga tggggggcggg ggggggggggg gcgcgcgcca ggcggggcgg ggcggggcga    5760
ggggcggggc ggggcgaggc ggagaggtgc ggcggcagcc aatcagagcg gcgcgctccg    5820
aaagtttcct tttatggcga ggcggcggcg gcggcggccc tataaaaagc gaagcgcgcg    5880
gcgggcggga gtcgctgcgt tgccttcgcc ccgtgccccg ctccgcgccg cctcgcgccg    5940
cccgccccgg ctctgactga ccgcgttact cccacaggtg agcgggcggg acggcccttc    6000
tcctccgggc tgtaattagc gcttggttta atgacggctc gtttcttttc tgtggctgcg    6060
tgaaagcctt aaagggctcc gggagggccc tttgtgcggg ggggagcggc tcgggggtg    6120 cgtgcgtgtg tgtgtgcgtg gggagcgccg cgtgcgccc gcgctgcccg gcggctgtga    6180
gcgctgcggg cgcggcgcgg ggctttgtgc gctccgcgtg tgcgcgaggg gagcgcggcc    6240
gggggcggtg ccccgcggtg cggggggggct gcgaggggaa caaaggctgc gtgcggggtg    6300
tgtgcgtggg ggggtgagca gggggtgtgg gcgcggcggt cgggctgtaa ccccccctg    6360 caccccctc cccgagttgc tgagcacggc ccggcttcgg gtgcgggggct ccgtgcgggg    6420 cgtggcgcgg ggctcgccgt gccgggcggg gggtggcgg aggtgggggt gccgggcggg    6480
gcggggccgc ctcgggccgg ggagggctcg gggaggggc gcggcggccc cggagcgccg    6540
gcggctgtcg aggcgcggcg agccgcagcc attgcctttt atggtaatcg tgcgagaggg    6600
cgcagggact tcctttgtcc caaatctggc ggagccgaaa tctgggaggc gccgccgcac    6660
cccctctagc gggcgcgggc gaagcggtgc ggcgccggca ggaaggaaat gggcggggag    6720
ggccttcgtg cgtcgccgcg ccgccgtccc cttctccatc tccagcctcg gggctgccgc    6780 aggggacgg ctgccttcgg gggggacggg gcagggcggg gttcggcttc tggcgtgtga    6840
ccggcggctc tagagcctct gctaaccatg ttcatgcctt cttctttttc ctacagctcc    6900
tgggcaacgt gctggttatt gtgctgtctc atcattttgg caaagaattc gccaccatgg    6960
tgagcaaggg cgaggagctg ttcaccgggg tggtgcccat cctggtcgag ctggacggcg    7020
acgtaaacgg ccacaagttc agcgtgtccg gcgagggcga gggcgatgcc acctacggca    7080
agctgaccct gaagttcatc tgcaccaccg gcaagctgcc cgtgccctgg cccaccctcg    7140
tgaccaccct gacctacggc gtgcagtgct tcagccgcta ccccgaccac atgaagcagc    7200
acgacttctt caagtccgcc atgcccgaag gctacgtcca ggagcgcacc atcttcttca    7260
aggacgacgg caactacaag acccgcgccg aggtgaagtt cgagggcgac accctggtga    7320
accgcatcga gctgaagggc atcgacttca aggaggacgg caacatcctg gggcacaagc    7380
tggagtacaa ctacaacagc cacaacgtct atatcatggc cgacaagcag aagaacggca    7440
tcaaggtgaa cttcaagatc cgccacaaca tcgaggacgg cagcgtgcag ctcgccgacc    7500
actaccagca gaacaccccc atcggcgacg gccccgtgct gctgcccgac aaccactacc    7560
tgagcaccca gtccgccctg agcaaagacc ccaacgagaa gcgcgatcac atggtcctgc    7620
tggagttcgt gaccgccgcc gggatcactc tcggcatgga cgagctgtac aagtaaagcg    7680
gccgcgactc tagatcataa tcagccatac cacatttgta gaggttttac ttgctttaaa    7740
aaacctccca cacctccccc tgaacctgaa acataaaatg aatgcaattg ttgttgttaa    7800
cttgtttatt gcagcttata atggttacaa ataaagcaat agcatcacaa atttcacaaa    7860
taaagcattt ttttcactgc attctagttg tggtttgtcc aaactcatca atgtatctta    7920
agataacttc gtataatgta tgctatacga agttatataa cttcgtataa tgtgtactat    7980
acgaagttat aaatgaagtt cctattccga agttcctatt ctctagaaag tataggaact    8040
tcgaagcagc tccagcctac acaatcgctc aagacgtgta atgctctatg gtaggtcgat    8100
```

```
ataatagcaa tcaacgcaag caaatgtgtc agtcctgctt acaggaacga ttctatttag   8160
taattttcgt tgtataaagt aattatgtat gtatgtaagc cccataaatc tgaaacaatt   8220
aggcaaaacc atgcgacggc cgatctcgag agatctgaca atgttcagtg cagagactcg   8280
gctacgcctc gtggactttg aagttgacca acaatgttta ttcttacctc taatagtcct   8340
ctgtggcaag gtcaagattc tgttagaagc caatgaagaa cctggttgtt caataacatt   8400
ttgttcgtct aatatttcac taccgcttga cgttggctgc acttcatgta cctcatctat   8460
aaacgcttct tctgtatcgc tctggacgtc atcttcactt acgtgatctg atatttcact   8520
gtcagaatcc tcaccaacaa gctcgtcatc gctttgcaga agagcagaga ggatatgctc   8580
atcgtctaaa gaactaccca ttttattata tattagtcac gatatctata acaagaaaat   8640
atatatataa taagttatca cgtaagtaga acatgaaata acaatataat tatcgtatga   8700
gttaaatctt aaaagtcacg taaaagataa tcatgcgtca ttttgactca cgcggtcgtt   8760
atagttcaaa atcagtgaca cttaccgcat tgacaagcac gcctcacggg agctccaagc   8820
ggcgactgag atgtcctaaa tgcacagcga cggattcgcg ctatttagaa agagagagca   8880
atatttcaag aatgcatgcg tcaattttac gcagactatc tttctagggt taaaaaagat   8940
ttgcgcttta ctcgacctaa actttaaaca ggtcatagaa tcttcgtttg acaaaaacca   9000
cattgtgggg taccgagctc gaattcatcg atgatatcag atctgccggt ctccctatag   9060
tgagtcgtat taatttcgat aagccaggtt aacctgcatt aatgaatcgg ccaacgcgcg   9120
gggagaggcg gtttgcgtat tgggcgctct tccgcttcct cgctcactga ctcgctgcgc   9180
tcggtcgttc ggctgcggcg agcggtatca gctcactcaa aggcggtaat acggttatcc   9240
acagaatcag gggataacgc aggaaagaac atgtgagcaa aaggccagca aaaggccagg   9300
aaccgtaaaa aggccgcgtt gctggcgttt ttccataggc tccgcccccc tgacgagcat   9360
cacaaaaatc gacgctcaag tcagaggtgg cgaaacccga caggactata agataccag    9420 gcgtttcccc ctggaagctc cctcgtgcgc tctcctgttc cgaccctgcc gcttaccgga   9480
tacctgtccg cctttctccc ttcgggaagc gtggcgcttt ctcatagctc acgctgtagg   9540
tatctcagtt cggtgtaggt cgttcgctcc aagctgggct gtgtgcacga accccccgtt   9600
cagcccgacc gctgcgcctt atccggtaac tatcgtcttg agtccaaccc ggtaagacac   9660
gacttatcgc cactggcagc agccactggt aacaggatta gcagagcgag gtatgtaggc   9720
ggtgctacag agttcttgaa gtggtggcct aactacggct acactagaag aacagtattt   9780
ggtatctgcg ctctgctgaa gccagttacc ttcggaaaaa gagttggtag ctcttgatcc   9840
ggcaaacaaa ccaccgctgg tagcggtggt ttttttgttt gcaagcagca gattacgcgc   9900
agaaaaaaag gatctcaaga agatcctttg atcttttcta cggggtctga cgctcagtgg   9960
aacgaaaact cacgttaagg gattttggtc atgagattat caaaaaggat cttcacctag  10020
atccttttaa attaaaaatg aagttttaaa tcaatctaaa gtatatatga gtaaacttgg  10080
tctgacagtt accaatgctt aatcagtgag gcacctatct cagcgatctg tctatttcgt  10140
tcatccatag ttgcctgact ccccgtcgtg tagataacta cgatacggga gggcttacca  10200
tctggcccca gtgctgcaat gataccgcga acccacgct caccggctcc agatttatca   10260
gcaataaacc agccagccgg aagggccgag cgcagaagtg gtcctgcaac tttatccgcc  10320
tccatccagt ctattaattg ttgccgggaa gctagagtaa gtagttcgcc agttaatagt  10380
ttgcgcaacg ttgttgccat tgctacaggc atcgtggtgt cacgctcgtc gtttggtatg  10440
gcttcattca gctccggttc ccaacgatca aggcgagtta catgatcccc catgttgtgc  10500
```

```
aaaaaagcgg ttagctcctt cggtcctccg atcgttgtca gaagtaagtt ggccgcagtg    10560
ttatcactca tggttatggc agcactgcat aattctctta ctgtcatgcc atccgtaaga    10620
tgcttttctg tgactggtga gtactcaacc aagtcattct gagaatagtg tatgcggcga    10680
ccgagttgct cttgcccggc gtcaatacgg gataataccg cgccacatag cagaacttta    10740
aaagtgctca tcattggaaa acgttcttcg gggcgaaaac tctcaaggat cttaccgctg    10800
ttgagatcca gttcgatgta acccactcgt gcacccaact gatcttcagc atctttttact   10860
ttcaccagcg tttctgggtg agcaaaaaca ggaaggcaaa atgccgcaaa aagggaata     10920
agggcgacac ggaaatgttg aatactcata ctcttccttt ttcaatatta ttgaagcatt    10980
tatcagggtt attgtctcat gagcggatac atatttgaat gtatttagaa aaataaacaa    11040
atagggggttc cgcgcacatt tccccgaaaa gtgccacctg acgtctaaga aaccattatt   11100
atcatgacat taacctataa aaataggcgt atcacgaggc cctttcgtct cgcgcgtttc    11160
ggtgatgacg gtgaaaacct ctgacacatg cagctcccgg agacggtcac agcttgtctg    11220
taagcggatg ccgggagcag acaagcccgt cagggcgcgt cagcgggtgt tggcgggtgt    11280
cggggctggc ttaactatgc ggcatcagag cagattgtac tgagagtgca ccatatggac    11340
atattgtcgt tagaacgcgg ctacaattaa tacataacct tatgtatcat acacatacga    11400
tttaggtgac actatagaac tcgacctcga ggctggcacg acaggtttcc cgactggaaa    11460
gcgggcagtg agcgcaacgc aattaatgtg agttagctca ctcattaggc accccaggct    11520
ttacacttta tgcttccggc tcgtatgttg tgtggaattg tgagcggata acaatttcac    11580
acaggaaaca gctatgacca tgattacgcc aagctcgaaa ttaaccctca ctaaagggaa    11640
caaaagctgg agctcgtctt tgatcaaaac gcaaatcgac gaaaatgtgt cggacaatat    11700
caagtcgatg agcgaaaaac taaaaaggct agaatacgac aatctcacag acagcgttga    11760
gatatacggt attcacgaca gcaggctgaa taataaaaaa attagaaact attat          11815
```

<210> SEQ ID NO 106
<211> LENGTH: 11277
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 106

```
ttaaccctag aaagataatc atattgtgac gtacgttaaa gataatcatg cgtaaaattg      60
acgcatgtgt tttatcggtc tgtatatcga ggtttattta ttaatttgaa tagatattaa    120
gttttattat atttcacactt acatactaat aataaattca acaaacaatt tatttatgtt    180
tatttattta ttaaaaaaaa acaaaaactc aaaatttctt ctataaagta acaaaacttt    240
taaacattct ctcttttaca aaaataaact tattttgtac tttaaaaaca gtcatgttgt    300
attataaaat aagtaattag cttaacttat acataataga aacaaattat acttattagt    360
cagtcagaaa caactttggc acatatcaat attatgctct cgacaaataa cttttttgca    420
tttttttgcac gatgcatttg cctttcgcct tattttaatc gcataacttc gtataatgta    480
tgctatacga agttatgcga ttaagggatc tgtagggcgc agtagtccag ggtttccttg    540
atgatgtcat acttatcctg tcccttttt ttccacagct cgcggttgag acaaactct      600
tcgcggtctt tccagtgggg atcgacggta tcgtagagtc gaggccgctc tagcggatct    660
gcccctctcc ctccccccc cctaacgtta ctggccgaag ccgcttggaa taaggccggt    720
gtgcgtttgt ctatatgtta ttttccacca tattgccgtc ttttggcaat gtgagggccc    780
```

-continued

```
ggaaacctgg ccctgtcttc ttgacgagca ttcctagggg tctttcccct ctcgccaaag    840
gaatgcaagg tctgttgaat gtcgtgaagg aagcagttcc tctggaagct tcttgaagac    900
aaacaacgtc tgtagcgacc ctttgcaggc agcggaaccc cccacctggc gacaggtgcc    960
tctgcggcca aaagccacgt gtataagata cacctgcaaa ggcggcacaa ccccagtgcc   1020
acgttgtgag ttggatagtt gtggaaagag tcaaatggct ctcctcaagc gtattcaaca   1080
aggggctgaa ggatgcccag aaggtacccc attgtatggg atctgatctg gggcctcggt   1140
gcacatgctt tacatgtgtt tagtcgaggt taaaaaaacg tctaggcccc ccgaaccacg   1200
gggacgtggt tttcctttga aaaacacgat gataatatgg ccacaaccat ggaccctgtt   1260
gtgctgcaaa ggagagactg ggagaaccct ggagtgaccc agctcaacag actggctgcc   1320
caccctccct ttgcctcttg gaggaactct gaggaagcca ggacagacag gcccagccag   1380
cagctcaggt ctctcaatgg agagtggagg tttgcctggt tccctgcccc tgaagctgtg   1440
cctgagtctt ggctggagtg tgacctccca gaggctgaca ctgttgtggt gccaagcaac   1500
tggcagatgc atggctatga tgcccccatc tacaccaatg tcacctaccc catcactgtg   1560
aaccccccct tgtgcccac tgagaacccc actggctgct acagcctgac cttcaatgtt   1620
gatgagagct ggctgcaaga aggccagacc aggatcatct ttgatggagt caactctgcc   1680
ttccacctct ggtgcaatgg caggtgggtt ggctatggcc aagacagcag gctgccctct   1740
gagtttgacc tctctgcctt cctcagagct ggagagaaca ggctggctgt catggtgctc   1800
aggtggtctg atggcagcta cctggaagac caagacatgt ggaggatgtc tggcatcttc   1860
agggatgtga gcctgctgca caagcccacc acccagattt ctgacttcca tgttgccacc   1920
aggttcaatg atgacttcag cagagctgtg ctggaggctg aggtgcagat gtgtggagaa   1980
ctcagagact acctgagagt cacagtgagc ctctggcaag gtgagaccca ggtggcctct   2040
ggcacagccc cctttggagg agagatcatt gatgagagag gaggctatgc tgacagagtc   2100
accctgaggc tcaatgtgga aaccccaag ctgtggtctg ctgagatccc caacctctac   2160
agggctgttg tggagctgca cactgctgat ggcaccctga ttgaagctga agcctgtgat   2220
gttggattca gagaagtcag gattgagaat ggcctgctgc tgctcaatgg caagcctctg   2280
ctcatcaggg gagtcaacag gcatgagcac caccctctgc atggacaagt gatggatgaa   2340
cagacaatgg tgcaagatat cctgctaatg aagcagaaca acttcaatgc tgtcaggtgc   2400
tctcactacc ccaaccaccc tctctggtac accctgtgtg acaggtatgg cctgtatgtt   2460
gttgatgaag ccaacattga gacacatggc atggtgccca tgaacaggct cacagatgac   2520
cccaggtggc tgcctgccat gtctgagaga gtgaccagga tggtgcagag agacaggaac   2580
cacccctctg tgatcatctg gtctctgggc aatgagtctg acatggagc caaccatgat   2640
gctctctaca ggtggatcaa gtctgttgac cccagcagac ctgtgcagta tgaaggaggt   2700
ggagcagaca ccacagccac agacatcatc tgccccatgt atgccagggt tgatgaggac   2760
cagcccttcc ctgctgtgcc caagtggagc atcaagaagt ggctctctct gcctggagag   2820
accagacctc tgatcctgtg tgaatatgca catgcaatgg gcaactctct gggaggcttt   2880
gccaagtact ggcaagcctt cagacagtac cccaggctgc aaggaggatt tgtgtgggac   2940
tgggtggacc aatctctcat caagtatgat gagaatggca cccctggtc tgcctatgga   3000
ggagactttg gtgacacccc caatgacagg cagttctgca tgaatggcct ggtctttgca   3060
gacaggaccc ctcaccctgc cctcacagag gccaagcacc agcaacagtt cttccagttc   3120
aggctgtctg gacagaccat tgaggtgaca tctgagtacc tcttcaggca ctctgacaat   3180
```

-continued

```
gagctcctgc actggatggt ggccctggat ggcaagcctc tggcttctgg tgaggtgcct    3240
ctggatgtgg cccctcaagg aaagcagctg attgaactgc ctgagctgcc tcagccagag    3300
tctgctggac aactgtggct aacagtgagg gtggttcagc ccaatgcaac agcttggtct    3360
gaggcaggcc acatctctgc atggcagcag tggaggctgg ctgagaacct ctctgtgacc    3420
ctgcctgctg cctctcatgc catccctcac ctgacaacat ctgaaatgga cttctgcatt    3480
gagctgggca acaagagatg gcagttcaac aggcagtctg gcttcctgtc tcagatgtgg    3540
attggagaca agaagcagct cctcaccct ctcaggga cc aattcaccag ggctcctctg    3600
gacaatgaca ttggagtgtc tgaggccacc aggattgacc caaatgcttg ggtggagagg    3660
tggaaggctg ctggacacta ccaggctgag gctgccctgc tccagtgcac agcagacacc    3720
ctggctgatg ctgttctgat caccacagcc catgcttggc agcaccaagg caagaccctg    3780
ttcatcagca gaaagaccta caggattgat ggctctggac agatggcaat cacagtggat    3840
gtggaggttg cctctgacac acctcaccct gcaaggattg gcctgaactg tcaactggca    3900
caggtggctg agagggtgaa ctggctgggc ttaggccctc aggagaacta ccctgacagg    3960
ctgacagctg cctgctttga caggtgggac ctgcctctgt ctgacatgta cacccttat    4020
gtgttcccct ctgagaatgg cctgaggtgt ggcaccaggg agctgaacta tggtcctcac    4080
cagtggaggg gagacttcca gttcaacatc tccaggtact ctcagcaaca gctcatggaa    4140
acctctcaca ggcacctgct ccatgcagag gagggaacct ggctgaacat tgatggcttc    4200
cacatgggca ttgaggagaga tgactcttgg tctccttctg tgtctgctga gttccagtta    4260
tctgctggca ggtaccacta tcagctggtg tggtgccaga agtaaaccta atctagcagc    4320
tcgctgatca gcctcgactg tgccttctag ttgccagcca tctgttgttt gcccctcccc    4380
cgtgccttcc ttgaccctgg aaggtgccac tcccactgtc cttcctaat aaaatgagga    4440
aattgcatcg cattgtctga gtaggtgtca ttctattctg gggggtgggg tgggcagga    4500
cagcaagggg gaggattggg aagacaatag caggcatgct ggggatgcgg tgggctctat    4560
ggcttctgag gcggaaagaa ccagctgggg ctcgatcctc tagttggcgc gtcatggtcc    4620
atatgaatat cctccttagt tcctattccg aagttcctat tctctagaaa gtataggaac    4680
ttcggcgcgt cgacattgat tattgactag ttattaatag taatcaatta cggggtcatt    4740
agttcatagc ccatatatgg agttccgcgt tacataactt acggtaaatg gcccgcctgg    4800
ctgaccgccc aacgaccccc gcccattgac gtcaataatg acgtatgttc ccatagtaac    4860
gccaataggg actttccatt gacgtcaatg ggtggactat ttacggtaaa ctgcccactt    4920
ggcagtacat caagtgtatc atatgccaag tacgcccct attgacgtca atgacggtaa    4980
atggcccgcc tggcattatg cccagtacat gaccttatgg actttccta cttggcagta    5040
catctacgta ttagtcatcg ctattaccat gggtcgaggt gagccccacg ttctgcttca    5100
ctctccccat ctccccccc tccccacccc caattttgta tttatttatt ttttaattat    5160
tttgtgcagc gatggggggcg gggggggggg gggcgcgcgc caggcggggc ggggcggggc    5220
gaggggcggg gcggggcgag gcggagaggt gcggcggcag ccaatcagag cggcgcgctc    5280
cgaaagtttc cttttatggc gaggcggcgg cggcggcggc cctataaaaa gcgaagcgcg    5340
cggcgggcgg gagtcgctgc gttgccttcg ccccgtgccc cgctccgcgc cgcctcgcgc    5400
cgcccgcccc ggctctgact gaccgcgtta ctcccacagg tgagcgggcg gacggccct    5460
tctcctccgg gctgtaatta gcgcttggtt taatgacggc tcgtttcttt tctgtggctg    5520
cgtgaaagcc ttaaagggct ccgggagggc cctttgtgcg ggggggagcg gctcgggggg    5580
```

```
tgcgtgcgtg tgtgtgtgcg tggggagcgc cgcgtgcggc ccgcgctgcc cggcggctgt    5640
gagcgctgcg ggcgcggcgc ggggctttgt gcgctccgcg tgtgcgcgag gggagcgcgg    5700
ccgggggcgg tgccccgcgg tgcggggggg ctgcgagggg aacaaaggct gcgtgcgggg    5760
tgtgtgcgtg ggggggtgag caggggtgt gggcgcggcg gtcgggctgt aaccccccccc   5820 tgcaccccccc tccccgagtt gctgagcacg gcccggcttc gggtgcgggg ctccgtgcgg   5880
ggcgtggcgc ggggctcgcc gtgccgggcg ggggtggcg gcaggtgggg gtgccgggcg    5940
gggcggggcc gcctcgggcc ggggagggct cggggaggg gcgcggcggc cccggagcgc    6000
cggcggctgt cgaggcgcgg cgagccgcag ccattgcctt ttatggtaat cgtgcgagag    6060
ggcgcaggga cttcctttgt cccaaatctg gcggagccga aatctgggag gcgccgccgc    6120 acccctcta gcgggcgcgg gcgaagcggt gcggcgccgg caggaaggaa atgggcgggg    6180
agggccttcg tgcgtcgccg cgccgccgtc cccttctcca tctccagcct cggggctgcc    6240 gcaggggac ggctgccttc gggggggacg ggcagggcg gggttcggct tctggcgtgt    6300
gaccggcggc tctagagcct ctgctaacca tgttcatgcc ttcttctttt tcctacagct    6360
cctgggcaac gtgctggtta ttgtgctgtc tcatcatttt ggcaaagaat tcgccaccat    6420
ggtgagcaag ggcgaggagc tgttcaccgg ggtggtgccc atcctggtcg agctggacgg    6480
cgacgtaaac ggccacaagt tcagcgtgtc cggcgagggc gagggcgatg ccacctacgg    6540
caagctgacc ctgaagttca tctgcaccac cggcaagctg cccgtgccct ggcccaccct    6600
cgtgaccacc ctgacctacg gcgtgcagtg cttcagccgc tacccccgacc acatgaagca    6660 gcacgacttc ttcaagtccg ccatgcccga aggctacgtc caggagcgca ccatcttctt    6720
caaggacgac ggcaactaca agacccgcgc cgaggtgaag ttcgagggcg acaccctggt    6780
gaaccgcatc gagctgaagg gcatcgactt caaggaggac ggcaacatcc tggggcacaa    6840
gctggagtac aactacaaca gccacaacgt ctatatcatg gccgacaagc agaagaacgg    6900
catcaaggtg aacttcaaga tccgccacaa catcgaggac ggcagcgtgc agctcgccga    6960
ccactaccag cagaacaccc ccatcggcga cggccccgtg ctgctgcccg acaaccacta    7020
cctgagcacc cagtccgccc tgagcaaaga ccccaacgag aagcgcgatc acatggtcct    7080
gctggagttc gtgaccgccg ccgggatcac tctcggcatg gacgagctgt acaagtaaag    7140
cggccgcgac tctagatcat aatcagccat accacatttg tagaggtttt acttgcttta    7200
aaaaacctcc cacacctccc cctgaacctg aaacataaaa tgaatgcaat tgttgttgtt    7260
aacttgttta ttgcagctta taatggttac aaataaagca atagcatcac aaatttcaca    7320
aataaagcat ttttttcact gcattctagt tgtggtttgt ccaaactcat caatgtatct    7380
taagataact tcgtataatg tatgctatac gaagttatat aacttcgtat aatgtgtact    7440
atacgaagtt ataaatgaag ttcctattcc gaagttccta ttctctagaa agtataggaa    7500
cttcgaagca gctccagcct acacaatcgc tcaagacgtg taatgctcta tggtaggtcg    7560
atataatagc aatcaacgca agcaaatgtg tcagtcctgc ttacaggaac gattctattt    7620
agtaattttc gttgtataaa gtaattatgt atgtatgtaa gccccataaa tctgaaacaa    7680
ttaggcaaaa ccatgcgacg gccgatctcg agagatctga caatgttcag tgcagagact    7740
cggctacgcc tcgtggactt tgaagttgac caacaatgtt tattcttacc tctaatagtc    7800
ctctgtggca aggtcaagat tctgttagaa gccaatgaag aacctggttg ttcaataaca    7860
ttttgttcgt ctaatatttc actaccgctt gacgttggct gcacttcatg tacctcatct    7920
ataaacgctt cttctgtatc gctctggacg tcatcttcac ttacgtgatc tgatatttca    7980
```

```
ctgtcagaat cctcaccaac aagctcgtca tcgctttgca gaagagcaga gaggatatgc   8040
tcatcgtcta aagaactacc cattttatta tatattagtc acgatatcta taacaagaaa   8100
atatatatat aataagttat cacgtaagta gaacatgaaa taacaatata attatcgtat   8160
gagttaaatc ttaaaagtca cgtaaaagat aatcatgcgt cattttgact cacgcggtcg   8220
ttatagttca aaatcagtga cacttaccgc attgacaagc acgcctcacg ggagctccaa   8280
gcggcgactg agatgtccta atgcacagc gacggattcg cgctatttag aaagagagag    8340
caatatttca agaatgcatg cgtcaatttt acgcagacta tctttctagg gttaaaaaag   8400
atttgcgctt tactcgacct aaactttaaa caggtcatag aatcttcgtt tgacaaaaac   8460
cacattgtgg ggtaccgagc tcgaattcat cgatgatatc agatctgccg gtctccctat   8520
agtgagtcgt attaatttcg ataagccagg ttaacctgca ttaatgaatc ggccaacgcg   8580
cggggagagg cggtttgcgt attgggcgct cttccgcttc ctcgctcact gactcgctgc   8640
gctcggtcgt tcggctgcgg cgagcggtat cagctcactc aaaggcggta atacggttat   8700
ccacagaatc aggggataac gcaggaaaga acatgtgagc aaaaggccag caaaaggcca   8760
ggaaccgtaa aaaggccgcg ttgctggcgt ttttccatag gctccgcccc cctgacgagc   8820
atcacaaaaa tcgacgctca agtcagaggt ggcgaaaccc gacaggacta taaagatacc   8880
aggcgtttcc ccctggaagc tccctcgtgc gctctcctgt tccgaccctg ccgcttaccg   8940
gatacctgtc cgcctttctc ccttcgggaa gcgtggcgct ttctcatagc tcacgctgta   9000
ggtatctcag ttcggtgtag tcgttcgct ccaagctggg ctgtgtgcac gaaccccccg     9060
ttcagcccga ccgctgcgcc ttatccggta actatcgtct tgagtccaac ccggtaagac   9120
acgacttatc gccactggca gcagccactg gtaacaggat tagcagagcg aggtatgtag   9180
gcggtgctac agagttcttg aagtggtggc ctaactacgg ctacactaga agaacagtat   9240
ttggtatctg cgctctgctg aagccagtta ccttcggaaa aagagttggt agctcttgat   9300
ccggcaaaca aaccaccgct ggtagcggtg gtttttttgt ttgcaagcag cagattacgc   9360
gcagaaaaaa aggatctcaa gaagatcctt tgatcttttc tacggggtct gacgctcagt   9420
ggaacgaaaa ctcacgttaa gggattttgg tcatgagatt atcaaaaagg atcttcacct   9480
agatcctttt aaattaaaaa tgaagtttta atcaatcta aagtatatat gagtaaactt     9540
ggtctgacag ttaccaatgc ttaatcagtg aggcacctat ctcagcgatc tgtctatttc   9600
gttcatccat agttgcctga ctccccgtcg tgtagataac tacgatacgg gagggcttac   9660
catctggccc cagtgctgca atgataccgc gagacccacg ctcaccggct ccagatttat   9720
cagcaataaa ccagccagcc ggaagggccg agcgcagaag tggtcctgca actttatccg   9780
cctccatcca gtctattaat tgttgccggg aagctagagt aagtagttcg ccagttaata   9840
gtttgcgcaa cgttgttgcc attgctacag gcatcgtggt gtcacgctcg tcgtttggta   9900
tggcttcatt cagctccggt tcccaacgat caaggcgagt tacatgatcc cccatgttgt   9960
gcaaaaaagc ggttagctcc ttcggtcctc cgatcgttgt cagaagtaag ttggccgcag  10020
tgttatcact catggttatg gcagcactgc ataattctct tactgtcatg ccatccgtaa  10080
gatgcttttc tgtgactggt gagtactcaa ccaagtcatt ctgagaatag tgtatgcggc  10140
gaccgagttg ctcttgcccg gcgtcaatac gggataatac cgcgccacat agcagaactt  10200
taaaagtgct catcattgga aaacgttctt cggggcgaaa actctcaagg atcttaccgc  10260
tgttgagatc cagttcgatg taacccactc gtgcacccaa ctgatcttca gcatctttta  10320 cttttcaccag cgtttctggg tgagcaaaaa caggaaggca aaatgccgca aaaaagggaa  10380
```

```
taagggcgac acggaaatgt tgaatactca tactcttcct tttcaatat tattgaagca    10440 tttatcaggg ttattgtctc atgagcggat acatatttga atgtatttag aaaaataaac    10500 aaatagggt  tccgcgcaca tttccccgaa aagtgccacc tgacgtctaa gaaaccatta    10560
ttatcatgac attaacctat aaaaataggc gtatcacgag gcccttcgt  ctcgcgcgtt    10620 tcggtgatga cggtgaaaac ctctgacaca tgcagctccc ggagacggtc acagcttgtc    10680
tgtaagcgga tgccgggagc agacaagccc gtcagggcgc gtcagcgggt gttggcgggt    10740
gtcggggctg gcttaactat gcggcatcag agcagattgt actgagagtg caccatatgg    10800
acatattgtc gttagaacgc ggctacaatt aatacataac cttatgtatc atacacatac    10860
gatttaggtg acactataga actcgacctc gaggctggca cgacaggttt cccgactgga    10920
aagcgggcag tgagcgcaac gcaattaatg tgagttagct cactcattag gcaccccagg    10980
ctttacactt tatgcttccg gctcgtatgt tgtgtggaat tgtgagcgga taacaatttc    11040
acacaggaaa cagctatgac catgattacg ccaagctcga aattaaccct cactaaaggg    11100
aacaaaagct ggagctcgtc tttgatcaaa acgcaaatcg acgaaaatgt gtcggacaat    11160
atcaagtcga tgagcgaaaa actaaaaagg ctagaatacg acaatctcac agacagcgtt    11220
gagatatacg gtattcacga cagcaggctg aataataaaa aaattagaaa ctattat      11277
```

<210> SEQ ID NO 107
<211> LENGTH: 10662
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 107

```
ttaaccctag aaagataatc atattgtgac gtacgttaaa gataatcatg cgtaaaattg      60
acgcatgtgt tttatcgatc tgtatatcga ggtttattta ttaatttgaa tagatattaa     120
gttttattat atttacactt acatactaat aataaattca acaacaatt  tatttatgtt    180 tatttattta ttaaaaaaaa acaaaaactc aaaatttctt ctataaagta acaaaacttt    240
taaacattct ctcttttaca aaaataaact tattttgtac tttaaaaaca gtcatgttgt    300
attataaaat aagtaattag cttaacttat acataataga aacaaattat acttattaat    360
cgcataactt cgtataatgt atgctatacg aagttatgcg attaagggat ctgtagggcg    420
cagtagtcca gggtttcctt gatgatgtca tacttatcct gtcccttttt tttccacagc    480
tcgcggttga ggacaaactc ttcgcggtct ttccagtggg gatcgacggt atcgtagagt    540
cgaggccgct ctagcggatc tgcccctctc cctccccccc ccctaacgtt actggccgaa    600
gccgcttgga ataaggccgg tgtgcgtttg tctatatgtt attttccacc atattgccgt    660
cttttggcaa tgtgagggcc cggaaacctg gccctgtctt cttgacgagc attcctaggg    720
gtctttcccc tctcgccaaa ggaatgcaag gtctgttgaa tgtcgtgaag gaagcagttc    780
ctctggaagc ttcttgaaga caacaacgt ctgtagcgac cctttgcagg cagcggaacc    840
ccccacctgg cgacaggtgc ctctgcggcc aaaagccacg tgtataagat acacctgcaa    900
aggcggcaca accccagtgc cacgttgtga gttggatagt tgtggaaaga gtcaaatggc    960
tctcctcaag cgtattcaac aaggggctga aggatgccca aaggtaccc  cattgtatgg   1020 gatctgatct ggggcctcgg tgcacatgct ttacatgtgt ttagtcgagg ttaaaaaaac    1080
gtctaggccc cccgaaccac ggggacgtgg ttttcctttg aaaacacga  tgataatatg    1140
```

```
gccacaacca tggaccctgt tgtgctgcaa aggagagact gggagaaccc tggagtgacc    1200
cagctcaaca gactggctgc ccaccctccc tttgcctctt ggaggaactc tgaggaagcc    1260
aggacagaca ggcccagcca gcagctcagg tctctcaatg gagagtggag gtttgcctgg    1320
ttccctgccc ctgaagctgt gcctgagtct tggctggagt gtgacctccc agaggctgac    1380
actgttgtgg tgccaagcaa ctggcagatg catggctatg atgcccccat ctacaccaat    1440
gtcacctacc ccatcactgt gaaccccccct tttgtgccca ctgagaaccc cactggctgc    1500
tacagcctga ccttcaatgt tgatgagagc tggctgcaag aaggccagac caggatcatc    1560
tttgatggag tcaactctgc cttccacctc tggtgcaatg gcaggtgggt tggctatggc    1620
caagacagca ggctgccctc tgagtttgac ctctctgcct tcctcagagc tggagagaac    1680
aggctggctg tcatggtgct caggtggtct gatggcagct acctggaaga ccaagacatg    1740
tggaggatgt ctggcatctt cagggatgtg agcctgctgc acaagcccac cacccagatt    1800
tctgacttcc atgttgccac caggttcaat gatgacttca gcagagctgt gctggaggct    1860
gaggtgcaga tgtgtggaga actcagagac tacctgagag tcacagtgag cctctggcaa    1920
ggtgagaccc aggtggcctc tggcacagcc cctttggag  gagagatcat tgatgagaga    1980
ggaggctatg ctgacagagt caccctgagg ctcaatgtgg agaaccccaa gctgtggtct    2040
gctgagatcc ccaacctcta cagggctgtt gtggagctgc acactgctga tgcaccctg    2100 attgaagctg aagcctgtga tgttggattc agagaagtca ggattgagaa tggcctgctg    2160
ctgctcaatg gcaagcctct gctcatcagg ggagtcaaca ggcatgagca ccaccctctg    2220
catggacaag tgatggatga acagacaatg gtgcaagata tcctgctaat gaagcagaac    2280
aacttcaatg ctgtcaggtg ctctcactac cccaaccacc ctctctggta cacccctgtgt    2340 gacaggtatg gcctgtatgt tgttgatgaa gccaacattg agacacatgg catggtgccc    2400
atgaacaggc tcacagatga cccccaggtgg ctgcctgcca tgtctgagag agtgaccagg    2460
atggtgcaga gagacaggaa ccacccctct gtgatcatct ggtctctggg caatgagtct    2520
ggacatggag ccaaccatga tgctctctac aggtggatca agtctgttga ccccagcaga    2580
cctgtgcagt atgaaggagg tggagcagac accacagcca cagacatcat ctgccccatg    2640
tatgccaggg ttgatgagga ccagcccttc cctgctgtgc ccaagtggag catcaagaag    2700
tggctctctc tgcctggaga gaccagacct ctgatcctgt gtgaatatgc acatgcaatg    2760
ggcaactctc tgggaggctt tgccaagtac tggcaagcct tcagacagta ccccaggctg    2820
caaggaggat ttgtgtggga ctgggtggac caatctctca tcaagtatga tgagaatggc    2880 aaccccctggt ctgcctatgg aggagacttt ggtgacaccc ccaatgacag gcagttctgc    2940
atgaatggcc tggtctttgc agacaggacc cctcaccctg ccctcacaga ggccaagcac    3000
cagcaacagt tcttccagtt caggctgtct ggacagacca ttgaggtgac atctgagtac    3060
ctcttcaggc actctgacaa tgagctcctg cactggatgg tggccctgga tggcaagcct    3120
ctggcttctg gtgaggtgcc tctggatgtg gcccctcaag gaaagcagct gattgaactg    3180
cctgagctgc ctcagccaga gtctgctgga caactgtggc taacagtgag ggtggttcag    3240
cccaatgcaa cagcttggtc tgaggcaggc cacatctctg catggcagca gtggaggctg    3300
gctgagaacc tctctgtgac cctgcctgct gcctctcatg ccatccctca cctgacaaca    3360
tctgaaatgg acttctgcat tgagctgggc aacaagagat ggcagttcaa caggcagtct    3420
ggcttcctgt ctcagatgtg gattggagac aagaagcagc tcctcaccccc tctcagggac    3480 caattcacca gggctcctct ggacaatgac attggagtgt ctgaggccac caggattgac    3540
```

```
ccaaatgctt gggtggagag gtggaaggct gctggacact accaggctga ggctgccctg   3600
ctccagtgca cagcagacac cctggctgat gctgttctga tcaccacagc ccatgcttgg   3660
cagcaccaag gcaagaccct gttcatcagc agaaagacct acaggattga tggctctgga   3720
cagatggcaa tcacagtgga tgtggaggtt gcctctgaca cacctcaccc tgcaaggatt   3780
ggcctgaact gtcaactggc acaggtggct gagagggtga actggctggg cttaggccct   3840
caggagaact accctgacag gctgacagct gcctgctttg acaggtggga cctgcctctg   3900
tctgacatgt acaccccctta tgtgttccct tctgagaatg gcctgaggtg tggcaccagg   3960
gagctgaact atggtcctca ccagtggagg ggagacttcc agttcaacat ctccaggtac   4020
tctcagcaac agctcatgga aacctctcac aggcacctgc tccatgcaga ggagggaacc   4080
tggctgaaca ttgatggctt ccacatgggc attggaggag atgactcttg gtctccttct   4140
gtgtctgctg agttccagtt atctgctggc aggtaccact atcagctggt gtggtgccag   4200
aagtaaacct aatctagcag ctcgctgatc agcctcgact gtgccttcta gttgccagcc   4260
atctgttgtt tgcccctccc ccgtgccttc cttgaccctg gaaggtgcca ctcccactgt   4320
cctttcctaa taaaatgagg aaattgcatc gcattgtctg agtaggtgtc attctattct   4380
gggggggtggg gtggggcagg acagcaaggg ggaggattgg gaagacaata gcaggcatgc   4440
tggggatgcg gtgggctcta tggcttctga ggcggaaaga accagctggg gctcgatcct   4500
ctagttggcg cgtcatggtc catatgaata tcctccttag ttcctattcc gaagttccta   4560
ttctctagaa agtataggaa cttcggcgcg tcgacattga ttattgacta gttattaata   4620
gtaatcaatt acggggtcat tagttcatag cccatatatg gagttccgcg ttacataact   4680
tacggtaaat ggcccgcctg gctgaccgcc caacgacccc cgcccattga cgtcaataat   4740
gacgtatgtt cccatagtaa cgccaatagg gactttccat tgacgtcaat gggtggacta   4800
tttacggtaa actgcccact tggcagtaca tcaagtgtat catatgccaa gtacgccccc   4860
tattgacgtc aatgacggta aatggcccgc ctggcattat gcccagtaca tgaccttatg   4920
ggactttcct acttggcagt acatctacgt attagtcatc gctattacca tgggtcgagg   4980
tgagccccac gttctgcttc actctcccca tctcccccccc ctcccacccc caatttttgt   5040
atttatttat tttttaatta ttttgtgcag cgatggggggc gggggggggg ggggcgcgcg   5100
ccaggcgggg cggggcgggg cgaggggcgg ggcggggcga ggcggagagg tgcggcggca   5160
gccaatcaga gcggcgcgct ccgaaagttt cctttttatgg cgaggcggcg gcggcggcgg   5220
ccctataaaa agcgaagcgc gcggcgggcg ggagtcgctg cgttgccttc gccccgtgcc   5280
ccgctccgcg ccgcctcgcg ccgcccgccc cggctctgac tgaccgcgtt actcccacag   5340
gtgagcgggc gggacggccc ttctcctccg ggctgtaatt agcgcttggt ttaatgacgg   5400
ctcgtttctt ttctgtggct gcgtgaaagc cttaaagggc tccgggaggg cctttgtgc    5460
ggggggagc ggctcggggg gtgcgtgcgt gtgtgtgtgc gtggggagcg ccgcgtgcgg   5520
cccgcgctgc ccggcggctg tgagcgctgc gggcgcggcg cggggctttg tgcgctccgc   5580
gtgtgcgcga ggggagcgcg gccggggggcg gtgcccgcg gtgcggggg gctgcgaggg   5640
gaacaaaggc tgcgtgcggg gtgtgtgcgt gggggggtga gcaggggtg tgggcgcggc   5700
ggtcgggctg taaccccccc ctgcaccccc ctccccgagt tgctgagcac ggcccggctt   5760
cgggtgcggg gctccgtgcg gggcgtggcg cggggctcgc cgtgccgggc gggggtggc    5820
ggcaggtggg ggtgccgggc ggggcggggc cgctcgggc cggggagggc tcggggagg    5880
ggcgcggcgg ccccggagcg ccggcggctg tcgaggcgcg gcgagccgca gccattgcct   5940
```

```
tttatggtaa tcgtgcgaga gggcgcaggg acttcctttg tcccaaatct ggcggagccg    6000
aaatctggga ggcgccgccg cacccctct agcgggcgcg ggcgaagcgg tgcggcgccg     6060
gcaggaagga aatgggcggg gagggccttc gtgcgtcgcc gcgccgccgt cccttctcc     6120 atctccagcc tcgggctgc cgcagggga cggctgcctt cgggggggac ggggcagggc      6180
ggggttcggc ttctggcgtg tgaccggcgg ctctagagcc tctgctaacc atgttcatgc    6240
cttcttcttt ttcctacagc tcctgggcaa cgtgctggtt attgtgctgt ctcatcattt    6300
tggcaaagaa ttcgccacca tggtgagcaa gggcgaggag ctgttcaccg ggtggtgcc     6360 catcctggtc gagctggacg gcgacgtaaa cggccacaag ttcagcgtgt ccggcgaggg    6420
cgagggcgat gccacctacg gcaagctgac cctgaagttc atctgcacca ccggcaagct    6480
gcccgtgccc tggcccaccc tcgtgaccac cctgacctac ggcgtgcagt gcttcagccg    6540
ctaccccgac cacatgaagc agcacgactt cttcaagtcc gccatgcccg aaggctacgt    6600
ccaggagcgc accatcttct tcaaggacga cggcaactac aagacccgcg ccgaggtgaa    6660
gttcgagggc gacaccctgg tgaaccgcat cgagctgaag ggcatcgact tcaaggagga    6720
cggcaacatc ctggggcaca gctggagta caactacaac agccacaacg tctatatcat     6780
ggccgacaag cagaagaacg gcatcaaggt gaacttcaag atccgccaca acatcgagga    6840
cggcagcgtg cagctcgccg accactacca gcagaacacc cccatcggcg acggccccgt    6900
gctgctgccc gacaaccact acctgagcac ccagtccgcc ctgagcaaag accccaacga    6960
gaagcgcgat cacatggtcc tgctggagtt cgtgaccgcc gccgggatca ctctcggcat    7020
ggacgagctg tacaagtaaa gcggccgcga ctctagatca taatcagcca taccacattt    7080
gtagaggttt tacttgcttt aaaaaacctc ccacacctcc ccctgaacct gaaacataaa    7140
atgaatgcaa ttgttgttgt taacttgttt attgcagctt ataatggtta caaataaagc    7200
aatagcatca caatttcac aaataaagca ttttttcac tgcattctag ttgtggtttg      7260
tccaaactca tcaatgtatc ttaagataac ttcgtataat gtatgctata cgaagttata    7320
taacttcgta taatgtgtac tatacgaagt tataaatgaa gttcctattc cgaagttcct    7380
attctctaga aagtatagga acttcgaagc agctccagcc tacacaatcg ctcaagacgt    7440
gtaatgcttt tattatatat tagtcacgat atctataaca agaaaatata tataataa     7500 gttatcacgt aagtagaaca tgaaataaca atataattat cgtatgagtt aaatcttaaa    7560
agtcacgtaa aagataatca tgcgtcattt tgactcacgc ggtcgttata gttcaaaatc    7620
agtgacactt accgcattga caagcacgcc tcacgggagc tccaagcggc gactgagatg    7680
tcctaaatgc acagcgacgg attcgcgcta tttagaaaga gagagcaata tttcaagaat    7740
gcatgcgtca attttacgca gactatcttt ctagggttaa aaaagatttg cgctttactc    7800
gacctaaact ttaaacacgt catagaatct tcgtttgaca aaaaccacat tgtggggtac    7860
cgagctcgaa ttcatcgatg atatcagatc tgccggtctc cctatagtga gtcgtattaa    7920
tttcgataag ccaggttaac ctgcattaat gaatcggcca acgcgcgggg agaggcggtt    7980
tgcgtattgg gcgctcttcc gcttcctcgc tcactgactc gctgcgctcg gtcgttcggc    8040
tgcggcgagc ggtatcagct cactcaaagg cggtaatacg ttatccaca gaatcagggg     8100 ataacgcagg aaagaacatg tgagcaaaag gccagcaaaa ggccaggaac cgtaaaaagg    8160
ccgcgttgct ggcgtttttc cataggctcc gcccccctga cgagcatcac aaaaatcgac    8220
gctcaagtca gaggtggcga aacccgacag gactataaag ataccaggcg tttccccctg    8280
gaagctccct cgtgcgctct cctgttccga cctgccgct taccggatac ctgtccgcct     8340
```

| | |
|---|---|
| ttctcccttc gggaagcgtg gcgctttctc atagctcacg ctgtaggtat ctcagttcgg | 8400 |
| tgtaggtcgt tcgctccaag ctgggctgtg tgcacgaacc ccccgttcag cccgaccgct | 8460 |
| gcgccttatc cggtaactat cgtcttgagt ccaacccggt aagacacgac ttatcgccac | 8520 |
| tggcagcagc cactggtaac aggattagca gagcgaggta tgtaggcggt gctacagagt | 8580 |
| tcttgaagtg gtggcctaac tacggctaca ctagaagaac agtatttggt atctgcgctc | 8640 |
| tgctgaagcc agttaccttc ggaaaaagag ttggtagctc ttgatccggc aaacaaacca | 8700 |
| ccgctggtag cggtggtttt tttgtttgca agcagcagat tacgcgcaga aaaaaggat | 8760 |
| ctcaagaaga tcctttgatc ttttctacgg ggtctgacgc tcagtggaac gaaaactcac | 8820 |
| gttaagggat tttggtcatg agattatcaa aaaggatctt cacctagatc cttttaaatt | 8880 |
| aaaaatgaag ttttaaatca atctaaagta tatatgagta aacttggtct gacagttacc | 8940 |
| aatgcttaat cagtgaggca cctatctcag cgatctgtct atttcgttca tccatagttg | 9000 |
| cctgactccc cgtcgtgtag ataactacga tacgggaggg cttaccatct ggccccagtg | 9060 |
| ctgcaatgat accgcgagac ccacgctcac cggctccaga tttatcagca ataaaccagc | 9120 |
| cagccggaag ggccgagcgc agaagtggtc ctgcaacttt atccgcctcc atccagtcta | 9180 |
| ttaattgttg ccgggaagct agagtaagta gttcgccagt taatagtttg cgcaacgttg | 9240 |
| ttgccattgc tacaggcatc gtggtgtcac gctcgtcgtt tggtatggct tcattcagct | 9300 |
| ccggttccca acgatcaagg cgagttacat gatcccccat gttgtgcaaa aaagcggtta | 9360 |
| gctccttcgg tcctccgatc gttgtcagaa gtaagttggc cgcagtgtta tcactcatgg | 9420 |
| ttatggcagc actgcataat tctcttactg tcatgccatc cgtaagatgc ttttctgtga | 9480 |
| ctggtgagta ctcaaccaag tcattctgag aatagtgtat gcggcgaccg agttgctctt | 9540 |
| gcccggcgtc aatacgggat aataccgcgc cacatagcag aactttaaaa gtgctcatca | 9600 |
| ttggaaaacg ttcttcgggg cgaaaactct caaggatctt accgctgttg agatccagtt | 9660 |
| cgatgtaacc cactcgtgca cccaactgat cttcagcatc ttttactttc accagcgttt | 9720 |
| ctgggtgagc aaaaacagga aggcaaaatg ccgcaaaaaa gggaataagg gcgacacgga | 9780 |
| aatgttgaat actcatactc ttccttttc aatattattg aagcatttat cagggttatt | 9840 |
| gtctcatgag cggatacata tttgaatgta tttagaaaaa taaacaaata ggggttccgc | 9900 |
| gcacatttcc ccgaaaagtg ccacctgacg tctaagaaac cattattatc atgacattaa | 9960 |
| cctataaaaa taggcgtatc acgaggccct ttcgtctcgc gcgtttcggt gatgacggtg | 10020 |
| aaaacctctg acacatgcag ctcccggaga cggtcacagc ttgtctgtaa gcggatgccg | 10080 |
| ggagcagaca agcccgtcag ggcgcgtcag cgggtgttgg cgggtgtcgg ggctggctta | 10140 |
| actatgcggc atcagagcag attgtactga gagtgcacca tatggacata ttgtcgttag | 10200 |
| aacgcggcta caattaatac ataaccttat gtatcataca catacgattt aggtgacact | 10260 |
| atagaactcg acctcgaggc tggcacgaca ggtttcccga ctggaaagcg ggcagtgagc | 10320 |
| gcaacgcaat taatgtgagt tagctcactc attaggcacc ccaggcttta cactttatgc | 10380 |
| ttccggctcg tatgttgtgt ggaattgtga gcggataaca atttcacaca ggaaacagct | 10440 |
| atgaccatga ttacgccaag ctcgaaatta accctcacta aagggaacaa agctggagc | 10500 |
| tcgtctttga tcaaaacgca aatcgacgaa aatgtgtcgg acaatatcaa gtcgatgagc | 10560 |
| gaaaaactaa aaaggctaga atacgacaat ctcacagaca gcgttgagat atacggtatt | 10620 |
| cacgacagca ggctgaataa taaaaaaatt agaaactatt at | 10662 |

<210> SEQ ID NO 108

<211> LENGTH: 3144
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 108

| | | | | | |
|---|---|---|---|---|---|
| ccaaataatg | attttatttt | gactgatagt | gacctgttcg | ttgcaacaaa | ttgataagca | 60 |
| atgctttttt | ataatgccaa | ctttgtacaa | aaaagcaggc | tttaaaggaa | ccaattcagt | 120 |
| cgactggatc | cggtaccgaa | ttcgcttact | aaaagccaga | taacagtatg | cgtatttgcg | 180 |
| cgctgatttt | tgcggtataa | gaatatatac | tgatatgtat | acccgaagta | tgtcaaaaag | 240 |
| aggtgtgctt | ctagaatgca | gtttaaggtt | tacacctata | aaagagagag | ccgttatcgt | 300 |
| ctgtttgtgg | atgtacagag | tgatattatt | gacacgcccg | ggcgacggat | agtgatcccc | 360 |
| ctggccagtg | cacgtctgct | gtcagataaa | gtctcccgtg | aactttaccc | ggtggtgcat | 420 |
| atcggggatg | aaagctggcg | catgatgacc | accgatatgg | ccagtgtgcc | ggtctccgtt | 480 |
| atcgggggaag | aagtggctga | tctcagccac | cgcgaaaatg | acatcaaaaa | cgccattaac | 540 |
| ctgatgttct | ggggaatata | gaattcgcgg | ccgcactcga | gatatctaga | cccagctttc | 600 |
| ttgtacaaag | ttggcattat | aagaaagcat | tgcttatcaa | tttgttgcaa | cgaacaggtc | 660 |
| actatcagtc | aaaataaaat | cattatttgc | catccagctg | cagctgtcaa | acatgagaat | 720 |
| tacaacttat | atcgtatggg | gctgacttca | ggtgctacat | ttgaagagat | aaattgcact | 780 |
| gaaatctaga | atatttttat | ctgattaata | agatgatctt | cttgagatcg | ttttggtctg | 840 |
| cgcgtaatct | cttgctctga | aaacgaaaaa | accgccttgc | agggcggttt | ttcgaaggtt | 900 |
| ctctgagcta | ccaactcttt | gaaccgaggt | aactggcttg | gaggagcgca | gtcaccaaaa | 960 |
| cttgtccttt | cagtttagcc | ttaaccggcg | catgacttca | agactaactc | tctaaatca | 1020 |
| attaccagtg | gctgctgcca | gtggtgcttt | tgcatgtctt | tccgggttgg | actcaagacg | 1080 |
| atagttaccg | gataaggcgc | agcggtcgga | ctgaacgggg | ggttcgtgca | tacagtccag | 1140 |
| cttggagcga | actgcctacc | cggaactgag | tgtcaggcgt | ggaatgagac | aaacgcggcc | 1200 |
| ataacagcgg | aatgacaccg | gtaaaccgaa | aggcaggaac | aggagagcgc | acgagggagc | 1260 |
| cgccaggggg | aaacgcctgg | tatctttata | gtcctgtcgg | gtttcgccac | cactgatttg | 1320 |
| agcgtcagat | ttcgtgatgc | ttgtcagggg | ggcggagcct | atggaaaaac | ggctttgccg | 1380 |
| cggccctctc | acttccctgt | taagtatctt | cctggcatct | tccaggaaat | ctccgccccg | 1440 |
| ttcgtaagcc | atttccgctc | gccgcagtcg | aacgaccgag | cgtagcgagt | cagtgagcga | 1500 |
| ggaagcggaa | tatatcctgt | atcacatatt | ctgctgacgc | accggtgcag | cctttttttct | 1560 |
| cctgccacat | gaagcacttc | actgacaccc | tcatcagtgc | caacatagta | agccagtata | 1620 |
| cactccgcta | gcgctgaggt | ctgcctcgtg | aagaaggtgt | tgctgactca | taccaggcct | 1680 |
| gaatcgcccc | atcatccagc | cagaaagtga | gggagccacg | gttgatgaga | gctttgttgt | 1740 |
| aggtggacca | gttggtgatt | ttgaactttt | gctttgccac | ggaacggtct | gcgttgtcgg | 1800 |
| gaagatgcgt | gatctgatcc | ttcaactcag | caaaagttcg | atttattcaa | caaagccacg | 1860 |
| ttgtgtctca | aaatctctga | tgttacattg | cacaagataa | aaatatatca | tcatgaacaa | 1920 |
| taaaactgtc | tgcttacata | aacagtaata | caaggggtgt | tatgagccat | attcaacggg | 1980 |
| aaacgtcttg | ctcgaggccg | cgattaaatt | ccaacatgga | tgctgattta | tatgggtata | 2040 |
| aatgggctcg | cgataatgtc | gggcaatcag | gtgcgacaat | ctatcgattg | tatgggaagc | 2100 |
| ccgatgcgcc | agagttgttt | ctgaaacatg | gcaaaggtag | cgttgccaat | gatgttacag | 2160 |

```
atgagatggt cagactaaac tggctgacgg aatttatgcc tcttccgacc atcaagcatt      2220
ttatccgtac tcctgatgat gcatggttac tcaccactgc gatccccggg aaaacagcat      2280
tccaggtatt agaagaatat cctgattcag gtgaaaatat tgttgatgcg ctggcagtgt      2340
tcctgcgccg gttgcattcg attcctgttt gtaattgtcc ttttaacagc gatcgcgtat      2400
ttcgtctcgc tcaggcgcaa tcacgaatga ataacggttt ggttgatgcg agtgattttg      2460
atgacgagcg taatggctgg cctgttgaac aagtctggaa agaaatgcat aagcttttgc      2520
cattctcacc ggattcagtc gtcactcatg gtgatttctc acttgataac cttattttg      2580 acgagggaa attaataggt tgtattgatg ttggacgagt cggaatcgca gaccgatacc       2640
aggatcttgc catcctatgg aactgcctcg gtgagttttc tccttcatta cagaaacggc      2700
tttttcaaaa atatggtatt gataatcctg atatgaataa attgcagttt catttgatgc      2760
tcgatgagtt tttctaatca gacatgttct ttcctgcgtt atcccctgat tctgtggata      2820
accgtattac cgctagcatg gatctcgggg acgtctaact actaagcgag agtagggaac      2880
tgccaggcat caaataaaac gaaaggctca gtcggaagac tgggcctttc gttttatctg      2940
ttgtttgtcg gtgaacgctc tcctgagtag gacaaatccg ccgggagcgg atttgaacgt      3000
tgtgaagcaa cggcccggag ggtggcgggc aggacgcccg ccataaactg ccaggcatca      3060
aactaagcag aaggccatcc tgacggatgg ccttttgcg tttctacaaa ctcttcctgt       3120
tagttagtta cttaagctcg ggcc                                             3144

<210> SEQ ID NO 109
<211> LENGTH: 3048
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 109
agaaggccat cctgacggat ggccttttg cgtttctaca aactcttcct gttagttagt        60
tacttaagct cgggccccaa ataatgattt tattttgact gatagtgacc tgttcgttgc       120
aacaaattga taagcaatgc ttttttataa tgccaacttt gtacaaaaaa gcaggcttta      180
aaggaaccaa ttcagtcgac tggatccggt accgaattcg cttactaaaa gccagataac      240
agtatgcgta tttgcgcgct gattttgcg gtataagaat atatactgat atgtataccc       300
gaagtatgtc aaaaagaggt gtgcttctag aatgcagttt aaggtttaca cctataaaag      360
agagagccgt tatcgtctgt ttgtggatgt acagagtgat attattgaca cgcccgggcg      420
acggatagtg atccccctgg ccagtgcacg tctgctgtca gataaagtct cccgtgaact      480
ttacccggtg gtgcatatcg gggatgaaag ctggcgcatg atgaccaccg atatggccag      540
tgtgccggtc tccgttatcg gggaagaagt ggctgatctc agccaccgcg aaaatgacat      600
caaaaacgcc attaacctga tgttctgggg aatatagaat tcgcggccgc actcgagata      660
tctagaccca gctttcttgt acaaagttgg cattataaga aagcattgct tatcaatttg      720
ttgcaacgaa caggtcacta tcagtcaaaa taaaatcatt atttgccatc cagctgcagc      780
tgtcaaacat gagaattaca acttatatcg tatgggctg acttcaggtg ctacatttga       840
agagataaat tgcactgaaa tctagaaata ttttatctga ttaataagat gatcttcttg      900
agatcgtttt ggtctgcgcg taatctcttg ctctgaaaac gaaaaaaccg ccttgcaggg      960
cggtttttcg aaggttctct gagctaccaa ctctttgaac cgaggtaact ggcttggagg     1020
```

| | | | | | |
|---|---|---|---|---|---|
| agcgcagtca | ccaaaacttg | tcctttcagt | ttagccttaa | ccggcgcatg | acttcaagac | 1080 |
| taactcctct | aaatcaatta | ccagtggctg | ctgccagtgg | tgcttttgca | tgtctttccg | 1140 |
| ggttggactc | aagacgatag | ttaccggata | aggcgcagcg | gtcggactga | acggggggtt | 1200 |
| cgtgcataca | gtccagcttg | gagcgaactg | cctacccgga | actgagtgtc | aggcgtggaa | 1260 |
| tgagacaaac | gcggccataa | cagcggaatg | acaccggtaa | accgaaaggc | aggaacagga | 1320 |
| gagcgcacga | gggagccgcc | aggggaaac | gcctggtatc | tttatagtcc | tgtcgggttt | 1380 |
| cgccaccact | gatttgagcg | tcagatttcg | tgatgcttgt | caggggggcg | gagcctatgg | 1440 |
| aaaaacggct | ttgccgcggc | cctctcactt | ccctgttaag | tatcttcctg | gcatcttcca | 1500 |
| ggaaatctcc | gccccgttcg | taagccattt | ccgctcgccg | cagtcgaacg | accgagcgta | 1560 |
| gcgagtcagt | gagcgaggaa | gcggaatata | tcctgtatca | catattctgc | tgacgcaccg | 1620 |
| gtgcagcctt | ttttctcctg | ccacatgaag | cacttcactg | acaccctcat | cagtgccaac | 1680 |
| atagtaagcc | agtatacact | ccgctagcgc | tgatgtccgg | cggtgctttt | gccgttacgc | 1740 |
| accaccccgt | cagtagctga | acaggaggga | cagctgatag | aaacagaagc | cactggagca | 1800 |
| cctcaaaaac | accatcatac | actaaatcag | taagttggca | gcatcacccg | acgcactttg | 1860 |
| cgccgaataa | atacctgtga | cggaagatca | cttcgcagaa | taaataaatc | ctggtgtccc | 1920 |
| tgttgatacc | gggaagccct | gggccaactt | ttggcgaaaa | tgagacgttg | atcggcacgt | 1980 |
| aagaggttcc | aactttcacc | ataatgaaat | aagatcacta | ccgggcgtat | tttttgagtt | 2040 |
| atcgagattt | tcaggagcta | aggaagctaa | aatggagaaa | aaaatcactg | gatataccac | 2100 |
| cgttgatata | tcccaatggc | atcgtaaaga | acattttgag | gcatttcagt | cagttgctca | 2160 |
| atgtacctat | aaccagaccg | ttcagctgga | tattacggcc | tttttaaaga | ccgtaaagaa | 2220 |
| aaataagcac | aagttttatc | cggcctttat | tcacattctt | gcccgcctga | tgaatgctca | 2280 |
| tccggaattc | cgtatggcaa | tgaaagacgg | tgagctggtg | atatgggata | gtgttcaccc | 2340 |
| ttgttacacc | gttttccatg | agcaaactga | aacgttttca | tcgctctgga | gtgaatacca | 2400 |
| cgacgatttc | cggcagtttc | tacacatata | ttcgcaagat | gtggcgtgtt | acggtgaaaa | 2460 |
| cctggcctat | ttccctaaag | ggtttattga | gaatatgttt | ttcgtctcag | ccaatccctg | 2520 |
| ggtgagtttc | accagttttg | atttaaacgt | ggccaatatg | gacaacttct | tcgcccccgt | 2580 |
| tttcaccatg | ggcaaatatt | atacgcaagg | cgacaaggtg | ctgatgccgc | tggcgattca | 2640 |
| ggttcatcat | gccgtctgtg | atggcttcca | tgtcggcaga | atgcttaatg | aattacaaca | 2700 |
| gtactgcgat | gagtggcagg | gcggggcgta | atttttttaa | ggcagttatt | ggtgccctta | 2760 |
| aacatgttct | ttcctgcgtt | atcccctgat | tctgtggata | accgtattac | cgctagcatg | 2820 |
| gatctcgggg | acgtctaact | actaagcgag | agtaggaac | tgccaggcat | caaataaaac | 2880 |
| gaaaggctca | gtcggaagac | tgggcctttc | gttttatctg | ttgtttgtcg | gtgaacgctc | 2940 |
| tcctgagtag | gacaaatccg | ccgggagcgg | atttgaacgt | tgtgaagcaa | cggcccggag | 3000 |
| ggtggcgggc | aggacgcccg | ccataaactg | ccaggcatca | aactaagc | | 3048 |

<210> SEQ ID NO 110
<211> LENGTH: 7904
<212> TYPE: DNA
<213> ORGANISM: Artificial Sequence
<220> FEATURE:
<223> OTHER INFORMATION: Description of Artificial Sequence:  note = Synthetic Construct

<400> SEQUENCE: 110
gaactcgacg gcgcgccgcg attaaccccca agaagaagag gaaggtgagc aagcagatcc      60

```
tgaagaacac cggcctgcag gagatcatga gcttcaaggt gaacctggag ggcgtggtga    120
acaaccacgt gttcaccatg gagggctgcg gcaagggcaa catcctgttc ggcaaccagc    180
tggtgcagat ccgcgtgacc aagggcgccc ccctgccctt cgccttcgac atcctgagcc    240
ccgccttcca gtacggcaac cgcaccttca ccaagtaccc cgaggacatc agcgacttct    300
tcatccagag cttccccgcc ggcttcgtgt acgagcgcac cctgcgctac gaggacggcg    360
gcctggtgga gatccgcagc gacatcaacc tgatcgagga gatgttcgtg taccgcgtgg    420
agtacaaggg ccgcaacttc cccaacgacg gccccgtgat gaagaagacc atcaccggcc    480
tgcagcccag cttcgaggtg gtgtacatga cgacggcgt gctggtgggc caggtgatcc    540
tggtgtaccg cctgaacagc ggcaagttct acagctgcca catgcgcacc ctgatgaaga    600
gcaagggcgt ggtgaaggac ttccccgagt accacttcat ccagcaccgc ctggagaaga    660
cctacgtgga ggacggcggc ttcgtggagc agcacgagac cgccatcgcc cagctgacca    720
gcctgggcaa gcccctgggc agcctgcacg agtgggtgta ataggaattc gcccttgtta    780
attaagcggc gcgccgtgag caagggcgag gagctgttca ccggggtggt gcccatcctg    840
gtcgagctgg acggcgacgt aaacggccac aagttcagcg tgtccggcga gggcgagggc    900
gatgccacct acggcaagct gaccctgaag ttcatctgca ccaccggcaa gctgcccgtg    960
ccctggccca cccctcgtga cacccctgacc tacggcgtgc agtgcttcag ccgctacccc    1020
gaccacatga agcagcacga cttcttcaag tccgccatgc ccgaaggcta cgtccaggag    1080
cgcaccatct tcttcaagga cgacggcaac tacaagaccc gcgccgaggt gaagttcgag    1140
ggcgacaccc tggtgaaccg catcgagctg aagggcatcg acttcaagga ggacggcaac    1200
atcctggggc acaagctgga gtacaactac aacagccaca acgtctatat catggccgac    1260
aagcagaaga acggcatcaa ggtgaacttc aagatccgcc acaacatcga ggacggcagc    1320
gtgcagctcg ccgaccacta ccagcagaac ccccccatcg gcgacggccc cgtgctgctg    1380
cccgacaacc actacctgag cacccagtcc gccctgagca agacccccaa cgagaagcgc    1440
gatcacatgg tcctgctgga gttcgtgacc gccgccggga tcactctcgg catggacgag    1500
ctgtacaagt aaagcggccg cgactctaga tcataatcag ccataccaca tttgtagagg    1560
ttttacttgc tttaaaaaac ctcccacacc tccccctgaa cctgaaacat aaaatgaatg    1620
caattgttgt tgttaacttg tttattgcag cttataatgg ttacaaataa agcaatagca    1680
tcacaaattt cacaaataaa gcatttttt cactgcattc tagttgtggt ttgtccaaac    1740
tcatcaatgt atcttaagga tccgccgata agggcgaatt cataacttcg tataatgtat    1800
gctatacgaa gttatggatc tgtcgatcga cggatcgatc cgaacaaacg acccaacacc    1860
cgtgcgtttt attctgtctt tttattgccg atcccctcag aagaactcgt caagaaggcg    1920
atagaaggcg atgcgctgcg aatcgggagc ggcgataccg taaagcacga ggaagcggtc    1980
agcccattcg ccgccaagct cttcagcaat atcacgggta gccaacgcta tgtcctgata    2040
gcggtccgcc acacccagcc ggccacagtc gatgaatcca gaaaagcggc cattttccac    2100
catgatattc ggcaagcagg catcgccatg ggtcacgacg agatcctcgc cgtcgggcat    2160
gcgcgccttg agcctggcga acagttcggc tggcgcgagc ccctgatgct cttcgtccag    2220
atcatcctga tcgacaagac cggcttccat ccgagtacgt gctcgctcga tgcgatgttt    2280
cgcttggtgg tcgaatgggc aggtagccgg atcaagcgta tgcagccgcc gcattgcatc    2340
agccatgatg gatactttct cggcaggagc aaggtgagat gacaggagat cctgccccgg    2400
cacttcgccc aatagcagcc agtcccttcc cgcttcagtg acaacgtcga gcacagctgc    2460
```

```
gcaaggaacg cccgtcgtgg ccagccacga tagccgcgct gcctcgtcct gcagttcatt    2520
cagggcaccg gacaggtcgg tcttgacaaa aagaaccggg cgcccctgcg ctgacagccg    2580
gaacacggcg gcatcagagc agccgattgt ctgttgtgcc cagtcatagc cgaatagcct    2640
ctccacccaa gcggccggag aacctgcgtg caatccatct tgttcaatgg ccgatcccat    2700
attggctgca cggatcctga acggcagagg ttacggcagt ttgtctctcc cccttccggg    2760
agccaccttc ttctccaacc gtcccggtcg cgctctcggc gcttctgagg agagaactgg    2820
ctgagtgacg ccctttatag attcgccctt gtgtcccgcc ccttcctttc ccgccctccc    2880
ttgcgctacg gggccgcccg caccggccta cacggagcgc gcgcggcgga gttgttgacg    2940
ctagggctcc ggctccctgg ttgggtgttc tttctgacgc gacaggagga ggagaatgtc    3000
ctggtcctgt cgtcctcctt tcgggtttcc cgtgcactca aaccgaggac ttacagaacg    3060
gaggataaag ttaggccatt tttactcagc ttcggagttc aggctcattt ttcagctaaa    3120
gtctctcatt agtatcccc cacacacatc gggaaaatgg tttgtcctac gcatcggtaa    3180
tgaaggcggg gcccttcggg tcctccggag cgggttccgg gggtggggggg aaggagggag    3240 ggacgggacg ggcctcgttc atgaatattc agttcaccgc tgaatatgca taaggcaggc    3300
aagatggcgc gtccaatcaa ttggaagtag ccgttattag tggagaggcc ccaggacgtt    3360
ggggcaccgc ctgtgctcta gtagctttac ggagccctgg cgctcgatgt tcaagcccaa    3420
gctttcgcga gctcgaccga acaaacgacc caacacccgt gcgtttttatt ctgtcttttt    3480 attgccgctc agctttacag tgacaatgac ggctggcgac tgaatattag tgcttacaga    3540
cagcactaca tattttccgt cgatgttgaa atcctttctc atatgtcacc ataaatatca    3600
aataattata gcaatcattt acgcgttaat ggctaatcgc catcttccag caggcgcacc    3660
attgcccctg tttcactatc caggttacgg atatagttca tgacaatatt tacattggtc    3720
cagccaccag cttgcatgat ctccggtatt gaaactccag cgcgggccat atctcgcgcg    3780
gctccgacac gggcactgtg tccagaccag gccaggtatc tctgaccaga gtcatcctaa    3840
aatacacaaa caattagaat cagtagttta acacattata cacttaaaaa tttttatattt    3900 accttagcgc cgtaaatcaa tcgatgagtt gcttcaaaaa tcccttccag ggcgcgagtt    3960
gatagctggc tggtggcaga tggcgcggca acaccatttt ttctgacccg gcaaaacagg    4020
tagttattcg gatcatcagc tacaccagag acggaaatcc atcgctcgac cagtttagtt    4080
acccccaggc taagtgcctt ctctacacct gcggtgctaa ccagcgtttt cgttctgcca    4140
atatggatta acattctccc accgtcagta cgtgagatat ctttaaccct gatcctggca    4200
atttcggcta tacgtaacag ggtgttataa gcaatcccca gaaatgccag attacgtata    4260
tcctggcagc gatcgctatt ttccatgagt gaacgaacct ggtcgaaatc agtgcgttcg    4320
aacgctagag cctgttttgc acgttcaccg gcatcaacgt tttctttttcg gatccgccgc    4380 ataaccagtg aaacagcatt gctgtcactt ggtcgtggca gcccggaccg acgatgaagc    4440
atgtttagct ggcccaaatg ttgctggata gtttttactg ccagaccgcg cgcctgaaga    4500
tatagaagat aatcgcgaac atcttcaggt tctgcgggaa accatttccg gttattcaac    4560
ttgcaccatg ccgcccacga ccggcaaacg gacagaagca ttttccaggt atgctcagaa    4620
aacgcctggc gatccctgaa catgtccatc aggttcttgc gaacctcatc actcgttgca    4680
tcgaccggta atgcaggcaa attttggtgt acggtcagta aattggacac cttcctcttc    4740
ttcttgggca tggccgcagg aaagcagagc cctgaagctc ccatcaccgg ccaataagag    4800
ccaagcctgc agtgtgacct catagagcaa tgtgccagcc agcctgaccc caagggccct    4860
```

```
caggcttggg cacactgtct ctaggaccct gagagaaaga catacccatt tctgcttagg    4920
gccctgagga tgagcccagg ggtggcttgg cactgaagca aaggacactg gggctcagct    4980
ggcagcaaag tgaccaggat gctgaggctt tgacccagaa gccagaggcc agaggccagg    5040
acttctcttg gtcccagtcc accctcactc agagctttac caatgccctc tggatagttg    5100
tcgggtaacg gtggacgcca ctgattctct ggccagccta ggacttcgcc attccgctga    5160
ttctgctctt ccagccactg gctgaccggt tggaagtact ccagcagtgc cttggcatcc    5220
agggcatctg agcctaccag gtccttcagt acctcctgcc agggcctgga gcagccagcc    5280
tgcaacacct gcctgccaag cagagtgacc actgtgggca caggggacac agggtggggc    5340
ccacaacagc accattgtcc acttgtccct cactagtaaa agaactctag ggttgcgggg    5400
ggtgggggag gtctctgtga ggctggtaag ggatatttgc ctggcccatg gagatccata    5460
acttcgtata atgtatgcta tacgaagtta taagctttcg cgagctcgag atcctgcagg    5520
cgcgccggat ctgccggtct ccctatagtg agtcgtatta atttcgataa gccaggttaa    5580
cctgcattaa tgaatcggcc aacgcgcggg gagaggcggt ttgcgtattg ggcgctcttc    5640
cgcttcctcg ctcactgact cgctgcgctc ggtcgttcgg ctgcggcgag cggtatcagc    5700
tcactcaaag gcggtaatac ggttatccac agaatcaggg gataacgcag gaaagaacat    5760
gtgagcaaaa ggccagcaaa aggccaggaa ccgtaaaaag gccgcgttgc tggcgttttt    5820
ccataggctc cgcccccctg acgagcatca caaaaatcga cgctcaagtc agaggtggcg    5880
aaacccgaca ggactataaa gataccaggc gtttccccct ggaagctccc tcgtgcgctc    5940
tcctgttccg accctgccgc ttaccggata cctgtccgcc tttctccctt cgggaagcgt    6000
ggcgctttct catagctcac gctgtaggta tctcagttcg gtgtaggtcg ttcgctccaa    6060
gctgggctgt gtgcacgaac cccccgttca gcccgaccgc tgcgccttat ccggtaacta    6120
tcgtcttgag tccaacccgg taagacacga cttatcgcca ctggcagcag ccactggtaa    6180
caggattagc agagcgaggt atgtaggcgg tgctacagag ttcttgaagt ggtggcctaa    6240
ctacggctac actagaagaa cagtatttgg tatctgcgct ctgctgaagc cagttacctt    6300
cggaaaaaga gttggtagct cttgatccgg caaacaaacc accgctggta gcggtggttt    6360
ttttgtttgc aagcagcaga ttacgcgcag aaaaaaagga tctcaagaag atcctttgat    6420
cttttctacg gggtctgacg ctcagtggaa cgaaaactca cgttaaggga ttttggtcat    6480
gagattatca aaaaggatct tcacctagat ccttttaaat taaaaatgaa gttttaaatc    6540
aatctaaagt atatatgagt aaacttggtc tgacagttac caatgcttaa tcagtgaggc    6600
acctatctca gcgatctgtc tatttcgttc atccatagtt gcctgactcc ccgtcgtgta    6660
gataactacg atacgggagg gcttaccatc tggccccagt gctgcaatga taccgcgaga    6720
cccacgctca ccggctccag atttatcagc aataaaccag ccagccggaa gggccgagcg    6780
cagaagtggt cctgcaactt tatccgcctc catccagtct attaattgtt gccgggaagc    6840
tagagtaagt agttcgccag ttaatagttt gcgcaacgtt gttgccattg ctacaggcat    6900
cgtggtgtca cgctcgtcgt ttggtatggc ttcattcagc tccggttccc aacgatcaag    6960
gcgagttaca tgatccccca tgttgtgcaa aaaagcggtt agctccttcg gtcctccgat    7020
cgttgtcaga agtaagttgg ccgcagtgtt atcactcatg gttatggcag cactgcataa    7080
ttctcttact gtcatgccat ccgtaagatg cttttctgtg actggtgagt actcaaccaa    7140
gtcattctga gaatagtgta tgcggcgacc gagttgctct tgcccggcgt caatacggga    7200
taataccgcg ccacatagca gaactttaaa agtgctcatc attggaaaac gttcttcggg    7260
```

-continued

```
gcgaaaactc tcaaggatct taccgctgtt gagatccagt tcgatgtaac ccactcgtgc    7320
acccaactga tcttcagcat cttttacttt caccagcgtt tctgggtgag caaaaacagg    7380
aaggcaaaat gccgcaaaaa agggaataag ggcgacacgg aaatgttgaa tactcatact    7440
cttccttttt caatattatt gaagcattta tcagggttat tgtctcatga gcggatacat    7500
atttgaatgt atttagaaaa ataaacaaat aggggttccg cgcacatttc cccgaaaagt    7560
gccacctgac gtctaagaaa ccattattat catgacatta acctataaaa ataggcgtat    7620
cacgaggccc tttcgtctcg cgcgtttcgg tgatgacggt gaaaacctct gacacatgca    7680
gctcccggag acggtcacag cttgtctgta agcggatgcc gggagcagac aagcccgtca    7740
gggcgcgtca gcgggtgttg gcgggtgtcg ggctggctt aactatgcgg catcagagca    7800
gattgtactg agagtgcacc atatggacat attgtcgtta gaacgcggct acaattaata    7860 cataaccta tgtatcatac acatacgatt taggtgacac tata    7904
```

<210> SEQ ID NO 111
<211> LENGTH: 7904
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 111

```
gaactcgacg gcgcgccgcg attaacccca agaagaagag gaaggtgagc aagcagatcc      60
tgaagaacac cggcctgcag gagatcatga gcttcaaggt gaacctggag ggcgtggtga     120
acaaccacgt gttcaccatg gagggctgcg gcaagggcaa catcctgttc ggcaaccagc     180
tggtgcagat ccgcgtgacc aagggcgccc ccctgccctt cgccttcgac atcctgagcc     240
ccgccttcca gtacggcaac cgcaccttca ccaagtaccc cgaggacatc agcgacttct     300
tcatccagag cttccccgcc ggcttcgtgt acgagcgcac cctgcgctac gaggacggcg     360
gcctggtgga gatccgcagc gacatcaacc tgatcgagga gatgttcgtg taccgcgtgg     420
agtacaaggg ccgcaacttc cccaacgacg gccccgtgat gaagaagacc atcaccggcc     480
tgcagcccag cttcgaggtg gtgtacatga cgacggcgt gctggtgggc caggtgatcc     540
tggtgtaccg cctgaacagc ggcaagttct acagctgcca catgcgcacc ctgatgaaga     600
gcaagggcgt ggtgaaggac ttccccgagt accacttcat ccagcaccgc ctggagaaga     660
cctacgtgga ggacgcggc ttcgtggagc agcacgagc cgccatcgcc cagctgacca     720
gcctgggcaa gccctgggc agcctgcacg agtgggtgta ataggaattc gcccttgtta     780
attaagcggc gcgccgtgag caagggcgag gagctgttca ccggggtggt gcccatcctg     840
gtcgagctgg acggcgacgt aaacggccac aagttcagcg tgtccggcga gggcgagggc     900
gatgccacct acggcaagct gaccctgaag ttcatctgca ccaccggcaa gctgccgtg     960 ccctggccca ccctcgtgac cacctgacc tgggggtgc agtgcttcag ccgctacccc    1020
gaccacatga gcagcacga cttcttcaag tccgccatgc ccgaaggcta cgtccaggag    1080
cgcaccatct tcttcaagga cgacggcaac tacaagaccc gcgccgaggt gaagttcgag    1140
ggcgacaccc tggtgaaccg catcgagctg aagggcatcg acttcaagga ggacggcaac    1200
atcctggggc acaagctgga gtacaactac atcagccaca acgtctatat caccgccgac    1260
aagcagaaga acggcatcaa ggccaacttc aagatccgcc acaacatcga ggacggcagc    1320
gtgcagctcg ccgaccacta ccagcagaac acccccatcg gcgacggccc cgtgctgctg    1380
```

```
cccgacaacc actacctgag cacccagtcc gccctgagca agaccccaa cgagaagcgc    1440 gatcacatgg tcctgctgga gttcgtgacc gccgccggga tcactctcgg catggacgag    1500
ctgtacaagt aaagcggccg cgactctaga tcataatcag ccataccaca tttgtagagg    1560
ttttacttgc tttaaaaaac ctcccacacc tccccctgaa cctgaaacat aaaatgaatg    1620
caattgttgt tgttaacttg tttattgcag cttataatgg ttacaaataa agcaatagca    1680
tcacaaattt cacaaataaa gcattttttt cactgcattc tagttgtggt ttgtccaaac    1740
tcatcaatgt atcttaagga tccgccgata agggcgaatt cataacttcg tataatgtat    1800
gctatacgaa gttatggatc tgtcgatcga cggatcgatc cgaacaaacg acccaacacc    1860
cgtgcgtttt attctgtctt tttattgccg atccctcag aagaactcgt caagaaggcg    1920
atagaaggcg atgcgctgcg aatcgggagc ggcgataccg taaagcacga ggaagcggtc    1980
agcccattcg ccgccaagct cttcagcaat atcacgggta gccaacgcta tgtcctgata    2040
gcggtccgcc acacccagcc ggccacagtc gatgaatcca gaaaagcggc catttccac    2100 catgatattc ggcaagcagg catcgccatg ggtcacgacg agatcctcgc cgtcgggcat    2160
gcgcgccttg agcctggcga acagttcggc tggcgcgagc ccctgatgct cttcgtccag    2220
atcatcctga tcgacaagac cggcttccat ccgagtacgt gctcgctcga tgcgatgttt    2280
cgcttggtgg tcgaatgggc aggtagccgg atcaagcgta tgcagccgcc gcattgcatc    2340
agccatgatg gatactttct cggcaggagc aaggtgagat gacaggagat cctgccccgg    2400
cacttcgccc aatagcagcc agtcccttcc cgcttcagtg acaacgtcga gcacagctgc    2460
gcaaggaacg cccgtcgtgg ccagccacga tagccgcgct gcctcgtcct gcagttcatt    2520
cagggcaccg gacaggtcgg tcttgacaaa aagaaccggg cgcccctgcg ctgacagccg    2580
gaacacggcg gcatcagagc agccgattgt ctgttgtgcc cagtcatagc cgaatagcct    2640
ctccacccaa gcggccggag aacctgcgtg caatccatct tgttcaatgg ccgatcccat    2700
attggctgca cggatcctga acggcagagg ttacggcagt ttgtctctcc cccttccggg    2760
agccaccttc ttctccaacc gtcccggtcg cgctctcggc gcttctgagg agagaactgg    2820
ctgagtgacg ccctttatag attcgccctt gtgtcccgcc ccttcctttc ccgccctccc    2880
ttgcgctacg gggccgcccg caccggccta cacggagcgc gcgcggcgga gttgttgacg    2940
ctagggctcc ggctccctgg ttgggtgttc tttctgacgc gacaggagga ggagaatgtc    3000
ctggtcctgt cgtcctcctt tcgggttttcc cgtgcactca aaccgaggac ttacagaacg    3060
gaggataaag ttaggccatt tttactcagc ttcggagttc aggctcattt ttcagctaaa    3120
gtctctcatt agtatccccc cacacacatc gggaaaatgg tttgtcctac gcatcggtaa    3180
tgaaggcggg gcccttcggg tcctccggag cgggttccgg gggtgggggg aaggagggag    3240
ggacgggacg ggcctcgttc atgaatattc agttcaccgc tgaatatgca taaggcaggc    3300
aagatggcgc gtccaatcaa ttggaagtag ccgttattag tggagaggcc ccaggacgtt    3360
ggggcaccgc ctgtgctcta gtagctttac ggagccctgg cgctcgatgt tcaagcccaa    3420
gctttcgcga gctcgaccga acaaacgacc caacacccgt gcgttttatt ctgtcttttt    3480
attgccgctc agctttacag tgacaatgac ggctggcgac tgaatattag tgcttacaga    3540
cagcactaca tattttccgt cgatgttgaa atccttctc atatgtcacc ataaatatca    3600
aataattata gcaatcattt acgcgttaat ggctaatcgc catcttccag caggcgcacc    3660
attgcccctg tttcactatc caggttacgg atatagttca tgacaatatt tacattggtc    3720
cagccaccag cttgcatgat ctccggtatt gaaactccag cgcgggccat atctcgcgcg    3780
```

```
gctccgacac gggcactgtg tccagaccag gccaggtatc tctgaccaga gtcatcctaa   3840
aatacacaaa caattagaat cagtagttta acacattata cacttaaaaa ttttatattt   3900
accttagcgc cgtaaatcaa tcgatgagtt gcttcaaaaa tcccttccag ggcgcgagtt   3960
gatagctggc tggtggcaga tggcgcggca acaccatttt ttctgacccg gcaaaacagg   4020
tagttattcg gatcatcagc tacaccagag acggaaatcc atcgctcgac cagtttagtt   4080 accccccaggc taagtgcctt ctctacacct gcggtgctaa ccagcgtttt cgttctgcca   4140
atatggatta acattctccc accgtcagta cgtgagatat ctttaaccct gatcctggca   4200
atttcggcta tacgtaacag ggtgttataa gcaatcccca gaaatgccag attacgtata   4260
tcctggcagc gatcgctatt ttccatgagt gaacgaacct ggtcgaaatc agtgcgttcg   4320
aacgctagag cctgttttgc acgttcaccg gcatcaacgt tttcttttcg gatccgccgc   4380
ataaccagtg aaacagcatt gctgtcactt ggtcgtggca gcccggaccg acgatgaagc   4440
atgtttagct ggcccaaatg ttgctggata gttttttactg ccagaccgcg cgcctgaaga   4500
tatagaagat aatcgcgaac atcttcaggt tctgcgggaa accatttccg gttattcaac   4560
ttgcaccatg ccgcccacga ccggcaaacg gacagaagca ttttccaggt atgctcagaa   4620
aacgcctggc gatccctgaa catgtccatc aggttcttgc gaacctcatc actcgttgca   4680
tcgaccggta atgcaggcaa attttggtgt acgtcagta aattggacac cttcctcttc   4740
ttcttgggca tggccgcagg aaagcagagc cctgaagctc ccatcaccgg ccaataagag   4800
ccaagcctgc agtgtgacct catagagcaa tgtgccagcc agcctgaccc caagggccct   4860
caggcttggg cacactgtct ctaggaccct gagagaaaga catacccatt tctgcttagg   4920
gccctgagga tgagcccagg ggtggcttgg cactgaagca aggacactg gggctcagct    4980 ggcagcaaag tgaccaggat gctgaggctt tgacccagaa gccagaggcc agaggccagg   5040
acttctcttg gtcccagtcc accctcactc agagctttac caatgccctc tggatagttg   5100
tcgggtaacg gtggacgcca ctgattctct ggccagccta ggacttcgcc attccgctga   5160
ttctgctctt ccagccactg gctgaccggt tggaagtact ccagcagtgc cttggcatcc   5220
agggcatctg agcctaccag gtccttcagt acctcctgcc agggcctgga gcagccagcc   5280
tgcaacacct gcctgccaag cagagtgacc actgtgggca caggggacac agggtggggc   5340
ccacaacagc accattgtcc acttgtccct cactagtaaa agaactctag gttgcgggg    5400 ggtgggggag gtctctgtga ggctggtaag ggatatttgc ctggcccatg gagatccata   5460
acttcgtata atgtatgcta tacgaagtta taagctttcg cgagctcgag atcctgcagg   5520
cgcgccggat ctgccggtct ccctatagtg agtcgtatta atttcgataa gccaggttaa   5580
cctgcattaa tgaatcggcc aacgcgcggg gagaggcggt ttgcgtattg ggcgctcttc   5640
cgcttcctcg ctcactgact cgctgcgctc ggtcgttcgg ctgcggcgag cggtatcagc   5700
tcactcaaag gcggtaatac ggttatccac agaatcaggg gataacgcag aaagaacat    5760 gtgagcaaaa ggccagcaaa aggccaggaa ccgtaaaaag gccgcgttgc tggcgttttt   5820
ccataggctc cgcccccctg acgagcatca caaaaatcga cgctcaagtc agaggtggcg   5880
aaacccgaca ggactataaa gataccaggc gtttccccct ggaagctccc tcgtgcgctc   5940
tcctgttccg accctgccgc ttaccggata cctgtccgcc tttctccctt cgggaagcgt   6000
ggcgctttct catagctcac gctgtaggta tctcagttcg gtgtaggtcg ttcgctccaa   6060
gctgggctgt gtgcacgaac cccccgttca gcccgaccgc tgcgccttat ccggtaacta   6120
tcgtcttgag tccaacccgg taagacacga cttatcgcca ctggcagcag ccactggtaa   6180
```

```
caggattagc agagcgaggt atgtaggcgg tgctacagag ttcttgaagt ggtggcctaa    6240
ctacggctac actagaagaa cagtatttgg tatctgcgct ctgctgaagc cagttacctt    6300
cggaaaaaga gttggtagct cttgatccgg caaacaaacc accgctggta gcggtggttt    6360
ttttgtttgc aagcagcaga ttacgcgcag aaaaaaagga tctcaagaag atcctttgat    6420
cttttctacg gggtctgacg ctcagtggaa cgaaaactca cgttaaggga ttttggtcat    6480
gagattatca aaaaggatct tcacctagat ccttttaaat taaaaatgaa gttttaaatc    6540
aatctaaagt atatatgagt aaacttggtc tgacagttac caatgcttaa tcagtgaggc    6600
acctatctca gcgatctgtc tatttcgttc atccatagtt gcctgactcc ccgtcgtgta    6660
gataactacg atacgggagg gcttaccatc tggccccagt gctgcaatga taccgcgaga    6720
cccacgctca ccggctccag atttatcagc aataaaccag ccagccggaa gggccgagcg    6780
cagaagtggt cctgcaactt tatccgcctc catccagtct attaattgtt gccgggaagc    6840
tagagtaagt agttcgccag ttaatagttt gcgcaacgtt gttgccattg ctacaggcat    6900
cgtggtgtca cgctcgtcgt ttggtatggc ttcattcagc tccggttccc aacgatcaag    6960
gcgagttaca tgatccccca tgttgtgcaa aaaagcggtt agctccttcg gtcctccgat    7020
cgttgtcaga agtaagttgg ccgcagtgtt atcactcatg gttatggcag cactgcataa    7080
ttctcttact gtcatgccat ccgtaagatg cttttctgtg actggtgagt actcaaccaa    7140
gtcattctga aatagtgta tgcggcgacc gagttgctct tgcccggcgt caatacggga    7200
taataccgcg ccacatagca gaactttaaa agtgctcatc attggaaaac gttcttcggg    7260
gcgaaaactc tcaaggatct taccgctgtt gagatccagt tcgatgtaac ccactcgtgc    7320
acccaactga tcttcagcat cttttacttt caccagcgtt tctgggtgag caaaaacagg    7380
aaggcaaaat gccgcaaaaa agggaataag ggcgacacgg aaatgttgaa tactcatact    7440
cttccttttt caatattatt gaagcattta tcagggttat tgtctcatga gcggatacat    7500
atttgaatgt atttagaaaa ataaacaaat aggggttccg cgcacatttc cccgaaaagt    7560
gccacctgac gtctaagaaa ccattattat catgacatta acctataaaa ataggcgtat    7620
cacgaggccc tttcgtctcg cgcgtttcgg tgatgacggt gaaaacctct gacacatgca    7680
gctcccggag acggtcacag cttgtctgta gcggatgcc gggagcagac aagcccgtca    7740
gggcgcgtca gcgggtgttg gcgggtgtcg ggctggctt aactatgcgg catcagagca    7800
gattgtactg agagtgcacc atatggacat attgtcgtta aacgcggct acaattaata    7860 cataacctta tgtatcatac acatacgatt taggtgacac tata                    7904

<210> SEQ ID NO 112
<211> LENGTH: 7904
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 112
gaactcgacg gcgcgccgcg attaacccca agaagaagag gaaggtgagc aagcagatcc      60
tgaagaacac cggcctgcag gagatcatga gcttcaaggt gaacctggag gcgtggtga     120 acaaccacgt gttcaccatg gagggctgcg gcaagggcaa catcctgttc ggcaaccagc     180
tggtgcagat ccgcgtgacc aagggcgccc ccctgccctt cgccttcgac atcctgagcc     240
ccgccttcca gtacggcaac cgcacccttca ccaagtaccc cgaggacatc agcgacttct     300
tcatccagag cttccccgcc ggcttcgtgt acgagcgcac cctgcgctac gaggacgcg     360
```

```
gcctggtgga gatccgcagc gacatcaacc tgatcgagga gatgttcgtg taccgcgtgg    420
agtacaaggg ccgcaacttc cccaacgacg gccccgtgat gaagaagacc atcaccggcc    480
tgcagcccag cttcgaggtg gtgtacatga cgacggcgt gctggtgggc caggtgatcc    540
tggtgtaccg cctgaacagc ggcaagttct acagctgcca catgcgcacc ctgatgaaga    600
gcaagggcgt ggtgaaggac ttccccgagt accacttcat ccagcaccgc ctggagaaga    660
cctacgtgga ggacggcggc ttcgtggagc agcacgagac cgccatcgcc cagctgacca    720
gcctgggcaa gccctgggc agcctgcacg agtgggtgta ataggaattc gcccttgtta    780
attaagcggc gcgccgtgag caagggcgag gagctgttca ccggggtggt gcccatcctg    840
gtcgagctgg acggcgacgt aaacggccac aagttcagcg tgtccggcga gggcgagggc    900
gatgccacct acggcaagct gaccctgaag ttcatctgca ccaccggcaa gctgcccgtg    960
ccctggccca ccctcgtgac caccttcggc tacggcctgc agtgcttcgc ccgctacccc   1020
gaccacatga agcagcacga cttcttcaag tccgccatgc ccgaaggcta cgtccaggag   1080
cgcaccatct tcttcaagga cgacggcaac tacaagaccc gcgccgaggt gaagttcgag   1140
ggcgacaccc tggtgaaccg catcgagctg aagggcatcg acttcaagga ggacggcaac   1200
atcctggggc acaagctgga gtacaactac aacagccaca cgtctatat catggccgac   1260 aagcagaaga cggcatcaa ggtgaacttc aagatccgcc acaacatcga ggacggcagc   1320
gtgcagctcg ccgaccacta ccagcagaac ccccatcg gcgacggccc cgtgctgctg   1380
cccgacaacc actacctgag ctaccagtcc gccctgagca agacccccaa cgagaagcgc   1440
gatcacatgg tcctgctgga gttcgtgacc gccgccggga tcactctcgg catggacgag   1500
ctgtacaagt aaagcggccg cgactctaga tcataatcag ccataccaca tttgtagagg   1560
ttttacttgc tttaaaaaac ctcccacacc tccccctgaa cctgaaacat aaaatgaatg   1620
caattgttgt tgttaacttg tttattgcag cttataatgg ttacaaataa agcaatagca   1680
tcacaaattt cacaaataaa gcatttttt cactgcattc tagttgtggt ttgtccaaac   1740
tcatcaatgt atcttaagga tccgccgata agggcgaatt cataacttcg tataatgtat   1800
gctatacgaa gttatggatc tgtcgatcga cggatcgatc cgaacaaacg acccaacacc   1860
cgtgcgtttt attctgtctt tttattgccg atccctcag aagaactcgt caagaaggcg   1920
atagaaggcg atgcgctgcg aatcgggagc ggcgataccg taaagcacga ggaagcggtc   1980
agcccattcg ccgccaagct cttcagcaat atcacgggta gccaacgcta tgtcctgata   2040
gcggtccgcc acacccagcc ggccacagtc gatgaatcca gaaaagcggc catttccac   2100 catgatattc ggcaagcagg catcgccatg ggtcacgacg agatcctcgc cgtcgggcat   2160
gcgcgccttg agcctggcga acagttcggc tggcgcgagc cctgatgct cttcgtccag   2220 atcatcctga tcgacaagac cggcttccat ccgagtacgt gctcgctcga tgcgatgttt   2280
cgcttggtgg tcgaatgggc aggtagccgg atcaagcgta tgcagccgcc gcattgcatc   2340
agccatgatg gatactttct cggcaggagc aaggtgagat gacaggagat cctgccccgg   2400
cacttcgccc aatagcagcc agtcccttcc cgcttcagtg acaacgtcga gcacagctgc   2460
gcaaggaacg cccgtcgtgg ccagccacga tagccgcgct gcctcgtcct gcagttcatt   2520
cagggcaccg gacaggtcgg tcttgacaaa agaaccgggc gcccctgcg ctgacagccg   2580 gaacacggcg gcatcagagc agccgattgt ctgttgtgcc cagtcatagc cgaatagcct   2640
ctccacccaa gcggccggag aacctgcgtg caatccatct tgttcaatgg ccgatcccat   2700
attggctgca cggatcctga acggcagagg ttacggcagt ttgtctctcc cccttccggg   2760
```

```
agccaccttc ttctccaacc gtcccggtcg cgctctcggc gcttctgagg agagaactgg    2820
ctgagtgacg cccttt atag attcgcccttg tgtcccgcc ccttcctttc ccgccctccc    2880
ttgcgctacg gggccgcccg caccggccta cacggagcgc gcgcggcgga gttgttgacg    2940
ctagggctcc ggctccctgg ttgggtgttc tttctgacgc gacaggagga ggagaatgtc    3000
ctggtcctgt cgtcctcctt tcgggtttcc cgtgcactca aaccgaggac ttacagaacg    3060
gaggataaag ttaggccatt tttactcagc ttcggagttc aggctcattt ttcagctaaa    3120
gtctctcatt agtatccccc cacacacatc gggaaaatgg tttgtcctac gcatcggtaa    3180
tgaaggcggg gcccttcggg tcctccggag cgggttccgg gggtggggggg aaggagggag    3240 ggacgggacg ggcctcgttc atgaatattc agttcaccgc tgaatatgca taaggcaggc    3300
aagatggcgc gtccaatcaa ttggaagtag ccgttattag tggagaggcc ccaggacgtt    3360
ggggcaccgc ctgtgctcta gtagctttac ggagccctgg cgctcgatgt tcaagcccaa    3420
gctttcgcga gctcgaccga acaaacgacc caacacccgt gcgttttatt ctgtcttttt    3480
attgccgctc agctttacag tgacaatgac ggctggcgac tgaatattag tgcttacaga    3540
cagcactaca tattttccgt cgatgttgaa atcctttctc atatgtcacc ataaatatca    3600
aataattata gcaatcattt acgcgttaat ggctaatcgc catcttccag caggcgcacc    3660
attgcccctg tttcactatc caggttacgg atatagttca tgacaatatt tacattggtc    3720
cagccaccag cttgcatgat ctccggtatt gaaactccag cgcgggccat atctcgcgcg    3780
gctccgacac gggcactgtg tccagaccag gccaggtatc tctgaccaga gtcatcctaa    3840
aatacacaaa caattagaat cagtagttta acacattata cacttaaaaa tttta tattt    3900 accttagcgc cgtaaatcaa tcgatgagtt gcttcaaaaa tcccttccag ggcgcgagtt    3960
gatagctggc tggtggcaga tggcgcggca acaccatttt ttctgacccg gcaaaacagg    4020
tagttattcg gatcatcagc tacaccagag acggaaatcc atcgctcgac cagtttagtt    4080 accccccaggc taagtgcctt ctctacacct gcggtgctaa ccagcgtttt cgttctgcca    4140
atatggatta acattctccc accgtcagta cgtgagatat cttta accct gatcctggca    4200 atttcggcta tacgtaacag ggtgttataa gcaatcccca gaaatgccag attacgtata    4260
tcctggcagc gatcgctatt ttccatgagt gaacgaacct ggtcgaaatc agtgcgttcg    4320
aacgctagag cctgttttgc acgttcaccg gcatcaacgt tttcttttcg gatccgccgc    4380
ataaccagtg aaacagcatt gctgtcactt ggtcgtggca gcccggaccg acgatgaagc    4440
atgtttagct ggcccaaatg ttgctggata gttttt actg ccagaccgcg cgcctgaaga    4500
tatagaagat aatcgcgaac atcttcaggt tctgcgggaa accatttccg gttattcaac    4560
ttgcaccatg ccgcccacga ccggcaaacg gacagaagca ttttccaggt atgctcagaa    4620
aacgcctggc gatccctgaa catgtccatc aggttcttgc gaacctcatc actcgttgca    4680
tcgaccggta atgcaggcaa attttggtgt acggtcagta aattggacac cttcctcttc    4740
ttcttgggca tggccgcagg aaagcagagc cctgaagctc ccatcaccgg ccaataagag    4800
ccaagcctgc agtgtgacct catagagcaa tgtgccagcc agcctgaccc caagggccct    4860
caggcttggg cacactgtct ctaggaccct gagagaaaga catacccatt tctgcttagg    4920
gccctgagga tgagccaggg gtggcttgg cactgaagca aaggacactg gggctcagct    4980
ggcagcaaag tgaccaggat gctgaggctt tgacccagaa gccagaggcc agaggccagg    5040
acttctcttg gtcccagtcc accctcactc agagctttac caatgccctc tggatagttg    5100
tcgggtaacg gtggacgcca ctgattctct ggccagccta ggacttcgcc attccgctga    5160
```

```
ttctgctctt ccagccactg gctgaccggt tggaagtact ccagcagtgc cttggcatcc    5220
agggcatctg agcctaccag gtccttcagt acctcctgcc agggcctgga gcagccagcc    5280
tgcaacacct gcctgccaag cagagtgacc actgtgggca caggggacac agggtggggc    5340
ccacaacagc accattgtcc acttgtccct cactagtaaa agaactctag ggttgcgggg    5400
ggtgggggag gtctctgtga ggctggtaag ggatatttgc ctggcccatg gagatccata    5460
acttcgtata atgtatgcta tacgaagtta taagctttcg cgagctcgag atcctgcagg    5520
cgcgccggat ctgccggtct ccctatagtg agtcgtatta atttcgataa gccaggttaa    5580
cctgcattaa tgaatcggcc aacgcgcggg gagaggcggt ttgcgtattg ggcgctcttc    5640
cgcttcctcg ctcactgact cgctgcgctc ggtcgttcgg ctgcggcgag cggtatcagc    5700
tcactcaaag gcggtaatac ggttatccac agaatcaggg gataacgcag gaaagaacat    5760
gtgagcaaaa ggccagcaaa aggccaggaa ccgtaaaaag gccgcgttgc tggcgttttt    5820
ccataggctc cgcccccctg acgagcatca caaaaatcga cgctcaagtc agaggtggcg    5880
aaacccgaca ggactataaa gataccaggc gtttccccct ggaagctccc tcgtgcgctc    5940
tcctgttccg accctgccgc ttaccggata cctgtccgcc tttctccctt cgggaagcgt    6000
ggcgctttct catagctcac gctgtaggta tctcagttcg gtgtaggtcg ttcgctccaa    6060
gctgggctgt gtgcacgaac cccccgttca gcccgaccgc tgcgccttat ccggtaacta    6120
tcgtcttgag tccaacccgg taagacacga cttatcgcca ctggcagcag ccactggtaa    6180
caggattagc agagcgaggt atgtaggcgg tgctacagag ttcttgaagt ggtggcctaa    6240
ctacggctac actagaagaa cagtatttgg tatctgcgct ctgctgaagc cagttacctt    6300
cggaaaaaga gttggtagct cttgatccgg caaacaaacc accgctggta gcggtggttt    6360
ttttgtttgc aagcagcaga ttacgcgcag aaaaaaagga tctcaagaag atcctttgat    6420
cttttctacg gggtctgacg ctcagtggaa cgaaaactca cgttaaggga ttttggtcat    6480
gagattatca aaaaggatct tcacctagat ccttttaaat taaaaatgaa gttttaaatc    6540
aatctaaagt atatatgagt aaacttggtc tgacagttac caatgcttaa tcagtgaggc    6600
acctatctca gcgatctgtc tatttcgttc atccatagtt gcctgactcc ccgtcgtgta    6660
gataactacg atacgggagg gcttaccatc tggccccagt gctgcaatga taccgcgaga    6720
cccacgctca ccggctccag atttatcagc aataaaccag ccagccggaa gggccgagcg    6780
cagaagtggt cctgcaactt tatccgcctc catccagtct attaattgtt gccgggaagc    6840
tagagtaagt agttcgccag ttaatagttt gcgcaacgtt gttgccattg ctacaggcat    6900
cgtggtgtca cgctcgtcgt ttggtatggc ttcattcagc tccggttccc aacgatcaag    6960
gcgagttaca tgatccccca tgttgtgcaa aaaagcggtt agctccttcg gtcctccgat    7020
cgttgtcaga agtaagttgg ccgcagtgtt atcactcatg gttatggcag cactgcataa    7080
ttctcttact gtcatgccat ccgtaagatg cttttctgtg actggtgagt actcaaccaa    7140
gtcattctga gaatagtgta tgcggcgacc gagttgctct tgcccggcgt caatacggga    7200
taataccgcg ccacatagca gaactttaaa agtgctcatc attggaaaac gttcttcggg    7260
gcgaaaactc tcaaggatct taccgctgtt gagatccagt tcgatgtaac ccactcgtgc    7320
acccaactga tcttcagcat cttttacttt caccagcgtt tctgggtgag caaaaacagg    7380
aaggcaaaat gccgcaaaaa agggaataag ggcgacacgg aaatgttgaa tactcatact    7440 cttcctttt caatattatt gaagcattta tcagggttat tgtctcatga gcggatacat    7500
atttgaatgt atttagaaaa ataaacaaat aggggttccg cgcacatttc cccgaaaagt    7560
```

| | | | |
|---|---|---|---|
| gccacctgac | gtctaagaaa | ccattattat | catgacatta | acctataaaa | ataggcgtat | 7620 |
| cacgaggccc | tttcgtctcg | cgcgtttcgg | tgatgacggt | gaaaacctct | gacacatgca | 7680 |
| gctcccggag | acggtcacag | cttgtctgta | agcggatgcc | gggagcagac | aagcccgtca | 7740 |
| gggcgcgtca | gcgggtgttg | gcgggtgtcg | gggctggctt | aactatgcgg | catcagagca | 7800 |
| gattgtactg | agagtgcacc | atatggacat | attgtcgtta | gaacgcggct | acaattaata | 7860 |
| cataacctta | tgtatcatac | acatcgatt | taggtgacac | tata | | 7904 |

```
<210> SEQ ID NO 113
<211> LENGTH: 8196
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 113
```

| | | | | | | |
|---|---|---|---|---|---|---|
| tcattaatgc | aggttaacct | ggcttatcga | aattaatacg | actcactata | gggagaccgg | 60 |
| cagatccggc | gcgcctgcag | gatctcctgc | tgctgctgct | gctgctgggc | ctgaggctac | 120 |
| agctctccct | gggcatcatc | ccagttgagg | aggagaaccc | ggacttctgg | aaccgcgagg | 180 |
| cagccgaggc | cctgggtgcc | gccaagaagc | tgcagcctgc | acagacagcc | gccaagaacc | 240 |
| tcatcatctt | cctgggcgat | gggatggggg | tgtctacggt | gacagctgcc | aggatcttaa | 300 |
| aagggcagaa | gaaggacaaa | ctggggcctg | agatacccct | ggccatggac | cgcttcccat | 360 |
| atgtggctct | gtccaagaca | tacaatgtag | acaaacatgt | gccagacagt | ggagccacag | 420 |
| ccacggccta | cctgtgcggg | gtcaagggca | acttccagac | cattggcttg | agtgcagccg | 480 |
| cccgctttaa | ccagtgcaac | acgacacgcg | gcaacgaggt | catctccgtg | atgaatcggg | 540 |
| ccaagaaagc | agggaagtca | gtgggagtgg | taaccaccac | acgagtgcag | cacgcctcgc | 600 |
| cagccggcac | ctacgcccac | acggtgaacc | gcaactggta | ctcggacgcc | gacgtgcctg | 660 |
| cctcggcccg | ccaggagggg | tgccaggaca | tcgctacgca | gctcatctcc | aacatggaca | 720 |
| ttgacgtgat | cctaggtgga | ggccgaaagt | acatgttccg | catgggaacc | ccagaccctg | 780 |
| agtacccaga | tgactacagc | caaggtggga | ccaggctgga | cgggaagaat | ctggtgcagg | 840 |
| aatggctggc | gaagcgccag | ggtgcccggt | atgtgtggaa | ccgcactgag | ctcatgcagg | 900 |
| cttccctgga | cccgtctgtg | acccatctca | tgggtctctt | tgagcctgga | gacatgaaat | 960 |
| acgagatcca | ccgagactcc | acactggacc | cctccctgat | ggagatgaca | gaggctgccc | 1020 |
| tgcgcctgct | gagcaggaac | ccccgcggct | tcttcctctt | cgtggagggt | ggtcgcatcg | 1080 |
| accatggtca | tcatgaaagc | agggcttacc | gggcactgac | tgagacgatc | atgttcgacg | 1140 |
| acgccattga | gagggcgggc | cagctcacca | gcgaggagga | cacgctgagc | ctcgtcactg | 1200 |
| ccgaccactc | ccacgtcttc | tccttcggag | gctaccccct | gcgagggagc | tccatcttcg | 1260 |
| ggctggcccc | tggcaaggcc | cgggacagga | aggcctacac | ggtcctccta | tacggaaacg | 1320 |
| gtccaggcta | tgtgctcaag | gacgcgcccc | ggccggatgt | taccgagagc | gagagcggga | 1380 |
| gccccgagta | tcggcagcag | tcagcagtgc | cctggacga | agagacccac | gcaggcgagg | 1440 |
| acgtggcggt | gttcgcgcgc | ggcccgcagg | cgcacctggt | tcacggcgtg | caggagcaga | 1500 |
| ccttcatagc | gcacgtcatg | gccttcgccg | cctgcctgga | gccctacacc | gcctgcgacc | 1560 |
| tggcgccccc | cgccggcacc | accgacgccg | cgcaccggg | gcggtccgtg | gtccccgcgt | 1620 |
| tgcttcctct | gctggccggg | accctgctgc | tgctggagac | ggccactgct | ccctgagatc | 1680 |

```
gaattaattc gatagcttct agaagctcgc tttcttgctg tccaatttct attaaaggtt    1740
cctttgttcc ctaagtccaa ctactaaact gggggatatt atgaagggcc ttgagcatct    1800
ggattctgcc taataaaaaa catttatttt cattgcaatg atgtatttaa attatttctg    1860
aatattttac taaaaggga atgtgggagg tcagtgcatt taaaacataa agaaatgaag     1920
agctagttca aaccttggga aaatacacta tatcttaaac tccatgaaag aaggtgaggc    1980
tgcaaacagc taatgcacat tggcaacagc ccctgatgcc tatgccttat tcatccctca    2040
gaaaaggatt caagtagagg cttgatttgg aggttaaagt tttgctatgc tgtattttaa    2100
ttaagaattc ataacttcgt ataatgtatg ctatacgaag ttatggatct gtcgatcgac    2160
ggatcgatcc gaacaaacga cccaacaccc gtgcgtttta ttctgtcttt ttattgccga    2220
tcccctcaga agaactcgtc aagaaggcga tagaaggcga tgcgctgcga atcgggagcg    2280
gcgataccgt aaagcacgag gaagcggtca gcccattcgc cgccaagctc ttcagcaata    2340
tcacgggtag ccaacgctat gtcctgatag cggtccgcca cacccagccg ccacagtcg     2400 atgaatccag aaaagcggcc attttccacc atgatattcg gcaagcaggc atcgccatgg    2460
gtcacgacga gatcctcgcc gtcgggcatg cgcgccttga gcctggcgaa cagttcggct    2520
ggcgcgagcc cctgatgctc ttcgtccaga tcatcctgat cgacaagacc ggcttccatc    2580
cgagtacgtg ctcgctcgat gcgatgtttc gcttggtggt cgaatgggca ggtagccgga    2640
tcaagcgtat gcagccgccg cattgcatca gccatgatgg atactttctc ggcaggagca    2700
aggtgagatg acaggagatc ctgccccggc acttcgccca atagcagcca gtcccttccc    2760
gcttcagtga acaacgtcga cacagctgcg caaggaacgc ccgtcgtggc cagccacgat    2820
agccgcgctg cctcgtcctg cagttcattc agggcaccgg acaggtcggt cttgacaaaa    2880
agaaccgggc gcccctgcgc tgacagccgg aacacggcgg catcagagca gccgattgtc    2940
tgttgtgccc agtcatagcc gaatagcctc tccacccaag cggccggaga acctgcgtgc    3000
aatccatctt gttcaatggc cgatcccata ttggctgcac ggatcctgaa cggcagaggt    3060
tacggcagtt tgtctctccc ccttccggga gccaccttct tctccaaccg tcccggtcgc    3120
gctctcggcg cttctgagga gagaactggc tgagtgacgc cctttataga ttcgcccttg    3180
tgtcccgccc cttcctttcc cgccctccct tgcgctacgg ggccgcccgc accggcctac    3240
acggagcgcg cgcggcggag ttgttgacgc tagggctccg gctccctggt tgggtgttct    3300
ttctgacgcg acaggaggag gagaatgtcc tggtcctgtc gtcctccttt cgggtttccc    3360
gtgcactcaa accgaggact tacagaacgg aggataaagt taggccattt ttactcagct    3420
tcggagttca ggctcatttt tcagctaaag tctctcatta gtatcccccc acacacatcg    3480
ggaaaatggt ttgtcctacg catcggtaat gaaggcgggg cccttcgggt cctccggagc    3540
gggttccggg ggtgggggga aggagggagg gacgggacgg gcctcgttca tgaatattca    3600
gttcaccgct gaatatgcat aaggcaggca agatggcgcg tccaatcaat tggaagtagc    3660
cgttattagt ggagaggccc caggacgttg gggcaccgcc tgtgctctag tagctttacg    3720
gagccctggc gctcgatgtt caagcccaag ctttcgcgag ctcgaccgaa caaacgaccc    3780
aacacccgtg cgttttattc tgtctttta ttgccgctca gctttacagt gacaatgacg     3840
gctggcgact gaatattagt gcttacagac agcactacat attttccgtc gatgttgaaa    3900
tcctttctca tatgtcacca taaatatcaa ataattatag caatcattta cgcgttaatg    3960
gctaatcgcc atcttccagc aggcgcacca ttgcccctgt ttcactatcc aggttacgga    4020
tatagttcat gacaatattt acattggtcc agccaccagc ttgcatgatc tccggtattg    4080
```

```
aaactccagc gcgggccata tctcgcgcgg ctccgacacg ggcactgtgt ccagaccagg    4140
ccaggtatct ctgaccagag tcatcctaaa atacacaaac aattagaatc agtagtttaa    4200
cacattatac acttaaaaat tttatattta ccttagcgcc gtaaatcaat cgatgagttg    4260
cttcaaaaat cccttccagg gcgcgagttg atagctggct ggtggcagat ggcgcggcaa    4320
caccattttt tctgacccgg caaaacaggt agttattcgg atcatcagct acaccagaga    4380
cggaaatcca tcgctcgacc agtttagtta cccccaggct aagtgccttc tctacacctg    4440
cggtgctaac cagcgttttc gttctgccaa tatggattaa cattctccca ccgtcagtac    4500
gtgagatatc tttaaccctg atcctggcaa tttcggctat acgtaacagg gtgttataag    4560
caatccccag aaatgccaga ttacgtatat cctggcagcg atcgctattt ccatgagtg    4620 aacgaacctg gtcgaaatca gtgcgttcga acgctagagc ctgttttgca cgttcaccgg    4680
catcaacgtt ttcttttcgg atccgccgca taaccagtga aacagcattg ctgtcacttg    4740
gtcgtggcag cccggaccga cgatgaagca tgtttagctg gcccaaatgt tgctggatag    4800
tttttactgc cagaccgcgc gcctgaagat atagaagata atcgcgaaca tcttcaggtt    4860
ctgcgggaaa ccatttccgg ttattcaact tgcaccatgc cgcccacgac cggcaaacgg    4920
acagaagcat tttccaggta tgctcagaaa acgcctggcg atccctgaac atgtccatca    4980
ggttcttgcg aacctcatca ctcgttgcat cgaccggtaa tgcaggcaaa ttttggtgta    5040
cggtcagtaa attggacacc ttcctcttct tcttgggcat ggccgcagga aagcagagcc    5100
ctgaagctcc catcaccggc caataagagc caagcctgca gtgtgacctc atagagcaat    5160
gtgccagcca gcctgacccc aagggccctc aggcttgggc acactgtctc taggaccctg    5220
agagaaagac atacccattt ctgcttaggg ccctgaggat gagcccaggg gtggcttggc    5280
actgaagcaa aggacactgg ggctcagctg gcagcaaagt gaccaggatg ctgaggcttt    5340
gacccagaag ccagaggcca gaggccagga cttctcttgg tcccagtcca ccctcactca    5400
gagctttacc aatgccctct ggatagttgt cgggtaacgg tggacgccac tgattctctg    5460
gccagcctag gacttcgcca ttccgctgat tctgctcttc cagccactgg ctgaccggtt    5520
ggaagtactc cagcagtgcc ttggcatcca gggcatctga gcctaccagg tccttcagta    5580
cctcctgcca gggcctggag cagccagcct gcaacacctg cctgccaagc agagtgacca    5640
ctgtgggcac aggggacaca gggtggggcc cacaacagca ccattgtcca cttgtccctc    5700
actagtaaaa gaactctagg gttgcggggg gtggggaagg tctctgtgag gctggtaagg    5760
gatatttgcc tggcccatgg agatccataa cttcgtataa tgtatgctat acgaagttat    5820
aagctttcgc gagctcgaga tcccagtcag tcagtctcga gcgatcgcgg cgcgccgtcg    5880
agttctatag tgtcacctaa atcgtatgtg tatgatacat aaggttatgt attaattgta    5940
gccgcgttct aacgacaata tgtccatatg gtgcactctc agtacaatct gctctgatgc    6000
cgcatagtta agccagcccc gacacccgcc aacacccgct gacgcgccct gacgggcttg    6060
tctgctcccg gcatccgctt acagacaagc tgtgaccgtc tccgggagct gcatgtgtca    6120
gaggttttca ccgtcatcac cgaaacgcgc gagacgaaag gcctcgtga tacgcctatt    6180 tttataggtt aatgtcatga taataatggt ttcttagacg tcaggtggca cttttcgggg    6240
aaatgtgcgc ggaacccta tttgttatt tttctaaata cattcaaata tgtatccgct    6300
catgagacaa taaccctgat aaatgcttca ataatattga aaaggaaga gtatgagtat    6360 tcaacatttc cgtgtcgccc ttattccctt ttttgcggca ttttgccttc ctgttttgc    6420 tcacccagaa acgctggtga agtaaaagat gctgaagatc agttgggtg cacgagtggg    6480
```

```
ttacatcgaa ctggatctca acagcggtaa gatccttgag agttttcgcc ccgaagaacg    6540
ttttccaatg atgagcactt ttaaagttct gctatgtggc gcggtattat cccgtattga    6600
cgccgggcaa gagcaactcg gtcgccgcat acactattct cagaatgact tggttgagta    6660
ctcaccagtc acagaaaagc atcttacgga tggcatgaca gtaagagaat tatgcagtgc    6720
tgccataacc atgagtgata acactgcggc caacttactt ctgacaacga tcggaggacc    6780
gaaggagcta accgcttttt tgcacaacat ggggatcat gtaactcgcc ttgatcgttg     6840
ggaaccggag ctgaatgaag ccataccaaa cgacgagcgt gacaccacga tgcctgtagc    6900
aatggcaaca acgttgcgca aactattaac tggcgaacta cttactctag cttcccggca    6960
acaattaata gactggatgg aggcggataa agttgcagga ccacttctgc gctcggccct    7020
tccggctggc tggtttattg ctgataaatc tggagccggt gagcgtgggt ctcgcggtat    7080
cattgcagca ctggggccag atggtaagcc ctcccgtatc gtagttatct acacgacggg    7140
gagtcaggca actatggatg aacgaaatag acagatcgct gagataggtg cctcactgat    7200
taagcattgg taactgtcag accaagttta ctcatatata ctttagattg atttaaaact    7260
tcatttttaa tttaaaagga tctaggtgaa gatcctttt gataatctca tgaccaaaat     7320
cccttaacgt gagttttcgt tccactgagc gtcagacccc gtagaaaaga tcaaaggatc    7380
ttcttgagat ccttttttc tgcgcgtaat ctgctgcttg caaacaaaaa aaccaccgct     7440
accagcggtg gtttgtttgc cggatcaaga gctaccaact ctttttccga aggtaactgg    7500
cttcagcaga gcgcagatac caaatactgt tcttctagtg tagccgtagt taggccacca    7560
cttcaagaac tctgtagcac cgcctacata cctcgctctg ctaatcctgt taccagtggc    7620
tgctgccagt ggcgataagt cgtgtcttac cgggttggac tcaagacgat agttaccgga    7680
taaggcgcag cggtcgggct gaacggggg ttcgtgcaca cagcccagct tggagcgaac     7740
gacctacacc gaactgagat acctacagcg tgagctatga aaagcgcca cgcttcccga    7800 agggagaaag gcggacaggt atccggtaag cggcagggtc ggaacaggag agcgcacgag    7860
ggagcttcca gggggaaacg cctggtatct ttatagtcct gtcgggtttc gccacctctg    7920
acttgagcgt cgatttttgt gatgctcgtc aggggggcgg agcctatgga aaacgccag    7980 caacgcggcc tttttacggt tcctggcctt ttgctggcct tttgctcaca tgttctttcc    8040
tgcgttatcc cctgattctg tggataaccg tattaccgcc tttgagtgag ctgataccgc    8100
tcgccgcagc cgaacgaccg agcgcagcga gtcagtgagc gaggaagcgg aagagcgccc    8160
aatacgcaaa ccgcctctcc ccgcgcgttg gccgat                              8196

<210> SEQ ID NO 114
<211> LENGTH: 9645
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 114
tcattaatgc aggttaacct ggcttatcga aattaatacg actcactata gggagaccgg      60
cagatccggc gcgcctgcag gccatggacc ctgttgtgct gcaaaggaga gactgggaga    120
accctggagt gacccagctc aacagactgg ctgcccaccc tcccttgcc tcttggagga     180 actctgagga agccaggaca gacaggccca gccagcagct caggtctctc aatggagagt    240
ggaggtttgc ctggttccct gcccctgaag ctgtgcctga gtcttggctg gagtgtgacc    300
tcccagaggc tgacactgtt gtggtgccaa gcaactggca gatgcatggc tatgatgccc    360
```

```
ccatctacac caatgtcacc tacccccatca ctgtgaaccc cccttttgtg cccactgaga    420
accccactgg ctgctacagc ctgaccttca atgttgatga gagctggctg caagaaggcc    480
agaccaggat catctttgat ggagtcaact ctgccttcca cctctggtgc aatggcaggt    540
gggttggcta tggccaagac agcaggctgc cctctgagtt tgacctctct gccttcctca    600
gagctggaga gaacaggctg gctgtcatgg tgctcaggtg gtctgatggc agctacctgg    660
aagaccaaga catgtggagg atgtctggca tcttcaggga tgtgagcctg ctgcacaagc    720
ccaccaccca gatttctgac ttccatgttg ccaccaggtt caatgatgac ttcagcagag    780
ctgtgctgga ggctgaggtg cagatgtgtg agaactcag agactacctg agagtcacag      840
tgagcctctg gcaaggtgag acccaggtgg cctctggcac agccccccttt ggaggagaga   900 tcattgatga gagaggaggc tatgctgaca gagtcaccct gaggctcaat gtggagaacc    960
ccaagctgtg gtctgctgag atccccaacc tctacagggc tgttgtggag ctgcacactg    1020
ctgatggcac cctgattgaa gctgaagcct gtgatgttgg attcagagaa gtcaggattg    1080
agaatggcct gctgctgctc aatggcaagc ctctgctcat caggggagtc aacaggcatg    1140
agcaccaccc tctgcatgga caagtgatgg atgaacagac aatggtgcaa gatatcctgc    1200
taatgaagca gaacaacttc aatgctgtca ggtgctctca ctaccccaac caccctctct    1260 ggtacacccct gtgtgacagg tatggcctgt atgttgttga tgaagccaac attgagacac   1320
atggcatggt gcccatgaac aggctcacag atgacccccag gtggctgcct gccatgtctg   1380
agagagtgac caggatggtg cagagagaca ggaaccaccc ctctgtgatc atctggtctc    1440
tgggcaatga gtctggacat ggagccaacc atgatgctct ctacaggtgg atcaagtctg    1500
ttgaccccag cagacctgtg cagtatgaag gaggtggagc agacaccaca gccacagaca    1560
tcatctgccc catgtatgcc agggttgatg aggaccagcc cttccctgct gtgcccaagt    1620
ggagcatcaa gaagtggctc tctctgcctg gagagaccag acctctgatc ctgtgtgaat    1680
atgcacatgc aatgggcaac tctctgggag ctttgccaa gtactggcaa gccttcagac    1740
agtaccccag gctgcaagga ggatttgtgt gggactgggt ggaccaatct ctcatcaagt    1800
atgatgagaa tggcaacccc tggtctgcct atggaggaga cttttggtgac acccccaatg    1860 acaggcagtt ctgcatgaat ggcctggtct ttgcagacag gaccctcac cctgccctca     1920 cagaggccaa gcaccagcaa cagttcttcc agttcaggct gtctggacag accattgagg    1980
tgacatctga gtacctcttc aggcactctg acaatgagct cctgcactgg atggtggccc    2040
tggatggcaa gcctctggct tctggtgagg tgcctctgga tgtggcccct caaggaaagc    2100
agctgattga actgcctgag ctgcctcagc cagagtctgc tggacaactg tggctaacag    2160
tgagggtggt tcagcccaat gcaacagctt ggtctgaggc aggccacatc tctgcatggc    2220
agcagtggag gctggctgag aacctctctg tgaccctgcc tgctgcctct catgccatcc    2280
ctcacctgac aacatctgaa atggacttct gcattgagct gggcaacaag agatggcagt    2340
tcaacaggca gtctggcttc ctgtctcaga tgtggattgg agacaagaag cagctcctca    2400
cccctctcag ggaccaattc accagggctc tctggacaa tgacattgga gtgtctgagg    2460
ccaccaggat tgacccaaat gcttgggtgg agaggtggaa ggctgctgga cactaccagg    2520
ctgaggctgc cctgctccag tgcacagcag acacctggc tgatgctgtt ctgatccaca    2580
cagcccatgc ttggcagcac caaggcaaga ccctgttcat cagcagaaag acctacagga    2640
ttgatggctc tggacagatg gcaatcacag tggatgtgga ggttgcctct gacacacctc    2700 acccctgcaag gattggcctg aactgtcaac tggcacaggt ggctgagagg gtgaactggc    2760
```

```
tgggcttagg ccctcaggag aactaccctg acaggctgac agctgcctgc tttgacaggt   2820
gggacctgcc tctgtctgac atgtacaccc cttatgtgtt cccttctgag aatggcctga   2880
ggtgtggcac cagggagctg aactatggtc ctcaccagtg gaggggagac ttccagttca   2940
acatctccag gtactctcag caacagctca tggaaacctc tcacaggcac ctgctccatg   3000
cagaggaggg aacctggctg aacattgatg gcttccacat gggcattgga ggagatgact   3060
cttggtctcc ttctgtgtct gctgagttcc agttatctgc tggcaggtac cactatcagc   3120
tggtgtggtg ccagaagtaa acctaatcta gaagctcgct ttcttgctgt ccaatttcta   3180
ttaaaggttc ctttgttccc taagtccaac tactaaactg ggggatatta tgaagggcct   3240
tgagcatctg gattctgcct aataaaaaac atttattttc attgcaatga tgtatttaaa   3300
ttatttctga atattttact aaaaagggaa tgtgggaggt cagtgcattt aaaacataaa   3360
gaaatgaaga gctagttcaa accttgggaa aatacactat atcttaaact ccatgaaaga   3420
aggtgaggct gcaaacagct aatgcacatt ggcaacagcc cctgatgcct atgccttatt   3480
catccctcag aaaaggattc aagtagaggc ttgatttgga ggttaaagtt ttgctatgct   3540
gtattttaat taagaattca taacttcgta taatgtatgc tatacgaagt tatggatctg   3600
tcgatcgacg gatcgatccg aacaaacgac ccaacacccg tgcgttttat tctgtcttt    3660 tattgccgat cccctcagaa gaactcgtca agaaggcgag agaaggcgat gcgctgcgaa   3720
tcgggagcgg cgataccgta agcacgagg aagcggtcag cccattcgcc gccaagctct    3780
tcagcaatat cacgggtagc caacgctatg tcctgatagc ggtccgccac acccagccgg   3840
ccacagtcga tgaatccaga aaagcggcca ttttccacca tgatattcgg caagcaggca   3900
tcgccatggg tcacgacgag atcctcgccg tcgggcatgc gcgccttgag cctggcgaac   3960
agttcggctg gcgcgagccc ctgatgctct tcgtccagat catcctgatc gacaagaccg   4020
gcttccatcc gagtacgtgc tcgctcgatg cgatgtttcg cttggtggtc gaatgggcag   4080
gtagccggat caagcgtatg cagccgccgc attgcatcag ccatgatgga tactttctcg   4140
gcaggagcaa ggtgagatga caggagatcc tgccccggca cttcgcccaa tagcagccag   4200
tcccttcccg cttcagtgac aacgtcgagc acagctgcgc aaggaacgcc cgtcgtggcc   4260
agccacgata gccgcgctgc ctcgtcctgc agttcattca gggcaccgga caggtcggtc   4320
ttgacaaaaa gaaccgggcg cccctgcgct gacagccgga acacggcggc atcagagcag   4380
ccgattgtct gttgtgccca gtcatagccg aatagcctct ccacccaagc ggccggagaa   4440
cctgcgtgca atccatcttg ttcaatggcc gatcccatat tggctgcacg gatcctgaac   4500
ggcagaggtt acggcagttt gtctctcccc cttccgggag ccaccttctt ctccaaccgt   4560
cccggtcgcg ctctcggcgc ttctgaggag agaactggct gagtgacgcc ctttatagat   4620
tcgcccttgt gtcccgcccc ttcctttccc gccctccctt gcgctacggg gccgccgca    4680 ccggcctaca cggagcgcgc gcggcggagt tgttgacgcg agggctccgg ctccctggtt   4740
gggtgttctt tctgacgcga caggaggagg agaatgtcct ggtcctgtcg tcctcctttc   4800 ggggtttcccg tgcactcaaa ccgaggactt acagaacgga ggataaagtt aggccatttt   4860
tactcagctt cggagttcag gctcattttt cagctaaagt ctctcattag tatcccccca   4920
cacacatcgg gaaaatggtt tgtcctacgc atcggtaatg aaggcggggc ccttcgggtc   4980
ctccggagcg ggttccgggg gtgggggaa ggagggaggg acgggacggg cctcgttcat    5040
gaatattcag ttcaccgctg aatatgcata aggcaggcaa gatggcgcgt ccaatcaatt   5100
ggaagtagcc gttattagtg gagaggcccc aggacgttgg ggcaccgcct gtgctctagt   5160
```

```
agctttacgg agccctggcg ctcgatgttc aagcccaagc tttcgcgagc tcgaccgaac   5220
aaacgaccca acaccegtgc gttttattct gtctttttat tgccgctcag ctttacagtg   5280
acaatgacgg ctggcgactg aatattagtg cttacagaca gcactacata ttttccgtcg   5340
atgttgaaat cctttctcat atgtcaccat aaatatcaaa taattatagc aatcatttac   5400
gcgttaatgg ctaatcgcca tcttccagca ggcgcaccat tgccctgtt tcactatcca    5460 ggttacggat atagttcatg acaatattta cattggtcca gccaccagct tgcatgatct   5520
ccggtattga aactccagcg cgggccatat ctcgcgcggc tccgacacgg gcactgtgtc   5580
cagaccaggc caggtatctc tgaccagagt catcctaaaa tacacaaaca attagaatca   5640
gtagtttaac acattataca cttaaaaatt ttatatttac cttagcgccg taaatcaatc   5700
gatgagttgc ttcaaaaatc ccttccaggg cgcgagttga tagctggctg gtggcagatg   5760
gcgcggcaac accatttttt ctgacccggc aaaacaggta gttattcgga tcatcagcta   5820
caccagagac ggaaatccat cgctcgacca gtttagttac ccccaggcta agtgccttct   5880
ctacacctgc ggtgctaacc agcgttttcg ttctgccaat atggattaac attctcccac   5940
cgtcagtacg tgagatatct ttaaccctga tcctggcaat ttcggctata cgtaacaggg   6000
tgttataagc aatccccaga aatgccagat tacgtatatc ctggcagcga tcgctatttt   6060
ccatgagtga acgaacctgg tcgaaatcag tgcgttcgaa cgctagagcc tgttttgcac   6120
gttcaccggc atcaacgttt tcttttcgga tccgccgcat aaccagtgaa acagcattgc   6180
tgtcacttgg tcgtggcagc ccggaccgac gatgaagcat gtttagctgg cccaaatgtt   6240
gctggatagt ttttactgcc agaccgcgcg cctgaagata tagaagataa tcgcgaacat   6300
cttcaggttc tgcgggaaac catttccggt tattcaactt gcaccatgcc gcccacgacc   6360
ggcaaacgga cagaagcatt ttccaggtat gctcagaaaa cgcctggcga tccctgaaca   6420
tgtccatcag gttcttgcga acctcatcac tcgttgcatc gaccggtaat gcaggcaaat   6480
tttggtgtac ggtcagtaaa ttggacacct tcctcttctt cttgggcatg ccgcaggaa    6540 agcagagccc tgaagctccc atcaccggcc aataagagcc aagcctgcag tgtgacctca   6600
tagagcaatg tgccagccag cctgacccca agggccctca ggcttgggca cactgtctct   6660
aggaccctga gagaaagaca tacccatttc tgcttagggc cctgaggatg agcccagggg   6720
tggcttggca ctgaagcaaa ggacactggg gctcagctgg cagcaaagtg accaggatgc   6780
tgaggctttg acccagaagc cagaggccag aggccaggac ttctcttggt cccagtccac   6840
cctcactcag agctttacca atgccctctg gatagttgtc gggtaacggt ggacgccact   6900
gattctctgg ccagcctagg acttcgccat tccgctgatt ctgctcttcc agccactggc   6960
tgaccggttg gaagtactcc agcagtgcct tggcatccag ggcatctgag cctaccaggt   7020
ccttcagtac ctcctgccag ggcctggagc agccagcctg caacacctgc ctgccaagca   7080
gagtgaccac tgtgggcaca ggggacacag ggtggggccc acaacagcac cattgtccac   7140
ttgtccctca ctagtaaaag aactctaggg ttgcgggggg tggggaggt ctctgtgagg    7200 ctggtaaggg atatttgcct ggcccatgga gatccataac ttcgtataat gtatgctata   7260
cgaagttata agcttcgcg agctcgagat cccagtcagt cagtctcgag cgatcgcggc    7320
gcgccgtcga gttctatagt gtcacctaaa tcgtatgtgt atgatacata aggttatgta   7380
ttaattgtag ccgcgttcta acgacaatat gtccatatgg tgcactctca gtacaatctg   7440
ctctgatgcc gcatagttaa gccagccccg acacccgcca acaccegctg acgcgccctg   7500 acgggcttgt ctgctcccgg catccgctta cagacaagct gtgaccgtct ccgggagctg   7560
```

```
catgtgtcag aggttttcac cgtcatcacc gaaacgcgcg agacgaaagg gcctcgtgat   7620
acgcctattt ttataggtta atgtcatgat aataatggtt tcttagacgt caggtggcac   7680
ttttcgggga aatgtgcgcg gaacccctat ttgtttattt ttctaaatac attcaaatat   7740
gtatccgctc atgagacaat aaccctgata aatgcttcaa taatattgaa aaaggaagag   7800
tatgagtatt caacatttcc gtgtcgccct tattccctt ttttgcggcat tttgccttcc   7860
tgttttgct cacccagaaa cgctggtgaa agtaaaagat gctgaagatc agttgggtgc   7920
acgagtgggt tacatcgaac tggatctcaa cagcggtaag atccttgaga gttttcgccc   7980
cgaagaacgt tttccaatga tgagcacttt taaagttctg ctatgtggcg cggtattatc   8040
ccgtattgac gccgggcaag agcaactcgg tcgccgcata cactattctc agaatgactt   8100
ggttgagtac tcaccagtca cagaaaagca tcttacggat ggcatgacag taagagaatt   8160
atgcagtgct gccataacca tgagtgataa cactgcggcc aacttacttc tgacaacgat   8220
cggaggaccg aaggagctaa ccgcttttttt gcacaacatg gggatcatg taactcgcct   8280
tgatcgttgg gaaccggagc tgaatgaagc cataccaaac gacgagcgtg acaccacgat   8340
gcctgtagca atggcaacaa cgttgcgcaa actattaact ggcgaactac ttactctagc   8400
ttcccggcaa caattaatag actggatgga ggcggataaa gttgcaggac cacttctgcg   8460
ctcggccctt ccggctggct ggtttattgc tgataaatct ggagccggtg agcgtgggtc   8520
tcgcggtatc attgcagcac tggggccaga tggtaagccc tcccgtatcg tagttatcta   8580
cacgacgggg agtcaggcaa ctatggatga acgaaataga cagatcgctg agataggtgc   8640
ctcactgatt aagcattggt aactgtcaga ccaagtttac tcatatatac tttagattga   8700
tttaaaactt catttttaat ttaaaaggat ctaggtgaag atccttttg ataatctcat   8760
gaccaaaatc ccttaacgtg agttttcgtt ccactgagcg tcagaccccg tagaaaagat   8820
caaaggatct tcttgagatc ctttttttct gcgcgtaatc tgctgcttgc aaacaaaaaa   8880
accaccgcta ccagcggtgg tttgtttgcc ggatcaagag ctaccaactc tttttccgaa   8940
ggtaactggc ttcagcagag cgcagatacc aaatactgtt cttctagtgt agccgtagtt   9000
aggccaccac ttcaagaact ctgtagcacc gcctacatac ctcgctctgc taatcctgtt   9060
accagtggct gctgccagtg gcgataagtc gtgtcttacc gggttggact caagacgata   9120
gttaccggat aaggcgcagc ggtcgggctg aacggggggt tcgtgcacac agcccagctt   9180
ggagcgaacg acctacaccg aactgagata cctacagcgt gagctatgag aaagcgccac   9240
gcttcccgaa gggagaaagg cggacaggta tccggtaagc ggcagggtcg gaacaggaga   9300
gcgcacgagg gagcttccag ggggaaacgc ctggtatctt tatagtcctg tcgggtttcg   9360
ccacctctga cttgagcgtc gatttttgtg atgctcgtca gggggggcgga gcctatggaa   9420
aaacgccagc aacgcggcct ttttacggtt cctggccttt tgctggcctt ttgctcacat   9480
gttctttcct gcgttatccc ctgattctgt ggataaccgt attaccgcct tgagtgagc    9540
tgataccgct cgccgcagcc gaacgaccga gcgcagcgag tcagtgagcg aggaagcgga   9600
agagcgccca atacgcaaac cgcctctccc cgcgcgttgg ccgat                  9645
```

<210> SEQ ID NO 115
<211> LENGTH: 8491
<212> TYPE: DNA
<213> ORGANISM: Artificial Sequence
<220> FEATURE:
<223> OTHER INFORMATION: Description of Artificial Sequence: note = Synthetic Construct

```
<400> SEQUENCE: 115
atgagtattc aacatttccg tgtcgccctt attcccttttt ttgcggcatt ttgccttcct    60
gtttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
cgtattgacg ccgggcaaga gcaactcggt cgccgcatac actattctca gaatgacttg   300
gttgagtact caccagtcac agaaaagcat cttacggatg gcatgacagt aagagaatta   360
tgcagtgctg ccataaccat gagtgataac actgcggcca acttacttct gacaacgatc   420
ggaggaccga aggagctaac cgcttttttg cacaacatgg gggatcatgt aactcgcctt   480
gatcgttggg aaccggagct gaatgaagcc ataccaaacg acgagcgtga caccacgatg   540
cctgtagcaa tggcaacaac gttgcgcaaa ctattaactg gcgaactact tactctagct   600
tcccggcaac aattaataga ctggatggag gcggataaag ttgcaggacc acttctgcgc   660
tcggcccttc cggctggctg gtttattgct gataaatctg gagccggtga gcgtgggtct   720
cgcggtatca ttgcagcact ggggccagat ggtaagccct cccgtatcgt agttatctac   780
acgacgggga gtcaggcaac tatggatgaa cgaaatagac agatcgctga gataggtgcc   840
tcactgatta gcattggta actgtcagac caagtttact catatatact ttagattgat   900
ttaaaacttc atttttaatt taaaaggatc taggtgaaga tccttttga taatctcatg   960
accaaaatcc cttaacgtga gttttcgttc cactgagcgt cagacccgt agaaaagatc   1020
aaaggatctt cttgagatcc ttttttttctg cgcgtaatct gctgcttgca acaaaaaaa   1080
ccaccgctac cagcggtggt ttgtttgccg gatcaagagc taccaactct ttttccgaag   1140
gtaactggct tcagcagagc gcagatacca atactgttc ttctagtgta gccgtagtta   1200
ggccaccact tcaagaactc tgtagcaccg cctacatacc tcgctctgct aatcctgtta   1260
ccagtggctg ctgccagtgg cgataagtcg tgtcttaccg ggttggactc aagacgatag   1320
ttaccggata aggcgcagcg tcgggctga acggggggtt cgtgcacaca gcccagcttg   1380
gagcgaacga cctacaccga actgagatac ctacagcgtg agctatgaga aagcgccacg   1440
cttcccgaag ggagaaaggc ggacaggtat ccggtaagcg gcagggtcgg aacaggagag   1500
cgcacgaggg agcttccagg gggaaacgcc tggtatcttt atagtcctgt cgggtttcgc   1560
cacctctgac ttgagcgtcg atttttgtga tgctcgtcag ggggggcggag cctatggaaa   1620
aacgccagca acgcggcctt tttacggttc ctggccttttt gctggccttt tgctcacatg   1680
ttctttcctg cgttatcccc tgattctgtg gataaccgta ttaccgcctt tgagtgagct   1740
gataccgctc gccgcagccg aacgaccgag cgcagcgagt cagtgagcga ggaagcggaa   1800
gagcgcccaa tacgcaaacc gcctctcccc gcgcgttggc cgattcatta atgcaggtta   1860
acctggctta tcgaaattaa tacgactcac tataggggaga ccgcagatc cggcgcgcct   1920
gcaggcgcgc cactagttaa ttaatttaaa tcgatgcgat cgctagcggc gcgctttaaa   1980
cggccctcga ctctagtcga gcagtgtggt tttcaagagg aagcaaaaag cctctccacc   2040
caggcctgga atgtttccac ccaatgtcga gcagtgtggt tttgcaagag gaagcaaaaa   2100
gcctctccac ccaggcctgg aatgtttcca cccaatgtcg agcaaacccc gcccagcgtc   2160
ttgtcattgg cgaattcgaa cacgcagatg cagtctgggc ggcgcggccc gaggtccact   2220
tcgcatatta aggtgacgcg cgtggcctcg aacagcgagc gaccctgcag cgacccgctc   2280
atcagcgtca gcagcgttcc acaaatcctg gtggcgttga actcccgcac ctctcgggcg   2340
```

```
aacgccttgt agaagcgggt atggcttctc acgccggcca acagcacgcg cctgcgttcg    2400
gtcaggctgc tcgtgcgagc gggcctaccg acggccgcgc ggcgtcccgt cctagccatc    2460
gccagggggc ctccgaagcc cgcggggatc cggagctgcc cacgctgctg cgggtttata    2520
tagacggacc ccacggggtg gggaagacca ccacctccgc gcagctgatg gaggccctgg    2580
ggccgcgcga caatatcgtc tacgtccccg agccgatgac ttactggcag gtgctggggg    2640
cctccgagac cctgacgaac atctacaaca cgcagcaccg tctggaccgc ggcgagatat    2700
cggccgggga ggcggcggtg gtaatgacca gcgcccagat aacaatgagc acgccttatg    2760
cggcgacgga cgccgttttg gctcctcata tcggggggga ggctgtgggc ccgcaagccc    2820
cgcccccggc cctcacccct tgttttcgac cggcaccctat cgcctccctg ctgtgctacc    2880
cggccgcgcg gtacctcatg gaagcatga  ccccccaggc cgtgttggcg ttcgtggccc    2940
tcatgccccc gaccgcgccc ggcacgaacc tggtcctggg tgtccttccg gaggccgaac    3000
acgccgaccg cctggccaga cgccaacgcc cgggcgagcg gcttgacctg gccatgctgt    3060
ccgccattcg ccgtgtctac gatctactcg ccaacacggt gcggtacctg cagcgcggcg    3120
ggaggtggcg ggaggactgg ggccggctga cggggtcgc cgcggcgacc ccgcgccccg    3180
accccgagga cggcgcgggg tctctgcccc gcatcgagga cacgctgttt gccctgttcc    3240
gcgttcccga gctgctggcc cccaacgggg acttgtacca cattttttgcc tgggtcttgg    3300
acgtcttggc cgaccgcctc cttccgatgc atctatttgt cctggattac gatcagtcgc    3360
ccgtcgggtg tcgagacgcc ctgttgcgcc tcaccgccgg gatgatccca acccgcgtca    3420
caaccgccgg gtccatcgcc gagatacgcg acctggcgcg cacgtttgcc cgcgaggtgg    3480
ggggagttta gttcaaacac ggaagcccga acggaaggcc tcccggcgat gacggcaata    3540
aaagaacaga ataaaaggca ttgttgtcgt gtggtgtgtc cataagcgcg ggggttcggg    3600
gccagggctg gcaccgtatc agcaccccac cgaaaaacgg agcgggccga tccgtccttg    3660
ttttcggtct ggtactccct ttgtgctttt accctcaccc caccccatcc tttggcccgc    3720
gcttacggca acaaagggcc tccgatagcc tccgaggtgc ggagcctctt tgggccgtgg    3780
gtacggacac ccccccatct gcggactggc agccgggacg gacgaccatg gccccggtc    3840
tgtgggtggt gatggggtc ctggtgggcg ttgccggggg ccatgacacg tactggacgg    3900
agcaaatcga cccgtggttt ttgcacggtc tggggttggc ccgcacgtac tggcgcgaca    3960
caaacaccgg gcgtctgtgg ttgcccaaca cccccgacgc cagcgacccc cagcgcggac    4020
gcttggcgcc cccgggcgaa ctcaacctga ctacggcatc cgtgcccatg cttcggtggt    4080
acgccgagcg cttttgtttc gtgttggtca ccacggccga gtttcctcgg accccgggc    4140
agctgcttta catcccaaag acctatctgc tcggccggcc tcgaacgcg agcctgcccg    4200
gaagatcccc gggtaccgag ctcgaattca tcgtcaccat cacctcgaat caacaagttt    4260
gtacaaaaaa gctgaacgag aaacgtaaaa tgatataaat atcaatatat taaattagat    4320
tttgcataaa aaacagacta cataatactg taaaacacaa catatccagt cactatggcg    4380
gccgcattag gcaccccagg ctttacactt tatgcttccg gctcgtataa tgtgtggatt    4440
ttgagttagg atccgtcgag attttcagga gctaaggaag ctaaaatgga gaaaaaatc    4500
actggatata ccaccgttga tatatcccaa tggcatcgta aagaacattt tgaggcattt    4560
cagtcagttg ctcaatgtac ctataaccag accgttcagc tggatattac ggccttttta    4620
aagaccgtaa agaaaaataa gcacaagttt tatccggcct ttattcacat tcttgcccgc    4680
ctgatgaatg ctcatccgga attccgtatg gcaatgaaag acggtgagct ggtgatatgg    4740
```

```
gatagtgttc acccttgtta caccgttttc catgagcaaa ctgaaacgtt ttcatcgctc   4800
tggagtgaat accacgacga tttccggcag tttctacaca tatattcgca agatgtggcg   4860
tgttacggtg aaaacctggc ctatttccct aaagggttta ttgagaatat gttttcgtc    4920
tcagccaatc cctgggtgag tttcaccagt tttgatttaa acgtggccaa tatggacaac   4980
ttcttcgccc ccgttttcac catgggcaaa tattatacgc aaggcgacaa ggtgctgatg   5040
ccgctggcga ttcaggttca tcatgccgtc tgtgatggct tccatgtcgg cagaatgctt   5100
aatgaattac aacagtactg cgatgagtgg cagggcgggg cgtaaagatc tggatccggc   5160
ttactaaaag ccagataaca gtatgcgtat ttgcgcgctg attttttgcgg tataagaata   5220
tatactgata tgtatacccg aagtatgtca aaaagaggtg tgctatgaag cagcgtatta   5280
cagtgacagt tgacagcgac agctatcagt tgctcaaggc atatatgatg tcaatatctc   5340
cggtctggta agcacaacca tgcagaatga agcccgtcgt ctgcgtgccg aacgctggaa   5400
agcggaaaat caggaaggga tggctgaggt cgcccggttt attgaaatga acggctcttt   5460
tgctgacgag aacagggact ggtgaaatgc agtttaaggt ttacacctat aaaagagaga   5520
gccgttatcg tctgtttgtg gatgtacaga gtgatattat tgacacgccc gggcgacgga   5580
tggtgatccc cctggccagt gcacgtctgc tgtcagataa agtctcccgt gaactttacc   5640
cggtggtgca tatcggggat gaaagctggc gcatgatgac caccgatatg gccagtgtgc   5700
cggtctccgt tatcggggaa gaagtggctg atctcagcca ccgcgaaaat gacatcaaaa   5760
acgccattaa cctgatgttc tggggaatat aaatgtcagg ctcccttata cacagccagt   5820
ctgcaggtcg accatagtga ctggatatgt tgtgttttac agtattatgt agtctgtttt   5880
ttatgcaaaa tctaatttaa tatattgata tttatatcat tttacgtttc tcgttcagct   5940
ttcttgtaca aagtggttga ttcgaggctg ctaacaaatc gagtcgagca tcgagcagtg   6000
tggttttcaa gaggaagcaa aaagcctctc cacccaggcc tggaatgttt ccacccaatg   6060
tcgagcagtg tggttttgca agaggaagca aaaagcctct ccacccaggc ctggaatgtt   6120
tccacccaat gtcgagcaaa ccccgcccag cgtcttgtca ttggcgaatt cgaacacgca   6180
gatgcagtcg gggcggcgcg gtcccaggtc cacttcgcat attaaggtga cgcgtgtggc   6240
ctcgaacacc gagcgaccct gcagcgaccc gcttaacagc gtcaacagcg tgccgcagat   6300
cttggtggcg tgaaactccc gcacctcttc ggccagcgcc ttgtagaagc gcgtatggct   6360
tcgtaccccg gccatcaaca cgcgtctgcg ttcgaccagg ctgcgcgttc tcgcggccat   6420
agcaaccgac gtacggcgtt gcgccctcgc cggcagcaag aagccacgga agtccgcccg   6480
gagcagaaaa tgcccacgct actgcgggtt tatatagacg gtccccacgg gatggggaaa   6540
accaccacca cgcaactgct ggtggccctg ggttcgcgcg acgatatcgt ctacgtaccc   6600
gagccgatga cttactggcg ggtgctgggg gcttccgaga caatcgcgaa catctacacc   6660
acacaacacc gcctcgacca gggtgagata tcggccgggg acgcggcggt ggtaatgaca   6720
agcgcccaga taacaatggg catgccttat gccgtgaccg acgccgttct ggctcctcat   6780
atcggggggg aggctgggag ctcacatgcc ccgcccccgg ccctcaccct catcttcgac   6840
cgccatccca tcgccgccct cctgtgctac ccggccgcgc ggtaccttat gggcagcatg   6900
acccccagg ccgtgctggc gttcgtggcc ctcatcccgc cgaccttgcc cggcaccaac   6960
atcgtgcttg gggcccttcc ggaggacaga cacatcgacc gcctggccaa acgccagcgc   7020
cccgcgagc ggctgaccct ggctatgctg gctgcgattc gccgcgttta cgggctactt   7080
gccaatacgg tgcggtatct gcagtgcggc gggtcgtggc gggaggactg gggacagctt   7140
```

```
tcggggacgg ccgtgccgcc ccagggtgcc gagccccaga gcaacgcggg cccacgaccc    7200
catatcgggg acacgttatt taccctgttt cgggcccccg agttgctggc ccccaacggc    7260
gacctgtata acgtgtttgc ctgggccttg acgtcttgg ccaaacgcct ccgttccatg     7320
cacgtcttta tcctggatta cgaccaatcg cccgccggct gccgggacgc cctgctgcaa    7380
cttacctccg ggatggtcca gacccacgtc accaccccg gctccatacc gacgatatgc     7440
gacctggcgc gcacgtttgc ccgggagatg ggggaggcta actgaaacac ggaaggagac    7500
aataccggaa ggaacccgcg ctatgacggc aataaaaaga cagaataaaa cgcacgggtg    7560
ttgggtcgtt tgttcataaa cgcggggttc ggtcccaggg ctggcactct gtcgataccc    7620
caccgagacc ccattggggc caatacgccc gcgtttcttc cttttcccca ccccaccccc    7680
caagttcggg tgaaggccca gggctcgcag ccaacgtcgg ggcggcaggc cctgccatag    7740
ccactggccc cgtgggttag ggacggggtc ccccatgggg aatggtttat ggttcgtggg    7800
ggttattatt ttgggcgttg cgtggggtca ggtccacgac ccaagcttgg ctgcaggtcg    7860
agctcgcgaa agcttggcac tggccgtcgt tttggcactg gccgtcgttt tacaacgtcg    7920
tgactgggaa aaccctggcg ttacccaact taatcgcctt gcagcacatc cccctttcgc    7980
cagctggcgt aatagcgaag aggcccgcac cgatcgccct tcccaacagt tgcgcagcct    8040
gaatggcgaa tggcgcctga tgcggtattt tctccttacg catctgtgcg gtatttcaca    8100
ccgcatatgg tgcactctca gtacaatctg ctctgatgcc gcatagttaa gccagccccg    8160
acacccgcca cacccgctg acgcgccctg acgggcttgt ctgctcccgg catccgctta    8220
cagacaagct gtgaccgtct ccgggagctg catgtgtcag aggttttcac cgtcatcacc    8280
gaaacgcgcg agacgaaagg gcctcgtgat acgcctattt ttataggtta atgtcatgat    8340
aataatggtt tcttagacgt caggtggcac ttttcgggga atgtgcgcg gaacccctat     8400 ttgtttattt ttctaaatac attcaaatat gtatccgctc atgagacaat aaccctgata    8460
aatgcttcaa taatattgaa aaaggaagag t                                   8491
```

<210> SEQ ID NO 116
<211> LENGTH: 6379
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 116

```
atgagtattc aacatttccg tgtcgccctt attcccttt ttgcggcatt ttgccttcct      60 gttttgctc acccagaaac gctggtgaaa gtaaaagatg ctgaagatca gttgggtgca     120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg ggatcatgt aactcgcctt    480 gatcgttggg aaccggagct gaatgaagcc ataccaaacg acgagcgtga ccacacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
```

-continued

```
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta actgtcagac caagtttact catatatact ttagattgat    900
ttaaaacttc atttttaatt taaaaggatc taggtgaaga tccttttttga taatctcatg   960
accaaaatcc cttaacgtga gttttcgttc cactgagcgt cagacccgt agaaaagatc    1020
aaaggatctt cttgagatcc ttttttttctg cgcgtaatct gctgcttgca aacaaaaaaa   1080
ccaccgctac cagcggtggt ttgtttgccg gatcaagagc taccaactct ttttccgaag   1140
gtaactggct tcagcagagc gcagatacca atactgttc ttctagtgta gccgtagtta   1200
ggccaccact tcaagaactc tgtagcaccg cctacatacc tcgctctgct aatcctgtta   1260
ccagtggctg ctgccagtgg cgataagtcg tgtcttaccg ggttggactc aagacgatag   1320
ttaccggata aggcgcagcg tcgggctga acggggggtt cgtgcacaca gcccagcttg   1380
gagcgaacga cctacaccga actgagatac ctacagcgtg agctatgaga aagcgccacg   1440
cttcccgaag ggagaaaggc ggacaggtat ccggtaagcg gcagggtcgg aacaggagag   1500
cgcacgaggg agcttccagg gggaaacgcc tggtatcttt atagtcctgt cgggtttcgc   1560
cacctctgac ttgagcgtcg attttttgtga tgctcgtcag ggggggcggag cctatggaaa   1620
aacgccagca acgcggcctt tttacggttc ctggccttttt gctggccttt tgctcacatg   1680
ttctttcctg cgttatcccc tgattctgtg ataaccgta ttaccgcctt tgagtgagct   1740
gataccgctc gccgcagccg aacgaccgag cgcagcgagt cagtgagcga ggaagcggaa   1800
gagcgcccaa tacgcaaacc gcctctcccc gcgcgttggc cgattcatta atgcaggtta   1860
acctggctta tcgaaattaa tacgactcac tataggaga ccggcagatc cggcgcgcct   1920
gcaggcgcgc cactagttaa ttaattttaaa tcgatgcgat cgctagcggc cgcgtttgct   1980
tttgtttcgt gttggtcacc acggccgagt ttcctcggga ccccgggcag ctgctttaca   2040
tcccaaagac ctatctgctc ggccggcctc ggaacgcgag cctgcccgga agatccccgg   2100
gtaccgagct cgaattcatc gtcaccatca cctcgaatca acaagtttgt acaaaaaagc   2160
tgaacgagaa acgtaaaatg atataaatat caatatatta aattagattt tgcataaaaa   2220
acagactaca taatactgta aaacacaaca tatccagtca ctatggcggc cgcattaggc   2280
accccaggct ttacacttta tgcttccggc tcgtataatg tgtggatttt gagttaggat   2340
ccgtcgagat tttcaggagc taaggaagct aaaatggaga aaaaaatcac tggatatacc   2400
accgttgata tatcccaatg gcatcgtaaa gaacattttg aggcatttca gtcagttgct   2460
caatgtacct ataaccagac cgttcagctg gatattacgg ccttttttaaa gaccgtaaag   2520
aaaaataagc acaagtttta tccggccttt attcacattc ttgcccgcct gatgaatgct   2580
catccggaat tccgtatggc aatgaaagac ggtgagctgg tgatatggga tagtgttcac   2640
ccttgttaca ccgttttcca tgagcaaact gaaacgtttt catcgctctg gagtgaatac   2700
cacgacgatt tccggcagtt tctacacata tattcgcaag atgtggcgtg ttacggtgaa   2760
aacctggcct atttccctaa agggtttatt gagaatatgt ttttcgtctc agccaatccc   2820
tgggtgagtt tcaccagttt tgatttaaac gtggccaata tggacaactt cttcgccccc   2880
gttttcacca tgggcaaata ttatacgcaa ggcgacaagg tgctgatgcc gctggcgatt   2940
caggttcatc atgccgtctg tgatggcttc catgtcggca gaatgcttaa tgaattacaa   3000
cagtactgcg atgagtggca gggcggggcg taaagatctg gatccggctt actaaaagcc   3060
agataacagt atgcgtattt gcgcgctgat ttttgcggta taagaatata tactgatatg   3120
```

```
tatacccgaa gtatgtcaaa aagaggtgtg ctatgaagca gcgtattaca gtgacagttg    3180
acagcgacag ctatcagttg ctcaaggcat atatgatgtc aatatctccg gtctggtaag    3240
cacaaccatg cagaatgaag cccgtcgtct gcgtgccgaa cgctggaaag cggaaaatca    3300
ggaagggatg gctgaggtcg cccggtttat tgaaatgaac ggctcttttg ctgacgagaa    3360
cagggactgg tgaaatgcag tttaaggttt acacctataa aagagagagc cgttatcgtc    3420
tgtttgtgga tgtacagagt gatattattg acacgcccgg gcgacggatg gtgatccccc    3480
tggccagtgc acgtctgctg tcagataaag tctcccgtga actttacccg gtggtgcata    3540
tcggggatga aagctggcgc atgatgacca ccgatatggc cagtgtgccg gtctccgtta    3600
tcggggaaga agtggctgat ctcagccacc gcgaaaatga catcaaaaac gccattaacc    3660
tgatgttctg gggaatataa atgtcaggct cccttataca cagccagtct gcaggtcgac    3720
catagtgact ggatatgttg tgttttacag tattatgtag tctgtttttt atgcaaaatc    3780
taatttaata tattgatatt tatatcattt tacgtttctc gttcagcttt cttgtacaaa    3840
gtggttgatt cgaggctgct aacaaatcga gtcgagcatc gagcagtgtg gttttcaaga    3900
ggaagcaaaa agcctctcca cccaggcctg gaatgtttcc acccaatgtc gagcagtgtg    3960
gttttgcaag aggaagcaaa aagcctctcc acccaggcct ggaatgtttc cacccaatgt    4020
cgagcaaacc ccgcccagcg tcttgtcatt ggcgaattcg aacacgcaga tgcagtcggg    4080
gcggcgcggt cccaggtcca cttcgcatat taaggtgacg cgtgtggcct cgaacaccga    4140
gcgaccctgc agcgacccgc ttaacagcgt caacagcgtg ccgcagatct tggtggcgtg    4200
aaactcccgc acctcttcgg ccagcgcctt gtagaagcgc gtatggcttc gtaccccggc    4260
catcaacacg cgtctgcgtt cgaccaggct gcgcgttctc gcggccatag caaccgacgt    4320
acggcgttgc gccctcgccg gcagcaagaa gccacggaag tccgcccgga gcagaaaatg    4380
cccacgctac tgcgggttta tatagacggt ccccacggga tggggaaaac caccaccacg    4440
caactgctgg tggccctggg ttcgcgcgac gatatcgtct acgtacccga gccgatgact    4500
tactggcggg tgctggggc ttccgagaca atcgcgaaca tctacaccac acaacaccgc    4560
ctcgaccagg gtgagatatc ggccggggac gcggcggtgg taatgacaag cgcccagata    4620
acaatgggca tgccttatgc cgtgaccgac gccgttctgg ctcctcatat cgggggggag    4680
gctgggagct cacatgcccc gccccggcc ctcaccctca tcttcgaccg ccatcccatc    4740
gccgccctcc tgtgctaccc ggccgcgcgg taccttatgg gcagcatgac ccccaggcc    4800 gtgctggcgt tcgtggccct catcccgccg accttgcccg gcaccaacat cgtgcttggg    4860
gcccttccgg aggacagaca catcgaccgc ctggccaaac gccagcgccc cggcgagcgg    4920
ctggacctgg ctatgctggc tgcgattcgc cgcgtttacg ggctacttgc caatacggtg    4980
cggtatctgc agtgcggcgg gtcgtggcgg gaggactggg gacagctttc ggggacggcc    5040
gtgccgcccc agggtgccga gccccagagc aacgcgggcc cacgacccca tatcggggac    5100 acgttatttta ccctgtttcg ggcccccgag ttgctggccc ccaacggcga cctgtataac    5160
gtgtttgcct gggccttgga cgtcttggcc aaacgcctcc gttccatgca cgtctttatc    5220
ctggattacg accaatcgcc cgccggctgc cgggacgccc tgctgcaact tacctccggg    5280
atggtccaga cccacgtcac cacccccggc tccataccga cgtatgcga cctggcgcgc    5340 acgtttgccc gggagatggg ggaggctaac tgaaacacgg aaggagacaa taccggaagg    5400
aacccgcgct atgacggcaa taaaaagaca gaataaaacg cacgggtgtt gggtcgtttg    5460
ttcataaacg cggggttcgg tcccagggct ggcactctgt cgatacccca ccgagacccc    5520
```

```
attggggcca atacgcccgc gtttcttcct tttccccacc ccaccccca agttcgggtg    5580 aaggcccagg gctcgcagcc aacgtcgggg cggcaggccc tgccatagcc actggccccg    5640
tgggttaggg acgggtccc ccatggggaa tggtttatgg ttcgtggggg ttattatttt    5700
gggcgttgcg tggggtcagg tccacgaccc aagcttggct gcaggtcgag ctcgcgaaag    5760
cttggcactg gccgtcgttt tggcactggc cgtcgtttta caacgtcgtg actgggaaaa    5820
ccctggcgtt acccaactta atcgccttgc agcacatccc cctttcgcca gctggcgtaa    5880
tagcgaagag gcccgcaccg atcgcccttc ccaacagttg cgcagcctga atggcgaatg    5940
gcgcctgatg cggtattttc tccttacgca tctgtgcggt atttcacacc gcatatggtg    6000
cactctcagt acaatctgct ctgatgccgc atagttaagc cagccccgac acccgccaac    6060
acccgctgac gcgccctgac gggcttgtct gctcccggca tccgcttaca gacaagctgt    6120
gaccgtctcc gggagctgca tgtgtcagag gttttcaccg tcatcaccga aacgcgcgag    6180
acgaaagggc ctcgtgatac gcctattttt ataggttaat gtcatgataa taatggtttc    6240
ttagacgtca ggtggcactt ttcggggaaa tgtgcgcgga acccctattt gtttattttt    6300
ctaaatacat tcaaatatgt atccgctcat gagacaataa ccctgataaa tgcttcaata    6360
atattgaaaa aggaagagt                                                 6379
```

<210> SEQ ID NO 117
<211> LENGTH: 6355
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 117

```
tttcgttcc actgagcgtc agaccccta ataagatgat cttcttgaga tcgttttggt      60
ctgcgcgtaa tctcttgctc tgaaaacgaa aaaaccgcct tgcagggcgg ttttttcgaag   120 gttctctgag ctaccaactc tttgaaccga ggtaactggc ttggaggagc gcagtcacca   180
aaacttgtcc tttcagttta gccttaaccg gcgcatgact tcaagactaa ctcctctaaa   240
tcaattacca gtggctgctg ccagtggtgc ttttgcatgt cttccgggt tggactcaag   300 acgatagtta ccggataagg cgcagcggtc ggactgaacg ggggtcgt gcatacagtc   360 cagcttggag cgaactgcct acccggaact gagtgtcagg cgtggaatga gacaaacgcg   420
gccataacag cggaatgaca ccggtaaacc gaaaggcagg aacaggagag cgcacgaggg   480
agccgccagg ggaaacgcct ggtatcttta gtcctgtc gggtttcgcc accactgatt   540
tgagcgtcag atttcgtgat gcttgtcagg gggcggagc ctatggaaaa acggctttgc   600
cgcggccctc tcacttccct gttaagtatc ttcctggcat cttccaggaa atctccgccc   660
cgttcgtaag ccatttccgc tcgccgcagt cgaacgaccg agcgtagcga gtcagtgagc   720
gaggaagcgg aatatatcct gtatcacata ttctgctgac gcaccggtgc agccttttt   780 ctcctgccac atgaagcact tcactgacac cctcatcagt gccaacatag taagccagta   840
tacactccgc tagcaacctg gcttatcgaa attaatacga ctcactatag ggagaccggc   900
agatccggcg cgcctgcagg cgcgccacta gttaattaat ttaaatcgat gcgatcgcta   960
gcggccgcgt ttgcttttgt ttcgtgttgg tcaccacggc cgagtttcct cgggacccg   1020 ggcagctgct ttacatccca aagacctatc tgctcggccg gcctcggaac gcgagcctgc   1080
ccggaagatc cccgggtacc gagctcgaat tcatcgtcac catcacctcg aatcaacaag   1140
```

```
tttgtacaaa aaagctgaac gagaaacgta aaatgatata aatatcaata tattaaatta    1200
gattttgcat aaaaaacaga ctacataata ctgtaaaaca caacatatcc agtcactatg    1260
gcggccgcat taggcacccc aggctttaca ctttatgctt ccggctcgta taatgtgtgg    1320
attttgagtt aggatccgtc gagattttca ggagctaagg aagctaaaat ggagaaaaaa    1380
atcactggat ataccaccgt tgatatatcc caatggcatc gtaaagaaca ttttgaggca    1440
tttcagtcag ttgctcaatg tacctataac cagaccgttc agctggatat tacgccttt     1500 ttaaagaccg taaagaaaaa taagcacaag ttttatccgg cctttattca cattcttgcc    1560
cgcctgatga atgctcatcc ggaattccgt atggcaatga agacggtga gctggtgata     1620 tgggatagtg ttcacccttg ttacaccgtt ttccatgagc aaactgaaac gttttcatcg    1680
ctctggagtg aataccacga cgatttccgg cagtttctac acatatattc gcaagatgtg    1740
gcgtgttacg gtgaaaacct ggcctatttc cctaaagggt ttattgagaa tatgtttttc    1800
gtctcagcca atccctgggt gagtttcacc agttttgatt taaacgtggc caatatggac    1860
aacttcttcg cccccgtttt caccatgggc aaatattata cgcaaggcga aggtgctg     1920 atgccgctgg cgattcaggt tcatcatgcc gtctgtgatg gcttccatgt cggcagaatg    1980
cttaatgaat tacaacagta ctgcgatgag tggcagggcg gggcgtaaag atctggatcc    2040
ggcttactaa aagccagata acagtatgcg tatttgcgcg ctgattttg cggtataaga     2100 atatatactg atatgtatac ccgaagtatg tcaaaaagag gtgtgctatg aagcagcgta    2160
ttacagtgac agttgacagc gacagctatc agttgctcaa ggcatatgt gatgtcaatat    2220 ctccggtctg gtaagcacaa ccatgcagaa tgaagcccgt cgtctgcgtg ccgaacgctg    2280
gaaagcggaa aatcaggaag ggatggctga ggtcgcccgg tttattgaaa tgaacggctc    2340
ttttgctgac gagaacaggg actggtgaaa tgcagtttaa ggtttacacc tataaaagag    2400
agagccgtta tcgtctgttt gtggatgtac agagtgatat tattgacacg cccgggcgac    2460
ggatggtgat cccctggcc agtgcacgtc tgctgtcaga taaagtctcc cgtgaacttt     2520
acccggtggt gcatatcggg gatgaaagct ggcgcatgat gaccaccgat atggccagtg    2580
tgccggtctc cgttatcggg gaagaagtgg ctgatctcag ccaccgcgaa atgacatca     2640 aaaacgccat taacctgatg ttctggggaa tataaatgtc aggctccctt atacacagcc    2700
agtctgcagg tcgaccatag tgactggata tgttgtgttt tacagtatta tgtagtctgt    2760 ttttatgca aaatctaatt taatatattg atatttatat cattttacgt ttctcgttca     2820
gctttcttgt acaaagtggt tgattcgagg ctgctaacaa atcgagtcga gcatcgagca    2880
gtgtggtttt caagaggaag caaaaagcct ctccacccag gcctggaatg tttccaccca    2940
atgtcgagca gtgtggtttt gcaagaggaa gcaaaaagcc tctccaccca ggcctggaat    3000
gtttccaccc aatgtcgagc aaaccccgcc cagcgtcttg tcattggcga attcgaacac    3060
gcagatgcag tcgggcggc gcggtcccag gtccacttcg catattaagg tgacgcgtgt     3120
ggcctcgaac accgagcgac cctgcagcga cccgcttaac agcgtcaaca gcgtgccgca    3180
gatcttggtg gcgtgaaact cccgcacctc ttcggccagc gccttgtaga agcgcgtatg    3240
gcttcgtacc ccggccatca acacgcgtct gcgttcgacc aggctgcgcg ttctcgcggc    3300
catagcaacc gacgtacggc gttgcgccct cgccggcagc aagaagccac ggaagtccgc    3360
ccggagcaga aaatgcccac gctactgcgg gtttatatag acggtcccca cgggatgggg    3420
aaaaccacca ccacgcaact gctggtggcc ctggttcgc gcgacgatat cgtctacgta     3480
cccgagccga tgacttactg gcgggtgctg ggggcttccg agacaatcgc gaacatctac    3540
```

```
accacacaac accgcctcga ccagggtgag atatcggccg gggacgcggc ggtggtaatg    3600
acaagcgccc agataacaat gggcatgcct tatgccgtga ccgacgccgt tctggctcct    3660
catatcgggg gggaggctgg gagctcacat gccccgcccc cggccctcac cctcatcttc    3720
gaccgccatc ccatcgccgc cctcctgtgc tacccgccg cgcggtacct tatgggcagc     3780
atgaccccc aggccgtgct ggcgttcgtg gccctcatcc cgccgacctt gcccggcacc     3840
aacatcgtgc ttggggccct tccggaggac agacacatcg accgcctggc caaacgccag    3900
cgccccggcg agcggctgga cctggctatg ctggctgcga ttcgccgcgt ttacgggcta    3960
cttgccaata cggtgcggta tctgcagtgc ggcgggtcgt ggcgggagga ctggggacag    4020
cttccggga cggccgtgcc gccccagggt gccgagcccc agagcaacgc gggcccacga     4080
ccccatatcg gggacacgtt atttaccctg tttcgggccc ccgagttgct ggccccaac     4140
ggcgacctgt ataacgtgtt tgcctgggcc ttggacgtct tggccaaacg cctccgttcc    4200
atgcacgtct ttatcctgga ttacgaccaa tcgcccgccg gctgccggga cgccctgctg    4260
caacttacct ccgggatggt ccagacccac gtcaccaccc ccggctccat accgacgata    4320
tgcgacctgg cgcgcacgtt tgcccgggag atggggagg ctaactgaaa cacgaagga     4380
gacaataccg gaaggaaccc gcgctatgac ggcaataaaa agacagaata aaacgcacgg    4440
gtgttgggtc gtttgttcat aaacgcgggg ttcggtccca gggctggcac tctgtcgata    4500
ccccaccgag accccattgg ggccaatacg cccgcgtttc ttccttttcc ccaccccacc    4560
ccccaagttc gggtgaaggc ccagggctcg cagccaacgt cggggcggca ggccctgcca    4620
tagccactgg ccccgtgggt tagggacggg gtccccccatg gggaatggtt tatggttcgt   4680
gggggttatt atttgggcg ttgcgtgggg tcaggtccac gacccaagct tggctgcagg    4740
tcgagctcgc gaaagcttgg cactggccgt cgttttggca ctggccgtcg ttttacaacg    4800
tcgtgactgg gaaaaccctg gcgttaccca acttaatcgc cttgcagcac atccccttt     4860
cgccagctgg cgtaatagcg aagaggcccg caccgatcgc ccttcccaac agttgcgcag    4920
cctgaatggc gaatggcgcc tgatgcggta ttttctcctt acgcatctgt gcggtatttc    4980
acaccgcata tggtgcactc tcagtacaat ctgctctgat gccgcatagt taagccagcc    5040
ccgacacccg ccaacacccg ctgacgcgcc ctgacgggct tgtctgctcc cggcatccgc    5100
ttacagacaa gctgtgaccg tctccgggag ctgcatgtgt cagaggtttt caccgtcatc    5160
accgaaacgc gcgagacgaa agggcctcgt gatacgccta ttttttatagg ttaatgtcat   5220
gataataatg gtttcttaga cgtcaggtgg cacttttcgg ggaaatgtgc gcggaacccc    5280
tatttgttta ttttttctaaa tacattcaaa tatgtatccg ctcatgagac aataacccctg  5340
ataaatgctt caataatatt gaaaaaggaa gagtatgagt attcaacatt tccgtgtcgc    5400
ccttattccc ttttttgcgg cattttgcct tcctgttttt gctcacccag aaacgctggt    5460
gaaagtaaaa gatgctgaag atcagttggg tgcacgagtg ggttacatcg aactggatct    5520
caacagcggt aagatccttg agagttttcg ccccgaagaa cgttttccaa tgatgagcac    5580
ttttaaagtt ctgctatgtg gcgcggtatt atcccgtgtt gacgccgggc aagagcaact    5640
cggtcgccgc atacactatt ctcagaatga cttggttgag tactcaccag tcacagaaaa    5700
gcatcttacg gatggcatga cagtaagaga attatgcagt gctgccataa ccatgagtga    5760
taacactgcg gccaacttac ttctgacaac gatcggagga ccgaaggagc taaccgcttt    5820
tttgcacaac atgggggatc atgtaactcg ccttgatcgt tgggaaccgg agctgaatga    5880
agccatacca aacgacgagc gtgacaccac gatgcctgca gcaatggcaa caacgttgcg    5940
```

```
caaactatta actggcgaac tacttactct agcttcccgg caacaattaa tagactggat    6000
ggaggcggat aaagttgcag gaccacttct gcgctcggcc cttccggctg gctggtttat    6060
tgctgataaa tctggagccg gtgagcgtgg gtctcgcggt atcattgcag cactggggcc    6120
agatggtaag ccctcccgta tcgtagttat ctacacgacg gggagtcagg caactatgga    6180
tgaacgaaat agacagatcg ctgagatagg tgcctcactg attaagcatt ggtaactgtc    6240
agaccaagtt tactcatata tactttagat tgatttaaaa cttcattttt aatttaaaag    6300
gatctaggtg aagatccttt ttgataatct catgaccaaa atcccttaac gtgag         6355

<210> SEQ ID NO 118
<211> LENGTH: 6911
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 118
tagttattac tagcgctacc ggactcagat ctcgagctca agcttcgaat tctgcagtcg      60
acattgatta ttgactagtt attaatagta atcaattacg gggtcattag ttcatagccc     120
atatatggag ttccgcgtta cataacttac ggtaaatggc ccgcctggct gaccgcccaa     180
cgacccccgc ccattgacgt caataatgac gtatgttccc atagtaacgc caatagggac     240
tttccattga cgtcaatggg tggactattt acggtaaact gcccacttgg cagtacatca     300
agtgtatcat atgccaagta cgccccctat tgacgtcaat gacggtaaat ggcccgcctg     360
gcattatgcc cagtacatga ccttatggga ctttcctact tggcagtaca tctacgtatt     420
agtcatcgct attaccatgg gtcgaggtga gccccacgtt ctgcttcact ctccccatct     480
cccccccctc cccacccccca attttgtatt tatttatttt ttaattattt tgtgcagcga     540
tgggggcggg gggggggggg gcgcgcgcca ggcggggcgg ggcggggcga ggggcggggc     600
ggggcgaggc ggagaggtgc ggcggcagcc aatcagagcg gcgcgctccg aaagtttcct     660
tttatggcga ggcggcggcg gcggcggccc tataaaaagc gaagcgcgcg gcgggcggga     720
gtcgctgcgt tgccttcgcc ccgtgccccg ctccgcgccg cctcgcgccg cccgccccgg     780
ctctgactga ccgcgttact cccacaggtg agcgggcggg acggcccttc tcctccgggc     840
tgtaattagc gcttggttta atgacggctc gtttcttttc tgtggctgcg tgaaagcctt     900
aaagggctcc ggggagggcc cttcgtgcggg gggagcggc tcgggggtg cgtgcgtgtg     960 tgtgtgcgtg gggagcgccg cgtgcggccc gcgctgcccg gcggctgtga gcgctgcggg    1020
cgcggcgcgg ggctttgtgc gctccgcgtg tgcgcgaggg gagcgcggcc ggggcggtg    1080 ccccgcggtg cggggggct gcgaggggaa caaaggctgc gtgcggggtg tgtgcgtggg    1140
ggggtgagca ggggtgtgg gcgcggcggt cgggctgtaa ccccccctg cacccccctc    1200 cccgagttgc tgagcacggc ccggcttcgg gtgcggggct ccgtgcgggg cgtggcgcgg    1260
ggctcgccgt gccgggcggg gggtggcggc aggtgggggt gccgggcggg gcggggccgc    1320
ctcgggccgg ggagggctcg ggggagggc gcggcggccc cggagcgccg gcggctgtcg    1380
aggcgcggcg agccgcagcc attgcctttt atggtaatcg tgcgagaggg cgcagggact    1440
tcctttgtcc caaatctggc ggagccgaaa tctgggaggc gccgccgcac ccctctagc    1500 gggcgcgggc gaagcggtgc ggcgccggca ggaaggaaat gggcggggag ggccttcgtg    1560
cgtcgccgcg ccgccgtccc cttctccatc tccagcctcg ggctgccgc aggggacgg     1620 ctgccttcgg ggggacgggg cagggcgggg gttcggcttc tggcgtgtga ccggcggctc    1680
```

```
tagagcctct gctaaccatg ttcatgcctt cttctttttc ctacagctcc tgggcaacgt    1740
gctggttatt gtgctgtctc atcattttgg caaagaattc cgcggccacc atgggtagtt    1800 cttagacga tgagcatatc ctctctgctc ttctgcaaag cgatgacgag cttgttggtg    1860
aggattctga cagtgaaata tcagatcacg taagtgaaga tgacgtccag agcgatacag    1920
aagaagcgtt tatagatgag gtacatgaag tgcagccaac gtcaagcggt agtgaaatat    1980
tagacgaaca aaatgttatt gaacaaccag gttcttcatt ggcttctaac agaatcttga    2040
ccttgccaca gaggactatt agaggtaaga ataaacattg ttggtcaact tcaaagtcca    2100
cgaggcgtag ccgagtctct gcactgaaca ttgtcagatc tcaaagaggt ccgacgcgta    2160
tgtgccgcaa tatatatgac ccacttttat gcttcaaact attttttact gatgagataa    2220
tttcggaaat tgtaaaatgg acaaatgctg agatatcatt gaaacgtcgg aatctatga     2280 caggtgctac atttcgtgac acgaatgaag atgaaatcta tgctttcttt ggtattctgg    2340
taatgacagc agtgagaaaa gataaccaca tgtccacaga tgacctcttt gatcgatctt    2400
tgtcaatggt gtacgtctct gtaatgagtc gtgatcgttt tgatttttg atacgatgtc     2460 ttagaatgga tgacaaaagt atacggccca cacttcgaga aaacgatgta tttactcctg    2520
ttagaaaaat atgggatctc tttatccatc agtgcataca aaattacact ccaggggctc    2580
atttgaccat agatgaacag ttacttggtt ttagaggacg tgtccgtttt aggatgtata    2640
tcccaaacaa gccaagtaag tatggaataa aaatcctcat gatgtgtgac agtggtacga    2700
agtatatgat aaatggaatg ccttatttgg gaagaggaac acagaccaac ggagtaccac    2760
tcggtgaata ctacgtgaag gagttatcaa agcctgtgca cggtagttgt cgtaatatta    2820
cgtgtgacaa ttggttcacc tcaatccctt tggcaaaaaa cttactacaa gaaccgtata    2880
agttaaccat tgtgggaacc gtgcgatcaa acaaacgcga gataccggaa gtactgaaaa    2940
acagtcgctc caggccagtg ggaacatcga tgttttgttt tgacggaccc cttactctcg    3000
tctcatataa accgaagcca gctaagatgg tatacttatt atcatcttgt gatgaggatg    3060
cttctatcaa cgaaagtacc ggtaaaccgc aaatggttat gtattataat caaactaaag    3120
gcggagtgga cacgctagac caaatgtgtt ctgtgatgac ctgcagtagg aagacgaata    3180
ggtggcctat ggcattattg tacggaatga taaacattgc ctgcataaat tcttttatta    3240
tatacagcca taatgtcagt agcaagggag aaaaggttca aagtcgcaaa aaatttatga    3300
gaaaccttta catgagcctg acgtcatcgt ttatgcgtaa gcgtttagaa gctcctactt    3360
tgaagagata tttgcgcgat aatatctcta atattttgcc aaatgaagtg cctggtacat    3420
cagatgacag tactgaagag ccagtaatga aaaaacgtac ttactgtact tactgccct     3480 ctaaaataag gcgaaaggca aatgcatcgt gcaaaaaatg caaaaaagtt atttgtcgag    3540
agcataatat tgatatgtgc caaagttgtt tctgatagcg gccgcgactc tagatcataa    3600
tcagccatac cacatttgta gaggttttac ttgctttaaa aaacctccca cacctccccc    3660
tgaacctgaa acataaaatg aatgcaattg ttgttgttaa cttgtttatt gcagcttata    3720
atggttacaa ataaagcaat agcatcacaa atttcacaaa taaagcattt ttttcactgc    3780
attctagttg tggtttgtcc aaactcatca atgtatctta aggcgtaaat tgtaagcgtt    3840
aatattttgt taaaattcgc gttaaatttt tgttaaatca gctcattttt taaccaatag    3900
gccgaaatcg gcaaaatccc ttataaatca aagaataga ccgagatagg gttgagtgtt    3960
gttccagttt ggaacaagag tccactatta agaacgtgg actccaacgt caagggcga     4020 aaaccgtctt atcagggcga tggcccacta cgtgaaccat cacccctaatc aagttttttg   4080
```

```
gggtcgaggt gccgtaaagc actaaatcgg aaccctaaag ggagccccg atttagagct    4140
tgacggggaa agccggcgaa cgtggcgaga aggaaggga agaaagcgaa aggagcgggc    4200
gctagggcgc tggcaagtgt agcggtcacg ctgcgcgtaa ccaccacacc cgccgcgctt    4260
aatgcgccgc tacagggcgc gtcaggtggc acttttcggg gaaatgtgcg cggaacccct    4320
atttgtttat ttttctaaat acattcaaat atgtatccgc tcatgagaca ataaccctga    4380
taaatgcttc aataatattg aaaaggaag agtcctgagg cggaaagaac cagctgtgga    4440
atgtgtgtca gttagggtgt ggaaagtccc caggctcccc agcaggcaga agtatgcaaa    4500
gcatgcatct caattagtca gcaaccaggt gtggaaagtc cccaggctcc ccagcaggca    4560
gaagtatgca aagcatgcat ctcaattagt cagcaaccat agtcccgccc ctaactccgc    4620
ccatcccgcc cctaactccg cccagttccg cccattctcc gccccatggc tgactaattt    4680
tttttattta tgcagaggcc gaggccgcct cggcctctga gctattccag aagtagtgag    4740
gaggcttttt tggaggccta ggcttttgca aagatcgatc aagagacagg atgaggatcg    4800
tttcgcatga ttgaacaaga tggattgcac gcaggttctc cggccgcttg ggtggagagg    4860
ctattcggct atgactgggc acaacagaca atcggctgct ctgatgccgc cgtgttccgg    4920
ctgtcagcgc aggggcgccc ggttcttttt gtcaagaccg acctgtccgg tgccctgaat    4980
gaactgcaag acgaggcagc gcggctatcg tggctggcca cgacgggcgt tccttgcgca    5040
gctgtgctcg acgttgtcac tgaagcggga agggactggc tgctattggg cgaagtgccg    5100
gggcaggatc tcctgtcatc tcaccttgct cctgccgaga agtatccat catggctgat    5160
gcaatgcggc ggctgcatac gcttgatccg gctacctgcc cattcgacca ccaagcgaaa    5220
catcgcatcg agcgagcacg tactcggatg gaagccggtc ttgtcgatca ggatgatctg    5280
gacgaagagc atcagggct cgcgccagcc gaactgttcg ccaggctcaa ggcgagcatg    5340
cccgacggcg aggatctcgt cgtgacccat ggcgatgcct gcttgccgaa tatcatggtg    5400
gaaaatggcc gcttttctgg attcatcgac tgtggccggc tgggtgtggc ggaccgctat    5460
caggacatag cgttggctac ccgtgatatt gctgaagagc ttggcggcga atgggctgac    5520
cgcttcctcg tgctttacgg tatcgccgct cccgattcgc agcgcatcgc cttctatcgc    5580
cttcttgacg agttcttctg agcgggactc tggggttcga atgaccgac caagcgacgc    5640
ccaacctgcc atcacgagat ttcgattcca ccgccgcctt ctatgaaagg ttgggcttcg    5700
gaatcgtttt ccgggacgcc ggctggatga tcctccagcg cggggatctc atgctggagt    5760
tcttcgccca ccctaggggg aggctaactg aaacacggaa ggagacaata ccggaaggaa    5820
cccgcgctat gacggcaata aaaagacaga ataaaacgca cggtgttggg tcgtttgttc    5880
ataaacgcgg ggttcggtcc cagggctggc actctgtcga taccccaccg agaccccatt    5940
ggggccaata cgcccgcgtt tcttcctttt ccccacccca cccccaagt tcgggtgaag    6000
gcccagggct cgcagccaac gtcggggcgg caggccctgc catagcctca ggttactcat    6060
atatacttta gattgattta aaacttcatt tttaatttaa aaggatctag gtgaagatcc    6120
tttttgataa tctcatgacc aaaatccctt aacgtgagtt ttcgttccac tgagcgtcag    6180
accccgtaga aaagatcaaa ggatcttctt gagatccttt ttttctgcgc gtaatctgct    6240
gcttgcaaac aaaaaaacca ccgctaccag cggtggtttg tttgccggat caagagctac    6300
caactctttt tccgaaggta actggcttca gcagagcgca gataccaaat actgtccttc    6360
tagtgtagcc gtagttaggc caccacttca agaactctgt agcaccgcct acatacctcg    6420
ctctgctaat cctgttacca gtggctgctg ccagtggcga taagtcgtgt cttaccgggt    6480
```

```
tggactcaag acgatagtta ccggataagg cgcagcggtc gggctgaacg ggggggttcgt    6540 gcacacagcc cagcttggag cgaacgacct acaccgaact gagataccta cagcgtgagc    6600
tatgagaaag cgccacgctt cccgaaggga gaaaggcgga caggtatccg gtaagcggca    6660
gggtcggaac aggagagcgc acgagggagc ttccaggggg aaacgcctgg tatctttata    6720
gtcctgtcgg gtttcgccac ctctgacttg agcgtcgatt tttgtgatgc tcgtcagggg    6780
ggcggagcct atggaaaaac gccagcaacg cggcctttttt acggttcctg gccttttgct    6840
ggccttttgc tcacatgttc tttcctgcgt tatcccctga ttctgtggat aaccgtatta    6900
ccgccatgca t                                                         6911
```

<210> SEQ ID NO 119
<211> LENGTH: 5960
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 119

```
agttattact agcgctaccg gactcagatc tcgagctcaa gcttggtacc gagctcggat      60
ccactagtaa cggccgccag tgtgctggaa ttcgcccttg tctagagttt cctgtccacc     120
tttcagcttc cctctcaggc tgggagcagg ggccagtagc agcacccacg tccaccttct     180
gtctagtaat gtccaacacc tccctcagtc caaacactgc tctgcatcca tgtggctccc     240
atttatacct gaagcacttg atggggcctc aatgttttac tagagcccac cccctgcaa     300 ctctgagacc ctctggattt gtctgtcagt gcctcactgg ggcgttggat aatttcttaa     360
aaggtcaagt tccctcagca gcattctctg agcagtctga agatgtgtgc ttttcacagt     420
tcaaatccat gtggctgttt cacccacctg cctggccttg ggttatctat caggacctag     480
cctagaagca ggtgtgtggc acttaacacc taagctgagt gactaactga acactcaagt     540
ggatgccatc tttgtcactt cttgactgtg acacaagcaa ctcctgatgc caaagccctg     600 cccaccctc tcatgccat atttggacat ggtacaggtc tcactggcc atggtctgtg      660 aggtcctggt cctctttgac ttcataattc ctaggggcca ctagtatcta aagaggaag    720 agggtgctgg ctcccaggcc acagcccaca aaattccacc tgctcacagg ttggctggct    780
cgacccaggt ggtgtcccct gctctgagcc agctcccggc caagccagcc gcggccacca    840
tgggtagttc tttagacgat gagcatatcc tctctgctct tctgcaaagc gatgacgagc    900
ttgttggtga ggattctgac agtgaaatat cagatcacgt aagtgaagat gacgtccaga    960
gcgatacaga agaagcgttt atagatgagg tacatgaagt gcagccaacg tcaagcggta   1020
gtgaaatatt agacgaacaa aatgttattg aacaaccagg ttcttcattg gcttctaaca   1080
gaatcttgac cttgccacag aggactatta gaggtaagaa taaacattgt tggtcaactt   1140
caaagtccac gaggcgtagc cgagtctctg cactgaacat tgtcagatct caaagaggtc   1200
cgacgcgtat gtgccgcaat atatatgacc cacttttatg cttcaaacta tttttttactg   1260 atgagataat ttcggaaatt gtaaaatgga caaatgctga gatatcattg aaacgtcggg   1320
aatctatgac aggtgctaca tttcgtgaca cgaatgaaga tgaaatctat gctttcttg    1380 gtattctggt aatgacagca gtgagaaaag ataaccacat gtccacagat gacctctttg   1440
atcgatcttt gtcaatggtg tacgtctctg taatgagtcg tgatcgtttt gattttttga   1500
tacgatgtct tagaatggat gacaaaagta tacggcccac acttcgagaa aacgatgtat   1560
```

```
ttactcctgt tagaaaaata tgggatctct ttatccatca gtgcatacaa aattacactc   1620
caggggctca tttgaccata gatgaacagt tacttggttt tagaggacgg tgtccgttta   1680
ggatgtatat cccaaacaag ccaagtaagt atggaataaa aatcctcatg atgtgtgaca   1740
gtggtacgaa gtatatgata aatggaatgc cttatttggg aagaggaaca cagaccaacg   1800
gagtaccact cggtgaatac tacgtgaagg agttatcaaa gcctgtgcac ggtagttgtc   1860
gtaatattac gtgtgacaat tggttcacct caatcccttt ggcaaaaaac ttactacaag   1920
aaccgtataa gttaaccatt gtgggaaccg tgcgatcaaa caaacgcgag ataccggaag   1980
tactgaaaaa cagtcgctcc aggccagtgg gaacatcgat gttttgtttt gacggacccc   2040
ttactctcgt ctcatataaa ccgaagccag ctaagatggt atacttatta tcatcttgtg   2100
atgaggatgc ttctatcaac gaaagtaccg gtaaaccgca aatggttatg tattataatc   2160
aaactaaagg cggagtggac acgctagacc aaatgtgttc tgtgatgacc tgcagtagga   2220
agacgaatag gtggcctatg gcattattgt acggaatgat aaacattgcc tgcataaatt   2280
cttttattat atacagccat aatgtcagta gcaagggaga aaaggttcaa agtcgcaaaa   2340
aatttatgag aaacctttac atgagcctga cgtcatcgtt tatgcgtaag cgtttagaag   2400
ctcctacttt gaagagatat ttgcgcgata atatctctaa tattttgcca aatgaagtgc   2460
ctggtacatc agatgacagt actgaagagc cagtaatgaa aaaacgtact tactgtactt   2520
actgcccctc taaaataagg cgaaaggcaa atgcatcgtg caaaaaatgc aaaaaagtta   2580
tttgtcgaga gcataatatt gatatgtgcc aaagttgttt ctgatagcgg ccgcgactct   2640
agatcataat cagccatacc acatttgtag aggttttact tgctttaaaa aacctcccac   2700
acctccccct gaacctgaaa cataaaatga atgcaattgt tgttgttaac ttgtttattg   2760
cagcttataa tggttacaaa taagcaata gcatcacaaa tttcacaaat aaagcatttt   2820
tttcactgca ttctagttgt ggtttgtcca aactcatcaa tgtatcttaa ggcgtaaatt   2880
gtaagcgtta atattttgtt aaaattcgcg ttaaattttt gttaaatcag ctcattttttt   2940
aaccaatagg ccgaaatcgg caaaatccct tataaatcaa aagaatagac cgagataggg   3000
ttgagtgttg ttccagtttg gaacaagagt ccactattaa agaacgtgga ctccaacgtc   3060
aaagggcgaa aaaccgtcta tcagggcgat ggcccactac gtgaaccatc accctaatca   3120
agttttttgg ggtcgaggtg ccgtaaagca ctaaatcgga accctaaagg agccccccga   3180
tttagagctt gacggggaaa gccggcgaac gtggcgagaa aggaagggaa gaaagcgaaa   3240
ggagcgggcg ctagggcgct ggcaagtgta gcggtcacgc tgcgcgtaac caccacaccc   3300
gccgcgctta atgcgccgct acagggcgcg tcaggtggca cttttcgggg aaatgtgcgc   3360
ggaaccccta tttgtttatt tttctaaata cattcaaata tgtatccgct catgagacaa   3420
taaccctgat aaatgcttca ataatattga aaaggaaga gtcctgaggc ggaaagaacc   3480
agctgtggaa tgtgtgtcag ttagggtgtg gaaagtcccc aggctcccca gcaggcagaa   3540
gtatgcaaag catgcatctc aattagtcag caaccaggtg tggaaagtcc ccaggctccc   3600
cagcaggcag aagtatgcaa agcatgcatc tcaattagtc agcaaccata gtcccgcccc   3660
taactccgcc catcccgccc ctaactccgc ccagttccgc ccattctccg ccccatggct   3720
gactaatttt ttttatttat gcagaggccg aggccgcctc ggcctctgag ctattccaga   3780
agtagtgagg aggcttttttt ggaggcctag gcttttgcaa agatcgatca agagacagga   3840
tgaggatcgt ttcgcatgat tgaacaagat ggattgcacg caggttctcc ggccgcttgg   3900
gtggagaggc tattcggcta tgactgggca caacagacaa tcggctgctc tgatgccgcc   3960
```

```
gtgttccggc tgtcagcgca ggggcgcccg gttcttttg tcaagaccga cctgtccggt      4020
gccctgaatg aactgcaaga cgaggcagcg cggctatcgt ggctggccac gacgggcgtt      4080
ccttgcgcag ctgtgctcga cgttgtcact gaagcgggaa gggactggct gctattgggc      4140
gaagtgccgg ggcaggatct cctgtcatct caccttgctc ctgccgagaa agtatccatc      4200
atggctgatg caatgcggcg gctgcatacg cttgatccgg ctacctgccc attcgaccac      4260
caagcgaaac atcgcatcga gcgagcacgt actcggatgg aagccggtct tgtcgatcag      4320
gatgatctgg acgaagagca tcaggggctc gcgccagccg aactgttcgc caggctcaag      4380
gcgagcatgc ccgacggcga ggatctcgtc gtgacccatg gcgatgcctg cttgccgaat      4440
atcatggtgg aaaatggccg cttttctgga ttcatcgact gtggccggct gggtgtggcg      4500
gaccgctatc aggacatagc gttggctacc cgtgatattg ctgaagagct tggcggcgaa      4560
tgggctgacc gcttcctcgt gctttacggt atcgccgctc ccgattcgca gcgcatcgcc      4620
ttctatcgcc ttcttgacga gttcttctga gcgggactct ggggttcgaa atgaccgacc      4680
aagcgacgcc caacctgcca tcacgagatt tcgattccac cgccgccttc tatgaaaggt      4740
tgggcttcgg aatcgttttc cgggacgccg gctggatgat cctccagcgc ggggatctca      4800
tgctggagtt cttcgcccac cctaggggga ggctaactga aacacggaag gagacaatac      4860
cggaaggaac ccgcgctatg acggcaataa aagacagaa taaaacgcac ggtgttgggt       4920
cgtttgttca taaacgcggg gttcggtccc agggctggca ctctgtcgat accccaccga      4980 gacccattg gggccaatac gcccgcgttt cttccttttc cccacccac ccccaagtt        5040 cgggtgaagg cccagggctc gcagccaacg tcgggcggc aggccctgcc atagcctcag      5100
gttactcata tactttag attgatttaa aacttcattt ttaatttaaa aggatctagg       5160
tgaagatcct ttttgataat ctcatgacca aaatcccta acgtgagttt tcgttccact       5220
gagcgtcaga ccccgtagaa aagatcaaag gatcttcttg agatccttt tttctgcgcg      5280 taatctgctg cttgcaaaca aaaaaaccac cgctaccagc ggtggtttgt ttgccggatc      5340
aagagctacc aactctttt ccgaaggtaa ctggcttcag cagagcgcag ataccaaata     5400
ctgtccttct agtgtagccg tagttaggcc accacttcaa gaactctgta gcaccgccta     5460
catacctcgc tctgctaatc ctgttaccag tggctgctgc cagtggcgat aagtcgtgtc     5520
ttaccgggtt ggactcaaga cgatagttac cggataaggc gcagcggtcg ggctgaacgg     5580
ggggttcgtg cacacagccc agcttggagc gaacgaccta caccgaactg agatacctac     5640
agcgtgagct atgagaaagc gccacgcttc ccgaagggag aaaggcggac aggtatccgg     5700
taagcggcag ggtcggaaca ggagagcgca cagggagct tccaggggga aacgcctggt      5760
atctttatag tcctgtcggg tttcgccacc tctgacttga gcgtcgattt ttgtgatgct     5820
cgtcaggggg gcggagccta tggaaaaacg ccagcaacgc ggcctttta cggttcctgg      5880 ccttttgctg gccttttgct cacatgttct ttcctgcgtt atcccctgat tctgtggata    5940
accgtattac cgccatgcat                                                 5960

<210> SEQ ID NO 120
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 120
ccctatctcc cagaaccggc tattagcctc tgcaggcttc catgcacctg cgactgaatt       60
```

```
ggttccttta aagc                                                      74

<210> SEQ ID NO 121
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 121
gcgctgtctg tatgtccggt agcaagcacc agactttaag atatatgtct gccgcactcg   60
agatatctag accca                                                     75

<210> SEQ ID NO 122
<211> LENGTH: 84
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 122
gtcttcttgt agttctcctg attctggagc ctgccaggat ggggcctctg aggcgcgcca   60
gcattacacg tcttgagcga ttgt                                           84

<210> SEQ ID NO 123
<211> LENGTH: 84
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 123
ctccctcatg atctagtcga tcatggcggg taagacacac ctgctctatc aggcgcgccc   60
acttaacggc tgacatggga atta                                           84

<210> SEQ ID NO 124
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 124
aaacatatca ctgaattatc ttattgttgt gacttaaagg ctaaataagt cgactgaatt   60
ggttccttta aagc                                                      74

<210> SEQ ID NO 125
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 125
caattgtcca attaaaagac ataggctaac agactggatc tataaacagg tcgagatatc   60
tagacccagc tttc                                                      74

<210> SEQ ID NO 126
```

<211> LENGTH: 75
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 126
gagctggcgg cagctgaggg gagtgcactg gtgaggaatc atgggagctt ctagagggcg    60
cgcctacctg tgacg    75

<210> SEQ ID NO 127
<211> LENGTH: 68
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 127
gatggactat aacatcctgt ttctcttctc atgagagatg ttagccagaa ggcgcgcctt    60
acgccccg    68

<210> SEQ ID NO 128
<211> LENGTH: 74
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 128
ttttagtaag gatgtgttga tgcagtattg gatgatttgg agaaaatatt cgactgaatt    60 ggttcccttta aagc    74

<210> SEQ ID NO 129
<211> LENGTH: 74
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 129
acttgtactc atttctggaa ggtcctgtca tgggaagaga gtgtgcaaag tcgagatatc    60
tagacccagc tttc    74

<210> SEQ ID NO 130
<211> LENGTH: 83
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 130
gtctggatac ccttgtaccc tgggtgcaga agcaaagatg aagattggaa ggcgcgccag    60
cattacacgt cttgagcgat tgt    83

<210> SEQ ID NO 131
<211> LENGTH: 84
<212> TYPE: DNA
<213> ORGANISM: Artificial Sequence
<220> FEATURE:
<223> OTHER INFORMATION: Description of Artificial Sequence: note =

-continued

Synthetic Construct

<400> SEQUENCE: 131
gttttgagta gaaacgcagt gccaacaggg ctattctcta tgattttcac ggcgcgccca      60
cttaacggct gacatgggaa ttag                                            84

<210> SEQ ID NO 132
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 132
ttaatccagc ggatcacaac tggacaaacc gctaagaata ataacgagt cgactgaatt       60 ggttccttta aagc                                                       74

<210> SEQ ID NO 133
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 133
ccgctagtat ttaagatgga gataaccaat ttatgtaggt caaaagttgc tcgagatatc      60
tagacccagc tttc                                                       74

<210> SEQ ID NO 134
<211> LENGTH: 69
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 134
cgccgcggct gttgacccgg ctggccggga acaggagag atgcggagcc ggcgcgccta       60
cctgtgacg                                                             69

<210> SEQ ID NO 135
<211> LENGTH: 68
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 135
ctcctgaact ttggggttgc cttggtgact gactctaagg gtcagggctg ggcgcgcctt     60
acgccccg                                                              68

<210> SEQ ID NO 136
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 136
gtcgctccca atgcacttcc tggaaagaga aaatgagga gcctaaagga cgactgaatt      60

```
ggttccttta aagcc                                                         75

<210> SEQ ID NO 137
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 137
gttttggcca cagtaccctg taccccgggg ggccttgggt gagtatgtgg gccgcactcg        60
agatatctag accca                                                         75

<210> SEQ ID NO 138
<211> LENGTH: 83
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 138
cccgggcggg gggcggcgga ggccgtgacg ggaggcgggg gtgatggcga ggcgcgccag        60
cattacacgt cttgagcgat tgt                                                83

<210> SEQ ID NO 139
<211> LENGTH: 89
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 139
agctctgtct cacagaagtc tcccgtgaag ccaggagggc agcggcagcg actagtggcg        60
cgcccactta acggctgaca tgggaatta                                          89

<210> SEQ ID NO 140
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 140
gttgtaaggt cccccggact cattcaggca tggctctctg aactatatac cgactgaatt        60
ggttccttta aagc                                                          74

<210> SEQ ID NO 141
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 141
caggtgaggc ccagaaaagct ggaggaacag ggatatatag atctacaaag tcgagatatc       60
tagacccagc tttc                                                          74

<210> SEQ ID NO 142
```

```
<211> LENGTH: 69
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 142
acctgaaccc tttccctctt cttacccagg agctttcacc atgacgcttg ggcgcgccta      60
cctgtgacg                                                             69

<210> SEQ ID NO 143
<211> LENGTH: 68
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 143
cctgagttca aatctcagca accacatggt ggctcacaac cacccataat ggcgcgcctt      60
acgccccg                                                              68

<210> SEQ ID NO 144
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 144
actgtgaagt attcatcttc tggtagtgag tttaagtatg tgaatttaac cgactgaatt      60 ggttcccttta aagc                                                      74

<210> SEQ ID NO 145
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 145
tattttagaa taaagatcaa atttggcaaa tatttcattt ccaaaatcta tcgagatatc      60
tagacccagc tttc                                                       74

<210> SEQ ID NO 146
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 146
acggacatgt gatatgatga gtgtgactat gggacactgt atgggcacaa ggatccggcg      60
cgcctacctg tgacg                                                      75

<210> SEQ ID NO 147
<211> LENGTH: 74
<212> TYPE: DNA
<213> ORGANISM: Artificial Sequence
<220> FEATURE:
<223> OTHER INFORMATION: Description of Artificial Sequence:  note =
```

-continued

Synthetic Construct

<400> SEQUENCE: 147
agccattcta agacatgtca tttctactca aatggagact tccccatctg gaattcggcg   60
cgccttacgc cccg   74

<210> SEQ ID NO 148
<211> LENGTH: 74
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 148
caccaaatcg taattagtta tgaaaatggt tgtcaagtca gagctttaac cgactgaatt   60
ggttccttta aagc   74

<210> SEQ ID NO 149
<211> LENGTH: 73
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 149
ggccctctta tgttcccttg aaactctcca agggcttcct gatgaagagc cgcactcgag   60
atatctagac cca   73

<210> SEQ ID NO 150
<211> LENGTH: 90
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 150
tcttcttctc caggttcctg gaaactagga ccatgaactt ggccgcaaac ggatcccggc   60
gcgccagcat tacacgtctt gagcgattgt   90

<210> SEQ ID NO 151
<211> LENGTH: 87
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 151 agaaagaat ttttaagcct attgagaaca aataaaagaa tacaagctct agaggcgcgc   60
ccacttaacg gctgacatgg gaattag   87

<210> SEQ ID NO 152
<211> LENGTH: 74
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 152
cacaacccac agaaggtgat agacccataa tgatagagac tggtcaagac cgactgaatt   60
ggttccttta aagc                                                            74

<210> SEQ ID NO 153
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 153
ccacggcaga acaccatggg gatggaatca acgcaagctt tcagagaaca gccgcactcg         60
agatatctag accca                                                          75

<210> SEQ ID NO 154
<211> LENGTH: 83
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 154
gctcgctggc tcgctggctc gcgggaggcc gggcagcagc aggggcatgt ggcgcgccag         60
cattacacgt cttgagcgat tgt                                                 83

<210> SEQ ID NO 155
<211> LENGTH: 85
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 155
ccatcccccg ggccccttcc cagacaggaa tcagcacaga ccgcaaggct cggcgcgccc         60
acttaacggc tgacatggga attag                                               85

<210> SEQ ID NO 156
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 156
ccttctccta actagtcagc atacagatgt aattactgcc tccctgatcc cgactgaatt         60
ggttccttta aagc                                                            74

<210> SEQ ID NO 157
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 157
gcacccttga tgactgggga caagaggata gcatcctcct gatgcctaca gccgcactcg         60
agatatctag accca                                                          75

<210> SEQ ID NO 158

<211> LENGTH: 85
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 158
cggggccatt tgaaaggaaa caatccctac gcaaaatctt acaccttggt agggcgcgcc    60
agcattacac gtcttgagcg attgt    85

<210> SEQ ID NO 159
<211> LENGTH: 84
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 159
gctcgtttaa attgtattta caaccgctgt ccatcaggtg ccatgtgtta ggcgcgccca    60
cttaacggct gacatgggaa ttag    84

<210> SEQ ID NO 160
<211> LENGTH: 74
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 160
ttgctgtatg gctttgttgt aaaaaggatc agctgcagaa acaacctaag cgactgaatt    60 ggttcccttta aagc    74

<210> SEQ ID NO 161
<211> LENGTH: 75
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 161
atgagggcag cctggtgcag agagctctgc ccaaggactc tacccgtgtg gccgcactcg    60
agatatctag accca    75

<210> SEQ ID NO 162
<211> LENGTH: 83
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 162
cccacatgcc ccaggacccc ccagcatccg ggcaatgagg aacatcacgg ggcgcgccag    60
cattacacgt cttgagcgat tgt    83

<210> SEQ ID NO 163
<211> LENGTH: 85
<212> TYPE: DNA
<213> ORGANISM: Artificial Sequence
<220> FEATURE:
<223> OTHER INFORMATION: Description of Artificial Sequence: note =

Synthetic Construct

<400> SEQUENCE: 163
acctgtgcca gcagcctagg aggcaggcag gctgcaggcg gggagggacc tggcgcgccc    60
acttaacggc tgacatggga attag    85

<210> SEQ ID NO 164
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 164
gcaatttgga agtacacttt tagccccact gcagcagact actgaacgaa cgactgaatt    60
ggttccttta aagc    74

<210> SEQ ID NO 165
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 165
cactggtttt cccccttagt aagatgcaca aggtctagaa attcagatag gccgcactcg    60
agatatctag accca    75

<210> SEQ ID NO 166
<211> LENGTH: 83
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 166
ttctcagaaa caggggggctg gcgcctattc caaatcctac accctggtgg ggcgcgccag    60
cattacacgt cttgagcgat tgt    83

<210> SEQ ID NO 167
<211> LENGTH: 85
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 167
gaggcgcaga ggtcccagtg tggagcccct ctccatttgt cggccatcct aggcgcgccc    60
acttaacggc tgacatggga attag    85

<210> SEQ ID NO 168
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 168
tgtcctacca aagacgtgtt tccaagaggc actccaggga gaggctgagg cgactgaatt    60

<210> SEQ ID NO 169
<211> LENGTH: 75
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 169
cagcagtgta atgaatactt tctgtaaaga tcagacatat atgctggaat gccgcactcg     60
agatatctag accca                                                     75

<210> SEQ ID NO 170
<211> LENGTH: 84
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 170
gtctggtgtg gagctggagc ttcagctgga ctggccctgc catgcagaag gggcgcgcca     60
gcattacacg tcttgagcga ttgt                                           84

<210> SEQ ID NO 171
<211> LENGTH: 80
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 171
cctctgtgac cctcacaccc actgctgctc acagtgctgt ggacaggggc gcgcccactt     60
aacggctgac atgggaatta                                                80

<210> SEQ ID NO 172
<211> LENGTH: 74
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 172
catgtcatta atgttggctc aagaaactac ccagtctgcc ttcggtaggc cgactgaatt     60
ggttccttta aagc                                                      74

<210> SEQ ID NO 173
<211> LENGTH: 75
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 173
gaaaacttaa agacaaaaca cactgccacc tcgcacctaa gacatattga gccgcactcg     60
agatatctag accca                                                     75

<210> SEQ ID NO 174

```
<211> LENGTH: 84
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 174
gcattgacac actgtcttat ttttcaggca ccatattcac tactaattct gggcgcgcca    60
gcattacacg tcttgagcga ttgt                                          84

<210> SEQ ID NO 175
<211> LENGTH: 83
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 175
tgtctgagct gagagatggg cgagcaggca cggagtcagc atcaggtcta ggcgcgccca    60
cttaacggct gacatgggaa tta                                           83

<210> SEQ ID NO 176
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 176
gtgcacatgc ccagctgagc aacctgattc attataatac cactggctca cgactgaatt    60
ggttccttta aagc                                                     74

<210> SEQ ID NO 177
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 177
gagcatcatc ttgagaggcc tctgcagtaa gggagtcagc agatagagag gccgcactcg    60
agatatctag accca                                                    75

<210> SEQ ID NO 178
<211> LENGTH: 85
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 178
aattgtctca ttttcgcgct gatttgctta actggtggga ccatgccaga aaggcgcgcc    60
agcattacac gtcttgagcg attgt                                         85

<210> SEQ ID NO 179
<211> LENGTH: 84
<212> TYPE: DNA
<213> ORGANISM: Artificial Sequence
<220> FEATURE:
<223> OTHER INFORMATION: Description of Artificial Sequence:  note =
```

Synthetic Construct

<400> SEQUENCE: 179
catttaaaga ccaggaacag gccctgaaat ggtagtttta aaatgaagct tggcgcgccc    60
acttaacggc tgacatggga atta    84

<210> SEQ ID NO 180
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 180
caatggcagg ccagccaagt ccaagtctca agaggccctc tctgcttcag cgactgaatt    60
ggttccttta aagc    74

<210> SEQ ID NO 181
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 181
gttgcatggg catggggtat tggccctgtg ggtaagagtg tttgttgtac gccgcactcg    60
agatatctag accca    75

<210> SEQ ID NO 182
<211> LENGTH: 83
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 182
gaatgcaaac gccgccaggc gcttcttcta gtcgggcaag atgcagccga ggcgcgccag    60
cattacacgt cttgagcgat tgt    83

<210> SEQ ID NO 183
<211> LENGTH: 83
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 183
ctgaatgcag aaagctggtg ggagcgcgct gactgcggct cacattccct ggcgcgccca    60
cttaacggct gacatgggaa tta    83

<210> SEQ ID NO 184
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 184
cacattttct ggtaacatag agaaagctac tgtagaagac accagaattt cgactgaatt    60

```
ggttccttta aagc                                                     74

<210> SEQ ID NO 185
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 185
gaatggaaag atatgtttac agggtgtgga attttggaaa tatggtggga gccgcactcg   60
agatatctag accca                                                    75

<210> SEQ ID NO 186
<211> LENGTH: 83
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 186
caggccacga agacaagaag gactgtgaac gggaagcgat cttacaatga ggcgcgccag   60
cattacacgt cttgagcgat tgt                                           83

<210> SEQ ID NO 187
<211> LENGTH: 83
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 187
ctcaagagag aaaaactaac aatcaattcc aaagaaatca aaacaaactt ggcgcgccca   60
cttaacggct gacatgggaa tta                                           83

<210> SEQ ID NO 188
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 188
atgaacatat ctgacgttac tcatagaaca acatggcttc agagtttaga cgactgaatt   60
ggttccttta aagc                                                     74

<210> SEQ ID NO 189
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 189
tagaatgagg tgcagtgaat ttgtatttct taactgaatt taattttaag gccgcactcg   60
agatatctag accc                                                     74

<210> SEQ ID NO 190
```

<211> LENGTH: 83
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 190
cctttctaga ataagagctg gaatcctaat acacaccaga atgaattatt ggcgcgccag    60
cattacacgt cttgagcgat tgt    83

<210> SEQ ID NO 191
<211> LENGTH: 84
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 191
cacttcacat ctttacaaat tcatctattg taacttttc agaaacaag tggcgcgccc    60 acttaacggc tgacatggga atta    84

<210> SEQ ID NO 192
<211> LENGTH: 74
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 192
acctgccaca gacagtcgag aagagcctgt acaaggagtg aaacaggtgg cgactgaatt    60
ggttccttta aagc    74

<210> SEQ ID NO 193
<211> LENGTH: 75
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 193
tccaatgcct gttagttctg agttcttaag attcaaagac atgaacaatg gccgcactcg    60
agatatctag accca    75

<210> SEQ ID NO 194
<211> LENGTH: 83
<212> TYPE: DNA
<213> ORGANISM: Artificial Sequence
<220> FEATURE:
<223> OTHER INFORMATION: Description of Artificial Sequence: note = Synthetic Construct

<400> SEQUENCE: 194
cattctactt gacttctgaa actcctgcaa gcccatgtgg actacgggta ggcgcgccag    60
cattacacgt cttgagcgat tgt    83

<210> SEQ ID NO 195
<211> LENGTH: 84
<212> TYPE: DNA
<213> ORGANISM: Artificial Sequence
<220> FEATURE:
<223> OTHER INFORMATION: Description of Artificial Sequence: note =

-continued

Synthetic Construct

<400> SEQUENCE: 195
catctcaaca ccagagaccc tgagaatttc tctttctcct gggcacatct tggcgcgccc    60
acttaacggc tgacatggga atta    84

<210> SEQ ID NO 196
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 196
attcatcccc ttgcttcttc cacttgacac tgcaggctta tgtgtgtcct cgactgaatt    60
ggttccttta aagc    74

<210> SEQ ID NO 197
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 197
gacaggaaag gaatgctgat tcacagtaag aacctactgt gtgctgtgag gccgcactcg    60
agatatctag accca    75

<210> SEQ ID NO 198
<211> LENGTH: 83
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 198
ctctggtcca tgctcagggg cttggccagc gccatcaagc atgaggccac ggcgcgccag    60
cattacacgt cttgagcgat tgt    83

<210> SEQ ID NO 199
<211> LENGTH: 80
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 199
gaaccgggac taccagtggg tgtccccaga gtcggggctg acagtgggc gcgcccactt    60 aacggctgac atgggaatta    80

<210> SEQ ID NO 200
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 200
agtctccctg ctgctgcaat gccctccatc tgcccacact gctcacagga cgactgaatt    60

```
ggttccttta aagc                                                         74

<210> SEQ ID NO 201
<211> LENGTH: 76
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 201
gtctgtctcc tgcccacatg tccctccctt ctctttgagt ccctgtgact ggccgcactc      60
gagatatcta gaccca                                                      76

<210> SEQ ID NO 202
<211> LENGTH: 83
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 202
cctggggcca gtgaacaaga gccctggctg gattacaaac atgtggggcc ggcgcgccag      60
cattacacgt cttgagcgat tgt                                              83

<210> SEQ ID NO 203
<211> LENGTH: 84
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 203
acatccaggg atagctctct gtatggtgct ccttagggcc cagggcttct cggcgcgccc      60
acttaacggc tgacatggga atta                                             84

<210> SEQ ID NO 204
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 204
ccctatctcc cagaaccggc tattagcctc tgcaggcttc catgcacctg cgactgaatt      60
ggttccttta aagc                                                        74

<210> SEQ ID NO 205
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 205
gcgctgtctg tatgtccggt agcaagcacc agactttaag atatatgtct gccgcactcg      60
agatatctag accca                                                       75

<210> SEQ ID NO 206
```

```
<211> LENGTH: 84
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 206
gtcttcttgt agttctcctg attctggagc ctgccaggat ggggcctctg aggcgcgcca    60
gcattacacg tcttgagcga ttgt                                          84

<210> SEQ ID NO 207
<211> LENGTH: 84
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 207
ctccctcatg atctagtcga tcatggcggg taagacacac ctgctctatc aggcgcgccc    60
acttaacggc tgacatggga atta                                          84

<210> SEQ ID NO 208
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 208
tacagcctat tggctaactg taaaacacag acacaaggcc agtgtgatac cgactgaatt    60
ggttccttta aagc                                                     74

<210> SEQ ID NO 209
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 209
atactctgtc ttcaccttgc ttctacgaca cctgctggag cctgcccttg gccgcactcg    60
agatatctag accca                                                    75

<210> SEQ ID NO 210
<211> LENGTH: 81
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 210
ggttagaagg agcagtagca gcagcagcaa gagaagatgc tgaggatgcg acgcgtagca    60
ttacacgtct tgagcgattg t                                             81

<210> SEQ ID NO 211
<211> LENGTH: 82
<212> TYPE: DNA
<213> ORGANISM: Artificial Sequence
<220> FEATURE:
<223> OTHER INFORMATION: Description of Artificial Sequence: note =
```

-continued

Synthetic Construct

<400> SEQUENCE: 211
ctgagtgatc agccctctct ggggtatgta aacacatctg ggatctatct tacgcgtcac    60
ttaacggctg acatgggaat ta    82

<210> SEQ ID NO 212
<211> LENGTH: 74
<212> TYPE: DNA
<213> ORGANISM: Artificial Sequence
<220> FEATURE:
<223> OTHER INFORMATION: Description of Artificial Sequence:  note = 
      Synthetic Construct

<400> SEQUENCE: 212
agacagagac ctctagaggt acagtaagat tcatctgaat cgccagcatg cgactgaatt    60
ggttccttta aagc    74

<210> SEQ ID NO 213
<211> LENGTH: 75
<212> TYPE: DNA
<213> ORGANISM: Artificial Sequence
<220> FEATURE:
<223> OTHER INFORMATION: Description of Artificial Sequence:  note = 
      Synthetic Construct

<400> SEQUENCE: 213
acgagaaata gatccactca ttttactgat aaaactggtg aaatactcag gccgcactcg    60
agatatctag accca    75

<210> SEQ ID NO 214
<211> LENGTH: 83
<212> TYPE: DNA
<213> ORGANISM: Artificial Sequence
<220> FEATURE:
<223> OTHER INFORMATION: Description of Artificial Sequence:  note = 
      Synthetic Construct

<400> SEQUENCE: 214
ggctggctgg ctacagggga gctgcttcct tttccttttg gaaatgattg ggcgcgccag    60
cattacacgt cttgagcgat tgt    83

<210> SEQ ID NO 215
<211> LENGTH: 85
<212> TYPE: DNA
<213> ORGANISM: Artificial Sequence
<220> FEATURE:
<223> OTHER INFORMATION: Description of Artificial Sequence:  note = 
      Synthetic Construct

<400> SEQUENCE: 215
gctaacacct gaaatacac agtgcaccag aagagatgca gggccgggct aggcgcgccc    60
acttaacggc tgacatggga attag    85

<210> SEQ ID NO 216
<211> LENGTH: 74
<212> TYPE: DNA
<213> ORGANISM: Artificial Sequence
<220> FEATURE:
<223> OTHER INFORMATION: Description of Artificial Sequence:  note = 
      Synthetic Construct

<400> SEQUENCE: 216
accataggat taactcagca aagacatgca aactaaacct gtgaggaatt cgactgaatt    60

```
ggttccttta aagc                                                        74

<210> SEQ ID NO 217
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 217
gtatttggct acgcgtttta tgccaagaag atgccactgg attagtctat gccgcactcg     60
agatatctag accca                                                       75

<210> SEQ ID NO 218
<211> LENGTH: 83
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 218
agtccggctg ctcctgttcc caccccaccg gtctgggatg taccttccca ggcgcgccag     60
cattacacgt cttgagcgat tgt                                              83

<210> SEQ ID NO 219
<211> LENGTH: 85
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 219
tggagttaag tggaggggag cccccgtccc gggccacaat ggtcacattg tggcgcgccc     60
acttaacggc tgacatggga attag                                            85

<210> SEQ ID NO 220
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 220
gctatgaggc tgttttctgg aaatccagat gcttagctct ttgctactca cgactgaatt     60
ggttccttta aagc                                                        74

<210> SEQ ID NO 221
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 221
tgttgctagg ggctgtagaa agaaatcaac acttaggagt actgaagtct gccgcactcg     60
agatatctag accca                                                       75

<210> SEQ ID NO 222
```

```
<211> LENGTH: 83
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 222
ctaactcgcc ctgagaaggg aatctagcaa ctgaccaatg caccaaatga ggcgcgccag      60
cattacacgt cttgagcgat tgt                                             83

<210> SEQ ID NO 223
<211> LENGTH: 85
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 223
gcctctgagc atcagcatct ggcttgacca ggccctgtag tgtctgatct tggcgcgccc      60
acttaacggc tgacatggga attag                                           85

<210> SEQ ID NO 224
<211> LENGTH: 74
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 224
ctagacctca caagtggctt tatgtagttc cttaggactt ccagctgctc cgactgaatt      60 ggttcccttta aagc                                                      74

<210> SEQ ID NO 225
<211> LENGTH: 75
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 225
tcttcccaga tcttctagag ctgcttacta tcccatggga cactctggag gccgcactcg      60
agatatctag accca                                                      75

<210> SEQ ID NO 226
<211> LENGTH: 82
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 226
tcggaggggt gtggagaggc gaggcaaggc agagccccgc gcagccatgg aacgcgtagc      60
attacacgtc ttgagcgatt gt                                              82

<210> SEQ ID NO 227
<211> LENGTH: 82
<212> TYPE: DNA
<213> ORGANISM: Artificial Sequence
<220> FEATURE:
<223> OTHER INFORMATION: Description of Artificial Sequence:  note =
```

-continued

Synthetic Construct

<400> SEQUENCE: 227
catatcttac tcactcaaaa cacagaagaa aagaaagaaa acttggctct acgcgtcact    60
taacggctga catgggaatt ag                                             82

<210> SEQ ID NO 228
<211> LENGTH: 74
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 228
atttgaattt cacgttcttc tttctcactt ctggcagagg tgataatgag cgactgaatt    60
ggttccttta aagc                                                      74

<210> SEQ ID NO 229
<211> LENGTH: 75
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 229
gcacagttta aaattatag aattggtaca aaacagtttg ataggcagtc gccgcactcg     60
agatatctag accca                                                     75

<210> SEQ ID NO 230
<211> LENGTH: 83
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 230
ccaccctccc ttctggagcg ctctgactgc agcctcccag ggaatgcgcg ggcgcgccag    60
cattacacgt cttgagcgat tgt                                            83

<210> SEQ ID NO 231
<211> LENGTH: 85
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 231
gactacctat ggcagttaca atgtccctcc atgttattcc acaatggcat aggcgcgccc    60
acttaacggc tgacatggga attag                                          85

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: note =
      Synthetic Construct

<400> SEQUENCE: 232
tagtgaaaca ggggcaatgg tg                                             22

```
<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 233
catggatgca gagcagtgtt tg                                              22

<210> SEQ ID NO 234
<211> LENGTH: 25
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 234
gccttcttga cgagttcttc tgagg                                           25

<210> SEQ ID NO 235
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 235
taccttcttg ggcaggaagc ag                                              22

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 236
tttctttcca ggcattccct ca                                              22

<210> SEQ ID NO 237
<211> LENGTH: 22
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 237
ttcttgcgaa cctcatcact cg                                              22

<210> SEQ ID NO 238
<211> LENGTH: 995
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 238
ccctagaaag ataatcatat tgtgacgtac gttaaagata atcatgcgta aaattgacgc     60
atgtgtttta tcggtctgta tatcgaggtt tatttattaa tttgaataga tattaagttt    120
tattatattt acacttacat actaataata aattcaacaa acaatttatt tatgtttatt    180
```

```
tatttattaa aaaaaaacaa aaactcaaaa tttcttctat aaagtaacaa aacttttaaa      240
cattctctct tttacaaaaa taaacttatt ttgtacttta aaaacagtca tgttgtatta      300
taaaataagt aattagctta acttatacat aatagaaaca aattatactt attagtcagt      360
cagaaacaac tttggcacat atcaatatta tgctctcgac aaataacttt tttgcatttt      420
ttgcacgatg catttgcctt tcgccttatt ttagaggggc agtaagtaca gtaagtacgt      480
tttttcatta ctggctcttc agtactgtca tctgatgtac caggcacttc atttggcaaa      540
atattagaga tattatcgcg caaatatctc ttcaaagtag gagcttctaa acgcttacgc      600
ataaacgatg acgtcaggct catgtaaagg tttctcataa atttttttgcg actttgaacc      660 ttttctccct tgctactgac attatggctg tatataataa aagaatttat gcaggcaatg      720
tttatcattc cgtacaataa tgccataggc cacctattcg tcttcctact gcaggtcatc      780
acagaacaca tttggtctag cgtgtccact ccgcctttag tttgattata atacataacc      840
atttgcggtt taccggtact ttcgttgata gaagcatcct catcacaaga tgataataag      900
tataccatct tagctggctt cggtttatat gagacgagag taagggggtcc gtcaaaacaa      960 aacatcgatg ttcccactgg cctggagcga ctgtt                                995

<210> SEQ ID NO 239
<211> LENGTH: 680
<212> TYPE: DNA
<213> ORGANISM: Artificial Sequence
<220> FEATURE:
<223> OTHER INFORMATION: Description of Artificial Sequence:  note =
      Synthetic Construct

<400> SEQUENCE: 239
gagatctgac aatgttcagt gcagagactc ggctacgcct cgtggacttt gaagttgacc       60
aacaatgttt attcttacct ctaatagtcc tctgtggcaa ggtcaagatt ctgttagaag      120
ccaatgaaga acctggttgt tcaataacat tttgttcgtc taatatttca ctaccgcttg      180
acgttggctg cacttcatgt acctcatcta taaacgcttc ttctgtatcg ctctggacgt      240
catcttcact tacgtgatct gatatttcac tgtcagaatc ctcaccaaca agctcgtcat      300
cgctttgcag aagagcagag aggatatgct catcgtctaa agaactaccc attttattat      360
atattagtca cgatatctat aacaagaaaa tatatatata ataagttatc acgtaagtag      420
aacatgaaat aacaatataa ttatcgtatg agttaaatct taaaagtcac gtaaaagata      480
atcatgcgtc attttgactc acgcggtcgt tatagttcaa aatcagtgac acttaccgca      540
ttgacaagca cgcctcacgg gagctccaag cggcgactga gatgtcctaa atgcacagcg      600
acggattcgc gctatttaga aagagagagc aatatttcaa gaatgcatgc gtcaatttta      660
cgcagactat ctttctaggg                                                 680
```